(12) United States Patent
Kitamura et al.

(10) Patent No.: US 7,538,241 B2
(45) Date of Patent: May 26, 2009

(54) HSP90 FAMILY PROTEIN INHIBITORS

(75) Inventors: Yushi Kitamura, Sakai (JP); Shinji Nara, Sunto-gun (JP); Hiroshi Nakagawa, Sunto-gun (JP); Rieko Nakatsu, Yokohama (JP); Takayuki Nakashima, Sunto-gun (JP); Shiro Soga, Machida (JP); Jiro Kajita, Sunto-gun (JP); Yukimasa Shiotsu, Sunto-gun (JP); Yutaka Kanda, Machida (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 114 days.

(21) Appl. No.: 10/584,234

(22) PCT Filed: Dec. 24, 2004

(86) PCT No.: PCT/JP2004/019742

§ 371 (c)(1),
(2), (4) Date: Jun. 26, 2006

(87) PCT Pub. No.: WO2005/063222

PCT Pub. Date: Jul. 14, 2005

(65) Prior Publication Data

US 2007/0155813 A1    Jul. 5, 2007

(30) Foreign Application Priority Data

Dec. 26, 2003    (JP)    ............... 2003-432776

(51) Int. Cl.
C07C 225/00    (2006.01)
C07C 211/00    (2006.01)
C07C 69/76    (2006.01)

(52) U.S. Cl. .................... 558/414; 564/338; 560/69
(58) Field of Classification Search ............... 558/414; 564/338; 560/89
See application file for complete search history.

(56) References Cited

U.S. PATENT DOCUMENTS

| | | | |
|---|---|---|---|
| 3,118,887 A | 1/1964 | Hardy et al. | 260/248 |
| 3,268,474 A | 8/1966 | Hardy et al. | 260/45.8 |
| 4,868,306 A * | 9/1989 | Ince et al. | 546/165 |
| 6,914,074 B2 | 7/2005 | Mewshaw et al. | 514/524 |
| 2003/0181519 A1 | 9/2003 | Mewshaw et al. | 514/520 |
| 2004/0016063 A1 | 1/2004 | Chassot et al. | 8/405 |
| 2004/0167127 A1 | 8/2004 | Steffan et al. | 514/227.8 |
| 2005/0049263 A1 | 3/2005 | Kasibhatla et al. | 514/263.21 |
| 2005/0222230 A1 | 10/2005 | Drysdale et al. | 514/381 |

FOREIGN PATENT DOCUMENTS

| | | |
|---|---|---|
| EP | 1 642 880 | 4/2006 |
| JP | 52151133 * | 12/1977 |
| JP | 2000-287697 | 10/2000 |
| WO | WO 2004/072051 | 8/2004 |
| WO | WO 2004/081008 | 9/2004 |

OTHER PUBLICATIONS

Evans et al. Tetrahedron Letters (1992), 33(9), 1189-92.*
Kashiwada et al. Bioorganic & Medicinal Chemistry Letters (1992), 2(3), 235-8.*
Chester et al. Australian Journal of Chemistry (1986), 39(11), 1759-64.*
Ling et al. STN Accession No. 2003:53748; Document No. 138:237722 Abstract of Journal of Organic Chemistry (2003), 68(4), 1358-1366.*
ApSimon et al.STN Accession No. 1965:445881, Document No. 63:45881 Abstract of Journal of the Chemical Society (1965), (July),4156-63.*
Bringmann, et al., "On the Verge of Axial Chirality: Atroposelective Synthesis of the AB-Biaryl Fragment of Vancomycin", Organic Letters, vol. 4, No. 17 (2002) 2833-36.
Furstner, et al., "Total Synthesis of the Turrianes and Evaluation of Their DNA-Cleaving Properties", Chem. Eur. J., vol. 8, No. 8 (2002) 1856-71.
Bringmann, et al., "Atropo-Enantioselective Synthesis of the Natural Bicoumarin(+)-IsokotaninA via a Configurationally Stable Biaryl Lactone", Eur. J. Org. Chem., Issue 6 (2002) 1096-1106.

(Continued)

*Primary Examiner*—D. Margaret Seaman
*Assistant Examiner*—Nizal S Chandrakumar
(74) *Attorney, Agent, or Firm*—Fitzpatrick, Cella, Harper & Scinto

(57) ABSTRACT

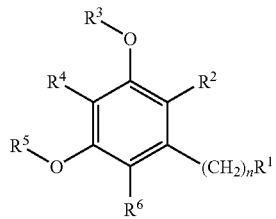

(wherein n is an integer of 0 to 10; $R^1$ represents substituted or unsubstituted lower alkyl, substituted or unsubstituted lower alkoxy, substituted or unsubstituted cycloalkyl, substituted or unsubstituted lower alkoxycarbonyl, substituted or unsubstituted heterocyclic-alkyl, substituted or unsubstituted aryl, —$CONR^7R^8$, —$NR^9R^{10}$, etc.; $R^2$ represents substituted or unsubstituted aryl or a substituted or unsubstituted heterocyclic group, etc.; $R^3$ and $R^5$ may be the same or different, each represent a hydrogen atom, substituted or unsubstituted lower alkyl, etc.; $R^4$ and $R^6$ may be the same or different, each represent a hydrogen atom, halogen, substituted or unsubstituted lower alkyl, etc.)

Provided are an Hsp90 family protein inhibitor comprising, as an active ingredient, a benzene derivative of formula (I) or a prodrug thereof or a pharmaceutically-acceptable salt thereof, etc.

20 Claims, 1 Drawing Sheet

OTHER PUBLICATIONS

Baker, et al., "Formal Synthesis of Both Atropomers of Desertorin C and an Example of Chirality Transfer from a Biphenyl Axis to a Spiro Centre and its Reverse", Aust. J. Chem., vol. 53, No. 6 (2000) 487-506.

Neuville, et al., "Synthesis of a model 22-membered AB-C-O-D ring of vancomycin containing biaryl and biaryl ether linkages", Tetrahedron Letters, vol. 41, No. 11 (2000) 1747-51.

Wachtmeister, "Studies on the Chemistry of Lichens", Acta Chem. Scand., vol. 12, No. 2 (1958) 147-64.

McClanahan, et al., "Microbial Transformation of Olivetol by *Fusarium Roseum*", *Journal of Natural Products*, vol. 48, No. 4 (1985), pp. 660-663.

Balachari, et al., "Efficient synthesis of 5-aryl-2-vinylfurans by palladium catalyzed cross-coupling strategies", *Tetrahedron Letters*, vol. 40 (1999), pp. 4769-4773.

Schulte, et al., "Antibiotic radicicol binds to the N-terminal domain of Hsp90 and . . . ", *Cell Stress & Chaperones*, vol. 3, No. 2 (1998), pp. 100-108.

Roe, et al., "Structural Basis for Inhibition of the Hsp90 Molecular Chaperone . . . ", *J. Med. Chem.*, vol. 42 (1999), pp. 260-266.

Csermely, et al., "The 90-kDa Molecular Chaperone Family: Structure, Function, and . . . ", *Pharmacol. Ther.*, vol. 79, No. 2 (1998), pp. 129-168.

Schulte, et al., "Interaction of Radicicol with Members of the Heat Shock Protein 90 Family of Molecular Chaperones", *Mol. Endo*, vol. 13, No. 9 (1999), pp. 1435-1448.

\* cited by examiner

HSP90 FAMILY PROTEIN INHIBITORS

TECHNICAL FIELD

The present invention relates to heat shock protein 90 (Hsp90) family protein inhibitors comprising, as an active ingredient, a benzene derivative or a prodrug thereof, or a pharmaceutically acceptable salt thereof.

BACKGROUND ART

As benzene derivatives, known are compound A (see J. Nat. Prod., 1985, Vol. 48, pp. 660-663), compound B, (see U.S. Pat. Nos. 3,118,887, 3,268,474, and the like), compound C (see Tetrahedron Lett., 1999, Vol. 40, pp. 4769-4773), etc.

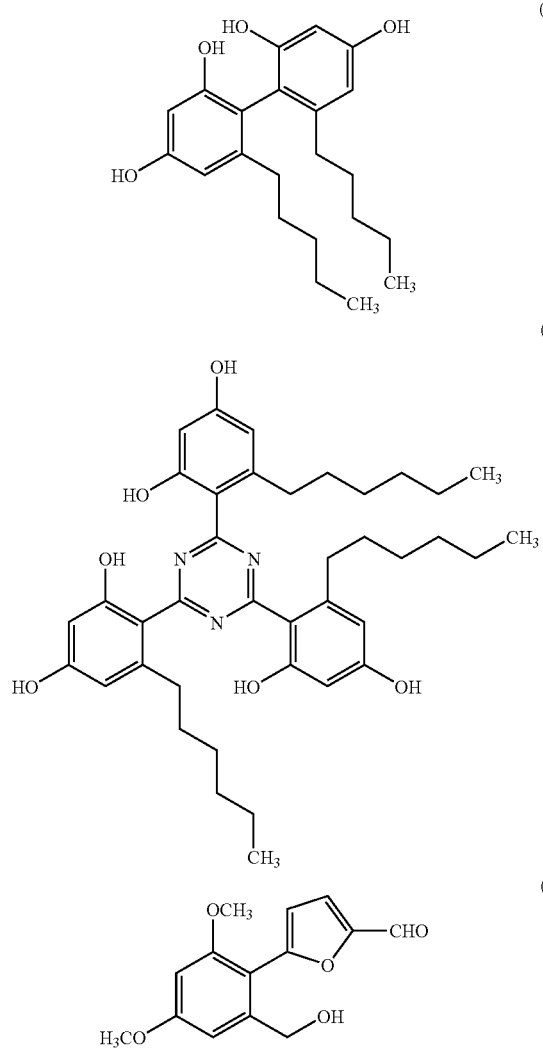

Benzoquinone ansamycin antibiotics such as Geldanamycin, Herbimycin, etc. and Radicicol are known as compounds which are bound to heat shock protein 90 (Hsp90) family proteins (Cell Stress & Chaperones, 1998, Vol., 3, pp. 100-108; J. Med. Chem., 1999, Vol., 42, pp. 260-266); and purine derivatives and pyrazole derivatives are also known (WO03/037860, WO03/055860). It is reported that these compounds are all bound to Hsp90 family proteins and inhibit the functions of Hsp90 family proteins, thereby exhibiting pharmacological activities such as anti-tumor activity. Therefore, compounds capable of being bound to Hsp90 family proteins are considered to be useful as therapeutic agents for diseases associated with Hsp90 family proteins or proteins to which Hsp90 family proteins are bound (Hsp90 client proteins).

Examples of known Hsp90 family proteins include Hsp90α protein, Hsp90β protein, grp94 and hsp75/TRAP1 (Pharmacology & Therapeutics, 1998, Vol., 79, pp. 129-168; Molecular Endocrinology, 1999, Vol., 13, pp. 1435-1448; etc.).

DISCLOSURE OF THE INVENTION

An object of the present invention is to provide Hsp90 family protein inhibitors comprising, as an active ingredient, for example, a benzene derivative or a prodrug thereof, or a pharmaceutically acceptable salt thereof.

The present invention relates to the following (1) to (41).

(1) An Hsp90 family protein inhibitor comprising, as an active ingredient, a benzene derivative represented by general formula (I):

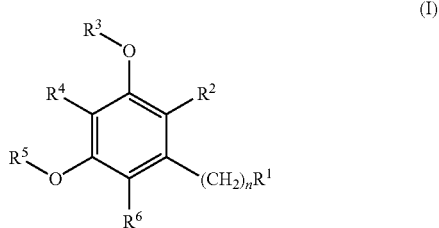

{wherein n represents an integer of 0 to 10;

$R^1$ represents a hydrogen atom, hydroxy, cyano, carboxy, nitro, halogen, substituted or unsubstituted lower alkyl, substituted or unsubstituted lower alkenyl, substituted or unsubstituted lower alkynyl, substituted or unsubstituted cycloalkyl, substituted or unsubstituted lower alkoxycarbonyl, substituted or unsubstituted aroyl, substituted or unsubstituted lower alkanoyl, substituted or unsubstituted heterocyclic-alkyl, substituted or unsubstituted aryl, substituted or unsubstituted aralkyl, substituted or unsubstituted arylsulfonyl, a substituted or unsubstituted heterocyclic group, —$CONR^7R^8$ (wherein $R^7$ and $R^8$, which may be the same or different, each represent a hydrogen atom, substituted or unsubstituted lower alkyl, substituted or unsubstituted cycloalkyl, substituted or unsubstituted lower alkanoyl, substituted or unsubstituted aryl, a substituted or unsubstituted heterocyclic group, substituted or unsubstituted aralkyl, substituted or unsubstituted heterocyclic-alkyl or substituted or unsubstituted aroyl, or $R^7$ and $R^8$ form a substituted or unsubstituted heterocyclic group together with the adjacent nitrogen atom), —$NR^9R^{10}$ [wherein. $R^9$ and $R^{10}$, which may be the same or different, each represent a hydrogen atom, substituted or unsubstituted lower alkylsulfonyl, substituted or unsubstituted lower alkyl, substituted or unsubstituted cycloalkyl, substituted or unsubstituted lower alkanoyl, substituted or unsubstituted aryl, a substituted or unsubstituted heterocyclic group, substituted or unsubstituted aralkyl, substituted or unsubstituted heterocyclic-alkyl, substituted or unsubstituted aroyl, or —$CONR^{11}R^{12}$ (wherein $R^{11}$ and $R^{12}$ have the same meanings as the above $R^7$ and $R^8$, respectively), or $R^9$ and $R^{10}$ form a substituted or unsubstituted heterocyclic group together with the adjacent nitrogen atom], or —OR$^{13}$ (wherein R$^{13}$ represents substituted or unsubstituted lower alkyl, substituted or unsubstituted lower alkenyl, substituted or unsubstituted lower alkanoyl, substituted or unsubstituted aryl, a substituted or unsubstituted heterocyclic group, substituted or unsubstituted aralkyl or substituted or unsubstituted heterocyclic-alkyl);

R$^2$ represents substituted or unsubstituted lower alkyl, substituted or unsubstituted lower alkenyl, substituted or unsubstituted lower alkynyl, substituted or unsubstituted aryl or a substituted or unsubstituted heterocyclic group (excluding substituted or unsubstituted pyrazolyl);

R$^3$ and R$^5$, which may be the same or different, each represent a hydrogen atom, substituted or unsubstituted lower alkyl, substituted or unsubstituted lower alkenyl, substituted or unsubstituted lower alkanoyl, substituted or unsubstituted cycloalkyl, substituted or unsubstituted lower alkylsulfonyl, substituted or unsubstituted arylsulfonyl, carbamoyl, sulfamoyl, substituted or unsubstituted lower alkylaminocarbonyl, substituted or unsubstituted di-lower alkylaminocarbonyl, substituted or unsubstituted lower alkoxycarbonyl, substituted or unsubstituted heterocyclic-carbonyl, substituted or unsubstituted aralkyl or substituted or unsubstituted aroyl;

R$^4$ and R$^6$, which may be the same or different, each represent a hydrogen atom, hydroxy, halogen, cyano, nitro, substituted or unsubstituted lower alkyl, substituted or unsubstituted lower alkenyl, substituted or unsubstituted lower alkynyl, substituted or unsubstituted lower alkoxy, substituted or unsubstituted cycloalkyl, amino, lower alkylamino, di-lower alkylamino, carboxy, substituted or unsubstituted lower alkoxycarbonyl, substituted or unsubstituted aryloxy, substituted or unsubstituted aryl, a substituted or unsubstituted heterocyclic group (excluding substituted or unsubstituted pyrazolyl), substituted or unsubstituted lower alkanoyl, substituted or unsubstituted aralkyl, or substituted or unsubstituted heterocyclic-alkyl}, or a prodrug thereof, or a pharmaceutically acceptable salt thereof.

(2) An Hsp90 family protein inhibitor comprising, as an active ingredient, a benzene derivative represented by general formula (I):

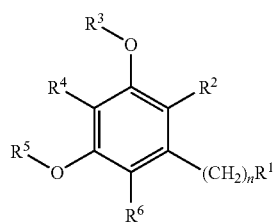

(I)

(wherein n, R$^1$, R$^2$, R$^3$, R$^4$, R$^5$ and R$^6$ have the same meanings as those defined above, respectively) or a pharmaceutically acceptable salt thereof.

(3) The Hsp90 family protein inhibitor according to the above (1) or (2), wherein R$^1$ is a hydrogen atom, hydroxy, cyano, carboxy, nitro, halogen, substituted or unsubstituted lower alkyl, substituted or unsubstituted lower alkynyl, substituted or unsubstituted lower alkoxy, substituted or unsubstituted cycloalkyl, substituted or unsubstituted lower alkoxycarbonyl, substituted or unsubstituted lower alkanoyloxy, substituted or unsubstituted heterocyclic-alkyl, substituted or unsubstituted aryl, substituted or unsubstituted arylsulfonyl, —CONR$^7$R$^8$ (wherein R$^7$ and R$^8$ have the same meanings as those defined above, respectively) or —NR$^9$R$^{10}$ (wherein R$^9$ and R$^{10}$ have the same meanings as those defined above, respectively).

(4) The Hsp90 family protein inhibitor according to the above (1) or (2), wherein R$^1$ is substituted or unsubstituted lower alkyl, substituted or unsubstituted lower alkynyl, substituted or unsubstituted lower alkoxy, substituted or unsubstituted cycloalkyl, substituted or unsubstituted lower alkoxycarbonyl, substituted or unsubstituted heterocyclic-alkyl, substituted or unsubstituted aryl, —CONR$^7$R$^8$ (wherein R$^7$ and R$^8$ have the same meanings as those defined above, respectively), or —NR$^9$R$^{10}$ (wherein R$^9$ and R$^{10}$ have the same meanings as those defined above, respectively).

(5) The Hsp90 family protein inhibitor according to any of the above (1) to (4), wherein R$^2$ is substituted or unsubstituted aryl, or a substituted or unsubstituted aromatic heterocyclic group.

(6) The Hsp90 family protein inhibitor according to any of the above (1) to (4), wherein R$^2$ is substituted or unsubstituted aryl.

(7) The Hsp90 family protein inhibitor according to any of the above (1) to (4), wherein R$^2$ is substituted or unsubstituted phenyl.

(8) The Hsp90 family protein inhibitor according to any of the above (1) to (4), wherein R$^2$ is substituted or unsubstituted furyl.

(9) The Hsp90 family protein inhibitor according to any of the above (1) to (8), wherein R$^4$ is a hydrogen atom, hydroxy, or halogen.

(10) The Hsp90 family protein inhibitor according to any of the above (1) to (9), wherein R$^3$ and R$^5$, which may be the same or different, each represent a hydrogen atom, substituted or unsubstituted lower alkyl, substituted or unsubstituted lower alkenyl, substituted or unsubstituted lower alkanoyl, substituted or unsubstituted aroyl, substituted or unsubstituted lower alkylaminocarbonyl, substituted or unsubstituted di-lower alkylaminocarbonyl, substituted or unsubstituted lower alkoxycarbonyl, or substituted or unsubstituted heterocyclic-carbonyl.

(11) The Hsp90 family protein inhibitor according to any of the above (1) to (8), wherein R$^3$, R$^4$ and R$^5$ are hydrogen atoms.

(12) A benzene derivative represented by general formula (IA):

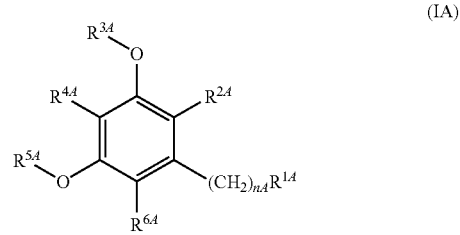

(IA)

[wherein R$^{2A}$ represents substituted or unsubstituted aryl, or a substituted or unsubstituted aromatic heterocyclic group (excluding substituted or unsubstituted pyrazolyl);

R$^{3A}$ and R$^{5A}$, which may be the same or different, each represent a hydrogen atom, substituted or unsubstituted lower alkyl, substituted or unsubstituted lower alkenyl, substituted or unsubstituted lower alkanoyl, carbamoyl, sulfamoyl, substituted or unsubstituted lower alkylsulfonyl, substituted or unsubstituted lower alkylaminocarbonyl, substituted or unsubstituted di-lower alkylaminocarbonyl, substituted or unsubstituted lower alkoxycarbonyl, substituted or unsubstituted heterocyclic-carbonyl, substituted or unsubstituted aralkyl, or substituted or unsubstituted aroyl;

$R^{4A}$ represents a hydrogen atom, hydroxy, or halogen;

nA represents an integer of 0 to 5;

provided that;

(1) when nA is 0, then $R^{1A}$ is a hydrogen atom, methyl, hydroxy, methoxy, carboxy, methoxycarbonyl, carbamoyl, —CONHCH$_3$, —CON(CH$_3$)$_2$, —CONHCH$_2$Ph (wherein Ph represents phenyl), —CH(OCH$_3$)Ph (wherein Ph has the same meaning as that defined above), propionyl, benzoyl, dioxolanyl, substituted or unsubstituted vinyl, or substituted or unsubstituted prop-1-en-1-yl;

and when $R^{1A}$ is a hydrogen atom, then $R^{6A}$ is substituted or unsubstituted lower alkyl;

when $R^{1A}$ is methyl, hydroxy, methoxy, carboxy, methoxycarbonyl, carbamoyl, —CONHCH$_3$, —CON(CH$_3$)$_2$, —CONHCH$_2$Ph (wherein Ph has the same meaning as that defined above), propionyl, benzoyl, dioxolanyl, substituted or unsubstituted vinyl, or substituted or unsubstituted prop-1-en-1-yl, then $R^{6A}$ is halogen;

(2) when nA is an integer of 1 to 5, then $R^{1A}$ is hydroxy, cyano, carboxyl, halogen, substituted or unsubstituted lower alkyl, substituted or unsubstituted lower alkenyl, substituted or unsubstituted lower alkynyl, substituted or unsubstituted cycloalkyl, substituted or unsubstituted lower alkanoyl, substituted or unsubstituted lower alkoxycarbonyl, substituted or unsubstituted aryl, substituted or unsubstituted aroyl, substituted or unsubstituted heterocyclic-alkyl, substituted or unsubstituted aralkyl, substituted or unsubstituted arylsulfonyl, a substituted or unsubstituted heterocyclic group, —CONR$^7$R$^8$ (wherein R$^7$ and R$^8$ have the same meanings as those defined above, respectively), —NR$^9$R$^{10}$ (wherein R$^9$ and R$^{10}$ have the same meanings as those defined above, respectively), or —OR$^{13}$ (wherein R$^{13}$ has the same meaning as that defined above), $R^{6A}$ is a hydrogen atom, halogen, cyano, nitro, substituted or unsubstituted lower alkyl, substituted or unsubstituted lower alkenyl, substituted or unsubstituted lower alkynyl, substituted or unsubstituted lower alkoxy, substituted or unsubstituted cycloalkyl, substituted or unsubstituted lower alkanoyl, amino, lower alkylamino, di-lower alkylamino, carboxy, substituted or unsubstituted lower alkoxycarbonyl, substituted or unsubstituted aryloxy, substituted or unsubstituted aryl, a substituted or unsubstituted heterocyclic group (excluding substituted or unsubstituted pyrazolyl), substituted or unsubstituted aralkyl, or substituted or unsubstituted heterocyclic-alkyl; and provided that;

(i) when $R^{3A}$ and $R^{5A}$ are isopropyl, then $R^{6A}$ is not a hydrogen atom;

(ii) when $R^{3A}$ and $R^{5A}$ are methyl, then $R^{6A}$ is not the group selected from a hydrogen atom, bromo, ethyl, 1-hydroxyethyl, 1-(dimethylamino)ethyl, vinyl and carboxy;

(iii) when $R^{4A}$ and $R^{6A}$ are hydrogen atoms, and when $R^{3A}$ and $R^{5A}$ are the same and are tert-butyl or benzyl, Then —(CH$_2$)$_{nA}$R$^{1A}$ is not the group selected from hydroxymethyl and 2-chloroallyl;

(iv) when $R^{4A}$ and $R^{6A}$ are hydrogen atoms, and when $R^{3A}$ is benzyl or acetyl and $R^{5A}$ is methyl, or when $R^{3A}$, $R^{4A}$ and $R^{6A}$ are hydrogen atoms, and when $R^{5A}$ is methyl, then —(CH$_2$)$_{nA}$R$^{1A}$ is not the group selected from 2-(acetylamino)propyl and 2-(substituted lower alkanoylamino)propyl;

(v) when $R^{3A}$, $R^{4A}$ and $R^{5A}$ are hydrogen atoms, and when $R^{6A}$ is carboxy, or when $R^{4A}$, $R^{5A}$ and $R^{6A}$ are hydrogen atoms, and when $R^{3A}$ is methyl, then —(CH$_2$)$_{nA}$R$^{1A}$ is not n-pentyl;

(vi) when $R^{3A}$ and $R^{4A}$ are hydrogen atoms, $R^{5A}$ is methyl, and $R^{6A}$ is ethyl, then —(CH$_2$)$_{nA}$R$^{1A}$ is not n-propyl;

(vii) when $R^{3A}$ is methyl, $R^{4A}$ and $R^{6A}$ are hydrogen atoms, and $R^{5A}$ is 4-methoxybenzyl, then —(CH$_2$)$_{nA}$R$^{1A}$ is not the group selected from —(CH$_2$)$_3$CH=CH$_2$ and —(CH$_2$)$_5$CH=CH$_2$;

(viii) when $R^{3A}$, $R^{4A}$, $R^{5A}$ and $R^{6A}$ are hydrogen atoms, and when —(CH$_2$)$_{nA}$R$^{1A}$ is (a) n-pentyl, then $R^{2A}$ is not 2,4-dihydroxy-6-pentylphenyl, (b) n-hexyl, then $R^{2A}$ is not the group selected from 4,6-di(substituted phenyl)triazol-2-yl and 3,6-di(substituted phenyl)-1,2,4-triazin-5-yl, (c) n-heptyl, then $R^{2A}$ is not substituted triazolyl;

(ix) when $R^{3A}$ is a hydrogen atom or acetyl, $R^{5A}$ is methyl, and $R^{4A}$ and $R^{6A}$ are hydrogen atoms, and when —(CH$_2$)$_{nA}$R$^{1A}$ is ethyl or n-propyl, then $R^{2A}$ is not 2-aminopyrimidin-4-yl having a substituent at the 5-position thereof, (x) when $R^{3A}$, $R^{4A}$ and $R^{5A}$ are hydrogen atoms, $R^{6A}$ is methoxy, and —(CH$_2$)$_{nA}$R$^{1A}$ is 3-methylbut-2-en-1-yl, or 3-hydroxy-3-methylbutyl, then $R^{2A}$ is not the group selected from 7-hydroxy-4-oxo-4H-1-benzopyran-3-yl and 6-methoxy-2,2-dimethyl-2H-1-benzopyran-8-yl], or a pharmaceutically acceptable salt thereof.

(13) The benzene derivative according to the above (12), wherein $R^{2A}$ is substituted or unsubstituted phenyl, or a pharmaceutically acceptable salt thereof.

(14) The benzene derivative according to the above (12), wherein $R^{2A}$ is substituted or unsubstituted furyl, or a pharmaceutically acceptable salt thereof.

(15) The benzene derivative according to any of the above (12) to (14), wherein $R^{3A}$ and $R^{5A}$, which may be the same or different, each represent a hydrogen atom, substituted or unsubstituted lower alkanoyl, substituted or unsubstituted aroyl, substituted or unsubstituted lower alkenyl, substituted or unsubstituted lower alkylaminocarbonyl, substituted or unsubstituted di-lower alkylaminocarbonyl, substituted or unsubstituted lower alkoxycarbonyl, or substituted or unsubstituted heterocyclic-carbonyl, or a pharmaceutically acceptable salt thereof.

(16) The benzene derivative according to any of the above (12) to (14), wherein $R^{3A}$, $R^{4A}$ and $R^{5A}$ are hydrogen atoms, or a pharmaceutically acceptable salt thereof.

(17) The benzene derivative according to any of the above (12) to (16), wherein nA is an integer of 1 to 5, or a pharmaceutically acceptable salt thereof.

(18) A pharmaceutical composition comprising, as an active ingredient, the benzene derivative according to any of the above (12) to (17) or a pharmaceutically acceptable salt thereof.

(19) An Hsp90 family protein inhibitor comprising, as an active ingredient, the benzene derivative according to any of the above (12) to (17) or a pharmaceutically acceptable salt thereof.

(20) A therapeutic agent for a disease associated with an Hsp90 family protein or a protein to which an Hsp90 family protein is bound (Hsp90 client protein) comprising, as an active ingredient, the benzene derivative according to any of the above (12) to (17) or a pharmaceutically acceptable salt thereof.

(21) An anti-tumor agent comprising, as an active ingredient, the benzene derivative according to any of the above (12) to (17) or a pharmaceutically acceptable salt thereof.

(22) A pharmaceutical composition comprising, as an active ingredient, the benzene derivative according to any of the above (12) to (17) or a prodrug thereof, or a pharmaceutically acceptable salt thereof.

(23) An Hsp90 family protein inhibitor comprising, as an active ingredient, the benzene derivative according to any of the above (12) to (17) or a prodrug thereof, or a pharmaceutically acceptable salt thereof.

(24) A therapeutic agent for a disease associated with an Hsp90 family protein or a protein to which an Hsp90 family protein is bound (Hsp90 client protein) comprising, as an active ingredient, the benzene derivative according to any of the above (12) to (17) or a prodrug thereof, or a pharmaceutically acceptable salt thereof.

(25) An anti-tumor agent comprising, as an active ingredient, the benzene derivative according to any of the above (12) to (17) or a prodrug thereof, or a pharmaceutically acceptable salt thereof.

(26) A method of inhibiting a heat shock protein 90 (Hsp90) family protein, which comprises administering an effective amount of a benzene derivative represented by general formula (I):

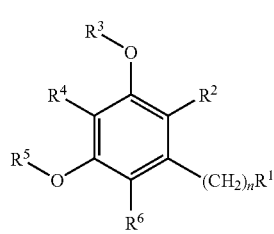

(I)

(wherein n, $R^1$, $R^2$, $R^3$, $R^4$, $R^5$ and $R^6$ have the same meanings as those defined above, respectively) or a prodrug thereof, or a pharmaceutically acceptable salt thereof.

(27) A method of inhibiting a heat shock protein 90 (Hsp90) family protein, which comprises administering an effective amount of the benzene derivative represented by general formula (I):

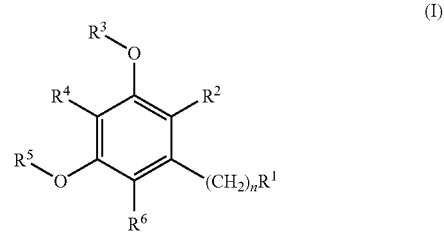

(I)

(wherein n, $R^1$, $R^2$, $R^3$, $R^4$, $R^5$ and $R^6$ have the same meanings as those defined above, respectively) or a pharmaceutically acceptable salt thereof.

(28) A method of inhibiting an Hsp90 family protein, which comprises administering an effective amount of the benzene derivative according to any of the above (12) to (17) or a prodrug thereof, or a pharmaceutically acceptable salt thereof.

(29) A method of inhibiting an Hsp90 family protein, which comprises administering an effective amount of the benzene derivative according to any of the above (12) to (17) or a pharmaceutically acceptable salt thereof.

(30) A method of treating a disease associated with an Hsp90 family protein or a protein to which an Hsp90 family protein is bound (Hsp90 client protein), which comprises administering an effective amount of the benzene derivative according to any of the above (12) to (17) or a prodrug thereof, or a pharmaceutically acceptable salt thereof.

(31) A method of treating a disease associated with an Hsp90 family protein or a protein to which an Hsp90 family protein is bound (Hsp90 client protein), which comprises administering an effective amount of the benzene derivative according to any of the above (12) to (17) or a pharmaceutically acceptable salt thereof.

(32) A method of treating malignant tumors, which comprises administering an effective amount of the benzene derivative according to any of the above (12) to (17) or a prodrug thereof, or a pharmaceutically acceptable salt thereof.

(33) A method of treating malignant tumors, which comprises administering an effective amount of the benzene derivative according to any of the above (12) to (17) or a pharmaceutically acceptable salt thereof.

(34) Use of a benzene derivative represented by general formula (I):

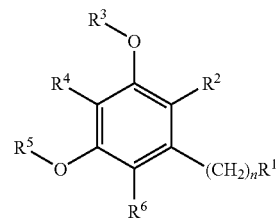

(I)

(wherein n, $R^1$, $R^2$, $R^3$, $R^4$, $R^5$ and $R^6$ have the same meanings as those defined above, respectively) or a prodrug thereof, or a pharmaceutically acceptable salt thereof for the manufacture of a heat shock protein 90 (Hsp90) family protein inhibitor.

(35) Use of a benzene derivative represented by general formula (I):

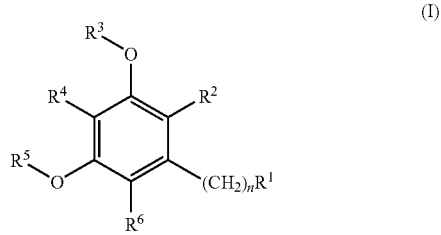

(wherein n, R¹, R², R³, R⁴, R⁵ and R⁶ have the same meanings as those defined above, respectively) or a pharmaceutically acceptable salt thereof for the manufacture of a heat shock protein 90 (Hsp90) family protein inhibitor.

(36) Use of the benzene derivative according to any of the above (12) to (17) or a prodrug thereof, or a pharmaceutically acceptable salt thereof for the manufacture of an Hsp90 family protein inhibitor.

(37) Use of the benzene derivative according to any of the above (12) to (17) or a pharmaceutically acceptable salt thereof for the manufacture of an Hsp90 family protein inhibitor.

(38) Use of the benzene derivative according to any one of the above (12) to (17) or a prodrug thereof, or a pharmaceutically acceptable salt thereof for the manufacture of a therapeutic agent for diseases associated with an Hsp90 family protein or a protein to which an Hsp90 family protein is bound (Hsp90 client protein).

(39) Use of the benzene derivative according to any one of the above (12) to (17) or a pharmaceutically acceptable salt thereof for the manufacture of a therapeutic agent for diseases associated with an Hsp90 family protein or a protein to which an Hsp90 family protein is bound (Hsp90 client protein).

(40) Use of the benzene derivative according to any one of the above (12) to (17) or a prodrug thereof, or a pharmaceutically acceptable salt thereof for the manufacture of an anti-tumor agent.

(41) Use of the benzene derivative according to any one of the above (12) to (17) or a pharmaceutically acceptable salt thereof for the manufacture of an anti-tumor agent.

In the definitions of the groups in general formulae (I) and (IA):

Examples of the lower alkyl moiety of the lower alkyl, lower alkoxy, lower alkoxycarbonyl, lower alkoxysulfonyl, lower alkylaminocarbonyl, di-lower alkylaminocarbonyl, lower alkylamino and di-lower alkylamino include straight-chain or branched alkyl having 1 to 8 carbon atoms, concretely methyl, ethyl, propyl, isopropyl, butyl, sec-butyl, tert-butyl, pentyl, isopentyl, neopentyl, hexyl, heptyl, octyl, etc. The two lower alkyl moieties of the di-lower alkylamino and di-lower alkylaminocarbonyl may be the same or different.

Examples of the lower alkenyl include straight-chain or branched alkenyl having 2 to 8 carbon atoms, concretely vinyl, allyl, prop-1-en-1-yl, isopropenyl, crotyl, but-1-en-1-yl, but-2-en-1-yl, but-3-en-1-yl, pent-2-en-1-yl, 3-methylbut-1-en-1-yl, 3-methylbut-2-en-1-yl, pent-4-en-1-yl, hex-2-en-1-yl, hex-5-en-1-yl, hept-2-en-1-yl, oct-2-en-1-yl, etc.

Examples of the lower alkynyl include straight-chain or branched alkynyl having 2 to 8 carbon atoms, concretely ethynyl, propynyl, butynyl, pentynyl, hexynyl, heptynyl, octynyl, etc.

Examples of the lower alkanoyl moiety of the lower alkanoyl, lower alkanoyloxy and 2-(substituted lower alkanoylamino)propyl include straight-chain or branched alkanoyl having 1 to 7 carbon atoms, concretely formyl, acetyl, propionyl, butyryl, isobutyryl, valeryl, isovaleryl, pivaloyl, hexanoyl, heptanoyl, etc.

Examples of the cycloalkyl include cycloalkyl having 3 to 8 carbon atoms, concretely cyclopropyl, cyclobutyl, cyclopentyl, cyclohexyl, cycloheptyl, cyclooctyl, etc.

Examples of the aryl moiety of the aryl, arylsulfonyl, aryloxy and aroyl include monocyclic, bicyclic or tricyclic aryl having 6 to 14 carbon atoms, concretely phenyl, indenyl, naphthyl, anthryl, etc.

Examples of the aralkyl include aralkyl having 7 to 15 carbon atoms, concretely benzyl, phenethyl, benzhydryl, naphthylmethyl, etc.

Examples of the aromatic heterocyclic group include 5- or 6-membered monocyclic aromatic heterocyclic groups containing at least one atom selected from a nitrogen atom, an oxygen atom and a sulfur atom, and bicyclic or tricyclic condensed-ring aromatic heterocyclic groups containing at least one atom selected from a nitrogen atom, an oxygen atom and a sulfur atom in which 3- to 8-membered rings are condensed, concretely pyridyl, pyrazinyl, pyrimidinyl, pyridazinyl, quinolinyl, isoquinolinyl, phthalazinyl, quinazolinyl, quinoxalinyl, naphthyridinyl, cinnolinyl, pyrrolyl, pyrazolyl, imidazolyl, triazolyl, tetrazolyl, thienyl, furyl, thiazolyl, isothiazolyl, oxazolyl, isoxazolyl, oxadiazolyl, thiadiazolyl, indolyl, indazolyl, benzimidazolyl, benzotriazolyl, benzothiazolyl, benzoxazolyl, purinyl, dibenzofuranyl, etc.

Examples of the heterocyclic group moiety of the heterocyclic group, heterocyclic alkyl and heterocyclic carbonyl include the groups described in the above definition of the aromatic heterocyclic group and also alicyclic heterocyclic groups.

Examples of the alicyclic heterocyclic group include 5- or 6-membered monocyclic alicyclic heterocyclic groups containing at least one atom selected from a nitrogen atom, an oxygen atom and a sulfur atom, and bicyclic or tricyclic condensed-ring alicyclic heterocyclic groups containing at least one atom selected from a nitrogen atom, an oxygen atom and a sulfur atom in which 3- to 8-membered rings are condensed, concretely pyrrolidinyl, piperidino, piperidinyl, piperazinyl, morpholino, morpholinyl, thiomorpholino, thiomorpholinyl, homopiperidino, homopiperidinyl, homopiperazinyl, tetrahydropyridinyl, tetrahydroquinolinyl, tetrahydroisoquinolinyl, oxazolinyl, oxazolidinyl, oxoxazolidinyl, oxadiazolinyl, oxoxadiazolinyl, oxiranyl, tetrahydrofuranyl, tetrahydropyranyl, dihydrobenzofuranyl, oxopiperazinyl, 2-oxopyrrolidinyl, dioxolanyl, benzodioxolanyl, benzopyranyl, etc.

Examples of the heterocyclic group formed together with the adjacent nitrogen atom include 5- or 6-membered monocyclic heterocyclic groups containing at least one nitrogen atom (the monocyclic heterocyclic groups may also contain any other nitrogen atom, oxygen atom or sulfur atom), and bicyclic or tricyclic condensed-ring heterocyclic groups containing at least one nitrogen atom in which 3- to 8-membered rings are condensed (the condensed-ring heterocyclic groups may also contain any other nitrogen atom, oxygen atom or sulfur atom), concretely pyrrolidinyl, piperidino, piperazinyl, morpholino, thiomorpholino, homopiperidino, homopiperazinyl, tetrahydropyridinyl, tetrahydroquinolinyl, tetrahydroisoquinolinyl, 2-oxopyrrolidinyl, oxoxazolidinyl, oxazolidinyl, imidazolyl, etc.

The alkylene moiety of the heterocyclic alkyl has the same meaning as the group produced by removing one hydrogen atom from the above-described lower alkyl.

The halogen means fluorine, chlorine, bromine and iodine atoms.

The substituent (A) in the substituted lower alkyl may be the same or different in number of 1 to 3, and includes, for example, hydroxy, oxo, cyano, nitro, carboxy, carbamoyl, amino, hydroxyimino, lower alkoxyimino, halogen, substituted or unsubstituted lower alkoxy, cycloalkyl, lower alkanoyl, lower alkoxycarbonyl, substituted or unsubstituted lower alkylaminocarbonyl, substituted or unsubstituted di-lower alkylaminocarbonyl, lower alkylamino, di-lower alkylamino, substituted or unsubstituted lower alkanoylamino, etc. The position(s) to be substituted by the substituent(s) is/are not particularly limited.

The halogen, the lower alkoxy, the cycloalkyl, the lower alkanoyl, the lower alkoxycarbonyl, the lower alkylaminocarbonyl, the di-lower alkylaminocarbonyl, the lower alkylamino and the di-lower alkylamino described as examples of the substituents (A) have the same meanings as those defined above, respectively. The lower alkoxy moiety of the lower alkoxyimino has the same meaning as the above-described lower alkoxy; and the lower alkanoyl moiety of the lower alkanoylamino has the same meaning as the above-described lower alkanoyl.

The substituent (a) in the substituted lower alkoxy, the substituted lower alkylaminocarbonyl and the substituted di-lower alkylaminocarbonyl described as examples of the substituents (A) are the same or different in number of 1 to 3, and includes, for example, hydroxy, halogen, lower alkoxy, etc. The halogen and the lower alkoxy described as examples of the substituents (a) have the same meanings as those defined above, respectively. The substituent (b) of the substituted lower alkanoylamino described as an example of the substituents (A) includes, for example, the substituents that are mentioned hereinunder as examples of substituents (B).

The substituent (B) in the substituted lower alkoxy, the substituted lower alkoxycarbonyl, the substituted lower alkylaminocarbonyl, the substituted di-lower alkylaminocarbonyl, the substituted lower alkylsulfonyl, the substituted lower alkanoyl, the substituted lower alkenyl, the substituted lower alkynyl, the substituted lower alkanoyloxy, the substituted vinyl, the substituted prop-1-en-1-yl and the 2-(substituted lower alkanoylamino)propyl may the same or different in number of 1 to 3, and includes, for example, hydroxy, cyano, nitro, carboxy, amino, halogen, substituted or unsubstituted lower alkoxy, cycloalkyl, lower alkanoyl, lower alkoxycarbonyl, lower alkylamino, di-lower alkylamino and the like. The position(s) to be substituted by substituent(s) is/are not particularly limited.

The halogen, the lower alkoxy, the cycloalkyl, the lower alkanoyl, the lower alkoxycarbonyl, the lower alkylamino and the di-lower alkylamino described as examples of the substituents (B) have the same meanings as those defined above, respectively.

The substituent (c) in the substituted lower alkoxy described as an example of the substituents (B) may be the same or different in number of 1 to 3, and includes, for example, hydroxy, halogen, etc. The halogen described as an example of the substituent (c) has the same meaning as that defined above.

The substituent (C) in the substituted cycloalkyl, the substituted arylsulfonyl, the substituted aryloxy, the substituted aralkyl, the substituted aroyl, the substituted heterocyclic alkyl and the substituted heterocyclic group formed together with the adjacent nitrogen atom may be the same or different in number of 1 to 3, and includes, for example, hydroxy, halogen, nitro, cyano, amino, carboxy, carbamoyl, substituted or unsubstituted lower alkyl, substituted or unsubstituted lower alkoxy, aralkyloxy, lower alkylsulfonyl, cycloalkyl, lower alkoxycarbonyl, heterocyclic-carbonyl, lower alkylamino, di-lower alkylamino, lower alkanoyl, a substituted or unsubstituted heterocyclic group, substituted or unsubstituted heterocyclic-alkyl, substituted or unsubstituted aryl, etc. The position(s) to be substituted by substituent(s) is/are not particularly limited.

The halogen, the lower alkyl, the lower alkoxy, the lower alkylsulfonyl, the cycloalkyl, the lower alkoxycarbonyl, the lower alkylamino, the di-lower alkylamino, the lower alkanoyl, the heterocyclic group, the heterocyclic-alkyl and the aryl described as examples of the substituents (C) have the same meanings as those defined above, respectively; the aralkyl moiety of the aralkyloxy has the same meaning as the above-described aralkyl; and the heterocyclic group moiety of the heterocyclic-carbonyl has the same meaning as the above-described heterocyclic group.

The substituents in the substituted lower alkyl and the substituted lower alkoxy described as examples of the substituents (C) include the substituents described hereinabove as examples of the substituents (a). The substituent (d) in the substituted heterocyclic group, the substituted heterocyclic-alkyl and the substituted aryl described as examples of the substituents (C) may be the same or different in number of 1 to 3, and includes, for example, hydroxy, cyano, halogen, lower alkyl, lower alkoxy, etc. The halogen, the lower alkyl and the lower alkoxy described as examples of the substituents (d) have the same meanings as those defined above, respectively.

The substituent (D) in the substituted aryl, the substituted phenyl, the substituted heterocyclic group, the substituted aromatic heterocyclic group, the substituted pyrazolyl, the substituted furyl, the substituted triazolyl and the 2-aminopyrimidin-4-yl having a substituent at the 5-position thereof may be the same or different in number of 1 to 4, and includes for example, hydroxy, halogen, nitro, cyano, amino, carboxy, carbamoyl, substituted or unsubstituted lower alkyl, substituted or unsubstituted lower alkenyl, substituted or unsubstituted lower alkoxy, substituted or unsubstituted aryloxy, substituted or unsubstituted aralkyloxy, substituted or unsubstituted heterocyclic-alkyloxy, substituted or unsubstituted lower alkylsulfonyl, substituted or unsubstituted cycloalkyl, substituted or unsubstituted lower alkoxycarbonyl, substituted or unsubstituted lower alkylaminocarbonyl, substituted or unsubstituted di-lower alkylaminocarbonyl, substituted or unsubstituted cycloalkylaminocarbonyl, substituted or unsubstituted lower alkylamino, substituted or unsubstituted di-lower alkylamino, substituted or unsubstituted lower alkylsulfonylamino, substituted or unsubstituted arylsulfonylamino, substituted or unsubstituted lower alkanoylamino, substituted or unsubstituted aroylamino, substituted or unsubstituted lower alkylaminocarbonylamino, substituted or unsubstituted di-lower alkylaminocarbonylamino, substituted or unsubstituted lower alkanoyl, a substituted or unsubstituted heterocyclic group, substituted or unsubstituted aryl, substituted or unsubstituted aralkyl, substituted or unsubstituted heterocyclic-alkyl, etc. The position(s) to be substituted by substituent(s) is/are not particularly limited.

The halogen, the lower alkyl, the lower alkenyl, the lower alkoxy, the lower alkylsulfonyl, the aryloxy, the cycloalkyl, the lower alkoxycarbonyl, the lower alkylaminocarbonyl, the di-lower alkylaminocarbonyl, the lower alkylamino, the di-lower alkylamino, the lower alkanoyl, the heterocyclic group, the aryl, the aralkyl and the heterocyclic-alkyl described as examples of the substituents (D) have the same meanings as those defined above, respectively; the aralkyl moiety of the aralkyloxy has the same meaning as the above-described aralkyl; the heterocyclic-alkyl moiety of the heterocyclic-alkyloxy has the same meaning as the above-described heterocyclic-alkyl; the lower alkyl moiety of the lower alkylsulfonylamino, the lower alkylaminocarbonylamino and the di-lower alkylaminocarbonylamino has the same meaning as the above-described lower alkyl; the cycloalkyl moiety of the substituted or unsubstituted cycloalkylaminocarbonyl has the same meaning as the above-described cycloalkyl; the aryl moiety of the arylsulfonylamino has the same meaning as the above-described aryl; the lower alkanoyl moiety of the lower alkanoylamino has the same meaning as the above-described lower alkanoyl; the lower aroyl moiety of the aroylamino has the same meaning as the above-described aroyl. The two lower alkyl moieties in the di-lower alkylaminocarbonyl may be the same or different.

The substituent in the substituted lower alkoxy, the substituted lower alkylsulfonyl, the substituted cycloalkyl, the substituted lower alkoxycarbonyl, the substituted lower alkylaminocarbonyl, the substituted di-lower alkylaminocarbonyl, the substituted cycloalkylaminocarbonyl, the substituted lower alkylamino, the substituted di-lower alkylamino, the substituted lower alkylsulfonylamino, the substituted lower alkylaminocarbonylamino, the substituted di-lower alkylaminocarbonylamino, the substituted lower alkanoylamino and the substituted lower alkanoyl described as examples of the substituents (D) includes the substituents described hereinabove as the examples of the substituents (a). Examples of the substituent in the substituted aryl, the substituted aralkyl, the substituted heterocyclic group, the substituted heterocyclic-alkyl, the substituted aryloxy, the substituted aralkyloxy, the substituted heterocyclic-alkyloxy, the substituted arylsulfonylamino and the substituted aroylamino as examples of the substituents (D) include the substituents described hereinabove as examples of the substituents (d).

The substituent (e) in the substituted lower alkyl described as an example of the substituents (D) may be the same or different in number of 1 to 3, and includes, for example, hydroxy, halogen, lower alkoxy, lower alkanoyl, aroyl, lower alkoxycarbonyl, carboxy, cyano, hydroxyimino, lower alkoxyimino, and —$NR^{14}R^{15}$ (wherein $R^{14}$ and $R^{15}$ are the same or different, each represent a hydrogen atom, lower alkyl, lower alkanoyl or heterocyclic-alkyl). The halogen, the lower alkyl, the lower alkoxy, the lower alkanoyl, the aroyl, the lower alkoxycarbonyl and the heterocyclic-alkyl described as examples of the substituents (e) have the same meanings as those defined above, respectively; and the lower alkoxy moiety of the lower alkoxyimino has the same meaning as the above-described lower alkoxy.

The substituent (f) in the substituted lower alkenyl described as an example of the substituents (D) may be the same or different in number of 1 to 3, and includes, for example, hydroxy, halogen, lower alkoxy, lower alkanoyl, aroyl, lower alkoxycarbonyl, carboxy, cyano, etc. The halogen, the lower alkoxy, the lower alkanoyl, the aroyl and the lower alkoxycarbonyl described as examples of the substituents (f) have the same meanings as those defined above, respectively.

Examples of the substituents in the 4,6-di(substituted phenyl)triazol-2-yl and the 3,6-di(substituted phenyl)-1,2,4-triazin-5-yl include the substituents described hereinabove as examples of the substituents (d).

Hereinafter, the compounds represented by general formula (I) are referred to as Compounds (I), and the same applies to the compounds of the other formula numbers.

The prodrugs of Compounds (I) include compounds which are converted in vivo, for example, by various mechanisms such as hydrolysis in blood to form Compounds (I) of the present invention. Such compounds can be specified by techniques well known in the art (e.g. J. Med. Chem., 1997, Vol. 40, pp. 2011-2016; Drug Dev. Res., 1995, Vol. 34, pp. 220-230; Advances in Drug Res., 1984, Vol. 13, pp. 224-331; Bundgaard, Design of Prodrugs, 1985, Elsevier Press).

Specifically, when Compound (I) has carboxy in its structure, the prodrug of Compound (I) includes, for example, compounds in which the hydrogen atom of the carboxy is substituted by the group selected from lower alkyl, lower alkanoyloxyalkyl [e.g. lower alkanoyloxymethyl, 1-(lower alkanoyloxy)ethyl and 1-methyl-1-(lower alkanoyloxy)ethyl], lower alkoxycarbonyloxyalkyl [e.g. lower alkoxycarbonyloxymethyl, 1-(lower alkoxycarbonyloxy)ethyl, and 1-methyl-1-(lower alkoxycarbonyloxy)ethyl], N-(lower alkoxycarbonyl)aminoalkyl (e.g. N-(lower alkoxycarbonyl)aminomethyl and 1-[N-(lower alkoxycarbonyl)amino]ethyl}, 3-phthalidyl, 4-crotonolactonyl, γ-butyrolacton-4-yl, di-lower alkylaminoalkyl, carbamoylalkyl, di-lower alkylcarbamoylalkyl, piperidinoalkyl, pyrrolidinoalkyl, morpholinoalkyl and the like.

Also, when Compound (I) has an alcoholic hydroxy in its structure, the prodrug of Compound (I) includes, for example, compounds in which the hydrogen atom of the hydroxy is substituted by the group selected from lower alkanoyloxyalkyl, 1-(lower alkanoyloxy)ethyl, 1-methyl-1-(lower alkanoyloxy)ethyl, lower alkoxycarbonyloxyalkyl, N-lower alkoxycarbonylaminoalkyl, succinoyl, lower alkanoyl, α-amino lower alkanoyla and the like.

Also, when Compound (I) has amino in its structure, the prodrug of Compound (I) includes, for example, compounds in which one or two hydrogen atoms of the amino are substituted by the group selected from lower alkylcarbonyl, lower alkoxycarbonyl, lower alkylcarbamoyl, di-lower alkylcarbamoyl and the like.

The lower alkyl moiety of the above-described lower alkyl, lower alkoxycarbonyloxyalkyl, lower alkoxycarbonyloxymethyl, 1-(lower alkoxycarbonyloxy)ethyl, 1-methyl-1-(lower alkoxycarbonyloxy)ethyl, N-(lower alkoxycarbonyl)aminoalkyl, N-(lower alkoxycarbonyl)aminomethyl, 1-[N-(lower alkoxycarbonyl)amino]ethyl, di-lower alkylaminoalkyl, di-lower alkylcarbamoylalkyl, lower alkoxycarbonyloxymethyl, N-lower alkoxycarbonylaminomethyl, lower alkylcarbonyl, lower alkoxycarbonyl, lower alkylcarbamoyl and di-lower alkylcarbamoyl has the same meaning as the above-described lower alkyl. The two lower alkyl moieties of the di-lower alkylaminoalkyl, di-lower alkylcarbamoylalkyl and di-lower alkylcarbamoyl may be the same or different.

Also, the lower alkanoyl moiety of the above-described lower alkanoyloxyalkyl, lower alkanoyloxymethyl, 1-(lower alkanoyloxy)ethyl, 1-methyl-1-(lower alkanoyloxy)ethyl, lower alkanoyl and α-amino lower alkanoyl has the same meaning as the above-described lower alkanoyl.

Also, the alkylene moiety of the above-described lower alkanoyloxyalkyl, lower alkoxycarbonyloxyalkyl, N-(lower alkoxycarbonyl)aminoalkyl, di-lower alkylaminoalkyl, carbamoylalkyl, di-lower alkylcarbamoylalkyl, piperidinoalkyl, pyrrolidinoalkyl and morpholinoalkyl has the same meaning as the group produced by removing a hydrogen atom from the above-described lower alkyl.

These prodrugs of Compounds (I) can be prepared from Compounds (I) according to, for example, the methods described in Protective Groups in Organic Synthesis, T. W. Greene, third edition, John Wiley & Sons Inc. (1999), or methods similar thereto.

The pharmaceutically acceptable salts of Compounds (I) or prodrugs thereof include, for example, pharmaceutically acceptable acid addition salts, metal salts, ammonium salts, organic amine addition salts and amino acid addition salts.

Examples of the pharmaceutically acceptable acid addition salts of Compounds (I) or prodrugs thereof include inorganic acid addition salts such as hydrochloride, sulfate, nitrate and phosphate, and organic acid addition salts such as acetate, maleate, fumarate and citrate. Examples of the pharmaceutically acceptable metal salts include alkali metal salts such as sodium salt and potassium salt, alkaline earth metal salts such as magnesium salt and calcium salt, aluminum salt, and zinc salt. Examples of the pharmaceutically acceptable ammonium salts include ammonium and tetramethylammonium salts. Examples of the pharmaceutically acceptable organic amine addition salts include an addition salt of morpholine or piperidine. Examples of the pharmaceutically acceptable amino acid addition salts include an addition salt of glycine, phenylalanine, lysine, aspartic acid or glutamic acid.

The term "inhibition of Hsp90 family protein" refers to inhibition of the binding of an Hsp90 family protein to a protein to which the Hsp90 family protein may be bound (Hsp90 client protein).

Examples of Hsp90 family proteins include Hsp90α protein, Hsp90β protein, grp94 and hsp75/TRAP1.

The proteins to which Hsp90 family proteins is bound include any proteins to which Hsp90 family proteins may be bound, for example, EGFR, Erb-B2, Bcr-Abl, src, raf-1, AKT, Flt-3, PLK, Wee1, FAK, cMET, hTERT, HIF1-α, mutant p53, estrogen receptors, androgen receptors and the like (Expert Opinion on Biological Therapy, 2002, Vol. 2, pp. 3-24).

The processes for preparing Compounds (I) are described below.

In the processes shown below, when the defined groups undergo changes under the reaction conditions or are not suitable for carrying out the processes, then the production can be easily performed by applying methods generally used in synthetic organic chemistry, such as protection of functional groups, and removal of protecting groups [e.g. T. W. Greene, Protective Groups in Organic Synthesis, third edition, John Wiley & Sons Inc. (1999)].

If necessary, the order of the reaction steps such as introduction of a substituent may be changed.

Compounds (I) and their intermediates can be obtained, for example, according to Production Processes 1 to 5 shown below.

Production Process 1

Compound (I) can be produced in the following process.

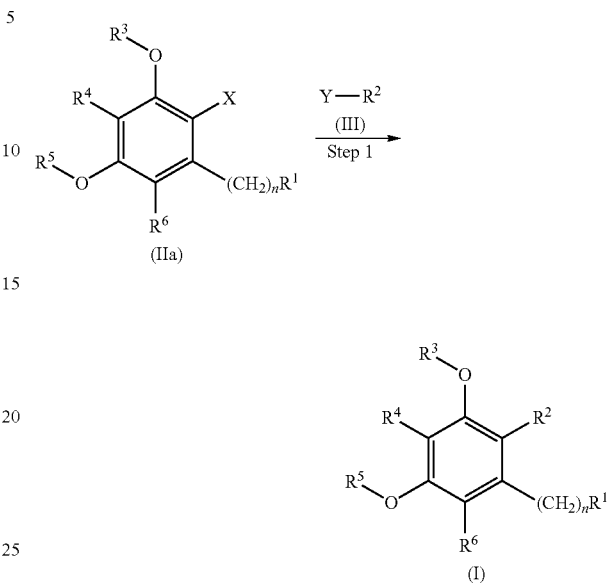

[wherein $R^1$ to $R^6$ and n have the same meanings as those defined above, respectively; X represents halogen (the halogen has the same meaning as that defined above); Y represents —$B(OR^x)_2$ (wherein $R^x$ represents a hydrogen atom or lower alkyl, and the lower alkyl has the same meaning as that defined above) or —$Sn(R^y)_3$ (wherein $R^y$ represents lower alkyl, and the lower alkyl has the same meaning as that defined above).]

(Step 1)

Compound (I) can be obtained by reacting Compound (IIa) with 1 to 10 equivalents of Compound (III) in the presence of a catalyst and optionally in the presence of a carbonate such as cesium carbonate, sodium carbonate, cesium fluorocarbonate, etc., in an inert solvent.

The catalyst includes, for example, transition metal catalysts such as bis(tri-o-tolylphosphine)palladium(II) dichloride, bis(triphenylphosphine)palladium(II) dichloride, tetrakis(triphenylphosphine)palladium(II) and the like; a combination of tris(dibenzylideneacetone)dipalladium and 2-(di-tert-butylphosphino)biphenyl; and a combination of tris(dibenzylideneacetone)dipalladium and triphenylphosphine and the like, and its amount to be used is preferably 0.001 to 1 equivalent based on Compound (IIa). The inert solvent includes, for example, dichloromethane, N,N-dimethylformamide, 1,2-dimethoxyethane, water, their mixed solvents, etc. The reaction is carried out generally at a temperature between −50° C. and the boiling point of the solvent used for 5 minutes to 24 hours.

The starting Compound (IIa) can be obtained according to a known method [e.g., R. C. Larock, Comprehensive Organic Transformations, second edition, John Wiley & Sons Inc. (1999), etc.] or methods similar thereto. For example, it can be produced according to the following process:

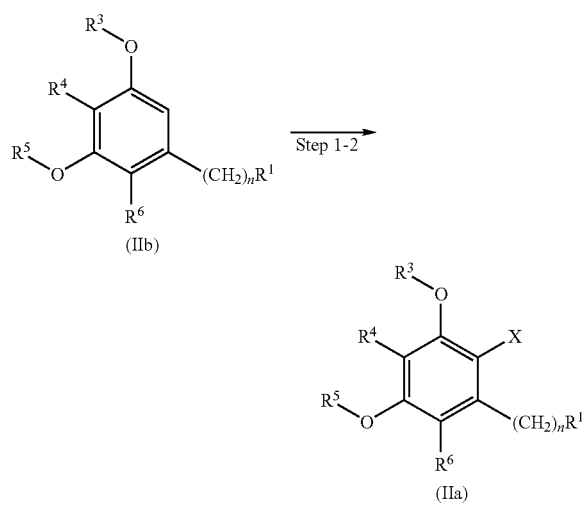

(wherein $R^1$, $R^3$ to $R^6$, n and X have the same meanings as those defined above, respectively.)

Compound (IIa) can be obtained by treating Compound (IIb) with 1 to 2 equivalents of a corresponding halogenating agent, such as N-bromosuccinimide, N-chlorosuccinimide, chlorine, bromine, iodine, a combination of iodine and [bis(trifluoroacetoxy)iodo]benzene, etc. in an inert solvent. The inert solvent includes, for example, dichloromethane, chloroform, carbon tetrachloride, N,N-dimethylformamide, etc. The reaction is carried out generally at a temperature between 0° C. and 50° C. for 5 minutes to 24 hours.

The starting Compound (IIb) and the starting Compound (III) can be obtained according to a known method [e.g., R. C. Larock, Comprehensive Organic Transformations, second edition, John Wiley & Sons Inc. (1999), etc.] or methods similar thereto.

Production Process 2

Compound (Ia) of Compound (I) where $R^1$ is —$CONR^7R^8$ can also be produced according to the following process:

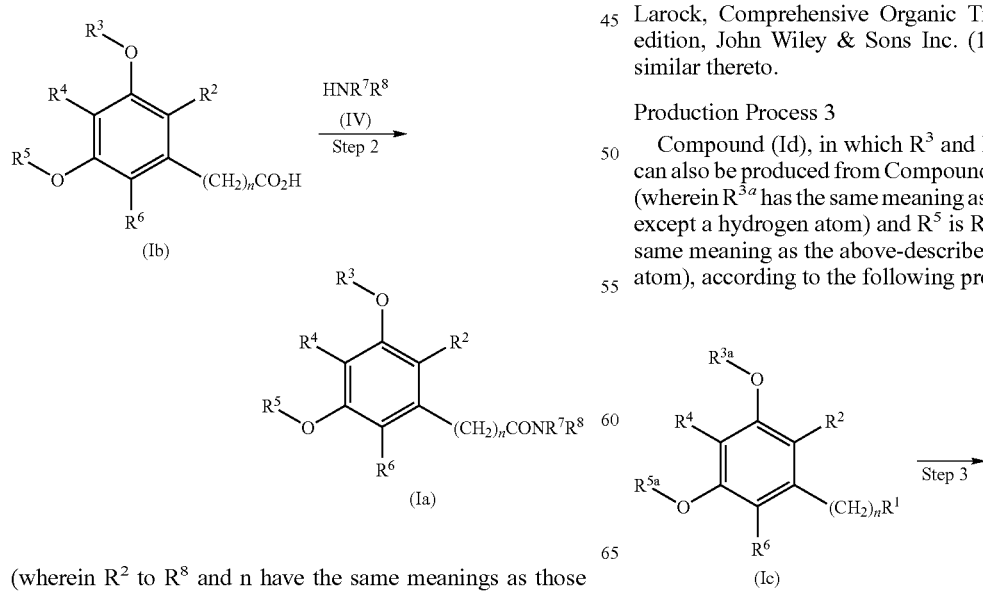

(wherein $R^2$ to $R^8$ and n have the same meanings as those defined above, respectively.)

(Step 2)

Compound (Ia) can be obtained through condensation of Compound (Ib) and Compound (IV).

For example, Compound (Ia) can be obtained by reacting Compound (Ib) with Compound (IV) in a solvent in the presence of an activator such as 1-hydroxybenzotriazole, N-hydroxysuccinimide, etc. and a condensing agent. If necessary, 1 to 20 equivalents of a base may be added thereto when the reaction is carried out. In general, the condensing agent, the activator and Compound (IV) are used in an amount of 1 to 20 equivalents based on Compound (Ib), and the reaction is carried out at a temperature between −20° C. and the boiling point of the solvent used for 1 minute to 24 hours.

Examples of the solvent include halogenated hydrocarbons such as dichloromethane, chloroform, etc.; esters such as methyl acetate, ethyl acetate, isobutyl acetate, etc.; ethers such as diethyl ether, tetrahydrofuran, 1,4-dioxane, etc.; aromatic hydrocarbons such as benzene, toluene, etc.; acetonitrile; N,N-dimethylformamide; N-methylpiperidone; mixtures thereof, and the like. Examples of the condensing agent include dicyclohexylcarbodiimide, 1-[3-(dimethylamino)propyl]-3-ethylcarbodiimide hydrochloride, polymer-bound-1-[3-(dimethylamino)propyl]-3-ethylcarbodiimide, triphenylphosphine oxide trifluoromethanesulfonic anhydride, etc. Examples of the base include alkylamines such as triethylamine, diisopropyl ethylamine, N-methylmorpholine, etc.; pyridines such as pyridine, lutidine, collidine, 4-dimethylaminopyridine, etc.; alkali metal carbonates such as potassium carbonate, sodium hydrogencarbonate, etc.; alkali metal hydroxides such as potassium hydroxide, sodium hydroxide, lithium hydroxide, etc.; and the like.

Prior to use in the reaction, Compound (Ib) may be treated with the activator, or the carboxyl group of Compound (Ib) may be converted to a highly reactive group such as acid chloride, acid bromide, p-nitrophenoxycarbonyl, pentafluorophenoxycarbonyl, pentafluorothiophenoxycarbonyl, etc. according to an ordinary method.

The starting Compound (Ib) can be obtained according to Production Process 1, a known method (e.g., J. Am. Chem. Soc., 93, 6708-9 (1971), etc.) or methods similar thereto. The starting Compound (IV) can be obtained as a commercially available product, or according to a known method [e.g., R. C. Larock, Comprehensive Organic Transformations, second edition, John Wiley & Sons Inc. (1999), etc.] or methods similar thereto.

Production Process 3

Compound (Id), in which $R^3$ and $R^5$ are hydrogen atoms, can also be produced from Compound (Ic), in which $R^3$ is $R^{3a}$ (wherein $R^{3a}$ has the same meaning as the above-described $R^3$ except a hydrogen atom) and $R^5$ is $R^{5a}$ (wherein $R^{5a}$ has the same meaning as the above-described $R^5$ except a hydrogen atom), according to the following process:

-continued

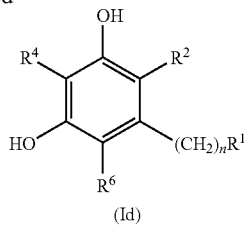

(Id)

(wherein $R^1$, $R^2$, $R^{3a}$, $R^4$, $R^{5a}$, $R^6$ and n have the same meanings as those defined above, respectively.)

(Step 3)

Compound (Id) can be obtained by treating Compound (Ic) with a Lewis acid such as boron tribromide, boron trichloride, boron trifluoride, aluminum trichloride, titanium tetrachloride, a complex thereof, etc. in an inert solvent such as dichloromethane, and the like. In general, the Lewis acid is used in an amount of 1 to 20 equivalents based on Compound (Ic), and the reaction is carried out at a temperature between $-78°$ C. and the boiling point of the solvent used for 1 minute to 24 hours.

Compound (Ic-i) of Compound (Ic) where $R^{3a}$ and $R^{5a}$ are allyl may give Compound (Id) by treating Compound (Ic-i) with a nucleophilic reagent, for example, a combination of a palladium complex such as bis(triphenylphosphine)palladium(II) dichloride, etc. with a formate such as ammonium formate, etc., with a typical metal hydride such as tributyltin hydride, etc., with a secondary amine such as morpholine, etc., and with an active methylene compound such as dimedone, etc., in an inert solvent. Examples of the inert solvent include tetrahydrofuran, acetic acid and 1,4-dioxane. These reactions are generally carried out at a temperature between room temperature and the boiling point of the solvent used for 1 minute to 24 hours.

Compound (Id) can also be obtained by treating Compound (Ic-i) with palladium(II) acetate in the presence or absence of a ligand such as triphenylphosphine, etc. or with a palladium complex such as tetrakis(triphenylphosphine)palladium(II), etc., selenium dioxide or the like, in an organic acid such as acetic acid or formic acid or in a mixed solvent of such an organic acid and tetrahydrofuran. These reactions are generally carried out at a temperature between room temperature and the boiling point of the solvent used for 1 minute to 24 hours.

Compound (Ic-ii) of Compound (Ic) where $R^{3a}$ and $R^{5a}$ are methoxymethyl may give Compound (Id) by treating Compound (Ic-ii) with an acid such as hydrochloric acid, acetic acid, etc., in a solvent. Examples of the solvent include protic solvents such as water, methanol, isopropyl alcohol, etc., mixed solvents of such a protic solvent and an inert solvent such as 1,4-dioxane, etc., and the like. These reactions are generally carried out at a temperature between 0° C. and the boiling point of the solvent used for 5 minutes to 24 hours.

Compound (Ic-iii) of Compound (Ic) where $R^{3a}$ and $R^{5a}$ are benzyl can give Compound (Id) by treating Compound (Ic-iii) with hydrogen or a hydrogen source such as ammonium formate, triethylammonium formate, sodium dihydrogenphosphate, hydrazine, etc., in the presence of a metal catalyst such as palladium-carbon, platinum oxide, Raney nickel, etc., in a solvent. Examples of the solvent include protic solvents such as water, methanol, isopropyl alcohol, etc.; aprotic solvents such as ethyl acetate, tetrahydrofuran, N,N-dimethylformamide, etc., and the like. These reactions are generally carried out at a temperature between 0° C. and the boiling point of the solvent used under a pressure between 0.01 MPa and 1 MPa for 5 minutes to 200 hours.

When $R^{3a}$ and $R^{5a}$ in Compound (Ic) are different from each other, the desired Compound (Id) can be obtained by appropriately combining the above processes.

Compound (Ie) of Compound (I) in which either $R^3$ or $R^5$ is a hydrogen atom, can be obtained from Compound (Ic) according to the above processes by adjusting the equivalent amount of the reagents used, the reaction temperature, and the like.

The starting Compound (Ic) can be obtained according to Production Process 1, Production Process 2, a known method [e.g., R. C. Larock, Comprehensive Organic Transformations, second edition, John Wiley & Sons Inc. (1999), etc.] or methods similar thereto.

Production Process 4

Compound (IIb-ii) of the starting Compound (IIb) in Production Process 1, in which $R^1$ is $-OR^{13}$ (wherein $R^{13}$ has the same meaning as defined above) and n is an integer of 1 to 10, can be produced according to the following process:

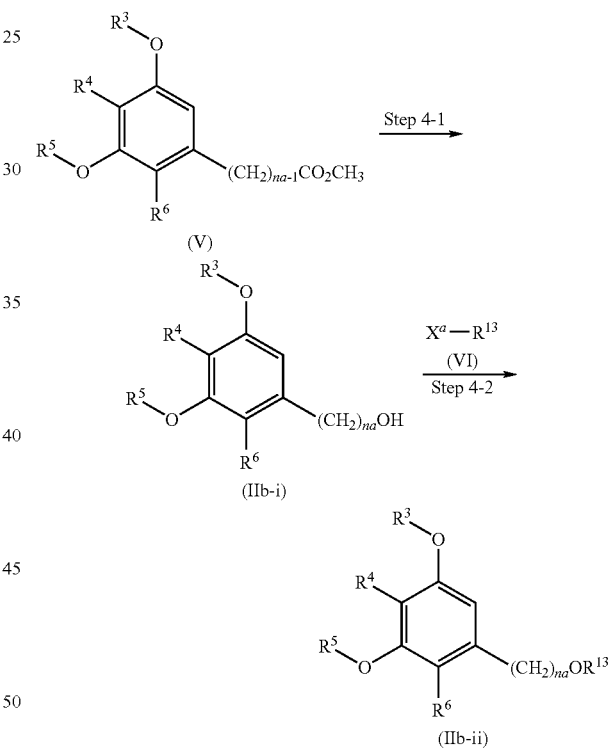

(wherein $R^3$ to $R^6$ and $R^{13}$ have the same meanings as those defined above, respectively; $X^a$ has the same meaning as the above-described X; and na represents an integer of 1 to 10.)

(Step 4-1)

Compound (IIb-i) can be obtained by treating Compound (V) with 1 to 5 equivalents of a reducing agent such as isobutyl aluminum hydride, lithium aluminum hydride, etc., in an inert solvent. Examples of the inert solvent include tetrahydrofuran, toluene, dichloromethane, etc. The reaction is generally carried out at a temperature between $-78°$ C. and the boiling point of the solvent used for 5 minutes to 24 hours.

The starting Compound (V) may be commercially available, or can be obtained according to a known method [e.g., R.

C. Larock, Comprehensive Organic Transformations, second edition, John Wiley & Sons Inc. (1999), etc.] or methods similar thereto.

(Step 4-2)

Compound (IIb-ii) can be obtained by treating Compound (IIb-i) with 1 to 5 equivalents of sodium hydride or the like in an inert solvent and then reacting the resulting compound with 1 to 5 equivalents of Compound (VI). Examples of the inert solvent include tetrahydrofuran, dichloromethane, N,N-dimethylformamide, etc. The reaction is generally carried out at a temperature between 0° C. and the boiling point of the solvent used for 5 minutes to 24 hours.

Production Process 5

Of Compound (I), those of Compound (If) where $R^6$ is halogen, Compound (Ig) where $R^6$ is $R^{6a}$ (wherein $R^{6a}$ represents substituted or unsubstituted lower alkyl, substituted or unsubstituted lower alkenyl, substituted or unsubstituted lower alkynyl, substituted or unsubstituted cycloalkyl, substituted or unsubstituted aryl, a substituted or unsubstituted heterocyclic group, substituted or unsubstituted aralkyl, or substituted or unsubstituted heterocyclic-alkyl, falling within the definition of $R^6$) or Compound (Ij) where $R^6$ is $R^{6b}$ (wherein $R^{6b}$ represents substituted or unsubstituted lower alkanoyl in which the carbon atom adjacent to the carbonyl moiety has at least one hydrogen atom, falling within the definition of the substituted or unsubstituted lower alkanoyl group of $R^6$) may be produced according to the following process:

alkyl moiety of the substituted or unsubstituted alkanoyl, adjacent to the carbonyl moiety of the lower alkanoyl.)

(Step 5-1)

Compound (If) can be obtained by treating Compound (Ih) with 1 to 2 equivalents of a corresponding halogenating agent, such as N-bromosuccinimide, N-chlorosuccinimide, chlorine, bromine, iodine, or a combination of iodine and [bis(trifluoroacetoxy)iodo]benzene, in an inert solvent. The inert solvent includes, for example, dichloromethane, chloroform, N,N-dimethylformamide, etc. The reaction is carried out generally at a temperature between 0° C. and 50° C. for 5 minutes to 24 hours.

The starting Compound (Ih) can be obtained according to Production Processes 1 to 3, or a known method [e.g., R. C. Larock, Comprehensive Organic Transformations, second edition, John Wiley & Sons Inc. (1999), etc.] or methods similar thereto.

(Step 5-2)

Compound (Ig) can be obtained by reacting Compound (If) with 1 to 5 equivalents of Compound (VII) in an inert solvent in the presence of 0.01 to 1 equivalent of, for example, bis(tri-o-tolylphosphine)palladium(II) dichloride, bis(triphenylphosphine)palladium(II) dichloride, a combination of tris(dibenzylideneacetone)dipalladium and 2-(di-tert-butylphosphino)biphenyl or a combination of tris(dibenzylideneacetone)dipalladium and triphenylphosphine, and optionally treating the resulting product with an acid such as

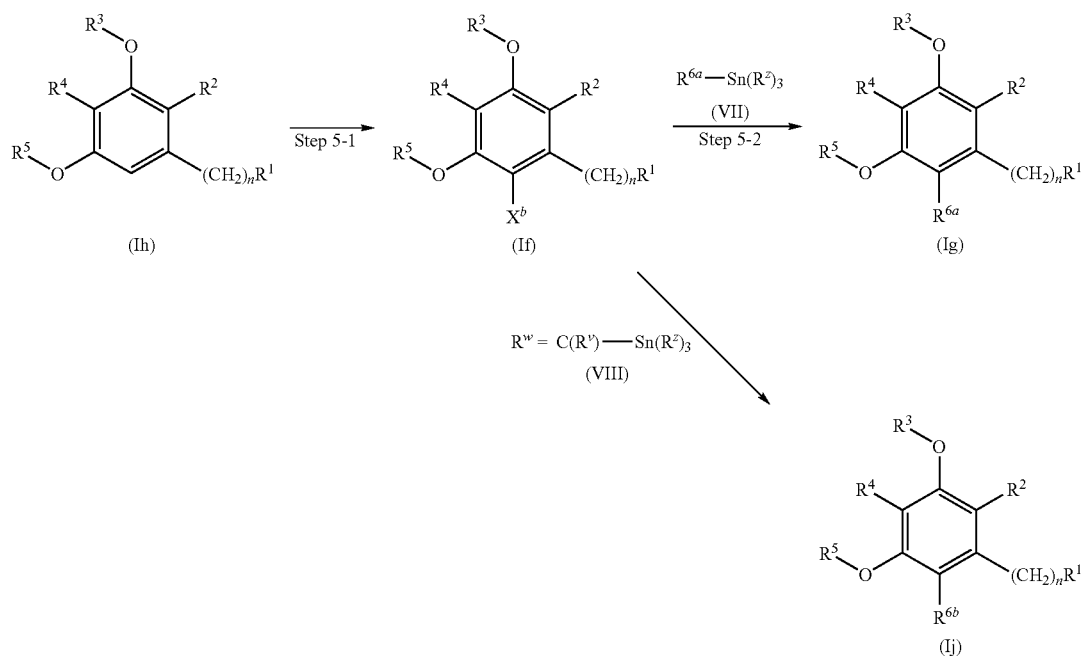

(wherein $R^1$ to $R^5$, $R^{6a}$, $R^{6b}$ and n have the same meanings as those defined above, respectively; $X^b$ has the same meaning as the above-described X; $R^z$ represents lower alkyl, and the lower alkyl has the same meaning as that defined above; $R^v$ represents methoxy or ethoxy; $R^w$ represents the same meaning as that of the group derived from the substituted or unsubstituted alkanoyl of $R^{6b}$ by removing one hydrogen atom on the carbon atom in the substituted or unsubstituted lower hydrochloric acid, etc. The inert solvent includes, for example, 1,2-dimethoxymethane, tetrahydrofuran, dichloromethane, chloroform, toluene, their mixed solvents and the like. The reaction is generally carried out at a temperature between 50° C. and the boiling point of the solvent used for 5 minutes to 24 hours.

Compound (Ij) can be obtained in the same manner as above, by reacting Compound (VIII) in place of Compound (VII) with Compound (If) and treating the resulting compound with an acid such as hydrochloric acid, etc.

The starting Compound (VII) and the starting Compound (VIII) may be commercially available or can be obtained according to a known method [e.g., R. C. Larock, Comprehensive Organic Transformations, second edition, John Wiley & Sons Inc. (1999), etc.] or methods similar thereto.

The functional groups in Compound (I) and in the starting compounds and the intermediate compounds and the functional groups in the substituents therein can be converted according to a known method [e.g., R. C. Larock, Comprehensive Organic Transformations, second edition, John Wiley & Sons Inc. (1999)] or methods similar thereto.

By appropriately combining the above-described processes and others, Compounds (I) having desired functional groups at desired positions can be obtained.

The intermediates and the intended compounds in the above-described production processes can be isolated and purified by appropriately combining separation and purification methods generally used in synthetic organic chemistry, for example, filtration, extraction, washing, drying, concentration, recrystallization, and various kinds of chromatography. The intermediates can also be subjected to the subsequent reactions without purification.

For some of Compounds (I) and their prodrugs, there may exist stereoisomers such as geometrical isomers and optical isomers, and all possible isomers including them and mixtures thereof can be used for the Hsp90 family protein inhibitors of the present invention.

When it is desired to obtain a salt of Compound (I) or its prodrug, in the case where Compound (I) or its prodrug is produced in the form of a salt thereof, it can be purified as such, but where it is produced as a free form thereof, it can be converted into a salt by dissolving or suspending it in an appropriate solvent and then adding an acid or a base thereto.

Further, Compounds (I) and their prodrugs as well as pharmaceutically acceptable salts thereof may exist in the form of adducts with water or various solvents, and these adducts can also be used for the Hsp90 family protein inhibitors of the present invention.

Examples of Compounds (I) obtained by the present invention are shown in Tables 1 to 3. In the Tables, Ph represents a phenyl, and the numbers preceding the groups in $R^{2b}$ refer to the substituted positions.

TABLE 1

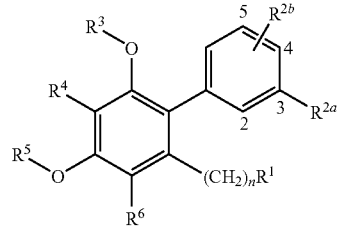

(I-i)

| Compound | $R^1$ | n | $R^{2a}$ | $R^{2b}$ |
|---|---|---|---|---|
| 1 | $CO_2CH_3$ | 1 | H | H |
| 2 | $CO_2CH_3$ | 1 | $CH=CHCOCH_3$ | H |
| 3 | $CO_2CH_3$ | 1 | $CH=NOH$ | H |
| 4 | $CO_2CH_3$ | 1 | $CH=NOCH_3$ | H |
| 5 | $CO_2CH_3$ | 1 | $(CH_2)_2COCH_3$ | H |
| 6 | $CO_2CH_3$ | 1 | H | 2-$OCH_3$ |
| 7 | $CO_2CH_3$ | 1 | H | 2-Cl |
| 8 | $CO_2CH_3$ | 1 | $COCH_3$ | H |
| 9 | $CONH(CH_2)_2N(CH_3)_2$ | 1 | H | H |
| 10 | $CO_2CH_3$ | 1 | H | H |
| 11 | $CO_2CH_3$ | 1 | H | H |
| 12 | $CO_2H$ | 1 | H | H |
| 13 | $CO_2CH_3$ | 1 | H | H |
| 14 | $CO_2CH_3$ | 1 | H | H |
| 15 | OH | 1 | H | H |
| 16 | $CONH(CH_2)_2NHCOCH_3$ | 1 | H | H |
| 17 | 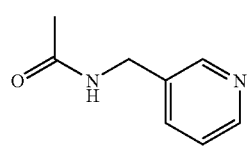 | 1 | H | H |
| 18 | 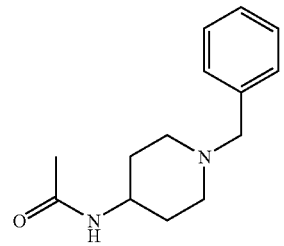 | 1 | H | H |

TABLE 1-continued
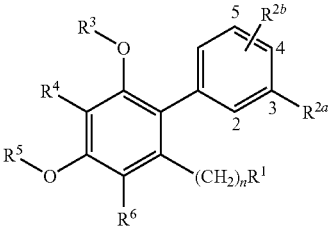
(I-i)
| # | R¹ group | n | R²ᵃ/R²ᵇ | |
|---|---|---|---|---|
| 19 | 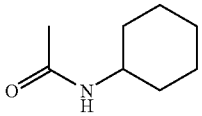 | 1 | H | H |
| 20 | CONHCH₂CH(CH₃)₂ | 1 | H | H |
| 21 | CONH(CH₂)₂CH₃ | 1 | H | H |
| 22 | 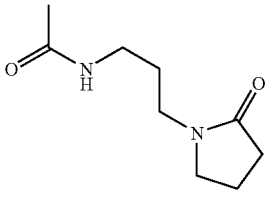 | 1 | H | H |
| 23 | 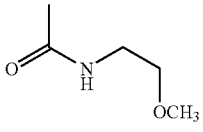 | 1 | H | H |
| 24 | 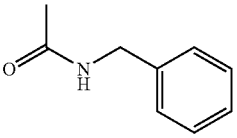 | 1 | H | H |
| 25 | 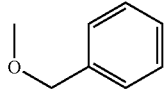 | 1 | H | H |
| 26 | OCH₃ | 1 | H | H |
| 27 | OCH₂CH=CH₂ | 1 | H | H |
| 28 | 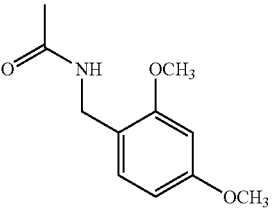 | 1 | H | H |
| 29 | 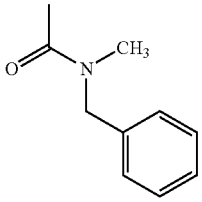 | 1 | H | H |

TABLE 1-continued
(I-i)
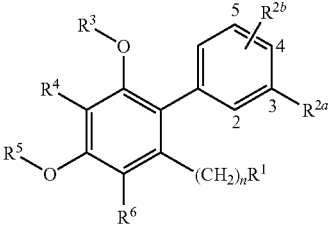
| | | | | |
|---|---|---|---|---|
| 30 | 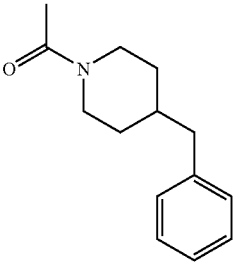 | 1 | H | H |
| 31 | 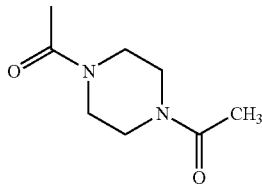 | 1 | H | H |
| 32 | 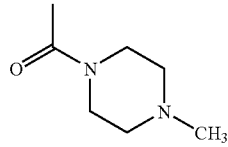 | 1 | H | H |
| 33 | 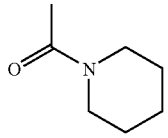 | 1 | H | H |
| 34 | 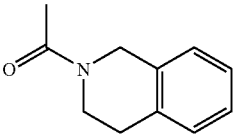 | 1 | H | H |
| 35 | 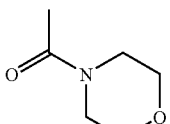 | 1 | H | H |
| 36 | 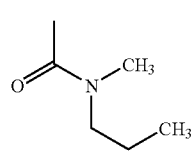 | 1 | H | H |

TABLE 1-continued
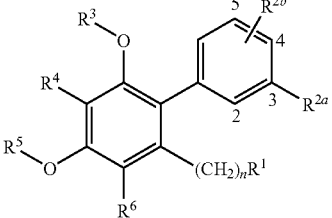
(I-i)
| | $R^1$ | n | $R^{2a}$ | $R^{2b}$ |
|---|---|---|---|---|
| 37 | 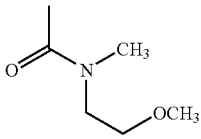 | 1 | H | H |
| 38 | 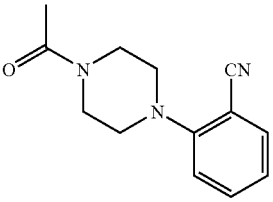 | 1 | H | H |
| 39 | 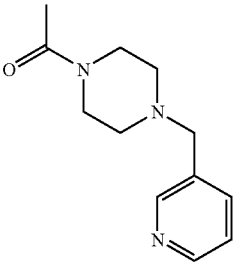 | 1 | H | H |
| 40 | 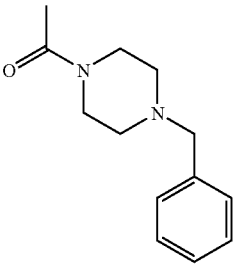 | 1 | H | H |
| 41 | $CONH_2$ | 1 | H | H |
| 42 | $CONHCH_3$ | 1 | H | H |
| 43 | $CON(CH_3)_2$ | 1 | H | H |
| 44 | 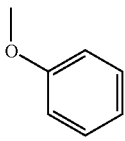 | 1 | H | H |
| 45 | $CH_3$ | 0 | H | H |
| 46 | $CO_2H$ | 0 | H | H |
| 47 | $CO_2CH_3$ | 0 | H | H |
| 48 | $CONHCH_3$ | 0 | H | H |
| 49 | $CON(CH_3)_2$ | 0 | H | H |
| 50 | $CONH_2$ | 0 | H | H |

TABLE 1-continued (I-i)

| # | R¹ | n | R²ᵇ | R²ᵃ |
|---|---|---|---|---|
| 51 | -C(=O)NH-CH₂-C₆H₅ (benzylaminocarbonyl) | 0 | H | H |
| 52 | CO₂CH₃ | 1 | H | H |
| 53 | -C(=O)NH-CH₂-(2-pyridyl) | 1 | H | H |
| 54 | -C(=O)NH-CH₂-(4-pyridyl) | 1 | H | H |
| 55 | CO₂CH₃ | 1 | H | H |
| 56 | CO₂CH₃ | 1 | H | H |
| 57 | COCH₂CH₃ | 0 | H | H |
| 58 | -C(=O)-C₆H₅ | 0 | H | H |
| 59 | CH=CHCO₂CH₃ | 0 | H | H |
| 60 | CH=CHCOCH₃ | 0 | H | H |
| 61 | OCH₃ | 0 | H | H |
| 62 | OH | 2 | H | H |
| 63 | OH | 0 | H | H |
| 64 | OCH₃ | 2 | H | H |
| 65 | COCH₃ | 1 | H | H |
| 66 | CO₂CH₃ | 1 | CH=CHCO₂H | H |
| 67 | CO₂CH₃ | 1 | CH₂CH₂CO₂H | H |
| 68 | CO₂CH₃ | 1 | CH₂CH₂CO₂H | H |
| 69 | CO₂CH₃ | 1 | H | H |
| 70 | CO₂CH₃ | 1 | H | H |
| 71 | OCH₂CH₂OCH₃ | 1 | H | H |
| 72 | O(CH₂CH₂O)₂CH₃ | 1 | H | H |
| 73 | CO₂CH₃ | 1 | H | 4-COCH₃ |
| 74 | CO₂CH₃ | 1 | OCF₃ | H |
| 75 | CO₂CH₃ | 1 | H | 4-OCF₃ |
| 76 | CO₂CH₃ | 1 | CH₂OH | H |
| 77 | CO₂CH₃ | 1 | NO₂ | H |
| 78 | CO₂CH₃ | 1 | CN | H |
| 79 | CO₂CH₃ | 1 | H | 4-Ph |
| 80 | CO₂CH₃ | 1 | H | 4-OPh |
| 81 | CO₂CH₃ | 1 | OCH₃ | H |
| 82 | CO₂CH₃ | 1 | H | 4-OCH₃ |
| 83 | OCH₃ | 2 | H | H |
| 84 | OH | 2 | H | H |

TABLE 1-continued (I-i)

[Structure: biphenyl compound with R³O, R⁴, R⁵O, R⁶, (CH₂)ₙR¹ substituents on one ring and R²ᵃ, R²ᵇ on the other ring at positions 2,3,4,5]

| # | R¹ | n | R²ᵃ | R²ᵇ |
|---|---|---|---|---|
| 85 | (2-methoxymethyl-tetrahydrofuran group) | 1 | H | H |
| 86 | OCH₂CH₂OCH₃ | 2 | H | H |
| 87 | CO₂CH₃ | 2 | H | H |
| 88 | 1-acetyl-4-(2-methoxyphenyl)piperazine | 1 | H | H |
| 89 | N-methyl-N-(2-(pyridin-2-yl)ethyl)acetamide | 1 | H | H |
| 90 | 1-acetyl-4-(3-cyanopyridin-2-yl)piperazine | 1 | H | H |
| 91 | 1-acetyl-4-(furan-2-carbonyl)piperazine | 1 | H | H |
| 92 | OCH₃ | 2 | H | H |
| 93 | OCH₃ | 2 | H | H |
| 94 | OCH₃ | 2 | H | H |
| 95 | OCH₃ | 2 | H | H |
| 96 | OCH₃ | 2 | H | H |
| 97 | OCH₃ | 3 | H | H |
| 98 | NHCH₃ | 2 | H | H |
| 99 | N(CH₃)₂ | 2 | H | H |
| 100 | NHCH₂CH₂OCH₃ | 2 | H | H |
| 101 | NHCH₃ | 1 | H | H |
| 102 | N(CH₃)₂ | 1 | H | H |
| 103 | NHCH₂CH₂OCH₃ | 1 | H | H |
| 104 | OH | 3 | H | H |
| 105 | OCH₃ | 2 | OCH₃ | H |
| 106 | OCH₃ | 2 | CO₂H | H |
| 107 | C(=NOH)CH₃ | 1 | H | H |

TABLE 1-continued (I-i)

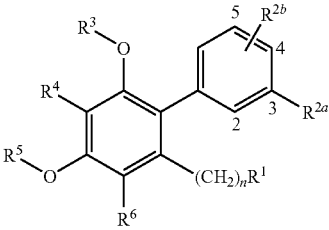

| | | | | |
|---|---|---|---|---|
| 108 | 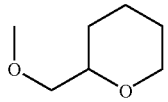 | 2 | H | H |
| 109 | 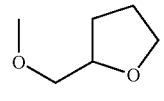 | 2 | H | H |
| 110 | OCH$_2$CH$_2$OH | 2 | H | H |
| 111 | OCH$_2$OCH$_3$ | 2 | H | H |
| 112 | 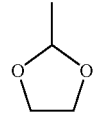 | 0 | H | H |
| 113 | OCH$_2$CH$_2$OCH$_3$ | 2 | H | H |
| 114 | COCH$_3$ | 2 | H | H |
| 115 | CH(OH)CH$_3$ | 2 | H | H |
| 116 | OCH$_3$ | 2 | OCH$_3$ | H |
| 117 | OCH$_3$ | 2 | CONH$_2$ | H |
| 118 | OCH$_3$ | 2 | OCH$_3$ | H |
| 119 | OCH$_3$ | 2 | CO$_2$CH$_3$ | H |
| 120 | OCH$_3$ | 2 | Ph | H |
| 121 | OCH$_3$ | 2 | OCH$_2$CH$_3$ | H |
| 122 | OCH$_3$ | 2 | CH$_3$ | H |
| 123 | OH | 3 | H | H |
| 124 | OH | 3 | H | H |
| 125 | OCH$_3$ | 2 | H | H |
| 126 | CO$_2$CH$_3$ | 1 | H | H |
| 127 | OCH$_3$ | 2 | H | H |
| 128 | OCH$_3$ | 2 | H | H |
| 129 | OCH$_3$ | 2 | H | H |
| 130 | OCH$_3$ | 2 | CH$_3$ | H |
| 131 | OCH$_3$ | 2 | CO$_2$CH$_3$ | H |
| 132 | OCH$_3$ | 2 | Ph | H |
| 133 | OCH$_3$ | 2 | OCH$_2$CH$_3$ | H |
| 134 | OCH$_3$ | 2 | OH | H |
| 135 | OCH$_3$ | 2 | OCH$_2$Ph | H |
| 136 | OCH$_2$CH$_2$OCH$_3$ | 2 | H | H |
| 137 | OCH$_2$CH$_2$OCH$_3$ | 2 | OCH$_3$ | H |
| 138 | OCH$_2$CH$_2$OCH$_3$ | 2 | OCH$_3$ | H |
| 139 | OCH$_2$CH$_2$OCH$_3$ | 2 | CH$_3$ | H |
| 140 | OCH$_2$CH$_2$OCH$_3$ | 2 | H | H |
| 141 | CON(CH$_3$)(CH$_2$CH$_2$OCH$_3$) | 1 | OCH$_3$ | H |
| 142 | CO$_2$CH$_3$ | 1 | OCH$_3$ | H |
| 143 | OH | 2 | OCH$_3$ | H |
| 144 | OCH$_2$CH=CH$_2$ | 2 | H | H |
| 145 | OCH$_2$CH=CH$_2$ | 3 | H | H |
| 146 | OCH$_2$CH$_2$OCH$_3$ | 3 | H | H |
| 147 | OCH$_2$CH(OH)CH$_2$OH | 2 | H | H |
| 148 | OCH$_2$CH(OH)CH$_2$OH | 3 | H | H |
| 149 | OCH$_2$CH$_2$OCH$_3$ | 2 | CH$_3$ | H |
| 150 | CON(CH$_3$)(CH$_2$CH$_2$OCH$_3$) | 1 | OCH$_3$ | H |
| 151 | OCH$_3$ | 2 | H | H |
| 152 | OCH$_2$CH$_2$OCH$_3$ | 2 | H | H |
| 153 | OCH$_2$CH$_2$OCH$_3$ | 2 | (CH$_2$)$_2$COCH$_3$ | H |
| 154 | OCH$_2$CH$_2$OCH$_3$ | 2 | (CH$_2$)$_2$CH(OH)CH$_3$ | H |
| 155 | OCH$_2$CONH$_2$ | 2 | H | H |
| 156 | OCH$_2$CONHCH$_3$ | 2 | H | H |
| 157 | OCH$_2$CON(CH$_3$)$_2$ | 2 | H | H |

TABLE 1-continued (I-i)

| | R³O group | n | R²ᵇ | R²ᵃ |
|---|---|---|---|---|
| 158 | OCH₂CONH₂ | 3 | H | H |
| 159 | OCH₂CONHCH₃ | 3 | H | H |
| 160 | OCH₂CON(CH₃)₂ | 3 | H | H |
| 161 | OCH₂CH₂OH | 2 | H | H |
| 162 | OCH₂CH₂OH | 3 | H | H |
| 163 | OCH(CH₂OH)₂ | 3 | H | H |
| 164 | [1-(3-methoxypropyl)pyrrolidin-2-one] | 3 | H | H |
| 165 | OCH₂CH₂OCH₃ | 2 | OH | H |
| 166 | OCH₂CH₂OCH₃ | 2 | OH | H |
| 167 | OCH₂CONHCH₂CH₂OH | 3 | H | H |
| 168 | OCH₂CONHCH₂CH₂OCH₃ | 3 | H | H |
| 169* | CH(OH)CH₂CH(OH)CH₂OH | 2 | H | H |
| 170* | CH(OH)CH₂CH(OH)CH₂OH | 2 | H | H |
| 171 | OCH₃ | 2 | OH | H |
| 172 | OH | 2 | OH | H |
| 173 | OCH₂CH(OH)CH₂OH | 2 | OH | H |
| 174 | OCH₂CH₂OH | 2 | OH | H |
| 175 | OCH₂CH₂CH₂OH | 2 | H | H |
| 176 | OCH₂CH₂CH₂OCH₃ | 2 | H | H |
| 177* | CH(OH)CH₂CH(OH)CH₂OH | 1 | H | H |
| 178* | CH(OH)CH₂CH(OH)CH₂OH | 1 | H | H |
| 179 | OCH₂CH(OH)CH₂OCH₂CH₂OH | 2 | H | H |
| 180 | CH(OH)CH(OH)CH₂OH | 1 | H | H |
| 181 | CH(OH)CH(OH)CH₂OH | 2 | H | H |
| 182 | CH(OH)CH₂OH | 1 | H | H |
| 183 | [methyl glucopyranoside group] | 2 | H | H |
| 184 | CH(OH)CH(CO₂CH₂CH₃)₂ | 2 | H | H |
| 185 | CH(OH)CH(CH₂OH)₂ | 2 | H | H |
| 186 | CON(CH₂CH₂OH)₂ | 2 | H | H |
| 187 | CON(CH₂CH₂OH)₂ | 2 | H | H |
| 188 | [3-(methoxymethyl)pyridine] | 2 | H | H |
| 189 | OCH₂CH(OH)CH₂OH | 2 | OCH₃ | H |
| 190 | OCH₂CH(OH)CH₂OH | 2 | [2-(methoxymethyl)pyridine] | H |
| 191 | OCH₂CH(OH)CH₂OH | 2 | [3-(methoxymethyl)pyridine] | H |

TABLE 1-continued (I-i)

| | R⁵O / R⁴ / R³O / R² / R²ᵇ / R²ᵃ / (CH₂)ₙR¹ / R⁶ structure | | | |
|---|---|---|---|---|
| 192 | OCH₂CH(OH)CH₂OH | 2 | (methoxymethyl pyridine) | H |
| 193 | OCH₂CH(OH)CH₂OH | 2 | (methoxymethyl 2-methyl thiazole) | H |
| 194 | OCH₂CH(OH)CH₂OH | 2 | OCH₂CH₂OH | H |
| 195 | OCH₂CH(OH)CH₂OH | 2 | (2-methoxyethyl morpholine) | H |
| 196 | OCH₂CH(OH)CH₂OH | 2 | (2-methoxyethyl pyrrolidinone) | H |
| 197 | OCH₂CH(OH)CH₂OH | 2 | NH₂ | H |
| 198 | CON(CH₂CH₂OH)₂ | 1 | H | H |
| 199 | C(OH)(CH₂CH₂OH)₂ | 1 | H | H |
| 200 | (5-methyl oxazole-4-CO₂CH₃) | 1 | H | H |
| 201 | (methyl deoxy sugar) | 2 | H | H |
| 202 | OCH₂CH(OH)CH₂OH | 2 | NHSO₂CH₃ | H |
| 203 | OCH₂CH(OH)CH₂OH | 2 | (N-methyl tosylsulfonamide) | H |
| 204 | OCH₂CH(OH)CH₂OH | 2 | NHCOCH₃ | H |
| 205 | OCH₂CH(OH)CH₂OH | 2 | NHCOPh | H |
| 206 | OCH₂CH(OH)CH₂OH | 2 | NHCONHCH₂CH₃ | H |
| 207 | OCH₂CH(OH)CH₂OH | 2 | NHCOC(CH₃)(CH₂OH)₂ | H |
| 208 | (5-methyl oxazole-4-CH₂OH) | 1 | H | H |

TABLE 1-continued
(I-i)
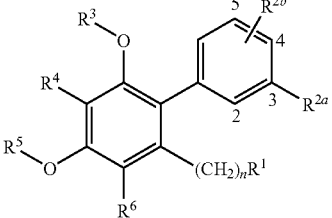
| | $R^1$ | n | $R^{2b}$ | $R^{2a}$ |
|---|---|---|---|---|
| 209 | 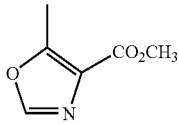 | 2 | H | H |
| 210 | 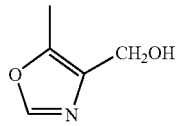 | 2 | H | H |
| 211 | 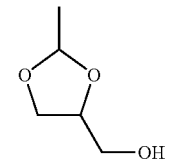 | 1 | H | H |
| 212 | $CONH_2$ | 2 | H | H |
| 213 | $CH(CO_2CH_3)_2$ | 2 | H | H |
| 214 | $CH=CHCH(CH_2OH)_2$ | 0 | H | H |
| 215 | $CH(CH_2OH)_2$ | 2 | H | H |
| 216 | 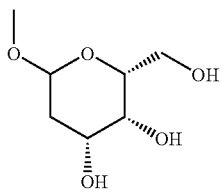 | 2 | H | H |
| 217 | $CH(CH_2OH)_2$ | 3 | H | H |
| 218 | 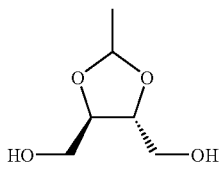 | 1 | H | H |
| 219 | 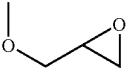 | 2 | OH | H |
| 220 | $CONHCH_2CH_2OH$ | 2 | H | H |
| 221 | $CONHCH_2CH_2NHCOCH_3$ | 2 | H | H |
| 222 | 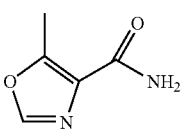 | 2 | H | H |

TABLE 1-continued
(I-i)
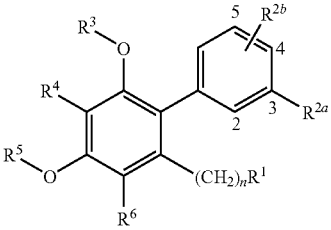
| | | | | |
|---|---|---|---|---|
| 223 | 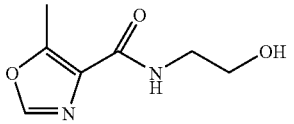 | 2 | H | H |
| 224 | 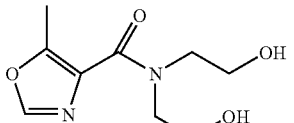 | 2 | H | H |
| 225 | 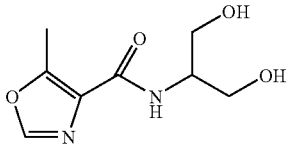 | 2 | H | H |
| 226 | 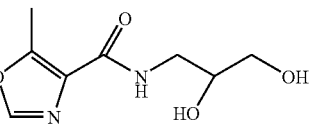 | 2 | H | H |
| 227 | 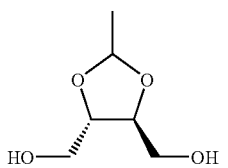 | 1 | H | H |
| 228 | 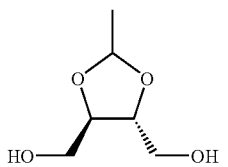 | 1 | CH$_3$ | H |
| 229 | 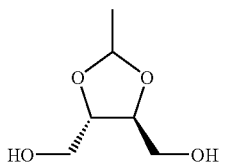 | 1 | CH$_3$ | H |
| 230 | 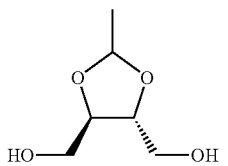 | 1 | H | H |

TABLE 1-continued (I-i)

| | | n | $R^{2b}$ | $R^{2a}$ |
|---|---|---|---|---|
| 231 | [dioxolane-CH3 with two CH2OH] | 1 | H | H |
| 232 | [dioxolane-CH3 with two CH2OH] | 1 | H | H |
| 233 | [dioxolane-CH3 with two CH2OH] | 1 | OCH3 | H |
| 234 | [dioxolane-CH3 with two CH2OH] | 1 | H | H |
| 280 | [dioxolane-CH3 with two CH2OH] | 1 | H | H |
| 281 | [dioxolane-CH3 with two CH2OH] | 1 | OH | H |
| 282 | [dioxolane-CH3 with two CH2OH] | 1 | F | H |

TABLE 1-continued
(I-i)
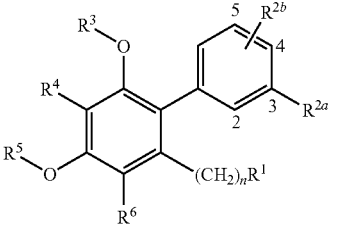
| 283 | 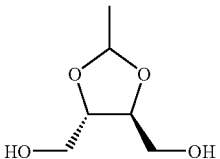 | 1 | CH$_3$ | 5-CH$_3$ |
| --- | --- | --- | --- | --- |
| 284 | 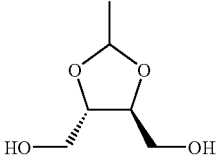 | 1 | NHCOCH$_3$ | H |
| 285 | 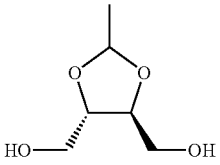 | 1 | H | H |
| 286 | 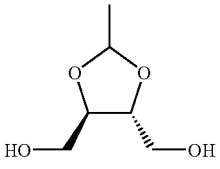 | 1 | OCH$_3$ | H |
| 287 | 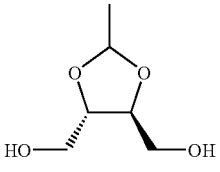 | 1 | H | H |
| 288 | 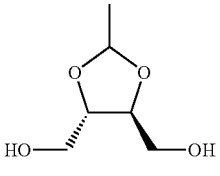 | 1 | CONH$_2$ | H |
| 289 | 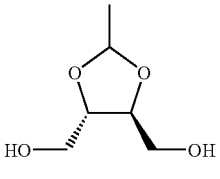 | 1 | CONHCH$_3$ | H |

TABLE 1-continued (I-i)

| | | n | R¹ | R²ᵃ | R²ᵇ |
|---|---|---|---|---|---|
| 290 | dioxolane-diol | 1 | CON(CH₃)₂ | H | |
| 291 | dioxolane-diol | 1 | CH₃ | 4-F | |
| 292 | dioxolane-diol | 1 | CON(CH₃)₂ | H | |
| 293 | dioxolane-diol | 1 | Cl | 4-F | |
| 294 | dioxolane-diol | 1 | CONHCH₃ | H | |
| 295 | dioxolane-diol | 1 | CONH₂ | H | |
| 296 | dioxolane-diol | 1 | F | H | |

TABLE 1-continued
(I-i)
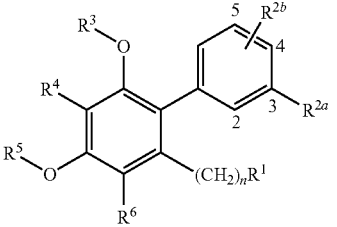
| | R¹ | n | R²ᵃ | R²ᵇ |
|---|---|---|---|---|
| 297 | 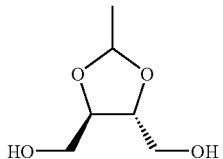 | 1 | F | 4-F |
| 298 | 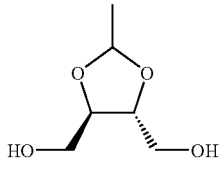 | 1 | OH | H |
| 299 | 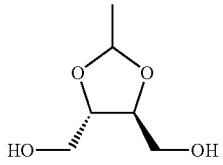 | 1 | F | 4-F |
| 300 | 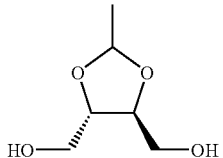 | 1 | CH₃ | 4-F |
| 301 | 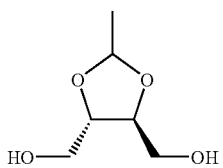 | 1 | Cl | 4-F |
| 302 | 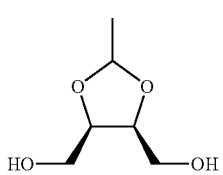 | 1 | H | H |
| 303 | 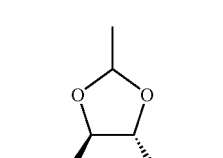 | 1 | CONHCH₂CH₂OCH₃ | H |

TABLE 1-continued
(I-i)
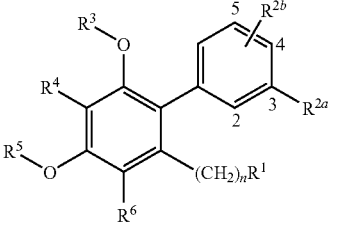
| | | n | R²ᵃ (3) | R²ᵇ |
|---|---|---|---|---|
| 304 | 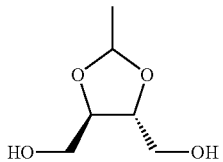 | 1 | CONHCH₂CH₂OH | H |
| 305 | 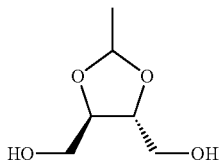 | 1 | 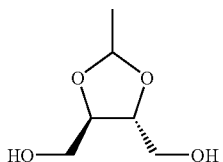 | H |
| 306 | 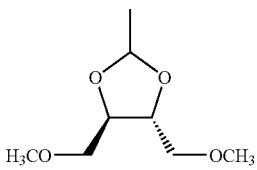 | 1 | CONHCH₂CH₃ | H |
| 307 | 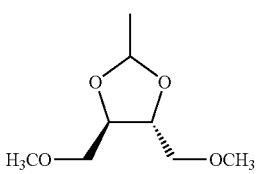 | 1 | OH | H |
| 308 | 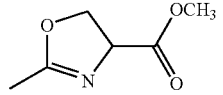 | 1 | H | H |
| 309 | OCH₂CH₂OH | 2 | OCH₃ | 4-OCH₃ |
| 310 | OCH₂CH₂OH | 2 | OH | H |
| 311 | OCH₂CH₂OH | 2 | OCH₃ | H |
| 312 | OCH₂CH₂OH | 2 | Cl | 4-F |
| 313 | 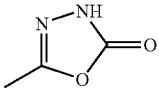 | 1 | H | H |
| 314 | OCH₂CH₂OH | 2 | CH₃ | 4-F |
| 315 |  | 1 | H | H |

TABLE 1-continued
(I-i)
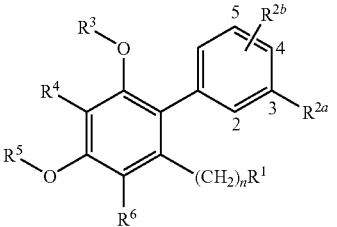
| | | n | R²ᵇ (5) | R²ᵃ (3) |
|---|---|---|---|---|
| 316 | 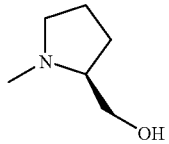 | 2 | H | H |
| 317 | 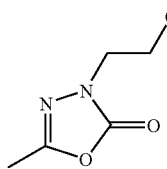 | 1 | H | H |
| 318 | 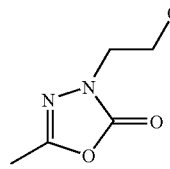 | 1 | H | H |
| 319 | 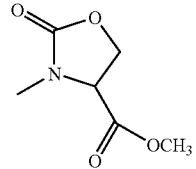 | 2 | H | H |
| 320 | 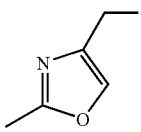 | 1 | H | H |
| 321 | 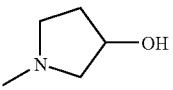 | 2 | H | H |
| 322 | CON(CH₂CH₂OH)(CH₂CH₂CH₂OCH₃) | 1 | H | H |
| 323 | 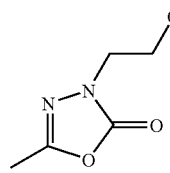 | 1 | OCH₃ | H |
| 324 | 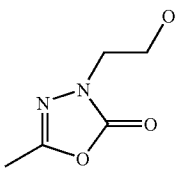 | 1 | OH | H |

TABLE 1-continued (I-i)

[Structure: biphenyl with R³O at position, R⁴, R⁵O, R⁶, (CH₂)ₙR¹ substituents; R²ᵃ at position 3, R²ᵇ at positions 4/5]

| | | | | |
|---|---|---|---|---|
| 325 | OCH$_2$CH$_2$OCH$_3$ | 2 | H | H |
| 326 | OCH$_2$CH$_2$OCH$_3$ | 2 | H | H |
| 327 | OCH$_2$CH$_2$OCH$_3$ | 2 | H | H |
| 328 | OCH$_2$CH$_2$OCH$_3$ | 2 | H | H |

| Compound | R³ | R⁴ | R⁵ | R⁶ |
|---|---|---|---|---|
| 1 | H | H | H | H |
| 2 | H | H | H | H |
| 3 | H | H | H | H |
| 4 | H | H | H | H |
| 5 | H | H | H | H |
| 6 | H | H | H | H |
| 7 | H | H | H | H |
| 8 | H | H | H | H |
| 9 | H | H | H | Br |
| 10 | H | H | H | Br |
| 11 | H | H | H | Ph |
| 12 | H | H | H | Br |
| 13 | H | H | H | I |
| 14 | H | H | H | N-ethylmorpholine |
| 15 | H | H | H | Br |
| 16 | H | H | H | Br |
| 17 | H | H | H | Br |
| 18 | H | H | H | Br |
| 19 | H | H | H | Br |
| 20 | H | H | H | Br |
| 21 | H | H | H | Br |
| 22 | H | H | H | Br |
| 23 | H | H | H | Br |
| 24 | H | H | H | Br |
| 25 | H | H | H | Br |
| 26 | H | H | H | Br |
| 27 | H | H | H | Br |
| 28 | H | H | H | Br |
| 29 | H | H | H | Br |
| 30 | H | H | H | Br |
| 31 | H | H | H | Br |
| 32 | H | H | H | Br |
| 33 | H | H | H | Br |
| 34 | H | H | H | Br |
| 35 | H | H | H | Br |
| 36 | H | H | H | Br |
| 37 | H | H | H | Br |
| 38 | H | H | H | Br |
| 39 | H | H | H | Br |
| 40 | H | H | H | Br |
| 41 | H | H | H | Br |
| 42 | H | H | H | Br |
| 43 | H | H | H | Br |
| 44 | H | H | H | Br |
| 45 | H | H | H | Br |
| 46 | H | H | H | Br |
| 47 | H | H | H | Br |
| 48 | H | H | H | Br |
| 49 | H | H | H | Br |
| 50 | H | H | H | Br |
| 51 | H | H | H | Br |
| 52 | H | H | H | CH$_2$CH$_3$ |
| 53 | H | H | H | Br |

TABLE 1-continued (I-i)

| # | | | | |
|---|---|---|---|---|
| 54 | H | H | H | Br |
| 55 | H | H | H | CHO |
| 56 | H | H | H | $CH_3$ |
| 57 | H | H | H | Br |
| 58 | H | H | H | Br |
| 59 | H | H | H | Br |
| 60 | H | H | H | Br |
| 61 | H | H | H | Br |
| 62 | H | H | H | Br |
| 63 | H | H | H | Br |
| 64 | H | H | H | Br |
| 65 | H | H | H | Br |
| 66 | H | H | H | H |
| 67 | H | H | H | H |
| 68 | H | H | H | Br |
| 69 | H | H | H | $COCH_3$ |
| 70 | H | H | H | $CH_2Ph$ |
| 71 | H | H | H | Br |
| 72 | H | H | H | Br |
| 73 | H | H | H | H |
| 74 | H | H | H | H |
| 75 | H | H | H | H |
| 76 | H | H | H | H |
| 77 | H | H | H | H |
| 78 | H | H | H | H |
| 79 | H | H | H | H |
| 80 | H | H | H | H |
| 81 | H | H | H | H |
| 82 | H | H | H | H |
| 83 | H | H | H | $CH_2CH_3$ |
| 84 | H | H | H | $CH_2CH_3$ |
| 85 | H | H | H | Br |
| 86 | H | H | H | Br |
| 87 | H | H | H | Br |
| 88 | H | H | H | Br |
| 89 | H | H | H | Br |
| 90 | H | H | H | Br |
| 91 | H | H | H | Br |
| 92 | H | H | H | $COCH_3$ |
| 93 | H | H | H | $COCH(CH_3)_2$ |
| 94 | H | H | H | $COCH_2CH_3$ |
| 95 | H | H | H | $(CH_2)_2CH_3$ |
| 96 | H | H | H | $CH_2CH(CH_3)_2$ |
| 97 | H | H | H | Br |
| 98 | H | H | H | Br |
| 99 | H | H | H | Br |
| 100 | H | H | H | Br |
| 101 | H | H | H | Br |
| 102 | H | H | H | Br |
| 103 | H | H | H | Br |
| 104 | H | H | H | Br |
| 105 | H | H | H | Br |
| 106 | H | H | H | Br |
| 107 | H | H | H | Br |
| 108 | H | H | H | Br |
| 109 | H | H | H | Br |
| 110 | H | H | H | Br |
| 111 | H | H | H | Br |
| 112 | H | H | H | Br |
| 113 | H | H | H | $CH_2CH_3$ |
| 114 | H | H | H | Br |
| 115 | H | H | H | Br |
| 116 | H | H | H | $COCH_3$ |
| 117 | H | H | H | Br |
| 118 | H | H | H | $CH_2CH_3$ |
| 119 | H | H | H | $COCH_3$ |

TABLE 1-continued

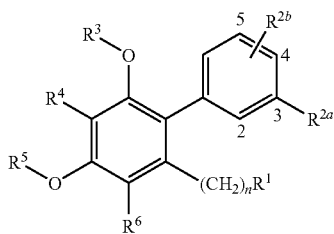

(I-i)

| | | | | |
|---|---|---|---|---|
| 120 | H | H | H | COCH$_3$ |
| 121 | H | H | H | COCH$_3$ |
| 122 | H | H | H | COCH$_3$ |
| 123 | H | H | H | CH$_2$CH$_3$ |
| 124 | H | H | H | COCH$_3$ |
| 125 | H | H | H | COCF$_3$ |
| 126 | H | H | CH$_3$ | CH$_2$CH$_3$ |
| 127 | H | H | H | CO$_2$H |
| 128 | H | H | H | CO$_2$CH$_3$ |
| 129 | H | H | H | OCH$_3$ |
| 130 | H | H | H | CH$_2$CH$_3$ |
| 131 | H | H | H | CH$_2$CH$_3$ |
| 132 | H | H | H | CH$_2$CH$_3$ |
| 133 | H | H | H | CH$_2$CH$_3$ |
| 134 | H | H | H | COCH$_3$ |
| 135 | H | H | H | COCH$_3$ |
| 136 | H | H | H | COCH$_3$ |
| 137 | H | H | H | COCH$_3$ |
| 138 | H | H | H | CH$_2$CH$_3$ |
| 139 | H | H | H | COCH$_3$ |
| 140 | H | H | SO$_2$CF$_3$ | H |
| 141 | H | H | H | COCH$_3$ |
| 142 | H | H | H | CH$_2$CH$_3$ |
| 143 | H | H | H | CH$_2$CH$_3$ |
| 144 | H | H | H | CH$_2$CH$_3$ |
| 145 | H | H | H | CH$_2$CH$_3$ |
| 146 | H | H | H | CH$_2$CH$_3$ |
| 147 | H | H | H | CH$_2$CH$_3$ |
| 148 | H | H | H | CH$_2$CH$_3$ |
| 149 | H | H | H | CH$_2$CH$_3$ |
| 150 | H | H | H | CH$_2$CH$_3$ |
| 151 | H | H | H | CH(CH$_3$)$_2$ |
| 152 | H | H | SO$_2$NH$_2$ | H |
| 153 | H | H | H | CH$_2$CH$_3$ |
| 154 | H | H | H | CH$_2$CH$_3$ |
| 155 | H | H | H | CH$_2$CH$_3$ |
| 156 | H | H | H | CH$_2$CH$_3$ |
| 157 | H | H | H | CH$_2$CH$_3$ |
| 158 | H | H | H | CH$_2$CH$_3$ |
| 159 | H | H | H | CH$_2$CH$_3$ |
| 160 | H | H | H | CH$_2$CH$_3$ |
| 161 | H | H | H | CH$_2$CH$_3$ |
| 162 | H | H | H | CH$_2$CH$_3$ |
| 163 | H | H | H | CH$_2$CH$_3$ |
| 164 | H | H | H | CH$_2$CH$_3$ |
| 165 | H | H | H | COCH$_3$ |
| 166 | H | H | H | CH$_2$CH$_3$ |
| 167 | H | H | H | CH$_2$CH$_3$ |
| 168 | H | H | H | CH$_2$CH$_3$ |
| 169* | H | H | H | CH$_2$CH$_3$ |
| 170* | H | H | H | CH$_2$CH$_3$ |
| 171 | H | H | H | CH$_2$CH$_3$ |
| 172 | H | H | H | CH$_2$CH$_3$ |
| 173 | H | H | H | CH$_2$CH$_3$ |
| 174 | H | H | H | CH$_2$CH$_3$ |
| 175 | H | H | H | CH$_2$CH$_3$ |
| 176 | H | H | H | CH$_2$CH$_3$ |
| 177* | H | H | H | CH$_2$CH$_3$ |
| 178* | H | H | H | CH$_2$CH$_3$ |
| 179 | H | H | H | CH$_2$CH$_3$ |
| 180 | H | H | H | CH$_2$CH$_3$ |
| 181 | H | H | H | CH$_2$CH$_3$ |
| 182 | H | H | H | CH$_2$CH$_3$ |
| 183 | H | H | H | CH$_2$CH$_3$ |
| 184 | H | H | H | CH$_2$CH$_3$ |
| 185 | H | H | H | CH$_2$CH$_3$ |

TABLE 1-continued (I-i)

| | | | | |
|---|---|---|---|---|
| 186 | H | H | H | COCH$_3$ |
| 187 | H | H | H | CH$_2$CH$_3$ |
| 188 | H | H | H | CH$_2$CH$_3$ |
| 189 | H | H | H | CH$_2$CH$_3$ |
| 190 | H | H | H | CH$_2$CH$_3$ |
| 191 | H | H | H | CH$_2$CH$_3$ |
| 192 | H | H | H | CH$_2$CH$_3$ |
| 193 | H | H | H | CH$_2$CH$_3$ |
| 194 | H | H | H | CH$_2$CH$_3$ |
| 195 | H | H | H | CH$_2$CH$_3$ |
| 196 | H | H | H | CH$_2$CH$_3$ |
| 197 | H | H | H | CH$_2$CH$_3$ |
| 198 | H | H | H | CH$_2$CH$_3$ |
| 199 | H | H | H | CH$_2$CH$_3$ |
| 200 | H | H | H | CH$_2$CH$_3$ |
| 201 | H | H | H | CH$_2$CH$_3$ |
| 202 | H | H | H | CH$_2$CH$_3$ |
| 203 | H | H | H | CH$_2$CH$_3$ |
| 204 | H | H | H | CH$_2$CH$_3$ |
| 205 | H | H | H | CH$_2$CH$_3$ |
| 206 | H | H | H | CH$_2$CH$_3$ |
| 207 | H | H | H | CH$_2$CH$_3$ |
| 208 | H | H | H | CH$_2$CH$_3$ |
| 209 | H | H | H | CH$_2$CH$_3$ |
| 210 | H | H | H | CH$_2$CH$_3$ |
| 211 | H | H | H | CH$_2$CH$_3$ |
| 212 | H | H | H | CH$_2$CH$_3$ |
| 213 | H | H | H | CH$_2$CH$_3$ |
| 214 | H | H | H | CH$_2$CH$_3$ |
| 215 | H | H | H | CH$_2$CH$_3$ |
| 216 | H | H | H | CH$_2$CH$_3$ |
| 217 | H | H | H | CH$_2$CH$_3$ |
| 218 | H | H | H | CH$_2$CH$_3$ |
| 219 | H | H | H | CH$_2$CH$_3$ |
| 220 | H | H | H | CH$_2$CH$_3$ |
| 221 | H | H | H | CH$_2$CH$_3$ |
| 222 | H | H | H | CH$_2$CH$_3$ |
| 223 | H | H | H | CH$_2$CH$_3$ |
| 224 | H | H | H | CH$_2$CH$_3$ |
| 225 | H | H | H | CH$_2$CH$_3$ |
| 226 | H | H | H | CH$_2$CH$_3$ |
| 227 | H | H | H | CH$_2$CH$_3$ |
| 228 | H | H | H | CH$_2$CH$_3$ |
| 229 | H | H | H | CH$_2$CH$_3$ |
| 230 | H | H | H | H |
| 231 | H | Br | H | Br |
| 232 | H | H | H | Br |
| 233 | H | H | H | CH$_2$CH$_3$ |
| 234 | H | H | H | COCH$_3$ |
| 280 | H | H | H | Cl |
| 281 | H | H | H | CH$_2$CH$_3$ |
| 282 | H | H | H | CH$_2$CH$_3$ |
| 283 | H | H | H | CH$_2$CH$_3$ |
| 284 | H | H | H | CH$_2$CH$_3$ |
| 285 | H | H | H | Cl |
| 286 | H | H | H | CH$_2$CH$_3$ |
| 287 | H | H | H | COCH$_3$ |
| 288 | H | H | H | CH$_2$CH$_3$ |
| 289 | H | H | H | CH$_2$CH$_3$ |
| 290 | H | H | H | CH$_2$CH$_3$ |
| 291 | H | H | H | CH$_2$CH$_3$ |
| 292 | H | H | H | CH$_2$CH$_3$ |
| 293 | H | H | H | CH$_2$CH$_3$ |
| 294 | H | H | H | CH$_2$CH$_3$ |
| 295 | H | H | H | CH$_2$CH$_3$ |
| 296 | H | H | H | CH$_2$CH$_3$ |

TABLE 1-continued (I-i)

|  |  |  |  |  |
|---|---|---|---|---|
| 297 | H | H | H | CH$_2$CH$_3$ |
| 298 | H | H | H | CH$_2$CH$_3$ |
| 299 | H | H | H | CH$_2$CH$_3$ |
| 300 | H | H | H | CH$_2$CH$_3$ |
| 301 | H | H | H | CH$_2$CH$_3$ |
| 302 | H | H | H | CH$_2$CH$_3$ |
| 303 | H | H | H | CH$_2$CH$_3$ |
| 304 | H | H | H | CH$_2$CH$_3$ |
| 305 | H | H | H | CH$_2$CH$_3$ |
| 306 | H | H | H | CH$_2$CH$_3$ |
| 307 | H | H | H | CH$_2$CH$_3$ |
| 308 | H | H | H | CH$_2$CH$_3$ |
| 309 | H | H | H | CH$_2$CH$_3$ |
| 310 | H | H | H | COCH$_3$ |
| 311 | H | H | H | COCH$_3$ |
| 312 | H | H | H | CH$_2$CH$_3$ |
| 313 | H | H | H | CH$_2$CH$_3$ |
| 314 | H | H | H | CH$_2$CH$_3$ |
| 315 | H | H | H | CH$_2$CH$_3$ |
| 316 | H | H | H | CH$_2$CH$_3$ |
| 317 | H | H | H | CH$_2$CH$_3$ |
| 318 | H | H | H | CH$_2$CH$_3$ |
| 319 | H | H | H | CH$_2$CH$_3$ |
| 320 | H | H | H | CH$_2$CH$_3$ |
| 321 | H | H | H | CH$_2$CH$_3$ |
| 322 | H | H | H | CH$_2$CH$_3$ |
| 323 | H | H | H | CH$_2$CH$_3$ |
| 324 | H | H | H | CH$_2$CH$_3$ |
| 325 | CO$_2$CH$_2$CH$_3$ | H | CO$_2$CH$_2$CH$_3$ | CH$_2$CH$_3$ |
| 326 | CON(CH$_3$)$_2$ | H | CON(CH$_3$)$_2$ | CH$_2$CH$_3$ |
| 327 | H | H | 1-acetyl-4-methylpiperazinyl | CH$_2$CH$_3$ |
| 328 | COCH$_3$ | H | COCH$_3$ | CH$_2$CH$_3$ |

*Compound 170 is a diastereomer of Compound 169; Compound 178 is a diastereomer of Compound 177.

TABLE 2

(I-ii)

| Compound | R$^1$ | n | R$^{2c}$ | R$^3$ | R$^4$ | R$^5$ | R$^6$ |
|---|---|---|---|---|---|---|---|
| 235 | OCH$_2$Ph | 1 | CHO | H | H | H | H |
| 236 | OCH$_2$Ph | 1 | CH$_2$CH$_2$CO$_2$CH$_2$CH$_3$ | H | H | H | H |
| 237 | CH(OCH$_3$)Ph | 0 | CH$_2$CH$_2$CO$_2$CH$_3$ | H | H | H | H |
| 238 | CO$_2$CH$_3$ | 1 | H | H | H | H | Br |
| 239 | CONHCH$_2$CH$_2$CH$_3$ | 1 | H | H | H | H | Br |

TABLE 2-continued (I-ii)

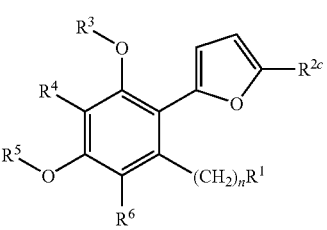

| Compound | R¹ | n | R$^{2c}$ | R³ | R⁴ | R⁵ | R⁶ |
|---|---|---|---|---|---|---|---|
| 240 | (1-acetylpyrrolidinyl) | 1 | H | H | H | H | Br |
| 241 | CON(CH$_2$CH$_3$)$_2$ | 1 | H | H | H | H | Br |
| 242 | (N-acetyl-3,5-dimethoxyanilinyl) | 1 | H | H | H | H | Br |
| 243 | OCH$_3$ | 2 | H | H | H | H | Br |
| 244 | OCH$_3$ | 2 | H | H | H | H | CH$_2$CH$_3$ |
| 245 | CO$_2$CH$_3$ | 1 | (N-ethylmorpholinyl) | H | H | H | H |
| 246 | CO$_2$CH$_3$ | 1 | (ethylamino-propyl-imidazolyl) | H | H | H | H |
| 247 | CO$_2$CH$_3$ | 1 | (ethylamino-propyl-morpholinyl) | H | H | H | H |
| 248 | CO$_2$CH$_3$ | 1 | (N-ethyl-N-acetyl-propyl-morpholinyl) | H | H | H | H |
| 249 | CO$_2$CH$_3$ | 1 | (ethylamino-propyl-pyrrolidinonyl) | H | H | H | H |
| 250 | CO$_2$CH$_3$ | 1 | CH$_2$CH$_2$COPh | H | H | H | H |

TABLE 2-continued (I-ii)

[Structure: benzene ring with R³O, R⁴, R⁵O, R⁶ substituents, furan ring with R²ᶜ, and (CH₂)ₙR¹]

| Compound | R¹ | n | R²ᶜ | R³ | R⁴ | R⁵ | R⁶ |
|---|---|---|---|---|---|---|---|
| 251 | $CO_2CH_3$ | 1 | [CH₂-piperazine-N-CH₃ group] | H | H | H | H |
| 252 | $CO_2CH_3$ | 1 | $CH_2N(CH_2CH_3)_2$ | H | H | H | H |
| 253 | $CO_2CH_3$ | 1 | CH=NOH | H | H | H | H |
| 254 | $CO_2CH_3$ | 1 | $CH=NOCH_3$ | H | H | H | H |
| 255 | $CO_2CH_3$ | 1 | H | H | H | H | H |
| 256 | $OCH_2CH_2OH$ | 2 | H | H | H | H | $CH_2CH_3$ |
| 257 | $CON(CH_3)CH_2CH_2OCH_3$ | 1 | H | H | H | H | $CH_2CH_3$ |
| 258 | $CO_2CH_3$ | 1 | $CH_2OH$ | H | H | H | H |
| 259 | $CO_2CH_3$ | 1 | $CH_2CH_2CH(OH)Ph$ | H | H | H | H |
| 260 | $CO_2CH_3$ | 1 | $CH_2CH_2CO_2CH_3$ | H | H | H | H |
| 261 | $CO_2CH_3$ | 1 | $CH_2CH_2COCH_3$ | H | H | H | H |
| 262 | $CO_2H$ | 1 | $CH_2CH_2COCH_3$ | H | H | H | H |
| 263 | $CO_2CH_3$ | 1 | $CH_2NH_2$ | H | H | H | H |
| 264 | $CO_2CH_3$ | 1 | $CH_2NHCOCH_3$ | H | H | H | H |
| 265 | $CO_2CH_3$ | 1 | $CH_2CH_2COCH_3$ | H | H | H | Br |
| 266 | $CO_2H$ | 1 | $CH_2NHCOCH_3$ | H | H | H | H |
| 267 | $CO_2CH_3$ | 1 | $CH_2CH_2CO_2CH_3$ | H | H | H | Br |
| 268 | $CO_2CH_3$ | 1 | $CH_2CH_2C(=NOH)CH_3$ | H | H | H | H |
| 269 | $CO_2CH_3$ | 1 | $CH_2CH_2C(=NOCH_3)CH_3$ | H | H | H | H |

TABLE 3

(I-iii)

[Structure: benzene ring with R³O, R⁴, R⁵O, R², R⁶ substituents and (CH₂)ₙR¹]

| Compound | R¹ | n | R² | R³ | R⁴ | R⁵ | R⁶ |
|---|---|---|---|---|---|---|---|
| 270 | $CO_2CH_3$ | 1 | [2-naphthyl group] | H | H | H | H |
| 271 | $CO_2CH_3$ | 1 | [dibenzofuran-4-yl group] | H | H | H | H |

TABLE 3-continued (I-iii)

| Compound | R¹ | n | R² | R³ | R⁴ | R⁵ | R⁶ |
|---|---|---|---|---|---|---|---|
| 272 | CO$_2$CH$_3$ | 1 | 1-methylnaphthyl | H | H | H | H |
| 273 | CO$_2$CH$_3$ | 1 | 6-methyl-1,3-benzodioxole | H | H | H | H |
| 274 | CO$_2$CH$_3$ | 1 | 2-methylthiophene | H | H | H | H |
| 275 | OCH$_2$CH$_2$OH | 2 | 2-methylthiophene | H | H | H | CH$_2$CH$_3$ |
| 276 | H | 0 | 3-methyl-6-methoxy-1H-indazole | H | H | H | CH$_2$CH$_3$ |
| 277 | H | 0 | 3-methyl-5-nitro-1H-indazole | H | H | H | CH$_2$CH$_3$ |
| 278 | H | 0 | 2-methyl-1H-benzimidazole | H | H | H | CH$_2$CH$_3$ |
| 279 | H | 0 | 2-methyl-1-phenyl-benzimidazole | H | H | H | CH$_2$CH$_3$ |
| 329 | CO$_2$CH$_3$ | 1 | 2-methyl-5-phenyloxazole | H | H | H | CH$_2$CH$_3$ |

TABLE 3-continued

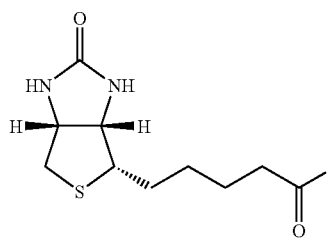

(I-iii)

| Compound | R¹ | n | R² | R³ | R⁴ | R⁵ | R⁶ |
|---|---|---|---|---|---|---|---|
| 330 | OCH$_2$CH(OH)CH$_2$OH | 2 | 3-methyl-6-methoxy-1H-indazol-5-yl | H | H | H | CH$_2$CH$_3$ |

The pharmacological activity of Compounds (I) is more concretely illustrated below referring to Test Examples.

TEST EXAMPLE 1

Hsp90 Protein Binding Assay (1) Human N-terminal recombinant Hsp90 protein (region of amino acids 9 to 236) prepared according to the method described in "Cell", 89, 239-250 (1997) was diluted to 1 μg/mL with Tris-buffered physiological saline (TBS, pH 7.5) and added to each well of a 96-well ELISA assay plate (Greiner) in an amount of 70 μL/well. The plate was incubated overnight at 4° C. to obtain a solid phase.

(2) The supernatant was removed, and Tris-buffered physiological saline containing 1% bovine serum albumin (BSA) was added in an amount of 350 μL/well for blocking.

(3) After the blocking solution was removed, each resulting solid phase was washed by the addition of Tris-buffered physiological saline containing 0.05% Tween 20 (TBST) in an amount of 500 μL/well. This washing procedure was repeated three times.

(4) A test compound having the highest concentration of 0.1 mmol/L was diluted with TBST to prepare eight √10-fold serial dilutions in separate vials. Each of these test compound solutions was added, in an amount of 10 μL/well, to the assay plate containing TBST (90 μL/well) previously added thereto, and the plate was allowed to stand at 24° C. for 1 hour. In this assay, a positive control using dimethyl sulfoxide (final concentration: 0.1 μL/well) and a negative control using Radicicol (final concentration: 0.29 μmol/L) were subjected to the same procedure as that for the test compound, and these controls were on the same plate on which was placed the test compound.

(5) Biotinylated Radicicol represented by formula (D) was added to give a final concentration of 0.1 μmol/L, and the plate was incubated at 24° C. for further 1 hour for competitive binding reaction to measure the binding activity of the test compound to the immobilized Hsp90 protein.

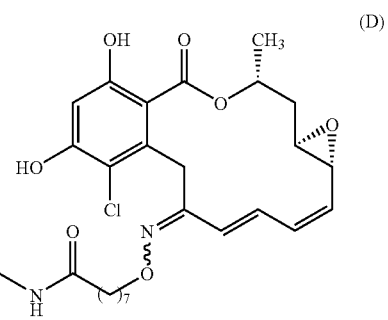

(D)

(6) After the reaction liquid of (5) was removed, each resulting solid phase was washed by the addition of TBST in an amount of 500 μL/well. This washing procedure was repeated three times.

(7) Europium-labeled streptoavidin (Wallac Oy) was diluted to a final concentration of 0.1 μg/mL with Assay Buffer (Wallac Oy) and added to the wells of the plate in an amount of 100 μL/well. The plate was incubated at room temperature for 1 hour to carry out biotin-avidin binding reaction.

(8) After the reaction mixture of (7) was removed, each resulting solid phase was washed by the addition of TBST in an amount of 500 μL/well. This washing procedure was repeated five times.

(9) Fluorescence enhancement solution (Wallac Oy) was added thereto in an amount of 100 μL/well and color developing reaction was carried out at room temperature for 5 minutes, followed by measurement of time-resolved fluorescence (excitation wavelength: 340 nm, measurement wavelength: 615 nm) using Multilabel Counter (ARVO 1420, Wallac Oy).

The binding rate in each well treated with the test compound was calculated from the time-resolved fluorescence measured for each well based on the time-resolved fluorescence measured with the positive control taken as 100% binding rate and that with the negative control taken as 0% binding rate.

In the above method, it was revealed that Compounds 1, 2, 5, 8 to 10, 17 to 18, 25 to 26, 36 to 38, 50, 59, 61, 63 to 67, 70, 71, 80 to 100, 112 to 125, 131 to 138, 141 to 165, 167 to 234, 237, 243, 270, 272, 280 to 282, 284 to 324, 329 and 330 inhibited the binding of biotinylated Radicicol to the Hsp90 protein by at least 30% at concentrations of at most 10 μmol/L and thus have Hsp90 protein-binding activity.

As described above, benzoquinone ansamycin antibiotics such as Geldanamycin and Herbimycin, and Radicicol are known as compounds which are bound to Hsp90 family proteins (Cell Stress & Chaperones, 1998, Vol., 3, pp. 100-108; J. Med. Chem., 1999, Vol., 42, pp. 260-266), and these compounds are all reported to bind to Hsp90 family proteins and inhibit the functions of Hsp90 family proteins, thereby exhibiting pharmacological activities such as anti-tumor activity. Further, it is reported that a Geldanamycin derivative (17-AAG; Invest. New Drugs, 1999, Vol. 17, pp. 361-373) and Radicicol derivatives (Cancer Research, 1999, Vol. 59, pp. 2931-2938; Blood, 2000, Vol. 96, pp. 2284-2291; Cancer Chemotherapy and Pharmacology, 2001, Vol. 48, pp. 35-445; WO96/33989; WO98/18780; WO99/55689; WO02/16369) show anti-tumor effect.

Therefore, Compounds (I) are considered to be useful as therapeutic agents for diseases associated with Hsp90 family proteins or proteins to which Hsp90 family proteins are bound (Hsp90 client proteins) (e.g. anti-tumor agents).

TEST EXAMPLE 2

Cell Growth Inhibition Test with Human Mammary Cancer-Derived KPL-4 Cells

In a 96-well plate (Nunc), human mammary cancer-derived KPL-4 cells were sown in an amount of 2000 cells/well, and pre-incubated in 10% fetal calf serum (FCS)-containing Dulbecco Modified Eagle Medium (DMEM) (incubation medium) in a 5% carbon dioxide incubator at 37° C. for 24 hours. A dimethylsulfoxide (DMSO) solution of a test compound controlled at 10 mmol/L was stepwise diluted with the incubation medium, and added to each well in a total amount of 100 μL/well, and incubated in the 5% carbon dioxide incubator at 37° C. for 72 hours. After the incubation, WST-1 {4-[3-(4-Iodophenyl)-2-(4-nitrophenyl)-2H-5-tetrazolio]-1,3-benzene disulfonate}-labeled mixture (Rosh Diagnostic) diluted 2-fold with the incubation medium was added thereto in an amount of 20 μL/well, and incubated in the 5% carbon dioxide incubator at 37° C. for 1 hour. Using a microplate spectrophotometer (Biorad's Model 550), the absorbance at 450 nm and 655 nm of each well was measured. The cell growth inhibition activity of the test compound was indicated by the 50% growth inhibition concentration ($GI_{50}$) thereof. A method of calculating $GI_{50}$ is described. The absorbance at 655 nm of each well was subtracted from the absorbance at 450 nm thereof to give a value (absorbance difference). The absorbance difference obtained with the cells without being treated with the test compound was taken as 100%, and this was compared with the absorbance difference obtained with the cells treated with the test compound to give the concentration of the compound for 50% cell growth inhibition, and this is referred to as $GI_{50}$.

In the above method, it was revealed that Compounds 1, 3, 8, 10, 11, 13, 17, 18, 23, 25, 26, 35 to 38, 41, 43, 47, 51, 52, 54 to 62, 64, 65, 69 to 100, 103 to 105, 107 to 126, 128 to 194, 236 to 238, 241 to 244, 257, 260, 265, 267, 270, 273, 276 to 279, 329 and 330 have the $GI_{50}$ value of at most 50 μmol/L, thus showing a cell growth inhibition activity against human mammary cancer-derived KPL-4 cells, and are therefore considered to be useful as anti-tumor agents, for example, for solid tumors.

TEST EXAMPLE 3

Cell Growth Inhibition Test with Human Chronic Myelocytic Leukemia-Derived K562 Cells In a 96-well plate (Nunc), human chronic myelocytic leukemia-derived K562 cells were sown in an amount of 1500 cells/well, and pre-incubated in 10% FCS-containing Rosewell Park Memorial Institute's Medium (RPMI) 1640 (Nissui) (incubation medium) in a 5% carbon dioxide incubator at 37° C. for 5 hours. Next, a DMSO solution of a test compound controlled at 10 mmol/L was stepwise diluted with the incubation medium, and added to each well in a total amount of 100 μL/well, and further incubated in the 5% carbon dioxide incubator at 37° C. for 72 hours. After the incubation, WST-1-labeled mixture (Rosh Diagnostic) diluted 2-fold with the incubation medium was added thereto in an amount of 20 μL/well, and incubated in the 5% carbon dioxide incubator at 37° C. for 2 hours. Using a microplate spectrophotometer (Biorad's Model 550), the absorbance at 450 nm and 655 nm of each well was measured. The cell growth inhibition activity of the test compound was indicated by the 50% growth inhibition concentration ($GI_{50}$) thereof, like in Test Example 2.

In the above method, it was revealed that Compounds 37, 69, 83, 84, 92, 104, 113, 116, 118, 122, 123, 130, 134, 136 to 139, 143, 145 to 149, 156, 159, 161 to 163, 165 to 167, 170 to 175, 189, 195 to 230, 232 to 234, 238, 256, 261, 265, 270, 275 and 280 to 328 have the $GI_{50}$ value of at most 50 μmol/L, thus showing a cell growth inhibition activity against human chronic myelocytic leukemia-derived K562 cells, and are therefore considered to be useful as anti-tumor agents, for example, for hematopoietic tumors.

TEST EXAMPLE 4

Cell Growth Inhibition Test with Human Multiple Myeloma-Derived KMS-11 Cells

In a 96-well plate (Nunc), human multiple myeloma-derived KMS-11 cells were sown in an amount of 4000 cells/well, and pre-incubated in 10% FCS-containing RPMI 1640 (Nissui) (incubation medium) in a 5% carbon dioxide incubator at 37° C. for 24 hours. Next, a DMSO solution of a test compound controlled at 10 mmol/L was stepwise diluted with the incubation medium, and added to each well in a total amount of 100 μL/well, and further incubated in the 5% carbon dioxide incubator at 37° C. for 72 hours. After the incubation, WST-1-labeled mixture (Rosh Diagnostic) diluted 2-fold with the incubation medium was added thereto in an amount of 20 μL/well, and incubated in the 5% carbon dioxide incubator at 37° C. for 2 hours. Using a microplate spectrophotometer (Biorad's Model 550), the absorbance at 450 nm and 655 nm of each well was measured. The cell growth inhibition activity of the test compound was indicated by the 50% growth inhibition concentration ($GI_{50}$) thereof, like in Test Example 2.

In the above method, it was revealed that Compounds 52, 84, 92, 113, 116, 118, 122, 134, 138, 139, 147, 159, 166, 174, 201, 209, 210, 218, 227, 229, 238, 256, 265, 275, 276, 300 and 317 have the $GI_{50}$ value of at most 50 μmol/L, thus showing a cell growth inhibition activity against human multiple myeloma-derived KMS-11 cells, and are therefore considered to be useful as anti-tumor agents, for example, for hematopoietic tumors.

TEST EXAMPLE 5

Deletion of Protein Encoded by Partner Gene Through Translocation of Immunoglobulin Gene in Cells, by Hsp90-Inhibiting Compound It is reported that tumors of B-cell lines (including transformants) are often accompanied by translocation of an immunoglobulin gene in the q32 region of the 14-th chromosome (hereinafter referred to as "14q32"). (The term "translocation" as referred to herein is meant to indicate genetic abnormality caused by movement of a part of a chromosome to any other site of the same chromosome or to, any other chromosome.) For example, in hematopoietic cell tumors such as multiple myeloma, the proportion of translocation of the immunoglobulin gene in 14q32 increases with the development of the disease. It is reported that, when tumor cells collected from cases of multiple myeloma are assayed for the immunoglobulin gene translocation in 14q32 therein, then the translocation is found in 50% of the cases of monoclonal gammopathy, in 60 to 65% of the cases of intramedullary myeloma, and in 70 to 80% of the cases of extramedullary myeloma; and that the translocation is found in at least 90% of the immunoglobulin gene in 14q32 of the myeloma cells in the established cell line thereof [Oncogene, 20, 5611-5622 (2001)]. In the cells having immunoglobulin gene translocation therein, the protein that is encoded by a partner gene, of which the expression is abnormally promoted by the immunoglobulin gene translocation, can be deleted by the addition of Compound (I) to the cells, and this was confirmed by the following Western blotting.

Human multiple myeloma-derived KMS-11 cells [In Vitro Cell. Dev. Biol., 25, 723 (1989)], which had been diluted with a 10% fetal calf serum-containing RPMI 1640 (incubation medium) to 100,000 cell/mL, were put in a 6-well plastic plate for cell incubation (Nunc), in an amount of 3 mL/well. It is reported that the KMS-11 cells express a large quantity of FGFR3 (fibroblast growth factor receptor 3) as a result of translocation between the immunoglobulin gene in 14q32 and the FGFR3 gene in 4p16.3 [Blood 90, 4062 (1997)]. A DMSO solution of a test compound that had been controlled to 10 mmol/L was further diluted with the incubation medium to 1/10 and 1/100, and added to the plate to a final concentration of 10 μmol/L and 1.0 μmol/L. In the control, the test compound solution was not added. This was incubated in a 5% carbon dioxide incubator at 37° C. for 24 hours, and the cells were collected through centrifugation at 1000 G for 5 minutes.

To the thus-collected cells, added was a cooled cytolysis buffer (50 mmol/L HEPES NaOH, pH 7.4, 250 mmol/L sodium chloride, 1 mmol/L ethylenediamine-tetraacetic acid, 1% Nonidet P-40, 1 mmol/L dithiothreitol, 1 mmol/L phenylmethylsulfonyl fluoride, 5 μg/mL leupeptin), and kept at 4° C. for 30 minutes for cytolysis. Then, this was centrifuged at 20000 G for 10 minutes. The protein concentration in the resulting supernatant was measured, and samples were prepared so as to have the same protein amount for each lane, and these were subjected to SDS (sodium dodecylsulfate)-polyacrylamide gel electrophoresis for protein separation.

Thus separated, the protein sample was transferred onto a polyvinylidene difluoride membrane (Millipore). Then, as a primary antibody, anti-FGFR3 antibody (Sigma) and Erk2 antibody (Upstate Biotechnology) were added thereto and reacted with the protein on the membrane. Next, as a secondary antibody, an enzyme-labeled antibody capable of reacting with the primary antibody [horse radish peroxidase-labeled anti-rabbit Ig antibody or anti-mouse Ig antibody (Amersham Biosciences)] was reacted with the protein. After further reaction with an ECL reagent (Amersham Biosciences), the protein bands were detected on an X-ray film. The result is shown in FIG. 1.

The result confirms the following: As in FIG. 1, the addition of Compound 166, 201, 209 or 218 resulted in deletion of FGFR3 encoded by the immunoglobulin gene-translocated partner gene. On the other hand, the addition caused no change in the protein amount of Erk2 that is a non-Hsp90 client protein. Accordingly, it is shown that Compounds 166, 201, 209 and 218 may selectively delete the protein that is encoded by the immunoglobulin gene-translocated partner gene, from cells. From the above, it is understood that Compounds (I) such as Compounds 166, 201, 209 and 218 may be useful as therapeutic agents for diseases associated with cells having immunoglobulin gene translocation, such as hematopoietic tumors (e.g., leukemia, multiple myeloma, lymphoma).

From the above results, it is considered that Compounds (I) is useful as anti-tumor agents, for example, for solid tumors such as mammary cancer, and hematopoietic tumors such as leukemia, multiple myeloma and lymphoma.

Although Compounds (I) or prodrugs thereof, or pharmaceutically acceptable salts thereof can be administered as such, it is generally preferred to offer them in the form of various pharmaceutical preparations. Such pharmaceutical preparations are to be used in animals and humans.

The pharmaceutical preparations of the present invention can comprise Compound (I) or a prodrug thereof, or a pharmaceutical salt thereof as the active ingredient alone or in combination with any other active ingredients for the therapy. These pharmaceutical preparations may be produced by any methods well known in the technical field of pharmaceutics by mixing the active ingredient with one or more pharmaceutically acceptable carriers.

It is desirable to select a route of administration that is most effective for therapy, examples thereof being oral administration and other parenteral administrations such as intravenous.

Examples of the dosage form include tablets and injections.

Preparations suitable for oral administration such as tablets can be produced using, for example, excipients (e.g., lactose and mannitol), disintegrators (e.g., starch), lubricants (e.g., magnesium stearate), binders (e.g., hydroxypropyl cellulose), surfactants (e.g., fatty acid esters) and plasticizers (e.g., glycerin).

Preparations suitable for parenteral administration preferably comprise a sterilized aqueous preparation containing an active compound which is isotonic to the recipient's blood. In the case of an injection, for example, a solution for injection is prepared using a carrier comprising a saline solution, a glucose solution, or a mixture of a saline solution and a glucose solution.

The parenteral preparations may also comprise one or more auxiliary components selected from the excipients, disintegrators, lubricants, binders, surfactants and plasticizers described in the above description of oral preparations, and diluents, antiseptics, flavors, etc.

The dose and the administration schedule of Compound (I) or a prodrug thereof, or a pharmaceutical salt thereof will vary depending upon the administration route, the age and body weight of a patient, and the nature and degree of seriousness of the symptom to be treated. In general, in the case of oral administration, the active ingredient is administered in a dose of 0.01 mg to 1 g, preferably 0.05 to 50 mg, per adult once to several times per day. In the case of parenteral administration such as intravenous administration, the active ingredient is administered in a dose of 0.001 to 500 mg, preferably 0.01 to 100 mg, per adult once to several times per day. However, the dose and the administration schedule may vary depending upon various conditions as given above.

BEST MODES FOR CARRYING OUT THE INVENTION

Figure 1:
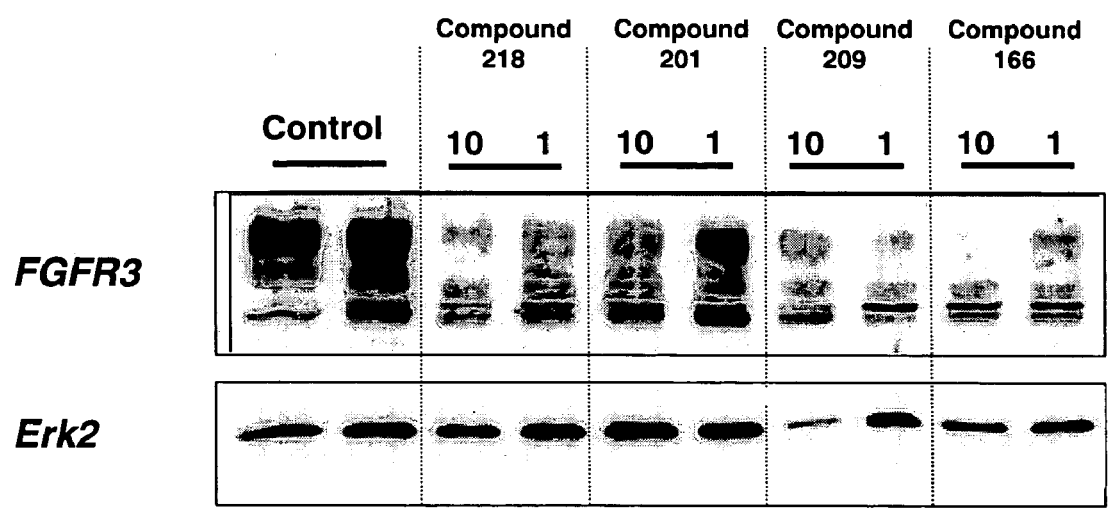
FIG. 1 shows the deletion of a protein (FGFR3) encoded by an immunoglobulin gene-translocated partner gene in cells. This shows the deletion of FGFR3 in KMS-11 cells to which Compound (I) was added. From the leftmost side thereof, the lanes indicate Western blotting with KMS-11 cells of control, and Compound 218 (concentration 10 μmol/L), Compound 218 (concentration 1 μmol/L), Compound 201 (concentration 10 μmol/L), Compound 201 (concentration 1 μmol/L), Compound 209 (concentration 10 μmol/L), Compound 209 (concentration 1 μmol/L), Compound 166 (concentration 10 μmol/L) or Compound 166 (concentration 1 μmol/L) added to the cells. The upper row indicates the detection of FGFR3; and the lower row indicates the detection of Erk2.

Embodiments of the invention are described below with reference to Examples.

EXAMPLE 1

Methyl 3,5-dihydroxy-2-phenylphenylacetate (Compound 1)

(Step 1)

Methyl 3,5-dihydroxyphenylacetate (5.0 g, 27 mmol) was dissolved in dichloromethane (0.15 L), and N,N-diisopropylethylamine (14 mL, 80 mmol) and chloromethyl methyl ether (5.6 mL, 60 mmol) were added thereto and stirred for 12 hours. Water (0.10 L) was added thereto for liquid-liquid separation. The organic layer was washed with aqueous saturated sodium hydrogencarbonate solution (0.10 L), and dried over anhydrous sodium sulfate, and the solvent was evaporated away under reduced pressure. The resulting residue was purified through silica gel column chromatography (ethyl acetate/n-hexane=1/4 to 2/1) to obtain methyl 3,5-bis(methoxymethoxy)phenylacetate (4.1 g, 56%).

$^1$H-NMR (270 MHz, CDCl$_3$) δ (ppm): 3.47 (s, 6H), 3.56 (s, 2H), 3.69 (s, 3H), 5.14 (s, 4H), 6.62-6.66 (m, 3H);

APCI-MS (m/z): 269 (M−H)$^−$.

(Step 2)

Methyl 3,5-bis(methoxymethoxy)phenylacetate (3.0 g, 11 mmol) obtained in the above was dissolved in carbon tetrachloride (0.15 L), and N-bromosuccinimide (2.0 g, 11 mmol) was added thereto and stirred with heating for 8 hours. The reaction mixture was cooled to room temperature, and then concentrated under reduced pressure. The resulting residue was purified through silica gel column chromatography (n-hexane to ethyl acetate/n-hexane=1/2) to obtain methyl 2-bromo-3,5-bis(methoxymethoxy)phenylacetate (3.7 g, 97%).

$^1$H-NMR (270 MHz, CDCl$_3$) δ (ppm): 3.47 (s, 3H), 3.51 (s, 3H), 3.71 (s, 3H), 3.78 (s, 2H), 5.14 (s, 2H), 5.22 (s, 2H), 6.69 (d, J=2.6 Hz, 1H), 6.81 (d, J=2.6 Hz, 1H);

APCI-MS (m/z): 349 ($^{79}$Br), 351 ($^{81}$Br) (M+H)$^+$.

(Step 3)

Methyl 2-bromo-3,5-bis(methoxymethoxy)phenylacetate (13 g, 38 mmol) obtained in the above was dissolved in a mixed solvent of 1,2-dimethoxyethane (120 mL) and water (10 mL), and cesium carbonate (37 g, 110 mmol), phenylboronic acid (6.5 g, 53 mmol) and bis(tri-o-tolylphosphine)palladium(II) dichloride (770 mg, 1.1 mmol) were added thereto, and stirred at 90° C. for 6 hours. The reaction mixture was concentrated under reduced pressure, water was added thereto, and extracted three times with ethyl acetate. The organic layers were combined, washed with aqueous saturated sodium chloride solution and dried over anhydrous sodium sulfate, and the solvent was evaporated away under reduced pressure. The resulting residue was purified through silica gel column chromatography (ethyl acetate/n-hexane=1/9 to 1/4) to obtain methyl 3,5-bis(methoxymethoxy)-2-phenylphenylacetate (13 g, 96%).

$^1$H-NMR (270 MHz, CDCl$_3$) δ (ppm): 3.28 (s, 3H), 3.51 (s, 2H), 3.54 (s, 3H), 3.57 (s, 3H), 5.00 (s, 2H), 5.19 (s, 2H), 6.72 (d, J=2.3 Hz, 1H), 6.83 (d, J=2.3 Hz, 1H), 7.17-7.38 (m, 5H).

(Step 4)

Methyl 3,5-bis(methoxymethoxy)-2-phenylphenylacetate (58 mg, 0.17 mmol) obtained in the above was dissolved in methanol (1.0 mL), and 1,4-dioxane solution (1.0 mL) of 4 mol/L hydrogen chloride was dropwise added thereto, and stirred at room temperature for 1 hour. The reaction solution was concentrated under reduced pressure, and the resulting residue was purified through silica gel column chromatography (ethyl acetate/n-hexane=1/4 to 1/1) to obtain Compound 1 (27 mg, 62%).

$^1$H-NMR (270 MHz, CDCl$_3$) δ (ppm): 3.35 (s, 2H), 3.57 (s, 3H), 6.39 (d, J=2.3 Hz, 1H), 6.41 (d, J=2.3 Hz, 1H), 7.22-7.23 (m, 2H), 7.35-7.48 (m, 3H);

FAB-MS (m/z): 258 (M+H)$^+$.

EXAMPLE 2

Methyl 3,5-dihydroxy-2-[3-(3-(oxobut-1-en-1-yl)phenyl]phenylacetate (Compound 2)

(Step 1)

Methyl 2-bromo-3,5-bis(methoxymethoxy)phenylacetate (630 mg, 1.8 mmol) obtained in the step 2 in Example 1 was dissolved in a mixed solvent of 1,2-dimethoxyethane (10 mL)

and water (2 mL), and in an argon atmosphere, 3-formylphenylboronic acid (400 mg, 2.7 mmol), bis(tri-o-tolylphosphine)palladium(II) dichloride (140 mg, 0.17 mmol) and cesium carbonate (1.1 g, 7.2 mmol) were added thereto, and stirred under heat for 10 hours. The reaction mixture was cooled to room temperature, then filtered, and the filtrate was concentrated under reduced pressure. Water was added to the resulting residue, and extracted twice with ethyl acetate. The organic layer was dried over anhydrous sodium sulfate, and the solvent was evaporated away under reduced pressure. The resulting residue was purified through silica gel column chromatography (ethyl acetate/n-hexane=1/4 to 1/2) to obtain methyl 2-(3-formylphenyl)-3,5-bis(methoxymethoxy)phenylacetate (500 mg, 75%).

$^1$H-NMR (270 MHz, CDCl$_3$) δ (ppm): 3.28 (s, 3H), 3.38 (s, 3H), 3.51 (s, 2H), 3.57 (s, 3H), 5.01 (s, 2H), 5.20 (s, 2H), 6.73 (d, J=2.3 Hz, 1H), 6.85 (d, J=2.3 Hz, 1H), 7.50 (dt, J=7.5, 1.6 Hz, 1H), 7.56 (dd, J=7.5, 7.5 Hz, 1H), 7.73 (dd, J=1.6, 1.6 Hz, 1H), 7.86 (dt, J=7.5, 1.6 Hz, 1H), 10.2 (s, 1H);

APCI-MS (m/z): 375 (M+H)$^+$.

(Step 2)

Methyl 2-(3-formylphenyl)-3,5-bis(methoxymethoxy)phenylacetate (260 mg, 0.70 mmol) obtained in the above was dissolved in toluene (7.0 mL), and acetylmethylene triphenylphosphine (320 mg, 1.0 mmol) was added thereto and stirred with heating for 8 hours. The reaction mixture was concentrated under reduced pressure, and the resulting residue was purified through silica gel column chromatography (ethyl acetate/n-hexane=1/4 to 1/2) to obtain methyl 3,5-bis(methoxymethoxy)-2-[3-(3-oxobut-1-en-1-yl)phenyl]phenylacetate (290 mg, 99%).

$^1$H-NMR (270 MHz, CDCl$_3$) δ (ppm): 3.25 (s, 3H), 3.36 (s, 2H), 3.47 (s, 3H), 3.54 (s, 3H), 4.98 (s, 2H), 5.17 (s, 2H), 6.70 (d, J=16.5 Hz, 1H), 6.71 (d, J=2.3 Hz, 1H), 6.82 (d, J=2.3 Hz, 1H), 7.24 (m, 1H), 7.36-7.54 (m, 4H);

APCI-MS (m/z): 415 (M+H)$^+$.

(Step 3)

In the same manner as in the step 4 in Example 1, Compound 2 (37 mg, 39%) was obtained from methyl 3,5-bis(methoxymethoxy)-2-[3-(3-oxobut-1-en-1-yl)phenyl]phenylacetate (120 mg, 0.29 mmol) obtained in the above, using methanol (2.0 mL) and 1,4-dioxane solution (1.0 mL) of 4 mol/L hydrogen chloride.

$^1$H-NMR (270 MHz, CDCl$_3$) δ (ppm): 2.35 (s, 3H), 3.32 (s, 2H), 3.55 (s, 3H), 6.38 (br s, 1H), 6.40 (br s, 1H), 6.67 (d, J=15.4 Hz, 1H), 7.25 (m, 1H), 7.40-7.53 (m, 4H);

APCI-MS (m/z): 325 (M−H)$^−$.

EXAMPLE 3

Methyl 3,5-dihydroxy-2-[3-(hydroxyiminomethyl)phenyl]phenylacetate (Compound 3)

(Step 1)

Methyl 2-(3-formylphenyl)-3,5-bis(methoxymethoxy)phenylacetate (57 mg, 0.15 mmol) obtained in the step 1 in Example 2 was dissolved in pyridine (1.0 mL), and hydroxyamine hydrochloride (15 mg, 0.22 mmol) was added thereto and stirred at room temperature for 1 hour. The solvent was evaporated away under reduced pressure, and the residue was purified through silica gel column chromatography (ethyl acetate/n-hexane=1/4 to 1/2) to obtain methyl 2-[3-(hydroxyiminomethyl)phenyl]-3,5-bis(methoxymethoxy)phenylacetate (60 mg, 92%).

$^1$H-NMR (270 MHz, CDCl$_3$) δ (ppm): 3.19 (s, 3H), 3.19 (s, 3H), 3.31 (s, 2H), 3.42 (s, 3H), 3.48 (s, 3H), 5.11 (s, 2H), 4.92 (s, 2H), 6.64 (d, J=2.3 Hz, 1H), 6.75 (d, J=2.3 Hz, 1H), 7.13 (m, 1H), 7.28-7.34 (m, 2H), 7.46 (m, 1H), 8.06 (s, 1H);

APCI-MS (m/z): 390 (M+H)$^+$.

(Step 2)

In the same manner as in the step 4 in Example 1, Compound 3 (40 mg, 94%) was obtained from methyl 2-[3-(hydroxyiminomethyl)phenyl]-3,5-bis(methoxymethoxy)phenylacetate (55 mg, 0.14 mmol) obtained in the above, using methanol (1.0 mL) and 1,4-dioxane solution (1.0 mL) of 4 mol/L hydrogen chloride.

$^1$H-NMR (270 MHz, CDCl$_3$) δ (ppm): 3.30 (s, 3H), 3.51 (s, 3H), 6.30 (d, J=2.0 Hz, 1H), 6.32 (d, J=2.0 Hz, 1H), 7.15 (m, 1H), 7.36 (m, 1H), 7.51 (m, 1H), 8.07 (s, 1H);

APCI-MS (m/z): 300 (M−H)$^−$.

EXAMPLE 4

Methyl 3,5-dihydroxy-2-[3-(methoxyiminomethyl)phenyl]phenylacetate (Compound 4)

(Step 1)

In the same manner as in the step 1 in Example 3, methyl 2-[3-(methoxyiminomethyl)phenyl]-3,5-bis(methoxymethoxy)phenylacetate (60 mg, 85%) was obtained from methyl 2-(3-formylphenyl)-3,5-bis(methoxymethoxy)phenylacetate (58 mg, 0.15 mmol) obtained in the step 1 in Example 2, using O-methylhydroxyamine hydrochloride (20 mg, 0.22 mmol) and pyridine (1.0 mL).

$^1$H-NMR (270 MHz, CDCl$_3$) δ (ppm): 3.28 (s, 3H), 3.38 (s, 2H), 3.50 (s, 3H), 3.57 (s, 3H), 3.94 (s, 3H), 5.00 (s, 2H), 5.19 (s, 2H), 6.71 (d, J=2.3 Hz, 1H), 6.82 (d, J=2.3 Hz, 1H), 7.20 (m, 1H), 7.36-7.41 (m, 2H), 7.54 (m, 1H), 8.06 (s, 1H);

APCI-MS (m/z): 404 (M+H)$^+$.

(Step 2)

In the same manner as in the step 4 in Example 1, Compound 4 (23 mg, 55%) was obtained from methyl 2-[3-(methoxyiminomethyl)phenyl]-3,5-bis(methoxymethoxy)phenylacetate (53 mg, 0.13 mmol) obtained in the above, using methanol (1.0 mL) and 1,4-dioxane solution (1.0 mL) of 4 mol/L hydrogen chloride.

$^1$H-NMR (270 MHz, CDCl$_3$) δ (ppm): 3.31 (s, 2H), 3.55 (s, 3H), 3.93 (s, 3H), 5.32 (br s, 1H), 6.35 (d, J=2.3 Hz, 1H), 6.37 (d, J=2.3 Hz, 1H), 6.40 (br s, 1H), 7.22 (m, 2H), 7.40 (m, 2H), 7.52 (m, 1H), 8.03 (s, 1H);

APCI-MS (m/z): 314 (M−H)$^−$.

EXAMPLE 5

Methyl 2-[3-(2-acetylethyl)phenyl]-3,5-dihydroxyphenylacetate (Compound 5)

(Step 1)

Methyl 3,5-bis(methoxymethoxy)-2-[3-(3-oxobut-1-en-1-yl)phenyl]phenylacetate (120 mg, 0.29 mmol) obtained in the step 2 in Example 2 was dissolved in toluene (4.0 mL), and tris(triphenylphosphine)rhodium(I) chloride (20 mg, 0.22 mmol) and triethylsilane (0.13 mL, 0.81 mmol) were added thereto and stirred with heating for 1 hour. The reaction mixture was cooled to room temperature, and then filtered through Celite, and the filtrate was concentrated under reduced pressure. The resulting residue was purified through silica gel column chromatography (ethyl acetate/n-hexane=1/4 to 1/2) to obtain methyl 2-[3-(2-acetylethyl)phenyl]-3,5-bis(methoxymethoxy)phenylacetate (70 mg, 53%).

$^1$H-NMR (270 MHz, CDCl$_3$) δ (ppm): 2.68 (m, 2H), 2.83 (m, 2H), 3.20 (s, 3H), 3.29 (s, 2H), 3.42 (s, 3H), 3.50 (s, 3H), 4.91 (s, 2H), 5.10 (s, 2H), 6.63 (d, J=2.5 Hz, 1H), 6.75 (d, J=2.5 Hz, 1H), 6.93-6.96 (m, 2H), 7.05 (m, 1H), 7.21 (m, 1H);

APCI-MS (m/z): 434 (M+NH$_4$)$^+$.

(Step 2)

In the same manner as in the step 4 in Example 1, Compound 5 (48 mg, 98%) was obtained from methyl 2-[3-(2-acetylethyl)phenyl]-3,5-bis(methoxymethoxy)phenylacetate (62 mg, 0.15 mmol) obtained in the above, using methanol (1.0 mL) and 1,4-dioxane solution (1.0 mL) of 4 mol/L hydrogen chloride.

$^1$H-NMR (270 MHz, CDCl$_3$) δ (ppm): 2.15 (s, 3H), 2.80 (t, J=7.3 Hz, 2H), 2.89 (t, J=7.3 Hz, 2H), 3.35 (s, 2H), 3.57 (s, 3H), 5.29 (br s, 1H), 6.39 (d, J=2.6 Hz, 1H), 6.41 (d, J=2.6 Hz, 1H), 6.66 (br s, 1H), 7.08 (m, 2H), 7.21 (m. 1H), 7.35 (t, J=7.9 Hz, 1H);

APCI-MS (m/z): 329 (M+H)$^+$.

EXAMPLE 6

Methyl 3,5-dihydroxy-2-(2-methoxyphenyl)phenylacetate (Compound 6)

In the same manner as in the step 3 in Example 1, methyl 3,5-bis(methoxymethoxy)-2-(2-methoxyphenyl)phenylacetate was obtained from methyl 2-bromo-3,5-bis(methoxymethoxy)phenylacetate (88 mg, 0.25 mmol) obtained in the step 2 in Example 1, using 2-methoxyphenylboronic acid (57 mg, 0.38 mmol), tetrakis(triphenylphosphine)palladium(II) (15 mg, 0.013 mmol), aqueous 2 mol/L sodium carbonate solution (0.4 mL) and 1,2-dimethoxyethane (3.0 mL). Then, in the same manner as in the step 4 in Example 1, Compound 6 (51 mg, 71%) was obtained from the resulting compound, using methanol (2.0 mL) and 1,4-dioxane solution (1.0 mL) of 4 mol/L hydrogen chloride.

$^1$H-NMR (270 MHz, CDCl$_3$) δ (ppm): 3.31 (d, J=15.1 Hz, 1H), 3.32 (d, J=15.1 Hz, 1H), 3.54 (s, 3H), 3.73 (s, 3H), 5.13 (br s, 1H), 6.15 (br s, 1H), 6.38 (d, J=2.5 Hz, 1H), 6.44 (d, J=2.5 Hz, 1H), 6.98-7.06 (m, 2H), 7.15 (dd, J=7.4, 1.8 Hz, 1H), 7.38 (td, J=7.4, 1.8 Hz, 1H);

FAB-MS (m/z): 288 (M+H)$^+$.

EXAMPLE 7

Methyl 2-(2-chlorophenyl)-3,5-dihydroxyphenylacetate (Compound 7)

In the same manner as in the step 3 in Example 1, methyl 2-(2-chlorophenyl)-3,5-bis(methoxymethoxy)phenylacetate was obtained from methyl 2-bromo-3,5-bis(methoxymethoxy)phenylacetate (89 mg, 0.25 mmol) obtained in the step 2 in Example 1, using 2-chlorophenylboronic acid (59 mg, 0.38 mmol), tetrakis(triphenylphosphine)palladium(II) (15 mg, 0.013 mmol), aqueous 2 mol/L sodium carbonate solution (0.4 mL) and 1,2-dimethoxyethane (3 mL). Then, in the same manner as in the step 4 in Example 1, Compound 7 (23 mg, 32%) was obtained from the resulting compound, using methanol (2 mL) and 1,4-dioxane solution (1.0 mL) of 4 mol/L hydrogen chloride.

$^1$H-NMR (270 MHz, CDCl$_3$) δ (ppm): 3.20 (d, J=15.1 Hz, 1H), 3.27 (d, J=15.1 Hz, 1H), 3.49 (s, 3H), 6.31 (d, J=2.4 Hz, 1H), 6.31 (d, J=2.4 Hz, 1H), 7.15 (m, 1H), 7.27-7.35 (m, 2H), 7.43 (m, 1H);

FAB-MS (m/z): 292 (M+H)$^+$.

EXAMPLE 8

Methyl 2-(3-acetylphenyl)-3,5-dihydroxyphenylacetate (Compound 8)

In the same manner as in the step 3 in Example 1, methyl 2-(3-acetylphenyl)-3,5-bis(methoxymethoxy)phenylacetate was obtained from methyl 2-bromo-3,5-bis(methoxymethoxy)phenylacetate (75 mg, 0.22 mmol) obtained in the step 2 in Example 1, using 3-acetylphenylboronic acid (52 mg, 0.32 mol), tetrakis(triphenylphosphine)palladium(II) (15 mg, 0.013 mmol), aqueous 2 mol/L fluorocesium carbonate solution (0.4 mL) and 1,2-dimethoxyethane (3.0 mL). Then, in the same manner as in the step 4 in Example 1, Compound 8 (60 mg, 90%) was obtained from the resulting compound, using methanol (2.0 mL) and 1,4-dioxane solution (1.0 mL) of 4 mol/L hydrogen chloride.

$^1$H-NMR (270 MHz, CDCl$_3$) δ (ppm): 2.55 (s, 3H), 3.30 (s, 2H), 3.54 (s, 3H), 6.21 (br s, 1H), 6.35 (d, J=2.3 Hz, 1H), 6.39 (d, J=2.3 Hz, 1H), 7.13 (br s, 1H), 7.44 (dt, J=7.3 Hz, 1.7 Hz, 1H), 7.49 (t, J=7.3 Hz, 1H), 7.83 (m, 1H), 7.90 (dt, J=7.3, 1.7 Hz, 1H);

APCI-MS (m/z): 301 (M+H)$^+$.

EXAMPLE 9

2-(2-Bromo-3,5-dihydroxy-6-phenylphenyl)-N-[2-(dimethylamino)ethyl]acetamide (Compound 9)

(Step 1)

Methyl 3,5-bis(methoxymethoxy)-2-phenylphenylacetate (10 g, 29 mmol) obtained in the step 3 in Example 1 was dissolved in N,N-dimethylformamide (150 mL), and N-bromosuccinimide (5.7 g, 32 mmol) was added thereto and stirred at room temperature for 2 hours. The reaction mixture was concentrated under reduced pressure, and the resulting residue was purified through silica gel column chromatography (ethyl acetate/n-hexane=1/9 to 1/4) to obtain methyl 2-bromo-3,5-bis(methoxymethoxy)-6-phenylphenylacetate (13 g, 99%).

$^1$H-NMR (270 MHz, CDCl$_3$) δ (ppm): 2.21 (s, 3H), 2.67 (s, 3H), 3.55 (s, 2H), 4.99 (s, 2H), 3.63 (s, 3H), 5.27 (s, 2H), 7.03 (s, 1H), 7.11-7.14 (m, 2H), 7.33-7.43 (m, 3H).

(Step 2)

Methyl 2-bromo-3,5-bis(methoxymethoxy)-6-phenylphenylacetate (5.6 g, 13 mmol) obtained in the above was dissolved in methanol (60 mL), and aqueous 2 mol/L sodium hydroxide solution (30 mL) was added thereto and stirred with heating for 4 hours. Methanol was evaporated away under reduced pressure from the reaction solution, and 2 mol/L hydrochloric acid was added thereto to render the reaction solution acidic, and the reaction solution was then extracted three times with ethyl acetate. The organic layers were combined, washed with aqueous saturated sodium chloride solution, and dried over anhydrous magnesium sulfate, and the solvent was evaporated away under reduced pressure. The resulting residue was triturated with n-hexane to obtain 2-bromo-3,5-bis(methoxymethoxy)-6-phenylphenylacetic acid (5.0 g, 92%).

$^1$H-NMR (270 MHz, DMSO-d$_6$) δ (ppm): 3.14 (s, 3H), 3.40 (s, 2H), 3.44 (s, 3H), 5.04 (s, 2H), 5.31 (s, 2H), 7.00 (s, 1H), 7.11-7.14 (m, 2H), 7.33-7.43 (m, 3H).

(Step 3)
2-Bromo-3,5-bis(methoxymethoxy)-6-phenylphenylacetic acid (20 mg, 0.050 mmol) obtained in the above was dissolved in N,N-dimethylformamide (0.25 mL), and N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L N,N-dimethylethylenediamine (0.75 mL, 0.075 mmol) were added thereto in order, and stirred at room temperature for 8 hours. The reaction solution was concentrated under reduced pressure, and subjected to liquid-liquid separation with chloroform (0.4 mL) and aqueous saturated sodium hydrogencarbonate solution was added thereto. The organic layer was washed with aqueous saturated sodium chloride solution, and washed over anhydrous magnesium sulfate, and the solvent was evaporated away under reduced pressure. To the resulting residue, added were chloroform (0.5 mL), poly(4-vinylpyridine) (PVP) and polystyrenecarbonyl chloride (PS—COCl), and the mixture was stirred at room temperature for 8 hours. The reaction solution was filtered, and the filtrate was concentrated under reduced pressure to obtain 2-[2-bromo-3,5-bis(methoxymethoxy)-6-phenylphenyl]-N-[2-(dimethylamino)ethyl]acetamide. Then, in the same manner as in the step 4 in Example 1, Compound 9 (14 mg, 70%) was obtained from the resulting compound, using methanol (0.3 mL) and 1,4-dioxane solution (0.3 mL) of 4 mol/L hydrogen chloride.
APCI-MS (m/z): 393, 395 (M+H)$^+$.

EXAMPLE 10

Methyl 2-bromo-3,5-dihydroxy-6-phenylphenylacetate (Compound 10)

In the same manner as in the step 4 in Example 1, Compound 10 (92 mg, 71%) was obtained from methyl 2-bromo-3,5-bis(methoxymethoxy)-6-phenylphenylacetate (110 mg, 0.26 mmol) obtained in the step 1 in Example 9, using methanol (2.0 mL) and 1,4-dioxane solution (1.0 mL) of 4 mol/L hydrogen chloride.
$^1$H-NMR (270 MHz, CDCl$_3$) δ (ppm): 3.56 (s, 2H), 3.64 (s, 3H), 5.01 (s, 1H), 5.94 (s, 1H), 6.61 (s, 1H), 7.22-7.25 (m, 2H), 7.40-7.46 (m, 3H);
APCI-MS (m/z): 334, 336 (M−H)$^-$.

EXAMPLE 11

Methyl 3,5-dihydroxy-2,6-diphenylphenylacetate (Compound 11)

In the same manner as in the step 3 in Example 1, methyl 3,5-bis(methoxymethoxy)-2,6-diphenylphenylacetate was obtained from methyl 2-bromo-3,5-bis(methoxymethoxy)-6-phenylphenylacetate (130 mg, 0.30 mmol) obtained in the step 1 in Example 9, using phenylboronic acid (54 mg, 0.44 mmol), bis(tri-o-tolylphosphine)palladium(II) dichloride (10 mg, 0.017 mmol), cesium carbonate (300 mg, 0.92 mmol), 1,2-dimethoxyethane (3.0 mL) and water (0.5 mL). Then, in the same manner as in the step 4 in Example 1, Compound 11 (75 mg, 74%) was obtained from the resulting compound, using methanol (2.0 mL) and 1,4-dioxane solution (1.0 mL) of 4 mol/L hydrogen chloride.
$^1$H-NMR (270 MHz, CDCl$_3$) δ (ppm): 3.18 (s, 2H), 3.40 (s, 3H), 6.61 (s, 1H), 7.26-7.31 (m, 4H), 7.36-7.49 (m, 6H);
FAB-MS (m/z): 334 (M+H)$^+$.

EXAMPLE 12

2-Bromo-3,5-dihydroxy-6-phenylphenylacetic acid (Compound 12)

In the same manner as in the step 4 in Example 1, Compound 12 (86 mg, 95%) was obtained from 2-bromo-3,5-bis(methoxymethoxy)-6-phenylphenylacetic acid (120 mg, 0.28 mmol) obtained in the step 2 in Example 9, using methanol (2.0 mL) and 1,4-dioxane solution (1.0 mL) of 4 mol/L hydrogen chloride.
$^1$H-NMR (270 MHz, CD$_3$OD) δ (ppm): 3.38 (s, 2H), 6.37 (s, 1H), 7.08 (m, 2H), 7.17-7.24 (m, 3H);
APCI-MS (m/z): 322, 324 (M+H)$^+$.

EXAMPLE 13

Methyl 3,5-dihydroxy-2-iodo-6-phenylphenylacetate (Compound 13)

(Step 1)
Methyl 3,5-bis(methoxymethoxy)-2-phenylphenylacetate (0.23 g, 0.67 mmol) obtained in the step 3 in Example 1 was dissolved in chloroform (10 mL), and the solution was cooled to −10° C., and then iodine (0.17 g, 0.67 mmol) and [bis(trifluoroacetoxy)iodo]benzene (0.29 g, 0.68 mmol) were added thereto and stirred for 8 hours with heating up to room temperature. The reaction solution was concentrated under reduced pressure, and the resulting residue was purified through silica gel column chromatography (n-hexane to n-hexane/ethyl acetate=1/2) to obtain methyl 2-iodo-3,5-bis(methoxymethoxy)-6-phenylphenylacetate (0.25 g, 80%).
$^1$H-NMR (270 MHz, CDCl$_3$) δ (ppm): 3.27 (s, 3H), 3.56 (s, 3H), 3.64 (s, 3H), 3.69 (s, 2H), 5.00 (s, 2H), 5.27 (s, 2H), 6.96 (s, 1H), 7.14-7.40 (m, 5H);
APCI-MS (m/z): 473 (M+H)$^+$.

(Step 2)
In the same manner as in the step 4 in Example 1, Compound 13 (66 mg, 68%) was obtained from methyl 2-iodo-3,5-bis(methoxymethoxy)-6-phenylphenylacetate (0.12 g, 0.25 mmol) obtained in the above, using methanol (3.0 mL) and 1,4-dioxane solution (3.0 mL) of 4 mol/L hydrogen chloride.
$^1$H-NMR (270 MHz, CDCl$_3$) δ (ppm): 3.62 (s, 2H), 3.65 (s, 3H), 4.76 (s, 1H), 5.50 (s, 1H), 6.68 (s, 1H), 7.23-7.26 (m, 2H), 7.43-7.52 (m, 3H);
APCI-MS (m/z): 383 (M−H)$^-$.
Elementary Analysis (as $C_{15}H_{13}IO_4 \cdot 0.1H_2O$):
Measured (%): C:46.68, H:3.38, N:0
Calculated (%): C:46.68, H:3.45, N:0

EXAMPLE 14

Methyl 3,5-dihydroxy-2-(morpholinomethyl)-6-phenylphenylacetate (Compound 14)

Compound 1 (0.19 g, 0.74 mmol) obtained in Example 1 was dissolved in 2-propanol (3.0 mL), and morpholine (0.065 mL, 0.75 mmol) and aqueous 37% formalin solution (0.063 mL, 0.78 mmol) were added thereto and stirred at room temperature for 4 hours. The reaction solution was concentrated under reduced pressure, and then purified through preparative thin-layer chromatography (methanol/chloroform=1/9) to obtain Compound 14 (0.091 g, 35%) as a colorless oily substance.

$^1$H-NMR (270 MHz, CDCl$_3$) δ (ppm): 2.64 (br s, 4H), 3.32 (s, 2H), 3.57 (s, 3H), 3.77 (br s, 4H), 3.83 (s, 2H), 6.40 (s, 1H), 7.24-7.27 (m, 2H), 7.40-7.50 (m, 3H); APCI-MS (m/z): 358 (M+H)$^+$.

EXAMPLE 15

5-(Hydroxymethyl)-6-bromo-4-phenylbenzene-1,3-diol (Compound 15)

(Step 1)

In the same manner as in the step 3 in Example 1, [3,5-bis(methoxymethoxy)-2-phenylphenyl]methanol (724 mg, 67 was obtained from [2-bromo-3,5-bis(methoxymethoxy)phenyl]methanol (1.09 g, 3.53 mmol) obtained according to the method described in Tetrahedron, Vol. 59, pp. 7345-7355 (2003) or methods similar thereto, using phenylboronic acid (652 mg, 5.34 mmol), cesium carbonate (3.46 g, 10.6 mmol) and bis(tri-o-tolylphosphine)palladium(II) dichloride (129 mg, 0.164 mmol).

$^1$H-NMR (270 MHz, CDCl$_3$) δ (ppm): 1.55-1.65 (m, 1H), 3.28 (s, 3H), 3.51 (s, 3H), 4.39 (d, J=5.9 Hz, 2H), 5.00 (s, 2H), 5.21 (s, 2H), 6.83 (d, J=2.3 Hz, 1H), 6.94 (d, J=2.6 Hz, 1H), 7.18-7.26 (m, 2H), 7.28-7.45 (m, 3H).

(Step 2)

[3,5-Bis(methoxymethoxy)-2-phenylphenyl]methanol (384 mg, 1.26 mmol) obtained in the above was dissolved in N,N-dimethylformamide (10 mL), and N-bromosuccinimide (268 mg, 1.51 mmol) was added thereto and stirred at room temperature for 5 hours. Water was added to the reaction mixture, and extracted with chloroform. The organic layer was washed with aqueous saturated sodium chloride solution, and dried over anhydrous sodium sulfate, and the solvent was evaporated away under reduced pressure. The residue was purified through silica gel column chromatography (n-hexane/ethyl acetate=4/1 to 3/1) to obtain [2-bromo-3,5-bis(methoxymethoxy)-6-phenylphenyl]methanol (421 mg, 87%).

$^1$H-NMR (270 MHz, CDCl$_3$) δ (ppm): 2.11 (t, J=6.9 Hz, 1H), 3.27 (s, 3H), 3.56 (s, 3H), 4.52 (d, J=6.9 Hz, 2H), 5.00 (s, 2H), 5.28 (s, 2H), 7.03 (s, 1H), 7.20-7.46 (m, 5H).

(Step 3)

[2-Bromo-3,5-bis(methoxymethoxy)-6-phenylphenyl]methanol (63.3 mg, 0.165 mmol) obtained in the above was dissolved in methanol (10 mL), and D,L-camphorsulfonic acid (279 mg, 1.20 mmol) was added thereto and stirred under heat for 2.5 hours. The reaction solution was concentrated under reduced pressure, and the resulting residue was purified through preparative thin-layer chromatography (chloroform/methanol=20/1) to obtain Compound 15 (46.6 mg, 96%).

$^1$H-NMR (270 MHz, CDCl$_3$) δ (ppm): 1.81 (br t, J=4.9 Hz, 1H), 4.48 (d, J=4.9 Hz, 2H), 4.87 (s, 1H), 5.69 (s, 1H), 6.71 (s, 1H), 7.30-7.38 (m, 2H), 7.40-7.58 (m, 3H);
ESI-MS (m/z): 296 (M+H)$^+$.

EXAMPLE 16

N-[2-(acetylamino)ethyl]-2-(2-bromo-3,5-dihydroxy-6-phenylphenyl)acetamide (Compound 16)

In the same manner as in the step 3 in Example 9, N-[2-(acetylamino)ethyl]-2-[3,5-bis(methoxymethoxy)-2-bromo-6-phenylphenyl]acetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L N-acetylethylenediamine (0.75 mL, 0.075 mmol) and N,N-dimethylformamide (0.25 mL); and the resulting compound was treated with 1,4-dioxane solution (0.3 mL) of 4 mol/L hydrogen chloride and methanol (0.3 mL) to obtain Compound 16 (14 mg, 70%).
APCI-MS (m/z): 407, 409 (M+H)$^+$.

EXAMPLE 17

2-(2-Bromo-3,5-dihydroxy-6-phenylphenyl)-N-(pyridin-3-ylmethyl)acetamide (Compound 17)

In the same manner as in the step 3 in Example 9, 2-[2-bromo-3,5-bis(methoxymethoxy)-6-phenylphenyl]-N-(pyridin-3-ylmethyl)acetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L 3-picolylamine (0.75 mL, 0.075 mmol) and N,N-dimethylformamide (0.25 mL); and the resulting compound was treated with 1,4-dioxane solution (0.3 mL) of 4 mol/L hydrogen chloride and methanol (0.3 mL) to obtain Compound 17 (14 mg, 70%).
APCI-MS (m/z): 413, 415 (M+H)$^+$.

EXAMPLE 18

N-(1-benzylpiperidin-4-yl)-2-(2-bromo-3,5-dihydroxy-6-phenylphenyl)acetamide (Compound 18)

In the same manner as in the step 3 in Example 9, N-(1-benzylpiperidin-4-yl)-2-[2-bromo-3,5-bis(methoxymethoxy)-6-phenylphenyl]acetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L 4-amino-1-benzylpiperidine (0.75 mL, 0.075 mmol) and N,N-dimethylformamide (0.25 mL); and the resulting compound was treated with 1,4-dioxane solution (0.3 mL) of 4 mol/L hydrogen chloride and methanol (0.3 mL) to obtain Compound 18 (17 mg, 70%).
APCI-MS (m/z): 495, 497 (M+H)$^+$.

EXAMPLE 19

2-(2-Bromo-3,5-dihydroxy-6-phenylphenyl)-N-cyclohexylacetamide (Compound 19)

In the same manner as in the step 3 in Example 9, 2-[2-bromo-3,5-bis(methoxymethoxy)-6-phenylphenyl]-N-cyclohexylacetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L cyclohexylamine (0.75 mL, 0.075 mmol) and N,N-dimethylformamide (0.25 mL); and the resulting compound was treated with 1,4-dioxane solution (0.3 mL) of 4 mol/L hydrogen chloride and methanol (0.3 mL) to obtain Compound 19 (15 mg, 70%).

APCI-MS (m/z): 404, 406 (M+H)$^+$.

EXAMPLE 20

2-(2-Bromo-3,5-dihydroxy-6-phenylphenyl)-N-(2-methylpropyl)acetamide (Compound 20)

In the same manner as in the step 3 in Example 9, 2-[2-bromo-3,5-bis(methoxymethoxy)-6-phenylphenyl]-N-(2-methylpropyl)acetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L isobutylamine (0.75 mL, 0.075 mmol) and N,N-dimethylformamide (0.25 mL); and the resulting compound was treated with 1,4-dioxane solution (0.3 mL) of 4 mol/L hydrogen chloride and methanol (0.3 mL) to obtain Compound 20 (13 mg, 70%).

APCI-MS (m/z): 378, 379 (M+H)$^+$.

EXAMPLE 21

2-(2-Bromo-3,5-dihydroxy-6-phenylphenyl)-N-propylacetamide (Compound 21)

In the same manner as in the step 3 in Example 9, 2-[2-bromo-3,5-bis(methoxymethoxy)-6-phenylphenyl]-N-propylacetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L propylamine (0.75 mL, 0.075 mmol) and N,N-dimethylformamide (0.25 mL); and the resulting compound was treated with 1,4-dioxane solution (0.3 mL) of 4 mol/L hydrogen chloride and methanol (0.3 mL) to obtain Compound 21 (13 mg, 70%).

APCI-MS (m/z): 364, 366 (M+H)$^+$.

EXAMPLE 22

2-(2-Bromo-3,5-dihydroxy-6-phenylphenyl)-N-[3-(2-oxopyrrolidin-1-yl)propyl]acetamide (Compound 22)

In the same manner as in the step 3 in Example 9, 2-[2-bromo-3,5-bis(methoxymethoxy)-6-phenylphenyl]-N-[3-(2-oxopyrrolidin-1-yl)propyl]acetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L 1-(3-aminopropyl)-2-pyrrolidone (0.75 mL, 0.075 mmol) and N,N-dimethylformamide (0.25 mL); and the resulting compound was treated with 1,4-dioxane solution (0.3 mL) of 4 mol/L hydrogen chloride and methanol (0.3 mL) to obtain Compound 22 (35 mg, 70%).

APCI-MS (m/z): 447 449 (M+H)$^+$.

EXAMPLE 23

2-(2-Bromo-3,5-dihydroxy-6-phenylphenyl)-N-(2-methoxyethyl)acetamide (Compound 23)

In the same manner as in the step 3 in Example 9, 2-[2-bromo-3,5-bis(methoxymethoxy)-6-phenylphenyl]-N-(2-methoxyethyl)acetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L 2-methoxyethylamine (0.75 mL, 0.075 mmol) and N,N-dimethylformamide (0.25 mL); and the resulting compound was treated with 1,4-dioxane solution (0.3 mL) of 4 mol/L hydrogen chloride and methanol (0.3 mL) to obtain Compound 23 (13 mg, 70%).

APCI-MS (m/z): 380/382 (M+H)$^+$.

EXAMPLE 24

N-benzyl-2-(2-bromo-3,5-dihydroxy-6-phenylphenyl)acetamide (Compound 24)

In the same manner as in the step 3 in Example 9, N-benzyl-2-[2-bromo-3,5-bis(methoxymethoxy)-6-phenylphenyl]acetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L benzylamine (0.75 mL, 0.075 mmol) and N,N-dimethylformamide (0.25 mL); and the resulting compound was treated with 1,4-dioxane solution (0.3 mL) of 4 mol/L hydrogen chloride and methanol (0.3 mL) to obtain Compound 24 (15 mg, 70%).

APCI-MS (m/z): 412, 414 (M+H)$^+$.

EXAMPLE 25

5-(Benzyloxymethyl)-6-bromo-4-phenylbenzene-1,3-diol (Compound 25)

(Step 1)

[2-Bromo-3,5-bis(methoxymethoxy)-6-phenylphenyl]methanol (121 mg, 0.317 mmol) obtained in the step 2 in Example 15 was dissolved in N,N-dimethylformamide (6 mL), and 60% sodium hydride/mineral oil dispersion (39.5 mg, 0.988 mmol) and benzyl bromide (0.200 mL, 1.68 mmol) were added thereto and stirred at room temperature for 2 hours. Water and methanol were added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer chromatography (n-hexane/ethyl acetate=2/1) to obtain 3-(benzyloxymethyl)-4-bromo-1,5-bis(methoxymethoxy)-2-phenylbenzene (138 mg, 92%).

$^1$H-NMR (270 MHz, CDCl$_3$) δ (ppm): 3.26 (s, 3H), 3.55 (s, 3H), 4.33 (s, 2H), 4.41 (s, 2H), 4.97 (s, 2H), 5.27 (s, 2H), 7.03 (s, 1H), 7.20-7.40 (m, 10H).

(Step 2)

3-(Benzyloxymethyl)-4-bromo-1,5-bis(methoxymethoxy)-2-phenylbenzene (133 mg, 0.280 mmol) obtained in the above was dissolved in methanol (8 mL), and concentrated hydrochloric acid (0.2 mL) was added thereto and stirred at 60° C. for 1.2 hours. The reaction solution was concentrated under reduced pressure, and the resulting residue was purified through preparative thin-layer chromatography (chloroform/methanol=20/1) to obtain Compound 25 (102 mg, 94%).

$^1$H-NMR (270 MHz, CDCl$_3$) δ (ppm): 4.27 (s, 2H), 4.40 (s, 2H), 4.86 (br s, 1H), 5.74 (s, 1H), 6.69 (s, 1H), 7.20-7.36 (m, 7H), 7.40-7.52 (m, 3H);

FAB-MS (m/z): 385, 387 (M+H)$^+$.

EXAMPLE 26

6-Bromo-5-(methoxymethoxy)-4-phenylbenzene-1,3-diol (Compound 26)

(Step 1)

In the same manner as in the step 1 in Example 25, 4-bromo-1,5-bis(methoxymethoxy)-3-(methoxymethyl)-2-phenylbenzene (108 mg, 100%) was obtained from [2-bromo-3,5-bis(methoxymethoxy)-6-phenylphenyl]methanol (104 mg, 0.271 mmol) obtained in the step 2 in Example 15, using 60% sodium hydride/mineral oil dispersion (53.0 mg, 1.33 mmol) and methyl iodide (0.200 mL, 3.21 mmol).

$^1$H-NMR (270 MHz, CDCl$_3$) δ (ppm): 3.24 (s, 3H), 3.27 (s, 3H), 3.55 (s, 3H), 4.23 (s, 2H), 4.98 (s, 2H), 5.27 (s, 2H), 7.04 (s, 1H), 7.22-7.45 (m, 5H).

(Step 2)

In the same manner as in the step 2 in Example 25, Compound 26 (70.3 mg, 88%) was obtained from 4-bromo-1,5-bis(methoxymethoxy)-3-(methoxymethyl)-2-phenylbenzene (103 mg, 0.258 mmol) obtained in the above, using ethanol (8 mL) and concentrated hydrochloric acid (0.2 mL).

$^1$H-NMR (270 MHz, CDCl$_3$) δ (ppm): 3.24 (s, 3H), 4.18 (s, 2H), 4.87 (br s, 1H), 5.74 (br s, 1H), 6.70 (s, 1H), 7.28-7.36 (m, 2H), 7.40-7.55 (m, 3H);

FAB-MS (m/z): 309, 311 (M+H)$^+$.

EXAMPLE 27

5-(Allyloxymethyl)-6-bromo-4-phenylbenzene-1,3-diol (Compound 27)

(Step 1)

In the same manner as in the step 1 in Example 25, 3-(allyloxymethyl)-4-bromo-1,5-bis(methoxymethoxy)-2-phenylbenzene (87.9 mg, 84%) was obtained from [2-bromo-3,5-bis(methoxymethoxy)-6-phenylphenyl]methanol (94.6 mg, 0.247 mmol) obtained in the step 2 in Example 15, using 60% sodium hydride/mineral oil dispersion (34.8 mg, 0.870 mmol) and allyl bromide (0.100 mL, 1.18 mmol).

$^1$H-NMR (270 MHz, CDCl$_3$) δ (ppm): 3.26 (s, 3H), 3.55 (s, 3H), 3.87 (ddd, J=1.3, 1.3, 5.9 Hz, 2H), 4.28 (s, 2H), 4.97 (s, 2H), 5.09 (ddt, J=1.6, 10.2, 1.6 Hz, 1H), 5.17 (ddt, J=1.6, 17.3, 1.6 Hz, 1H), 5.27 (s, 2H), 5.83 (ddt, J=10.2, 17.3, 5.9 Hz, 1H), 7.03 (s, 1H), 7.22-7.42 (m, 5H).

(Step 2)

In the same manner as in the step 2 in Example 25, Compound 27 (63.2 mg, 93%) was obtained from 3-(allyloxymethyl)-4-bromo-1,5-bis(methoxymethoxy)-2-phenylbenzene (85.3 mg, 0.202 mmol) obtained in the above, using ethanol (8 mL) and concentrated hydrochloric acid (0.2 mL).

$^1$H-NMR (270 MHz, CDCl$_3$) δ (ppm): 3.86 (ddd, J=1.3, 1.3, 1.6 Hz, 2H), 4.23 (s, 2H), 4.84 (s, 1H), 5.10 (ddt, J=1.6, 10.6, 1.6 Hz, 1H), 5.17 (ddt, J=1.6, 17.3, 1.6 Hz, 1H), 5.73 (s, 1H), 5.81 (ddt, J=10.6, 17.3, 5.6 Hz, 1H), 7.30-7.37 (m, 2H), 7.40-7.54 (m, 3H); FAB-MS (m/z): 335, 337 (M+H)$^+$.

EXAMPLE 28

2-(2-Bromo-3,5-dihydroxy-6-phenylphenyl)-N-(2,4-dimethoxybenzyl)acetamide (Compound 28)

In the same manner as in the step 3 in Example 9, 2-[2-bromo-3,5-bis(methoxymethoxy)-6-phenylphenyl]-N-(2,4-dimethoxybenzyl)acetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L 2,4-dimethoxybenzylamine (0.75 mL, 0.075 mmol), and N,N-dimethylformamide (0.25 mL); and the resulting compound was treated with 1,4-dioxane solution (0.3 ml) of 4 mol/L hydrogen chloride and methanol (0.3 mL) to obtain Compound 28 (17 mg, 70%).

APCI-MS (m/z): 472, 474 (M+H)$^+$.

EXAMPLE 29

N-benzyl-2-(2-bromo-3,5-dihydroxy-6-phenylphenyl)-N-methylacetamide (Compound 29)

In the same manner as in the step 3 in Example 9, N-benzyl-2-[2-bromo-3,5-bis(methoxymethoxy)-6-phenylphenyl]-N-methylacetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L N-methylbenzylamine (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 29 (15 mg, 70%).

APCI-MS (m/z): 426, 428 (M+H)$^+$.

EXAMPLE 30

1-(4-Benzylpiperidino)-2-(2-bromo-3,5-dihydroxy-6-phenylphenyl)ethanone (Compound 30)

In the same manner as in the step 3 in Example 9, 1-(4-benzylpiperidino)-2-[2-bromo-3,5-bis(methoxymethoxy)-6-phenylphenyl]ethanone was obtained from 2-bromo-3,5-bis (methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino) propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), chloroform solution of 0.5 mol/L benzotriazole hydrate (0.15 mL, 0.075 mmol), N,N-dimethylformamide solution of 1 mol/L 4-benzylpiperidine (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 30 (17 mg, 70%).

APCI-MS (m/z): 480, 482 (M+H)$^+$.

EXAMPLE 31

1-(4-Acetylpiperazin-1-yl)-2-(2-bromo-3,5-dihydroxy-6-phenylphenyl)ethanone (Compound 31)

In the same manner as in the step 3 in Example 9, 1-(4-acetylpiperazin-1-yl)-2-[2-bromo-3,5-bis(methoxymethoxy)-6-phenylphenyl]ethanone was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L N-acetylpiperazine (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 31 (15 mg, 70%).

APCI-MS (m/z): 432, 434 (M−H)$^-$.

EXAMPLE 32

2-(2-Bromo-3,5-dihydroxy-6-phenylphenyl)-1-(4-methylpiperazin-1-yl)ethanone (Compound 32)

In the same manner as in the step 3 in Example 9, 2-[2-bromo-3,5-bis(methoxymethoxy)-6-phenylphenyl]-1-(4-methylpiperazin-1-yl)ethanone was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L N-methylpiperazine (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 32 (14 mg, 70%).

APCI-MS (m/z): 405, 407 (M+H)$^+$.

EXAMPLE 33

2-(2-Bromo-3,5-dihydroxy-6-phenylphenyl)-1-piperidinoethanone (Compound 33)

In the same manner as in the step 3 in Example 9, 2-[2-bromo-3,5-bis(methoxymethoxy)-6-phenylphenyl]-1-piperidinoethanone was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L piperidine (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 33 (14 mg, 70%).

APCI-MS (m/z): 390, 392 (M+H)$^+$.

EXAMPLE 34

2-(2-Bromo-3,5-dihydroxy-6-phenylphenyl)-[(1,2,3,4-tetrahydroisoquinolin-2-yl)ethanone (Compound 34)

In the same manner as in the step 3 in Example 9, 2-[2-bromo-3,5-bis(methoxymethoxy)-6-phenylphenyl]-1-(1,2,3,4-tetrahydroisoquinolin-2-yl)ethanone was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L 1,2,3,4-tetrahydroisoquinoline (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 34 (15 mg, 70%).

APCI-MS (m/z): 438, 440 (M+H)$^+$.

EXAMPLE 35

2-(2-Bromo-3,5-dihydroxy-6-phenylphenyl)-1-morpholinoethanone (Compound 35)

In the same manner as in the step 3 in Example 9, 2-[2-bromo-3,5-bis(methoxymethoxy)-6-phenylphenyl]-1-morpholinoethanone was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L morpholine (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 35 (14 mg, 70%).

APCI-MS (m/z): 392, 394 (M+H)$^+$.

EXAMPLE 36

2-(2-Bromo-3,5-dihydroxy-6-phenylphenyl)-N-methyl-N-propylacetamide (Compound 36)

In the same manner as in the step 3 in Example 9, 2-[2-bromo-3,5-bis(methoxymethoxy)-6-phenylphenyl]-N-methyl-N-propylacetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino) propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L N-methylpropylamine (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 36 (13 mg, 70%).

APCI-MS (m/z): 378, 380 (M+H)$^+$.

EXAMPLE 37

2-(2-Bromo-3,5-dihydroxy-6-phenylphenyl)-N-(2-methoxyethyl)-N-methylacetamide (Compound 37)

In the same manner as in the step 3 in Example 9, 2-[2-bromo-3,5-bis(methoxymethoxy)-6-phenylphenyl]-N-(2-methoxyethyl)-N-methylacetamide was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L N-(2-methoxyethyl)methylamine (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 37 (14 mg, 70%).

APCI-MS (m/z): 394, 396 (M+H)$^+$.

EXAMPLE 38

2-(2-Bromo-3,5-dihydroxy-6-phenylphenyl)-1-[4-(2-cyanophenyl)piperazin-1-yl]ethanone (Compound 38)

In the same manner as in the step 3 in Example 9, 2-[2-bromo-3,5-bis(methoxymethoxy)-6-phenylphenyl]-1-[4-(2-cyanophenyl)piperazin-1-yl]ethanone was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L 1-(2-cyanophenyl)piperazine (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 38 (17 mg, 70%).

APCI-MS (m/z): 493, 495 (M+H)$^+$.

EXAMPLE 39

2-(2-Bromo-3,5-dihydroxy-6-phenylphenyl)-1-[4-(pyridin-3-ylmethyl)piperazin-1-yl]ethanone (Compound 39)

In the same manner as in the step 3 in Example 9, 2-[2-bromo-3,5-bis(methoxymethoxy)-6-phenylphenyl]-1-[4-(pyridin-3-ylmethyl)piperazin-1-yl]ethanone was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L 1-(3-pyridylmethyl)piperazine (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 39 (17 mg, 70%).

APCI-MS (m/z): 482, 484 (M+H)$^+$.

EXAMPLE 40

2-(2-Bromo-3,5-dihydroxy-6-phenylphenyl)-1-(4-benzylpiperazin-1-yl)ethanone (Compound 40)

In the same manner as in the step 3 in Example 9, 2-[2-bromo-3,5-bis(methoxymethoxy)-6-phenylphenyl]-1-(4-benzylpiperazin-1-yl)ethanone was obtained from 2-bromo-3,5-bis(methoxymethoxy)-6-phenylphenylacetic acid (20 mg, 0.050 mmol) obtained in the step 2 in Example 9, using N,N-dimethylformamide solution of 0.5 mol/L 1-[3-(dimethylamino)propyl]-3-ethylcarbodiimide hydrochloride (0.15 mL, 0.075 mmol), chloroform solution of 0.5 mol/L 1-hydroxybenzotriazole hydrate (0.15 mL, 0.075 mmol), N,N-dimethylformamide solution of 1 mol/L 1-benzylpiperazine (0.75 mL, 0.075 mmol), and N,N-dimethylformamide (0.25 mL); and the resulting compound was treated with 1,4-dioxane solution (0.3 mL) of 4 mol/L hydrogen chloride and methanol (0.3 mL) to obtain Compound 40 (17 mg, 70%).

APCI-MS (m/z): 482, 484 (M+H)$^+$.

EXAMPLE 41

2-(2-Bromo-3,5-dihydroxy-6-phenylphenyl)acetamide (Compound 41)

In the same manner as in the step 3 in Example 9, 2-[2-bromo-3,5-bis(methoxymethoxy)-6-phenylphenyl]acetamide was obtained from 2-bromo-3,5-bis(methoxymethoxy)-6-phenylphenylacetic acid (110 mg, 0.26 mmol) obtained in the step 2 in Example 9, using 1-[3-(dimethylamino)propyl]-3-ethylcarbodiimide hydrochloride (75 mg, 0.38 mmol), 1-hydroxybenzotriazole hydrate (50 mg, 0.38 mmol), methanol solution of 7 mol/L ammonia (0.1 mL, 0.7 mmol), N,N-dimethylformamide (1.5 mL) and chloroform (1.5 mL); and the resulting compound was treated with 1,4-dioxane solution (1.5 mL) of 4 mol/L hydrogen chloride and methanol (1.5 mL) to obtain Compound 41 (80 mg, 97%).

$^1$H-NMR (270 MHz, DMSO-$d_6$) δ (ppm): 3.23 (s, 2H), 6.54 (s, 1H), 6.69 (br s, 1H), 7.02 (br s, 1H), 7.12-7.15 (m, 2H), 7.25-7.34 (m, 3H), 9.20 (br s, 1H), 9.92 (br s, 1H);

APCI-MS (m/z): 322, 324 (M+H)$^+$.

EXAMPLE 42

2-(2-Bromo-3,5-dihydroxy-6-phenylphenyl)-N-methylacetamide (Compound 42)

In the same manner as in the step 3 in Example 9, 2-[2-bromo-3,5-bis(methoxymethoxy)-6-phenylphenyl]-N-methylacetamide was obtained from 2-bromo-3,5-bis(methoxymethoxy)-6-phenylphenylacetic acid (110 mg, 0.26 mmol) obtained in the step 2 in Example 9, using 1-[3-(dimethylamino)propyl]-3-ethylcarbodiimide hydrochloride (75 mg, 0.38 mmol), 1-hydroxybenzotriazole hydrate (50 mg, 0.38 mmol), methanol solution of 40% methylamine (0.4 mL, 5.1 mmol), N,N-dimethylformamide (1.5 mL) and chloroform (1.5 mL); and the resulting compound was treated with 1,4-dioxane solution (1.5 mL) of 4 mol/L hydrogen chloride and methanol (1.5 mL) to obtain Compound 42 (81 mg, 94%).

$^1$H-NMR (270 MHz, DMSO-d$_6$) δ (ppm): 2.49 (s, 3H), 3.55 (s, 2H), 6.56 (s, 1H), 7.11-7.14 (m, 2H), 7.21-7.39 (m, 4H), 9.22 (br s, 1H), 9.94 (br s, 1H);

APCI-MS (m/z): 336, 338 (M+H)$^+$.

EXAMPLE 43

2-(2-Bromo-3,5-dihydroxy-6-phenylphenyl)-N,N-dimethylacetamide (Compound 43)

In the same manner as in the step 3 in Example 9, 2-[2-bromo-3,5-bis(methoxymethoxy)-6-phenylphenyl]-N,N-dimethylacetamide was obtained from 2-bromo-3,5-bis(methoxymethoxy)-6-phenylphenylacetic acid (110 mg, 0.26 mmol) obtained in the step 2 in Example 9, using 1-[3-(dimethylamino)propyl]-3-ethylcarbodiimide hydrochloride (75 mg, 0.38 mmol), 1-hydroxybenzotriazole hydrate (50 mg, 0.38 mmol), tetrahydrofuran solution of 2 mol/L dimethylamine (0.3 mL, 0.6 mmol), N,N-dimethylformamide (1.5 mL) and chloroform (1.5 mL); and the resulting compound was treated with 1,4-dioxane solution (1.5 mL) of 4 mol/L hydrogen chloride and methanol (1.5 mL) to obtain Compound 43 (83 mg, 94%).

$^1$H-NMR (270 MHz, DMSO-d$_6$) δ (ppm): 2.75 (s, 3H), 2.76 (s, 3H), 3.40 (s, 2H), 6.54 (s, 1H), 7.07-7.10 (m, 2H), 7.24-7.34 (m, 3H), 9.20 (br s, 1H), 9.91 (br s, 1H);

APCI-MS (m/z): 350, 352 (M+H)$^+$.

EXAMPLE 44

6-Bromo-5-(phenoxymethyl)-4-phenylbenzene-1,3-diol (Compound 44)

(Step 1)

[2-Bromo-3,5-bis(methxoymethoxy)-6-phenylphenyl]methanol (553 mg, 1.44 mmol) obtained in the step 2 in Example 15 was dissolved in dichloromethane (20 mL), and triphenylphosphine (1.01 g, 3.85 mmol) and carbon tetrabromide (2.01 g, 6.06 mmol) were added thereto and stirred at room temperature for 2 hours. Water and aqueous saturated sodium hydrogencarbonate solution were added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through silica gel column chromatography (n-hexane/ethyl acetate=10/1 to 5/1 to 3/1) to obtain 4-Bromo-3-bromomethyl-1,5-bis(methoxymethoxy)-2-phenylbenzene (563 mg, 88%).

$^1$H-NMR (270 MHz, CDCl$_3$) δ (ppm): 3.28 (s, 3H), 3.57 (s, 3H), 4.39 (s, 2H), 4.99 (s, 2H), 5.28 (s, 2H), 7.04 (s, 1H), 7.25-7.48 (m, 5H).

(Step 2)

Phenol (70.1 mg, 0.745 mmol) was dissolved in N,N-dimethylformamide (4 mL), and 60% sodium hydride/mineral oil dispersion (26.3 mg, 0.65 8 mmol) and 4-Bromo-3-bromomethyl-1,5-bis(methoxymethoxy)-2-phenylbenzene (98.4 mg, 0.221 mmol) obtained in the above were added thereto and stirred at room temperature for 1 hour. Water and methanol were added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through partitioning thin-layer chromatography (n-hexane/ethyl acetate=4/1) to obtain 4-bromo-1,5-bis(methoxymethoxy)-3-phenoxy-2-phenylbenzene (108 mg, 100%).

$^1$H-NMR (270 MHz, CDCl$_3$) δ (ppm): 3.28 (s, 3H), 3.57 (s, 3H), 4.82 (s, 2H), 5.01 (s, 2H), 5.30 (s, 2H), 6.80-6.98 (m, 4H), 7.11 (s, 1H), 7.18-7.40 (m, 6H).

(Step 3)

In the same manner as in the step 2 in Example 25, Compound 44 (79.5 mg, 96%) was obtained from 4-bromo-1,5-bis(methoxymethoxy)-3-phenoxy-2-phenylbenzene (102 mg, 0.222 mmol) obtained in the above, using ethanol (8 mL) and concentrated hydrochloric acid (0.2 mL).

$^1$H-NMR (276 MHz, CDCl$_3$) δ (ppm): 4.76 (s, 2H), 4.92 (s, 1H), 5.75 (s, 1H), 6.77 (s, 1H), 6.78-7.00 (m, 3H, 7.15-7.50 (m, 7H);

APCI-MS (m/z): 369, 371 (M−H)$^-$.

EXAMPLE 45

6-Bromo-5-methyl-4-phenyl-1,3-diol (Compound 45)

(Step 1)

4-Bromo-3-bromomethyl-1,5-bis(methoxymethoxy)-2-phenylbenzene (91.5 mg, 0.205 mmol) obtained in the step 1 in Example 44 was dissolved in dimethylsulfoxide (2 mL), and sodium borohydride (27.0 mg, 0.714 mmol) was added thereto and stirred at room temperature for 1 hour. The reaction mixture was purified through column chromatography with HP-20 resin (Mitsubishi Chemical) (water to methanol to acetonitrile) and partitioning thin-layer chromatography (n-hexane/ethyl acetate=4/1) to obtain 4-bromo-1,5-bis(methoxymethoxy)-3-methyl-2-phenylbenzene (69.6 mg, 92%).

$^1$H-NMR (270 MHz, CDCl$_3$) δ (ppm): 2.17 (s, 3H), 3.26 (s, 3H), 3.56 (s, 3H), 4.97 (s, 2H), 5.27 (s, 2H), 6.92 (s, 1H), 7.12-7.20 (m, 2H), 7.28-7.45 (m, 3H).

(Step 2)

In the same manner as in the step 2 in Example 25, Compound 45 (46.9 mg, 97%) was obtained from 4-bromo-1,5-bis(methoxymethoxy)-3-methyl-2-phenylbenzene (63.5 mg, 0.173 mmol) obtained in the above, using ethanol (8 mL) and concentrated hydrochloric acid (0.2 mL).

$^1$H-NMR (270 MHz, CDCl$_3$) δ (ppm): 2.14 (s, 3H), 4.73 (s, 1H), 5.64 (s, 1H), 6.60 (s, 1H), 7.20-7.30 (m, 2H), 7.38-7.56 (m, 3H);

APCI-MS (m/z): 279, 281 (M+H)$^+$.

EXAMPLE 46

2-Bromo-3,5-dihydroxy-6-phenylbenzoic acid (Compound 46)

(Step 1)

[2-Bromo-3,5-bis(methoxymethoxy)-6-phenylphenyl]methanol (1.12 g, 2.92 mmol) obtained in the step 2 in Example 15 was dissolved in dichloromethane (50 mL), and pyridinium dichromate (2.29 g, 6.10 mmol) was added thereto and stirred with heating under reflux for 7 hours. The reaction mixture was filtered, and the filtrate was concentrated under reduced pressure. The resulting residue was purified through silica gel column chromatography (n-hexane/ethyl acetate=10/1 to 5/1) to obtain 2-bromo-3,5-bis(methoxymethoxy)-6-phenylbenzaldehyde (1.07 g, 88%).

¹H-NMR (270 MHz, CDCl₃) δ (ppm): 3.31 (s, 3H), 3.57 (s, 3H), 5.05 (s, 2H), 5.31 (s, 2H), 7.23 (s, 1H), 7.15-7.25 (m, 2H), 7.35-7.45 (m, 3H), 9.85 (s, 1H).

(Step 2)

2-Bromo-3,5-bis(methoxymethoxy)-6-phenylbenzaldehyde (448 mg, 1.08 mmol) obtained in the above was dissolved in a mixed solvent of 2-methyl-2-propanol (40 mL) and dichloromethane (5 mL), and sodium chlorite (1.00 g, 11.1 mmol), sodium dihydrogenphosphate (1.00 g, 7.10 mmol), water (10 mL) and 2-methyl-2-butene (5.00 mL, 47.2 mmol) were added thereto and stirred at room temperature for 10 hours. Water was added to the reaction mixture, and extracted with chloroform. The organic layer was washed with aqueous saturated sodium chloride solution, and dried over anhydrous sodium sulfate, and the solvent was evaporated away under reduced pressure to obtain 2-bromo-3,5-bis(methoxymethoxy)-6-phenylbenzoic acid (536 mg, 100%).

¹H-NMR (270 MHz, CDCl₃) δ (ppm): 3.30 (s, 3H), 3.55 (s, 3H), 5.02 (s, 2H), 5.29 (s, 2H), 7.11 (s, 1H), 7.25-7.50 (m, 5H).

(Step 3)

2-Bromo-3,5-bis(methoxymethoxy)-6-phenylbenzoic acid (52.2 mg, 0.131 mmol) obtained in the above was dissolved in methanol (8 mL), and concentrated hydrochloric acid (0.2 mL) was added thereto and stirred at 60° C. for 1.2 hours. The reaction solution was concentrated under reduced pressure to obtain Compound 46 (31.1 mg, 77%).

¹H-NMR (270 MHz, CDCl₃) δ (ppm): 5.08 (br s, 1H), 5.71 (br s, 1H), 6.77 (s, 1H), 7.30-7.38 (m, 2H), 7.40-7.50 (m, 3H);

APCI-MS (m/z): 307, 309 (M−H)⁻.

EXAMPLE 47

Methyl 2-bromo-3,5-dihydroxy-6-phenylbenzoate (Compound 47)

(Step 1)

2-Bromo-3,5-bis(methoxymethoxy)-6-phenylbenzoic acid (52.2 mg, 0.131 mmol) obtained in the step 2 in Example 46 was dissolved in methanol (4 mL), and n-hexane solution of 2.0 mol/L trimethylsilyldiazomethane (0.800 mL, 1.60 mmol) was added thereto and stirred at room temperature for 0.5 hours. The reaction solution was concentrated under reduced pressure to obtain methyl 2-bromo-3,5-bis(methoxymethoxy)-6-phenylbenzoate (53.9 mg, 100%).

¹H-NMR (270 MHz, CDCl₃) δ (ppm): 3.31 (s, 3H), 3.55 (s, 3H), 3.57 (s, 3H), 5.03 (s, 2H), 5.28 (s, 2H), 7.10 (s, 1H), 7.20-7.40 (m, 5H).

(Step 2)

Methyl 2-bromo-3,5-bis(methoxymethoxy)-6-phenylbenzoate (53.9 mg, 0.131 mmol) obtained in the above was dissolved in methanol (8 mL), and concentrated hydrochloric acid (0.2 mL) was added thereto and stirred at 60° C. for 1.2 hours. The reaction solution was concentrated under reduced pressure, and the resulting residue was purified through preparative thin-layer chromatography (chloroform/methanol=20/1) to obtain Compound 47 (52.2 mg, 100%).

¹H-NMR (270 MHz, CDCl₃) δ (ppm): 3.57 (s, 3H), 5.07 (br s, 1H), 5.68 (br s, 1H), 6.76 (s, 1H), 7.27-7.35 (m, 2H), 7.40-7.52 (m, 3H);

APCI-MS (m/z): 321, 323 (M−H)⁻.

EXAMPLE 48

2-Bromo-3,5-dihydroxy-N-methyl-6-phenylbenzamide (Compound 48)

(Step 1)

2-Bromo-3,5-bis(methoxymethoxy)-6-phenylbenzoic acid (90.5 mg, 0.228 mmol) obtained in the step 2 in Example 46 was dissolved in a mixed solvent of dichloromethane (4 mL) and N,N-dimethylformamide (0.5 mL); and 1-hydroxybenzotriazole hydrate (148 mg, 0.963 mmol), 1-[3-(dimethylamino)propyl]-3-ethylcarbodiimide hydrochloride (265 mg, 1.38 mmol), and methanol solution of 40% methylamine (0.100 mL, 0.988 mmol) were added thereto and stirred at room temperature for 20 hours. Water was added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer chromatography (n-hexane/ethyl acetate=1/1) to obtain 2-bromo-3,5-bis(methoxymethoxy)-N-methyl-6-phenylbenzamide (89.7 mg, 96%).

¹H-NMR (270 MHz, CDCl₃) δ (ppm): 2.62 (d, J=4.9 Hz, 3H), 3.30 (s, 3H), 3.55 (s, 3H), 5.01 (s, 2H), 5.28 (s, 2H), 7.07 (s, 1H), 7.20-7.40 (m, 6H).

(Step 2)

In the same manner as in the step 2 in Example 25, Compound 48 (14.6 mg, 21%) was obtained from 2-bromo-3,5-bis(methoxymethoxy)-N-methyl-6-phenylbenzamide (86.7 mg, 0.211 mmol) obtained in the above, using ethanol (8 mL) and concentrated hydrochloric acid (0.2 mL).

¹H-NMR (270 MHz, DMSO-d₆) δ (ppm): 2.36 (s, 1H), 6.55-6.65 (m, 2H), 7.10-7.30 (m, 5H), 9.48 (br s, 1H), 10.14 (br s, 1H);

APCI-MS (m/z): 320, 322 (M−H)⁻.

EXAMPLE 49

2-Bromo-3,5-dihydroxy-N,N-dimethyl-6-phenylbenzamide (Compound 49)

(Step 1)

In the same manner as in the step 1 in Example 48, 2-bromo-3,5-bis(methoxymethoxy)-N,N-dimethyl-6-phenylbenzamide (69.3 mg, 72%) was obtained from 2-bromo-3,5-bis(methoxymethoxy)-6-phenylbenzoic acid (90.5 mg, 0.228 mmol) obtained in the step 2 in Example 46, using 1-hydroxybenzotriazole hydrate (148 mg, 0.963 mmol), 1-[3-(dimethylamino)propyl]-3-ethylcarbodiimide hydrochloride (265 mg, 1.38 mmol) and aqueous 50% dimethylamine solution (0.100 mL, 0.954 mmol).

¹H-NMR (270 MHz, CDCl₃) δ (ppm): 2.65 (s, 3H), 2.76 (s, 3H), 3.30 (s, 3H), 3.55 (s, 3H), 5.01 (s, 2H), 5.22-5.32 (m, 2H), 7.06 (s, 1H), 7.20-7.40 (m, 5H).

(Step 2)

In the same manner as in the step 2 in Example 25, Compound 49 (64.2 mg, 100%) was obtained from 2-bromo-3,5-bis(methoxymethoxy)-N,N-dimethyl-6-phenylbenzamide (66.2 mg, 0.156 mmol) obtained in the above, using ethanol (8 mL) and concentrated hydrochloric acid (0.2 mL).

¹H-NMR (270 MHz, CDCl₃) δ (ppm): 2.68 (s, 3H), 2.78 (s, 3H), 5.12 (br s, 1H), 5.75 (br s, 1H), 6.71 (s, 1H), 7.30-7.50 (m, 5H);

APCI-MS (m/z): 334, 336 (M−H)⁻.

EXAMPLE 50

2-Bromo-3,5-dihydroxy-6-phenylbenzamide
(Compound 50)

(Step 1)

In the same manner as in the step 1 in Example 48, 2-bromo-3,5-bis(methoxymethoxy)-6-phenylbenzamide (31.5 mg, 35%) was obtained from 2-bromo-3,5-bis(methoxymethoxy)-6-phenylbenzoic acid (90.5 mg, 0.228 mmol) obtained in the step 2 in Example 46, using 1-hydroxybenzotriazole hydrate (148 mg, 0.963 mmol), 1-[3-(dimethylamino)propyl]-3-ethylcarbodiimide hydrochloride (265 mg, 1.38 mmol) and methanol solution of 7 mol/L ammonia (0.100 mL, 0.700 mmol).

$^1$H-NMR (270 MHz, CDCl$_3$) δ (ppm): 3.30 (s, 3H), 3.55 (s, 3H), 5.02 (s, 2H), 5.29 (s, 2H), 5.15-5.50 (m, 2H), 7.09 (s, 1H), 7.30-7.40 (m, 5H).

(Step 2)

In the same manner as in the step 2 in Example 25, Compound 50 (27.1 mg, 100%) was obtained from 2-bromo-3,5-bis(methoxymethoxy)-6-phenylbenzamide (30.4 mg, 0.0767 mmol) obtained in the above, using ethanol (8 mL) and concentrated hydrochloric acid (0.2 mL).

$^1$H-NMR (270 MHz, DMSO-d$_6$) δ (ppm): 6.59 (s, 1H), 7.11 (br s, 1H), 7.18-7.30 (m, 5H), 7.49 (br s, 1H), 9.42 (br s, 1H), 10.11 (br s, 1H);

APCI-MS (m/z): 306, 308 (M−H)$^-$.

EXAMPLE 51

N-benzyl-2-bromo-3,5-dihydroxy-6-phenylbenzamide
(Compound 51)

(Step 1)

In the same manner as in the step 1 in Example 48, N-benzyl-2-bromo-3,5-bis(methoxymethoxy)-6-phenylbenzamide (89.3 mg, 81%) was obtained from 2-bromo-3,5-bis(methoxymethoxy)-6-phenylbenzoic acid (90.5 mg, 0.228 mmol) obtained in the step 2 in Example 46, using 1-hydroxybenzotriazole hydrate (148 mg, 0.963 mmol), 1-[3-(dimethylamino)propyl]-3-ethylcarbodiimide hydrochloride (265 mg, 1.38 mmol) and benzylamine (0.200 mL, 1.83 mmol).

$^1$H-NMR (270 MHz, CDCl$_3$) δ (ppm): 3.29 (s, 3H), 3.54 (s, 3H), 4.30 (d, J=5.6 Hz, 2H), 5.00 (s, 2H), 5.28 (s, 2H), 5.51 (bt, J=5.6 Hz, 1H), 6.75-6.82 (m, 2H), 7.07 (s, 1H), 7.14-7.42 (m, 8H).

(Step 2)

In the same manner as in the step 2 in Example 25, Compound 51 (48.3 mg, 68%) was obtained from N-benzyl-2-bromo-3,5-bis(methoxymethoxy)-6-phenylbenzamide (87.1 mg, 0.179 mmol) obtained in the above, using ethanol (8 mL) and concentrated hydrochloric acid (0.2 mL).

$^1$H-NMR (270 MHz, CDCl$_3$) δ (ppm): 4.31 (d, J=5.8 Hz, 2H), 5.06 (s, 1H), 5.56 (br t, J=5.8 Hz, 1H), 5.71 (s, 1H), 6.73 (s, 1H), 6.76-6.82 (m, 2H), 7.10-7.22 (m, 3H), 7.32-7.40 (m, 2H), 7.42-7.50 (m, 3H);

APCI-MS (m/z): 396, 398 (M−H)$^-$.

EXAMPLE 52

Methyl 2-ethyl-3,5-dihydroxy-6-phenylphenylacetate
(Compound 52)

(Step 1)

In an argon atmosphere, methyl 2-iodo-3,5-bis(methoxymethoxy)-6-phenylphenylacetate (8.7 g, 18 mmol) obtained in the step 1 in Example 13 was dissolved in toluene (0.15 L), and tributylvinyltin (7.0 g, 24 mmol) and bis(triphenylphosphine)palladium(II) dichloride (1.0 g, 1.4 mmol) were added thereto and stirred at 90° C. for 11 hours. The reaction solution was cooled to room temperature, and aqueous saturated ammonium fluoride solution (0.10 L) was added thereto and stirred at room temperature for 2 hours. The reaction mixture was filtered under reduced pressure, and the filtered residue was washed with ethyl acetate (0.10 L). Then, the filtrate and the wash were combined and subjected to liquid-liquid separation. The organic layer was washed with aqueous saturated sodium chloride solution (10 mL), and dried over anhydrous sodium sulfate, and the solvent was evaporated away under reduced pressure. The resulting residue was purified through silica gel column chromatography (ethyl acetate/n-hexane=1/9 to 1/2) to obtain methyl 3,5-bis(methoxymethoxy)-6-phenyl-2-vinylphenylacetate (5.4 g, 80%).

$^1$H-NMR (CDCl$_3$, 270 MHz) δ (ppm): 3.27 (s, 3H), 3.56 (s, 3H), 3.51 (s, 5H), 5.00 (s, 2H), 5.22 (s, 2H), 5.45-5.53 (m, 2H), 6.64 (m, 1H), 6.97 (s, 1H), 7.15-7.41 (m, 5H);

APCI-MS (m/z): 373 (M+H)$^+$.

(Step 2)

Methyl 3,5-bis(methoxymethoxy)-6-phenyl-2-vinylphenylacetate (5.4 g, 15 mmol) obtained in the above was dissolved in methanol (0.20 L), and 10% palladium-carbon (50% wet., 7.0 g) was added thereto and stirred under hydrogen pressure (0.3 MPa) at room temperature for 10 hours. The reaction mixture was filtered through Celite, and the filtrate was concentrated under reduced pressure. The resulting residue was purified through silica gel column chromatography (ethyl acetate/n-hexane=1/9 to 1/2) to obtain methyl 2-ethyl-3,5-bis(methoxymethoxy)-6-phenylphenylacetate (4.1 g, 74%).

$^1$H-NMR (CDCl$_3$, 270 MHz) δ (ppm): 1.11 (t, J=7.5 Hz, 3H), 2.62 (q, J=7.5 Hz, 2H), 3.46 (s, 2H) 3.25 (s, 3H), 3.52 (s, 3H), 3.58 (s, 3H), 4.96 (s, 2H), 5.23 (s, 2H), 6.93 (s, 1H), 7.17-7.40 (m, 5H);

APCI-MS (m/z): 375 (M+H)$^+$.

(Step 3)

In the same manner as in the step 4 in Example 1, Compound 52 (2.5 g, 88%) was obtained from methyl 2-ethyl-3,5-bis(methoxymethoxy)-6-phenylphenylacetate (4.0 g, 11 mmol) obtained in the above, using methanol (0.10 L) and 1,4-dioxane solution (40 mL) of 4 mol/L hydrogen chloride.

$^1$H-NMR (CDCl$_3$, 270 MHz) δ (ppm): 1.12 (t, J=7.5 Hz, 3H), 2.57 (q, J=7.5 Hz, 2H), 3.44 (s, 2H) 3.60 (s, 3H), 4.58 (s, 1H), 5.24 (s, 1H), 6.36 (s, 1H), 7.26-7.50 (m, 5H);

APCI-MS (m/z): 285 (M−H)$^-$.

Elementary Analysis (as C$_{17}$H$_{18}$O$_4$):

Measured (%): C:71.20, H:6.54, N:0.01

Calculated (%): C:71.31, H:6.34, N:0

EXAMPLE 53

2-(2-Bromo-3,5-dihydroxy-6-phenylphenyl)-N-(pyridin-2-ylmethyl)acetamide (Compound 53)

In the same manner as in the step 3 in Example 9, Compound 53 (52 mg, 50%) was obtained from the carboxylic acid (110 mg, 0.26 mmol) obtained in the step 2 in Example 9, using 1-[3-(dimethylamino)propyl]-3-ethylcarbodiimide hydrochloride (75 mg, 0.38 mmol), 1-hydroxybenzotriazole hydrate (50 mg, 0.38 mmol), 2-picolylamine (0.04 mL, 0.39 mmol), N,N-dimethylformamide (1.5 mL), chloroform (1.5 mL), 1,4-dioxane solution (1.5 mL) of 4 mol/L hydrochloride, and methanol (1.5 mL).

$^1$H-NMR (270 MHz, DMSO-$d_6$) δ (ppm): 3.75 (s, 2H), 4.79 (s, 2H), 6.87 (s, 1H), 7.10-7.25 (m, 2H), 7.42-7.67 (m, 3H), 7.83-8.09 (m, 2H), 8.62-8.77 (m, 2H), 9.03 (br s, 1H), 9.63 (br s, 1H), 10.4 (br s, 1H);

APCI-MS (m/z): 413, 415 (M+H)$^+$.

EXAMPLE 54

2-(2-Bromo-3,5-dihydroxy-6-phenylphenyl)-N-(pyridin-4-ylmethyl)acetamide (Compound 54)

In the same manner as in the step 3 in Example 9, 2-[2-bromo-3,5-bis(methoxymethoxy)-6-phenylphenyl]-N-(pyridin-4-ylmethyl)acetamide was obtained from 2-bromo-3,5-bis(methoxymethoxy)-6-phenylphenylacetic acid (110 mg, 0.26 mmol) obtained in the step 2 in Example 9, using 1-[3-(dimethylamino)propyl]-3-ethylcarbodiimide hydrochloride (75 mg, 0.38 mmol), 1-hydroxybenzotriazole hydrate (50 mg, 0.38 mmol), 4-picolylamine (0.04 mL, 0.39 mmol), N,N-dimethylformamide (1.5 mL) and chloroform (1.5 mL); and the resulting compound was treated with 1,4-dioxane solution (1.5 mL) of 4 mol/L hydrochloride and methanol (1.5 mL) to obtain Compound 54 (52 mg, 50%).

$^1$H-NMR (270 MHz, DMSO-$d_6$) δ (ppm): 3.73 (s, 2H), 4.76 (s, 2H), 6.93 (s, 1H), 7.43-7.46 (m, 2H), 7.58-7.70 (m, 3H), 8.05-8.09 (m, 2H), 8.72 (br s, 1H), 9.14-9.17 (m, 2H), 9.64 (br s, 1H), 10.4 (br s, 1H);

APCI-MS (m/z): 413, 415 (M+H)$^+$.

EXAMPLE 55

Methyl 2-formyl-3,5-dihydroxy-6-phenylphenylacetate (Compound 55)

Compound 1 (0.25 g, 0.97 mmol) obtained in Example 1 was dissolved in dichloromethane (10 mL), and the solution was cooled to 4° C., and then dichloromethyl methyl ether (0.13 mL, 1.4 mmol) and tin(IV) chloride (0.17 g, 1.5 mmol) were added thereto and stirred at 4° C. for 5 minutes. Water (10 mL) and 3 mol/L hydrochloric acid (10 mL) were added to the reaction mixture, and extracted with chloroform (50 mL). The organic layer was dried over anhydrous sodium sulfate, and the solvent was evaporated away under reduced pressure. The residue was purified through preparative thin-layer chromatography (n-hexane/ethyl acetate=1/2) and crystallized (n-hexane/ethyl acetate=1/2) to obtain Compound 55 (0.21 g, 85%).

$^1$H-NMR (CDCl$_3$, 270 MHz) δ (ppm): 3.65 (s, 3H), 3.69 (s, 2H), 5.32 (s, 1H), 6.52 (s, 1H), 7.24-7.28 (2 m, H), 7.49-7.56 (m, 3H), 10.04 (s, 1H), 12.46 (s, 1H);

APCI-MS (m/z): 285 (M−H)$^−$.

Elementary Analysis (as $C_{16}H_{14}O_5 \cdot 0.1H_2O$):
Measured (%): C:66.65, H:4.90, N:0
Calculated (%): C:66.71, H:4.97, N:0

EXAMPLE 56

Methyl 3,5-dihydroxy-6-methyl-2-phenylphenylacetate (Compound 56)

Compound 55 (44 mg, 0.15 mmol) obtained in Example 55 was dissolved in methanol (10 mL), and 10% palladium-carbon (50% wet., 40 mg) was added thereto and stirred under hydrogen pressure (0.3 MPa) at room temperature for 8 hours. The reaction mixture was filtered, and the filtrate was concentrated under reduced pressure, purified through preparative thin-layer chromatography (methanol/chloroform 1/9) and crystallized (ethyl acetate/n-hexane=1/4) to obtain Compound 56 (31 mg, 74%).

$^1$H-NMR (CDCl$_3$, 270 MHz) δ (ppm): 2.11 (s, 3H), 3.42 (s, 2H), 3.62 (s, 3H), 4.56 (s, 1H), 4.95 (s, 1H), 6.41 (s, 1H), 7.24-7.28 (m, 2H), 7.41-7.51 (m, 3H);

FAB-MS (m/z): 273 (M+H)$^+$.

Elementary Analysis (as $C_{16}H_{16}O_4$):
Measured (%): C:70.43, H:5.92, N:0.35
Calculated (%): C:70.43, H:5.92, N:0

EXAMPLE 57

1-(2-Bromo-3,5-dihydroxy-6-phenylphenyl)propanone (Compound 57)

(Step 1)

2-Bromo-3,5-bis(methoxymethoxy)-6-phenylbenzaldehyde (328 mg, 0.860 mmol) obtained in the step 1 in Example 46 was dissolved in tetrahydrofuran (5 mL), and the solution was cooled to 0° C. Then, ether solution of 3.0 mol/L ethylmagnesium bromide (0.600 mL, 1.80 mmol) was added thereto and stirred at the same temperature for 1 hour. Methanol and water were added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through silica gel column chromatography (n-hexane/ethyl acetate=4/1 to 2/1) to obtain 1-[2-bromo-3,5-bis(methoxymethoxy)-6-phenylphenyl]propanol (171 mg, 48%).

$^1$H-NMR (270 MHz, CDCl$_3$) δ (ppm): 0.80 (t, J=7.4 Hz, 3H), 1.70-2.10 (m, 2H), 2.50-2.70 (m, 1H), 3.25 (s, 3H), 3.56 (s, 3H), 4.50-4.70 (m, 1H), 4.97 (s, 2H), 5.27 (s, 2H), 6.97 (s, 1H), 7.10-7.26 (m, 2H), 7.30-7.46 (m, 3H).

(Step 2)

1-[2-bromo-3,5-bis(methoxymethoxy)-6-phenylphenyl]propanol (78.1 mg, 0.190 mmol) obtained in the above was dissolved in dichloromethane (10 mL), and pyridinium dichromate (262 mg, 0.697 mmol) was added thereto and stirred at room temperature for 15 hours. The reaction mixture was filtered, and the filtrate was concentrated under reduced pressure. The resulting residue was purified through preparative thin-layer chromatography (n-hexane/ethyl acetate=2/1) to obtain 1-[2-bromo-3,5-bis(methoxymethoxy)-6-phenylphenyl]propanone (63.7 mg, 82%).

$^1$H-NMR (270 MHz, CDCl$_3$) δ (ppm): 0.82 (t, J=7.1 Hz, 3H), 2.27 (q, J=7.1 Hz, 2H), 3.31 (s, 3H), 3.56 (s, 3H), 5.03 (s, 2H), 5.29 (s, 2H), 7.07 (s, 1H), 7.20-7.40 (m, 5H).

(Step 3)

In the same manner as in the step 2 in Example 25, Compound 57 (46.2 mg, 98%) was obtained from 1-[2-bromo-3,5-bis(methoxymethoxy)-6-phenylphenyl]propanone (60.2 mg, 0.147 mmol) obtained in the above, using ethanol (8 mL) and concentrated hydrochloric acid (0.2 mL).

$^1$H-NMR (270 MHz, CDCl$_3$) δ (ppm): 0.83 (t, J=7.3 Hz, 3H), 2.28 (q, J=7.3 Hz, 2H), 5.06 (s, 1H), 5.68 (s, 1H), 6.73 (s, 1H), 7.20-7.30 (m, 2H), 7.35-7.50 (m, 3H);

APCI-MS (m/z): 319, 321 (M–H)$^-$.

EXAMPLE 58

2-Bromo-3,5-dihydroxy-6-phenylphenyl phenyl ketone (Compound 58)

(Step 1)

2-Bromo-3,5-bis(methoxymethoxy)-6-phenylbenzaldehyde (201 mg, 0.528 mmol) obtained in the step 1 in Example 46 was dissolved in tetrahydrofuran (10 mL), and the solution was cooled to 0° C. Then, ether solution of 3.0 mol/L phenylmagnesium bromide (0.500 mL, 1.50 mmol) was added thereto and stirred at the same temperature for 2 hours. Methanol and water were added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through silica gel column chromatography (n-hexane/ethyl acetate=4/1 to 2/1) to obtain 1-[2-bromo-13,5-bis(methoxymethoxy)-6-phenylphenyl]-1-phenylmethanol (244 mg, 100%).

$^1$H-NMR (270 MHz, CDCl$_3$) δ (ppm): 3.20-3.30 (m, 1H), 3.29 (s, 3H), 3.55 (s, 3H), 5.02 (s, 2H), 5.24-5.30 (m, 2H), 5.93 (br d, J=11.5 Hz, 1H), 7.00-7.30 (m, 10H), 7.07 (s, 1H).

(Step 2)

1-[2-Bromo-3,5-bis(methoxymethoxy)-6-phenylphenyl]-1-phenylmethanol (96.1 mg, 0.209 mmol) obtained in the above was dissolved in dichloromethane (10 mL), and pyridinium dichromate (238 mg, 0.637 mmol) was added thereto and stirred at room temperature for 15 hours. The reaction mixture was filtered, and the filtrate was concentrated under reduced pressure. The resulting residue was purified through preparative thin-layer chromatography (n-hexane/ethyl acetate=2/1) to obtain 3,5-bis(methoxymethoxy)-2-bromo-6-phenylphenyl phenyl ketone (87.2 mg, 91%).

$^1$H-NMR (270 MHz, CDCl$_3$) δ (ppm): 3.32 (s, 3H), 3.58 (s, 3H), 5.06 (s, 2H), 5.30-5.36 (m, 2H), 7.05-7.35 (m, 7H), 7.17 (s, 1H), 7.40-7.50 (m, 1H), 7.60-7.67 (m, 2H).

(Step 3)

In the same manner as in the step 2 in Example 25, Compound 58 (67.6 mg, 98%) was obtained from 2-bromo-3,5-bis(methoxymethoxy)-6-phenylphenyl phenyl ketone (85.2 mg, 0.186 mmol) obtained in the above, using ethanol (8 mL) and concentrated hydrochloric acid (0.2 mL).

$^1$H-NMR (270 MHz, CDCl$_3$) δ (ppm): 5.07 (s, 1H), 5.72 (s, 1H), 6.83 (s, 1H), 7.10-7.40 (m, 7H), 7.44-7.54 (m, 1H), 7.60-7.70 (m, 2H);

APCI-MS (m/z): 367, 369 (M–H)$^-$.

EXAMPLE 59

Methyl 3-(2-bromo-3,5-dihydroxy-6-phenylphenyl)acrylate (Compound 59)

(Step 1)

2-Bromo-3,5-bis(methoxymethoxy)-6-phenylbenzaldehyde (107 mg, 0.281 mmol) obtained in the step 1 in Example 46 was dissolved in toluene (10 mL), and methyl triphenylphospholanylidene-acetate (300 mg, 0.896 mmol) was added thereto and stirred at 80° C. for 7.5 hours. The reaction mixture was concentrated under reduced pressure, and the resulting residue was purified through preparative thin-layer chromatography (n-hexane/ethyl acetate=2/1) to obtain methyl 3-[2-bromo-3,5-bis(methoxymethoxy)-6-phenylphenyl]acrylate (113 mg, 92%).

$^1$H-NMR (270 MHz, CDCl$_3$) δ (ppm): 3.28 (s, 3H), 3.57 (s, 3H), 3.66 (s, 3H), 5.01 (s, 2H), 5.29 (s, 2H), 5.59 (d, J=16.5 Hz, 1H), 7.07 (s, 1H), 7.10-7.18 (m, 2H), 7.25-7.40 (m, 3H), 7.57 (d, J=16.3 Hz, 1H).

(Step 2)

In the same manner as in the step 2 in Example 25, Compound 59 (59.7 mg, 98%) was obtained from methyl 3-[2-bromo-3,5-bis(methoxymethoxy)-6-phenylphenyl]acrylate (76.6 mg, 0.175 mmol) obtained in the above, using ethanol (8 mL) and concentrated hydrochloric acid (0.2 mL).

$^1$H-NMR (270 MHz, CDCl$_3$) δ (ppm): 3.67 (s, 3H), 4.95 (s, 1H), 5.66 (d, J=16.3 Hz, 1H), 5.76 (s, 1H), 6.74 (s, 1H), 7.15-7.25 (m, 2H), 7.35-7.55 (m, 4H);

APCI-MS (m/z): 347, 349 (M–H)$^-$.

EXAMPLE 60

4-(2-Bromo-3,5-dihydroxy-6-phenylphenyl)but-3-en-2-one (Compound 60)

(Step 1)

2-Bromo-3,5-bis(methoxymethoxy)-6-phenylbenzaldehyde (108 mg, 0.284 mmol) obtained in the step 1 in Example 46 was dissolved in toluene (10 mL), and (acetylmethylene)triphenylphospholane (272 mg, 0.854 mmol) was added thereto and stirred at 80° C. for 7.5 hours. The reaction mixture was concentrated under reduced pressure, and the resulting residue was purified through preparative thin-layer chromatography (n-hexane/ethyl acetate=2/1) to obtain 4-[2-bromo-3,5-bis(methoxymethoxy)-6-phenylphenyl]but-3-en-2-one (129 mg, 100%).

$^1$H-NMR (270 MHz, CDCl$_3$) δ (ppm): 2.10 (s, 3H), 3.29 (s, 3H), 3.57 (s, 3H), 5.02 (s, 2H), 5.30 (s, 2H), 5.85 (d, J=16.6 Hz, 1H), 7.08 (s, 1H), 7.10-7.18 (m, 2H), 7.25-7.40 (m, 4H).

(Step 2)

In the same manner as in the step 2 in Example 25, Compound 60 (59.7 mg, 98%) was obtained from 4-[2-bromo-3,5-bis(methoxymethoxy)-6-phenylphenyl]but-3-en-2-one (76.6 mg, 0.175 mol) obtained in the above, using ethanol (8 mL) and concentrated hydrochloric acid (0.2 mL).

$^1$H-NMR (270 MHz, CDCl$_3$) δ (ppm): 2.10 (s, 3H), 4.97 (s, 1H), 5.76 (s, 1H), 5.92 (d, J=16.5 Hz, 1H), 6.75 (s, 1H), 7.16-7.34 (m, 6H);

APCI-MS (m/z): 347, 349 (M–H)$^-$.

EXAMPLE 61

6-Bromo-5-methoxy-4-phenylbenzene-1,3-diol (Compound 61)

(Step 1)
2-Bromo-3,5-bis(methoxymethoxy)-6-phenylbenzaldehyde (150 mg, 0.393 mmol) obtained in the step 1 in Example 46 was dissolved in dichloromethane (10 mL). m-Chloroperbenzoic acid (472 mg, 2.74 mmol) was added to the resulting solution, and stirred at room temperature for 48 hours. Aqueous saturated sodium hydrogencarbonate solution was added to the reaction mixture, and extracted with chloroform. The organic layer was washed with aqueous saturated sodium thiosulfate solution and aqueous saturated sodium chloride solution in order, and dried over anhydrous sodium sulfate, and the solvent was evaporated away under reduced pressure. Methanol solution of 7 mol/L ammonia (12.0 mL, 84.0 mmol) was added to the resulting residue, and stirred at room temperature for 4 hours, and then the reaction solution was concentrated under reduced pressure. The resulting residue was purified through preparative thin-layer chromatography (n-hexane/ethyl acetate=2/1) to obtain 2-bromo-3,5-bis(methoxymethoxy)-6-phenylphenol (115 mg, 79%).
$^1$H-NMR (270 MHz, CDCl$_3$) δ (ppm): 3.30 (s, 3H), 3.55 (s, 3H), 5.02 (s, 2H), 5.27 (s, 2H), 5.61 (s, 1H), 6.69 (s, 1H), 7.30-7.50 (m, 5H).

(Step 2)
2-Bromo-3,5-bis(methoxymethoxy)-6-phenylphenol (66.6 mg, 0.180 mmol) obtained in the above was dissolved in N,N-dimethylformamide (5 mL), and 60% sodium hydride/mineral oil dispersion (22.5 mg, 0.563 mmol) and dimethyl sulfate (0.0600 mL, 0.634 mmol) were added thereto and stirred at room temperature for 1 hour. Water was added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer chromatography (n-hexane/ethyl acetate=4/1) to obtain 4-bromo-3-methoxy-1,5-bis(methoxymethoxy)-2-phenylbenzene (66.3 mg, 96%).
$^1$H-NMR (270 MHz, CDCl$_3$) δ (ppm): 3.31 (s, 3H), 3.38 (s, 3H), 3.56 (s, 3H), 5.01 (s, 2H), 5.27 (s, 2H), 6.88 (s, 1H), 7.25-7.50 (m, 5H).

(Step 3)
In the same manner as in the step 2 in Example 25, Compound 61 (23.8 mg, 61%) was obtained from 4-bromo-3-methoxy-1,5-bis(methoxymethoxy)-2-phenylbenzene (50.8 mg, 0.133 mmol) obtained in the above, using ethanol (8 mL) and concentrated hydrochloric acid (0.2 mL).
$^1$H-NMR (270 MHz, CDCl$_3$) δ (ppm): 3.70 (s, 3H), 5.41 (s, 1H), 5.58 (s, 1H), 6.35 (s, 1H), 7.25-7.50 (m, 5H);
APCI-MS (m/z): 293, 295 (M−H)$^−$.

EXAMPLE 62

6-Bromo-5-(2-hydroxyethyl)-4-phenylbenzene-1,3-diol (Compound 62)

(Step 1)
2-Bromo-3,5-bis(methoxymethoxy)-6-phenylphenylacetic acid (376 mg, 0.885 mmol) obtained in the step 1 in Example 9 was dissolved in tetrahydrofuran (10 mL), and the solution was cooled to 0° C. Then, lithium aluminium hydride (39.3 mg, 1.04 mmol) was added thereto and stirred at the same temperature for 6 hours. Aqueous saturated sodium sulfate solution and anhydrous sodium sulfate were added to the reaction mixture, and stirred at room temperature for 1 hour. The reaction mixture was filtered, and the filtrate was concentrated under reduced pressure. The resulting residue was purified through silica gel column chromatography (n-hexane/ethyl acetate=10/1 to 5/1 to 3/1) to obtain 2-[2-bromo-3,5-bis(methoxymethoxy)-6-phenylphenyl]ethanol (344 mg, 98%).
$^1$H-NMR (270 MHz, CDCl$_3$) δ (ppm): 1.14 (t, J=5.3 Hz, 1H), 2.92 (t, J=7.9 Hz, 2H), 3.26 (s, 3H), 3.56 (s, 3H), 3.65 (dt, J=5.3, 7.9 Hz, 2H), 4.97 (s, 2H), 5.27 (s, 2H), 6.95 (s, 1H), 7.10-7.20 (m, 2H), 7.30-7.45 (m, 3H).

(Step 2)
In the same manner as in the step 2 in Example 25, Compound 62 (56.6 mg, 83%) was obtained from 2-[2-bromo-3,5-bis(methoxymethoxy)-6-phenylphenyl]ethanol (87.5 mg, 0.220 mmol) obtained in the above, using ethanol (8 mL) and concentrated hydrochloric acid (0.2 mL).
$^1$H-NMR (270 MHz, CDCl$_3$) δ (ppm): 1.10-1.24 (m, 1H), 2.85 (t, J=7.7 Hz, 2H), 3.56-3.70 (m, 2H), 4.65 (s, 1H), 5.67 (s, 1H), 6.63 (s, 1H), 7.20-7.30 (m, 2H), 7.40-7.56 (m, 3H);
APCI-MS (m/z): 307, 309 (M−H)$^−$.

EXAMPLE 63

4-Bromo-2-phenylbenzene-1,3,5-triol (Compound 63)

In the same manner as in the step 2 in Example 25, Compound 63 (22.0 mg, 87%) was obtained from 2-bromo-3,5-bis(methoxymethoxy)-6-phenylphenol (33.3 mg, 0.0902 mmol) obtained in the step 1 in Example 61, using ethanol (8 mL) and concentrated hydrochloric acid (0.2 mL).
$^1$H-NMR (270 MHz, CDCl$_3$) δ (ppm): 4.95 (s, 1H), 5.32 (s, 1H), 5.49 (s, 1H), 6.36 (s, 1H), 7.35-7.60 (m, 5H);
APCI-MS (m/z): 279, 281 (M−H)$^−$.

EXAMPLE 64

6-Bromo-5-(2-methoxyethyl)-4-phenylbenzene-1,3-diol (Compound 64)

(Step 1)
2-[2-Bromo-3,5-bis(methoxymethoxy)-6-phenylphenyl]ethanol (97.8 mg, 0.246 mmol) obtained in the step 1 in Example 62 was dissolved in N,N-dimethylformamide (4 mL), and 60% sodium hydride/mineral oil dispersion (39.0 mg, 0.975 mmol) and methyl iodide (0.100 mL, 1.61 mmol) were added thereto and stirred at room temperature for 1 hour. Water and methanol were added to the reaction mixture, and extracted with chloroform. The organic layer was washed with aqueous saturated sodium chloride solution, and dried over anhydrous sodium sulfate, and the solvent was evaporated away under reduced pressure to obtain 4-bromo-3-(2-methoxyethyl)-1,5-bis(methoxymethoxy)-2-phenylbenzene (115 mg, 100%).
$^1$H-NMR (270 MHz, CDCl$_3$) δ (ppm): 2.86-2.96 (m, 2H), 3.16 (s, 3H), 3.26 (s, 3H), 3.32-3.45 (m, 2H), 3.57 (s, 3H), 4.97 (s, 2H), 5.27 (s, 2H), 6.94 (s, 1H), 7.14-7.20 (m, 2H), 7.30-7.45 (m, 3H).

(Step 2)
In the same manner as in the step 2 in Example 25, Compound 64 (68.3 mg, 76%) was obtained from 4-bromo-3-(2- methoxyethyl)-1,5-bis(methoxymethoxy)-2-phenylbenzene (115 mg, 0.278 mmol) obtained in the above, using ethanol (8 mL) and concentrated hydrochloric acid (0.2 mL).

$^1$H-NMR (270 MHz, CDCl$_3$) δ (ppm): 2.80-2.88 (m, 2H), 3.17 (s, 3H), 3.30-3.40 (m, 2H), 4.65 (s, 1H), 5.68 (s, 1H), 6.62 (s, 1H), 7.20-7.30 (m, 2H), 7.40-7.55 (m, 3H);

APCI-MS (m/z): 321, 323 (M−H)$^-$.

EXAMPLE 65

1-(2-Bromo-3,5-dihydroxy-6-phenylphenyl)propan-2-one (Compound 65)

(Step 1)

In the same manner as in the step 3 in Example 9, 2-[2-bromo-3,5-bis(methoxymethoxy)-6-phenylphenyl]-N-(methoxymethyl)acetamide (520 mg, 47%) was obtained from 2-bromo-3,5-bis(methoxymethoxy)-6-phenylphenylacetic acid (1.0 g, 2.5 mmol) obtained in the step 2 in Example 9, using 1-[3-(dimethylamino)propyl]-3-ethylcarbodiimide hydrochloride (560 mg, 2.9 mmol), 1-hydroxybenzotriazole hydrate (400 mg, 3.0 mmol), triethylamine (0.45 mL, 3.2 mmol) and methoxymethylamine hydrochloride (300 mg, 3.1 mmol).

$^1$H-NMR (270 MHz, CDCl$_3$) δ (ppm): 3.13 (s, 3H), 3.26 (s, 3H), 3.46 (s, 3H), 3.55 (s, 3H), 3.72 (s, 2H), 4.98 (s, H), 5.27 (s, 2H), 7.01 (s, 1H), 7.19-7.23 (m, 2H), 7.30-7.37 (m, 3H).

(Step 2)

2-[2-Bromo-3,5-bis(methoxymethoxy)-6-phenylphenyl]-N-(methoxymethyl)acetamide (96 mg, 0.23 mmol) obtained in the above was dissolved in tetrahydrofuran (3.0 mL), and under stirring with ice-cooling, tetrahydrofuran solution of 1.0 mol/L methylmagnesium bromide (0.5 mL, 0.5 mmol) was dropwise added thereto, and further stirred at room temperature for 3 hours. Ice and ethyl acetate were added to the reaction solution for liquid-liquid separation. The organic layer was washed with 2 mol/L hydrochloric acid, aqueous saturated sodium hydrogencarbonate solution and aqueous saturated sodium chloride solution in order, and then dried over anhydrous magnesium sulfate, and the solvent was evaporated away under reduced pressure. The resulting residue was purified through silica gel column chromatography (ethyl acetate/n-hexane=1/4 to 1/2) to obtain 1-[2-bromo-3,5-bis(methoxymethoxy)-6-phenylphenyl]propan-2-one (63 mg, 67%).

$^1$H-NMR (270 MHz, CDCl$_3$) δ (ppm): 2.06 (s, 3H), 3.27 (s, 3H), 3.55 (s, 3H), 3.71 (s, 2H), 4.99 (s, 2H), 5.27 (s, 2H), 7.01 (s, 1H), 7.11-7.15 (m, 2H), 7.33-7.35 (m, 3H).

(Step 3)

In the same manner as in the step 4 in Example 1, Compound 65 (40 mg, 83%) was obtained from 1-[2-bromo-3,5-bis(methoxymethoxy)-6-phenylphenyl]propan-2-one (60 mg, 0.15 mmol) obtained in the above, using ethanol (8 mL) and concentrated hydrochloric acid (0.2 mL).

$^1$H-NMR (270 MHz, CDCl$_3$) δ (ppm): 2.06 (s, 3H), 3.00 (s, 2H), 6.65 (s, 1H), 7.19-7.23 (m, 2H), 7.44-7.48 (m, 3H); APCI-MS (m/z): 319, 321 (M−H)$^-$.

EXAMPLE 66

3-{3-[2,4-dihydroxy-6-(methoxycarbonylmethyl)phenyl]phenyl}acrylic acid (Compound 66)

(Step 1)

In the same manner as in the step 2 in Example 2, methyl 2-{3-[2-(tert-butoxycarbonyl)vinyl]phenyl}-3,5-bis(methoxymethoxy)phenylacetate (2.6 g, 99%) was obtained from methyl 2-(3-formylphenyl)-3,5-bis(methoxymethoxy)phenylacetate (2.1 g, 5.5 mmol) obtained in the step 1 in Example 2, using (tert-butoxycarbonylmethyl)triphenylphospholane (2.7 mg, 7.1 mmol) and toluene (50 mL).

$^1$H-NMR (270 MHz, CDCl$_3$) δ (ppm): 1.52 (s, 9H), 3.27 (s, 3H), 3.38 (s, 2H), 3.51 (s, 3H), 3.56 (s, 3H), 5.00 (s, 2H), 5.19 (s, 2H), 6.35 (d, J=16.5 Hz, 1H), 6.72 (d, J=2.5 Hz, 1H), 6.83 (d, J=2.5 Hz, 1H), 7.21 (m, 1H), 7.35-7.48 (m, 3H), 7.56 (d, J=16.5 Hz, 1H).

(Step 2)

In the same manner as in the step 4 in Example 1, a crude crystal of Compound 66 was obtained from methyl 2-{3-[2-(tert-butoxycarbonyl)vinyl]phenyl}-3,5-bis(methoxymethoxy)phenylacetate (58 mg, 0.12 mmol) obtained in the above, using 1,4-dioxane solution (1.0 mL) of 4 mol/L hydrogen chloride and isopropanol (1.0 mL); and the crude crystal of Compound 66 was recrystallized from dichloromethane to obtain Compound 66 (21 mg, 52%).

$^1$H-NMR (270 MHz, DMSO-d$_6$) δ (ppm): 3.27 (s, 3H), 3.45 (s, 3H), 6.22 (d, J=2.0 Hz, 1H), 6.32 (d, J=2.0 Hz, 1H), 6.45 (d, J=15.8 Hz, 1H), 7.12 (d, J=7.8 Hz, 1H), 7.34-7.40 (m, 2H), 7.54-7.60 (m, 2H), 9.27 (s, 1H), 9.12 (s, 1H);

APCI-MS (m/z): 328 (M−H)$^-$.

EXAMPLE 67

3-{3-[2,4-Dihydroxy-6-(methoxycarbonylmethyl)phenyl]phenyl}propanoic acid (Compound 67)

(Step 1)

Methyl 2-{3-[2-(tert-butoxycarbonyl)vinyl]phenyl}-3,5-bis(methoxymethoxy)phenylacetate (300 mg, 0.63 mmol) obtained in the step 1 in Example 66 was dissolved in ethyl acetate (20 mL), and 10% palladium-carbon (50% wet., 100 mg) was added thereto and stirred under hydrogen pressure (0.3 MPa) at room temperature for 30 minutes. The reaction mixture was filtered through Celite, and the filtrate was concentrated under reduced pressure. The resulting residue was purified through silica gel column chromatography (ethyl acetate/n-hexane=1/4 to 1/2) to obtain methyl 2-{3-[2-(tert-butoxycarbonyl)ethyl]phenyl}-3,5-bis(methoxymethoxy)phenylacetate (290 mg, 97%)

$^1$H-NMR (270 MHz, CDCl$_3$) δ (ppm): 1.41 (s, 9H), 2.53 (t, J=7.7 Hz, 2H), 2.91 (t, J=7.7 Hz, 2H), 3.28 (s, 3H), 3.37 (s, 2H), 3.50 (s, 3H), 3.58 (s, 3H), 4.99 (s, 2H), 5.18 (s, 2H), 6.71 (d, J=2.3 Hz, 1H), 6.81 (d, J=2.3 Hz, 1H), 7.01-7.03 (m, 2H), 7.15 (m, 1H), 7.29 (t, J=7.3 Hz, 1H).

(Step 2)

In the same manner as in the step 4 in Example 1, Compound 67 (56 mg, 62%) was obtained from methyl 2-{3-[2-(tert-butoxycarbonyl)ethyl]phenyl}-3,5-bis(methoxymethoxy)phenylacetate (130 mg, 0.27 mmol) obtained in the above, using 1,4-dioxane solution (1.0 mL) of 4 mol/L hydrogen chloride and isopropanol (2.0 mL).

$^1$H-NMR (270 MHz, CDCl$_3$) δ (ppm): 2.67 (d, J=7.3 Hz, 2H), 2.97 (t, J=7.3 Hz, 2H), 3.34 (s, 2H), 3.57 (s, 3H), 6.36 (d, J=2.3 Hz, 1H), 6.40 (d, J=2.3 Hz, 1H), 7.05 (m, 2H), 7.21 (m, 1H), 7.38 (t, J=7.6 Hz, 1H);

APCI-MS (m/z): 329 (M−H)$^-$.

EXAMPLE 68

3-[3-(5-Bromo-2,4-dihydroxy-6-methoxycarbonylmethylphenyl)phenyl]propanoic acid (Compound 68)

(Step 1)

In the same manner as in the step 2 in Example 1, methyl 6-bromo-2-{3-[2-(tert-butoxycarbonyl)ethyl]phenyl}-3,5-bis(methoxymethoxy)phenylacetate (110 mg, 68%) was obtained from methyl 2-{3-[2-(tert-butoxycarbonyl)ethyl]phenyl}-3,5-bis(methoxymethoxy)phenylacetate (140 mg, 0.28 mmol) obtained in the step 1 in Example 67, using N-bromosuccinimide (70 mg, 0.40 mmol) and carbon tetrachloride (4 mL).

$^1$H-NMR (270 MHz, CDCl$_3$) δ (ppm): 1.41 (s, 9H), 2.53 (t, J=7.7 Hz, 2H), 2.91 (t, J=7.7 Hz, 2H), 3.28 (s, 3H), 3.55 (s, 3H), 3.60 (s, 2H), 3.64 (s, 3H), 4.99 (s, 2H), 5.28 (s, 2H), 7.00-7.11 (m, 3H), 7.20 (m, 1H), 7.29 (t, J=7.6 Hz, 1H).

(Step 2)

In the same manner as in the step 4 in Example 1, Compound 68 (45 mg, 68%) was obtained from methyl 6-bromo-2-{3-[2-(tert-butoxycarbonyl)ethyl]phenyl}-3,5-bis(methoxymethoxy)phenylacetate (110 mg, 0.20 mmol) obtained in the above, using 1,4-dioxane solution (1.0 mL) of 4 mol/L hydrogen chloride and isopropanol (2.0 mL).

$^1$H-NMR (270 MHz, CDCl$_3$) δ (ppm): 2.68 (t, J=7.3 Hz, 2H), 2.98 (t, J=7.3 Hz, 2H), 3.55 (s, 2H), 3.65 (s, 3H), 6.63 (s, 1H), 7.08-7.11 (m, 2H), 7.29 (m, 1H), 7.41 (t, J=7.6 Hz, 1H);

APCI-MS (m/z): 407, 409 (M–H)$^-$.

EXAMPLE 69

Methyl 2-acetyl-3,5-dihydroxy-6-phenylphenylacetate (Compound 69)

(Step 1)

In an argon atmosphere, methyl 2-iodo-3,5-bis(methoxymethoxy)-6-phenylphenylacetate (4.8 g, 10 mmol) obtained in the step 1 in Example 13 was dissolved in toluene (0.10 L), and tributyl(1-ethoxyvinyl)tin (4.8 mL, 14 mmol) and bis(triphenylphosphine)palladium(II) dichloride (0.71 g, 1.0 mmol) were added thereto and stirred at 90° C. for 4 hours. The reaction mixture was cooled to room temperature, and then aqueous saturated potassium fluoride solution (50 mL) was added thereto and stirred for 2 hours. The reaction mixture was filtered under reduced pressure, and the filtrate was subjected to liquid-liquid separation. The organic layer was washed with aqueous saturated sodium chloride solution, and then dried over anhydrous sodium sulfate, and the solvent was evaporated away under reduced pressure. The resulting residue was dissolved in tetrahydrofuran (30 mL), and 3 mol/L hydrochloric acid (30 mL) was added thereto and stirred at room temperature for 2 hours. Ethyl acetate (0.10 L) was added to the reaction solution for liquid-liquid separation. The organic layer was washed with aqueous saturated sodium hydrogencarbonate solution (50 mL) and aqueous saturated sodium chloride solution (10 mL) in order, and then dried over anhydrous sodium sulfate, and the solvent was evaporated away under reduced pressure. The resulting residue was purified through silica gel column chromatography (n-hexane/ethyl acetate=1/9 to 1/2) to obtain methyl 2-acetyl-3,5-bis(methoxymethoxy)-6-phenylphenylacetate (3.4 g, 85%).

$^1$H-NMR (CDCl$_3$, 270 MHz) δ (ppm): 2.57 (s, 3H), 3.29 (s, 3H), 3.47 (s, 2H), 3.58 (s, 3H), 5.03 (s, 3H), 5.24 (s, 2H), 6.98 (s, 1H), 7.12-7.15 (m, 2H), 7.33-7.40 (m, 5H);

FAB-MS (m/z): 389 (M+H)$^+$.

(Step 2)

In the same manner as in the step 4 in Example 1, Compound 69 (1.4 g, 73%) was obtained from methyl 2-acetyl-3,5-bis(methoxymethoxy)-6-phenylphenylacetate (2.5 g, 6.4 mmol) obtained in the above, using methanol (40 mL) and 1,4-dioxane solution (40 mL) of 4 mol/L hydrogen chloride.

$^1$H-NMR (CDCl$_3$, 270 MHz) δ (ppm): 2.58 (s, 3H), 3.59 (s, 3H), 3.69 (s, 2H), 4.97 (s, 1H), 6.54 (s, 1H), 7.22-7.25 (m, 2H), 7.48-7.52 (m, 3H), 12.02 (s, 1H);

APCI-MS (m/z): 299 (M–H)$^-$.

Elementary Analysis (as C$_{17}$H$_{16}$O$_5$):

Measured (%): C:67.99, H:5.14, N:0

Calculated (%): C:67.99, H:5.37, N:0

EXAMPLE 70

Methyl 2-benzyl-3,5-dihydroxy-6-phenylphenylacetate (Compound 70)

(Step 1)

In an argon atmosphere, methyl 2-iodo-3,5-bis(methoxymethoxy)-6-phenylphenylacetate (0.40 g, 0.85 mmol) obtained in the step 1 in Example 13 was dissolved in tetrahydrofuran (10 mL), and tetrahydrofuran solution of 0.5 mol/L zinc benzyl bromide (3.0 mL, 1.5 mmol) and bis(triphenylphosphine)palladium(II) dichloride (60 mg, 0.085 mmol) were added thereto and stirred at 60° C. for 14 hours. The reaction mixture was cooled to room temperature, and 3 mol/L hydrochloric acid (10 mL) was added thereto, and extracted with ethyl acetate (0.10 L). The organic layer was washed with aqueous saturated sodium hydrogencarbonate solution (20 mL) and aqueous saturated sodium chloride solution (10 mL), then dried over anhydrous sodium sulfate, and concentrated under reduced pressure. The resulting residue was purified through silica gel column chromatography (n-hexane/ethyl acetate=1/9 to 1/3) to obtain methyl 2-benzyl-3,5-bis(methoxymethoxy)-6-phenylphenylacetate (0.31 g, 85%).

$^1$H-NMR (CDCl$_3$, 270 MHz) δ (ppm): 3.28 (s, 3H), 3.33 (s, 2H), 3.39 (s, 3H), 3.43 (s, 3H), 4.04 (s, 2H), 5.00, (s, 2H), 5.18 (s, 2H), 7.00 (s, 1H), 7.10-7.38 (m, 10H);

FAB-MS (m/z): 437 (M–H)$^-$.

(Step 2)

In the same manner as in the step 4 in Example 1, Compound 70 (76 mg, 82%) was obtained from methyl 2-benzyl-3,5-bis(methoxymethoxy)-6-phenylphenylacetate (0.12 g, 0.27 mmol) obtained in the above, using methanol (3.0 mL) and 1,4-dioxane solution (3.0 mL) of 4 mol/L hydrogen chloride.

$^1$H-NMR (CDCl$_3$, 270 MHz) δ (ppm): 3.39 (s, 2H), 3.45 (s, 3H), 4.00 (s, 2H), 4.63 (s, 1H), 5.02 (s, 1H), 6.46 (s, 1H), 7.15-7.50 (m, 10H);

FAB-MS (m/z): 349 (M+H)$^+$.

Elementary Analysis (as C$_{22}$H$_{20}$O$_4$·0.5H$_2$O):

Measured (%): C:74.04, H:6.05, N:0

Calculated (%): C:73.93, H:5.92, N:0

EXAMPLE 71

6-Bromo-5-[(2-methoxyethoxy)methyl]-4-phenyl-benzene-1,3-diol (Compound 71)

(Step 1)

4-Bromo-3-bromomethyl-1,5-bis(methoxymethoxy)-2-phenylbenzene (100 mg, 0.224 mmol) obtained in the step 1 in Example 44 was dissolved in N,N-dimethylformamide (5 mL), and 60% sodium hydride/mineral oil dispersion (29.6 mg, 0.740 mmol) and 2-methoxyethanol (0.0707 mL, 0.897 mmol) were added thereto and stirred at room temperature for 2 hours. Water and methanol was added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through partitioning thin-layer chromatography (n-hexane/ethyl acetate=2/1) to obtain 4-bromo-3-[(2-methoxyethoxy)methyl]-1,5-bis(methoxymethoxy)-2-phenylbenzene (73.6 mg, 74%).

$^1$H-NMR (270 MHz, CDCl$_3$) δ (ppm): 3.26 (s, 3H), 3.33 (s, 3H), 3.47 (s, 4H), 3.55 (s, 3H), 4.34 (s, 2H), 4.97 (s, 2H), 5.27 (s, 2H), 7.03 (s, 1H), 7.20-7.42 (m, 5H).

(Step 2)

In the same manner as in the step 2 in Example 25, Compound 71 (46.1 mg, 80%) was obtained from 4-bromo-3-[(2-methoxyethoxy)methyl]-1,5-bis(methoxymethoxy)-2-phenylbenzene (71.9 mg, 0.163 mmol) obtained in the above, using ethanol (8 mL) and concentrated hydrochloric acid (0.2 mL).

$^1$H-NMR (270 MHz, CDCl$_3$) δ (ppm): 3.32 (s, 3H), 3.46 (s, 4H), 4.30 (s, 2H), 4.85 (s, 1H), 5.73 (s, 1H), 6.69 (s, 1H), 7.20-7.38 (m, 2H), 7.40-7.50 (m, 3H);

APCI-MS (m/z): 351, 353 (M−H)$^-$.

EXAMPLE 72

6-Bromo-5-[2-(2-methoxyethoxy)ethoxymethyl]-4-phenylbenzene-1,3-diol (Compound 72)

(Step 1)

In the same manner as in the step 1 in Example 71, 4-bromo-3-[2-(2-methoxyethoxy)ethoxymethyl]-1,5-bis(methoxymethoxy)-2-phenylbenzene (64.1 mg, 59%) was obtained from 3,4-dibromo-1,5-bis(methoxymethoxy)-2-phenylbenzene (100 mg, 0.224 mmol) obtained in the step 1 in Example 44, using 60% sodium hydride/mineral oil dispersion (48.5 mg, 1.21 mmol) and diethylene glycol monomethyl ether (0.107 mL, 0.899 mmol).

$^1$H-NMR (270 MHz, CDCl$_3$) δ (ppm): 3.26 (s, 3H), 3.37 (s, 3H), 3.55 (s, 3H), 3.50-3.64 (m, 8H), 4.33 (s, 2H), 4.97 (s, 2H), 5.27 (s, 2H), 7.03 (s, 1H), 7.20-7.42 (m, 5H).

(Step 2)

In the same manner as in the step 2 in Example 25, Compound 72 (45.6 mg, 88%) was obtained from 4-bromo-3-[2-(2-methoxyethoxy)ethoxymethyl]-1,5-bis(methoxymethoxy)-2-phenylbenzene (63.0 mg, 0.130 mmol) obtained in the above, using ethanol (8 mL) and concentrated hydrochloric acid (0.2 mL).

$^1$H-NMR (270 MHz, CDCl$_3$) δ (ppm): 3.37 (s, 3H), 3.54-3.62 (m, 8H), 4.29 (s, 2H), 4.86 (s, 1H), 5.74 (s, 1H), 6.70 (s, 1H), 7.30-7.38 (m, 2H), 7.40-7.50 (m, 3H);

APCI-MS (m/z): 395, 397 (M−H)$^-$.

EXAMPLE 73

Methyl 2-(4-acetylphenyl)-3,5-dihydroxyphenylacetate (Compound 73)

In the same manner as in the step 3 in Example 1, methyl 2-(4-acetylphenyl)-3,5-bis(methoxymethoxy)phenylacetate was obtained from methyl 2-bromo-3,5-bis(methoxymethoxy)phenylacetate (120 mg, 0.34 mmol) obtained in the step 2 in Example 1, using 4-acetylphenylboronic acid (85 mg, 0.52 mmol), bis(tri-o-tolylphosphine)palladium(II) dichloride (10 mg, 0.017 mmol), cesium fluoride (420 mg, 1.0 mmol), 1,2-dimethoxyethane (3.0 mL) and water (0.5 mL). Then, from the resulting compound, obtained was Compound 73 (82 mg, 80%) in the same manner as in the step 4 in Example 1, using methanol (2.0 mL) and 1,4-dioxane solution (1.0 mL) of 4 mol/L hydrogen chloride.

$^1$H-NMR (270 MHz, DMSO-d$_6$) δ (ppm): 2.58 (s, 3H), 3.31 (s, 2H), 3.45 (s, 2H), 6.22 (d, J=1.7 Hz, 1H), 6.32 (d, J=1.7 Hz, 1H), 7.92 (d, J=8.2 Hz, 2H), 8.05 (d, J=8.2 Hz, 2H), 9.21 (s, 1H), 9.34 (s, 1H);

APCI-MS (m/z): 299 (M−H)$^-$.

EXAMPLE 74

Methyl 3,5-dihydroxy-2-[3-(trifluoromethoxy)phenyl]phenylacetate (Compound 74)

In the same manner as in the step 3 in Example 1, methyl 3,5-bis(methoxymethoxy)-2-[3-(trifluoromethoxy)phenyl]phenylacetate was obtained from methyl 2-bromo-3,5-bis(methoxymethoxy)phenylacetate (110 mg, 0.30 mmol) obtained in the step 2 in Example 1, using 3-trifluoromethoxyphenylboronic acid (100 mg, 0.49 mmol), bis(tri-o-tolylphosphine)palladium(II) dichloride (10 mg, 0.017 mmol), cesium carbonate (300 mg, 0.92 mmol), 1,2-dimethoxyethane (3.0 mL) and water (0.5 mL). Then, from the resulting compound, obtained was Compound 74 (60 mg, 58%) in the same manner as in the step 4 in Example 1, using methanol (2.0 mL) and 1,4-dioxane solution (1.0 mL) of 4 mol/L hydrogen chloride.

$^1$H-NMR (270 MHz, DMSO-d$_6$) δ (ppm): 3.28 (s, 3H), 3.29 (s, 2H), 6.21 (d, J=2.2 Hz, 1H), 6.31 (d, J=2.2 Hz, 1H), 7.01 (s, 1H), 7.12 (d, J=8.1 Hz, 1H), 7.24 (d, J=8.1 Hz, 1H), 7.46 (t, J=8.1 Hz, 1H), 9.23 (s, 1H), 9.34 (s, 1H);

APCI-MS (m/z): 341 (M−H)$^-$.

EXAMPLE 75

Methyl 3,5-dihydroxy-2-[4-(trifluoromethoxy)phenyl]phenylacetate (Compound 75)

In the same manner as in the step 3 in Example 1, methyl 3,5-bis(methoxymethoxy)-2-[4-(trifluoromethoxy)phenyl]phenylacetate was obtained from methyl 2-bromo-3,5-bis(methoxymethoxy)phenylacetate (110 mg, 0.30 mmol) obtained in the step 2 in Example 1, using 4-trifluoromethoxyphenylboronic acid (100 mg, 0.49 mmol), bis(tri-O-tolylphosphine)palladium(II) dichloride (10 mg, 0.017 mmol), cesium carbonate (300 mg, 0.92 mmol), 1,2-dimethoxyethane (3.0 mL) and water (0.5 mL). Then, from the resulting compound, obtained was Compound 75 (75 mg, 73%) in the same manner as in the step 4 in Example 1, using methanol (2.0 mL) and 1,4-dioxane solution (1.0 mL) of 4 mol/L hydrogen chloride.

APCI-MS (m/z): 341 (M−H)$^-$.

EXAMPLE 76

Methyl 3,5-dihydroxy-2-[3-(hydroxymethyl)phenyl]phenylacetate (Compound 76)

In the same manner as in the step 3 in Example 1, methyl 2-[3-(hydroxymethyl)phenyl]-3,5-bis(methoxymethoxy)phenylacetate was obtained from methyl 2-bromo-3,5-bis(methoxymethoxy)phenylacetate (110 mg, 0.30 mmol) obtained in the step 2 in Example 1, using 3-hydroxymethylphenylboronic acid (70 mg, 0.46 mmol), bis(tri-o-tolylphosphine)palladium(II) dichloride (10 mg, 0.017 mmol), cesium carbonate (300 mg, 0.92 mmol), 1,2-dimethoxyethane (3.0 mL) and water (0.5 mL). Then, from the resulting compound, obtained was Compound 76 (29 mg, 34%) in the same manner as in the step 4 in Example 1, using methanol (2.0 mL) and 1,4-dioxane solution (1.0 mL) of 4 mol/L hydrogen chloride.

$^1$H-NMR (270 MHz, CDCl$_3$) δ (ppm): 3.32 (s, 2H), 3.55 (s, 3H), 4.63 (s, 2H), 6.36 (s, 2H), 7.13 (d, J=7.3 Hz, 1H), 7.20 (s, 1H), 7.30-7.39 (m, 2H);
APCI-MS (m/z): 287 (M−H)$^-$.

EXAMPLE 77

Methyl 3,5-dihydroxy-2-(3-nitrophenyl)phenylacetate (Compound 77)

In the same manner as in the step 3 in Example 1, methyl 3,5-bis(methoxymethoxy)-2-(3-nitrophenyl)phenylacetate was obtained from methyl 2-bromo-3,5-bis(methoxymethoxy)phenylacetate (110 mg, 0.32 mmol), using 3-nitrophenylboronic acid (80 mg, 0.48 mmol), bis(tri-o-tolylphosphine)palladium(II) dichloride (10 mg, 0.017 mmol), cesium carbonate (300 mg, 0.92 mmol), 1,2-dimethoxyethane (3.0 mL) and water (0.5 mL). Then, from the resulting compound, obtained was Compound 77 (68 mg, 70%) in the same manner as in the step 4 in Example 1, using methanol (2.0 mL) and 1,4-dioxane solution (1.0 mL) of 4 mol/L hydrogen chloride.

$^1$H-NMR (270 MHz, DMSO-d$_6$) δ (ppm): 3.30 (s, 2H), 3.44 (s, 3H), 6.25 (d, J=1.4 Hz, 1H), 6.35 (d, J=1.4 Hz, 1H), 7.57 (dd, J=7.6, 1.4 Hz, 1H), 7.64 (t, J=7.6 Hz, 1H), 7.90 (br s, 1H), 8.15 (dt, J=7.6, 1.4 Hz, 1H), 9.36 (s, 1H), 9.47 (s, 1H);
APCI-MS (m/z): 302 (M−H)$^-$.

EXAMPLE 78

Methyl 2-(3-cyanophenyl)-3,5-dihydroxyphenylacetate (Compound 78)

In the same manner as in the step 3 in Example 1, methyl 2-(3-cyanophenyl)-3,5-bis(methoxymethoxy)phenylacetate was obtained from methyl 2-bromo-3,5-bis(methoxymethoxy)phenylacetate (110 mg, 0.31 mmol), using 3-cyanophenylboronic acid (70 mg, 0.48 mmol), bis(tri-o-tolylphosphine)palladium(II) dichloride (10 mg, 0.017 mmol), cesium carbonate (300 mg, 0.92 mmol), 1,2-dimethoxyethane (3.0 mL) and water (0.5 mL). Then, from the resulting compound, obtained was Compound 78 (72 mg, 82%) in the same manner as in the step 4 in Example 1, using methanol (2.0 mL) and 1,4-dioxane solution (1.0 mL) of 4 mol/L hydrogen chloride.

$^1$H-NMR (270 MHz, DMSO-d$_6$) δ (ppm): 3.21 (s, 2H), 3.44 (s, 3H), 6.23 (d, J=2.2 Hz, 1H), 6.33 (d, J=2.2 Hz, 1H), 7.43 (dt, J=7.8, 1.6 Hz, 1H), 7.49 (t, J=1.6 Hz, 1H), 7.54 (t, J=7.8 Hz, 1H), 7.73 (dt, J=7.8, 1.6 Hz, 1H), 9.38 (s, 1H), 9.28 (s, 1H);
APCI-MS (m/z): 282 (M−H)$^-$.

EXAMPLE 79

Methyl 3,5-dihydroxy-2-(4-phenylphenyl)phenylacetate (Compound 79)

In the same manner as in the step 3 in Example 1, methyl 3,5-bis(methoxymethoxy)-2-(4-phenylphenyl)phenylacetate was obtained from methyl 2-bromo-3,5-bis(methoxymethoxy)phenylacetate (110 mg, 0.31 mmol), using 4-biphenylboronic acid (91 mg, 0.46 mmol), bis(tri-o-tolylphosphine)palladium(II) dichloride (10 mg, 0.017 mmol), cesium carbonate (300 mg, 0.92 mmol), 1,2-dimethoxyethane (3.0 mL) and water (0.5 mL). Then, from the resulting compound, obtained was Compound 79 (31 mg, 30%) in the same manner as in the step 4 in Example 1, using methanol (2.0 mL) and 1,4-dioxane solution (1.0 mL) of 4 mol/L hydrogen chloride.

$^1$H-NMR (270 MHz, CDCl$_3$) δ (ppm): 3.37 (s, 2H), 3.60 (s, 3H), 4.92 (s, 1H), 5.51 (br s, 1H), 6.41 (s, 2H), 7.05-7.25 (m, 7H), 7.35-7.41 (m, 2H);
APCI-MS (m/z): 333 (M−H)$^-$.

EXAMPLE 80

Methyl 3,5-dihydroxy-2-(4-phenoxyphenyl)phenylacetate (Compound 80)

In the same manner as in the step 3 in Example 1, methyl 3,5-bis(methoxymethoxy)-2-(4-phenoxyphenyl)phenylacetate was obtained from methyl 2-bromo-3,5-bis(methoxymethoxy)phenylacetate (110 mg, 0.31 mmol), using 4-phenoxyphenylboronic acid (100 mg, 0.47 mmol), bis(tri-o-tolylphosphine)palladium(II) dichloride (10 mg, 0.017 mmol), cesium carbonate (300 mg, 0.92 mmol), 1,2-dimethoxyethane (3.0 mL) and water (0.5 mL). Then, from the resulting compound, obtained was Compound 80 (69 mg, 64%) in the same manner as in the step 4 in Example 1, using methanol (2.0 mL) and 1,4-dioxane solution (1.0 mL) of 4 mol/L hydrogen chloride.

$^1$H-NMR (270 MHz, DMSO-d$_6$) δ (ppm): 3.31 (s, 2H), 3.47 (s, 3H), 6.22 (d, J=1.7 Hz, 1H), 6.32 (d, J=1.7 Hz, 1H), 7.18-7.16 (m, 2H), 7.32-7.49 (m, 3H), 7.61-7.70 (m, 4H), 9.10 (s, 1H), 9.26 (s, 1H);
FAB-MS (m/z): 350 (M+H)$^+$.

EXAMPLE 81

Methyl 3,5-dihydroxy-2-(3-methoxyphenyl)phenylacetate (Compound 81)

In the same manner as in the step 3 in Example 1, methyl 3,5-bis(methoxymethoxy)-2-(3-phenoxyphenyl)phenylacetate was obtained from methyl 2-bromo-3,5-bis(methoxymethoxy)phenylacetate (110 mg, 0.31 mmol), using 3-phenoxyphenylboronic acid (71 mg, 0.47 mmol), bis(tri-o-tolylphosphine)palladium(II) dichloride (10 mg, 0.017 mmol), cesium carbonate (300 mg, 0.92 mmol), 1,2-dimethoxyethane (3.0 mL) and water (0.5 mL). Then, from the resulting compound, obtained was Compound 81 (50 mg, 56%) in the same manner as in the step 4 in Example 1, using methanol (2.0 mL) and 1,4-dioxane solution (1.0 mL) of 4 mol/L hydrogen chloride.

$^1$H-NMR (270 MHz, CDCl$_3$) δ (ppm): 3.37 (s, 2H), 3.60 (s, 3H), 3.80 (s, 3H), 6.40 (d, J=2.5 Hz, 1H), 6.41 (d, J=2.5 Hz, 1H), 6.80-6.84 (m, 2H), 6.94 (dd, J=7.9 1.0 Hz, 1H), 7.37 (t, J=7.9 Hz, 1H);

FAB-MS (m/z): 298 (M+H)$^+$.

EXAMPLE 82

Methyl 3,5-dihydroxy-2-(4-methoxyphenyl)phenylacetate (Compound 82)

In the same manner as in the step 3 in Example 1, methyl 3,5-bis(methoxymethoxy)-2-(4-methoxyphenyl)phenylacetate was obtained from methyl 2-bromo-3,5-bis(methoxymethoxy)phenylacetate (110 mg, 0.31 mmol), using 4-methoxyphenylboronic acid (71 mg, 0.47 mmol), bis(tri-o-tolylphosphine)palladium(II) dichloride (10 mg, 0.017 mmol), cesium carbonate (300 mg, 0.92 mmol), 1,2-dimethoxyethane (3.0 mL) and water (0.5 mL). Then, from the resulting compound, obtained was Compound 82 (36 mg, 40%) in the same manner as in the step 4 in Example 1, using methanol (2.0 mL) and 1,4-dioxane solution (1.0 mL) of 4 mol/L hydrogen chloride.

$^1$H-NMR (270 MHz, CDCl$_3$) δ (ppm): 3.35 (s, 2H), 3.59 (s, 3H), 3.84 (s, 3H), 4.95 (br s, 1H), 6.40 (s, 2H), 6.60 (br s, 1H), 6.98-7.01 (m, 2H), 7.15-7.19 (m, 2H);

FAB-MS (m/z): 288 (M+H)$^+$.

EXAMPLE 83

6-Ethyl-5-(2-methoxyethyl)-4-phenylbenzene-1,3-diol (Compound 83)

(Step 1)

In an argon atmosphere, methyl 2-ethyl-3,5-bis(methoxymethoxy)-6-phenylphenylacetate (9.7 g, 26 mmol) obtained in the step 2 in Example 52 was dissolved in tetrahydrofuran (50 mL), and the solution was cooled to 4° C., and then tetrahydrofuran (50 mL) suspension of lithium aluminium hydride (0.13 g, 34 mmol) was dropwise added thereto, taking 10 minutes. The reaction mixture was stirred at 4° C. for 1 hour, and then sodium sulfate 10-hydrate (20 g) was added thereto and stirred for 3 hours with heating up to room temperature. The white suspension was filtered, and the filtrate was concentrated under reduced pressure to obtain 2-[2-ethyl-3,5-bis(methoxymethoxy)-6-phenylphenyl]ethanol (8.4 g, 94%).

$^1$H-NMR (CDCl$_3$, 270 MHz) δ (ppm): 1.17 (t, J=7.4 Hz, 3H), 2.68-2.78 (m, 4H), 3.23 (s, 3H), 3.53 (s, 3H), 3.48-3.56 (m, 2H), 4.94 (s, 2H), 5.23 (s, 2H), 6.86 (s, 1H), 7.19-7.42 (m, 5H);

APCI-MS (m/z): 347 (M+H)$^+$.

(Step 2)

In an argon atmosphere, 2-[2-ethyl-3,5-bis(methoxymethoxy)-6-phenylphenyl]ethanol (0.44 g, 1.3 mmol) obtained in the above was dissolved in N,N-dimethylformamide (5.0 mL), and the solution was cooled to 4° C., and then 60% sodium hydride/mineral oil dispersion (0.10 g, 2.5 mmol) was added thereto and stirred at 4° C. for 1 hour. Methyl iodide (0.17 mL, 2.7 mmol) was added to the reaction mixture, and stirred for 1 hour with heating up to room temperature. Aqueous saturated ammonium chloride solution (30 mL) and water (0.10 L) were added to the reaction mixture, and extracted twice with ethyl acetate (0.10 L). The organic layer was dried over anhydrous sodium sulfate, and then concentrated under reduced pressure, and the resulting residue was purified through preparative thin-layer chromatography (ethyl acetate/n-hexane=1/2) to obtain 4-ethyl-3-(2-methoxyethyl)-1,5-bis(methoxymethoxy)-2-phenylbenzene (0.38 g, 83%).

$^1$H-NMR (CDCl$_3$, 270 MHz) δ (ppm): 1.17 (t, J=7.4 Hz, 3H), 2.67-2.77 (m, 4H), 3.10 (s, 3H), 3.22-3.28 (m, 2H), 3.23 (s, 3H), 3.52 (s, 3H), 4.94 (s, 2H), 5.22 (s, 2H), 6.85 (s, 1H), 7.18-7.42 (m, 5H);

FAB-MS (m/z): 361 (M+H)$^+$.

(Step 3)

In the same manner as in the step 4 in Example 1, Compound 83 (3.2 g, 90%) was obtained from 4-ethyl-3-(2-methoxyethyl)-1,5-bis(methoxymethoxy)-2-phenylbenzene (0.38 g, 1.0 mmol) obtained in the above, using methanol (5.0 mL) and 1,4-dioxane solution (70 mL) of 4 mol/L hydrogen chloride.

$^1$H-NMR (CDCl$_3$, 270 MHz) δ (ppm): 1.19 (t, J=7.5 Hz, 3H), 2.65-2.75 (m, 4H), 3.50-3.57 (m, 2H), 3.71 (s, 3H), 4.50 (s, 1H), 4.87 (s, 1H), 6.36 (s, 1H), 7.26-7.29 (m, 2H), 7.40-7.53 (m, 3H);

APCI-MS (m/z): 273 (M+H)$^+$.

Elementary Analysis (as C$_{17}$H$_{20}$O$_3$):

Measured (%): C:74.99, H:7.55, N:0

Calculated (%): C:74.97, H:7.40, N:0

EXAMPLE 84

6-Ethyl-5-(2-hydroxyethyl)-4-phenylbenzene-1,3-diol (Compound 84)

2-[2-Ethyl-3,5-bis(methoxymethoxy)-6-phenylphenyl]ethanol (5.2 g, 15 mmol) obtained in the step 1 in Example 83 was dissolved in methanol (70 mL), and the solution was cooled to 4° C., and then 1,4-dioxane solution (70 mL) of 4 mol/L hydrogen chloride was added thereto and stirred for 1 hour with heating up to room temperature. The reaction solution was concentrated under reduced pressure, and chloroform was added thereto, and the resulting crystal was taken out through filtration. The crystal was washed with a mixed solvent (ethyl acetate/n-hexane=1/99) to obtain Compound 84 (3.4 g, 88%)

$^1$H-NMR (CDCl$_3$, 270 MHz) δ (ppm): 1.19 (t, J=7.5 Hz, 3H), 2.65-2.75 (m, 4H), 3.48-3.56 (m, 2H), 4.50 (s, 1H), 4.80 (s, 1H), 6.37 (s, 1H), 7.28-7.53 (m, 5H);

FAB-MS (m/z): 259 (M+H)$^+$.

Elementary Analysis (as C$_{16}$H$_{18}$O$_3$.0.2H$_2$O):

Measured (%): C:73.66, H:6.99, N:0

Calculated (%): C:73.37, H:7.08, N:0

EXAMPLE 85

6-Bromo-5-[(oxolan-2-ylmethoxy)methyl]-4-phenylbenzene-1,3-diol (Compound 85)

(Step 1)

In the same manner as in the step 1 in Example 71, 4-bromo-1,5-bis(methoxymethoxy)-3-[(oxolan-2-ylmethoxy)methyl]-2-phenylbenzene (76.5 mg, 73%) was obtained from 3,4-dibromo-1,5-bis(methoxymethoxy)-2-phenylbenzene (100 mg, 0.224 mmol) obtained in the step 1 in Example 44, using 60% sodium hydride/mineral oil dispersion (44.9 mg, 1.12 mmol) and tetrahydrofurfuryl alcohol (0.0870 mL, 0.898 mmol).
$^1$H-NMR (270 MHz, CDCl$_3$) δ (ppm): 1.50-1.70 (m, 1H), 1.75-2.00 (m, 3H), 3.22-3.42 (m, 2H), 3.26 (s, 3H), 3.55 (s, 3H), 3.62-3.84 (m, 2H), 3.90-4.02 (m, 1H), 4.33 (s, 2H), 4.97 (s, 12H), 5.27 (s, 2H), 7.03 (s, 1H), 7.20-7.42 (m, 5H).

(Step 2)
In the same manner as in the step 2 in Example 25, Compound 85 (49.9 mg, 82%) was obtained from 4-bromo-1,5-bis(methoxymethoxy)-3-[(oxolan-2-ylmethoxy)methyl]-2-phenylbenzene (75.0 mg, 0.160 mmol) obtained in the above, using ethanol (8 mL) and concentrated hydrochloric acid (0.2 mL).
$^1$H-NMR (270 MHz, CDCl$_3$) δ (ppm): 1.50-1.70 (m, 1H), 1.76-1.98 (m, 3H), 3.25-3.40 (m, 2H), 3.60-3.85 (m, 2H), 3.88-4.00 (m, 1H), 4.29 (s, 2H), 4.84 (s, 1H), 5.73 (s, 1H), 6.70 (s, 1H), 7.20-7.37 (m, 2H), 7.42-7.55 (m, 3H);
FAB-MS (m/z): 401, 403 (M+Na)$^+$.

EXAMPLE 86

6-Bromo-5-[2-(2-methoxymethoxy)ethyl]-4-phenyl-benzene-1,3-diol (Compound 86)

(Step 1)
In the same manner as in the step 1 in Example 64, 4-bromo-3-[2-(2-methoxyethoxy)ethyl]-1,5-bis(methoxymethoxy)-2-phenylbenzene (40.4 mg, 46%) was obtained from 2-[2-bromo-3,5-bis(methoxymethoxy)-6-phenylphenyl]ethanol (75.9 mg, 0.191 mmol) obtained in the step 1 in Example 62, using 60% sodium hydride/mineral oil dispersion (21.0 mg, 0.525 mmol), 2-bromoethyl methyl ether (0.180 mL, 1.92 mmol) and sodium iodide (115 mg, 0.766 mmol).
$^1$H-NMR (270 MHz, CDCl$_3$) δ (ppm): 2.85-3.00 (m, 2H), 3.26 (s, 3H), 3.32 (s, 3H), 3.38-3.52 (m, 6H), 3.56 (s, 3H), 4.97 (s, 2H), 5.27 (s, 2H), 6.93 (s, 1H), 7.10-7.20 (m, 2H), 7.30-7.45 (m, 3H).

(Step 2)
In the same manner as in the step 2 in Example 25, Compound 86 (28.1 mg, 90%) was obtained from 4-bromo-3-[2-(2-methoxyethoxy)ethyl]-1,5-bis(methoxymethoxy)-2-phenylbenzene (38.8 mg, 0.0852 mmol) obtained in the above, using ethanol (8 mL) and concentrated hydrochloric acid (0.2 mL).
$^1$H-NMR (270 MHz, CDCl$_3$) δ (ppm): 2.80-2.92 (m, 2H), 3.33 (s, 3H), 3.42 (s, 4H), 3.40-3.50 (m, 2H), 4.64 (s, 1H), 5.66 (s, 1H), 6.61 (s, 1H), 7.20-7.60 (m, 5H);
APCI-MS (m/z): 365, 367 (M−H)$^-$.

EXAMPLE 87

Methyl 3-(2-bromo-3,5-dihydroxy-6-phenylphenyl)propanoate (Compound 87)

(Step 1)
[3,5-Bis(methoxymethoxy)-2-phenylphenyl]methanol (2.10 g, 6,89 mmol) obtained in the step 1 in Example 15 was dissolved in dichloromethane (100 mL), and pyridinium dichromate (5.19 g, 13.8 mmol) was added thereto and stirred for 6 hours under reflux with heating. The reaction mixture was filtered, and the filtrate was concentrated under reduced pressure. The resulting residue was purified through silica gel column chromatography (n-hexane/ethyl acetate=19/1 to 16/1 to 9/1) to obtain 3,5-bis(methoxymethoxy)-2-phenyl-benzaldehyde (628 mg, 30%).
$^1$H-NMR (270 MHz, CDCl$_3$) δ (ppm): 3.33 (s, 3H), 3.51 (s, 3H), 5.07 (s, 2H), 5.25 (s, 2H), 7.12 (d, J=2.6 Hz, 1H), 7.30-7.50 (m, 6H), 9.69 (s, 1H).

(Step 2)
3,5-Bis(methoxymethoxy)-2-phenylbenzaldehyde (237 mg, 0.785 mmol) obtained in the above was dissolved in toluene (10 mL), and methyl triphenylphospholanylidene-acetate (695 mg, 2.08 mmol) was added thereto and stirred at 80° C. for 6 hours. The reaction mixture was concentrated under reduced pressure, and the resulting residue was purified through silica gel column chromatography (n-hexane/ethyl acetate 20/1 to 9/1 to 4/1) to obtain methyl 3-[3,5-bis(methoxymethoxy)-2-phenylphenyl]acrylate (267 mg, 95%).
$^1$H-NMR (270 MHz, CDCl$_3$) δ (ppm): 33.30 (s, 3H), 3.52 (s, 3H), 3.70 (s, 3H), 5.02 (s, 2H), 5.22 (s, 2H), 6.30 (d, J=16.0 Hz, 1H), 7.05 (d, J=2.3 Hz, 1H), 7.19 (d, J=1.5 Hz, 1H), 7.15-7.45 (m, 6H).

(Step 3)
Methyl 3-[3,5-bis(methoxymethoxy)-2-phenylphenyl]acrylate (265 mg, 0.740 mmol) obtained in the above was dissolved in methanol (15 mL), and the solution was cooled to 0° C., and nickel(II) chloride 6-hydrate (524 mg, 2.20 mmol) and sodium borohydride (152 mg, 4.00 mmol) were added thereto and stirred at the same temperature for 6 hours. Water was added to the reaction mixture, dried over anhydrous sodium sulfate, and the solvent was evaporated away under reduced pressure to obtain methyl 3-[3,5-bis(methoxymethoxy)-2-phenylphenyl]propanoate (273 mg, 100%).
$^1$H-NMR (270 MHz, CDCl$_3$) δ (ppm): 2.30-2.40 (m, 2H), 2.65-2.75 (m, 2H), 3.27 (s, 3H), 3.51 (s, 3H), 3.59 (s, 3H), 4.98 (s, 2H), 5.18 (s, 2H), 6.66 (d, J=2.3 Hz, 1H), 6.75 (d, J=2.3 Hz, 1H), 7.15-7.42 (m, 5H).

(Step 4)
Methyl 3-[3,5-bis(methoxymethoxy)-2-phenylphenyl]propanoate (69.1 mg, 0.192 mmol) obtained in the above was dissolved in N,N-dimethylformamide (4 mL), and N-bromosuccinimide (47.6 mg, 0.267 mmol) was added thereto and stirred at room temperature for 4 hours. Water was added to the reaction mixture, and extracted with chloroform. The organic layer was washed with aqueous saturated sodium thiosulfate solution and aqueous saturated sodium chloride solution in order, and dried over anhydrous sodium sulfate, and the solvent was evaporated away under reduced pressure. The resulting residue was purified through preparative thin-layer chromatography (n-hexane/ethyl acetate=2/1) to obtain methyl 3-[2-bromo-3,5-bis(methoxymethoxy)-6-phenylphenyl]propanoate (69.4 mg, 82%).
$^1$H-NMR (270 MHz, CDCl$_3$) δ (ppm): 2.35-2.45 (m, 2H), 2.82-2.98 (m, 2H), 3.26 (s, 3H), 3.56 (s, 3H), 4.97 (s, 2H), 5.27 (s, 2H), 6.94 (s, 1H), 7.10-7.20 (m, 2H), 7.28-7.44 (m, 3H).

(Step 5)
In the same manner as in the step 2 in Example 25, Compound 87 (15.4 mg, 29%) was obtained from methyl 3-[2-bromo-3,5-bis(methoxymethoxy)-6-phenylphenyl]propanoate (65.4 mg, 0.149 mmol) obtained in the above, using methanol (8 mL) and concentrated hydrochloric acid (0.2 mL).
$^1$H-NMR (270 MHz, CDCl$_3$) δ (ppm): 2.35-2.45 (m, 2H), 2.80-2.90 (m, 2H), 3.59 (s, 3H), 4.66 (s, 1H), 5.67 (s, 1H), 6.62 (s, 1H), 7.20-7.30 (m, 2H), 7.40-7.55 (m, 3H);
APCI-MS (m/z): 349, 351 (M−H)$^-$.

EXAMPLE 88

2-(2-Bromo-3,5-dihydroxy-6-phenylphenyl)-1-[4-(2-methoxyphenyl)piperazin-1-yl]ethanone (Compound 88)

In the same manner as in the step 3 in Example 9, 2-[2-bromo-3,5-bis(methoxymethoxy)-6-phenylphenyl]-1-[4-(2-methoxyphenyl)piperazin-1-yl]ethanone was obtained from 2-bromo-3,5-bis(methoxymethoxy)-6-phenylphenylacetic acid (90 mg, 0.22 mmol) obtained in the step 2 in Example 9, using 1-[3-(dimethylamino)propyl]-3-ethylcarbodiimide hydrochloride (62 mg, 0.33 mmol), 1-hydroxybenzotriazole hydrate (45 mg, 0.33 mmol), 2-methoxyphenylpiperazine (65 mg, 0.33 mmol), N,N-dimethylformamide (1.5 mL) and chloroform (1.5 mL); and from the resulting compound, obtained was Compound 88 (45 mg, 41%), using 1,4-dioxane solution (1.5 mL) of 4 mol/L hydrogen chloride and methanol (1.5 mL).

$^1$H-NMR (270 MHz, DMSO-$d_6$) δ (ppm): 2.67-2.82 (m, 4H), 3.40-3.60 (m, 4H), 3.49 (s, 2H), 3.82 (s, 3H), 6.57 (s, 1H), 6.80-7.50 (m, 9H), 9.35 (s, 1H), 9.98 (s, 1H);
APCI-MS (m/z): 497, 499 (M+H)$^+$.

EXAMPLE 89

2-(2-Bromo-3,5-dihydroxy-6-phenylphenyl)-N-methyl-N-[2-(pyridin-2-yl)ethyl]acetamide (Compound 89)

In the same manner as in the step 3 in Example 9, 2-([2-bromo-3,5-bis(methoxymethoxy)-6-phenylphenyl]-N-methyl-N-[2-(pyridin-2-yl)ethyl]acetamide was obtained from 2-bromo-3,5-bis(methoxymethoxy)-6-phenylphenylacetic acid (90 mg, 0.22 mmol) obtained in the step 2 in Example 9, using 1-[3-(dimethylamino)propyl]-3-ethylcarbodiimide hydrochloride (62 mg, 0.33 mmol), 1-hydroxybenzotriazole hydrate (45 mg, 0.33 mmol), 2-(2-methylaminoethyl)pyridine (0.05 mL, 0.38 mmol), N,N-dimethylformamide (1.5 mL) and chloroform (1.5 mL); and from the resulting compound, obtained was Compound 89 (20 mg, 20%), using 1,4-dioxane solution (1.5 mL) of 4 mol/L hydrogen chloride and methanol (1.5 mL).

$^1$H-NMR (270 MHz, DMSO-$d_6$) δ (ppm): 2.61 (s, 3H), 3.17 (m, 2H), 3.32 (s, 2H), 3.69 (m, 2H), 6.56 (s, 1H), 6.98-7.06 (m, 3H), 7.25-7.33 (m, 2H), 7.74-7.87 (m, 2H), 8.41 (m, 1H), 8.69 (m, 1H), 9.25 (br s, 1H), 9.96 (br s, 1H);
APCI-MS (m/z): 441, 443 (M+H)$^+$.

EXAMPLE 90

2-(2-Bromo-3,5-dihydroxy-6-phenylphenyl)-1-[4-(3-cyanopyridin-2-yl)piperazin-1-yl]ethanone (Compound 90)

In the same manner as in the step 3 in Example 9, 2-[2-bromo-3,5-bis(methoxymethoxy)-6-phenylphenyl]-1-[4-(3-cyanopyridin-2-yl)piperazin-1-yl]ethanone was obtained from 2-bromo-3,5-bis(methoxymethoxy)-6-phenylphenylacetic acid (90 mg, 0.22 mmol) obtained in the step 2 in Example 9, using 1-[3-(dimethylamino)propyl]-3-ethylcarbodiimide hydrochloride (62 mg, 0.33 mmol), 1-hydroxybenzotriazole hydrate (45 mg, 0.33 mmol), 2-cyanopyridylpiperazine (65 mg, 0.35 mmol), N,N-dimethylformamide (1.5 mL) and chloroform (1.5 mL); and from the resulting compound, obtained was Compound 90 (65 mg, 60%), using 1,4-dioxane solution (1.5 mL) of 4 mol/L hydrogen chloride and methanol (1.5 mL).

$^1$H-NMR (270 MHz, DMSO-$d_6$) δ (ppm): 3.38-3.53 (m, 10H), 6.95 (dd, J=7.6, 5.0 Hz, 1H), 7.10 (m, 2H), 7.18-7.33 (m, 3H), 8.09 (dd, J=7.6, 2.0 Hz, 1H), 8.40 (dd, J=5.0, 2.0 Hz, 1H);
APCI-MS (m/z): 493, 495 (M+H)$^+$.

EXAMPLE 91

2-(2-Bromo-3,5-dihydroxy-6-phenylphenyl)-1-[4-(2-furoyl)piperazin-1-yl]ethanone (Compound 91)

In the same manner as in the step 3 in Example 9, 2-[2-bromo-3,5-bis(methoxymethoxy)-6-phenylphenyl]-1-[4-(2-furoyl)piperazin-1-yl]ethanone was obtained from 2-bromo-3,5-bis(methoxymethoxy)-6-phenylphenylacetic acid (90 mg, 0.22 mmol) obtained in the step 2 in Example 9, using 1-[3-(dimethylamino)propyl]-3-ethylcarbodiimide hydrochloride (62 mg, 0.33 mmol), 1-hydroxybenzotriazole hydrate (45 mg, 0.33 mmol), 1-(2-furoyl)piperazine (65 mg, 0.36 mmol), N,N-dimethylformamide (1.5 mL) and chloroform (1.5 mL); and from the resulting compound, obtained was Compound 91 (48 mg, 45%), using 1,4-dioxane solution (1.5 mL) of 4 mol/L hydrogen chloride and methanol (1.5 mL).

$^1$H-NMR (270 MHz, DMSO-$d_6$) δ (ppm): 3.33-3.55 (m, 10H), 6.57 (s, 1H), 6.62 (dd, J=3.3, 1.7 HZ, 1H), 7.00 (dd, J=3.3, 0.7 Hz, 1H), 7.07-7.11 (m, 2H), 7.22-7.35 (m, 3H), 7.83 (dd, J=1.7, 0.7 HZ, 1H), 9.24 (s, 1H), 9.95 (s, 1H);
APCI-MS (m/z): 403 (M-Br)$^-$.

EXAMPLE 92

1-[2,4-Dihydroxy-6-(2-methoxyethyl)-5-phenylphenyl]ethanone (Compound 92)

(Step 1)

In an argon atmosphere, methyl 3,5-bis(methoxymethoxy)-2-phenylphenylacetate (0.50 g, 1.4 mmol) obtained in the step 3 in Example 1 was dissolved in tetrahydrofuran (0.10 L), and the solution was cooled to 4° C., and then lithium aluminium hydride (0.10 g, 2.6 mmol) was added thereto and stirred at 4° C. for 0.5 hours. Sodium sulfate 10-hydrate was added to the reaction mixture, and stirred for 1.5 hours with heating up to room temperature. The white suspension was filtered, and the filtrate was concentrated under reduced pressure. The resulting crude product was purified through silica gel column chromatography (ethyl acetate/n-hexane=1/9 to 1/1) to obtain 2-[3,5-bis(methoxymethoxy)-2-phenylphenyl]ethanol (0.37 g, 81%).

$^1$H-NMR (270 MHz, CDCl$_3$) δ (ppm): 2.67 (t, J=7.2 Hz, 2H), 3.28 (s, 3H), 3.52 (s, 3H), 3.61 (t, J=7.2 Hz, 2H), 4.99 (s, 2H), 5.20 (s, 2H), 6.71 (d, J=2.4 Hz, 1H), 6.78 (d, J=2.4 Hz, 1H), 7.18-7.40 (m, 5H);
FAB-MS (m/z): 319 (M+H)$^+$.

(Step 2)

In an argon atmosphere, 2-[3,5-bis(methoxymethoxy)-2-phenylphenyl]ethanol (1.2 g, 3.7 mmol) obtained in the above was dissolved in N,N-dimethylformamide (15 mL), and the solution was cooled to 4° C., and then 60% sodium hydride/mineral oil suspension (0.30 g, 7.5 mmol) was added thereto and stirred at 4° C. for 45 minutes. Methyl iodide (0.17 mL, 2.7 mmol) was added to the reaction mixture, and stirred for 4 hours with heating up to room temperature. Aqueous saturated ammonium chloride solution (20 mL) and water (10 mL) were added to the reaction mixture, and extracted with ethyl acetate (0.10 L). The organic layer was washed with water (0.10 L), and then dried over anhydrous sodium sulfate, and the solvent was evaporated away under reduced pressure. The resulting residue was purified through silica gel column chromatography (ethyl acetate/n-hexane=1/9 to 1/2) to obtain 1-(2-methoxyethyl)-3,5-bis(methoxymethoxy)-2-phenylbenzene (1.1 g, 91%).

$^1$H-NMR (270 MHz, CDCl$_3$) δ (ppm): 2.66 (t, J=7.3 Hz, 2H), 3.19 (s, 3H), 3.27 (s, 3H), 3.38 (t, J=7.3 Hz, 2H), 3.51 (s, 3H), 4.98 (s, 2H), 5.19 (s, 2H), 6.71 (d, J=2.5 Hz, 1H), 6.76 (d, J=2.5 Hz, 1H), 7.18-7.41 (m, 5H);

FAB-MS (m/z): 333 (M+H)$^+$.

(Step 3)

1-(2-Methoxyethyl)-3,5-bis(methoxymethoxy)-2-phenylbenzene (4.3 g, 13 mmol) obtained in the above was dissolved in N,N-dimethylformamide (40 mL), and the solution was cooled to 4° C., and N-bromosuccinimide (2.3 g, 13 mmol) was added thereto and stirred for 40 minutes. Water (0.20 L) was added to the reaction solution, and extracted twice with a mixed solvent (n-hexane/ethyl acetate=1/2, 0.20 L), then dried over anhydrous sodium sulfate, and the solvent was evaporated away under reduced pressure. The resulting residue was purified through silica gel column chromatography (ethyl acetate/n-hexane=1/9 to 1/3) to obtain 4-bromo-3-(2-methoxyethyl)-1,5-bis(methoxymethoxy)-2-phenylbenzene (4.7 g, 88%).

$^1$H-NMR (270 MHz, CDCl$_3$) δ (ppm): 2.66 (dd, J=7.6, 8.6 Hz, 2H), 3.16 (s, 3H), 3.26 (s, 3H), 3.38 (dd, J=7.6, 8.6 Hz, 2H), 3.56 (s, 3H), 4.97 (s, 2H), 5.27 (s, 2H), 6.94 (s, 1H), 7.15-7.19 (m, 2H), 7.34-7.40 (m, 3H);

FAB-MS (m/z):; 411, 413 (M+H)$^+$.

(Step 4)

In an argon atmosphere, 4-bromo-3-(2-methoxyethyl)-1,5-bis(methoxymethoxy)-2-phenylbenzene (0.71 g, 1.7 mmol) obtained in the above was dissolved in tetrahydrofuran (10 mL), then the solution was cooled to −78° C., and n-hexane solution of 1.6 mol/L n-butyllithium (1.4 mL, 2.2 mmol) was added thereto and stirred for 5 minutes. Acetaldehyde (1.0 mL, 17.8 mmol) was added to the reaction solution, and stirred for 1 hour with heating from −78° C. up to room temperature. Water (5.0 mL) and aqueous saturated ammonium chloride solution (30 mL) were added in order to the reaction solution, and then extracted with ethyl acetate (0.10 L). The organic layer was dried over anhydrous sodium sulfate, and the solvent was evaporated away under reduced pressure. The resulting residue was purified through silica gel column chromatography (ethyl acetate/n-hexane=1/9 to 1/1) to obtain 1-[2-(2-methoxyethyl)-4,6-bis(methoxymethoxy)-3-phenylphenyl]ethanol (0.53 g, 82%).

$^1$H-NMR (270 MHz, CDCl$_3$) δ (ppm): 1.63 (d, J=6.6 Hz, 3H), 2.62-2.87 (m, 2H), 3.13 (s, 3H), 3.25 (s, 3H), 3.22-3.47 (m, 2H), 3.55 (s, 3H), 3.80 (d, J=10.2 Hz, 1H), 4.96 (s, 2H), 5.15 (m, 1H), 5.28 (d, J=6.8 Hz, 1H), 5.31 (d, J=6.8 Hz, 1H), 6.93 (s, 1H), 7.14-7.19 (m, 2H), 7.30-7.42 (m, 3H).

(Step 5)

1-[2-(2-Methoxyethyl)-4,6-bis(methoxymethoxy)-3-phenylphenyl]ethanol (0.52 g, 1.4 mmol) obtained in the above was dissolved in dichloromethane (10 mL), and Molecular Sieves 3 A (3.0 g) and pyridinium dichromate (1.3 g, 3.5 mmol) were added thereto and stirred at room temperature for 15 hours. The reaction mixture was filtered through Celite, the filtered residue was washed with chloroform, and the filtrate was concentrated under reduced pressure. The resulting residue was purified through silica gel column chromatography (ethyl acetate/n-hexane=1/9 to 1/2) to obtain 1-[2-(2-methoxyethyl)-4,6-bis(methoxymethoxy)-3-phenylphenyl]ethanone (0.44 g, 86%).

$^1$H-NMR (270 MHz, CDCl$_3$) δ (ppm): 2.56 (s, 3H), 2.66 (t, J=7.3 Hz, 2H), 3.08 (s, 3H), 3.22 (t, J=7.3 Hz, 2H), 3.27 (s, 3H), 3.50 (s, 3H), 5.00 (s, 2H), 5.20 (s, 2H), 6.88 (s, 1H), 7.16-7.20 (m, 2H), 7.32-7.42 (m, 3H);

APCI-MS (m/z): 375 (M+H)$^+$.

(Step 6)

In the same manner as in the step 4 in Example 1, Compound 92 (0.16 g, 67%) was obtained from 1-[2-(2-methoxyethyl)-4,6-bis(methoxymethoxy)-3-phenylphenyl]ethanone (0.30 g, 0.81 mmol) obtained in the above, using methanol (3.0 mL) and 1,4-dioxane solution (3.0 mL) of 4 mol/L hydrogen chloride.

$^1$H-NMR (270 MHz, CDCl$_3$) δ (ppm): 2.69 (s, 3H), 3.00 (t, J=7.3 Hz, 2H), 3.13 (s, 3H), 3.25 (t, J=7.3 Hz, 2H), 4.94 (s, 1H), 6.47 (s, 1H), 7.26-7.28 (m, 2H), 7.47-7.56 (m, 3H), 12.05 (br. s, 1H);

APCI-MS (m/z): 285 (M−H)$^-$.

Elementary Analysis (as C$_{17}$H$_{18}$O$_4$.0.2H$_2$O):
Measured (%): C:70.67, H:6.69, N:0.30
Calculated (%): C:70.43, H:6.40, N:0

EXAMPLE 93

1-[2,4-dihydroxy-6-(2-methoxyethyl)-5-phenylphenyl]-2-methylpropanone (Compound 93)

(Step 1)

In the same manner as in the step 4 in Example 92, 1-[2-(2-methoxyethyl)-4,6-bis(methoxymethoxy)-3-phenylphenyl]-2-methylpropanol (0.12 g, 69%) was obtained from 4-bromo-3-(2-methoxyethyl)-1,5-bis(methoxymethoxy)-2-phenylbenzene (0.18 g, 0.44 mmol) obtained in the step 3 in Example 92, using n-hexane solution of 1.6 mol/L n-butyllithium (0.32 mL, 0.51 mmol) and isobutylaldehyde (0.18 mL, 2.0 mmol).

$^1$H-NMR (270 MHz, CDCl$_3$) δ (ppm): 0.78 (d, J=6.8 Hz, 3H), 1.18 (d, J=6.8 Hz, 3H), 2.32 (m, 1H), 2.74-2.79 (m, 2H), 3.13 (s, 3H), 3.21-3.45 (m, 2H), 3.25 (s, 3H), 3.53 (s, 3H), 4.51 (m, 1H), 4.94 (d, J=6.7 Hz, 1H), 4.98 (d, J=6.7 Hz, 1H), 5.23 (d, J=6.8 Hz, 1H), 5.28 (d, J=6.8 Hz, 1H), 6.91 (s, 1H), 7.14-7.19 (m, 2H), 7.29-7.42 (m, 3H).

(Step 2)

In the same manner as in the step 5 in Example 92, 1-[2-(2-methoxyethyl)-4,6-bis(methoxymethoxy)-3-phenylphenyl]-2-methylpropanone (60 mg, 89%) was obtained from 1-[2-(2-methoxyethyl)-4,6-bis(methoxymethoxy)-3-phenylphenyl]-2-methylpropanol (68 mg, 0.17 mmol) obtained in the above, using Molecular Sieves 4 A (0.23 g) and pyridinium dichromate (0.18 g, 0.49 mmol).

$^1$H-NMR (270 MHz, CDCl$_3$) δ (ppm): 1.20 (d, J=6.9 Hz, 6H), 2.56 (t, J=8.0, 2H), 3.03 (s, 3H), 3.10-3.28 (m, 3H), 3.27 (s, 3H), 3.48 (s, 3H), 5.00 (s, 2H), 5.17 (s, 2H), 6.88 (s, 1H), 7.18-7.21 (m, 2H), 7.32-7.42 (m, 3H);

APCI-MS (m/z): 403 (M+H)$^+$.

(Step 3)

In the same manner as in the step 4 in Example 1, Compound 93 (33 mg, 85%) was obtained from 1-[2-(2-methoxyethyl)-4,6-bis(methoxymethoxy)-3-phenylphenyl]-2-methylpropanone (50 mg, 0.12 mmol) obtained in the above, using methanol (3.0 mL) and 1,4-dioxane-solution (3.0 mL) of 4 mol/L hydrogen chloride.

¹H-NMR (270 MHz, CDCl₃) δ (ppm): 1.20 (d, J=6.9 Hz, 6H), 2.86 (t, J=8.0, 2H), 3.09 (s, 3H), 3.20 (t, J=2H), 3.37 (m, 1H), 4.91 (s, 1H), 6.46 (s, 1H), 7.26-7.30 (m, 2H), 7.43-7.56 (m, 3H), 9.41 (s, 1H);
FAB-MS (m/z): 315 (M+H)⁺.
Elementary Analysis (as $C_{19}H_{22}O_4 \cdot 0.5H_2O$):
Measured (%): C:70.87, H:7.52, N:0.27
Calculated (%): C:70.57, H:7.17, N:0

EXAMPLE 94

1-[2,4-Dihydroxy-6-(2-methoxyethyl)-5-phenylphenyl]propanone (Compound 94)

(Step 1)

In the same manner as in the step 4 in Example 92, 1-[2-(2-methoxyethyl)-4,6-bis(methoxymethoxy)-3-phenylphenyl]propanol (53 mg, 29%) was obtained from 4-bromo-3-(2-methoxyethyl)-1,5-bis(methoxymethoxy)-2-phenylbenzene (0.19 g, 0.47 mmol) obtained in the step 3 in Example 92, using n-hexane solution of 1.6 mol/L n-butyllithium (0.35 mL, 0.56 mmol) and propionaldehyde (0.10 mL, 1.4 mmol).

¹H-NMR (270 MHz, CDCl₃) δ (ppm): 1.04 (t, J=7.4 Hz, 3H), 1.76-2.12 (m, 2H), 2.63-2.86 (m, 2H), 3.13 (s, 3H), 3.16-3.41 (m, 2H), 3.24 (s, 3H), 3.54 (s, 3H), 4.82 (m, 1H), 4.96 (s, 2H), 5.25 (d, J=6.9 Hz, 1H), 5.29 (d, J=6.9 Hz, 1H), 6.92 (s, 1H), 7.15-7.18 (m, 2H), 7.29-7.42 (m, 3H).

(Step 2)

In the same manner as in the step 5 in Example 92, 1-[2-(2-methoxyethyl)-4,6-bis(methoxymethoxy)-3-phenylphenyl]propanone (39 mg, 76%) was obtained from 1-[2-(2-methoxyethyl)-4,6-bis(methoxymethoxy)-3-phenylphenyl] propanol (52 mg, 0.13 mmol) obtained in the above, using Molecular Sieves 3 A (0.30 g) and pyridinium dichromate (0.20 g, 0.53 mmol).

¹H-NMR (270 MHz, CDCl₃) δ (ppm): 1.19 (t, J=7.3 Hz, 3H), 2.60 (t, J=7.6 Hz, 2H), 2.86 (q, J=7.3 Hz, 2H), 3.06 (s, 3H), 3.22 (t, J=7.6 Hz, 2H), 3.26 (s, 3H), 3.48 (s, 3H), 4.99 (s, 2H), 5.18 (s, 2H), 6.88 (s, 1H), 7.17-7.20 (m, 2H), 7.32-7.42 (m, 3H);
APCI-MS (m/z): 387 (M-H)⁻.

(Step 3)

In the same manner as in the step 4 in Example 1, Compound 94 (17 mg, 63%) was obtained from 1-[2-(2-methoxyethyl)-4,6-bis(methoxymethoxy)-3-phenylphenyl]propanone (35 mg, 0.090 mmol) obtained in the above, using methanol (2.0 mL) and 1,4-dioxane solution (2.0 mL) of 4 mol/L hydrogen chloride.

¹H-NMR (270 MHz, CDCl₃) δ (ppm): 1.22 (t, J=7.3 Hz, 3H), 2.95 (t, J=7.6 Hz, 2H), 2.98 (q, J=7.3 Hz, 2H), 3.11 (s, 3H), 3.23 (t, J=7.6 Hz, 2H), 4.91 (s, 1H), 6.47 (s, 1H), 7.25-7.28 (m, 2H), 7.46-7.56 (m, 3H), 11.07 (br s, 1H);
APCI-MS (m/z): 299 (M-H)⁻.
Elementary Analysis (as $C_{18}H_{20}O_4 \cdot 0.5H_2O$):
Measured (%): C:69.82, H:6.91, N:0.27
Calculated (%): C:69.86, H:6.84, N:0

EXAMPLE 95

5-(2-Methoxyethyl)-4-phenyl-6-propylbenzene-1,3-diol (Compound 95)

1-[2-(2-Methoxyethyl)-4,6-bis(methoxymethoxy)-3-phenylphenyl]propanol (59 mg, 0.19 mmol) obtained in the step 1 in Example 94 was dissolved in methanol (12 mL), and 10% palladium-carbon (50% wet., 50 mg) was added thereto and stirred under hydrogen pressure (0.3 MPa) at room temperature for 10 hours. The reaction mixture was filtered through Celite, and the filtrate was concentrated under reduced pressure. The resulting residue was dissolved in methanol (2.0 mL), and 1,4-dioxane solution (6.0 mL) of 4 mol/L hydrogen chloride was added thereto and stirred at room temperature for 1 hour. The reaction mixture was concentrated under reduced pressure, and the resulting residue was purified through preparative thin-layer chromatography (methanol/chloroform=1/9), and crystallized (n-hexane/ethyl acetate 1/9) to obtain Compound 95 (17 mg, 39%).

¹H-NMR (270 MHz, CDCl₃) δ (ppm): 1.03 (t, J=7.3 Hz, 3H), 1.54-1.63 (m, 2H), 2.57-2.74 (m, 4H), 3.12 (s, 3H), 3.24 (dd, J=6.3, 7.6 Hz, 2H), 4.47 (s, 1H), 4.70 (s, 1H), 6.35 (s, 1H), 7.26-7.29 (m, 2H), 7.41-7.52 (m, 3H);
APCI-MS (m/z): 285 (M-H)⁻.
Elementary Analysis (as $C_{18}H_{22}O_3 \cdot 0.7H_2O$):
Measured (%): C:72.35, H:7.88, N:0.32
Calculated (%): C:72.31, H:7.89, N:0

EXAMPLE 96

6-Isobutyl-5-(2-methoxyethyl)-4-phenylbenzene-1,3-diol (Compound 96)

In the same manner as in Example 95, Compound 96 (16 mg, 65%) was obtained from 1-[2-(2-methoxyethyl)-4,6-bis(methoxymethoxy)-3-phenylphenyl]-2-methylpropanol (0.11 g, 0.26 mmol) obtained in the step 1 in Example 93, using 10% palladium-carbon (50% wet., 70 mg) and 1,4-dioxane solution (2.0 mL) of 4 mol/L hydrogen chloride.

¹H-NMR (270 MHz, CDCl₃) δ (ppm): 0.95 (d, J=6.6 Hz, 6H), 1.91 (m, 1H), 2.51 (t, J=7.3 Hz, 2H), 2.73 (br t, J=8.0 Hz, 2H), 3.10 (s, 3H), 3.21 (br t, J=8.0 Hz, 2H), 4.54 (s, 1H), 5.04 (s, 1H), 6.33 (s, 1H), 7.25-7.29 (m, 2H), 7.38-7.51 (m, 3H);
APCI-MS (m/z): 299 (M-H)⁻.

EXAMPLE 97

6-Bromo-5-(3-methoxypropyl)-4-phenylbenzene-1,3-diol (Compound 97)

(Step 1)

Methyl 3-[3,5-bis(methoxymethoxy)-2-phenylphenyl]propanoate (200 mg, 0.555 mmol) obtained in the step 3 in Example 87 was dissolved in tetrahydrofuran (10 mL), and lithium aluminium hydride (32.1 mg, 0.846 mmol) was added thereto and stirred at room temperature for 6 hours. Anhydrous sodium sulfate and aqueous saturated sodium sulfate solution were added to the reaction mixture, and stirred for 1 hour. The reaction mixture was filtered, and the filtrate was concentrated under reduced pressure to obtain 3-[3,5-bis(methoxymethoxy)-2-phenylphenyl]propanol (205 mg, 100%).

¹H-NMR (270 MHz, CDCl₃) δ (ppm): 0.98 (br s, 1H), 1.60-1.72 (m, 2H), 2.40-2.52 (m, 2H), 3.28 (s, 3H), 3.40-3.50 (m, 2H), 3.51 (s, 3H), 4.99 (s, 2H), 5.19 (s, 2H), 6.68 (d, J=2.3 Hz, 1H), 6.75 (d, J=2.3 Hz, 1H), 7.15-7.25 (m, 2H), 7.30-7.45 (m, 3H).

(Step 2)

3-[3,5-Bis(methoxymethoxy)-2-phenylphenyl]propanol (194 mg, 0.583 mmol) obtained in the above was dissolved in N,N-dimethylformamide (5 mL), and N-bromosuccinimide (137 mg, 0.769 mmol) was added thereto, and stirred at room temperature for 4 hours. Water was added to the reaction mixture, and extracted with chloroform. The organic layer was washed with aqueous saturated sodium thiosulfate solution and aqueous saturated sodium chloride solution in order, and then dried over anhydrous sodium sulfate, and the solvent was evaporated away under reduced pressure. The resulting residue was purified through preparative thin-layer chromatography (n-hexane/ethyl acetate=2/1) to obtain 3-[2-bromo-3,5-bis(methoxymethoxy)-6-phenylphenyl]propanol (82.3 mg, 34%).

$^1$H-NMR (270 MHz, CDCl$_3$) δ (ppm): 0.94 (br s, 1H), 1.50-1.80 (m, 2H), 2.60-2.70 (m, 2H), 3.26 (s, 3H), 3.40-3.50 (m, 2H), 3.57 (s, 3H), 4.98 (s, 2H), 5.27 (s, 2H), 6.93 (s, 1H), 7.15-7.23 (m, 2H), 7.30-7.45 (m, 3H).

(Step 3)

3-[2-Bromo-3,5-bis(methoxymethoxy)-6-phenylphenyl]propanol (44.4 mg, 0.108 mmol) obtained in the above was dissolved in N,N-dimethylformamide (2 mL), and 60% sodium hydride/mineral oil dispersion (30.0 mg, 750 mmol) and methyl iodide (0.060 mL, 0.963 mmol) were added thereto, and stirred at room temperature for 52 hours. Water was added to the reaction mixture, and extracted with chloroform. The organic layer was washed with aqueous saturated sodium chloride solution, and then dried over anhydrous sodium sulfate, and the solvent was evaporated away under reduced pressure. The resulting residue was purified through preparative thin-layer chromatography (n-hexane/ethyl acetate=2/1) to obtain 4-bromo-1,5-bis(methoxymethoxy)-3-(3-methoxypropyl)-2-phenylbenzene (38.4 mg, 84%).

$^1$H-NMR (270 MHz, CDCl$_3$) δ (ppm): 1.62-1.76 (m, 2H), 2.55-2.65 (m, 2H), 3.17 (s, 3H), 3.20 (t, J=6.8 Hz, 2H), 3.26 (s, 3H), 3.56 (s, 3H), 4.97 (s, 2H), 5.27 (s, 2H), 6.92 (s, 1H), 7.14-7.22 (m, 2H), 7.28-7.44 (m, 3H).

(Step 4)

In the same manner as in the step 2 in Example 25, 4-bromo-1,5-bis(methoxymethoxy)-3-(3-methoxypropyl)-2-phenylbenzene (37.2 mg, 0.0875 mmol) was dissolved in ethanol (4 mL), and concentrated hydrochloric acid (0.1 mL) was added thereto and stirred at 60° C. for 1.1 hours. The reaction liquid was concentrated under reduced pressure, and the resulting residue was purified through partitioning thin-layer chromatography (chloroform/methanol=20/1) to obtain Compound 97 (28.7 mg, 97%).

$^1$H-NMR (270 MHz, CDCl$_3$) δ (ppm): 1.60-1.75 (m, 2H), 2.50-2.60 (m, 2H), 3.18 (s, 3H), 3.20 (t, J=6.6 Hz, 2H), 4.67 (s, 1H), 5.70 (s, 1H), 6.59 (s, 1H), 7.20-7.30 (m, 2H), 7.40-7.60 (m, 3H);

APCI-MS (m/z): 335, 337 (M−H)$^-$.

EXAMPLE 98

6-Bromo-5-[2-(N-methylamino)ethyl]-4-phenylbenzene-1,3-diol (Compound 98)

(Step 1)

2-[2-Bromo-3,5-bis(methoxymethoxy)-6-phenylphenyl]ethanol (185 mg, 0.465 mmol) obtained in the step 1 in Example 62 was dissolved in dichloromethane (10 mL), and pyridinium dichromate (376 mg, 1.00 mmol) was added thereto and stirred at room temperature for 24 hours. The reaction mixture was filtered, and the filtrate was concentrated under reduced pressure. Anhydrous sodium sulfate and aqueous saturated sodium sulfate solution were added to the resulting residue, and stirred for 1 hour. The mixture was filtered, the filtrate was concentrated under reduced pressure, and the resulting residue was purified through silica gel column chromatography (n-hexane/ethyl acetate=19/1 to 9/1) to obtain 2-[2-bromo-3,5-bis(methoxymethoxy)-6-phenylphenyl]ethanal (151 mg, 82%).

$^1$H-NMR (270 MHz, CDCl$_3$) δ (ppm): 3.28 (s, 3H), 3.56 (s, 3H), 3.73 (d, J=1.0 Hz, 2H), 5.01 (s, 2H), 5.29 (s, 2H), 7.04 (s, 1H), 7.10-7.15 (m, 2H), 7.30-7.45 (m, 3H), 9.62 (t, J=1.0 Hz, 1H).

(Step 2)

2-[2-bromo-3,5-bis(methoxymethoxy)-6-phenylphenyl]ethanal (47.9 mg, 0.121 mmol) obtained in the above was dissolved in 1,2-dichloroethane (2 mL); and acetic acid (0.200 mL), 1,2-dichloroethane solution of 2.0 mol/L methylamine (0.500 mL, 1.00 mmol) and sodium triacetoxyborohydride (67.8 mg, 0.320, mmol) were added thereto, and stirred at room temperature for 26 hours. Water was added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer chromatography (chloroform/methanol=9/1) to obtain 2-[2-bromo-3,5-bis(methoxymethoxy)-6-phenylphenyl]ethyl-N-methylamine (49.6 mg, 100%).

$^1$H-NMR (270 MHz, CDCl$_3$) δ (ppm): 2.24 (s, 3H, 2.29 (br s, 1H) m, 2.65-2.75 (m, 2H), 2.85-2.95 (m, 2H), 32.6 (s, 3H), 3.56 (s, 3H), 4.98 (s, 2H), 5.27 (s, 2H), 6.95 (s, 1H), 7.15-7.20 (m, 2H), 7.30-7.45 (m, 3H).

(Step 3)

In the same manner as in the step 2 in Example 25, Compound 98 (17.6 mg, 45%) was obtained from 2-[2-bromo-3,5-bis(methoxymethoxy)-6-phenylphenyl]ethyl-N-methylamine (49.6 mg, 0.121 mmol) obtained in the above, using ethanol (4 mL) and concentrated hydrochloric acid (0.1 mL).

$^1$H-NMR (270 MHz, DMSO-d$_6$) δ (ppm): 2.30 (s, 3H), 2.74 (s, 4H), 4.02 (br s, 1H), 6.57 (s, 1H), 7.10-7.18 (m, 2H), 7.28-7.44 (m, 3H), 9.36 (br s, 1H), 10.10 (br s, 1H); APCI-MS (m/z): 322, 324 (M+H)$^+$.

EXAMPLE 99

6-Bromo-5-[2-(N,N-dimethylamino)ethyl]-4-phenylbenzene-1,3-diol (Compound 99)

(Step 1)

In the same manner as in the step 2 in Example 98, 2-[2-bromo-3,5-bis(methoxymethoxy)-6-phenylphenyl]ethyl-N,N-dimethylamine (51.3 mg, 100%) was obtained from 2-[2-bromo-3,5-bis(methoxymethoxy)-6-phenylphenyl]ethanal (47.9 mg, 0.121 mmol) obtained in the step 1 in Example 98, using acetic acid (0.200 mL, 3.49 mmol), 1,2-dichloromethane solution of 2.0 mol/L dimethylamine (0.500 mL, 1.00 mmol) and sodium triacetoxyborohydride (93.6 mg, 0.442 mmol).

$^1$H-NMR (270 MHz, CDCl$_3$) δ (ppm): 2.06 (s, 6H), 2.30-2.44 (m, 2H), 2.72-2.86 (m, 2H), 3.27 (s, 3H), 3.56 (s, 3H), 4.98 (s, 2H), 5.27 (s, 2H), 6.93 (s, 1H), 7.15-7.25 (m, 2H), 7.30-7.45 (m, 3H).

(Step 2)

In the same manner as in the step 2 in Example 25, 2-[2-bromo-3,5-bis(methoxymethoxy)-6-phenylphenyl]ethyl-N,N-dimethylamine (51.3 mg, 0.121 mmol) obtained in the above was dissolved in ethanol (4 mL). Concentrated hydrochloric acid (0.1 mL) was added to the resulting solution, heated at 60° C. and stirred for 1.1 hours. The reaction mixture was concentrated under reduced pressure, and the resulting residue was purified through preparative thin-layer chromatography (chloroform/methanol=4/1) to obtain Compound 99 (24.3 mg, 60%).

$^1$H-NMR (270 MHz, DMSO-d$_6$) δ (ppm): 2.38 (s, 6H), 2.74 (s, 4H), 6.57 (s, 1H), 7.10-7.20 (m, 2H), 7.30-7.45 (m, 3H), 9.38 br s, 1H), 10.14 (br s, 1H);

APCI-MS (m/z): 336, 338 (M+H)$^+$.

EXAMPLE 100

6-Bromo-5-{2-[N-(2-methoxyethyl)amino]ethyl}-4-phenylbenzene-1,3-diol (Compound 100)

(Step 1)

In the same manner as in the step 2 in Example 98, 2-[2-bromo-3,5-bis(methoxymethoxy)-6-phenylphenyl]ethyl-N-(2-methoxyethyl)amine (55.0 mg, 100%) was obtained from 2-[2-bromo-3,5-bis(methoxymethoxy)-6-phenylphenyl]ethanal (47.9 mg, 0.121 mmol) obtained in the step 1 in Example 98, using acetic acid (0.200 mL, 3.49 mmol), (2-methoxyethyl)amine (0.0870 mL, 1.00 mmol) and sodium triacetoxyborohydride (57.6 mg, 0.272 mmol).

$^1$H-NMR (270 MHz, CDCl$_3$) δ (ppm): 2.61 (t, J=5.3 Hz, 2H), 2.65-2.85 (m, 4H), 3.26 (s, 3H), 3.31 (s, 3H), 3.39 (t, J=5.2 Hz, 2H), 3.56 (s, 3H), 4.97 (s, 2H), 5.27 (s, 2H), 6.93 (s, 1H), 7.10-7.20 (m, 2H), 7.30-7.45 (m, 3H).

(Step 2)

In the same manner as in the step 2 in Example 25, 2-[2-bromo-3,5-bis(methoxymethoxy)-6-phenylphenyl]ethyl-N-(2-methoxyethyl)amine (55.0 mg, 0.121 mmol) obtained in the above was dissolved in ethanol (4 mL), and concentrated hydrochloric acid (0.1 mL) was added thereto, and stirred at 60° C. for 1.1 hours. The reaction mixture was concentrated under reduced pressure, and the resulting residue was purified through preparative thin-layer chromatography (chloroform/methanol=4/1) to obtain Compound 100 (29.4 mg, 66%).

$^1$H-NMR (270 MHz, DMSO-d$_6$) δ (ppm): 2.72 (s, 4H), 2.76 (t, J=5.3 Hz, 2H), 3.22 (s, 3H), 6.56 (s, 1H), 7.10-7.20 (m, 2H), 7.25-7.45 (m, 3H), 9.33 (s, 1H), 10.10 (br s, 1H);

APCI-MS (m/z): 366, 368 (M+H)$^+$.

EXAMPLE 101

6-Bromo-5-(N-methylaminomethyl)-4-phenylbenzene-1,3-diol (Compound 101)

(Step 1)

In the same manner as in the step 2 in Example 98, 2-bromo-3,5-bis(methoxymethoxy)-6-phenylphenylmethyl-N-methylamine (68.6 mg, 100%) was obtained from 2-bromo-3,5-bis(methoxymethoxy)-6-phenylbenzaldehyde (66.1 mg, 0.173 mmol) obtained in the step 1 in Example 46, using acetic acid (0.200 mL, 3.49 mmol), 1,2-dichloroethane solution of 2.0 mol/L methylamine (0.500 mL, 1.00 mmol) and sodium triacetoxyborohydride (72.5 mg, 0.342 mmol).

$^1$H-NMR (270 MHz, CDCl$_3$) δ (ppm): 2.22 (s, 3H), 3.27 (s, 3H), 3.56 (s, 3H), 3.63 (s, 2H), 4.98 (s, 2H), 5.28 (s, 2H), 6.98 (s, 1H), 7.20-7.30 (m, 2H), 7.30-7.44 (m, 3H).

(Step 2)

In the same manner as in the step 2 in Example 25, 2-bromo-3,5-bis(methoxymethoxy)-6-phenylphenylmethyl-N-methylamine (68.6 mg, 0.173 mmol) obtained in the above was dissolved in ethanol (4 mL), and concentrated hydrochloric acid (0.1 mL) was added thereto, and stirred at 60° C. for 1.1 hours. The reaction mixture was concentrated under reduced pressure, and the resulting residue was purified through preparative thin-layer chromatography (chloroform/methanol=4/1) to obtain Compound 101 (54.2 mg, 100%).

$^1$H-NMR (270 MHz, DMSO-d$_6$) δ (ppm): 2.23 (s, 3H), 3.78 (s, 2H), 6.73 (s, 1H), 7.15-7.25 (m, 2H), 7.30-7.45 (m, 3H), 9.63 (br s, 1H), 10.39 (br s, 1H);

APCI-MS (m/z): 308, 310 (M+H)$^+$.

EXAMPLE 102

6-Bromo-5-(N,N-dimethylaminomethyl)-4-phenylbenzene-1,3-diol (Compound 102)

(Step 1)

In the same manner as in the step 2 in Example 98, 2-bromo-3,5-bis(methoxymethoxy)-6-phenylphenylmethyl-N,N-dimethylamine (72.6 mg, 100%) was obtained from 2-bromo-3,5-bis(methoxymethoxy)-6-phenylbenzaldehyde (67.6 mg, 0.177 mmol) obtained in the step 1 in Example 46, using acetic acid (0.200 mL, 3.49 mmol), 1,2-dichloroethane solution of 2.0 mol/L methylamine (0.500 mL, 1.00 mmol) and sodium triacetoxyborohydride (69.7 mg, 0.329 mmol).

$^1$H-NMR (270 MHz, CDCl$_3$) δ (ppm): 2.03 (s, 6H), 3.26 (s, 3H), 3.35 (s, 2H), 3.56 (s, 3H), 4.97 (s, 2H), 5.27 (s, 2H), 6.99 (s, 1H), 7.10-7.20 (m, 2H), 7.30-7.40 (m, 3H).

(Step 2)

In the same manner as in the step 2 in Example 25, 2-bromo-3,5-bis(methoxymethoxy)-6-phenylphenylmethyl-N,N-dimethylamine (72.6 mg, 0.177 mmol) obtained in the above was dissolved in ethanol (4 mL), and concentrated hydrochloric acid (0.1 mL) was added thereto, and stirred at 60° C. for 1.1 hours. The reaction mixture was concentrated under reduced pressure, and the resulting residue was purified through preparative thin-layer chromatography (chloroform/methanol=4/1) to obtain Compound 102 (12.9 mg, 24%).

$^1$H-NMR (270 MHz, DMSO-d$_6$) δ (ppm): 4.15 (br s, 2H), 6.74 (br s, 1H), 7.10-7.25 (m, 2H), 7.25-7.45 (m, 3H), 9.77 (br s, 1H), 10.55 (br s, 1H);

APCI-MS (m/z): 322, 324 (M+H)$^+$.

EXAMPLE 103

6-Bromo-5-[N-(2-methoxyethyl)aminomethyl]-4-phenylbenzene-1,3-diol (Compound 103)

(Step 1)

In the same manner as in the step 2 in Example 98, 2-bromo-3,5-bis(methoxymethoxy)-6-phenylphenylmethyl-N-(2-methoxyethyl)amine (73.5 mg, 100%) was obtained from 2-bromo-3,5-bis(methoxymethoxy)-6-phenylbenzaldehyde (63.8 mg, 0.167 mmol) obtained in the step 1 in Example 46, using acetic acid (0.200 mL, 3.49 mmol), 2-methoxyethylamine (0.0870 mL, 1.00 mmol) and sodium triacetoxyborohydride (81.5 mg, 0.385 mmol).

$^1$H-NMR (270 MHz, CDCl$_3$) δ (ppm): 2.57 (t, J=5.3 Hz, 2H), 3.26 (s, 3H), 3.26 (s, 3H), 3.32 (t, J=5.3 Hz, 2H), 3.55 (s, 3H), 3.71 (s, 2H), 4.97 (s, 2H), 5.27 (s, 2H), 6.97 (s, 1H), 7.20-7.30 (m, 2H), 7.30-7.45 (m, 3H).

(Step 2)

In the same manner as in the step 2 in Example 25, the methoxyethylamine (73.5 mg, 0.167 mmol) obtained in the above was dissolved in ethanol (4 mL), and concentrated hydrochloric acid (0.1 mL) was added thereto, and stirred at 60° C. for 1.1 hours. The reaction mixture was concentrated under reduced pressure, and the resulting residue was purified through preparative thin-layer chromatography (chloroform/methanol=4/1) to obtain Compound 103 (22.4 mg, 38%).

$^1$H-NMR (270 MHz, DMSO-$d_6$) δ (ppm): 2.62-2.74 (m, 2H), 3.12 (s, 3H), 3.84 (s, 2H), 6.71 (s, 1H), 7.15-7.25 (m, 2H), 7.30-7.45 (m, 3H), 9.59 (br s, 1H), 10.35 (br s, 1H);

APCI-MS (m/z): 352, 354 (M+H)$^+$.

EXAMPLE 104

6-Bromo-5-(3-hydroxypropyl)-4-phenylbenzene-1,3-diol (Compound 104)

In the same manner as in the step 2 in Example 25, 3-[2-bromo-3,5-bis(methoxymethoxy)-6-phenylphenyl]propanol (35.2 mg, 0.0856 mmol) obtained in the step 2 in Example 97 was dissolved in ethanol (4 mL), and concentrated hydrochloric acid (0.1 mL) was added thereto, and stirred at 60° C. for 1.1 hours. The reaction mixture was concentrated under reduced pressure, and the resulting residue was purified through preparative thin-layer chromatography (chloroform/methanol=20/1) to obtain Compound 104 (19.4 mg, 70%).

$^1$H-NMR (270 MHz, CDCl$_3$) δ (ppm): 0.80-1.20 (m, 1H), 1.60-1.74 (m, 2H), 2.55-2.65 (m, 2H), 3.46 (t, J=6.3 Hz, 2H), 4.66 (s, 1H), 5.68 (s, 1H), 6.61 (s, 1H), 7.20-7.30 (m, 2H), 7.40-7.55 (m, 3H);

APCI-MS (m/z): 321, 323 (M−H)$^-$.

EXAMPLE 105

6-Bromo-5-(2-methoxyethyl)-4-(3-methoxyphenyl)benzene-1,3-diol (Compound 105)

(Step 1)

In the same manner as in the step 3 in Example 1, 4-bromo-2-(3-methoxyphenyl)-3-(methoxyethyl)-11,5-bis(methoxymethoxy)benzene (28 mg, 21%) was obtained from 2,4-dibromo-3-(methoxyethyl)-1,5-bis(methoxymethoxy)benzene (110 mg, 0.27 mmol), using 3-methoxyphenylboronic acid (42 mg, 0.28 mmol), bis(tri-o-tolylphosphine)palladium(II) dichloride (10 mg, 0.013 mmol), cesium carbonate (200 mg, 0.62 mmol), 1,2-dimethoxyethane (3.0 mL) and water (1.5 mL).

$^1$H-NMR (270 MHz, CDCl$_3$) δ (ppm): 2.90 (m, 2H), 3.18 (s, 3H), 3.28 (s, 3H), 3.41 (m, 2H), 3.56 (s, 3H), 3.80 (s, 3H), 4.98 (s, 2H), 5.26 (s, 2H), 6.72-6.77 (m, 2H), 6.88 (m, 1H), 6.93 (s, 1H), 7.31 (t, J=7.8 Hz, 1H).

(Step 2)

In the same manner as in the step 4 in Example 1, Compound 105 (19 mg, 91%) was obtained from 4-bromo-2-(3-methoxyphenyl)-3-(methoxyethyl)-1,5-bis(methoxymethoxy)benzene (26 mg, 0.059 mmol) obtained in the above, using methanol (2.0 mL) and 1,4-dioxane solution (1.0 mL) of 4 mol/L hydrogen chloride.

$^1$H-NMR (270 MHz, CDCl$_3$) δ (ppm): 2.85 (t, J=8.9 Hz, 2H), 3.19 (s, 3H), 3.43-3.36 (m, 2H), 3.82 (s, 3H), 4.78 (s, 1H), 5.72 (s, 1H), 6.60 (s, 1H), 6.79-6.83 (m, 2H), 6.90 (dt, J=8.4, 2.5 Hz, 1H), 7.40 (t, J=8.4 Hz, 1H);

APCI-MS (m/z): 352 (M−H)$^-$.

EXAMPLE 106

3-[5-Bromo-2,4-dihydroxy-6-(2-methoxyethyl)phenyl]benzoic acid (Compound 106)

(Step 1)

In the same manner as in the step 3 in Example 1, 2-(3-formylphenyl)-1-(methoxyethyl)-3,5-bis(methoxymethoxy)benzene (350 mg, 94%) was obtained from 2-bromo-1-(methoxyethyl)-3,5-bis(methoxymethoxy)benzene (350 mg, 1.0 mmol), using 3-formylphenylboronic acid (180 mg, 1.2 mmol), bis(tri-o-tolylphosphine)palladium(II) dichloride (40 mg, 0.05 mmol), cesium carbonate (670 mg, 2.1 mmol), 1,2-dimethoxyethane (10 mL) and water (2.0 mL).

$^1$H-NMR (270 MHz, CDCl$_3$) δ (ppm): 2.63 (t, J=7.3 Hz, 2H), 3.19 (s, 3H), 3.26 (s, 3H), 3.38 (t, J=7.3 Hz, 2H), 3.51 (s, 3H), 4.99 (s, 2H), 5.20 (s, 2H), 6.72 (d, J=2.3 Hz, 1H), 6.78 (d, J=2.3 Hz, 1H), 7.50 (td, J=7.6, 1.5 Hz, 1H), 7.56 (t, J=7.6 Hz, 1H), 7.74 (t, J=1.5 Hz, 1H), 7.85 (dt, J=7.6, 1.5 Hz, 1H), 10.0 (s, 1H).

(Step 2)

In the same manner as in the step 2 in Example 1, 4-bromo-2-(3-formylphenyl)-3-(methoxyethyl)-1,5-bis(methoxymethoxy)benzene (370 mg, 84%) was obtained from 2-(3-formylphenyl)-1-(methoxyethyl)-3,5-bis(methoxymethoxy)benzene (350 mg, 0.97 mmol) obtained in the above, using N-bromosuccinimide (170 mg, 0.96 mmol) and N,N-dimethylformamide (5.0 mL).

$^1$H-NMR (270 MHz, CDCl$_3$) δ (ppm): 2.88 (t, J=7.8 Hz, 2H), 3.15 (s, 3H), 3.25 (s, 3H), 3.39 (t, J=7.8 Hz, 2H), 3.56 (s, 3H), 4.98 (s, 2H), 5.28 (s, 2H), 6.96 (s, 1H), 7.47 (dt J=7.6, 1.5 Hz, 1H), 7.59 (t, J=7.6 Hz, 1H), 7.73 (t, J=1.5 Hz, 1H), 7.88 (dt, J=7.6, 1.5 Hz, 1H), 10.0 (s, 1H).

(Step 3)

4-Bromo-2-(3-formylphenyl)-3-(methoxyethyl)-1,5-bis(methoxymethoxy)benzene (350 mg, 0.80 mmol) obtained in the above was dissolved in a mixed solvent of tert-butanol (7.0 mL) and dichloromethane (1.0 mL), and 2-methyl-2-butene (0.5 mL) was added thereto, and then aqueous solution (5.0 mL) of sodium hypochlorite (450 mg, 4.9 mmol) and sodium hydrogenphosphate (180 mg, 1.5 mmol) was dropwise added thereto, and stirred at room temperature for 9 hours. Water was added to the reaction solution, extracted twice with chloroform, and dried over anhydrous sodium hydrogensulfate. The solvent was evaporated away under reduced pressure to obtain 3-[5-bromo-6-(2-methoxyethyl)-2,4-bis(methoxymethoxy)phenyl]benzoic acid (360 mg, 99%).

$^1$H-NMR (270 MHz, CDCl$_3$) δ (ppm): 2.88 (m, 2H), 3.17 (s, 3H), 3.26 (s, 3H), 3.41 (m, 2H), 3.56 (s, 3H), 4.98 (s, 2H), 5.27 (s, 2H), 6.95 (s, 1H), 7.44 (dt J=7.6, 1.5 Hz, 1H), 7.52 (t, J=7.6 Hz, 1H), 7.96 (t, J=1.5 Hz, 1H), 8.09 (dt, J=7.6, 1.5 Hz, 1H).

(Step 4)

In the same manner as in the step 4 in Example 1, Compound 106 (70 mg, 83%) was obtained from 3-[5-bromo-6-(2-methoxyethyl)-2,4-bis(methoxymethoxy)phenyl]benzoic acid (104 mg, 0.23 mmol) obtained in the above, using methanol (2.0 mL) and 1,4-dioxane solution (1.0 mL) of 4 mol/L hydrogen chloride. In this, the product was crystallized with chloroform.

$^1$H-NMR (270 MHz, CDCl$_3$) δ (ppm): 2.82 (t, J=7.7 Hz, 2H), 3.18 (s, 3H), 3.39 (t, J=7.7 Hz, 2H), 5.72 (br s, 1H), 6.61 (s, 1H), 7.52 (d, J=7.7 Hz, 1H), 7.62 (t, J=7.7 Hz, 1H), 8.02 (br s, 1H), 8.17 (d, J=7.7 Hz, 1H);

APCI-MS (m/z): 365, 367 (M−H)$^-$.

EXAMPLE 107

6-Bromo-5-[2-(hydroxyimino)propyl]-4-(3-methoxyphenyl)benzene-1,3-diol (Compound 107)

(Step 1)

1-[2-Bromo-3,5-bis(methoxymethoxy)-6-phenylphenyl]propan-2-one (160 mg, 0.39 mmol) obtained in the step 2 in Example 65 was dissolved in pyridine (4.0 mL), and hydroxylamine hydrochloride (50 mg, 0.73 mmol) was added thereto and stirred at room temperature for 1 hour. The reaction solution was concentrated under reduced pressure, and the resulting residue was purified through silica gel column chromatography (ethyl acetate/n-hexane=1/4 to 1/2) to obtain 1-[2-bromo-3,5-bis(methoxymethoxy)-6-phenylphenyl]-2-(hydroxyimino)propane (150 mg, 91%).

APCI-MS (m/z): 409, 411 (M+H)$^+$ (Step 2)

In the same manner as in the step 4 in Example 1, Compound 107 (90 mg, 77%) was obtained from 1-[2-bromo-3,5-bis(methoxymethoxy)-6-phenylphenyl]-2-(hydroxyimino)propane (150 mg, 0.35 mmol) obtained in the above, using methanol (2.0 mL) and 1,4-dioxane solution (1.0 mL) of 4 mol/L hydrogen chloride.

$^1$H-NMR (270 MHz, CDCl$_3$) δ (ppm): 1.53 (s, 3H), 3.30 (s, 2H), 6.41 (s, 1H), 7.06-7.09 (m, 2H), 7.18-7.27 (m, 3H); APCI-MS (m/z): 336, 338 (M+H)$^+$.

EXAMPLE 108

6-Bromo-4-(3-methoxyphenyl)-5-[2-(tetrahydropyran-2-ylmethoxy)ethyl]benzene-1,3-diol (Compound 108)

(Step 1)

In the same manner as in the step 1 in Example 64, 4-bromo-1,5-bis(methoxymethoxy)-2-(3-methoxyphenyl)-3-[2-(tetrahydropyran-2-ylmethoxy)ethyl]benzene (14.0 mg, 16%) was obtained from 2-[2-bromo-3,5-bis(methoxymethoxy)-6-phenylphenyl]ethanol (67.7 mg, 0.170 mmol) obtained in the step 1 in Example 62, using 60% sodium hydride/mineral oil dispersion (108 mg, 2.71 mmol) and 2-(bromomethyl)tetrahydropyran (0.129 mL, 1.01 mmol).

$^1$H-NMR (270 MHz, CDCl$_3$) δ (ppm): 1.15-1.30 (m, 1H), 1.40-1.55 (m, 4H), 1.75-1.85 (m, 1H), 2.85-3.00 (m, 2H), 3.25 (s, 3H), 3.10-3.52 (m, 6H), 3.56 (s, 3H), 3.90-4.00 (m, 2H), 4.96 (s, 2H), 5.26 (s, 2H), 6.93 (s, 1H), 7.10-7.20 (m, 2H), 7.30-7.45 (m, 3H).

(Step 2)

In the same manner as in the step 2 in Example 25, 4-bromo-1,5-bis(methoxymethoxy)-2-(3-methoxyphenyl)-3-[2-(tetrahydropyran-2-ylmethoxy)ethyl]benzene (14.0 mg, 0.0266 mmol) obtained in the above was dissolved in ethanol (4 mL), and concentrated hydrochloric acid (0.1 mL) was added thereto and stirred at 60° C. for 1.1 hours. The reaction mixture was concentrated under reduced pressure, and the resulting residue was purified through preparative thin-layer chromatography (chloroform/methanol=20/1) to obtain Compound 108 (11.1 mg, 100%).

$^1$H-NMR (270 MHz, CDCl$_3$) δ (ppm): 1.10-1.30 (m, 1H), 1.40-1.60 (m, 4H), 1.75-1.90 (m, 1H), 2.80-2.90 (m, 2H), 3.15-3.50 (m, 6H), 3.90-4.00 (m, 1H), 4.65 (s, 1H), 5.68 (s, 1H), 6.61 (s, 1H), 7.20-7.28 (m, 2H), 7.40-7.60 (m, 3H); APCI-MS (m/z): 405, 407 (M–H)$^-$.

EXAMPLE 109

6-Bromo-5-[2-(oxolan-2-ylmethoxy)ethyl]-4-phenylbenzene-1,3-diol (Compound 109)

(Step 1)

In the same manner as in the step 1 in Example 64, 4-bromo-1,5-bis(methoxymethoxy)-2-(3-methoxyphenyl)-3-[2-(oxolan-2-ylmethoxy)ethyl]benzene (5.7 mg, 6%) was obtained from 2-[2-bromo-3,5-bis(methoxymethoxy)-6-phenylphenyl]ethanol (75.2 mg, 0.189 mmol) obtained in the step 1 in Example 62, using 60% sodium hydride/mineral oil dispersion (123 mg, 3.07 mmol) and tetrahydrofurfuryl bromide (0.106 mL, 0.944 mmol).

$^1$H-NMR (270 MHz, CDCl$_3$) δ (ppm): 1.40-1.54 (m, 1H), 1.74-1.94 (m, 3H), 2.90-3.00 (m, 2H), 3.26 (s, 3H), 3.20-3.40 (m, 2H), 3.44-3.54 (m, 2H), 3.56 (s, 3H), 3.65-3.97 (m, 3H), 4.97 (s, 2H), 5.27 (s, 2H), 6.93 (s, 1H), 7.10-7.20 (m, 2H), 7.30-7.45 (m, 3H).

(Step 2)

In the same manner as in the step 2 in Example 25, 4-bromo-1,5-bis(methoxymethoxy)-2-(3-methoxyphenyl)-3-[2-(oxolan-2-ylmethoxy)ethyl]benzene (5.7 mg, 0.0118 mmol) obtained in the above was dissolved in ethanol (4 mL). Concentrated hydrochloric acid (0.1 mL) was added to the resulting solution, heated at 60° C., and stirred for 1.1 hours. The reaction mixture was concentrated under reduced pressure, and the resulting residue was purified through preparative thin-layer chromatography (chloroform/methanol=20/1) to obtain Compound 109 (4.8 mg, 100%).

$^1$H-NMR (270 MHz, CDCl$_3$) δ (ppm): 1.42-1.60 (m, 1H), 1.76-1.94 (m, 3H), 2.80-2.90 (m, 2H), 3.24-3.30 (m, 2H), 3.42-3.52 (m, 2H), 3.65-3.97 (m, 3H), 4.65 (s, 1H), 5.68 (s, 1H), 6.61 (s, 1H), 7.20-7.30 (m, 2H), 7.40-7.54 (m, 3H); APCI-MS (m/z): 391, 393 (M–H)$^-$.

EXAMPLE 110

6-Bromo-5-[2-(2-hydroxyethoxy)ethyl]-4-phenylbenzene-1,3-diol (Compound 110)

(Step 1)

In the same manner as in the step 1 in Example 64, 4-bromo-3-{2-[2-(tert-butyldimethylsilyloxy)ethoxy]ethyl}-1,5-bis(methoxymethoxy)-2-(3-methoxyphenyl)benzene (35.1 mg, 25%) was obtained from 2-[2-bromo-3,5-bis(methoxymethoxy)-6-phenylphenyl]ethanol (99.3 mg, 0.250 mmol) obtained in the step 1 in Example 62, using 60% sodium hydride/mineral oil dispersion (106 mg, 2.66 mmol) and (2-bromoethoxy)-tert-butyldimethylsilane (0.268 mL, 1.25 mmol).

$^1$H-NMR (270 MHz, CDCl$_3$) δ (ppm): 0.30 (s, 6H), 0.87 (s, 9H), 2.80-3.00 (m, 2H), 3.26 (s, 3H), 3.32 (t, J=5.5 Hz, 2H), 3.40-3.50 (m, 2H), 3.57 (s, 3H), 3.63 (t, J=5.5 Hz, 2H), 4.97 (s, 2H), 5.27 (s, 2H), 6.94 (s, 1H), 7.12-7.20 (m, 2H), 7.30-7.45 (m, 3H).

(Step 2)

In the same manner as in the step 2 in Example 25, 4-bromo-3-{2-[2-(tert-butyldimethylsilyloxy)ethoxy]ethyl}-1,5-bis(methoxymethoxy)-2-(3-methoxyphenyl)benzene (35.0 mg, 0.0632 mmol) obtained in the above was dissolved in ethanol (4 mL), and concentrated hydrochloric acid (0.1 mL) was added thereto, and stirred at 60° C. for 1.1 hours. The reaction mixture was concentrated under reduced pressure, and the resulting residue was purified through preparative thin-layer chromatography (chloroform/methanol=9/1) to obtain Compound 110 (25.3 mg, 100%).

$^1$H-NMR (270 MHz, CDCl$_3$) δ (ppm): 1.77 (br s, 1H), 2.86 (t, J=7.3 Hz, 2H), 3.36 (t, J=4.6 Hz, 2H), 3.48 (t J=7.3 Hz, 2H), 3.56-3.68 (m, 2H), 4.66 (s, 1H), 5.68 (s, 1H), 6.63 (s, 1H), 7.20-7.40 (m, 2H), 7.42-7.58 (m, 3H);

APCI-MS (m/z): 351, 353 (M−H)$^-$.

EXAMPLE 111

6-Bromo-5-[2-(methoxymethoxy)ethyl]-4-phenyl-benzene-1,3-diol (Compound 111)

(Step 1)

In the same manner as in the step 1 in Example 64, 4-bromo-1,5-bis(methoxymethoxy)-3-[2-(methoxymethoxy)ethyl]-2-phenylbenzene (75.5 mg, 58%) was obtained from 2-[2-bromo-3,5-bis(methoxymethoxy)-6-phenylphenyl]ethanol (117 mg, 0.294 mmol) obtained in the step 1 in Example 62, using 60% sodium hydride/mineral oil dispersion (130 mg, 3.26 mmol) and chloromethyl methyl ether (0.111 mL, 1.47 mmol).

$^1$H-NMR (270 MHz, CDCl$_3$) δ (ppm): 2.85-2.98 (m, 2H), 3.20 (s, 3H), 3.26 (s, 3H), 3.56 (s, 3H), 3.48-3.60 (m, 2H), 4.43 (s, 2H), 4.97 (s, 2H), 5.27 (s, 2H), 6.94 (s, 1H), 7.15-7.23 (m, 2H), 7.30-7.45 (m, 3H).

(Step 2)

In the same manner as in the step 2 in Example 25, 4-bromo-1,5-bis(methoxymethoxy)-3-[2-(methoxymethoxy)ethyl]-2-phenylbenzene (74.0 mg, 0.168 mmol) obtained in the above was dissolved in methanol (8 mL), and concentrated hydrochloric acid (0.4 mL) was added thereto, and stirred at room temperature for 3 hours. Water was added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer chromatography (chloroform/methanol=20/1) to obtain Compound 111 (25.8 mg, 43%).

$^1$H-NMR (270 MHz, CDCl$_3$) δ (ppm): 2.80-2.90 (m, 2H), 3.19 (s, 3H), 3.48-3.58 (m, 2H), 4.44 (s, 2H), 4.66 (br s, 1H), 5.18 (s, 1H), 6.62 (s, 1H), 7.22-7.30 (m, 2H), 7.40-7.55 (m, 3H);

APCI-MS (m/z): 351, 353 (M−H)$^-$.

EXAMPLE 112

6-Bromo-5-(1,3-dioxolan-2-yl)-4-phenylbenzene-1,3-diol (Compound 112)

2-Bromo-3,5-bis(methoxymethoxy)-6-phenylbenzaldehyde (73.8 mg, 0.194 mmol) obtained in the step 1 in Example 46 was dissolved in ethylene glycol (4 mL), and concentrated hydrochloric acid (0.2 mL) was added thereto and stirred at 60° C. for 6 hours. Water was added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer chromatography (chloroform/methanol=20/1) to obtain Compound 112 (18.1 mg, 28%).

$^1$H-NMR (270 MHz, CDCl$_3$/CD$_3$OD) δ (ppm): 3.15-3.30 (m, 2H), 3.60-3.70 (m, 2H), 5.65 (s, 1H), 6.49 (s, 1H), 7.15-7.25 (m, 1H), 7.30-7.40 (m, 2H), 7.50-7.55 (m, 1H), 7.87-7.95 (m, 1H);

APCI-MS (m/z): 335, 337 (M−H)$^-$.

EXAMPLE 113

6-Ethyl-5-[2-(2-methoxymethoxy)ethyl]-4-phenyl-benzene-1,3-diol (Compound 113)

(Step 1)

In the same manner as in the step 1 in Example 71, 4-ethyl-3-[2-(2-methoxyethoxy)ethyl]-1,5-bis(methoxymethoxy)-2-phenylbenzene (163 mg, 35%) was obtained, using 2-[2-ethyl-3,5-bis(methoxymethoxy)-6-phenylphenyl]ethanol (398 mg, 1.15 mmol) obtained in the step 1 in Example 83, 60% sodium hydride/mineral oil dispersion (151 mg, 3.78 mmol) and 2-bromoethyl methyl ether (0.432 mL, 4.60 mmol).

$^1$H-NMR (270 MHz, CDCl$_3$) δ (ppm): 1.16 (t, J=7.4 Hz, 3H), 2.71 (q, J=7.3 Hz, 2H), 2.72-2.83 (m, 2H), 3.23 (s, 3H), 3.31 (s, 3H), 3.25-3.42 (m, 6H), 3.52 (s, 3H), 4.94 (s, 2H), 5.22 (s, 2H), 6.85 (s, 1H), 7.15-7.23 (m, 2H), 7.25 (m, 3H).

(Step 2)

In the same manner as in the step 2 in Example 25, 4-ethyl-3-[2-(2-methoxyethoxy)ethyl]-1,5-bis(methoxymethoxy)-2-phenylbenzene (160 mg, 0.395 mmol) obtained in the above was dissolved in ethanol (20 mL), and concentrated hydrochloric acid (0.5 mL) was added thereto, and stirred at 60° C. for 1.1 hours. The reaction mixture was concentrated under reduced pressure, and the resulting residue was purified through preparative thin-layer chromatography (chloroform/methanol=20/1) to obtain Compound 113 (135 mg, 100%).

$^1$H-NMR (270 MHz, CDCl$_3$) δ (ppm): 1.18 (t, J=7.7 Hz, 3H), 2.67 (q, J=7.7 Hz, 2H), 2.70-2.78 (m, 2H), 3.32 (s, 3H), 3.30-3.45 (m, 6H), 4.47 (s, 1H), 4.78 (br s, 1H), 6.35 (s, 1H), 7.22-7.30 (m, 2H), 7.35-7.52 (m, 3H);

APCI-MS (m/z): 315 (M−H)$^-$.

EXAMPLE 114

4-(2-Bromo-3,5-dihydroxy-6-phenylphenyl)butan-2-one (Compound 114)

(Step 1)

3,5-Bis(methoxymethoxy)-2-phenylbenzaldehyde (151 mg, 0.498 mmol) obtained in the step 1 in Example 87 was dissolved in toluene (10 mL), and (acetylmethylene)triphenylpholane (475 mg, 1.49 mmol) was added thereto and stirred at 80° C. for 10 hours. The reaction mixture was concentrated under reduced pressure, and the resulting residue was purified through preparative thin-layer chromatography (n-hexane/ethyl acetate=2/1) to obtain 4-[3,5-bis(methoxymethoxy)-2-phenylphenyl]but-3-en-2-one (148 mg, 87%).

$^1$H-NMR (270 MHz, CDCl$_3$) δ (ppm): 2.13 (s, 3H), 3.31 (s, 3H), 3.52 (s, 3H), 5.04 (s, 2H), 5.22 (s, 2H), 6.54 (d, J=16.2 Hz, 1H), 6.95 (d, J=2.3 Hz, 1H), 7.07 (d, J=2.3 Hz, 1H), 7.18-7.28 (m, 2H), 7.32-7.46 (m, 4H).

(Step 2)

4-[3,5-Bis(methoxymethoxy)-2-phenylphenyl]but-3-en-2-one (145 mg, 0.423 mmol) obtained in the above was dissolved in ethanol (5 mL), and 10% palladium-carbon catalyst (34.2 mg) was added thereto and stirred in a hydrogen atmosphere at room temperature for 15 hours. The reaction mixture was filtered, water was added to the filtrate, and extracted with chloroform. The organic layer was washed with aqueous saturated sodium chloride solution, dried over anhydrous sodium sulfate, and the solvent was evaporated away under reduced pressure. The resulting residue was purified through preparative thin-layer chromatography (n-hexane/ethyl acetate=2/1) to obtain 4-[3,5-bis(methoxymethoxy)-2-phenylphenyl]butan-2-one (90.1 mg, 62%).

$^1$H-NMR (270 MHz, CDCl$_3$) δ (ppm): 1.96 (s, 3H), 2.40-2.50 (m, 2H), 2.60-2.70 (m, 2H), 3.27 (s, 3H), 3.51 (s, 3H), 4.99 (s, 2H), 5.18 (s, 2H), 6.63 (d, J=2.5 Hz, 1H), 6.75 (d, J=2.5 Hz, 1H), 7.15-7.23 (m, 2H), 7.28-7.45 (m, 3H).

(Step 3)

4-[3,5-Bis(methoxymethoxy)-2-phenylphenyl]butan-2-one (88.0 mg, 0.256 mmol) obtained in the above was dissolved in N,N-dimethylformamide (4 mL), and N-bromosuccinimide (69.6 mg, 0.391 mmol) was added thereto and stirred at room temperature for 1 hour. Water was added to the reaction mixture, and extracted with chloroform. The organic layer was washed with aqueous saturated sodium thiosulfate solution and aqueous saturated sodium chloride solution, then dried over anhydrous sodium sulfate, and the solvent was evaporated away under reduced pressure. The resulting residue was purified through preparative thin-layer chromatography (n-hexane/ethyl acetate=2/1) to obtain 4-[2-bromo-3,5-bis(methoxymethoxy)-6-phenylphenyl]butan-2-one (101 mg, 93%).

$^1$H-NMR (270 MHz, CDCl$_3$) δ (ppm): 1.99 (s, 3H), 2.45-2.55 (m, 2H), 2.78-2.88 (m, 2H), 3.26 (s, 3H), 3.57 (s, 3H), 4.98 (s, 2H), 5.27 (s, 2H), 6.93 (s, 1H), 7.10-7.20 (m, 2H), 7.28-7.45 (m, 3H).

(Step 4)

In the same manner as in the step 2 in Example 25, 4-[2-bromo-3,5-bis(methoxymethoxy)-6-phenylphenyl]butan-2-one (47.4 mg, 0.112 mmol) obtained in the above was dissolved in ethanol (4 mL), and concentrated hydrochloric acid (0.1 mL) was added thereto and stirred at 60° C. for 1.1 hours. The reaction mixture was concentrated under reduced pressure, and the resulting residue was purified through preparative thin-layer chromatography (chloroform/methanol=20/1) to obtain Compound 114 (38.1 mg, 100%).

$^1$H-NMR (270 MHz, CDCl$_3$) δ (ppm): 2.00 (s, 3H), 2.45-2.55 (m, 2H), 2.72-2.82 (m, 2H), 4.65 (s, 1H), 5.65 (s, 1H), 6.61 (s, 1H), 7.20-7.28 (m, 2H), 7.40-7.55 (m, 3H);
FAB-MS (m/z): 335, 337 (M+H)$^+$.

EXAMPLE 115

5-(3-Hydroxybutyl)-6-bromo-4-phenylbenzene-1,3-diol (Compound 115)

(Step 1)

4-[2-Bromo-3,5-bis(methoxymethoxy)-6-phenylphenyl]butan-2-one (50.1 mg, 0.122 mmol) obtained in the step 3 in Example 114 was dissolved in methanol (10 mL), and sodium borohydride (12.1 mg, 0.320 mmol) was added thereto and stirred at room temperature for 2 hours. Methanol and water were added to the reaction mixture, and extracted with chloroform. The organic layer was washed with aqueous saturated sodium chloride solution, and dried over anhydrous sodium sulfate. The solvent was evaporated away under reduced pressure to obtain 4-[2-bromo-3,5-bis(methoxymethoxy)-6-phenylphenyl]butan-2-ol (52.2 mg, 100%).

$^1$H-NMR (270 MHz, CDCl$_3$) δ (ppm): 0.99 (d, J=5.9 Hz, 3H), 1.50-1.60 (m, 3H), 2.50-2.75 (m, 2H), 3.26 (s, 3H), 3.57 (s, 3H), 3.52-3.65 (m, 1H), 4.98 (s, 2H), 5.27 (s, 2H), 6.92 (s, 1H), 7.15-7.22 (m, 2H), 7.30-7.45 (m, 3H).

(Step 2)

In the same manner as in the step 2 in Example 25, 4-[2-bromo-3,5-bis(methoxymethoxy)-6-phenylphenyl]butan-2-ol (44.8 mg, 0.105 mmol) obtained in the above was dissolved in ethanol (4 mL), and concentrated hydrochloric acid (0.1 mL) was added thereto and stirred at 60° C. for 1.1 hours. The reaction mixture was concentrated under reduced pressure, and the resulting residue was purified through preparative thin-layer chromatography (chloroform/methanol=20/1) to obtain Compound 115 (30.2 mg, 85%).

$^1$H-NMR (270 MHz, CDCl$_3$) δ (ppm): 1.01 (d, J=6.1 Hz, 3H), 1.44-1.60 (m, 3H), 2.45-2.72 (m, 2H), 3.54-3.66 (m, 1H), 4.66 (s, 1H), 5.67 (s, 1H), 6.60 (s, 1H), 7.20-7.30 (m, 2H), 7.40-7.56 (m, 3H);
FAB-MS (m/z): 337, 339 (M+H)$^+$.

EXAMPLE 116

1-[2,4-Dihydroxy-6-(2-methoxyethyl)-5-(3-methoxyphenyl)phenyl]ethanone (Compound 116)

(Step 1)

In the same manner as in the step 1 in Example 62, 3,5-bis(methoxymethoxy)phenylethanol (3.8 g, 94%) was obtained from methyl 3,5-bis(methoxymethoxy)phenylacetate (4.5 g, 17 mmol) obtained in the step 1 in Example 1, using lithium aluminium hydride (640 mg, 17 mmol) and diethyl ether (100 mL).

$^1$H-NMR (270 MHz, CDCl$_3$) δ (ppm): 1.39 (br s, 1H), 2.81 (t, J=6.3 Hz, 2H), 3.48 (s, 6H), 3.85 (m, 2H), 5.14 (s, 4H), 6.57 (d, J=2.3 Hz, 2H), 6.62 (t, J=2.3 Hz, 1H).

(Step 2)

In the same manner as in the step 1 in Example 64, 5-(2-methoxyethyl)-1,3-bis(methoxymethoxy)benzene (2.9 g, 72%) was obtained from 3,5-bis(methoxymethoxy)phenylethanol (3.8 g, 16 mmol) obtained in the above, using 60% sodium hydride/mineral oil dispersion (1.3 g, 33 mmol), methyl iodide (3.1 mL, 50 mmol) and N,N-dimethylformamide (60 mL).

$^1$H-NMR (270 MHz, CDCl$_3$) δ (ppm): 2.82 (t, J=7.0 Hz, 2H), 3.35 (s, 3H), 3.47 (s, 6H), 3.59 (t, J=7.0 Hz, 2H), 5.13 (s, 4H), 6.57 (d, J=2.5 Hz, 2H), 6.60 (t, J=2.5 Hz, 1H).

(Step 3)

In the same manner as in the step 2 in Example 1, 2-bromo-1-(2-methoxyethyl)-3,5-bis(methoxymethoxy)benzene (3.8 g, 96%) was obtained from 5-(2-methoxyethyl)-1,3-bis(methoxymethoxy)benzene (3.0 g, 12 mmol) obtained in the above, using N-bromosuccinimide (2.1 g, 12 mmol) and N,N-dimethylformamide (50 mL).

$^1$H-NMR (270 MHz, CDCl$_3$) δ (ppm): 3.02 (t, J=7.1 Hz, 2H), 3.36 (s, 3H), 3.46 (s, 3H), 3.51 (s, 3H), 3.60 (t, J=7.1 Hz, 2H), 5.13 (s, 2H), 5.21 (s, 2H), 6.68 (d, J=2.7 Hz, 1H), 6.75 (d, J=2.7 Hz, 1H).

(Step 4)

In the same manner as in the step 1 in Example 13, 2-bromo-4-iodo-3-(2-methoxyethyl)-1,5-bis(methoxymethoxy)benzene (5.6 g, 62%) was obtained from 2-bromo-1-(2-methoxyethyl)-3,5-bis(methoxymethoxy) benzene (6.5 g, 20 mmol) obtained in the above, using chloroform (80 mL), iodine (5.0 g, 20 mmol) and [bis(trifluoroacetoxy)iodo]benzene (8.4 g, 20 mmol).

$^1$H-NMR (270 MHz, CDCl$_3$) δ (ppm): 3.42 (t, J=5.6 Hz, 2H), 3.55 (m, 2H), 3.50 (s, 9H), 5.20 (s, 2H), 5.22 (s, 2H), 6.87 (s, 1H).

(Step 5)

In the same manner as in the step 1 in Example 69, 2-bromo-4-iodo-3-(2-methoxyethyl)-1,5-bis(methoxymethoxy)benzene (5.4 g, 12 mmol) obtained in the above was treated with toluene (100 mL), tributyl(1-ethoxyvinyl)tin (4.4 mL, 13 mmol) and bis(triphenylphosphine)palladium(II) dichloride (0.4 g, 0.57 mmol), and then further treated with tetrahydrofuran (50 mL) and 1 mol/L hydrochloric acid (30 mL) to obtain 1-[3-bromo-2-(2-methoxyethyl)-4,6-bis(methoxymethoxy)phenyl]ethanone (3.9 g, 90%).

$^1$H-NMR (270 MHz, CDCl$_3$) δ (ppm): 2.51 (s, 3H), 3.02 (t, J=6.9 Hz, 2H), 3.31 (s, 3H), 3.45 (s, 3H), 3.51 (s, 3H), 3.54 (t, J=6.9 Hz, 2H), 5.16 (s, 2H), 5.24 (s, 2H), 6.89 (s, H).

(Step 6)

In the same manner as in the step 3 in Example 1, 1-[2-(2-methoxyethyl)-4,6-bis(methoxymethoxy)-3-(3-methoxyphenyl)phenyl]ethanone was obtained from 1-[3-bromo-2-(2-methoxyethyl)-4,6-bis(methoxymethoxy)phenyl]ethanone (150 mg, 0.22 mmol) obtained in the above, using 3-methoxyphenylboronic acid (45 mg, 0.29 mmol), bis(tri-o-tolylphosphine)palladium(II) dichloride (20 mg, 0.025 mmol), cesium carbonate (300 mg, 0.92 mmol), 1,2-dimethoxyethane (3.0 mL) and water (1.0 mL). Then, in the same manner as in the step 4 in Example 1, Compound 116 (19 mg, 30%) was obtained from the resulting compound, using methanol (1.0 mL) and 1,4-dioxane solution (1.0 mL) of 4 mol/L hydrogen chloride.

$^1$H-NMR (270 MHz, CDCl$_3$) δ (ppm): 2.69 (s, 3H), 3.02 (t, J=7.2 Hz, 2H), 3.15 (s, 3H), 3.28 (t, J=7.2 Hz, 2H), 3.83 (s, 3H), 5.05 (s, 1H), 6.46 (s, 1H), 9.84-6.78 (m, 2H), 7.00 (ddd, J=8.1, 2.6, 0.8, Hz, 1H), 7.44 (t, J=8.1 Hz, 1H), 12.0 (s, 1H); APCI-MS (m/z): 317 (M+H)$^+$.

EXAMPLE 117

3-[5-Bromo-2,4-dihydroxy-6-(2-methoxyethyl)phenyl]benzamide (Compound 117)

(Step 1)

In the same manner as in the step 1 in Example 48, 3-[5-bromo-6-(2-methoxyethyl)-2,4-bis(methoxymethoxy)phenyl]benzamide (120 mg, 41%) was obtained from 3-[5-bromo-6-(2-methoxyethyl)-2,4-bis(methoxymethoxy) phenyl]benzoic acid (290 mg, 0.64 mmol) obtained in the step 3 in Example 106, using 1-[3-(dimethylamino)propyl]-3-ethylcarbodiimide hydrochloride (130 mg, 0.96 mmol), 1-hydroxybenzotriazole hydrate (180 mg, 0.96 mmol) and methanol solution of 7 mol/L ammonia (0.2 mL, 1.4 mmol).

$^1$H-NMR (270 MHz, CDCl$_3$) δ (ppm): 2.88 (m, 2H), 3.17 (s, 3H), 3.25 (s, 3H), 3.44 (m, 2H), 3.56 (s, 3H), 4.98 (s, 2H), 5.27 (s, 2H), 5.98-6.50 (br d, 2H), 6.95 (s, 1H), 7.36 (dt J=7.6, 1.5 Hz, 1H), 7.48 (t, J=7.6 Hz, 1H), 7.68 (t, J=1.5 Hz, 1H), 7.81 (dt, J=7.6, 1.5 Hz, 1H).

(Step 2)

In the same manner as in the step 4 in Example 1, Compound 117 (30 mg, 76%) was obtained from 3-[5-bromo-6-(2-methoxyethyl)-2,4-bis(methoxymethoxy)phenyl]benzamide (50 mg, 0.11 mmol) obtained in the above, using methanol (2.0 mL) and 1,4-dioxane solution (1.0 mL) of 4 mol/L hydrogen chloride.

$^1$H-NMR (270 MHz, CDCl$_3$) δ (ppm): 2.83 (t, J=8.9 Hz, 2H), 3.16 (s, 3H), 3.38-3.44 (m, 2H), 6.49 (s, 1H), 7.40 (dt, J=7.7, 1.8 Hz, 1H), 7.51 (t, J=7.7 Hz, 1H), 7.69 (t, J=1.5 Hz, 1H), 7.82 (ddd, J=7.7, 1.8, 1.5 Hz, 1H); APCI-MS (m/z): 364, 366 (M–H)$^-$.

EXAMPLE 118

6-Ethyl-5-(2-methoxyethyl)-4-(3-methoxyphenyl)benzene-1,3-diol (Compound 118)

Compound 116 obtained in Example 116 was dissolved in tetrahydrofuran (10 mL), and triethylamine (0.35 mL, 2.5 mmol) and methyl chlorocarbonate (0.18 mL, 2.3 mmol) were added thereto and stirred at room temperature for 1 hour. The reaction solution was filtered, and the filtrate was concentrated under reduced pressure. The resulting residue was dissolved in tetrahydrofuran (10 mL), and under stirring with ice-cooling, aqueous solution (5 mL) of sodium borohydride (150 mg, 4.0 mmol) was dropwise added thereto, and stirred for 1 hour. Water was added to the reaction solution, and extracted twice with ethyl acetate. The organic layers were combined and dried over anhydrous magnesium sulfate, and the solvent was evaporated away under reduced pressure. The resulting residue was purified through silica gel column chromatography (ethyl acetate/n-hexane 1/1) to obtain a crude product. Methanol solution (10 mL) of 7 mol/L hydrochloric acid was added to the resulting crude product, and stirred at room temperature for 2 hours. The reaction solution was concentrated under reduced pressure, and the resulting residue was purified through silica gel column chromatography (ethyl acetate/n-hexane=1/4 to 1/1) to obtain Compound 118 (53 mg, 18%)

$^1$H-NMR (270 MHz, CDCl$_3$) δ (ppm): 1.10 (t, J=7.4 Hz, 3H), 2.66 (q, J=7.4 Hz, 2H), 2.74 (t, J=8.1 Hz, 2H), 3.30 (m, 2H), 3.82 (s, 3H), 4.62 (s, 1H), 5.18 (s, 1H), 6.33 (s, 1H), 6.80-6.89 (m, 2H), 6.95 (ddd, J=8.0, 2.5, 1.0 Hz, 1H), 7.39 (t, J=8.0 Hz, 1H); FAB-MS (m/z): 302 (M+H)$^+$.

EXAMPLE 119

Methyl 3-[5-acetyl-2,4-dihydroxy-6-(2-methoxyethyl)phenyl]benzoate (Compound 119)

In the same manner as in the step 3 in Example 1, methyl 3-[5-acetyl-6-(2-methoxyethyl)-2,4-bis(methoxymethoxy) phenyl]benzoate was obtained from 1-[3-bromo-2-(2-methoxyethyl)-4,6-bis(methoxymethoxy)phenyl]ethanone (220 mg, 0.58 mmol) obtained in the step 5 in Example 116, using 3-(methoxycarbonyl)phenylboronic acid (150 mg, 0.83 mmol), bis(tri-o-tolylphosphine)palladium(II) dichloride (20 mg, 0.025 mmol), cesium carbonate (570 mg, 1.8 mmol), 1,2-dimethoxyethane (5.0 mL) and water (1.0 mL). Then, in the same manner as in the step 4 in Example 1, Compound 119 (120 mg, 60%) was obtained from the resulting compound, using methanol (2.0 mL) and 1,4-dioxane solution (2.0 mL) of 4 mol/L hydrogen chloride.

$^1$H-NMR (270 MHz, CDCl$_3$) δ (ppm): 2.68 (s, 3H), 2.97 (t, J=7.8 Hz, 2H), 3.12 (s, 3H), 3.24 (t, J=7.8 Hz, 2H), 3.94 (s, 3H), 5.12 (br s, 1H), 6.47 (s, 1H), 7.47 (dt, J=7.8, 1.8 Hz, 1H), 7.60 (d, J=7.8 Hz, 1H), 7.97 (dd, J=1.8, 1.5 Hz, 1H), 8.13 (dt, J=7.8, 1.5 Hz, 1H), 11.9 (s, 1H); APCI-MS (m/z): 343 (M–H)$^-$.

EXAMPLE 120

1-[2,4-Dihydroxy-6-(2-methoxyethyl)-5-(3-phenylphenyl)phenyl]ethanone (Compound 120)

In the same manner as in the step 3 in Example 1, 1-[2-(2-methoxyethyl)-4,6-bis(methoxymethoxy)-3-(3-phenylphenyl)phenyl]ethanone was obtained from 1-[3-bromo-2-(2-methoxyethyl)-4,6-bis(methoxymethoxy)phenyl]ethanone (200 mg, 0.53 mmol) obtained in the step 5 in Example 116, using 3-biphenylboronic acid (150 mg, 0.76 mmol), bis(tri-o-tolylphosphine)palladium(II) dichloride (20 mg, 0.025 mmol), cesium carbonate (500 mg, 1.6 mmol), 1,2-dimethoxyethane (5.0 mL) and water (1.0 mL). Then, in the same manner as in the step 4 in Example 1, Compound 120 (130 mg, 67%) was obtained from the resulting compound, using methanol (2.0 mL) and 1,4-dioxane solution (2.0 mL) of 4 mol/L hydrogen chloride.

$^1$H-NMR (270 MHz, CDCl$_3$) δ (ppm): 2.70 (s, 3H), 3.08 (t, J=7.4 Hz, 2H), 3.13 (s, 3H), 3.29 (t, J=7.4 Hz, 2H), 5.10 (br s, 1H), 6.49 (s, 1H), 7.23-7.71 (m, 9H), 12.0 (br s, 1H);

APCI-MS (m/z): 361 (M–H)$^-$.

EXAMPLE 121

1-[2,4-Dihydroxy-5-(3-ethoxyphenyl)-6-(2-methoxyethyl)phenyl]ethanone (Compound 121)

In the same manner as in the step 3 in Example 1, 1-[3-(3-ethoxyphenyl)-2-(2-methoxyethyl)-4,6-bis(methoxymethoxy)phenyl]ethanone was obtained from 1-[3-bromo-2-(2-methoxyethyl)-4,6-bis(methoxymethoxy)phenyl]ethanone (230 mg, 0.61 mmol) obtained in the step 5 in Example 116, using 3-ethoxyphenylboronic acid (150 mg, 0.90 mmol), bis(tri-o-tolylphosphine)palladium(II) dichloride (20 mg, 0.025 mmol), cesium carbonate (580 mg, 1.8 mmol), 1,2-dimethoxyethane (5.0 mL) and water (1.0 mL). Then, in the same manner as in the step 4 in Example 1, Compound 121 (130 mg, 67%) was obtained from the resulting compound, using methanol (2.0 mL) and 1,4-dioxane solution (2.0 mL) of 4 mol/L hydrogen chloride.

$^1$H-NMR (270 MHz, CDCl$_3$) δ (ppm): 1.43 (t, J=7.0 HZ, 3H), 2.69 (s, 3H), 3.03 (t, J=7.5 Hz, 2H), 3.15 (s, 3H), 3.28 (t, J=7.5 Hz, 2H), 4.05 (q, J=7.0 Hz, 2H), 5.07 (br s, 1H), 6.40 (s, 1H), 6.77-6.82 (m, 2H), 6.97 (dd, J=7.8, 2.5 Hz, 1H), 7.42 (t, J=7.8 Hz, 1H), 12.1 (s, 1H);

APCI-MS (m/z): 329 (M–H)$^-$.

EXAMPLE 122

1-[2,4-Dihydroxy-6-(2-methoxyethyl)-5-(3-methylphenyl)phenyl]ethanone (Compound 122)

In the same manner as in the step 3 and the step 4 in Example 1, 1-[2-(2-methoxyethyl)-4,6-bis(methoxymethoxy)-3-(3-methylphenyl)phenyl]ethanone was obtained from 1-[3-bromo-2-(2-methoxyethyl)-4,6-bis(methoxymethoxy)phenyl]ethanone (590 mg, 1.6 mmol) obtained in the step 5 in Example 116, using 3-methylphenylboronic acid (320 mg, 2.4 mmol), bis(tri-o-tolylphosphine)palladium(II) dichloride (150 mg, 0.19 mmol), cesium carbonate (1.5 g, 4.6 mmol), 1,2-dimethoxyethane (10 mL) and water (2.0 mL). Then, in the same manner as in the step 4 in Example 1, Compound 122 (460 mg, 96%) was obtained from the resulting compound, using methanol (6.0 mL) and 1,4-dioxane solution (6.0 mL) of 4 mol/L hydrogen chloride.

$^1$H-NMR (270 MHz, CDCl$_3$) δ (ppm): 2.41 (s, 3H), 2.69 (s, 3H), 3.00 (t, J=7.5 Hz, 2H), 3.14 (s, 3H), 3.26 (t, J=7.5 Hz, 2H), 5.03 (br s, 1H), 6.46 (s, 1H), 7.06-7.03 (m, 2H), 7.28 (d, J=7.6 Hz, 1H), 7.40 (t, J=7.6 Hz, 1H), 12.1 (s, 1H);

APCI-MS (m/z): 299 (M–H)$^-$.

EXAMPLE 123

6-Ethyl-5-(3-hydroxypropyl)-4-phenylbenzene-1,3-diol (Compound 123)

(Step 1)

3-[2-Bromo-3,5-bis(methoxymethoxy)-6-phenylphenyl]propanol (137 mg, 0.333 mmol) obtained in the step 2 in Example 97 was dissolved in toluene (5 mL), and tris(dibenzylidene-acetone)dipalladium-chloroform adduct (15.6 mg, 0.0151 mmol), 2-(di-tert-butylphosphino)biphenyl (20.5 mg, 0.0687 mmol) and tributylvinyltin (0.150 mL, 0.513 mmol) were added thereto and stirred at 110° C. for 20 hours. Aqueous saturated potassium fluoride solution was added to the reaction mixture, and stirred at room temperature for 1 hour, and then filtered. Water was added to the filtrate, and extracted with chloroform. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=2/1) to obtain 3-[3,5-bis(methoxymethoxy)-6-phenyl-2-vinylphenyl]propanol (31.4 mg, 26%).

$^1$H-NMR (270 MHz, CDCl$_3$) δ (ppm): 0.80-1.00 (m, 1H), 1.50-1.80 (m, 2H), 2.50-2.60 (m, 2H), 3.26 (s, 3H), 3.32-3.42 (m, 2H), 3.52 (s, 3H), 4.99 (s, 2H), 5.21 (s, 2H), 5.51 (dd, J=2.4, 11.5 Hz, 1H), 5.65 (dd, J=2.4, 17.8 Hz, 1H), 6.71 (dd, J=11.5, 17.8 Hz, 1H), 6.88 (s, 1H), 7.15-7.23 (m, 2H), 7.28-7.45 (m, 3H).

(Step 2)

3-[3,5-Bis(methoxymethoxy)-6-phenyl-2-vinylphenyl]propanol (30.0 mg, 0.0837 mmol) obtained in the above was dissolved in ethanol (10 mL), and 10% palladium-carbon (52.6 mg) was added thereto and stirred in a hydrogen atmosphere at room temperature for 14 hours. The reaction mixture was filtered, and the filtrate was concentrated under reduced pressure. The resulting residue was purified through preparative thin-layer chromatography (n-hexane/ethyl acetate=2/1) to obtain 3-[2-ethyl-3,5-bis(methoxymethoxy)-6-phenylphenyl]propanol (15.2 mg, 50%).

$^1$H-NMR (270 MHz, CDCl$_3$) δ (ppm): 0.86 (br s, 1H), 1.17 (t, J=7.4 Hz, 3H), 1.50-1.64 (m, 2H), 2.45-2.55 (m, 2H), 2.69 (q, J=7.4 Hz, 2H), 3.24 (s, 3H), 3.39 (t, J=6.4 Hz, 2H), 3.53 (s, 3H), 4.95 (s, 2H), 5.23 (s, 2H), 6.84 (s, 1H), 7.17-7.25 (m, 2H), 7.27-7.45 (m, 3H).

(Step 3)

In the same manner as in the step 2 in Example 25, Compound 123 (11.9 mg, 100%) was obtained from 3-[2-ethyl-3,5-bis(methoxymethoxy)-6-phenylphenyl]propanol (15.2 mg, 0.0422 mmol) obtained in the above, using ethanol (4 mL) and concentrated hydrochloric acid (0.1 mL).

$^1$H-NMR (270 MHz, CDCl$_3$) δ (ppm): 1.19 (t, J=7.4 Hz, 3H), 1.40-1.80 (m, 3H), 2.40-2.50 (m, 2H), 2.65 (q, J=7.5 Hz, 2H), 3.41 (t, J=6.4 Hz, 2H), 4.50 (br s, 1H), 4.80 (br s, 1H), 6.35 (s, 1H), 7.22-7.33 (m, 2H), 7.37-7.55 (m, 3H);

FAB-MS (m/z): 273 (M+H)$^+$.

EXAMPLE 124

1-[2,4-Dihydroxy-6-(3-hydroxypropyl)-5-phenylphenyl]ethanone (Compound 124)

(Step 1)

3-[2-Bromo-3,5-bis(methoxymethoxy)-6-phenylphenyl]propanol (684 mg, 1.66 mmol) obtained in the step 2 in Example 97 was dissolved in N,N-dimethylformamide (4 mL), and imidazole (345 mg, 5.06 mmol) and tert-butyldimethylsilyl chloride (374 mg, 2.48 mmol) were added thereto and stirred at room temperature for 4 hours. Aqueous saturated sodium hydrogencarbonate solution was added to the reaction mixture, and extracted with chloroform. The organic layer was washed with aqueous saturated sodium chloride solution, then dried over anhydrous sodium sulfate, and the solvent was evaporated away under reduced pressure. The resulting residue was purified through silica gel column chromatography (n-hexane/ethyl acetate=9/1) to obtain 1-(tert-butyldimethylsilyloxypropyl)-3,5-bis(methoxymethoxy)-2-phenylbenzene (778 mg, 89%).

$^1$H-NMR (270 MHz, CDCl$_3$) δ (ppm): 0.05 (s, 6H), 0.81 (s, 9H), 1.54-1.70 (m, 2H), 2.50-2.60 (m, 2H), 3.26 (s, 3H), 3.44 (t, J=6.6 Hz, 2H), 3.57 (s, 3H), 4.97 (s, 2H), 5.27 (s, 2H), 6.91 (s, 1H), 7.13-7.20 (m, 2H), 7.27-7.42 (m, 3H).

(Step 2)

1-(Tert-butyldimethylsilyloxypropyl)-3,5-bis(methoxymethoxy)-2-phenylbenzene (147 mg, 0.280 mmol) obtained in the above was dissolved in toluene (10 mL), and tributyl(1-ethoxyvinyl)tin (0.200 mL, 0.592 mmol) and bis(tri-o-tolylphosphine)palladium(II) dichloride (75.5 mg, 0.0960 mmol) were added thereto and stirred at 130° C. for 60 hours. Aqueous saturated potassium fluoride solution was added to the reaction mixture, then stirred for 2 hours and filtered. Water was added to the filtrate, and extracted with chloroform. The organic layer was washed with aqueous saturated sodium chloride solution, then dried over anhydrous sodium sulfate, and the solvent was evaporated away under reduced pressure. The resulting residue was dissolved in tetrahydrofuran (6 mL), and 2 mol/L hydrochloric acid (6 mL) was added thereto and stirred at room temperature for 3 hours. Water was added to the reaction solution, and extracted with chloroform. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=2/1) to obtain 1-[2-(3-hydroxypropyl)-4,6-bis(methoxymethoxy)-3-phenylphenyl]ethanone (21.2 mg, 20%).

(Step 3)

In the same manner as in the step 2 in Example 25, Compound 124 (11.7 mg, 72%) was obtained from 1-[2-(3-hydroxypropyl)-4,6-bis(methoxymethoxy)-3-phenylphenyl]ethanone (21.2 mg, 0.0566 mmol) obtained in the above, using ethanol (8 mL) and concentrated hydrochloric acid (0.2 mL).

$^1$H-NMR (270 MHz, CDCl$_3$) δ (ppm): 1.04 (t, J=5.3 Hz, 1H), 1.50-1.64 (m, 2H), 2.71 (s, 3H), 2.75-2.86 (m, 2H), 3.39 (dt, J=5.3, 6.0 Hz, 2H), 4.96 (br s, 1H), 6.46 (s, 1H), 7.22-7.32 (m, 2H), 7.42-7.58 (m, 3H), 11.94 (s, 1H);

APCI-MS (m/z): 285 (M−H)$^-$.

EXAMPLE 125

1-[2,4-Dihydroxy-6-(2-methoxyethyl)-5-phenylphenyl]-2,2,2-trifluoroethanone (Compound 125)

In an argon atmosphere, 4-bromo-3-(2-methoxyethyl)-1,5-bis(methoxymethoxy)-2-phenylbenzene (0.33 g, 0.80 mmol) obtained in the step 3 in Example 92 was dissolved in tetrahydrofuran (7.0 mL), and the solution was cooled to −78° C., and thereafter n-hexane solution of 1.6 mol/L n-butyllithium (0.60 mL, 0.96 mmol) was dropwise added thereto, taking 5 minutes, and then stirred at −78° C. for 10 minutes. Ethyl trifluoroacetate (0.15 mL, 1.3 mmol) was added to the reaction mixture, and then with heating from −78° C. up to room temperature, the mixture was stirred for 2 hours. Water (10 mL) was added to the reaction mixture, and extracted twice with ethyl acetate (0.10 L). The organic layer was dried over anhydrous sodium sulfate, and the solvent was evaporated away under reduced pressure. The resulting residue was purified through silica gel column chromatography (ethyl acetate/n-hexane=1/9 to 1/2) to obtain 1-[2-(2-methoxyethyl)-4,6-bis(methoxymethoxy)-3-phenylphenyl]-2,2,2-trifluoroethanone. The resulting compound was dissolved in methanol (5.0 mL), and 1,4-dioxane solution (5.0 mL) of 4 mol/L hydrogen chloride was added thereto and stirred at room temperature for 1.5 hours. The reaction mixture was concentrated under reduced pressure, and purified through preparative thin-layer chromatography (ethyl acetate/n-hexane=1/2) to obtain Compound 125 (5.1 mg, 1.9%).

$^1$H-NMR (CDCl$_3$, 270 MHz) δ (ppm): 2.74 (t, J=6.7 Hz, 2H), 3.12 (s, 3H), 3.23 (t, J=6.7 Hz, 2H), 6.38 (s, 1H), 7.25-7.28 (m, 2H), 7.46-7.55 (m, 3H);

APCI-MS (m/z): 399 (M−H)$^-$.

EXAMPLE 126

Methyl 6-ethyl-3-hydroxy-5-methoxy-2-phenylphenylacetate (Compound 126)

(Step 1)

Compound 69 (0.12 g, 0.41 mmol) obtained in Example 69 was dissolved in tetrahydrofuran (10 mL), triethylamine (0.15 mL, 1.1 mmol) was added thereto, and the solution was cooled to 4° C. Then, methyl chlorocarbonate (0.081 mL, 1.1 mmol) was added thereto, and the mixture was stirred for 2 hours with heating up to room temperature. The reaction mixture was filtered, and the filtrate was concentrated under reduced pressure. The resulting methyl 2-acetyl-3,5-bis(methoxycarbonyloxy)-6-phenylphenylacetate was dissolved in a mixed solvent of tetrahydrofuran (5.0 mL) and water (5.0 mL), then the solution was cooled to 4° C., and sodium borohydride (73 mg, 1.9 mmol) was added thereto, taking 5 minutes, and then stirred for 1 hour. Water (10 mL) was added to the reaction mixture, and stirred for 10 minutes, and then extracted twice with ethyl acetate (0.10 L). The organic layer was washed with aqueous saturated sodium chloride solution, then dried over anhydrous sodium sulfate, and the solvent was evaporated away under reduced pressure. The resulting residue was purified through preparative thin-layer chromatography (ethyl acetate/n-hexane=1/2) to obtain methyl 6-ethyl-3-hydroxy-5-(methoxycarbonyloxy)-2-phenylphenylacetate (89 mg, 64%).

$^1$H-NMR (CDCl$_3$, 270 MHz) δ (ppm): 1.10 (t, J=7.4 Hz, 3H), 2.59 (q, J=7.4 Hz, 2H), 3.49 (s, 2H), 3.59 (s, 3H), 3.63 (s, 3H), 6.33 (s, 1H), 6.52 (s, 1H), 7.15-7.19 (m, 2H), 7.31-7.40 (m, 3H);

APCI-MS (m/z): 343 (M+H)$^+$.

(Step 2)

Methyl 6-ethyl-3-hydroxy-5-(methoxycarbonyloxy)-2-phenylphenylacetate (53 mg, 0.15 mmol) obtained in the above was dissolved in a mixed solvent of acetonitrile (3.6 mL) and methanol (0.4 mL), and N,N-diisopropylethylamine (0.053 mL, 0.30 mmol) and diethyl ether solution of 2.0 mol/L trimethylsilyldiazomethane (0.15 mL, 0.3 mmol) were added thereto, and stirred at room temperature for 6 hours. The reaction solution was concentrated under reduced pressure, and the resulting residue was purified through preparative thin-layer chromatography (ethyl acetate/n-hexane=1/2) to obtain methyl 2-ethyl-3-methoxy-5-(methoxycarbonyloxy)-6-phenylphenylacetate (51 mg, 92%).

$^1$H-NMR (CDCl$_3$, 270 MHz) δ (ppm): 1.10 (t, J=7.4 Hz, 3H), 2.65 (q, J=7.4 Hz, 2H), 3.49 (s, 2H), 3.57 (s, 3H), 3.64 (s, 3H), 3.84 (s, 3H), 6.68 (s, 1H), 7.15-7.19 (m, 2H), 7.31-7.39 (m, 3H).

(Step 3)

Methyl 2-ethyl-3-methoxy-5-(methoxycarbonyloxy)-6-phenylphenylacetate (39 mg, 0.11 mmol) obtained in the above was dissolved in methanol solution of 7.0 mol/L ammonia (4.0 mL, 28 mmol), and stirred at room temperature for 3 hours. The reaction solution was concentrated under reduced pressure, and the resulting residue was purified through preparative thin-layer chromatography (ethyl acetate/n-hexane=1/2) to obtain Compound 126 (28 mg, 85%).

$^1$H-NMR (CDCl$_3$, 270 MHz) δ (ppm): 1.07 (t, J=7.4 Hz, 3H), 2.58 (q, J=7.4 Hz, 2H), 3.44 (s, 2H), 3.58 (s, 3H), 3.83 (s, 3H), 4.62 (s, 1H), 6.35 (s, 1H), 7.26-7.29 (m, 2H), 7.40-7.50 (m, 3H);

FAB-MS (m/z): 301 (M+H)$^+$.

EXAMPLE 127

2,4-Dihydroxy-6-(2-methoxyethyl)-5-phenylbenzoic acid (Compound 127)

(Step 1)

In an argon atmosphere, 4-bromo-3-(2-methoxyethyl)-1,5-bis(methoxymethoxy)-2-phenylbenzene (0.71 g, 1.7 mmol) obtained in the step 3 in Example 92 was added to tetrahydrofuran (10 mL) and cooled to −78° C., and then n-hexane solution of 1.6 mol/L n-butyllithium (2.7 mL, 4.3 mmol) was dropwise added thereto, taking 1 minute, and then stirred for 5 minutes. Ground dry ice (1.0 g) was added to the reaction mixture, and stirred for 4 hours with heating from −78° C. up to room temperature. Aqueous saturated ammonium chloride solution (10 mL) was added to the reaction mixture, and extracted twice with ethyl acetate (0.10 L). The organic layer was dried over anhydrous sodium sulfate, and the solvent was evaporated away under reduced pressure. The resulting residue was purified through silica gel column chromatography (chloroform to methanol/chloroform=1/4) to obtain 2-(2-methoxyethyl)-4,6-bis(methoxymethoxy)-3-phenylbenzoic acid (0.40 g, 61%).

FAB-MS (m/z): 399 (M+Na)$^+$.

(Step 2)

In the same manner as in the step 4 in Example 1, Compound 127 (25 mg, 33%) was obtained from 2-(2-methoxyethyl)-4,6-bis(methoxymethoxy)-3-phenylbenzoic acid (0.10 g, 0.27 mmol) obtained in the above, using methanol (2.0 mL) and 1,4-dioxane solution (2.0 mL) of 4 mol/L hydrogen chloride.

APCI-MS (m/z): 287 (M−H)$^−$.

Elementary Analysis (as C$_{16}$H$_{16}$O$_5$·0.4H$_2$O):
Measured (%): C:65.25, H:5.69, N:0.18
Calculated (%): C:65.03, H:5.73, N:0

EXAMPLE 128

Methyl 2,4-dihydroxy-6-(2-methoxyethyl)-5-phenylbenzoate (Compound 128)

(Step 1)

2-(2-Methoxyethyl)-4,6-bis(methoxymethoxy)-3-phenylbenzoic acid (0.12 g, 0.32 mmol) obtained in the step-1 in Example 127 was dissolved in a mixed solvent of methanol (2.0 mL) and acetonitrile (2.0 mL), and diethyl ether solution of 2.0 mol/L trimethylsilyldiazomethane (0.5 mL, 1.0 mmol) was added thereto and stirred at room temperature for 11 hour. The reaction solution was concentrated under reduced pressure, and the resulting residue was purified through preparative thin-layer chromatography (n-hexane/ethyl acetate=1/2) to obtain methyl 2-(2-methoxyethyl)-4,6-bis(methoxymethoxy)-3-phenylbenzoate (81 mg, 65%).

$^1$H-NMR (270 MHz, CDCl$_3$) δ (ppm): 2.68 (t, J=8.0 Hz, 2H), 3.07 (s, 3H), 3.26 (s, 3H), 3.29 (t, J=8.0 Hz, 2H), 3.50 (s, 3H), 3.91 (s, 3H), 5.00 (s, 2H), 5.20 (s, 2H), 6.90 (s, 1H), 7.17-7.20 (m, 2H), 7.33-7.43 (m, 3H);

FAB-MS (m/z): 391 (M+H)$^+$.

(Step 2)

In the same manner as in the step 4 in Example 1, Compound 128 (52 mg, 84%) was obtained from methyl 2-(2-methoxyethyl)-4,6-bis(methoxymethoxy)-3-phenylbenzoate (80 mg, 0.21 mmol) obtained in the above, using methanol (2.0 mL) and 1,4-dioxane solution (2.0 mL) of 4 mol/L hydrogen chloride.

$^1$H-NMR (270 MHz, CDCl$_3$) δ (ppm): 3.03 (t, J=8.1 Hz, 2H), 3.12 (s, 3H), 3.33 (t, J=8.0 Hz, 2H), 3.95 (s, 3H), 4.92 (s, 1H), 6.51 (s, 1H), 7.23-7.27 (m, 2H), 7.46-7.54 (m, 3H), 11.48 (s, 1H);

APCI-MS (m/z): 301 (M−H)$^−$.
Elementary Analysis (as C$_{17}$H$_{18}$O$_5$·0.4H$_2$O):
Measured (%): C:66.16, H:6.03, N:0.10
Calculated (%): C:65.97, H:6.12, N:0

EXAMPLE 129

6-Methoxy-5-(2-methoxyethyl)-4-phenylbenzene-1,3-diol (Compound 129)

(Step 1)

In an argon atmosphere, 4-bromo-3-(2-methoxyethyl)-1,5-bis(methoxymethoxy)-2-phenylbenzene (1.2 g, 2.9 mmol) obtained in the step 3 in Example 92 was dissolved in tetrahydrofuran (20 mL), then the solution was cooled to −78° C., and n-hexane solution of 1.6 mol/L n-butyllithium (5.0 mL, 8.0 mmol) was dropwise added thereto, taking 5 minutes, and stirred at −78° C. for 10 minutes. 4-Formylmorpholine (1.2 mL, 12 mmol) was added thereto, and stirred for 2 hours with heating from −78° C. up to room temperature. Water (10 mL) was added to the reaction mixture, and extracted twice with ethyl acetate (0.10 L). The organic layer was dried over anhydrous sodium sulfate, and the solvent was evaporated away under reduced pressure. The resulting residue was purified through silica gel column chromatography (ethyl acetate/n-hexane=1/9 to 1/2) to obtain 2-(2-methoxyethyl)-4,6-bis(methoxymethoxy)-3-phenylbenzaldehyde (0.62 g, 59%).

¹H-NMR (300 MHz, CDCl₃) δ (ppm): 3.08 (t, J=7.3 Hz, 3H), 3.16 (s, 3H), 3.30 (s, 3H), 3.36 (t, J=7.3 Hz, 2H), 3.55 (s, 3H), 5.09 (s, 2H), 5.31 (s, 2H), 6.92 (s, 1H), 7.17-7.14 (m, 2H), 7.34-7.40 (m, 3H), 10.60 (s, 1H);
APCI-MS (m/z): 339 (M−H)⁻.

(Step 2)

2-(2-Methoxyethyl)-4,6-bis(methoxymethoxy)-3-phenylbenzaldehyde (0.18 g, 0.50 mmol) obtained in the above was dissolved in dichloromethane (10 mL), and m-chloroperbenzoic acid (0.26 g, 1.5 mmol) was added thereto and stirred at room temperature for 15 hours. Aqueous saturated sodium thiosulfate (10 mL) was added to the reaction solution for liquid-liquid separation. The organic layer was washed with aqueous saturated sodium hydrogencarbonate (10 mL), and dried over anhydrous sodium sulfate, and the solvent was evaporated away under reduced pressure. The resulting residue was dissolved in methanol solution (10 mL) of 7.0 mol/L ammonia, and stirred at room temperature for 4 hours. The reaction solution was concentrated under reduced pressure, and the resulting residue was purified through preparative thin-layer chromatography (ethyl acetate/n-hexane=1/2) to obtain 2-(2-methoxyethyl)-4,6-bis(methoxymethoxy)-3-phenylphenol (0.12 g, 68%).
¹H-NMR (270 MHz, CDCl₃) δ (ppm): 2.71 (t, J=6.3 Hz, 3H), 3.21 (s, 3H), 3.30 (s, 3H), 3.48 (t, J=6.3 Hz, 2H), 3.56 (s, 3H), 4.86 (s, 2H), 5.25 (s, 2H), 6.93 (s, 1H), 7.17-7.59 (m, 5H);
FAB-MS (m/z): 349 (M+H)⁺.

(Step 3)

2-(2-Methoxyethyl)-4,6-bis(methoxymethoxy)-3-phenylphenol (0.12 g, 0.35 mmol) obtained in the above was dissolved in a mixed solvent of ethanol (4.0 mL) and water (4.0 mL), and sodium hydroxide (40 mg, 1.0 mmol) and dimethyl sulfate (0.080 mL, 0.85 mmol) were added thereto and stirred at 80° C. for 4 hours. The reaction solution was cooled to room temperature, and 3 mol/L hydrochloric acid (5.0 mL) was added thereto and stirred for 1 hour, and then extracted twice with ethyl acetate (0.10 L). The organic layer was washed with water (50 mL), and dried over anhydrous sodium sulfate, and the solvent was evaporated away under reduced pressure. The resulting residue was purified through preparative thin-layer chromatography (ethyl acetate/n-hexane=1/2) to obtain Compound 129 (22 mg, 23%).
¹H-NMR (270 MHz, CDCl₃) δ (ppm): 2.73 (t, J=8.1 Hz, 2H), 3.15 (s, 3H), 3.27 (t, J=8.1 Hz, 2H), 3.81 (s, 3H), 4.55 (s, 1H), 5.56 (s, 1H), 6.52 (s, 1H), 7.26-7.30 (m, 2H), 7.42-7.53 (m, 3H);
FAB-MS (m/z): 275 (M+H)⁺.

EXAMPLE 130

6-Ethyl-5-(2-methoxyethyl)-4-(3-methylphenyl)benzene-1,3-diol (Compound 130)

In the same manner as in Example 118, 1-[4,6-bis(methoxycarbonyloxy)-2-(2-methoxyethyl)-3-(3-methylphenyl)phenyl]ethanone was obtained from Compound 122 (320 mg, 1.1 mmol) obtained in Example 122, using methyl chlorocarbonate (0.21 mL, 2.7 mmol), triethylamine (0.37 mL, 2.7 mmol) and tetrahydrofuran (10 mL); and from the resulting compound, obtained was 4-ethyl-1,5-bis(methoxycarbonyloxy)-3-(2-methoxyethyl)-2-(3-methylphenyl)benzene, using sodium borohydride (160 mg, 4.3 mmol), water (5.0 mL) and tetrahydrofuran (10 mL). Then, the resulting compound was treated with methanol solution (10 mL) of 7 mmol/L ammonia to obtain Compound 130 (70 mg, 23%).

¹H-NMR (270 MHz, CDCl₃) δ (ppm): 1.18 (t, J=7.3 Hz, 3H), 2.62-2.74 (m, 4H), 3.13 (s, 3H), 3.27 (t, J=7.7 Hz, 2H), 4.53 (s, 1H), 4.80 (br s, 1H), 6.34 (s, 1H), 7.04-7.08 (m, 2H), 7.21 (d, J=7.3 Hz, 1H), 7.37 (t, J=7.3 Hz, 1H);
FAB-MS (m/z): 286 (M+H)⁺.

EXAMPLE 131

Methyl 3-[5-ethyl-2,4-dihydroxy-6-(2-methoxyethyl)phenyl]benzoate (Compound 131)

In the same manner as in Example 118, methyl 3-[5-acetyl-2,4-bis(methoxycarbonyloxy)-6-(2-methoxyethyl)phenyl]benzoate was obtained from Compound 119 (100 mg, 0.30 mmol) obtained in Example 119, using methyl chlorocarbonate (0.05 mL, 0.65 mmol), triethylamine (0.09 mL, 0.65 mmol) and tetrahydrofuran (3.0 mL); and from the resulting compound, obtained was methyl 3-[5-ethyl-2,4-bis(methoxycarbonyloxy)-6-(2-methoxyethyl)phenyl]benzoate, using sodium borohydride (45 mg, 1.2 mmol), water (2.0 mL) and tetrahydrofuran (2.0 mL). Then, the resulting compound was treated with methanol solution (5.0 mL) of 7 mmol/L ammonia to obtain Compound 131 (37 mg, 37%).
¹H-NMR (270 MHz, CDCl₃) δ (ppm): 1.18 (t, J=7.3 Hz, 3H), 2.62-2.71 (m, 4H), 3.12 (s, 3H), 3.25 (t, J=7.5 Hz, 2H), 3.92 (s, 3H), 4.48 (br s, 1H), 5.16 (br s, 1H), 6.35 (s, 1H), 7.49 (dt, J=7.6, 1.4 Hz, 1H), 7.57 (t, J=7.6 Hz, 1H), 7.98 (t, J=1.7 Hz, 1H), 8.09 (m, 1H);
FAB-MS (m/z): 330 (M+H)⁺.

EXAMPLE 132

6-Ethyl-5-(2-methoxyethyl)-4-(3-phenylphenyl)benzene-1,3-diol (Compound 132)

In the same manner as in Example 118, 1-[4,6-bis(methoxycarbonyloxy)-2-(2-methoxyethyl)-3-(3-phenylphenyl)phenyl]ethanone was obtained from Compound 120 (65 mg, 0.18 mmol) obtained in Example 120, using methyl chlorocarbonate (0.03 mL, 0.39 mmol), triethylamine (0.06 mL, 0.43 mmol) and tetrahydrofuran (3.0 mL); and from the resulting compound, obtained was 4-ethyl-1,5-bis(methoxycarbonyloxy)-3-(2-methoxyethyl)-2-(3-phenylphenyl)benzene, using sodium borohydride (30 mg, 0.79 mmol), water (2.0 mL) and tetrahydrofuran (2.0 mL). Then, the resulting compound was treated with methanol solution (5.0 mL) of 7 mmol/L ammonia to obtain Compound 132 (33 mg, 52%).
¹H-NMR (270 MHz, CDCl₃) δ (ppm): 1.20 (t, J=7.6 Hz, 3H), 2.67 (q, J=7.6 Hz, 2H), 2.76 (t, J=7.9 Hz, 2H), 3.13 (s, 3H), 3.31 (t, J=7.9 Hz, 2H), 4.59 (s, 1H), 4.93 (br s, 1H), 6.37 (s, 1H), 7.36-7.76 (m, 7H), 7.24-7.27 (m, 2H);
APCI-MS (m/z): 347 (M−H)⁻.

EXAMPLE 133

4-(3-Ethoxyphenyl)-6-ethyl-5-(2-methoxyethyl)benzene-1,3-diol (Compound 133)

In the same manner as in Example 118, 1-[3-(3-ethoxyphenyl)-4,6-bis(methoxycarbonyloxy)-2-(2-methoxyethyl)phenyl]ethanone was obtained from Compound 121 (94 mg, 0.29 mmol) obtained in Example 121, using methyl chlorocarbonate (0.05 mL, 0.65 mmol), triethylamine (0.09 mL, 0.65 mmol) and tetrahydrofuran (3.0 mL); and from the resulting compound, obtained was 2-(3-ethoxyphenyl)-4-ethyl-1,5-bis(methoxycarbonyloxy)-3-(2-methoxyethyl)benzene, using sodium borohydride (30 mg, 0.79 mmol), water (2.0 mL) and tetrahydrofuran (2.0 mL). Then, the resulting compound was treated with methanol solution (5.0 mL) of 7 mmol/L ammonia to obtain Compound 133 (45 mg, 50%).

$^1$H-NMR (270 MHz, CDCl$_3$) δ (ppm): 1.18 (t, J=7.6 Hz, 3H), 1.42 (t, J=7.0 Hz, 3H), 2.65 (q, J=7.6 Hz, 2H), 2.73 (t, J=8.0 Hz, 2H), 3.15 (s, 3H), 3.30 (t, J=8.0 Hz, 2H), 4.04 (q, J=7.0 Hz, 2H), 4.60 (s, 1H), 4.98 (br s, 1H), 6.33 (s, 1H), 6.78-6.84 (m, 2H), 6.93 (ddd, J=7.9, 2.5, 0.8 Hz, 1H), 7.37 (t, J=7.9 Hz, 1H);

FAB-MS (m/z): 316 (M+H)$^+$.

EXAMPLE 134

1-[2,4-Dihydroxy-5-(3-hydroxyphenyl)-6-(2-methoxyethyl)phenyl]ethanone (Compound 134)

In the same manner as in the step 3 in Example 1, 1-[3-(3-hydroxyphenyl)-2-(2-methoxyethyl)-4,6-bis(methoxymethoxy)phenyl]ethanone was obtained from 1-[3-bromo-2-(2-methoxyethyl)-4,6-bis(methoxymethoxy)phenyl]ethanone (100 mg, 0.27 mmol) obtained in the step 5 in Example 116, using 2-(3-hydroxyphenyl)-4,4,5,5-tetramethyl-1,3,2-dioxaborolane (90 mg, 0.41 mmol), bis(tri-o-tolylphosphine)palladium(II) dichloride (20 mg, 0.025 mmol), cesium carbonate (200 mg, 0.61 mmol), 1,2-dimethoxyethane (2.0 mL) and water (0.5 mL). Then, in the same manner as in the step 4 in Example 1, Compound 134 (46 mg, 56%) was obtained from the resulting compound, using methanol (2.0 mL) and 1,4-dioxane solution (2.0 mL) of 4 mol/L hydrogen chloride.

$^1$H-NMR (270 MHz, CD$_3$OD) δ (ppm): 2.52 (s, 3H), 2.66 (t, J=7.8 Hz, 2H), 3.07 (s, 3H), 3.27 (t, J=7.8 Hz, 2H), 6.31 (s, 1H), 6.60-6.65 (m, 2H), 6.74 (m, 1H), 7.21 (t, J=7.5 Hz, 1H);

APCI-MS (m/z): 301 (M−H)$^-$.

EXAMPLE 135

1-[2,4-Dihydroxy-5-(3-benzyloxyphenyl)-6-(2-methoxyethyl)phenyl]ethanone (Compound 135)

(Step 1)

1-[3-(3-hydroxyphenyl)-2-(2-methoxyethyl)-4,6-bis(methoxymethoxy)phenyl]ethanone (25 mg, 0.064 mmol) obtained in Example 134 was dissolved in N,N-dimethylformamide (1.0 mL), and potassium carbonate (35 mg, 0.25 mmol) and benzyl bromide (0.02 mL, 0.17 mmol) were added thereto and stirred at room temperature for 1 hour. Water was added to the reaction solution, and extracted twice with diethyl ether. The organic layer was dried over anhydrous magnesium sulfate, and the solvent was evaporated away under reduced pressure. The resulting residue was purified through silica gel column chromatography (ethyl acetate/n-hexane=1/4 to 1/2) to obtain 1-[3-(3-benzyloxyphenyl)-2-(2-methoxyethyl)-4,6-bis(methoxymethoxy)phenyl]ethanone (30 mg, 97%).

$^1$H-NMR (270 MHz, CDCl$_3$) δ (ppm): 2.55 (s, 3H), 2.67 (t, J=7.2 Hz, 2H), 3.10 (s, 3H), 3.22 (t, J=7.2 Hz, 2H), 3.27 (s, 3H), 3.49 (s, 3H), 4.99 (s, 2H), 5.06 (s, 2H), 5.20 (s, 2H), 6.77-6.80 (m, 2H), 6.88 (s, 1H), 6.96 (m, 1H), 7.26-7.45 (m, 7H).

(Step 2)

In the same manner as in the step 4 in Example 1, Compound 135 (13 mg, 53%) was obtained from 1-[3-(3-benzyloxyphenyl)-2-(2-methoxyethyl)-4,6-bis(methoxymethoxy)phenyl]ethanone (30 mg, 0.062 mmol) obtained in the above, using methanol (2.0 mL) and 1,4-dioxane solution (2.0 mL) of 4 mol/L hydrogen chloride.

$^1$H-NMR (270 MHz, CDCl$_3$) δ (ppm): 2.68 (s, 3H), 3.00 (t, J=7.8 Hz, 2H), 3.13 (s, 3H), 3.22 (t, J=7.8 Hz, 2H), 5.07 (br s, 1H), 5.09 (s, 1H), 6.46 (s, 1H), 6.86-6.83 (m, 2H), 7.07 (m, 1H), 7.47-7.25 (m, 6H), 12.1 (s, 1H);

APCI-MS (m/z): 391 (M−H)$^-$.

EXAMPLE 136

1-[2,4-Dihydroxy-6-[2-(2-methoxyethoxy)ethyl]-5-phenylphenyl)ethanone (Compound 136)

(Step 1)

In the same manner as in the step 1 in Example 86, 1-[2-(2-methoxyethoxy)ethyl]-3,5-bis(methoxymethoxy)-2-phenylbenzene (3.8 g, 86%) was obtained from 2-[3,5-bis(methoxymethoxy)-2-phenylphenyl]ethanol (3.8 g, 12 mmol) obtained in the step 1 in Example 92, using 60% sodium hydride/mineral oil dispersion (1.9 g, 48 mmol) and 2-bromoethyl methyl ether (4.7 mL, 48 mmol).

$^1$HNMR (CDCl$_3$, 270 MHz) δ (ppm): 7.40-7.33 (m, 3H), 7.21-7.18 (m, 2H), 6.76 (d, J=2.3 Hz, 1H), 6.72 (d, J=2.3 Hz, 1H), 5.19 (s, 2H), 4.98 (s, 2H), 3.51 (s, 3H), 3.50-3.40 (m, 6H), 3.33 (s, 3H), 3.27 (s, 3H), 2.69 (t, J=7.5 Hz, 2H).

(Step 2)

1-[2-(2-Methoxyethoxy)ethyl]-3,5-bis(methoxymethoxy)-2-phenylbenzene (0.30 g, 0.81 mol) obtained in the above was dissolved in chloroform (5.0 mL), and [bis(trifluoroacetoxy)iodo]benzene (0.34 g, 0.81 mmol) and iodine (0.21 g, 0.81 mmol) were added thereto with ice-cooling, and stirred for 30 minutes. Water was added to the reaction solution, and extracted with ethyl acetate. The organic layer was washed with aqueous saturated sodium thiosulfate, and dried over magnesium sulfate, and the solvent was evaporated away under reduced pressure. The resulting residue was purified through silica gel column chromatography (ethyl acetate/n-hexane=1/3) to obtain 4-iodo-3-[2-(2-methoxyethoxy)ethyl]-1,5-bis(methoxymethoxy)-2-phenylbenzene (0.31 g, 76%).

ESI-MS (m/z): 503 (M+H)$^+$.

(Step 3)

In the same manner as in the step 1 in Example 69, 4-iodo-3-[2-(2-methoxyethoxy)ethyl]-1,5-bis(methoxymethoxy)-2-phenylbenzene (2.6 g, 5.2 mmol) obtained in the above was treated with toluene (50 mL), bis(triphenylphosphine)palladium(II) dichloride (370 mg, 0.52 mmol) and tributyl(1-ethoxyvinyl)tin (2.5 mL, 7.3 mmol), and then treated with tetrahydrofuran (50 mL) and 2 mol/L hydrochloric acid (30 mL) to obtain 1-{2-[2-(2-methoxyethoxy)ethyl]-4,6-bis(methoxymethoxy)-3-phenylphenyl}ethanone (2.4 g, quantitative).

$^1$H-NMR (270 MHz, CDCl$_3$) δ (ppm): 2.56 (s, 3H), 2.67 (dd, J=8.1, 7.2 Hz, 2H), 3.27 (s, 3H), 3.30 (s, 3H), 3.40-3.31 (m, 6H), 3.50 (s, 3H), 5.00 (s, 2H), 5.20 (s, 2H), 6.88 (s, 1H), 7.19-7.16 (m, 2H), 7.38-7.31 (m, 3H).

(Step 4)

1-{2-[2-(2-Methoxyethoxy)ethyl]-4,6-bis(methoxymethoxy)-3-phenylphenyl}ethanone (0.40 g) obtained in the above was dissolved in methanol (10 mL), and hydrochloric acid (3.0 mol/L, 1.0 mL) was added thereto and stirred at 40° C. for 30 minutes. The reaction solution was poured into water, and extracted with ethyl acetate. The organic layer was washed with aqueous saturated sodium chloride solution, and dried over sodium sulfate, and the solvent was evaporated away under reduced pressure. The resulting residue was purified through silica gel column chromatography (ethyl acetate/n-hexane=1/2) to obtain Compound 136 (0.11 g, 55%).

$^1$H-NMR (270 MHz, CDCl$_3$) δ (ppm): 2.70 (s, 3H), 3.02 (t, J=7.3 Hz, 2H), 3.47-3.31 (m, 9H), 5.19 (br s, 1H), 6.45 (s, 1H), 7.25-7.23 (m, 2H), 7.54-7.45 (m, 3H), 11.97 (br s, 1H);

FAB-MS (m/z): 331 (M+H)$^+$.

EXAMPLE 137

1-{2,4-dihydroxy-6-[2-(2-methoxyethoxy)ethyl]-5-(3-methoxyphenyl)phenyl}ethanone
(Compound 137)

(Step 1)

In the same manner as in the step 1 in Example 64, 1-[2-(2-methoxyethoxy)ethyl]-3,5-bis(methoxymethoxy)benzene (6.6 g, 55%) was obtained from 2-[3,5-bis(methoxymethoxy)phenyl]ethanol (5.4 g, 22 mmol) obtained in the step 1 in Example 116, using 60% sodium hydride/mineral oil dispersion (1.8 g, 45 mmol), 2-bromomethoxyethane (6.2 mL, 34 mmol) and N,N-dimethylformamide (70 mL).

$^1$H-NMR (270 MHz, CDCl$_3$) δ (ppm): 2.86 (t, J=7.4 Hz, 2H), 3.38 (s, 3H), 3.47 (s, 6H), 3.54-3.69 (m, 6H), 5.13 (s, 4H), 6.56-6.59 (m 3H);

APCI-MS (m/z): 301 (M+H)$^+$.

(Step 2)

In the same manner as in the step 2 in Example 1, 2-bromo-1-[2-(2-methoxyethoxy)ethyl]-3,5-bis(methoxymethoxy)benzene (4.6 g, 98%) was obtained from 1-[2-(2-methoxyethoxy)ethyl]-3,5-bis(methoxymethoxy)benzene (3.6 g, 12.0 mmol) obtained in the above, using N-bromosuccinimide (2.4 g, 13 mmol) and N,N-dimethylformamide (50 mL).

$^1$H-NMR (270 MHz, CDCl$_3$) δ (ppm): 3.06 (t, J=7.4 Hz, 2H), 3.39 (s, 3H), 3.46 (s, 3H), 3.51 (s, 3H), 3.72-3.35 (m, 6H), 5.13 (s, 2H), 5.21 (s, 2H), 6.75 (d, J=2.5 Hz, 1H), 6.69 (d, J=2.5 Hz, 1H);

FAB-MS (m/z): 380 (M+H)$^+$.

(Step 3)

In the same manner as in the step 1 in Example 13, 2-bromo-4-iodo-1-[2-(2-methoxyethoxy)ethyl]-3,5-bis(methoxymethoxy)benzene (5.6 g, 94%) was obtained from 2-bromo-1-[2-(2-methoxyethoxy)ethyl]-3,5-bis(methoxymethoxy)benzene (4.5 g, 12 mmol) obtained in the above, using chloroform (80 mL), iodine (3.0 g, 12 mmol) and [bis(trifluoroacetoxy)iodo]benzene (5.1 g, 12 mmol).

$^1$H-NMR (270 MHz, CDCl$_3$) δ (ppm): 3.41 (s, 3H), 3.507 (s, 3H), 3.508 (s, 3H), 3.57-3.72 (m, 8H), 5.20 (s, 2H), 5.21 (s, 2H), 6.87 (s, 1H);

FAB-MS (m/z): 506 (M+H)$^+$.

(Step 4)

In the same manner as in the step 1 in Example 69, 2-bromo-4-iodo-1-[2-(2-methoxyethoxy)ethyl]-3,5-bis(methoxymethoxy)benzene (5.5 g, 11 mmol) obtained in the above was treated with toluene (55 mL), tributyl(1-ethoxyvinyl)tin (4.4 mL, 13 mmol) and bis(triphenylphosphine)palladium(II) dichloride (0.77 g, 1.1 mmol), and then treated with tetrahydrofuran (50 mL) and 2 mol/L hydrochloric acid (30 mL) to obtain 1-{3-bromo-2-[2-(2-methoxyethoxy)ethyl]-4,6-bis(methoxymethoxy)phenyl}ethanone (3.3 g, 72%).

$^1$H-NMR (270 MHz, CDCl$_3$) δ (ppm): 2.51 (s, 3H), 3.02 (t, J=7.6 Hz, 2H), 3.36 (s, 3H), 3.45 (s, 3H), 3.52 (s, 3H), 3.51-3.54 (m, 2H), 3.58-3.67 (m, 4H), 5.15 (s, 2H), 5.24 (s, 2H), 6.89 (s, 1H);

APCI-MS (m/z): 421 (M+H)$^+$.

(Step 5)

In the same manner as in the step 3 in Example 1, 1-{2-[2-(2-methoxyethoxy)ethyl]-4,6-bis(methoxyethoxy)-3-(3-methoxyphenyl)phenyl}ethanone was obtained from 1-{3-bromo-2-[2-(2-methoxyethoxy)ethyl]-4,6-bis(methoxymethoxy)phenyl}ethanone (680 mg, 1.6 mmol) obtained in the above, using 3-methoxyphenylboronic acid (300 mg, 2.0 mmol), bis(tri-o-tolylphosphine)palladium(II) dichloride (20 mg, 0.025 mmol), cesium carbonate (1.6 g, 4.9 mmol), 1,2-dimethoxyethane (20 mL) and water (2.0 mL). Then, in the same manner as in the step 4 in Example 1, Compound 137 (390 mg, 68%) was obtained from the resulting compound, using methanol (5.0 mL) and 1,4-dioxane solution (5.0 mL) of 4 mol/L hydrogen chloride.

$^1$H-NMR (270 MHz, CDCl$_3$) δ (ppm): 2.78 (s, 3H), 3.06 (t, J=7.5 Hz, 2H), 3.31 (s, 3H), 3.42 (m, 6H), 3.83 (s, 3H), 5.06 (s, 1H), 6.47 (s, 1H), 6.77-6.84 (m, 2H), 7.00 (m, 1H), 7.43 (t, J=7.7 Hz, 1H), 12.0 (s, 1H);

APCI-MS (m/z): 359 (M−H)$^−$.

EXAMPLE 138

6-Ethyl-5-[2-(2-methoxyethoxy)ethyl]-4-(3-methoxyphenyl)benzene-1,3-diol (Compound 138)

In the same manner as in Example 118, 1-{4,6-bis(methoxycarbonyloxy)-2-[2-(2-methoxyethoxy)ethyl]-3-(3-methoxyphenyl)phenyl}ethanone was obtained from Compound 137 (250 mg, 0.69 mmol) obtained in Example 137, using methyl chlorocarbonate (0.15 mL, 1.9 mmol), triethylamine (0.26 mL, 1.9 mmol) and tetrahydrofuran (5.0 mL); and from the resulting compound, obtained was 4-ethyl-1,5-bis(methoxycarbonyloxy)-3-[2-(2-methoxyethoxy)ethyl]-2-(3-methoxyphenyl)benzene, using sodium borohydride (120 mg, 3.2 mmol), water (3.0 mL) and tetrahydrofuran (5.0 mL). Then, the resulting compound was treated with methanol solution (5.0 mL) of 7 mmol/L ammonia to obtain Compound 138 (110 mg, 46%).

$^1$H-NMR (270 MHz, CDCl$_3$) δ (ppm): 1.18 (t, J=7.6 Hz, 3H), 2.63-2.79 (m, 4H), 3.32 (s, 3H), 3.35-3.43 (m, 6H), 3.82 (s, 3H), 4.86 (s, 1H), 4.86 (s, 1H), 6.34 (s, 1H), 6.79-6.85 (m, 2H), 6.95 (m, 1H), 7.38 (t. J=7.7 Hz, 1H);

APCI-MS (m/z): 345 (M−H)$^−$.

EXAMPLE 139

1-{2,4-dihydroxy-6-[2-(2-methoxyethoxy)ethyl]-5-(3-methylphenyl)phenyl}ethanone (Compound 139)

In the same manner as in the step 3 in Example 1, 1-{2-[2-(2-methoxyethoxy)ethyl]-4,6-bis(methoxymethoxy)-3-(3-methylphenyl)phenyl}ethanone was obtained from 1-{3-bromo-2-[2-(2-methoxyethoxy)ethyl]-4,6-bis(methoxymethoxy)phenyl}ethanone (1.1 g, 2.5 mmol) obtained in the step 2 in Example 137, using 3-methylphenylboronic acid (420 mg, 3.1 mmol), bis(tri-o-tolylphosphine)palladium(II) dichloride (40 mg, 0.05 mmol), cesium carbonate (2.5 g, 7.7 mmol), 1,2-dimethoxyethane (30 mL) and water (3.0 mL). Then, in the same manner as in the step 4 in Example 1, Compound 139 (610 mg, 70%) was obtained from the resulting compound, using methanol (15 mL) and 1,4-dioxane solution (15 mL) of 4 mol/L hydrogen chloride.

$^1$H-NMR (270 MHz, CDCl$_3$) δ (ppm): 2.41 (s, 3H), 2.70 (s, 3H), 3.03 (t, J=7.9 Hz, 2H), 3.31 (s, 3H), 3.42-3.33 (m, 6H), 4.99 (br s, 1H), 6.46 (s, 1H), 7.06-7.03 (m, 2H), 7.28 (m, 1H), 7.39 (t, J=7.7 Hz, 1H), 12.1 (s, 1H);

APCI-MS (m/z): 343 (M−H)$^−$.

EXAMPLE 140

3-Hydroxy-5-(2-methoxyethyl)-4-phenylphenyl trifluoromethanesulfonate (Compound 140)

1-[(2-(2-Methoxyethoxy)ethyl)]-3,5-bis(methoxymethoxy)-2-phenylbenzene (410 mg, 1.2 mmol) obtained in the step 1 in Example 136 was dissolved in dichloromethane (10 mL), and pyridine (0.10 mL, 1.2 mmol) and trifluoromethanesulfonic acid anhydride (0.20 mL, 1.2 mmol) were added thereto with cooling with ice, and stirred at the same temperature for 1 hour. The reaction liquid was neutralized with diluted hydrochloric acid, and extracted with chloroform. The organic layer was washed with aqueous saturated sodium chloride solution, dried over sodium sulfate, and the solvent was evaporated away under reduced pressure. The resulting residue was purified through preparative thin layer silica gel column chromatography (n-hexane/ethyl acetate=2/1) to obtain Compound 140 (150 mg, yield 30%).

$^1$H-NMR (270 MHz, CDCl$_3$) δ (ppm): 7.53-7.46 (m, 3H), 7.28-7.25 (m, 2H), 6.83 (d, J=2.4 Hz, 1H), 6.79 (d, J=2.4 Hz, 1H), 5.03 (br s, 1H), 3.49-3.34 (m, 9H), 2.69 (t, J=7.1 Hz, 2H);

APCI-MS (m/z): 419 (M−H)$^−$.

EXAMPLE 141

2-[2-Acetyl-3,5-dihydroxy-6-(3-methoxyphenyl)phenyl]-N-(2-methoxyethyl)-N-methylacetamide (Compound 141)

(Step 1)

Methyl 2-bromo-3,5-bis(methoxymethoxy)phenylacetate (10 g, 28 mmol) obtained in the step 2 in Example 1 was dissolved in chloroform (240 mL), and with stirring at −30° C., iodine (7.3 g, 29 mmol) and [bis(trifluoroacetoxy)iodo]benzene (12 g, 29 mmol) were added thereto in order, and stirred at the same temperature for 1 hour. Aqueous saturated sodium thiosulfate solution and aqueous saturated sodium hydroxide solution were added to the reaction solution, then heated up to room temperature and stirred for 2 hours. The reaction mixture was subjected to liquid-liquid separation, and the aqueous layer was extracted twice with ethyl acetate. The organic layers were combined, washed with aqueous saturated sodium chloride solution, and dried over anhydrous sodium sulfate, and the solvent was evaporated away under reduced pressure. The resulting residue was purified through silica gel column chromatography (ethyl acetate/n-hexane=1/9 to 1/4) to obtain methyl 2-bromo-6-iodo-3,5-bis(methoxymethoxy)phenylacetate (10 g, 76%).

$^1$H-NMR (270 MHz, CDCl$_3$) δ (ppm): 3.51 (s, 6H), 3.73 (s, 3H), 4.29 (s, 2H), 5.22 (s, 2H), 5.23 (s, 2H), 6.94 (s, 1H);

FAB-MS (m/z): 475 (M+H)$^+$.

(Step 2)

In the same manner as in the step 1 in Example 69, methyl 2-bromo-6-iodo-3,5-bis(methoxymethoxy)phenylacetate (10.4 g, 22 mmol) obtained in the above was treated with tributyl(1-ethoxyvinyl)tin (11 mL, 33 mmol), bis(triphenylphosphine)palladium(II) dichloride (1.6 g, 2.2 mmol) and toluene (130 mL), and then treated with tetrahydrofuran (95 mL) and 2 mol/L hydrochloric acid (95 mL) to obtain methyl 2-acetyl-6-bromo-3,5-bis(methoxymethoxy)phenylacetate (6.6 g, 76%).

$^1$H-NMR (270 MHz, CDCl$_3$) δ (ppm): 2.52 (s, 3H), 3.47 (s, 3H), 3.51 (s, 3H), 3.70 (s, 3H), 3.94 (s, 2H), 5.19 (s, 2H), 5.25 (s, 2H), 6.98 (s, 1H);

APCI-MS (m/z): 391, 393 (M+H)$^+$.

(Step 3)

In the same manner as in the step 3 in Example 1, methyl 2-acetyl-3,5-bis(methoxymethoxy)-6-(3-methoxyphenyl)phenylacetate (1.1 g, 99%) was obtained from methyl 2-acetyl-6-bromo-3,5-bis(methoxymethoxy)phenylacetate (1.1 g, 2.8 mmol) obtained in the above, using 3-methoxyphenylboronic acid (630 mg, 4.1 mmol), bis(tri-o-tolylphosphine)palladium(II) dichloride (220 mg, 0.28 mmol), cesium carbonate (2.7 g, 8.3 mmol), dimethoxyethane (20 mL) and water (4 mL).

$^1$H-NMR (270 MHz, CDCl$_3$) δ (ppm): 2.57 (s, 3H), 2.31 (s, 3H), 3.49 (s, 2H), 3.52 (s, 3H), 3.59 (s, 3H), 3.78 (s, 3H), 5.05 (s, 2H), 5.24 (s, 2H), 6.69-6.73 (m, 2H), 6.87 (m, 1H), 6.98 (s, 1H), 7.29 (t, J=7.7 Hz, 1H);

FAB-MS (m/z): 418 (M+H)$^+$.

(Step 4)

In the same manner as in the step 2 in Example 9, 2-acetyl-3,5-bis(methoxymethoxy)-6-(3-methoxyphenyl)phenylacetic acid was obtained from methyl 2-acetyl-3,5-bis(methoxymethoxy)-6-(3-methoxyphenyl)phenylacetate (500 mg, 1.2 mmol) obtained in the above, using aqueous 1 mol/L sodium hydroxide solution (5.0 mL) and methanol (10 mL). Then, in the same manner as in the step 3 in Example 9, 2-[2-acetyl-3,5-bis(methoxymethoxy)-6-(3-methoxyphenyl)phenyl]-N-(2-methoxyethyl)-N-methylacetamide (90 mg, 15%) was obtained from the resulting compound, using 1-[3-(dimethylamino)propyl]-3-ethylcarbodiimide hydrochloride (230 mg, 1.2 mmol), 1-hydroxybenzotriazole hydrate (180 mg, 1.2 mmol), N-(2-methoxyethyl)methylamine (0.13 mL, 1.2 mmol) and chloroform (10 mL).

$^1$H-NMR (270 MHz, CDCl$_3$) δ (ppm): 2.58 (s, 3H), 2.69 (s, 1.5H), 2.86 (s, 1.5H), 3.11-3.55 (m, 15H), 3.75 (s, 1.5H), 3.77 (s, 1.5H), 5.03 (s, 2H), 5.22 (s, 2H), 6.72-6.75 (m, 2H), 6.87 (m, 1H), 6.94 (s, 1H), 7.28 (m, 1H).

(Step 5)

In the same manner as in the step 4 in Example 1, Compound 141 (30 mg, 41%) was obtained from 2-[2-acetyl-3,5-bis(methoxymethoxy)-6-(3-methoxyphenyl)phenyl]-N-(2-methoxyethyl)-N-methylacetamide (90 mg, 0.19 mmol) obtained in the above, using 1,4-dioxane solution (1.5 mL) of 4 mol/L hydrogen chloride and methanol (1.5 mL).

$^1$H-NMR (270 MHz, CDCl$_3$) δ (ppm): 2.54 (s, 3H), 2.90 (br s, 3H), 3.32-3.63 (m, 9H), 7.31 (m, 1H), 3.77 (m, 3H), 6.29 (m, 1H), 6.77-6.88 (m, 2H), 6.91 (m, 1H);

APCI-MS (m/z): 386 (M−H)$^−$.

EXAMPLE 142

Methyl 2-ethyl-3,5-dihydroxy-6-(3-methoxyphenyl)phenylacetate (Compound 142)

(Step 1)

In the same manner as in the step 4 in Example 1, methyl 2-acetyl-3,5-dihydroxy-6-(3-methoxyphenyl)phenylacetate (320 mg, 98%) was obtained from methyl 2-acetyl-3,5-bis(methoxymethoxy)-6-(3-methoxyphenyl)phenylacetate (410 mg, 0.98 mmol) obtained in the step 3 in Example 141, using methanol (4.0 mL) and 1,4-dioxane solution (4.0 mL) of 4 mol/L hydrogen chloride.

$^1$H-NMR (270 MHz, CDCl$_3$) δ (ppm): 2.56 (s, 3H), 3.46 (s, 2H), 3.61 (s, 3H), 3.79 (s, 3H), 6.37 (s, 1H), 6.82-6.84 (m, 2H), 6.94 (m, 1H), 7.37 (t, J=7.7 Hz, 1H);

APCI-MS (m/z): 331 (M+H)$^+$.

(Step 2)

In the same manner as in Example 118, methyl 2-acetyl-3,5-bis(methoxycarbonyloxy)-6-(3-methoxyphenyl)phenylacetate was obtained from methyl 2-acetyl-3,5-dihydroxy-6-(3-methoxyphenyl)phenylacetate (320 mg, 0.97 mmol) obtained in the above, using methyl chlorocarbonate (0.2 mL, 2.6 mmol), triethylamine (0.4 mL, 2.9 mmol) and tetrahydrofuran (5.0 mL); and from the resulting compound, obtained was methyl 2-ethyl-3,5-bis(methoxycarbonyloxy)-6-(3-methoxyphenyl)phenylacetate, using sodium borohydride (210 mg, 5.5 mmol), water (3.0 mL) and tetrahydrofuran (5.0 mL). Then, the resulting compound was treated with methanol solution (5.0 mL) of 7 mmol/L ammonia to obtain Compound 142 (170 mg, 55%).

$^1$H-NMR (270 MHz, CDCl$_3$) δ (ppm): 1.11 (t, J=7.5 Hz, 3H), 2.58 (q, J=7.5 Hz, 2H), 3.46 (s, 2H), 3.61 (s, 3H), 3.79 (s, 3H), 6.37 (s, 1H), 6.82-6.84 (m, 2H), 6.94 (m, 1H), 7.37 (t, J=7.7 Hz, 1H).

EXAMPLE 143

6-Ethyl-5-(2-hydroxyethyl)-4-(3-methoxyphenyl)benzene-1,3-diol (Compound 143)

In the same manner as in the step 1 in Example 62, Compound 143 (100 mg, 91%) was obtained from Compound 142 (120 mg, 0.38 mmol) obtained in Example 142, using lithium aluminium hydride (60 mg, 1.6 mmol) and tetrahydrofuran (5.0 mL).

$^1$H-NMR (270 MHz, CDCl$_3$) δ (ppm): 1.14 (t, J=7.3 Hz, 3H), 2.64 (q, J=7.3 Hz, 2H), 2.72 (t, J=7.7 Hz, 2H), 3.53 (t, J=7.7 Hz, 2H), 3.79 (s, 3H), 4.83 (s, 1H), 6.10 (br s, 1H), 6.29 (s, 1H), 6.78-6.84 (m, 2H), 6.92 (m, 1H), 7.36 (t, J=7.9 Hz, 1H);

FAB-MS (m/z): 288 (M+H)$^+$.

EXAMPLE 144

5-(2-Allyloxyethyl)-6-ethyl-4-phenylbenzene-1,3-diol (Compound 144)

(Step 1)

In the same manner as in the step 1 in Example 64, 3-(2-allyloxyethyl)-4-ethyl-1,5-bis(methoxymethoxy)-2-phenylbenzene (115 mg, 60%) was obtained from 2-[2-ethyl-3,5-bis(methoxymethoxy)-6-phenylphenyl]ethanol (172 mg, 0.497 mmol) obtained in the step 1 in Example 83, using 60% sodium hydride/mineral oil dispersion (78.2 mg, 1.95 mmol) and allyl bromide (0.100 mL, 1.18 mmol).

$^1$H-NMR (270 MHz, CDCl$_3$) δ (ppm): 1.17 (t, J=7.4 Hz, 3H), 2.64-2.84 (m, 4H), 3.23 (s, 3H), 3.26-3.36 (m, 2H), 3.52 (s, 3H), 3.71 (ddd, J=1.3, 1.6, 5.4 Hz, 2H), 4.94 (s, 2H), 5.02-5.16 (m, 2H), 5.22 (s, 2H), 5.76 (ddt, J=10.4, 17.3, 5.6 Hz, 1H), 6.85 (s, 1H), 7.15-7.23 (m, 2H), 7.27-7.45 (m, 3H).

(Step 2)

In the same manner as in the step 2 in Example 25, Compound 144 (27.4 mg, 87%) was obtained from 3-(2-allyloxyethyl)-4-ethyl-1,5-bis(methoxymethoxy)-2-phenylbenzene (40.7 mg, 0.105 mmol) obtained in the above, using ethanol (4 mL) and concentrated hydrochloric acid (0.2 mL).

$^1$H-NMR (300 MHz, CDCl$_3$) δ (ppm): 1.17 (t, J=7.5 Hz, 3H), 2.67 (q, J=7.5 Hz, 2H), 2.68-2.78 (m, 2H), 3.28-3.36 (m, 2H), 3.75 (ddd, J=1.3, 1.5, 5.7 Hz, 2H), 4.50 (s, 1H), 4.86 (s, 1H), 5.04-5.18 (m, 2H), 5.76 (ddt, J=10.5, 17.2, 5.7 Hz, 1H), 6.36 (s, 1H), 7.22-7.32 (m, 2H), 7.38-7.54 (m, 3H);

FAB-MS (m/z): 299 (M+H)$^+$.

EXAMPLE 145

5-(3-Allyloxypropyl)-6-ethyl-4-phenylbenzene-1,3-diol (Compound 145)

(Step 1)

In the same manner as in the step 1 in Example 64, 3-(3-allyloxypropyl)-4-ethyl-1,5-bis(methoxymethoxy)-2-phenylbenzene (181 mg, 81%) was obtained from 3-[2-ethyl-3,5-bis(methoxymethoxy)-6-phenylphenyl]propanol (204 mg, 0.566 mmol) obtained in the step 2 in Example 123, using 60% sodium hydride/mineral oil dispersion (88.3 mg, 2.21 mmol) and allyl bromide (0.100 mL, 1.18 mmol).

$^1$H-NMR (270 MHz, CDCl$_3$) δ (ppm): 1.17 (t, J=7.4 Hz, 3H), 1.50-1.65 (m, 2H), 2.40-2.50 (m, 2H), 2.69 (q, J=7.4 Hz, 2H), 3.20 (t, J=6.6 Hz, 2H), 3.24 (s, 3H), 3.53 (s, 3H), 3.78 (ddd, J=1.3, 1.6, 5.6 Hz, 2H), 4.94 (s, 2H), 5.22 (s, 2H), 5.06-5.24 (m, 2H), 5.82 (ddt, J=10.4, 17.3, 5.4 Hz, 1H), 6.83 (s, 1H), 7.10-7.23 (m, 2H), 7.26-7.42 (m, 3H).

(Step 2)

In the same manner as in the step 2 in Example 25, Compound 145 (28.4 mg, 61%) was obtained from 3-(3-allyloxypropyl)-1,5-bis(methoxymethoxy)-4-ethyl-2-phenylbenzene (46.8 mg, 0.150 mmol) obtained in the above, using ethanol (4 mL) and concentrated hydrochloric acid (0.2 mL).

$^1$H-NMR (300 MHz, CDCl$_3$) δ (ppm): 1.19 (t, J=7.4 Hz, 3H), 1.52-1.64 (m, 2H), 2.38-2.48 (m, 2H), 2.65 (q, J=7.5 Hz, 2H), 3.21 (t, J=6.5 Hz, 2H), 3.79 (ddd, J=1.5, 1.5, 5.5 Hz, 1H), 4.50 (s, 1H), 4.81 (s, 1H), 5.10 (ddd, J=1.3, 3.1, 10.3 Hz, 1H), 5.18 (ddd, J=1.7, 3.5, 17.2 Hz, 1H), 5.81 (ddt, 10.5, 17.2, 5.5 Hz, 1H), 6.35 (s, 1H), 7.24-7.31 (m, 2H), 7.36-7.53 (m, 3H);

FAB-MS (m/z): 313 (M+H)$^+$.

EXAMPLE 146

6-Ethyl-5-[3-(2-methoxyethoxy)propyl]-4-phenylbenzene-1,3-diol (Compound 146)

(Step 1)

In the same manner as in the step 1 in Example 64, 4-ethyl-3-[3-(2-methoxyethoxy)propyl]-1,5-bis(methoxymethoxy)-2-phenylbenzene (113 mg, 59%) was obtained from 3-[2-ethyl-3,5-bis(methoxymethoxy)-6-phenylphenyl]propanol (164 mg, 0.456 mmol) obtained in the step 2 in Example 123, using 60% sodium hydride/mineral oil dispersion (142 mg, 3.54 mmol) and 2-bromoethyl methyl ether (0.282 mL, 3.00 mmol).

$^1$H-NMR (270 MHz, CDCl$_3$) δ (ppm): 1.16 (t, J=7.4 Hz, 3H), 1.50-1.70 (m, 2H), 2.38-2.48 (m, 2H), 2.68° (q, J=7.5 Hz, 2H), 3.23 (s, 3H), 3.20-3.27 (m, 2H), 3.35 (s, 3H), 3.34-3.45 (m, 4H), 3.53 (s, 3H), 4.94 (s, 2H), 5.23 (s, 2H), 6.83 (s, 1H), 7.17-7.23 (m, 2H), 7.25-7.42 (m, 3H).

(Step 2)

In the same manner as in the step 2 in Example 25, Compound 146 (92.2 mg, 100%) was obtained from 4-ethyl-3-[3-(2-methoxyethoxy)propyl]-1,5-bis(methoxymethoxy)-2-phenylbenzene (111 mg, 0.264 mmol) obtained in the above, using ethanol (4 mL) and concentrated hydrochloric acid (0.2 mL).

$^1$H-NMR (300 MHz, CDCl$_3$) δ (ppm): 1.18 (t, J=7.4 Hz, 3H), 1.52-1.65 (m, 2H), 2.35-2.45 (m, 2H), 2.64 (q, J=7.5 Hz, 2H), 3.24 (t, J=6.7 Hz, 2H), 3.35 (s, 3H), 3.35-3.46 (m, 4H), 4.50 (s, 1H), 4.89 (br s, 1H), 6.34 (s, 1H), 7.23-7.30 (m, 2H), 7.37-7.52 (m, 3H);

APCI-MS (m/z): 329 (M−H)⁻.

EXAMPLE 147

5-[2-(2,3-Dihydroxypropoxy)ethyl]-6-ethyl-4-phenylbenzene-1,3-diol (Compound 147)

(Step 1)

3-(2-Allyloxyethyl)-4-ethyl-1,5-bis(methoxymethoxy)-2-phenylbenzene (71.1 mg, 0.184 mmol) obtained in the step 1 in Example 144 was dissolved in a mixed solvent of acetonitrile (4 mL) and water (1 mL), and N-methylmorpholine-N-oxide (56.4 mg, 0.481 mmol) and tert-butyl alcohol solution of 2.5% osmium tetroxide (0.100 mL, 0.00799 mmol) were added thereto and stirred at room temperature for 18 hours. Aqueous saturated sodium hydrogencarbonate solution and aqueous saturated sodium thiosulfate solution were added to the reaction mixture, and stirred at room temperature for 2 hours, and then the reaction mixture was extracted with ethyl acetate. The organic layer was washed with aqueous saturated sodium chloride solution, and dried over anhydrous sodium sulfate, and the solvent was evaporated away under reduced pressure. The resulting residue was purified through preparative thin-layer chromatography (chloroform/methanol=9/1) to obtain 3-{2-[2-ethyl-3,5-bis(methoxymethoxy)-6-phenylphenyl]ethoxy}propane-1,2-diol (72.6 mg, 94%).

¹H-NMR (300 MHz, CDCl₃) δ (ppm): 1.16 (t, J=7.4 Hz, 3H), 1.95 (br s, 1H), 2.36 (br s, 1H), 1.64-2.82 (m, 4H), 3.24 (s, 3H), 3.16-3.26 (m, 2H), 3.30-3.40 (m, 2H), 3.45-3.75 (m, 3H), 3.53 (s, 3H), 4.95 (s, 2H), 5.23 (s, 2H), 6.86 (s, 1H), 7.15-7.23 (m, 2H), 7.28-7.45 (m, 3H).

(Step 2)

In the same manner as in the step 2 in Example 25, Compound 147 (51.6 mg, 90%) was obtained from 3-{2-[2-ethyl-3,5-bis(methoxymethoxy)-6-phenylphenyl]ethoxy}propane-1,2-diol (72.5 mg, 0.172 mmol), using ethanol (4 mL) and concentrated hydrochloric acid (0.2 mL).

¹H-NMR (270 MHz, CDCl₃/CD₃OD) δ (ppm): 1.17 (t, J=7.4 Hz, 3H), 2.60-2.80 (m, 4H); 3.20-3.58 (m, 6H), 3.62-3.73 (m, 1H), 6.34 (s, 1H), 7.22-7.29 (m, 2H), 7.34-7.52 (m, 3H);

APCI-MS (m/z): 331 (M−H)⁻.

EXAMPLE 148

5-[3-(2,3-Dihydroxypropoxy)propyl]-6-ethyl-4-phenylbenzene-1,3-diol (Compound 148)

(Step 1)

3-(3-Allyloxypropyl)-4-ethyl-1,5-bis(methoxymethoxy)-2-phenylbenzene (65.2 mg, 0.163 mmol) obtained in the step 1 in Example 145 was dissolved in acetonitrile (4 mL) and water (1 mL), and N-methylmorpholine-N-oxide (58.4 mg, 0.499 mmol) and tert-butyl alcohol solution of 2.5% osmium tetroxide (0.100 mL, 0.00799 mmol) were added thereto and stirred at room temperature for 18 hours. Aqueous saturated sodium hydrogencarbonate solution and aqueous saturated sodium thiosulfate solution were added to the reaction mixture, then stirred at room temperature for 2 hours, and thereafter extracted with ethyl acetate. The organic layer was washed with aqueous saturated sodium chloride solution, dried over anhydrous sodium sulfate, and the solvent was evaporated away under reduced pressure. The resulting residue was purified through preparative thin-layer chromatography (chloroform/methanol=9/1) to obtain 3-{3-[2-ethyl-3,5-bis(methoxymethoxy)-6-phenylphenyl]propoxy}propane-1,2-diol (59.0 mg, 83%).

¹H-NMR (300 MHz, CDCl₃) δ (ppm): 1.17 (t, J=7.4 Hz, 3H), 1.50-1.60 (m, 2H), 2.05 (br s, 1H), 2.33 (br s, 1H), 3.24 (s, 3H), 3.20-3.35 (m, 4H), 3.53 (s, 3H), 3.50-3.78 (m, 3H), 4.95 (s, 2H), 5.23 (s, 2H), 6.84 8s, 1H), 7.16-7.24 (m, 2H), 7.28-7.44 (m, 3H).

(Step 2)

In the same manner as in the step 2 in Example 25, Compound 148 (42.3 mg, 92%) was obtained from 3-{3-[2-ethyl-3,5-bis(methoxymethoxy)-6-phenylphenyl]propoxy}propane-1,2-diol (58.0 mg, 0.133 mmol) obtained in the above, using ethanol (4 mL) and concentrated hydrochloric acid (0.2 mL).

¹H-NMR (270 MHz, CDCl₃/CD₃OD) δ (ppm): 1.17 (t, J=7.4 Hz, 3H), 1.48-1.64 (m, 2H), 2.34-2.46 (m, 2H), 2.63 (q, J=7.4 Hz, 2H), 3.20-3.76 (m, 7H), 6.32 (s, 1H), 7.20-7.28 (m, 2H), 7.33-7.50 (m, 3H);

APCI-MS (m/z): 345 (M−H)⁻.

EXAMPLE 149

6-Ethyl-5-[2-(2-methoxyethoxy)ethyl]-4-(3-methylphenyl)benzene-1,3-diol (Compound 149)

In the same manner as in Example 118, 1-{4,6-bis(methoxycarbonyloxy)-2-[2-(2-methoxyethoxy)ethyl]-3-(3-methylphenyl)phenyl}ethanone was obtained from Compound 139 (410 mg, 1.2 mmol) obtained in Example 139, using methyl chlorocarbonate (0.2 mL, 2.6 mmol), triethylamine (0.4 mL, 2.9 mmol) and tetrahydrofuran (5.0 mL); and from the resulting compound, obtained was 4-ethyl-1,5-bis(methoxycarbonyloxy)-3-[2-(2-methoxyethoxy)ethyl]-2-(3-methylphenyl)benzene, using sodium borohydride (210 mg, 5.5 mmol), water (3.0 mL) and tetrahydrofuran (5.0 mL). Then, the resulting compound was treated with methanol solution (5.0 mL) of 7 mmol/L ammonia to obtain Compound 149 (180 mg, 45%).

¹H-NMR (270 MHz, CDCl₃) δ (ppm): 1.17 (t, J=7.6 Hz, 3H), 2.38 (s, 3H), 2.77-2.62 (m, 4H), 3.32 (s, 3H), 3.43-3.32 (m, 6H), 4.53 (s, 1H), 4.89 (br s, 1H), 6.34 (s, 1H), 7.04-7.07 (m, 2H), 7.20 (m, 1H), 7.36 (t, J=7.7 Hz, 1H);

APCI-MS (m/z): 345 (M−H)⁻.

EXAMPLE 150

2-[2-Ethyl-3,5-dihydroxy-6-(3-methoxyphenyl)phenyl]-N-(2-methoxyethyl)-N-methylacetamide (Compound 150)

(Step 1)

Methyl 2-ethyl-3,5-bis(methoxymethoxy)phenylacetate (300 mg, 1.0 mmol) was dissolved in chloroform (9.0 mL), and with stirring at −30° C., iodine (260 mg, 1.0 mmol) and [bis(trifluoroacetoxy)iodo]benzene (440 mg, 1.0 mmol) were added thereto in order, and stirred at the same temperature for 1 hour. Aqueous saturated sodium thiosulfate solution and aqueous saturated sodium hydroxide solution were added to the reaction mixture, then heated up to room temperature, and stirred further for 2 hours. The reaction mixture was subjected to liquid-liquid separation, and the aqueous layer was washed twice with ethyl acetate. The organic layers were combined and washed with aqueous saturated sodium chloride solution, then dried over anhydrous sodium sulfate, and the solvent was evaporated away under reduced pressure. The residue was purified through silica gel column chromatography (ethyl acetate/n-hexane=1/9 to 1/4) to obtain methyl 2-ethyl-6-iodo-3,5-bis(methoxymethoxy)phenylacetate (230 mg, 53%).

$^1$H-NMR (270 MHz, CDCl$_3$) δ (ppm): 1.07 (t, J=7.5 Hz, 3H), 2.66 (q, J=7.5 Hz, 2H), 3.48 (s, 3H), 3.49 (s, 2H), 3.52 (s, 3H), 3.71 (s, 3H), 5.18 (s, 2H), 5.21 (s, 2H), 6.94 (s, 1H);

APCI-MS (m/z): 425 (M+H)$^+$.

(Step 2)

In the same manner as in the step 3 in Example 1, methyl 2-ethyl-3,5-bis(methoxymethoxy)-6-(3-methoxyphenyl)phenylacetate (170 mg, 85%) was obtained from methyl 2-ethyl-6-iodo-3,5-bis(methoxymethoxy)phenylacetate (210 mg, 0.49 mmol) obtained in the above, using 3-methoxyphenylboronic acid (110 mg, 0.72 mmol), bis(tri-o-tolylphosphine)palladium(II) dichloride (39 mg, 0.05 mmol), cesium carbonate (480 mg, 1.5 mmol), dimethoxyethane (4.0 mL) and water (0.5 mL).

$^1$H-NMR (270 MHz, CDCl$_3$) δ (ppm): 1.11 (t, J=7.3 Hz, 3H), 2.62 (q, J=7.3 Hz, 2H), 3.29 (s, 3H), 3.47 (s, 2H), 3.52 (s, 2H), 3.60 (s, 3H), 3.78 (s, 3H), 4.98 (s, 2H), 5.24 (s, 2H), 6.80-6.76 (m, 2H), 6.88 (m, 1H), 6.93 (s, 1H), 7.81 (t, J=7.7 Hz, 1H);

APCI-MS (m/z): 405 (M+H)$^+$.

(Step 3)

In the same manner as in the step 4 in Example 141, 3,5-bis(methoxymethoxy)-2-ethyl-6-(3-methoxyphenyl)phenylacetic acid was obtained from methyl 2-ethyl-3,5-bis(methoxymethoxy)-6-(3-methoxyphenyl)phenylacetate (170 mg, 0.42 mmol) obtained in the above, using methanol (3.0 mL) and aqueous solution of 2 mol/L sodium hydroxide. From the resulting compound, obtained was 2-[2-ethyl-3,5-bis(methoxymethoxy)-6-(3-methoxyphenyl)phenyl]-N-(2-methoxyethyl)-N-methylacetamide (93 mg, 46%), using 2-methoxy-N-methylethylamine (0.1 mL, 0.93 mmol), 1-[3-(dimethylamino)propyl]-3-ethylcarbodiimide hydrochloride (170 mg, 0.89 mmol) and 1-hydroxybenzotriazole hydrate (130 mg, 0.85 mmol).

$^1$H-NMR (270 MHz, CDCl$_3$) δ (ppm): 1.11 (m, 3H), 2.60 (m, 2H), 2.77 (s, 1.5H), 2.90 (s, 1.5H), 3.57-3.17 (m, 15H), 3.75 (s, 1.5H), 3.77 (s, 1.5H), 4.96 (s, 2H), 5.22 (s, 2H), 6.86-6.78 (m, 3H), 6.90 (s, 1H), 7.26 (t, J=7.7 Hz, 1H);

APCI-MS (m/z): 462 (M+H)$^+$.

(Step 4)

In the same manner as in the step 4 in Example 1, Compound 150 (55 mg, 77%) was obtained from 2-[2-ethyl-3,5-bis(methoxymethoxy)-6-(3-methoxyphenyl)phenyl]-N-(2-methoxyethyl)-N-methylacetamide (93 mg, 0.19 mmol) obtained in the above, using 1,4-dioxane solution (1.5 mL) of 4 mol/L hydrogen chloride and methanol (1.5 mL).

$^1$H-NMR (270 MHz, CDCl$_3$) δ (ppm): 1.07 (m, 3H), 2.53 (m, 2H), 2.82 (s, 1.5H), 2.95 (s, 1.5H), 3.23-3.51 (m, 9H), 3.78 (m, 3H), 6.14 (s, 1H), 6.88-6.91 (m, 2H), 7.30 (m, 1H);

APCI-MS (m/z): 374 (M+H)$^+$.

EXAMPLE 151

6-Isopropyl-5-(2-methoxyethyl)-4-phenylbenzene-1,3-diol (Compound 151)

(Step 1)

In an argon atmosphere, 1-[2-(2-methoxyethyl)-4,6-bis(methoxymethoxy)-3-phenylphenyl]ethanone (0.10 g, 0.27 mmol) obtained in the step 5 in Example 92 was dissolved in tetrahydrofuran (3.0 mL), and the solution was cooled to 4° C., and then toluene solution of 0.5 mol/L Tebbe reagent (μ-chloro-μ-methylene[bis(cyclopentadienyl)titanium]dimethylaluminum) (0.65 mL, 0.33 mmol) was added thereto and stirred for 0.5 hours with heating up to room temperature. Toluene solution of 0.5 mol/L Tebbe reagent (0.15 mL, 0.075 mmol) was further added to the reaction mixture, and stirred for 0.5 hours at room temperature. Diethyl ether (50 mL) was added to the reaction mixture to dilute it, and this was subjected to liquid-liquid separation with aqueous 0.1 mol/L sodium hydroxide solution (0.10 mL) added thereto. The organic layer was washed twice with aqueous 0.1 mol/L sodium hydroxide solution (0.10 mL), then dried over anhydrous magnesium sulfate, and filtered through Celite. The filtrate was concentrated under reduced pressure, and the resulting residue was purified through preparative thin-layer chromatography (ethyl acetate/n-hexane=1/4) to obtain 4-isopropyl-3-(2-methoxyethyl)-1,5-bis(methoxymethoxy)-2-phenylbenzene (87 mg, 87%).

$^1$H-NMR (270 MHz, CDCl$_3$) δ (ppm): 2.06 (s, 3H), 2.55-2.95 (m, 2H), 3.03 (s, 3H), 3.05-3.30 (m, 2H), 3.26 (s, 3H), 3.50 (s, 3H), 4.86 (br.s, 1H), 4.97 (s, 2H), 5.19 (s, 2H), 5.31 (br.s, 1H), 6.87 (s, 1H), 7.19-7.42 (m, 5H);

FAB-MS (m/z): 373 (M+H)$^+$.

(Step 2)

4-Isopropyl-3-(2-methoxyethyl)-1,5-bis(methoxymethoxy)-2-phenylbenzene (82 mg, 0.22 mmol) obtained in the above was dissolved in ethanol (15 mL), and 10% palladium-carbon (50% wet., 70 mg) was added thereto and stirred under hydrogen pressure (0.3 MPa) at room temperature for 12 hours. The reaction mixture was filtered through Celite, and the filtrate was exposed to reduced pressure. The resulting residue was dissolved in methanol (2.0 mL), and 1,4-dioxane solution (2.0 mL) of 4 mol/L hydrogen chloride was added thereto and stirred at room temperature for 3 hours. The reaction solution was concentrated under reduced pressure, and the resulting residue was purified through preparative thin-layer chromatography (methanol/chloroform=1/9) and crystallized (ethyl acetate/n-hexane=1/9) to obtain Compound 151 (39 mg, 62%).

$^1$H-NMR (270 MHz, CDCl$_3$) δ (ppm): 1.40 (d, J=7.1 Hz, 6H), 2.69 (t, J=8.2 Hz, 2H), 3.15 (s, 3H), 3.20-3.28 (m, 3H), 4.43 (s, 1H), 4.77 (s, 1H), 6.28 (s, 1H), 7.25-7.28 (m, 2H), 7.38-7.52 (m, 3H);

FAB-MS (m/z): 287 (M+H)$^+$.

Elementary Analysis (as C$_{18}$H$_{22}$O$_3$.0.1H$_2$O):
Measured (%): C:74.99, H:7.82, N:0
Calculated (%): C:75.02, H:7.76, N:0

EXAMPLE 152

3-(2-Methoxyethoxy)ethyl-2-phenyl-5-(sulfamoyloxy)phenol (Compound 152)

3,5-Bis(methoxymethoxy)-1-[(2-(2-methoxyethoxy)ethyl)]-2-phenylbenzene (0.080 g, 0.28 mmol) obtained in the step 1 in Example 136 was dissolved in N,N-dimethylformamide (2.0 mL), and sulfamoyl chloride (64 g, 0.56 mmol) was added thereto and stirred at room temperature for 1 day. The reaction liquid was poured into water, and extracted with ethyl acetate. The organic layer was dried over anhydrous sodium sulfate, and the solvent was evaporated away under reduced pressure. The resulting residue was purified through preparative thin-layer silica gel column chromatography (chloroform/methanol=15/1) to obtain Compound 152 (3.6 mg, 3.5%).

¹H-NMR (270 MHz, CDCl₃) δ (ppm): 2.66 (t, J=6.4 Hz, 2H), 3.35 (s, 3H), 3.52-3.45 (m, 6H), 4.88 (br s, 1H), 5.34 (br s, 2H), 6.85 (d, J=2.2 Hz, 1H), 7.02 (d, J=2.2 Hz, 1H), 7.27-7.26 (m, 2H), 7.55-7.45 (m, 3H);
APCI-MS (m/z): 366 (M−H)⁻.

EXAMPLE 153

4-(3-{5-Ethyl-2,4-dihydroxy-6-[2-(2-methoxyethoxy)ethyl]phenyl}phenyl)butan-2-one (Compound 153)

(Step 1)
In the same manner as in the step 1 in Example 62, 2-[2-ethyl-3,5-bis(methoxymethoxy)phenyl]ethanol (1.3 g, 96%) was obtained from methyl 2-ethyl-3,5-bis(methoxymethoxy)phenylacetate (1.5 g, 5.0 mmol), using lithium aluminium hydride (230 mg, 6.1 mmol) and diethyl ether (30 mL).

(Step 2)
In the same manner as in the step 1 in Example 64, 2-ethyl-1-[2-(2-methoxyethoxy)ethyl]-3,5-bis(methoxymethoxy)benzene (510 mg, 45%) was obtained from 2-[2-ethyl-3,5-bis(methoxymethoxy)phenyl]ethanol (1.0 g, 3.7 mmol) obtained in the above, using 60% sodium hydride/mineral oil dispersion (310 mg, 7.8 mmol), 2-bromomethoxyethane (1.1 mL, 12 mmol) and N,N-dimethylformamide (70 mL).
¹H-NMR (270 MHz, CDCl₃) δ (ppm): 1.10 (t, J=7.6 Hz, 3H), 2.63 (q, J=7.6 Hz, 2H), 2.92 (t, J=8.3 Hz, 2H), 3.39 (s, 3H), 3.47 (s, 6H), 3.66-3.54 (m, 6H), 5.12 (s, 2H), 5.16 (s, 2H), 6.56 (d, J=2.3 Hz, 1H), 6.67 (d, J=2.3 Hz, 1H);
APCI-MS (m/z): 329 (M+H)⁺.

(Step 3)
In the same manner as in the step 1 in Example 13, 2-ethyl-6-iodo-1-[2-(2-methoxyethoxy)ethyl]-3,5-bis(methoxymethoxy)benzene (440 mg, 62%) was obtained from 2-ethyl-1-[2-(2-methoxyethoxy)ethyl]-3,5-bis(methoxymethoxy)benzene (510 mg, 1.6 mmol) obtained in the above, using chloroform (15 mL), iodine (400 mg, 1.6 mmol) and [bis(trifluoroacetoxy)iodo]benzene (680 mg, 1.6 mmol).
¹H-NMR (270 MHz, CDCl₃) δ (ppm): 1.10 (t. J=7.6 Hz, 3H), 2.75 (q, J=7.6 Hz, 2H), 3.25 (t, J=8.1 Hz, 2H), 3.40 (s, 3H), 3.47 (s, 3H), 3.52 (s, 3H), 3.62-3.56 (m, 4H), 3.69 (t, J=6.0 Hz, 2H), 5.18 (s, 2H), 5.19 (s, 2H), 6.81 (s, 1H);
APCI-MS (m/z): 455 (M+H)⁺.

(Step 4)
In the same manner as in the step 3 in Example 1, 3-{5-ethyl-6-[2-(2-methoxyethoxy)ethyl]-2,4-bis(methoxymethoxy)phenyl}benzaldehyde (320 mg, 75%) was obtained from 2-ethyl-6-iodo-1-[2-(2-methoxyethoxy)ethyl]-3,5-bis(methoxymethoxy)benzene (440 mg, 0.98 mmol) obtained in the above, using 3-formylphenylboronic acid (220 mg, 1.5 mmol), bis(tri-o-tolylphosphine)palladium (II) dichloride (40 mg, 0.05 mmol), cesium carbonate (1.0 g, 3.1 mmol), 1,2-dimethoxyethane (10 mL) and water (1.0 mL).
¹H-NMR (270 MHz, CDCl₃) δ (ppm): 1.17 (t, J=7.3 Hz, 3H), 2.67-2.79 (m, 4H), 3.23 (s, 3H), 3.40 (s, 3H), 3.31-3.39 (m, 6H), 3.53 (s, 3H), 4.95 (s, 2H), 5.24 (s, 2H), 6.87 (s, 1H), 7.49 (m, 1H), 7.57 (t, J=7.6 Hz, 1H), 7.74 (m, 1H), 7.86 (m, 1H), 10.0 (s, 1H);
APCI-MS (m/z): 433 (M+H)⁺.

(Step 5)
In the same manner as in the step 2 in Example 2, 4-(3-{5-ethyl-6-[2-(2-methoxyethoxy)ethyl]-2,4-bis(methoxymethoxy)phenyl}phenyl)but-3-en-2-one (320 mg, 92%) was obtained from 3-{5-ethyl-6-[2-(2-methoxyethoxy)ethyl]-2,4-bis(methoxymethoxy)phenyl}benzaldehyde (320 mg, 0.73 mmol) obtained in the above, using (acetylmethylene)triphenylphospholane (350 mg, 1.1 mmol) and toluene (10 mL).
¹H-NMR (270 MHz, CDCl₃) δ (ppm): 1.16 (t, J=7.3 Hz, 3H), 2.38 (s, 3H), 2.66-2.78 (m, 4H), 3.20 (s, 3H), 3.30 (s, 3H), 3.33-3.40 (m, 6H), 3.52 (s, 3H), 4.95 (s, 2H), 5.23 (s, 2H), 6.70 (d, J=8.4 Hz, 1H), 6.86 (s, 1H), 7.56-7.24 (m, 5H);
APCI-MS (m/z): 473 (M+H)⁺.

(Step 6)
In the same manner as in the step 1 in Example 67, 4-(3-{5-ethyl-6-[2-(2-methoxyethoxy)ethyl]-2,4-bis(methoxymethoxy)phenyl}phenyl)butan-2-one (260 mg, 81%) was obtained from 4-(3-{5-ethyl-6-[2-(2-methoxyethoxy)ethyl]-2,4-bis(methoxymethoxy)phenyl}phenyl)but-3-en-2-one (320 mg, 0.68 mmol) obtained in the above, using 10% palladium-carbon (100 mg) and ethyl acetate (10 mL) and processing it under hydrogen pressure (0.3 MPa) at room temperature for 30 minutes.
¹H-NMR (270 MHz, CDCl₃) δ (ppm): 1.16 (t, J=7.3 Hz, 3H), 2.14 (s, 3H), 2.69-2.80 (m, 6H), 2.92 (s, 3H), 3.23 (s, 3H), 3.31 (s, 3H), 3.32-3.41 (m, 6H), 3.51 (s, 3H), 4.94 (s, 2H), 5.22 (s, 2H), 6.84 (s, 1H), 7.01-7.04 (m, 2H), 7.15 (m, 1H), 7.26 (t, J=8.4 Hz, 1H).

(Step 7)
In the same manner as in the step 4 in Example 1, Compound 153 (190 mg, 90%) was obtained from 4-(3-{5-ethyl-6-[2-(2-methoxyethoxy)ethyl]-2,4-bis(methoxymethoxy)phenyl}phenyl)butan-2-one (260 mg, 0.54 mmol) obtained in the above, using methanol (5.0 mL) and 1,4-dioxane solution (5.0 mL) of 4 mol/L hydrogen chloride.
¹H-NMR (270 MHz, CDCl₃) δ (ppm): 1.16 (t, J=7.4 Hz, 3H), 2.15 (s, 3H), 2.65 (q, J=7.4 Hz, 2H), 2.72-2.82 (m, 4H), 2.93 (t, J=7.3 Hz, 2H), 3.32 (s, 3H), 3.36 (m, 4H), 3.43 (m, 2H), 4.72 (br s, 1H), 5.78 (br s, 1H), 6.34 (s, 1H), 7.01-7.10 (m, 2H), 7.20 (&, J=8.0 Hz, 1H), 7.38 (t, J=8.0 Hz, 1H);
APCI-MS (m/z): 385 (M−H)⁻.

EXAMPLE 154

6-Ethyl-4-[3-(3-hydroxybutyl)phenyl]-5-[2-(2-methoxyethoxy)ethyl]benzene-1,3-diol (Compound 154)

(Step 1)
In the step 6 in Example 153, 4-ethyl-2-[3-(3-hydroxybutyl)phenyl]-3-[2-(2-methoxyethoxy)ethyl]-1,5-bis(methoxymethoxy)benzene (50 mg, 15%) was obtained as a side product.
¹H-NMR (270 MHz, CDCl₃) δ (ppm): 1.11 (t, J=7.4 Hz, 3H), 1.21 (m, 3H), 1.80 (m, 2H), 2.65 (q, J=7.4 Hz, 2H), 2.77-2.67 (m, 4H), 3.23 (s, 3H), 3.32 (s, 3H), 3.31 (s, 3H), 3.32-3.38 (m, 4H), 3.42 (m, 2H), 3.79 (m, 1H), 4.94 (s, 2H), 5.22 (s, 2H), 6.34 (s, 1H), 7.05-7.12 (m, 2H), 7.22 (d, J=7.3 Hz, 1H), 7.37 (t, J=7.8 Hz, 1H).

(Step 2)
In the same manner as in the step 4 in Example 1, Compound 154 (35 mg, 82%) was obtained from 4-ethyl-2-[3-(3-hydroxybutyl)phenyl]-3-[2-(2-methoxyethoxy)ethyl]-1,5-bis(methoxymethoxy)benzene (50 mg, 0.11 mmol) obtained in the above, using methanol (1.0 mL) and 1,4-dioxane solution (1.0 mL) of 4 mol/L hydrogen chloride.
¹H-NMR (270 MHz, CDCl₃) δ (ppm): 1.11 (t, J=7.4 Hz, 3H), 1.21 (m, 3H), 1.80 (m, 2H), 2.65 (q, J=7.4 Hz, 2H), 2.67-2.77 (m, 4H), 3.32 (s, 3H), 3.32-3.38 (m, 4H), 3.42 (m, 2H), 3.79 (m, 1H), 4.82 (br s, 1H), 5.94 (br s, 1H), 6.34 (s, 1H), 7.05-7.12 (m, 2H), 7.22 (d, J=7.3 Hz, 1H), 7.37 (t, J=7.8 Hz, 1H);

APCI-MS (m/z): 387 (M−H)−.

EXAMPLE 155

2-[2-(2-Ethyl-3,5-dihydroxy-6-phenylphenyl)ethoxy]acetamide (Compound 155)

(Step 1)

3-(2-Allyloxyethyl)-4-ethyl-1,5-bis(methoxymethoxy)-2-phenylbenzene (405 mg, 1.05 mmol) obtained in the step 1 in Example 144 was dissolved in a mixed solvent of 1,4-dioxane (5 mL) and water (1 mL), and tert-butyl alcohol solution of 2.5% osmium tetroxide (0.100 mL, 0.00799 mmol) and sodium periodate (719 mg, 3.36 mmol) were added thereto and stirred at room temperature for 18 hours. Aqueous saturated sodium hydrogencarbonate solution was added to the reaction mixture, and extracted with ethyl acetate. The organic layer was washed with aqueous saturated sodium thiosulfate solution and aqueous saturated sodium chloride solution in order, and dried over anhydrous sodium sulfate. The solvent was evaporated away under reduced pressure to obtain 2-{2-[2-ethyl-3,5-bis(methoxymethoxy)-6-phenylphenyl]ethoxy}ethanal (522 mg, 100%).

$^{1}$H-NMR (300 MHz, CDCl$_3$) δ (ppm): 1.17 (t, J=7.4 Hz, 3H), 2.66-2.88 (m, 4H), 3.24 (s, 3H), 3.35-3.45 (m, 2H), 3.52 (s, 3H), 3.68-3.75 (2H), 4.95 (s, 2H), 5.23 (s, 2H), 6.87 (s, 1H), 7.18-7.23 (m, 2H), 7.28-7.44 (m, 3H), 9.52 (t, J=1.8 Hz, 1H).

(Step 2)

2-{2-[2-Ethyl-3,5-bis(methoxymethoxy)-6-phenylphenyl]ethoxy}ethanal (326 mg, 0.840 mmol) obtained in the above was dissolved in a mixed solvent of tert-butyl alcohol (5 mL) and water (4 mL), and 2-methyl-2-butene (2.00 mL, 18.9 mmol), sodium chlorite (400 mg, 4.42 mmol) and sodium dihydrogenphosphate (400 mg, 3.33 mmol) were added thereto and stirred at room temperature for 12 hours. Water and 1 mol/L hydrochloric acid were added to the reaction mixture, and extracted with chloroform. The organic layer was washed with aqueous saturated sodium chloride solution, and dried over anhydrous sodium sulfate. The solvent was evaporated away under reduced pressure to obtain 2-[2-ethyl-3,5-bis(methoxymethoxy)-6-phenylphenyl]ethoxyacetic acid (494 mg, 100%).

(Step 3)

2-[2-Ethyl-3,5-bis(methoxymethoxy)-6-phenylphenyl]ethoxyacetic acid (125 mg, 0.309 mmol) obtained in the above was dissolved in dichloromethane (2 mL), and 1-hydroxybenzotriazole hydrate (108 mg, 0.800 mmol), methanol solution of 7.0 mol/L ammonia (0.900 mL, 6.30 mmol) and 1-[3-(dimethylamino)propyl]-3-ethylcarbodiimide hydrochloride (207 mg, 1.08 mmol) were added thereto and stirred at room temperature for 12 hours. Aqueous saturated sodium hydrogencarbonate solution was added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer chromatography (chloroform/methanol=20/1) to obtain 2-[2-ethyl-3,5-bis(methoxymethoxy)-6-phenylphenyl]ethoxyacetamide (52.1 mg, 42%).

$^{1}$H-NMR (270 MHz, CDCl$_3$) δ (ppm): 1.17 (t, J=7.4 Hz, 3H), 2.71 (q, J=7.4 Hz, 2H), 2.79 (t, J=7.4 Hz, 2H), 3.32-3.44 (m, 2H), 3.52 (s, 3H), 3.67 (s, 2H), 4.95 (s, 2H), 5.23 (s, 2H), 5.25 (br s, 1H), 6.14 (br s, 1H), 6.87 (s, 1H), 7.15-7.23 (m, 2H), 7.30-7.45 (m, 3H).

(Step 4)

In the same manner as in the step 2 in Example 25, 2-[2-ethyl-3,5-bis(methoxymethoxy)-6-phenylphenyl]ethoxyacetamide (50.0 mg, 0.124 mmol) obtained in the above was dissolved in ethanol (4 mL), and concentrated hydrochloric acid (0.2 mL) was added thereto and stirred at 60° C. for 1.1 hours. The reaction mixture was concentrated under reduced pressure, and the resulting residue was purified through preparative thin-layer chromatography (chloroform/methanol=9/1) to obtain Compound 155 (12.7 mg, 32%).

$^{1}$H-NMR (300 MHz, CDCl$_3$/CD$_3$OD) δ (ppm): 1.17 (t, J=7.5 Hz, 3H), 2.66 (q, J=7.5 Hz, 2H), 2.75 (t, J=7.5 Hz, 2H), 2.70-3.00 (m, 2H), 3.32-3.44 (m, 2H), 3.67 (s, 2H), 6.35 (s, 1H), 7.22-7.29 (m, 2H), 7.35-7.52 (m, 3H);

APCI-MS (m/z): 316 (M+H)+.

EXAMPLE 156

2-[2-(2-Ethyl-3,5-dihydroxy-6-phenylphenyl)ethoxy]-N-methylacetamide (Compound 156)

(Step 1)

In the same manner as in the step 3 in Example 155, 2-{2-[2-ethyl-3,5-bis(methoxymethoxy)-6-phenylphenyl]ethoxy}-N-methyladetamide (64.0 mg, 50%) was obtained from 2-[2-ethyl-3,5-bis(methoxymethoxy)-6-phenylphenyl]ethoxyacetic acid (125 mg, 0.309 mmol) obtained in the step 2 in Example 155, using 1-hydroxybenzotriazole hydrate (108 mg, 0.800 mmol), methanol solution of 40% methylamine (0.100 mL, 1.00 mmol) and 1-[3-(dimethylamino)propyl]-3-ethylcarbodiimide hydrochloride (207 mg, 1.08 mmol).

$^{1}$H-NMR (270 MHz, CDCl$_3$) δ (ppm): 1.17 (t, J=7.3 Hz, 3H), 2.65-2.83 (m, 7H), 3.24 (s, 3H), 3.36 (t, J=7.3 Hz, 2H), 3.52 (s, 3H), 3.68 (s, 2H), 4.95 (s, 2H), 5.24 (s, 2H), 6.26 (br s, 1H), 6.88 (s, 1H), 7.15-7.22 (m, 2H), 7.30-7.45 (m, 3H).

(Step 2)

In the same manner as in the step 2 in Example 25, 2-{2-[2-ethyl-3,5-bis(methoxymethoxy)-6-phenylphenyl]ethoxy}-N-methylacetamide (60.0 mg, 0.144 mmol) obtained in the above was dissolved in ethanol (4 mL), and concentrated acid (0.2 mL) was added thereto and stirred at 60° C. for 1.1 hours. The reaction mixture was concentrated under reduced pressure, and the resulting residue was purified through preparative thin-layer chromatography (chloroform/methanol=9/1) to obtain Compound 156 (49.4 mg, 100%).

$^{1}$H-NMR (270 MHz, CDCl$_3$/CD$_3$OD) δ (ppm): 1.17 (t, J=7.5 Hz, 3H), 2.60-2.80 (m, 7H), 3.36 (t, J=7.5 Hz, 2H), 3.68 (s, 2H), 6.31 (br s, 1H), 6.36 (s, 1H), 7.20-7.32 (m, 2H), 7.34-7.52 (m, 3H);

APCI-MS (m/z): 330 (M+H)+.

EXAMPLE 157

2-[2-(2-Ethyl-3,5-dihydroxy-6-phenylphenyl)ethoxy]-N,N-dimethylacetamide (Compound 157)

(Step 1)

In the same manner as in the step 3 in Example 155, 2-{2-[2-ethyl-3,5-bis(methoxymethoxy)-6-phenylphenyl]

ethoxy}-N,N-dimethylacetamide (58.4 mg, 44%) was obtained from 2-{2-[2-ethyl-3,5-bis(methoxymethoxy)-6-phenylphenyl]ethoxy}acetic acid (125 mg, 0.309 mmol) obtained in the step 2 in Example 155, using 1-hydroxybenzotriazole hydrate (108 mg, 0.800 mmol), aqueous solution of 50-% dimethylamine (0.100 mL, 1.00 mmol) and 1-[3-(dimethylamino)propyl]-3-ethylcarbodiimide hydrochloride (207 mg, 1.08 mmol).

$^1$H-NMR (270 MHz, CDCl$_3$) δ (ppm): 1.16 (t, J=7.4 Hz, 3H), 2.80 (s, 3H), 2.60-2.90 (m, 4H), 2.89 (s, 3H), 3.23 (s, 3H), 3.30-3.42 (m, 2H), 3.52 (s, 3H), 3.82 (s, 2H), 4.94 (s, 2H), 5.22 (s, 2H), 6.85 (s, 1H), 7.15-7.25 (m, 2H), 7.25-7.43 (m, 3H).

(Step 2)

In the same manner as in the step 2 in Example 25, Compound 157 (32.6 mg, 75%) was obtained from 2-{2-[2-ethyl-3,5-bis(methoxymethoxy)-6-phenylphenyl]ethoxy}-N,N-dimethylacetamide (55.0 mg, 0.127 mmol) obtained in the above, using ethanol (4 mL) and concentrated hydrochloric acid (0.2 mL).

$^1$H-NMR (270 MHz, CDCl$_3$) δ (ppm): 1.18 (t, J=7.5 Hz, 3H), 2.66 (q, J=7.5 Hz, 2H), 2.72-7.80 (m, 2H), 2.81 (s, 3H), 2.90 (s, 3H), 3.32-3.42 (m, 2H), 3.87 (s, 2H), 4.48 (s, 1H), 4.96 (s, 1H), 6.36 (s, 1H), 7.20-7.30 (m, 2H), 7.35-7.53 (m, 3H);

APCI-MS (m/z): 344 (M+H)$^+$.

EXAMPLE 158

2-[3-(2-Ethyl-3,5-dihydroxy-6-phenylphenyl)propoxy]acetamide (Compound 158)

(Step 1)

In the same manner as in the step 1 in Example 155, 2-{3-[2-ethyl-3,5-bis(methoxymethoxy)-6-phenylphenyl]propoxy}ethanal (434 mg, 100%) was obtained from 3-(3-allyloxypropyl)-4-ethyl-1,5-bis(methoxymethoxy)-2-phenylbenzene (352 mg, 0.878 mmol) obtained in the step 1 in Example 145, using tert-butyl alcohol solution of 2.5% osmium tetroxide (0.100 mL, 0.00799 mmol) and sodium periodate (732 mg, 3.42 mmol).

(Step 2)

In the same manner as in the step 2 in Example 155, 3-[2-ethyl-3,5-bis(methoxymethoxy)-6-phenylphenyl]propoxyacetic acid (463 mg, 100%) was obtained from 2-{3-[2-ethyl-3,5-bis(methoxymethoxy)-6-phenylphenyl]propoxy}ethanal (272 mg, 0.677 mmol) obtained in the above, using 2-methyl-2-butene (2.00 mL, 18.9 mmol), sodium chlorite (400 mg, 4.42 mmol) and sodium dihydrogenphosphate (400 mg, 3.33 mmol).

(Step 3)

In the same manner as in the step 3 in Example 155, 2-{3-[2-ethyl-3,5-bis(methoxymethoxy)-6-phenylphenyl]propoxy}acetamide (16.9 mg, 15%) was obtained from 3-[2-ethyl-3,5-bis(methoxymethoxy)-6-phenylphenyl]propoxyacetic acid (115 mg, 0.274 mmol) obtained in above, using 1-hydroxybenzotriazole hydrate (108 mg, 0.800 mmol), methanol solution of 7.0 mol/L ammonia (0.900 mL, 6.30 mmol) and 1-[3-(dimethylamino)propyl]-3-ethylcarbodiimide hydrochloride (207 mg, 1.08 mmol).

$^1$H-NMR (270 MHz, CDCl$_3$) δ (ppm): 1.17 (t, J=7.4 Hz, 3H), 1.50-1.66 (m, 2H), 2.40-2.60 (m, 2H), 2.68 (q, J=7.4 Hz, 2H), 3.24 (s, 3H), 3.30 (t, J=6.1 Hz, 2H), 3.53 (s, 3H), 3.73 (s, 2H), 4.95 (s, 2H), 5.23 (s, 2H), 5.23 (br s, 1H), 6.10 (br s, 1H), 6.84 (s, 1H), 7.15-7.45 (m, 5H).

(Step 4)

In the same manner as in the step 2 in Example 25, Compound 158 (6.0 mg, 51%) was obtained from 2-{3-[2-ethyl-3,5-bis(methoxymethoxy)-6-phenylphenyl]propoxy}acetamide (15.0 mg, 0.0359 mmol) obtained in the above, using ethanol (4 mL) and concentrated hydrochloric acid (0.2 mL).

$^1$H-NMR (300 MHz, CDCl$_3$/CD$_3$OD) δ (ppm): 1.18 (t, J=7.4 Hz, 3H), 1.50-1.65 (m, 2H), 2.30-2.70 (m, 4H), 3.30 (t, J=6.1 Hz, 2H), 3.72 (s, 2H), 6.33 (s, 1H), 7.25-7.35 (m, 2H), 7.35-7.50 (m, 3H);

APCI-MS (m/z): 328 (M−H)$^−$.

EXAMPLE 159

2-[3-(2-Ethyl-3,5-dihydroxy-6-phenylphenyl)propoxy]-N-methylacetamide (Compound 159)

(Step 1)

In the same manner as in the step 3 in Example 155, 2-{3-[2-ethyl-3,5-bis(methoxymethoxy)-6-phenylphenyl]propoxy}-N-methylacetamide (60.1 mg, 51%) was obtained from 3-[2-ethyl-3,5-bis(methoxymethoxy)-6-phenylphenyl]propoxyacetic acid (115 mg, 0.274 mmol) obtained in the step 2 in Example 158, using 1-hydroxybenzotriazole hydrate (108 mg, 0.800 mmol), methanol solution of 40% methylamine (0.100 mL, 1.00 mmol) and 1-[3-(dimethylamino)propyl]-3-ethylcarbodiimide hydrochloride (207 mg, 1.08 mmol).

$^1$H-NMR (270 MHz, CDCl$_3$) δ (ppm): 1.17 (t, J=7.4 Hz, 3H), 2.45-2.55 (m, 2H), 2.68 (q, J=7.4 Hz, 2H), 2.82 (d, J=4.9 Hz, 3H), 3.24 (s, 3H), 3.27 (t, J=4.7 Hz, 2H), 3.52 (s, 3H), 3.73 (s, 2H), 4.95 (s, 2H), 5.23 (s, 2H), 6.15 (be s, 1H), 6.85 (s, 1H), 7.25-7.30 (m, 2H), 7.30-7.45 (m, 3H).

(Step 2)

In the same manner as in the step 2 in Example 25, Compound 159 (20.7 mg, 45%) was obtained from 2-{3-[2-ethyl-3,5-bis(methoxymethoxy)-6-phenylphenyl]propoxy}-N-methylacetamide (58.0 mg, 0.134 mmol) obtained in the above, using ethanol (4 mL) and concentrated hydrochloric acid (0.2 mL).

$^1$H-NMR (270 MHz, CDCl$_3$/CD$_3$OD) δ (ppm): 1.18 (t, J=7.9 Hz, 3H), 1.50-1.65 (m, 2H), 2.40-2.70 (m, 4H), 2.81 (d, J=4.9 Hz, 3H), 3.29 (t, J=6.0 Hz, 2H), 3.72 (s, 2H), 6.29 (br s, 1H), 6.33 (s, 1H), 7.20-7.30 (m, 2H), 7.35-7.50 (m, 3H);

APCI-MS (m/z): 344 (M+H)$^+$.

EXAMPLE 160

2-[3-(2-Ethyl-3,5-dihydroxy-6-phenylphenyl)propoxy]-N,N-dimethylacetamide (Compound 160)

(Step 1)

In the same manner as in the step 3 in Example 155, 2-{3-[2-ethyl-3,5-bis(methoxymethoxy)-6-phenylphenyl]propoxy}-N,N-dimethylacetamide (60.2 mg, 49%) was obtained from 3-[2-ethyl-3,5-bis(methoxymethoxy)-6-phenylphenyl]propoxyacetic acid (115 mg, 0.274 mmol) obtained in the step 2 in Example 158, using 1-hydroxybenzotriazole hydrate (108 mg, 0.800 mmol), aqueous solution of 50% dimethylamine (0.100 mL, 1.00 mmol) and 1-[3-(dimethylamino)propyl]-3-ethylcarbodiimide hydrochloride (207 mg, 1.08 mmol).

$^1$H-NMR (270 MHz, CDCl$_3$) δ (ppm): 1.16 (t, J=7.3 Hz, 3H), 1.50-1.70 (m, 2H), 2.40-2.50 (m, 2H), 2.68 (q, J=7.3 Hz, 2H), 2.92 (s, 3H), 2.93 (s, 3H), 3.23 (s, 3H), 3.26 (t, J=6.7 Hz, 2H), 3.53 (s, 3H), 3.94 (s, 2H), 4.94 (s, 2H), 5.23 (s, 2H), 6.83 (s, 1H), 7.15-7.25 (m, 2H), 7.25-7.40 (m, 3H).

(Step 2)

In the same manner as in the step 2 in Example 25, Compound 160 (28.6 mg, 62%) was obtained from 2-{3-[2-ethyl-3,5-bis(methoxymethoxy)-6-phenylphenyl]propoxy}-N,N-dimethylacetamide (58.0 mg, 0.130 mmol) obtained in the above, using ethanol (4 mL) and concentrated hydrochloric acid (0.2 mL).

$^1$H-NMR (270 MHz, CDCl$_3$) δ (ppm): 1.18 (t, J=7.5 Hz, 3H), 1.50-1.68 (m, 2H), 2.38-2.47 (m, 2H), 2.64 (q, J=7.5 Hz, 2H), 2.92 (s, 3H), 2.93 (s, 3H), 3.27 (t, J=6.4 Hz, 2H), 3.96 (s, 2H), 4.49 (s, 1H), 4.90 (s, 1H), 6.35 (s, 1H), 7.20-7.30 (m, 2H), 7.35-7.50 (m, 3H);

APCI-MS (m/z): 358 (M+H)$^+$.

EXAMPLE 161

6-Ethyl-5-[2-(2-hydroxyethoxy)ethyl]-4-phenylbenzene-1,3-diol (Compound 161)

(Step 1)

2-{2-[2-Ethyl-3,5-bis(methoxymethoxy)-6-phenylphenyl]ethoxy}ethanal (104 mg, 0.269 mmol) obtained in the step 1 in Example 155 was dissolved in methanol (5 mL), and sodium borohydride (32.5 mg, 0.859 mmol) was added thereto and stirred at room temperature for 1 hour. Water was added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer chromatography (n-hexane/ethyl acetate=2/1) to obtain 2-{2-[2-ethyl-3,5-bis(methoxymethoxy)-6-phenylphenyl]ethoxy}ethanol (55.4 mg, 53%).

$^1$H-NMR (270 MHz, CDCl$_3$) δ (ppm): 1.17 (t, J=7.3 Hz, 3H), 1.76 (t, J=6.2 Hz, 1H), 2.65-2.82 (m, 4H), 3.24 (s, 3H), 3.36 (t, J=8.0 Hz, 2H), 3.53 (s, 3H), 3.52-3.62 (m, 2H), 4.95 (s, 2H), 5.23 (s, 2H), 6.86 (s, 1H), 7.15-7.25 (m, 2H), 7.30-7.45 (m, 3H).

(Step 2) in the same manner as in the step 2 in Example 25, Compound 161 (46.8 mg, 100%) was obtained from 2-{2-[2-ethyl-3,5-bis(methoxymethoxy)-6-phenylphenyl]ethoxy}ethanol (54.0 mg, 0.138 mmol) obtained in the above, using ethanol (4 mL) and concentrated hydrochloric acid (0.2 mL).

$^1$H-NMR (270 MHz, CDCl$_3$/CD$_3$OD) δ (ppm): 1.18 (t, J=7.4 Hz, 3H), 2.66 (q, J=7.6 Hz, 2H), 2.66-2.80 (m, 2H), 3.56 (t, j=4.6 Hz, 2H), 6.35 (s, 1H), 7.20-7.30 (m, 2H), 7.35-7.52 (m, 3H);

FAB-MS (m/z): 303 (M+H)$^+$.

EXAMPLE 162

6-Ethyl-5-[3-(2-hydroxyethoxy)propyl]-4-phenyl-benzene-1,3-diol (Compound 162)

(Step 1)

2-{3-[2-Ethyl-3,5-bis(methoxymethoxy)-6-phenylphenyl]propoxy}ethanal (99.4 mg, 0.247 mmol) obtained in the step 1 in Example 158 was dissolved in methanol (5 mL), and sodium borohydride (40.0 mg, 1.06 mmol) was added thereto and stirred at room temperature for 1 hour. Water was added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer chromatography (n-hexane/ethyl acetate=2/1) to obtain 2-{3-[2-ethyl-3,5-bis(methoxymethoxy)-6-phenylphenyl]propoxy}ethanol (44.8 mg, 45%).

$^1$H-NMR (270 MHz, CDCl$_3$) δ (ppm): 1.17 (t, J=7.4 Hz, 3H), 1.50-1.65 (m, 2H), 1.76 (t, J=6.2 Hz, 1H), 2.40-2.52 (m, 2H), 2.68 (q, J=7.4 Hz, 2H), 3.24 (s, 3H), 3.20-3.35 (m, 4H), 3.53 (s, 3H), 3.55-3.62 (m, 2H), 4.95 (s, 2H), 5.23 (s, 2H), 6.84 8s, 1H), 7.16-7.25 8m, 2H), 7.28-7.42 (m, 3H).

(Step 2)

In the same manner as in the step 2 in Example 25, Compound 162 (32.1 mg, 96%) was obtained from 2-{3-[2-ethyl-3,5-bis(methoxymethoxy)-6-phenylphenyl]propoxy}ethanol (43.0 mg, 0.106 mmol) obtained in the above, using ethanol (4 mL) and concentrated hydrochloric acid (0.2 mL).

$^1$H-NMR (270 MHz, CDCl$_3$/CD$_3$OD) δ (ppm): 1.18 (t, J=7.4 Hz, 3H), 1.50-1.64 (m, 2H), 2.38-2.55 (m, 2H), 2.64 (q, J=7.4 Hz, 2H), 3.26 (t, J=6.4 Hz, 2H), 3.28-3.35 (m, 2H), 3.58 (t, J=4.6 Hz, 2H), 6.32 (s, 1H), 7.23-7.35 (m, 2H), 7.35-7.50 (m, 3H);

FAB-MS (m/z): 317 (M+H)$^+$.

EXAMPLE 163

5-{3-[Bis(hydroxymethyl)methoxy]propyl}-6-ethyl-4-phenylbenzene-1,3-diol (Compound 163)

(Step 1)

3-(2-Ethyl-3,5-bis(methoxymethoxy)-6-phenylphenyl]propanol (3.18 g, 8.82 mmol) obtained in the step 2 in Example 123 was dissolved in toluene (50 mL). Triphenylphosphine (3.54 g, 13.5 mmol) and imidazole (1.96 g, 28.8 mmol) were dissolved in the resulting solution, and iodine (3.81 g, 15.0 mmol) was added thereto and stirred at room temperature for 1.5 hours. Aqueous saturated sodium hydrogencarbonate solution and aqueous saturated sodium thiosulfate solution were added to the reaction mixture, and extracted with ethyl acetate. The organic layer was washed with aqueous saturated sodium thiosulfate solution and aqueous saturated sodium chloride solution in order, and dried over anhydrous sodium sulfate, and the solvent was evaporated away under reduced pressure. The resulting residue was purified through silica gel column chromatography (n-hexane/ethyl acetate=20/1 to 9/1) to obtain 4-ethyl-3-(3-iodopropyl)-1,5-bis(methoxymethoxy)-2-phenylbenzene (3.65 g, 88%)

$^1$H-NMR (270 MHz, CDCl$_3$) δ (ppm): 1.17 (t, J=7.4 Hz, 3H), 1.70-1.85 (m, 2H), 2.44-2.54 (m, 2H), 2.68 (q, J=7.4 Hz, 2H), 2.93 (t, J=6.8 Hz, 2H), 3.24 (s, 3H), 4.94 (s, 2H), 5.23 (s, 2H), 6.84 (s, 1H), 7.15-7.22 (m, 2H), 7.27-7.45 (m, 3H).

(Step 2)

Cis-1,3-o-benzylidene-glycerol (1.15 g, 6.40 mmol) was dissolved in N,N-dimethylformamide (30 mL), and the solution was cooled to 0° C., then 60% sodium hydride/mineral oil dispersion (252 mg, 6.30 mmol) was added thereto and stirred at the same temperature for 1 hour. To the reaction mixture, added was 4-ethyl-3-(3-iodopropyl)-1,5-bis(methoxymethoxy)-2-phenylbenzene (1.33 g, 2.82 mmol) obtained in the above, and stirred at 40° C. for 8 hours. Methanol and water were added to the reaction mixture, and extracted with ethyl acetate. The organic layer was washed with aqueous saturated sodium chloride solution, and dried over anhydrous sodium sulfate, and the solvent was evaporated away under reduced pressure. The resulting residue was purified through silica gel column chromatography (n-hexane/ethyl acetate=20/1 to 9/1) to obtain 4-ethyl-1,5-bis(methoxymethoxy)-2-phenyl-3-[3-(2-phenyl-1,3-dioxan-5-yloxy)propyl]benzene (723 mg, 49%) and 3-allyl-4-ethyl-1,5-bis(methoxymethoxy)-2-phenylbenzene (484 mg, 50%).

4-Ethyl-1,5-bis(methoxymethoxy)-2-phenyl-3-[3-(2-phenyl-1,3-dioxan-5-yloxy)propyl]benzene $^1$H-NMR (270 MHz, CDCl$_3$) δ (ppm): 1.16 (t, J=7.4 Hz, 3H), 1.50-1.70 (m, 2H), 2.40-2.60 (m, 2H), 2.70 (q, J=7.4 Hz, 2H), 2.95-3.00 (m, 1H), 3.23 (s, 3H), 3.33 (t, J=6.5 Hz, 2H), 3.53 (s, 3H), 3.85-4.20 (m, 4H), 4.94 (s, 2H), 5.23 (s, 2H), 5.49 (s, 1H), 6.83 (s, 1H), 7.18-7.52 (m, 10H).

3-Allyl-4-ethyl-1,5-bis(methoxymethoxy)-2-phenylbenzene $^1$H-NMR (270 MHz, CDCl$_3$) δ (ppm): 1.12 (t, J=7.4 Hz, 3H), 2.64 (q, J=7.4 Hz, 2H), 3.15 (ddd, J=1.8, 1.8, 5.6 Hz, 2H), 3.23 (s, 3H), 3.51 (s, 3H), 4.70 (dq, J=17.1, 1.8 Hz, 1H), 4.90 (dq, J=10.2, 1.8 Hz, 1H), 4.93 (s, 2H), 5.22 (s, 2H), 5.73 (ddt, J=10.2, 17.1, 5.6 Hz, 1H), 7.15-7.40 (m, 5H).

(Step 3)

4-Ethyl-1,5-bis(methoxymethoxy)-2-phenyl-3-[3-(2-phenyl-1,3-dioxan-5-yloxy)propyl]benzene (705 mg, 1.35 mmol) obtained in the above was dissolved in methanol (30 mL), and 10% palladium-carbon (35.5 mg) was added thereto and stirred in a hydrogen atmosphere at room temperature for 1 hour. The reaction mixture was filtered, and the filtrate was concentrated under reduced pressure to obtain 2-{3-[2-ethyl-3,5-bis(methoxymethoxy)-6-phenylphenyl]propyl}propane-1,3-diol (620 mg, 100%).

$^1$H-NMR (300 MHz, CDCl$_3$) δ (ppm): 1.17 (t, J=7.4 Hz, 3H), 1.50-1.70 (m, 2H), 2.42-2.52 (m, 2H), 2.68 (q, J=7.4 Hz, 2H), 3.24 (s, 3H), 3.20-3.40 (m, 3H), 3.53 (s, 3H), 3.50-3.67 (m, 4H), 4.95 (s, 2H), 5.23 (s, 2H), 6.84 (s, 1H), 7.18-7.26 (m, 2H), 7.28-7.45 (m, 3H).

(Step 4)

In the same manner as in the step 2 in Example 25, Compound 163 (384 mg, 82%) was obtained from 2-{3-[2-ethyl-3,5-bis(methoxymethoxy)-6-phenylphenyl]propyl}propane-1,3-diol (620 mg, 1.43 mmol) obtained in the above, using ethanol (25 mL) and concentrated hydrochloric acid (0.5 mL).

$^1$H-NMR (270 MHz, CDCl$_3$/CD$_3$OD) δ (ppm): 1.17 (t, J=7.4 Hz, 3H), 1.50-1.65 (m, 2H), 2.36-2.48 (m, 2H), 2.63 (q, J=7.4 Hz, 2H), 3.10-3.65 (m, 7H), 6.32 (s, 1H), 7.20-7.50 (m, 5H);

FAB-MS (m/z): 347 (M+H)$^+$.

EXAMPLE 164

6-Ethyl-5-{3-[3-(2-oxopyrrolidon-1-yl)propoxy]propyl}-4-phenylbenzene-1,3-diol (Compound 164)

(Step 1)

1-(3-Hydroxypropyl)-2-oxopyrrolidone (136 mg, 0.949 mmol) was dissolved in N,N-dimethylformamide (5 mL), and the solution was cooled to 0° C., then 60% sodium hydride/mineral oil dispersion (64.7 mg, 1.62 mmol) was added thereto and stirred at the same temperature for 1 hour. To the reaction mixture, added was 1,5-bis(methoxymethoxy)-3-(3-iodopropyl)-2-phenyl-4-ethylbenzene (107 mg, 0.227 mmol) obtained in the step 1 in Example 163, and stirred at room temperature for 48 hours. Methanol and water were added to the reaction mixture and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=20/1 to 9/1) to obtain 4-ethyl-1,5-bis(methoxymethoxy)-3-{3-[3-(2-oxopyrrolidon-1-yl)propoxy]propyl}-2-phenylbenzene (38.6 mg, 35%).

$^1$H-NMR (300 MHz, CDCl$_3$) δ (ppm): 1.17 (t, J=7.4 Hz, 3H), 1.50-1.80 (m, 4H), 2.00 (tt, J=7.2, 7.6 Hz, 2H), 2.36 (t, J=8.2 Hz, 2H), 2.40-2.50 (m, 2H), 2.68 (Q, J=7.4 Hz, 2h), 3.17 (t, J=6.3 Hz, 2H), 3.20-3.30 (m, 4H), 3.35 (t, J=7.1 Hz, 2H), 3.53 (s, 3H), 4.94 (s, 2H), 5.23 (s, 2H), 6.83 (s, 1H), 7.15-7.25 (m, 2H), 7.25-7.42 (m, 3H).

(Step 2)

In the same manner as in the step 2 in Example 25, Compound 164 (25.2 mg, 82%) was obtained from 4-ethyl-1,5-bis(methoxymethoxy)-3-{3-[3-(2-oxopyrrolidon-1-yl)propoxy]propyl}-2-phenylbenzene (37.6 mg, 0.0774 mmol) obtained in the above, using ethanol (4 mL) and concentrated hydrochloric acid (0.1 mL).

$^1$H-NMR (270 MHz, CDCl$_3$/CD$_3$OD) δ (ppm): 1.17 (t, J=7.4 Hz, 3H), 1.50-1.75 (m, 4H), 1.90-2.10 (m, 4H), 2.32-2.46 (m, 4H), 2.64 (q, J=7.4 Hz, 2H), 3.10-3.50 (m, 8H), 6.34 (s, 1H), 7.20-7.30 (m, 2H), 7.35-7.50 (m, 3H);

FAB-MS (m/z): 398 (M+H)$^+$.

EXAMPLE 165

1-{2,4-Dihydroxy-5-(3-hydroxyphenyl)-6-[2-(2-methoxyethoxy)ethyl]phenyl}ethanone (Compound 165)

In the same manner as in the step 3 in Example 1, 1-{4,6-bis(methoxymethoxy)-3-(3-hydroxyphenyl)-2-[2-(2-methoxyethoxy)ethyl]phenyl}ethanone was obtained from 1-{3-bromo-2-[2-(2-methoxyethoxy)ethyl]-4,6-bis(methoxymethoxy)phenyl}ethanone (630 mg, 1.5 mmol) obtained in the step 4 in Example 137, using 2-(3-hydroxyphenyl)-4,4,5,5-tetramethyl-1,3,2-dioxaborolane (500 mg, 2.3 mmol), bis(tri-o-tolylphosphine)palladium(II) dichloride (200 mg, 0.25 mmol), cesium carbonate (1.5 g, 4.6 mmol), 1,2-dimethoxyethane (15 mL) and water (2.0 mL). Then, in the same manner as in the step 4 in Example 1, Compound 165 (420 mg, 81%) was obtained from the resulting compound, using methanol (7.0 mL) and 1,4-dioxane solution (7.0 mL) of 4 mol/L hydrogen chloride.

$^1$H-NMR (270 MHz, CDCl$_3$) δ (ppm): 2.66 (s, 3H), 3.02 (m, 2H), 3.36 (s, 3H), 3.37-3.52 (m, 6H), 5.20 (s, 1H), 6.26 (br s, 1H), 6.46 (s, 1H), 6.78 (dt, J=7.4, 1.0 Hz, 1H), 6.87 (m, 1H), 6.93 (ddd, J=7.4, 2.5, 1.0 Hz, 1H), 7.36 (t, J=7.4 Hz, 1H), 11.9 (s, 1H);

FAB-MS (m/z): 347 (M+H)$^+$.

EXAMPLE 166

6-Ethyl-4-(3-hydroxyphenyl)-5-[2-(2-methoxyethoxy)ethyl]benzene-1,3-diol (Compound 166)

In the same manner as in Example 118, 1-{3-(3-hydroxyphenyl)-2-[2-(2-methoxyethoxy)ethyl]-4,6-bis(methoxycarbonyloxy)phenyl]ethanone was obtained from Compound 165 (320 mg, 0.92 mmol) obtained in Example 165, using methyl chlorocarbonate (0.2 mL, 2.6 mmol), triethylamine (0.4 mL, 2.9 mmol) and tetrahydrofuran (10 mL); and from the resulting compound, obtained was 4-ethyl-2-(3-hydroxyphenyl)-3-[2-(2-methoxyethoxy)ethyl]-1,5-bis(methoxycarbonyloxy)benzene, using sodium borohydride (210 mg, 5.5 mmol), water (3.0 mL) and tetrahydrofuran (5.0 mL). Then, the resulting compound was treated with methanol solution (5.0 mL) of 7 mmol/L ammonia to obtain Compound 166 (72 mg, 24%).

$^1$H-NMR (270 MHz, CDCl$_3$) δ (ppm): 1.12 (t, J=7.4 Hz, 3H), 2.73-2.55 (m, 4H), 3.34 (s, 3H), 3.40-3.34 (m, 4H), 3.47 (m, 2H), 5.11 (br s, 1H), 6.12 (br-s, 1H), 6.31 (s, 1H), 6.75-6.71 (m, 2H), 6.80 (m, 1H), 7.00 (br s, 1H), 7.25 (t, J=7.8 Hz, 1H);

FAB-MS (m/z): 332 (M+H)$^+$.

EXAMPLE 167

2-[3-(2-Ethyl-3,5-dihydroxy-6-phenylphenyl)propoxy]-N-(2-hydroxyethyl)acetamide (Compound 167)

(Step 1)

In the same manner as in the step 3 in Example 155, 2-{3-[2-ethyl-3,5-bis(methoxymethoxy)-6-phenylphenyl]propoxy}-N-(2-hydroxyethyl)acetamide (65.0 mg, 64%) was obtained from 3-[3,5-bis(methoxymethoxy)-2-ethyl-6-phenylphenyl]propoxyacetic acid (92.1 mg, 0.220 mmol) obtained in the step 2 in Example 158, using 1-hydroxybenzotriazole hydrate (150 mg, 1.11 mmol), 2-aminoethanol (0.0500 mL, 0.828 mmol) and 1-[3-(dimethylamino)propyl]-3-ethylcarbodiimide hydrochloride (210 mg, 1.10 mmol).

$^1$H-NMR (300 MHz, CDCl$_3$) δ (ppm): 1.17 (t, J=7.3 Hz, 3H), 1.52-1.68 (m, 2H), 2.45-2.55 (m, 2H), 2.62-2.72 (m, 3H), 3.24 (s, 3H), 3.29 (t, J=6.1 Hz, 2H), 3.43 (dt, J=4.6, 5.5 Hz, 2H), 3.53 (s, 3H), 3.70-3.763 (m, 2H), 3.76 (s, 2H), 4.95 (s, 2H), 5.24 (s, 2H), 6.64 (br s, 1H), 6.85 (s, 1H), 7.15-7.25 (m, 2H), 7.30-7.45 8m, 3H).

(Step 2)

In the same manner as in the step 2 in Example 25, Compound 167 (26.7 mg, 51%) was obtained from 2-{3-[2-ethyl-3,5-bis(methoxymethoxy)-6-phenylphenyl]propoxy}-N-(2-hydroxyethyl)acetamide (64.0 mg, 0.139 mmol) obtained in the above, using ethanol (4 mL) and concentrated hydrochloric acid (0.2 mL).

$^1$H-NMR (300 MHz, CDCl$_3$/CD$_3$OD) δ (ppm): 1.17 (t, J=7.4 Hz, 3H), 1.55-1.65 (m, 2H), 2.40-2.50 (m, 2H), 2.64 (q, J=7.4 Hz, 2H), 3.00-3.50 (m, 4H), 3.65 (t, J=5.4 Hz, 2H), 3.74 (s, 2H), 6.33 (s, 1H), 7.24-7.50 8m, 5H);

APCI-MS (m/z): 374 (M+H)$^+$.

EXAMPLE 168

2-[3-(2-Ethyl-3,5-dihydroxy-6-phenylphenyl)propoxy]-N-(2-methoxyethyl)acetamide (Compound 168)

(Step 1)

In the same manner as in the step 3 in Example 155, 2-{3-[2-ethyl-3,5-bis(methoxymethoxy)-6-phenylphenyl]propoxy}-N-(2-methoxyethyl)acetamide (75.0 mg, 72%) was obtained from 3-[2-ethyl-3,5-bis(methoxymethoxy)-6-phenylphenyl]propoxyacetic acid (92.1 mg, 0.220 mmol) obtained in the step 2 in Example 158, using 1-hydroxybenzotriazole monohydrate (150 mg, 1.11 mmol), 2-methoxyethylamine (0.0500 mL, 0.575 mmol) and 1-[3-(dimethylamino)propyl]-3-ethylcarbodiimide hydrochloride (210 mg, 1.10 mmol).

$^1$H-NMR (300 MHz, CDCl$_3$) δ (ppm): 1.18 (t, J=7.4 Hz, 3H), 1.52-1.66 (m, 2H), 2.42 (m, 2H), 2.68 (q, J=7.5 Hz, 2H), 3.24 (s, 3H), 3.36 (s, 3H), 3.53 (s, 3H), 3.20-3.54 (m, 6H), 3.75 (s, 2H), 4.95 (s, 2H), 5.24 (s, 2H), 6.65 (br s, 1H), 6.85 (s, 1H), 7.16-7.24 (m, 2H), 7.30-7.44 (m, 3H).

(Step 2)

In the same manner as in the step 2 in Example 25, 2-{3-[2-ethyl-3,5-bis(methoxymethoxy)-6-phenylphenyl]propoxy}-N-(2-methoxyethyl)acetamide (74.0 mg, 0.156 mol) obtained in the above was dissolved in ethanol (4 mL), and concentrated hydrochloric acid (0.2 mL) was added thereto and stirred at 60° C. for 1.1 hours. The reaction mixture was concentrated under reduced pressure, and the resulting residue was purified through preparative thin-layer chromatography (chloroform/methanol=9/1) to obtain Compound 168 (46.3 mg, 77%).

$^1$H-NMR (300 MHz, CDCl$_3$/CD$_3$OD) δ (ppm): 1.18 (t, J=7.4 Hz, 3H), 1.52-1.66 (m, 2H), 2.40-2.50 (m, 2H), 2.60-2.80 (m, 2H), 3.28 (t, J=6.2 Hz, 2H), 3.36 (s, 3H), 3.38-3.48 8m, 4H), 3.74 8s, 2H), 6.33 (s, 1H), 6.75 (br s, 1H), 7.24-7.30 (m, 2H), 7.35-7.50 (m, 3H);

APCI-MS (m/z): 388 (M+H)$^+$.

EXAMPLE 169

6-Ethyl-4-phenyl-5-(3,5,6-trihydroxyhexyl)benzene-1,3-diol (Compound 169: diastereomer of Compound 170)

(Step 1)

3-[2-Ethyl-3,5-bis(methoxymethoxy)-6-phenylphenyl]propanol (394 mg, 1.09 mmol) obtained in the step 2 in Example 123 was dissolved in dichloromethane (25 mL), and pyridinium dichromate (806 mg, 2.14 mmol) was added thereto and stirred at room temperature for 18 hours. The reaction mixture was filtered, and the filtrate was concentrated under reduced pressure. The resulting residue was purified through silica gel column chromatography (n-hexane/ethyl acetate=20/1 to 9/1 to 4/1) to obtain 3-[2-ethyl-3,5-bis(methoxymethoxy)-6-phenylphenyl]propanal (270 mg, 69%).

$^1$H-NMR (300 MHz, CDCl$_3$) δ (ppm): 1.16 (t, J=7.4 Hz, 3H), 2.36-2.46 (m, 2H), 2.63 (q, J=7.5 Hz, 2H), 2.70-2.80 (m, 2H), 3.24 (s, 3H), 3.53 (s, 3H), 4.96 (s, 2H), 5.23 (s, 2H), 6.87 (s, 1H), 7.15-7.22 (m, 2H), 7.30-7.42 (m, 3H), 9.50 (t, J=1.4 Hz, 1H).

(Step 2)

3-[2-Ethyl-3,5-bis(methoxymethoxy)-6-phenylphenyl]propanal (267 mg, 0.745 mmol) obtained in the above was dissolved in ethanol (15 mL), and the solution was cooled to 0° C., then ether solution of 1.0 mol/L allylmagnesium bromide (2.00 mL, 2.00 mmol) was added thereto and stirred at the same temperature for 4 hours. Methanol and water were added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=4/1)

to obtain 1-[3,5-bis(methoxymethoxy)-2-ethyl-6-phenylphenyl]hex-5-en-3-ol (177 mg, 59%).

$^1$H-NMR (300 MHz, CDCl$_3$) δ (ppm): 1.17 (t, J=7.4 Hz, 3H), 1.40-1.52 (m, 2H), 1.90-2.10 (m, 2H), 2.38-2.65 (m, 2H), 2.69 (q, J=7.4 Hz, 2H), 3.24 (s, 3H), 3.35-3.45 (m, 1H), 3.53 (s, 3H), 4.95 (s, 2H), 4.95-5.10 (m, 2H), 5.23 (s, 2H), 5.44-5.72 (m, 2H), 6.84 (s, 1H), 7.17-7.30 (m, 2H), 7.30-7.45 (m, 3H).

(Step 3)

1-[2-Ethyl-3,5-bis(methoxymethoxy)-6-phenylphenyl]hex-5-en-3-ol (175 mg, 0.437 mmol) obtained in the above was dissolved in a mixed solvent of acetonitrile (6 mL) and water (2 mL), and N-methylmorpholine-N-oxide (100 mg, 0.855 mmol) and tert-butyl alcohol solution of 2.5% osmium tetroxide (0.0500 mL, 0.0004 mmol) were added thereto and stirred at the same temperature for 6 hours. Aqueous saturated sodium hydrogencarbonate solution and aqueous saturated sodium thiosulfate solution were added to the reaction mixture, and stirred at room temperature for 2 hours, and then extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (ethyl acetate) to obtain diastereomeric 1-[2-ethyl-3,5-bis(methoxymethoxy)-6-phenylphenyl]hexane-3,5,6-triol (triol A: 63.7 mg, 34% and triol B: 27.2 mg, 14%).

Triol A:

$^1$H-NMR (300 MHz, CDCl$_3$) δ (ppm): 1.17 (t, J=7.4 Hz, 3H), 1.20-1.40 (m, 2H), 1.45-1.60 (m, 2H), 1.90-2.06 (m, 2H), 2.40-2.65 (m, 2H), 2.68 (q, J=7.4 Hz, 2H), 3.24 8s, 3H), 3.53 (s, 3H), 3.30-3.85 (m, 5H), 4.96 (s, 2H), 5.23 (s, 2H), 6.85 (s, 1H), 7.20-7.27 (m, 2H), 7.30-7.45 (m, 3H).

Triol B:

$^1$H-NMR (300 MHz, CDCl$_3$) δ (ppm): 1.17 (t, J=7.4 Hz, 3H), 1.35-1.58 (m, 4H), 1.95 (br s, 2H), 2.36-2.76 (m, 5H), 3.24 (s, 3H), 3.53 (s, 3H), 3.35-3.55 (m, 2H), 3.60-3.80 (m, 2H), 4.96 (s, 2H), 5.23 (s, 2H), 6.85 (s, 1H), 7.18-7.25 (m, 2H), 7.30-7.45 (m, 3H).

(Step 4)

In the same manner as in the step 2 in Example 25, Compound 169 (33.9 mg, 84%) was obtained from the triol A (50.6 mg, 0.116 mmol) obtained in the above, using ethanol (4 mL) and concentrated hydrochloric acid (0.2 mL).

$^1$H-NMR (270 MHz, CDCl$_3$/CD$_3$OD) δ (ppm): 1.16 (t, J=7.4 Hz, 3H), 1.22-1.32 (m, 2H), 1.38-1.60 (m, 2H), 2.28-2.60 (m, 2H), 2.64 (q, J=7.4 Hz, 2H), 3.30-3.45 (m, 2H), 3.45-3.67 (m, 2H), 6.33 (s, 1H), 7.20-7.45 (m, 5H);

FAB-MS (m/z): 347 (M+H)$^+$.

EXAMPLE 170

6-Ethyl-4-phenyl-5-(3,5,6-trihydroxyhexyl)benzene-1,3-diol (Compound 170: diastereomer of Compound 169)

In the same manner as in the step 2 in Example 25, Compound 170 (16.9 mg, 79%) was obtained from the triol B (27.0 mg, 0.0621 mmol) obtained in the step 3 in Example 169, using ethanol (4 mL) and concentrated hydrochloric acid (0.2 mL).

$^1$H-NMR (270 MHz, CDCl$_3$/CD$_3$OD) δ (ppm): 1.17 (t, J=7.4 Hz, 3H), 1.10-1.34 (m, 4H), 2.27-2.60 (m, 2H), 2.64 (q, J=7.4 Hz, 2H), 3.30-3.70 (m, 4H), 6.31 (s, 1H), 7.20-7.30 (m, 2H), 7.30-7.50 (m, 3H);

FAB-MS (m/z): 347 (M+H)$^+$.

EXAMPLE 171

6-Ethyl-4-(3-hydroxyphenyl)-5-(2-methoxyethyl)benzene-1,3-diol (Compound 171)

(Step 1)

In the same manner as in the step 1 in Example 64, 2-ethyl-1-(2-methoxyethyl)-3,5-bis(methoxymethoxy)benzene (490 mg, 91%) was obtained from 2-[2-ethyl-3,5-bis(methoxymethoxy)phenyl]ethanol (500 mg, 1.9 mmol) obtained in the step 1 in Example 153, using 60% sodium hydride/mineral oil dispersion (150 mg, 3.8 mmol), methyl iodide (0.2 mL, 3.2 mmol) and N,N-dimethylformamide (10 mL).

$^1$H-NMR (270 MHz, CDCl$_3$) δ (ppm): 1.10 (t, J=7.5 Hz, 3H), 2.66 (q, J=7.5 Hz, 2H), 2.88 (t, J=7.7 Hz, 2H), 3.34 (s, 3H), 3.48 (s, 3H), 3.55 (t, J=7.7 Hz, 2H), 5.13 (s, 2H), 5.17 (s, 2H), 6.56 (d, J=2.5 Hz, 1H), 6.68 (d, J=2.5 Hz, 1H).

(Step 2)

In the same manner as in the step 1 in Example 13, 4-ethyl-2-iodo-3-(2-methoxyethyl)-1,5-bis(methoxymethoxy)benzene (350 mg, 50-%) was obtained from 2-ethyl-1-(2-methoxyethyl)-3,5-bis(methoxymethoxy)benzene (490 mg, 1.7 mmol) obtained in the above, using chloroform (15 mL), iodine (430 mg, 1.7 mmol) and [bis(trifluoroacetoxy)iodo]benzene (730 mg, 1.7 mmol).

$^1$H-NMR (270 MHz, CDCl$_3$) δ (ppm): 1.11 (t, J=7.3 Hz, 2H), 2.75 (q, J=7.3 Hz, 2H), 3.22 (t, J=8.0 Hz, 2H), 3.40 (s, 3H), 3.48 (s, 3H), 3.51 (t, J=8.0 Hz, 2H), 3.52 (s, 3H), 5.18 (s, 2H), 5.19 (s, 2H), 6.81 (s, 1H).

(Step 3)

In the same manner as in the step 3 in Example 1, 4-ethyl-2-(3-hydroxyphenyl)-3-(2-methoxyethyl)-1,5-bis(methoxycarbonyloxy)benzene was obtained from 4-ethyl-2-iodo-3-(2-methoxyethyl)-1,5-bis(methoxymethoxy)benzene (120 mg, 0.29 mmol) obtained in the above, using 2-(3-hydroxyphenyl)-4,4,5,5-tetramethyl-1,3,2-dioxaborolane (100 mg, 0.45 mmol), bis(tri-o-tolylphosphine)palladium(II) dichloride (20 mg, 0.025 mmol) and cesium carbonate (280 g, 0.87 mmol). Then, in the same manner as in the step 4 in Example 1, Compound 171 (70 mg, 84%) was obtained from the resulting compound, using methanol (2.0 mL) and 1,4-dioxane solution (2.0 mL) of 4 mol/L hydrogen chloride.

$^1$H-NMR (270 MHz, CDCl$_3$) δ (ppm): 1.16 (t, J=7.4 Hz, 3H), 2.60-2.77 (m, 4H), 3.15 (s, 3H), 3.30 (t, J=7.9 Hz, 2H), 6.32 (s, 1H), 6.71-6.77 (m, 2H), 6.85 (m, 1H), 7.29 (t, J=7.7 Hz, 1H);

APCI-MS (m/z): 288 (M+H)$^+$.

EXAMPLE 172

6-Ethyl-5-(2-hydroxyethyl)-4-(3-hydroxyphenyl)benzene-1,3-diol (Compound 172)

(Step 1)

In the same manner as in the step 2 in Example 1, methyl 6-bromo-2-ethyl-3,5-bis(methoxymethoxy)phenylacetate (12 g, 97%) was obtained from methyl 2-ethyl-3,5-bis(methoxymethoxy)phenylacetate (9.8 g, 33 mmol), using N-bromosuccinimide (6.5 g, 37 mmol) and N,N-dimethylformamide (130 mL).

$^1$H-NMR (270 MHz, CDCl$_3$) δ (ppm): 1.07 (t, J=7.5 Hz, 3H), 2.66 (q, J=7.5 Hz, 2H), 3.48 (s, 3H), 3.50 (s, 2H), 3.52 (s, 3H), 3.71 (s, 3H), 5.18 (s, 2H), 5.21 (s, 2H), 6.94 (s, 1H);

APCI-MS (m/z): 376, 378 (M+H)$^+$.

(Step 2)

In the same manner as in the step 3 in Example 1, methyl 2-ethyl-6-(3-hydroxyphenyl)-3,5-bis(methoxymethoxy)phenylacetate (3.9 g, 91%) was obtained from methyl 6-bromo-2-ethyl-3,5-bis(methoxymethoxy)phenylacetate (4.1 g, 11 mmol) obtained in the above, using 2-(3-hydroxyphenyl)-4,4,5,5-tetramethyl-1,3,2-dioxaborolane (3.0 g, 14 mmol), bis(tri-o-tolylphosphine)palladium(II) dichloride (860 mg, 1.1 mmol), cesium carbonate (11 g, 34 mmol), 1,2-dimethoxyethane (80 mL) and water (20 mL).

$^1$H-NMR (270 MHz, CDCl$_3$) δ (ppm): 1.10 (t, J=7.3 Hz, 3H), 2.61 (q, J=7.3 Hz, 2H), 3.27 (s, 3H), 3.51 (s, 2H), 3.52 (s, 3H), 3.60 (s, 3H), 4.98 (s, 2H), 5.23 (s, 2H), 6.68 (dd, J=2.7, 1.5 Hz, 1H), 6.73 (ddd, J=7.78, 1.5, 1.2 Hz, 1H), 6.78 (ddd, J=7.7, 2.7, 1.2 Hz, 1H), 7.22 (t, J=7.7 Hz, 1H), 6.92 (s, 1H);
APCI-MS (m/z): 391 (M+H)$^+$.

(Step 3)

In the same manner as in the step 1 in Example 1, methyl 2-ethyl-3,5-bis(methoxymethoxy)-6-[3-(methoxymethoxy)phenyl]phenylacetate (3.3 g, 77%) was obtained from methyl 2-ethyl-6-(3-hydroxyphenyl)-3,5-bis(methoxymethoxy)phenylacetate (3.9 g, 10 mmol), using chloromethyl methyl ether (3.0 mL, 40 mmol), diisopropylethylamine (7.0 mL, 41 mmol) and dichloromethane (80 mL).

$^1$H-NMR (270 MHz, CDCl$_3$) δ (ppm): 1.11 (t, J=7.3 Hz, 3H), 2.63 (q, J=7.3 Hz, 2H), 3.28 (s, 3H), 3.46 (s, 3H), 3.47 (s, 2H), 3.51 (s, 3H), 3.60 (s, 3H), 4.98 (s, 1H), 5.15 (s, 2H), 5.23 (s, 2H), 6.83-6.90 (m, 2H), 6.93 (s, 1H), 6.99 (m, 1H), 7.29 (t, J=7.6 Hz, 1H);
APCI-MS (m/z): 435 (M+H)$^+$.

(Step 4)

In the same manner as in the step 1 in Example 62, 2-{2-ethyl-3,5-bis(methoxymethoxy)-6-[3-(methoxymethoxy)phenyl]phenyl}ethanol (3.1 g, 99%) was obtained from methyl 2-ethyl-3,5-bis(methoxymethoxy)-6-[3-(methoxymethoxy)phenyl]phenylacetate (3.3 g, 7.6 mmol), using lithium aluminium hydride (0.5 g, 13 mmol) and tetrahydrofuran (50 mL).

$^1$H-NMR (270 MHz, CDCl$_3$) δ (ppm): 1.16 (t, J=7.3 Hz, 3H), 2.67-2.77 (m, 4H), 3.26 (s, 3H), 3.47 (s, 3H), 3.51 (s, 3H), 3.53 (m, 2H), 4.95 (s, 2H), 5.13 (d, J=6.6 Hz, 1H), 5.18 (d, J=6.6 Hz, 1H), 5.22 (s, 2H), 6.82-6.90 (m, 3H), 7.29 (t, J=7.9 Hz, 1H), 7.00 (m, 1H).

(Step 5)

In the same manner as in the step 4 in Example 1, Compound 172 (70 mg, 80%) was obtained from 2-{2-ethyl-3,5-bis(methoxymethoxy)-6-[3-(methoxymethoxy)phenyl]phenyl}ethanol (130 mg, 0.32 mmol) obtained in the above, using methanol (1.0 mL) and 1,4-dioxane solution (1.0 mL) of 4 mol/L hydrogen chloride.

$^1$H-NMR (270 MHz, CDCl$_3$) δ (ppm): 1.16 (J=7.2 Hz, 3H), 2.61-2.75 (m, 4H), 3.49 (t, J=8.1 Hz, 2H), 6.72-6.75 (m, 2H), 6.84 (m, 1H), 7.27 (t, J=8.1 Hz, 1H), 7.75 (s, 1H);
APCI-MS (m/z): 273 (M–H)$^-$.

EXAMPLE 173

5-[2-(2,3-dihydroxypropoxy)ethyl]-6-ethyl-4-(3-hydroxyphenyl)benzene-1,3-diol (Compound 173)

(Step 1)

In the same manner as in the step 1 in Example 64, 1-(2-allyloxyethyl)-2-ethyl-3,5-bis(methoxymethoxy)benzene (4.2 g, 81%) was obtained from 2-[2-ethyl-3,5-bis(methoxymethoxy)phenyl]ethanol (4.5 g, 6.8 mmol) obtained in the step 1 in Example 153, using 60% sodium hydride/mineral oil dispersion (2.7 g, 68 mmol), allyl bromide (5.8 mL, 67 mmol) and N,N-dimethylformamide (90 mL).

$^1$H-NMR (270 MHz, CDCl$_3$) δ (ppm): 1.10 (t, J=7.3 Hz, 3H), 2.63 (q, J=7.3 Hz, 2H), 2.90 (t, J=7.7 Hz, 2H), 3.47 (s, 3H), 3.48 (s, 3H), 3.60 (t, J=7.7 Hz, 2H), 4.00 (dt, J=5.9, 1.1 Hz, 2H), 5.12 (s, 2H), 5.17 (s, 2H), 5.19 (dq, J=10.8, 1.1 Hz, 1H), 5.27 (dq, J=17.2, 1.1 Hz, 1H), 5.93 (ddt, J=17.2, 10.8, 5.9 Hz, 1H), 6.56 (d, J=2.5 Hz, 1H), 6.67 (d, J=2.5 Hz, 1H).

(Step 2)

In the same manner as in the step 2 in Example 1, 3-(2-allyloxyethyl)-2-bromo-4-ethyl-1,5-bis(methoxymethoxy)benzene (5.0 g, 95%) was obtained from 1-(2-allyloxyethyl)-2-ethyl-3,5-bis(methoxymethoxy)benzene (4.2 g, 14 mmol) obtained in the above, using N-bromosuccinimide (2.6 g, 15 mmol) and N,N-dimethylformamide (60 mL).

$^1$H-NMR (270 MHz, CDCl$_3$) δ (ppm): 1.11 (t, J=7.3 Hz, 3H), 2.68 (q, J=7.3 Hz, 2H), 3.18 (t, J=7.9 Hz, 2H), 3.47 (S, 3H), 3.52 (s, 3H), 3.58 (t, J=7.9 Hz, 2H), 4.02 (dt, J=5.8, 1.5 Hz, 2H), 5.17-5.19 (m, 1H), 5.17 (s, 2H), 5.19 (s, 2H), 5.26 (dq, J=17.2, 1.5 Hz, 1H), 5.93 (ddt, J=17.2, 10.5, 5.8 Hz, 1H), 6.87 (s, 1H).

(Step 3)

3-(2-Allyloxyethyl)-2-bromo-4-ethyl-1,5-bis(methoxymethoxy)benzene (5.0 g, 13 mmol) obtained in the above was dissolved in a mixed solvent of tetrahydrofuran (50 mL) and water (10 mL), and with stirring at room temperature, N-methylmorpholine-N-oxide (1.9 g, 16 mmol) and tert-butanol solution (1 mL) of 2.5% osmium tetroxide were added thereto, and stirred overnight. Aqueous saturated sodium thiosulfate solution was added to the reaction mixture, and stirred further for 2 hours, and then extracted twice with ethyl acetate. The organic layer was washed with aqueous saturated sodium chloride solution, and dried over anhydrous sodium sulfate, and the solvent was evaporated away under reduced pressure to obtain 3-{2-[6-bromo-2-ethyl-3,5-bis(methoxymethoxy)phenyl]ethoxy}propane-1,2-diol. The resulting compound was dissolved in N,N-dimethylformamide (50 mL), and 2,2-dimethoxypropane (6.4 mL, 52 mmol) and p-toluenesulfonic acid dihydrate (0.12 g, 0.63 mmol) were added thereto and stirred at room temperature for 30 minutes. The reaction solution was neutralized with aqueous saturated sodium hydrogencarbonate solution, and then extracted twice with ethyl acetate. The organic layer was washed with aqueous saturated sodium chloride solution, then dried over anhydrous sodium sulfate, and the solvent was evaporated away under reduced pressure. The resulting residue was purified through silica gel column chromatography (n-hexane/ethyl acetate=9/1 to 4/1) to obtain 2-bromo-3-{2-[(2,2-dimethyl-1,3-dioxolan-4-yl)methoxy]ethyl}-4-ethyl-1,5-bis(methoxymethoxy)benzene (5.6 g, 93%).

$^1$H-NMR (270 MHz, CDCl$_3$) δ (ppm): 1.11 (t, J=7.4 Hz, 3H), 1.43 (s, 3H), 1.37 (s, 3H), 2.68 (q, J=7.4 Hz, 2H), 3.17 (t, J=7.9 Hz, 2H), 3.47 (s, 3H), 3.52 (s, 3H), 3.65-3.46 (m, 4H), 3.73 (dd, J=8.2, 6.4 Hz, 1H), 4.06 (dd, J=8.2, 6.4 Hz, 1H), 4.28 (m, 1H), 5.16 (s, 2H), 5.19 (s, 2H), 6.87 (s, 1H);
ESI-MS (m/z): 480, 482 (M+NH$_4$)$^+$.

(Step 4)

In the same manner as in the step 3 in Example 1, 3-{2-[(2,2-dimethyl-1,3-dioxolan-4-yl)methoxy]ethyl}-4-ethyl-2-(3-hydroxyphenyl)-1,5-bis(methoxymethoxy)benzene (1.8 g, 87%) was obtained from 2-bromo-3-{2-[(2,2-dimethyl-1,3-dioxolan-4-yl)methoxy]ethyl}-4-ethyl-1,5-bis(methoxymethoxy)benzene (2.0 g, 4.4 mmol) obtained in the above, using 2-(3-hydroxyphenyl)-4,4,5,5-tetramethyl-1,3, 2-dioxaborolane (1.0 g, 4.6 mmol), bis(tri-o-tolylphosphine) palladium(II) dichloride (0.2 g, 0.25 mmol), cesium carbonate (4.2 g, 13 mmol), 2-dimethoxymethane (30 mL) and water (5.0 mL).

$^1$H-NMR (270 MHz, CDCl$_3$) δ (ppm): 1.11 (t, J=7.3 Hz, 3H), 1.35 (s, 3H), 1.40 (s, 3H), 2.67 (q, J=7.3 Hz, 2H), 2.75 (t, J=7.0 Hz, 2H), 3.35-3.18 (m, 2H), 3.26 (s, 3H), 3.44 (m, 2H), 3.52 (s, 3H), 3.63 (m, 2H), 3.98 (t, J=6.6 Hz, 2H), 4.18 (m, 1H), 4.95 (s, 2H), 5.18 (s, 2H), 6.80-6.72 (m, 3H), 6.84 (s, 1H), 7.23 (m, 1H).

(Step 5)

In the same manner as in the step 4 in Example 1, Compound 173 (0.50 g, 75%) was obtained from 3-{2-[(2,2-dimethyl-1,3-dioxolan-4-yl)methoxy]ethyl}-4-ethyl-2-(3-hydroxyphenyl)-1,5-bis(methoxymethoxy)benzene (0.95 g, 2.0 mmol) obtained in the above, using methanol (7.0 mL) and 1,4-dioxane solution (7.0 mL) of 4 mol/L hydrogen chloride.

$^1$H-NMR (270 MHz, CD$_3$OD) δ, (ppm): 1.05 (t, J=7.4 Hz, 3H), 2.67-2.53 (m, 4H), 3.44-3.12 (m, 6H), 3.56 (m, 1H), 6.22 (s, 1H), 6.59-6.56 (m, 2H), 6.68 (m, 1H), 7.14 (t, J=7.8 Hz, 1H);

ESI-MS (m/z): 349 (M+H)$^+$.

EXAMPLE 174

6-Ethyl-5-[2-(2-hydroxyethoxy)ethyl]-4-(3-hydroxyphenyl)benzene-1,3-diol (Compound 174)

(Step 1)

In the same manner as in the step 1 in Example 64, 2-ethyl-3,5-bis(methoxymethoxy)-1-{2-[2-(tetrahydropyran-2-yloxy)ethoxy]ethyl}benzene (2.1 g, 58%) was obtained from 2-[2-ethyl-3,5-bis(methoxymethoxy)phenyl]ethanol (2.5 g, 9.2 mmol) obtained in the step 1 in Example 153, using 60% sodium hydride/mineral oil dispersion (1.0 g, 25 mmol), 2-(2-bromoethoxy)tetrahydro-2H-pyran (2.9 mL, 19 mmol) and N,N-dimethylformamide (50 mL).

$^1$H-NMR (270 MHz, CDCl$_3$) δ (ppm): 1.10 (t, J=7.5 Hz, 3H), 1.49-1.83 (m, 6H), 2.63 (q, J=7.5 Hz, 2H), 2.92 (t, J=7.5 Hz, 2H), 3.48 (s, 3H), 3.48 (s, 3H), 3.51 (m, 2H), 3.58-3.63 (m, 4H), 3.86 (m, 2H), 4.64 (dd, J=7.0, 3.1 Hz, 1H), 5.12 (s, 2H), 5.16 (s, 2H), 6.56 (d, J=2.4 Hz, 1H), 6.67 (d, J=2.4 Hz, 1H);

ESI-MS 416 (M+NH$_4$)$^+$.

(Step 2)

In the same manner as in the step 2 in Example 1, 2-bromo-4-ethyl-1,5-bis(methoxymethoxy)-3-{2-[2-(tetrahydropyran-2-yloxy)ethoxy]ethyl}benzene (2.1 g, 89%) was obtained from 2-ethyl-3,5-bis(methoxymethoxy)-1-{2-[2-(tetrahydropyran-2-yloxy)ethoxy]ethyl}benzene (2.1 g, 5.3 mmol) obtained in the above, using N-bromosuccinimide (1.0 g, 5.6 mmol) and N,N-dimethylformamide (50 mL).

$^1$H-NMR (270 MHz, CDCl$_3$) δ (ppm): 1.10 (t, J=7.5 Hz, 3H), 1.49-1.86 (m, 6H), 2.72 (q, J=7.5 Hz, 2H), 3.18 (t, J=7.5 Hz, 2H), 3.47 (s, 3H), 3.52 (s, 3H), 3.60-3.71 (m, 6H), 3.90 (m, 2H), 5.17 (s, 2H), 5.19 (s, 2H), 6.86 (s, 1H).

(Step 3)

In the same manner as in the step 3 in Example 1, 4-ethyl-1,5-bis(methoxymethoxy)-2-phenyl-3-{2-[2-(tetrahydropyran-2-yloxy)ethoxy]ethyl}benzene was obtained from 2-bromo-4-ethyl-1,5-bis(methoxymethoxy)-3-{2-[2-(tetrahydropyran-2-yloxy)ethyl]ethyl}benzene (1.3 g, 2.6 mmol) obtained in the above, using 2-(3-hydroxyphenyl)-4,4,5,5-tetramethyl-1,3,2-dioxaborolane (700 mg, 3.2 mmol), bis(tri-o-tolylphosphine)palladium(II) dichloride (100 mg, 0.13 mmol), cerium carbonate (2.0 g, 6.2 mmol), 1,2-dimethoxyethane (15 mL) and water (3.0 mL). Then, in the same manner as in the step 4 in Example 1, Compound 174 (420 mg, 49%) was obtained from the resulting compound, using methanol (10 mL) and 1,4-dioxane solution (5.0 mL) of 4 mol/L hydrogen chloride.

$^1$H-NMR (270 MHz, DMSO-d$_6$) δ (ppm): 1.04 (t, J=7.3 Hz, 3H), 2.49-2.56 (m, 4H), 3.16-3.38 (m, 6H), 4.48 (t, J=5.6 Hz, 1H), 6.30 (s, 1H), 6.52-6.47 (m, 2H), 6.64 (m, 1H), 7.11 (t, J=7.9 Hz), 8.56 (s, 1H), 9.00 (s, 1H), 9.20 (s, 1H);

ESI-MS (m/z): 319 (M+H)$^+$.

EXAMPLE 175

6-Ethyl-5-[2-(3-hydroxypropoxy)ethyl]-4-phenyl-benzene-1,3-diol (Compound 175)

(Step 1)

3-(2-Allyloxyethyl)-4-ethyl-1,5-bis(methoxymethoxy)-2-phenylbenzene (200 mg, 0.518 mmol) obtained in the step 1 in Example 144 was dissolved in tetrahydrofuran (5 mL), and the solution was cooled to 0° C., and then tetrahydrofuran solution of 1.0 mol/L borane-tetrahydrofuran complex (6.00 mL, 6.00 mmol) was added thereto and stirred at the same temperature for 10 hours. Aqueous 4.0 mol/L lithium hydroxide solution (5.00 mL, 20.0 mmol) and aqueous 35% hydrogen peroxide solution (5.0 mL) were added to the reaction mixture, and stirred at room temperature for 2 hours. Water was added to the reaction mixture, and extracted with ethyl acetate. The organic layer was washed with aqueous saturated sodium thiosulfate solution and aqueous saturated sodium chloride solution, then dried over anhydrous sodium sulfate, and the solvent was evaporated away under reduced pressure. The resulting residue was purified through preparative thin-layer chromatography (n-hexane/ethyl acetate=2/1) to obtain 4-ethyl-3-[2-(3-hydroxypropoxy)ethyl]-1,5-bis(methoxymethoxy)-2-phenylbenzene (146 mg, 70%).

$^1$H-NMR (270 MHz, CDCl$_3$/CD$_3$OD) δ (ppm): 1.16 (t, J=7.4 Hz, 3H), 1.68 (tt, J=5.6, 5.6 Hz, 2H), 2.10 (br s, 1H), 1.64-2.78 (m, 4H), 3.24 (s, 3H), 3.22-3.36 (m, 4H), 3.52 (s, 3H), 3.60-3.70 (m, 2H), 4.94 (s, 2H), 5.23 (s, 2H), 6.85 (s, 1H), 7.15-7.25 (m, 2H), 7.30-7.45 (m, 3H).

(Step 2)

In the same manner as in the step 2 in Example 25, Compound 175 (42.7 mg, 60%) was obtained from 4-ethyl-3-[2-(3-hydroxypropoxy)ethyl]-1,5-bis(methoxymethoxy)-2-phenylbenzene (91.5 mg, 0.226 mmol), using ethanol (4 mL) and concentrated hydrochloric acid (0.1 mL).

$^1$H-NMR (270 MHz, CDCl$_3$) δ (ppm): 1.17 (t, J=7.4 Hz, 3H), 1.67 (tt, J=5.9, 5.9 Hz, 2H), 2360-2.76 (m, 4H), 3.26-3.44 (m, 4H), 3.59 (t, J=5.9 Hz, 2H), 6.34 8s, 1H), 7.20-7.30 (m, 2H), 7.30-7.50 (m, 3H);

FAB-MS (m/z): 339 (M+Na)$^+$.

EXAMPLE 176

6-Ethyl-5-[2-(3-methoxypropoxy)ethyl]-4-phenyl-benzene-1,3-diol (Compound 176)

(Step 1)

In the same manner as in the step 1 in Example 64, 4-ethyl-3-[2-(3-methoxypropoxy)ethyl]-1,5-bis(methoxymethoxy)-2-phenylbenzene (28.4 mg, 51%) was obtained from 4-ethyl-3-[2-(3-hydroxypropoxy)ethyl]-1,5-bis(methoxymethoxy)-2-phenylbenzene (53.5 mg, 0.132 mmol) obtained in the step 1 in Example 175, using 60% sodium hydride/mineral oil dispersion (59.8 mg, 1.50 mmol) and methyl iodide (0.0810 mL, 1.30 mmol).

$^1$H-NMR (300 MHz, CDCl$_3$) δ (ppm): 1.16 (t, J=7.3 Hz, 3H), 1.68 (tt, J=5.9, 6.4 Hz, 2H), 2.64-2.80 (m, 4H), 3.23 (s, 3H), 3.59 (s, 3H), 3018-3.38 (m, 6H), 3.52 (s, 3H), 4.95 (s, 2H), 5.23 (s, 2H), 6.85 (s, 1H), 7.15-7.25 (m, 2H), 7.25-7.42 (m, 3H).

(Step 2)

In the same manner as in the step 2 in Example 25, 4-ethyl-3-[2-(3-methoxypropoxy)ethyl]-1,5-bis(methoxymethoxy)-2-phenylbenzene (28.4 mg, 0.0679 mmol) obtained in the above was dissolved in ethanol (4 mL), and concentrated hydrochloric acid (0.1 mL) was added thereto and stirred at 60° C. for 1.1 hours. The reaction mixture was concentrated under reduced pressure, and the resulting residue was purified twice through preparative thin-layer chromatography (chloroform/methanol=20/1) to obtain Compound 176 (19.5 mg, 87%).

$^1$H-NMR (270 MHz, CDCl$_3$) δ (ppm): 1.19 (t, J=7.4 Hz, 3H), 1.69 (tt, J=6.4, 6.4 Hz, 2H), 2.60-2.76 (m, 4H), 3.28 (s, 3H), 3.22-3.38 (m 6H), 4.51 (br s, 1H), 4.94 (br s, 1H), 6.35 (s, 1H), 7.22-7.30 (m, 2H), 7.36-7.52 (m, 3H);

FAB-MS (m/z): 353 (M+Na)$^+$.

EXAMPLE 177

6-Ethyl-4-phenyl-5-(2,4,5-trihydroxypentyl)benzene-1,3-diol (Compound 177: diastereomer of Compound 178)

(Step 1)

2-[2-Ethyl-3,5-bis(methoxymethoxy)-6-phenylphenyl]ethanol (187 mg, 0.540 mmol) obtained in the step 1 in Example 83 was dissolved in dichloromethane (10 mL), and pyridinium dichromate (549 mg, 1.46 mmol) was added thereto and stirred at room temperature for 12 hours. The reaction mixture was filtered, and the filtrate was concentrated under reduced pressure. The resulting residue was purified through preparative thin-layer chromatography (n-hexane/ethyl acetate=2/1) to obtain 2-[2-ethyl-3,5-bis(methoxymethoxy)-6-phenylphenyl]ethanal (139 mg, 75%).

$^1$H-NMR (270 MHz, CDCl$_3$) δ (ppm): 1.09 (t, J=7.4 Hz, 3H), 2.58 (q, J=7.4 Hz, 2H), 3.26 (s, 3H), 3.53 (s, 3H), 3.55 (d, J=1.6 Hz, 2H), 4.98 (s, 2H), 5.25 (s, 2H), 6.95 (s, 1H), 7.10-7.20 (m, 2H), 7.30-7.42 (m, 3H), 9.53 (t, J=1.6 Hz, 1H).

(Step 2)

2-[2-Ethyl-3,5-bis(methoxymethoxy)-6-phenylphenyl]ethanal (135 mg, 0.393 mmol) obtained in the above was dissolved in ether (10 mL), and the solution was cooled to 0° C., and ether solution of 1.0 mol/L allylmagnesium bromide (1.00 mL, 1.00 mmol) was added thereto and stirred at the same temperature for 3 hours. Methanol and water were added to the reaction mixture, and extracted with ethyl acetate. The organic layer was washed with aqueous saturated sodium chloride solution, dried over anhydrous sodium sulfate, and the solvent was evaporated away under reduced pressure. The resulting residue was purified through preparative thin-layer chromatography (n-hexane/ethyl acetate=2/1) to obtain 1-[2-ethyl-3,5-bis(methoxymethoxy)-6-phenylphenyl]pent-4-en-2-ol (134 mg, 88%).

$^1$H-NMR (270 MHz, CDCl$_3$) δ (ppm): 1.14 (t, J=7.4 Hz, 3H), 1.39 (br d, J=3.5 Hz, 1H), 1.94-2.04 (m, 2H), 2.66-2.84 (m, 4H), 3.24 (s, 3H), 3.53 (s, 3H), 3.50-3.60 (m, 1H), 4.95 (s, 2H), 4.90-5.00 (m, 2H), 5.23 (s, 2H), 5.40-5.58 (m, 1H), 6.88 (s, 1H), 7.15-7.25 (m, 2H), 7.25-7.42 (m, 3H).

(Step 3)

1-[2-Ethyl-3,5-bis(methoxymethoxy)-6-phenylphenyl]pent-4-en-2-ol (133 mg, 0.344 mmol) obtained in the above was dissolved in a mixed solvent of acetonitrile (6 mL) and water (2 mL), and N-methylmorpholine-N-oxide (101 mg, 0.861 mmol) and tert-butyl alcohol solution of 2.5% osmium tetroxide (0.0500 mL, 0.0004 mmol) were added thereto and stirred at room temperature for 17 hours. Aqueous saturated sodium hydrogencarbonate solution and aqueous saturated sodium thiosulfate solution were added to the reaction mixture, then stirred at room temperature for 2 hours, and thereafter extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (chloroform/ethyl acetate/methanol=50/50/1) to obtain diastereomeric 1-[2-ethyl-3,5-bis(methoxymethoxy)-6-phenylphenyl]pentane-2,4,5-triol (triol A: 101 mg, 70% and triol B: 111 mg, 77%).

Triol A:

$^1$H-NMR (300 MHz, CDCl$_3$) δ (ppm): 1.14 (t, J=7.4 Hz, 3HH), 1.30-1.70 (m, 2H), 2.00-2.10 8m, 2H), 2.70-2.85 (m, 4H), 3.24 (s, 3H), 3.30-3.40 (m, 2H), 3.46-3.54 (m, 1H), 3.53 (s, 3H), 3.64-3.80 (m, 2H), 4.96 (s, 2H), 5.24 (s, 2H), 6.89 (s, 1H), 7.15-7.25 (m, 2H), 7.30-7.45 (m, 3H).

Triol B:

$^1$H-NMR (300 MHz, CDCl$_3$) δ (ppm): 1.14 (t, J=7.4 Hz, 3H), 1.30-1.52 (m, 2H), 1.83 (br s, 1H), 1.95 (br s, 1H), 2.65-2.90 (m, 5H), 3.24 (s, 3H), 3.30-3.50 (m, 2H), 3.53 (s, 3H), 3.68-3.86 (m, 2H), 4.96 (s, 2H), 5.24 (s, 2H), 6.89 (s, 1H), 7.15-7.25 (m, 2H), 7.30-7.45 (m, 3H).

(Step 4)

In the same manner as in the step 2 in Example 25, Compound 177 (67.6 mg, 87%) was obtained from the triol A (98.0 mg, 0.233 mmol) obtained in the above, using ethanol (4 mL) and concentrated hydrochloric acid (0.1 mL).

$^1$H-NMR (270 MHz, CDCl$_3$/CD$_3$OD) δ (ppm): 1.14 (t, J=7.4 Hz, 3H), 1.25-1.35 (m, 2H), 2.60-2.80 (m, 4H), 3.00-3.46 (m, 2H), 3.60-3.78 (m, 2H), 6.35 (s, 1H), 7.20-7.30 (m, 2H), 7.30-7.50 (m, 3H);

FAB-MS (m/z): 333 (M+H)$^+$.

EXAMPLE 178

6-Ethyl-4-phenyl-5-(2,4,5-trihydroxypentyl)benzene-1,3-diol (Compound 178: diastereomer of Compound 177)

In the same manner as in the step 2 in Example 25, Compound 178 (60.3 mg, 70%) was obtained from the triol B (109 mg, 0.260 mmol) obtained in the step 3 in Example 177, using ethanol (4 mL) and concentrated hydrochloric acid (0.1 mL).

$^1$H-NMR (270 MHz, CDCl$_3$/CD$_3$OD) δ (ppm): 1.15 (t, J=7.4 Hz, 3H), 1.15-1.42 (m, 2H), 2.60-2.82 (m, 4H), 3.20-4.00 (m, 4H), 6.34 (s, 1H), 7.20-7.30 (m, 2H), 7.30-7.48 (m, 3H);

FAB-MS (m/z): 355 (M+Na)$^+$.

EXAMPLE 179

6-Ethyl-5-{2-[2-hydroxy-3-(2-hydroxyethoxy)propoxy]ethyl}-4-phenylbenzene-1,3-diol
(Compound 179)

(Step 1)

Methyl 2-ethyl-3,5-dihydroxyphenylacetate (1.70 g, 8.09 mmol) was dissolved in acetone (20 mL), and potassium carbonate (6.43 g, 46.5 mmol) and benzyl bromide (4.00 mL, 33.6 mmol) were added thereto ad stirred at room temperature for 6 hours. Water was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through silica gel column chromatography (n-hexane/ethyl acetate=20/1 to 9/1) to obtain methyl 3,5-bis(benzyloxy)-2-ethylphenylacetate (2.08 g, 66%).

$^1$H-NMR (270 MHz, CDCl$_3$) δ (ppm): 1.10 (t, J=7.4 Hz, 3H), 2.67 (q, J=7.4 Hz, 2H), 3.64 (s, 2H), 3.68 (s, 3H), 5.00 (s, 2H), 5.04 (s, 2H), 6.49 (d, J=2.5 Hz, 1H), 6.53 (d, J=2.5 Hz, 1H), 7.26-7.44 (m, 10H).

(Step 2)

Methyl 3,5-bis(benzyloxy)-2-ethylphenylacetate (2.06 g, 5.28 mmol) obtained in the above was dissolved in N,N-dimethylformamide (10 mL), and the solution was cooled to 0° C., and then N-bromosuccinimide (1.12 g, 6.29 mmol) was added thereto and stirred at the same temperature for 0.5 hour. Water was added to the reaction mixture, and extracted with ethyl acetate. The organic layer was washed with aqueous saturated sodium hydrogencarbonate solution and aqueous saturated sodium chloride solution in order, then dried over anhydrous sodium sulfate, and the solvent was evaporated away under reduced pressure. The resulting residue was purified through silica gel column chromatography (n-hexane/ethyl acetate=20/1 to 9/1) to obtain methyl 3,5-bis(benzyloxy)-6-bromo-2-ethylphenylacetate (2.39 g, 96%).

$^1$H-NMR (300 MHz, CDCl$_3$) δ (ppm): 1.08 (t, J=7.5 Hz, 3H), 2.70 (q, J=7.4 Hz, 2H), 3.72 (s, 3H), 3.97 (s, 3H), 5.00 (s, 2H), 5.08 (s, 2H), 6.54 (s, 1H), 7.20-7.50 (m, 10H).

(Step 3)

Methyl 3,5-bis(benzyloxy)-6-bromo-2-ethylphenylacetate (2.38 g, 5.07 mmol) obtained in the above was dissolved in a mixed solvent of 1,2-dimethoxyethane (20 mL) and water (1 mL), and phenylboronic acid (888 mg, 7.28 mmol), cesium carbonate (4.92 g, 15.1 mmol) and bis(tri-o-tolylphosphine)palladium(II) dichloride (232 mg, 0.296 mmol) were added thereto and stirred with heating under reflux for 10 hours. Water was added to the reaction mixture, and filtered, and the filtrate was extracted with ethyl acetate. The organic layer was washed with aqueous saturated sodium chloride solution, then dried over anhydrous sodium sulfate, and the solvent was evaporated away under reduced pressure. The resulting residue was purified through silica gel column chromatography (n-hexane/ethyl acetate=20/1 to 9/1) to obtain methyl 3,5-bis(benzyloxy)-2-ethyl-6-phenylphenylacetate (1.98 g, 84%).

$^1$H-NMR (300 MHz, CDCl$_3$) δ (ppm): 1.12 (t, J=7.4 Hz, 3H), 2.66 (q, J=7.4 Hz, 2H), 3.51 (s, 2H), 3.60 (s, 3H), 4.90 (s, 2H), 5.05 (s, 2H), 6.60 (s, 1H), 7.00-7.10 (m, 2H), 7.20-7.45 (m, 13H).

(Step 4)

Methyl 3,5-bis(benzyloxy)-2-ethyl-6-phenylphenylacetate (1.96 g, 4.20 mmol) obtained in the above was dissolved in tetrahydrofuran (100 mL), and the solution was cooled to 0° C., and lithium aluminium hydride (214 mg, 5.63 mmol) was added thereto and stirred at the same temperature for 1 hour. Sodium sulfate and aqueous saturated sodium sulfate were added to the reaction mixture, and stirred at room temperature for 2 hours. Then, the mixture was filtered, and the filtrate was concentrated under reduced pressure. The resulting residue was purified through silica gel column chromatography (n-hexane/ethyl acetate=20/1 to 9/1 to 4/1 to 2/1) to obtain 2-[3,5-bis(benzyloxy)-2-ethyl-6-phenylphenyl]ethanol (1.74 g, 95%).

$^1$H-NMR (300 MHz, CDCl$_3$) δ (ppm): 1.25 (t, J=6.7 Hz, 3H), 2.70-2.90 (m, 4H), 3.54-3.68 (m, 2H), 4.94 (s, 2H), 5.11 (s, 2H), 6.60 (s, 1H), 7.05-7.15 (m, 2H), 7.25-7.30 (m, 4H), 7.35-7.55 (m, 9H).

(Step 5)

2-[3,5-Bis(benzyloxy)-2-ethyl-6-phenylphenyl]ethanol (100 mg, 0.228 mmol) obtained in the above was dissolved in dichloromethane (5 mL), and allyl glycidyl ether (0.0271 mL, 0.228 mmol) and boron trifluoride/diethyl ether complex (0.0100 mL, 0.0794 mmol) were added thereto and stirred at room temperature for 15 hours. Aqueous saturated sodium hydrogencarbonate solution was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (chloroform/ethyl acetate=20/1) to obtain 3-allyloxy-1-{2-[3,5-bis(benzyloxy)-2-ethyl-6-phenylphenyl]ethoxy}propan-2-ol (44.6 mg, 35%).

$^1$H-NMR (270 MHz, CDCl$_3$) δ (ppm): 1.18 (t, J=7.4 Hz, 3H), 2.30-2.40 (m, 1H), 2.65-2.85 (m, 4H), 3.15-3.45 (m, 6H), 3.74-3.84 (m, 1H), 3.97 (ddd, J=1.3, 1.3, 5.6 Hz, 1H), 4.88 (s, 2H), 5.04 (s, 2H), 5.12-5.32 (m, 2H), 5.88 (ddt, J=10.4, 17.3, 5.6 Hz, 1H), 6.53 (s, 1H), 7.00-7.10 (m, 2H), 7.15-7.25 (m, 4H), 7.27-7.45 (m, 9H).

(Step 6)

3-Allyloxy-1-{2-[3,5-bis(benzyloxy)-2-ethyl-6-phenylphenyl]ethoxy}propan-2-ol (35.2 mg, 0.0637 mmol) obtained in the above was dissolved in 1,4-dioxane (4 mL) and water (1 mL), and tert-butyl alcohol solution of 2.5% osmium tetroxide (0.0500 mL, 0.004 mmol) and sodium periodate (124 mg, 0.581 mmol) were added thereto, and stirred at room temperature for 6 hours. Water was added to the reaction mixture, and extracted with ethyl acetate. The organic layer was washed with aqueous saturated sodium thiosulfate solution and aqueous saturated sodium chloride solution, then dried over anhydrous sodium sulfate, and the solvent was evaporated away under reduced pressure. The resulting residue was dissolved in methanol (4 mL), and sodium borohydride (52.4 mg, 1.39 mmol) was added thereto and stirred at room temperature for 4 hours. Water was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=1/2) to obtain 1-{2-[3,5-bis(benzyloxy)-2-ethyl-6-phenylphenyl]ethoxy}-3-(2-hydroxyethoxy)propan-2-ol (20.1 mg, 57%).

$^1$H-NMR (270 MHz, CDCl$_3$) δ (ppm): 1.18 (t, J=7.3 Hz), 3H), 2.33 (br s, 1H), 2.48 (br s, 1H), 2.68-2.86 (m, 4H), 3.10-3.85 (m, 11H), 4.87 (s, 2H), 5.04 (s, 2H), 6.53 (s, 1H), 7.00-7.10 (m, 2H), 7.20-7.45 (m, 13H).

(Step 7)

In the same manner as in the step 2 in Example 25, Compound 179 (13.8 mg, 100%) was obtained from 1-{2-[3,5-bis(benzyloxy)-2-ethyl-6-phenylphenyl]ethoxy}-3-(2-hydroxyethoxy)propan-2-ol (20.1 mg, 0.0361 mmol), using ethanol (4 mL) and concentrated hydrochloric acid (0.1 mL).

$^1$H-NMR (270 MHz, CD$_3$OD) δ (ppm): 1.12 (t, J=7.3 Hz, 3H), 2.56-2.72 (m, 4H), 3.13-3.75 (m, 11H), 6.29 (s, 1H), 7.13-7.20 (m, 2H), 7.30-7.42 (m, 3H);

APCI-MS (m/z): 377 (M+H)$^+$.

EXAMPLE 180

6-Ethyl-4-phenyl-5-(2,3,4-trihydroxybutyl)benzene-1,3-diol (Compound 180)

(Step 1)

2-[2-Ethyl-3,5-bis(methoxymethoxy)-6-phenylphenyl]ethanal (195 mg, 0.566 mmol) obtained in the step 1 in Example 177 was dissolved in tetrahydrofuran (5 mL), and the solution was cooled to 0° C., and tetrahydrofuran solution of 0.99 mol/L vinylmagnesium bromide (2.50 mL, 2.48 mmol) was added thereto and stirred at the same temperature for 2 hours. Water was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=4/1) to obtain 1-[2-ethyl-3,5-bis(methoxymethoxy)-6-phenylphenyl]but-3-en-2-ol (114 mg, 54%).

$^1$H-NMR (300 MHz, CDCl$_3$) δ (ppm): 1.14 (t, J=7.3 Hz, 3H), 1.36 (br d, J=3.1 Hz, 1H), 2.68-2.86, m, 4H), 3.24 (s, 3H), 3.53 (s, 3H), 3.92-4.04 (m, 1H), 4.86-5.00 (m, 2H), 4.96 (s, 2H), 5.24 (s, 2H), 5.63 (ddd, J=5.7, 10.1, 17.4 Hz, 1H), 6.89 (s, 1H), 7.15-7.45 (m, 5H).

(Step 2)

1-[2-Ethyl-3,5-bis(methoxymethoxy)-6-phenylphenyl]but-3-en-2-ol (111 mg, 0.298 mmol) obtained in the above was dissolved in a mixed solvent of acetonitrile (6 mL) and water (2 mL). To the resulting solution, added were N-methylmorpholine-N-oxide (85.4 mg, 0.729 mmol) and tert-butyl alcohol solution of 2.5% osmium tetroxide (0.0500 mL, 0.0040 mmol), and stirred at room temperature for 24 hours. Aqueous saturated sodium hydrogencarbonate solution and aqueous saturated sodium thiosulfate solution were added to the reaction mixture, and extracted with ethyl acetate. The organic layer was washed with aqueous saturated sodium thiosulfate solution and aqueous saturated sodium chloride solution in order, then dried over anhydrous sodium sulfate, and the solvent was evaporated away under reduced pressure. The resulting residue was purified through preparative thin-layer chromatography (ethyl acetate) to obtain 4-[2-ethyl-3,5-bis(methoxymethoxy)-6-phenylphenyl]butane-1,2,3-triol (109 mg, 90%).

$^1$H-NMR (300 MHz, CDCl$_3$) δ (ppm): 1.15 (t, J=7.4 Hz, 3H), 2.72-2.86 (m, 4H), 3.20-3.65 (m, 4H), 3.24 (s, 2H), 3.53 (s, 2H), 4.96 (s, 2H), 5.24 (s, 2H), 6.90 (s, 1H), 7.15-7.45 (m, 5H). 3.24 (s, 3H), 3.53 (s, 3H).

(Step 3)

In the same manner as in the step 2 in Example 25, 4-[2-ethyl-3,5-bis(methoxymethoxy)-6-phenylphenyl]butane-1,2,3,-triol (109 mg, 0.269 mmol) obtained in the above was dissolved in ethanol (4 mL), and concentrated hydrochloric acid (0.1 mL) was added thereto and stirred at 60° C. for 1.1 hours. The reaction solution was concentrated under reduced pressure, and the resulting residue was purified through preparative thin-layer chromatography (ethyl acetate) to obtain Compound 180 (59.5 mg, 69%).

$^1$H-NMR (270 MHz, CD$_3$OD) δ (ppm): 1.10 (t, J=7.4 Hz, 3H), 2.60-2.80 (m, 4H), 3.10-3.28 (m, 3H), 3.36-3.54 (m, 1H), 6.31 (s, 1H), 7.15-7.42 (m, 5H);

APCI-MS (m/z): 319 (M+H)$^+$.

EXAMPLE 181

6-Ethyl-4-phenyl-5-(3,4,5-trihydroxypentyl)benzene-1,3-diol (Compound 181)

(Step 1)

In the same manner as in the step 1 in Example 180, 5-[2-ethyl-3,5-bis(methoxymethoxy)-6-phenylphenyl]pent-1-en-3-ol (164 mg, 76%) was obtained from 3-[2-ethyl-3,5-bis(methoxymethoxy)-6-phenylphenyl]propanal (200 mg, 0.559 mmol)-obtained in the step 1 in Example 169, using tetrahydrofuran solution of 0.99 mol/L vinylmagnesium bromide (3.00 mL, 2.97 mmol).

$^1$H-NMR (270 MHz, CDCl$_3$) δ (ppm): 0.90 (br s, 1H), 1.16 (t, J=7.4 Hz, 3H), 1.46-1.64 (m, 2H), 2.35-2.60 (m, 2H), 2.68 (q, J=7.4 Hz, 2H), 3.24 (s, 3H), 3.52 (s, 3H), 3.75-3.88 (m, 1H), 4.95 (s, 2H), 4.96 (dt, J=10.4, 1.5 Hz, 1H), 5.05 (dt, J=17.2, 1.5 Hz, 1H), 5.23 (s, 2H), 5.55 (ddd, J=5.9, 10.4, 17.2 Hz, 1H), 6.83 (s, 1H), 7.16-7.23 (m, 2H), 7.27-7.43 (m, 3H).

(Step 2)

In the same manner as in the step 2 in Example 180, 5-[2-ethyl-3,5-bis(methoxymethoxy)-6-phenylphenyl]pentane-1,2,3-triol was obtained from 5-[2-ethyl-3,5-bis(methoxymethoxy)-6-phenylphenyl]pent-1-en-3-ol (162 mg, 0.420 mmol) obtained in the above, using N-methylmorpholine-N-oxide (99.9 mg, 0.853 mmol) and tert-butyl alcohol solution of 2.5% osmium tetroxide (0.0500 mL, 0.0040 mmol).

$^1$H-NMR (300 MHz, CDCl$_3$) δ (ppm): 1.17 (t, J=7.4 Hz, 3H), 1.60-1.70 (m, 1H), 1.84-1.92 (m, 1H), 2.26-2.34 (m, 1H), 2.40-2.76 (m, 4H), 3.24 (s, 3H), 3.53 (s, 3H), 3.20-3.60 (m, 4H), 4.96 (s, 2H), 5.23 (s, 2H), 6.85 (s, 1H), 7.20-7.28 (m, 2H), 7.30-7.46 (m, 3H).

(Step 3)

In the same manner as in the step 2 in Example 25, 5-[2-ethyl-3,5-bis(methoxymethoxy)-6-phenylphenyl]pentane-1,2,3-triol (135 mg, 0.320 mmol) obtained in the above was dissolved in ethanol (4 mL), and concentrated hydrochloric acid (0.1 mL) was added thereto and stirred at 60° C. for 1.1 hours. The reaction solution was concentrated under reduced pressure, and the resulting residue was purified through preparative thin-layer chromatography (ethyl acetate) to obtain Compound 181 (81.9 mg, 77%).

$^1$H-NMR (270 MHz, CD$_3$OD) δ (ppm): 1.12 (t, J=7.3 Hz, 3H), 1.30-1.70 (m, 2H), 2.20-2.36 (m, 1H), 2.56-2.74 (m, 3H), 3.15-3.56 8m, 4H), 6.26 (s, 1H), 7.14-7.22 (m, 2H), 7.22-7.42 (m, 3H);

FAB-MS (m/z): 333 (M+H)$^+$.

EXAMPLE 182

6-Ethyl-5-(2,3-dihydroxypropyl)-4-phenylbenzene-1,3-diol (Compound 182)

(Step 1)

3-Allyl-4-ethyl-1,5-bis(methoxymethoxy)-2-phenylbenzene (149 mg, 0.435 mmol) obtained in the step 2 in Example 163 was dissolved in a mixed solvent of acetonitrile (5 mL) and water (1 mL), and N-methylmorpholine-N-oxide (140 mg, 1.20 mmol) and tert-butyl alcohol solution of 2.5 osmium tetroxide (0.0500 mL, 0.0040 mmol) was added thereto and stirred at room temperature for 24 hours. Aqueous saturated sodium hydrogencarbonate solution and aqueous saturated sodium thiosulfate solution were added to the reaction mixture, and extracted with ethyl acetate. The organic layer was washed with aqueous saturated sodium thiosulfate solution and aqueous saturated sodium chloride solution in order, then dried over anhydrous sodium sulfate, and the solvent was evaporated away under reduced pressure. The resulting residue was purified through preparative thin-layer chromatography (n-hexane/ethyl acetate=1/1) to obtain 3-[2-ethyl-3,5-bis(methoxymethoxy)-6-phenylphenyl]propane-1,2-diol (116 mg, 71%).

$^1$H-NMR (300 MHz, CDCl$_3$) δ (ppm): 1.15 (t, J=7.3 Hz, 3H), 1.45-1.60 (m, 1H), 1.75 (d, J=4.6 Hz, 1H), 2.64-2.84 (m, 4H), 3.24 (s, 3H), 3.53 (s, 3H), 3.16-3.42 (m, 2H), 3.54-3.68 (m, 1H), 4.96 (s, 2H), 5.24 (s, 2H), 6.90 (s, 1H), 7.18-7.44 (m, 5H).

(Step 2)

In the same manner as in the step 2 in Example 25, Compound 182 (86.6 mg, 99%) was obtained from 3-[2-ethyl-3,5-bis(methoxymethoxy)-6-phenylphenyl]propane-1,2-diol (114 mg, 0.303 mmol) obtained in the above, using ethanol (4 mL) and concentrated hydrochloric acid (0.1 mL).

$^1$H-NMR (270 MHz, CD$_3$OD) δ (ppm): 1.11 (t, J=7.4 Hz, 3H), 2.55-2.80 (m, 4H), 3.01 (dd, J=7.8, 11.3 Hz, 1H), 3.19 (dd, J=3.3, 11.3 Hz, 1H), 3.48-3.60 8m, 1H), 6.31 (s, 1H), 7.12-7.42 (m, 5H);

APCI-MS (m/z): 287 (M−H)$^−$.

EXAMPLE 183

6-Ethyl-4-phenyl-5-{2-[3,4,5-trihydroxy-6-(hydroxymethyl)tetrahydropyran-2-yloxy]ethyl}benzene-1,3-diol (Compound 183)

(Step 1)

2-(3,5-Bis(benzyloxy)-2-ethyl-6-phenylphenyl)ethanol (85.3 mg, 0.194 mmol) obtained in the step 4 in Example 179 was dissolved in dichloromethane (5 mL), and O-(2,3,4,6-tetra-O-benzyl-α-D-glucopyranosyl)trichloroacetimidate (83.0 mg, 0.121 mmol) and boron trifluoride/diethyl ether complex (0.030 mL, 0.238 mmol) were added thereto and stirred at 40° C. for 4 hours. Aqueous saturated sodium hydrogencarbonate solution was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=4/1) to obtain 1,5-bis(benzyloxy)-4-ethyl-2-phenyl-3-{2-[3,4,5-trihydroxy-6-(hydroxymethyl)tetrahydropyran-2-yloxy]ethyl}phenylbenzene (17.9 mg, 9%).

$^1$H-NMR (300 MHz, CDCl$_3$) δ (ppm): 1.15 (t, J=7.3 Hz, 3H), 2.65-2.90 (m, 4H), 3.65-4.04 (m, 8H), 4.30-5.05 (m, 13H), 6.45-6.60 (m, 1H), 7.60-7.50 (m, 35H).

(Step 2)

1,5-Bis(benzyloxy)-4-ethyl-2-phenyl-3-{2-[3,4,5-trihydroxy-6-(hydroxymethyl)tetrahydropyran-2-yloxy]ethyl}phenylbenzene (20.0 mg, 0.205 mmol) obtained in the above was dissolved in methanol (5 mL), and 10% palladium-carbon (10.2 mg) was added thereto and stirred in a hydrogen atmosphere at room temperature for 26 hours. The reaction mixture was filtered, and the filtrate was concentrated under reduced pressure. The resulting residue was purified through preparative thin-layer chromatography (chloroform/methanol=4/1) to obtain Compound 183 (3.2 mg, 37%).

$^1$H-NMR (270 MHz, CD$_3$OD) δ (ppm): 1.12 (t, J=7.3 Hz, 3H), 2.60-2.80 (m, 4H), 3.20-3.85 (m, 8H), 4.80-5.00 (m, 1H), 6.30 (s, 1H), 7.15-7.45 (m, 5H);

FAB-MS (m/z): 421 (M+H)$^+$.

EXAMPLE 184

Diethyl 2-{3-[2-ethyl-3,5-dihydroxy-6-phenylphenyl]-1-hydroxypropyl}di-propanoate (Compound 184)

(Step 1)

Diethyl malonate (0.100 mL, 0.659 mmol) was dissolved in tetrahydrofuran (5 mL), and the solution was cooled to −78° C., and then heptane solution of 2.0 mol/L lithium diisopropylamide (0.350 mL, 0.70 mmol) and 3-[2-ethyl-3,5-bis(methoxymethoxy)-6-phenylphenyl]propanal (134 mg, 0.374 mmol) obtained in the step 1 in Example 169 were added thereto, and stirred at room temperature for 2 hours. Water was added to the reaction mixture, and extracted with ethyl acetate. The organic layer was washed with aqueous saturated sodium chloride solution, then dried over anhydrous sodium sulfate, and the solvent was evaporated-away under reduced pressure. The resulting residue was purified through preparative thin-layer chromatography (n-hexane/ethyl acetate=2/1) to obtain diethyl 2-{3-[2-ethyl-3,5-bis(methoxymethoxy)-6-phenylphenyl]-1-hydroxypropyl}di-propanoate (98.9 mg, 51%).

$^1$H-NMR (300 MHz, CDCl$_3$) δ (ppm): 1.16 (t, J=7.4 Hz, 3H), 1.24 (t, J=7.1 Hz, 3H), 1.25 (t, J=7.1 Hz, 3H), 1.45-1.60 (m, 2H), 2.30-2.80 (m, 2H), 2.68 (q, J=7.4 Hz, 2H), 2.84 (d, J=6.8 Hz, 1H), 3.24 (s, 3H), 3.53 (s, 3H), 3.80-3.92 (m, 1H), 4.10-4.26 (m, 4H), 4.95 (s, 2H), 5.23 (s, 2H), 6.84 (s, 1H), 7.15-7.45 (m, 5H).

(Step 2)

In the same manner as in the step 2 in Example 25, Compound 184 (9.1 mg, 47%) was obtained from diethyl 2-{3-[2-ethyl-3,5-bis(methoxymethoxy)-6-phenylphenyl]-1-hydroxypropyl}di-propanoate (23.5 mg, 0.0453 mmol), using ethanol (4 mL) and concentrated hydrochloric acid (0.1 mL).

$^1$H-NMR (270 MHz, CD$_3$OD) δ (ppm): 1.11 (t, J=7.3 Hz, 3H), 1.21 (t, J=7.3 Hz, 3H), 1.22 (t, J=7.3 Hz, 3H), 1.40-1.60 (m, 2H), 2.20-2.70 (m, 4H), 3.20-3.35 (m, 1H), 3.75-3.87 (m, 1H), 4.11 (q, J=7.3 Hz, 2H), 4.14 (q, J=7.3 Hz, 2H), 6.27 (s, 1H), 7.08-7.18 (m, 2H), 7.22-7.42 (m, 3H);

FAB-MS (m/z): 431 (M+H)$^+$.

EXAMPLE 185

6-Ethyl-5-[3,5-dihydroxy-4-(hydroxymethyl)pentyl]-4-phenylbenzene-1,3-diol (Compound 185)

(Step 1)

Diethyl 2-{3-[2-ethyl-3,5-bis(methoxymethoxy)-6-phenylphenyl]-1-hydroxypropyl}di-propanoate (57.3 mg, 0.110 mmol) obtained in the step 1 in Example 184 was dissolved in tetrahydrofuran (5 mL), and the solution was cooled to 0° C., and lithium aluminium hydride (20.3 mg, 0.535 mmol) was added thereto and stirred at the same temperature for 3 hours. Anhydrous sodium sulfate and aqueous saturated sodium sulfate solution were added to the reaction mixture, and stirred at room temperature for 1 hour. Then, the reaction mixture was filtered, and the filtrate was concentrated under reduced pressure. The resulting residue was purified through preparative thin-layer chromatography (n-hexane/ethyl acetate=2/1) to obtain 5-[2-ethyl-3,5-bis(methoxymethoxy)-6-phenylphenyl]-2-(hydroxymethyl)pentane-1,3-diol (5.3 mg, 11%).

$^1$H-NMR (300 MHz, CDCl$_3$) δ (ppm): 1.17 (t, J=7.3 Hz, 3H), 1.35-1.74 (m, 5H), 2.35-2.75 (m, 4H), 3.24 (s, 3H), 3.53 (s, 3H), 3.60-3.80 (m, 5H), 4.96 (s, 2H), 5.24 (s, 2H), 6.85 (s, 1H), 7.20-7.46 (m, 5H).

(Step 2)

In the same manner as in the step 2 in Example 25, Compound 185 (4.2 mg, 100%) was obtained from 5-[2-ethyl-3,5-bis(methoxymethoxy)-6-phenylphenyl]-2-(hydroxymethyl)pentane-1,3-diol (5.0 mg, 0.012 mmol) obtained in the above, using ethanol (4 mL) and concentrated hydrochloric acid (0.1 mL).

$^1$H-NMR (270 MHz, CD$_3$OD) δ (ppm): 1.12 (t, J=7.3 Hz, 3H), 1.40-1.56 (m, 3H), 2.20-2.70 (m, 4H), 3.40-3.60 (m, 5H), 6.27 (s, 1H), 7.14-7.22 (m, 2H), 7.24-7.42 (m, 3H);

FAB-MS (m/z): 347 (M+H)$^+$.

EXAMPLE 186

3-[3-(2-Acetyl-3,5-dihydroxy-6-phenylphenyl)]-N,N-bis(2-hydroxyethyl)propanamide (Compound 186)

(Step 1)

In the same manner as in the step 1 in Example 13, methyl 3-[2-iodo-3,5-bis(methoxymethoxy)-6-phenylphenyl]propanoate (32.7 g, 84%) was obtained from methyl 3-[3,5-bis(methoxymethoxy)-2-phenylphenyl]propanoate (29.0 g, 80.5 mmol) obtained in the step 3 of Example 87, using chloroform (200 mL), iodine (21.5 g, 84.7 mmol) and [bis(trifluoroacetoxy)iodo]benzene (35.7 g, 83.0 mmol).

$^1$H-NMR (300 MHz, CDCl$_3$) δ (ppm): 2.35-2.45 (m, 2H), 2.90-2.98 (m, 2H), 3.27 (s, 3H), 3.56 (s, 3H), 3.59 (s, 3H), 4.99 (s, 2H), 5.27 (s, 2H), 6.88 (s, 1H), 7.10-7.17 (m, 2H), 7.30-7.42 (m 3H).

(Step 2)

In an argon atmosphere, methyl 3-[2-iodo-3,5-bis(methoxymethoxy)-6-phenylphenyl]propanoate (1.5 g, 3.0 mmol) obtained in the above was dissolved in toluene (50 mL), and bis(triphenylphosphine)palladium(II) dichloride (210 mg, 0.3 mmol) and tributyl(1-ethoxyvinyl)tin (1.4 mL, 4.2 mmol) were added thereto and stirred at 90° C. for 2 hours. Aqueous saturated potassium fluoride solution (50 mL) was added to the reaction solution, and stirred for 12 hours, and then filtered through Celite. The filtrate was extracted with chloroform. The organic layer was washed with aqueous saturated sodium chloride solution, then dried over sodium sulfate, and the solvent was evaporated away under reduced pressure. The resulting residue was purified through silica gel column chromatography (eluted with ethyl acetate/n-hexane=1/8) to obtain methyl 3-[2-(1-ethoxyvinyl)-3,5-bis(methoxymethoxy)-6-phenylphenyl]propanoate (870 mg, 73%).

$^1$H-NMR (270 MHz, CDCl$_3$) δ (ppm): 1.07 (t, J=7.0 Hz, 3H), 2.35-2.29 (m, 2H), 2.79-2.73 (m, 2H), 3.24 (s, 3H), 3.50 (s, 3H), 3.53 (s, 3H), 3.89 (q, J=7.0 Hz, 2H), 4.14 (d, J=1.9 Hz, 1H), 4.45 (d, J=1.9 Hz, 1H), 4.98 (s, 2H), 5.19 (s, 2H), 6.86 (s, 1H), 7.21-7.17 (m, 2H), 7.41-7.31 (m, 3H).

(Step 3)

Methyl 3-[2-(1-ethoxyvinyl)-3,5-bis(methoxymethoxy)-6-phenylphenyl]propanoate (880 mg, 2.0 mmol) obtained in the above was dissolved in methanol (40 mL), and hydrochloric acid (6.0 mol/L, 10 mL) was added thereto and stirred at room temperature for half a day. Water was added to the reaction solution, and extracted with chloroform. The organic layer was washed with aqueous saturated sodium bicarbonate solution, then dried over anhydrous sodium sulfate, and the solvent was evaporated away under reduced pressure. The resulting residue was dissolved in methanol (50 mL), and aqueous 1.0 mol/L sodium hydroxide solution (5.0 mL) was added thereto and stirred at 60° C. for 4 hours. The reaction solution was concentrated under reduced pressure to obtain 3-[2-acetyl-3,5-dihydroxy-6-phenylphenyl]propanoic acid (550 mg, 92%).

$^1$H-NMR (270 MHz, CD$_3$OD) δ (ppm): 2.35-2.29 (m, 2H), 2.68 (s, 3H), 3.05-2.96 (m, 2H), 6.47 (s, 1H), 7.28-7.25 (m, 2H), 7.53-7.46 (m, 3H);

APCI-MS (m/z): 299 (M−H)$^−$.

(Step 4)

In an argon atmosphere, 3-[2-acetyl-3,5-dihydroxy-6-phenylphenyl]propanoic acid (200 mg, 6.66 mmol) obtained in the above was dissolved in dichloromethane (10 mL), and diethanolamine (150 mg, 1.4 mmol), 1-[3-(dimethylamino)propyl]-3-ethylcarbodiimide hydrochloride (130 mg, 0.70 mmol) and 1-hydroxybenzotriazole hydrate (110 mg, 0.70 mmol) were added thereto, and stirred at room temperature for 3 hours. The reaction solution was concentrated under reduced pressure, and the resulting residue was purified through silica gel column chromatography (chloroform/methanol=9/1) to obtain Compound 186 (120 mg, 73%).

$^1$H-NMR (270 MHz, CD$_3$OD/CDCl$_3$=1/9) δ (ppm): 2.36 (dd, J=8.6, 7.6 Hz, 2H), 2.63 (s, 3H), 2.75 (dd, J=8.6, 7.6 Hz, 2H), 3.14 (dd, J=5.1, 3.4 Hz, 2H), 3.39 (t, J=5.1 Hz, 2H), 3.55 (t, J=5.1 Hz, 2H), 3.66 (dd, J=5.1, 3.4 Hz, 2H), 6.36 (s, 1H), 7.23 (d, J=6.7 Hz, 2H), 7.46-7.35 (m, 3H);

APCI-MS (m/z): 386 (M−H)$^−$.

EXAMPLE 187

3-[3-(2-Ethyl-3,5-dihydroxy-6-phenylphenyl)]-N,N-bis(2-hydroxyethyl)propanamide (Compound 187)

Compound 186 (60 mg, 0.16 mmol) obtained in Example 186 was dissolved in trifluoroacetic acid (6.3 mL, 0.82 mmol), and stirred at room temperature for 30 minutes. Then, with ice-cooling, triethylsilane (0.039 mL, 0.26 mmol) was added thereto, and with heating up to room temperature, the mixture was stirred for 4 hours. The reaction solution was poured into water, and extracted with chloroform. The organic layer was washed with aqueous saturated sodium bicarbonate solution, then dried over anhydrous sodium sulfate, and the solvent was evaporated away under reduced pressure. The resulting residue was recrystallized with methanol to obtain Compound 187 (17 mg, 30%).

$^1$H-NMR (300 MHz, CD$_3$OD) δ (ppm): 7.40-7.29 (m, 3H), 7.22-7.20 (m, 2H), 6.30 (s, 1H), 4.56 (br s, 2H), 3.59 (t, J=5.7 Hz, 2H), 3.47 (t, J=5.4 Hz, 2H), 3.38 (t, J=5.7 Hz, 2H), 3.03 (t, J=5.4 Hz, 2H), 2.69-2.62 (m, 4H), 2.36-2.31 (m, 2H), 1.12 (t, J=7.4 Hz, 3H);

ESI-MS (m/z): 374 (M+H)$^+$.

EXAMPLE 188

6-Ethyl-4-phenyl-5-[2-(pyridin-3-ylmethoxy)ethyl]
benzene-1,3-diol (Compound 188)

(Step 1)
In an argon atmosphere, 2-[2-ethyl-3,5-bis(methoxymethoxy)-6-phenylphenyl]ethanol (70 mg, 0.20 mmol) obtained in the step 1 in Example 83 was dissolved in N,N-dimethylformamide (3.0 mL), and sodium hydride (15 mg, 0.60 mmol) was added thereto and stirred at room temperature for 1 hour. 2-Pyridylmethyl bromide (150 mg, 0.60 mmol) was added to the reaction mixture, and stirred at room temperature for 36 hours. Water was added to the reaction solution, and extracted with chloroform. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=2/1) to obtain 4-ethyl-1,5-bis(methoxymethoxy)-2-phenyl-3-[2-(pyridin-3-ylmethoxy)ethyl]benzene (78 mg, 90%).
$^1$H-NMR (270 MHz, CDCl$_3$) δ (ppm): 1.16 (t, J=7.2 Hz, 3H), 2.72 (q, J=7.2 Hz, 2H), 2.85 (t, J=8.2 Hz, 2H), 3.23 (s, 3H), 3.44 (t, J=8.2 Hz, 2H), 3.52 (s, 3H), 4.40 (s, 2H), 4.93 (s, 2H), 5.22 (s, 2H), 6.85 (s, 1H), 7.20-7.14 (m, 4H), 7.38-7.28 (m, 3H), 7.61 (m, 1H), 8.50 (d, J=4.6 Hz, 1H);
APCI-MS (m/z): 438 (M+H)$^+$.

(Step 2)
4-Ethyl-1,5-bis(methoxymethoxy)-2-phenyl-3-[2-(pyridin-3-ylmethoxy)ethyl]benzene (78 mg, 0.18 mmol) obtained in the above was dissolved in methanol (10 mL), and hydrochloric acid (1 mL, 6 mol/L) was added thereto and stirred for a half day at room temperature. The reaction liquid was neutralized with aqueous 1 mol/L sodium hydroxide solution, and then extracted with chloroform. The organic layer was washed with aqueous saturated sodium chloride solution, then dried over anhydrous sodium sulfate, and the solvent was evaporated away under reduced pressure. The resulting residue was purified through preparative thin-layer column chromatography (developed with n-hexane/ethyl acetate=1/1) to obtain Compound 188 (28 mg, 41%).
$^1$H-NMR (270 MHz, CD$_3$OD) δ (ppm): 1.18 (t, J=7.5 Hz, 3H), 2.79 (q, J=7.5 Hz, 2H), 2.81 (t, J=7.71 Hz, 2H), 3.43 (t, J=7.7 Hz, 2H), 4.42 (s, 2H), 4.47 (br s, 1H), 4.87 (br s, 1H), 6.36 (s, 1H), 7.26-7.13 (m, 4H), 7.46-7.41 (m, 3H), 7.59 (m, 1H), 8.50 (d, J=4.6 Hz, 1H);
APCI-MS (m/z): 350 (M+H)$^+$.

EXAMPLE 189

5-[2-(2,3-Dihydroxypropoxy)ethyl]-6-ethyl-4-(3-methoxyphenyl)benzene-1,3-diol (Compound 189)

In the same manner as in the step 3 in Example 1, 3-{2-[(2,2-dimethyl-1,3-dioxolan-4-yl)methoxy]ethyl}-4-ethyl-1,5-bis(methoxymethoxy)-2-(3-methoxyphenyl)benzene was obtained from 2-bromo-3-{2-[(2,2-dimethyl-1,3-dioxolan-4-yl)methoxy]ethyl}-4-ethyl-1,5-bis(methoxymethoxy)benzene (180 mg, 0.39 mmol) obtained in the step 3 in Example 173, using 3-methoxyphenylboronic acid (90 mg, 0.60 mmol), bis(tri-o-tolylphosphine)palladium(II) dichloride (20 mg, 0.025 mmol), cesium carbonate (350 mg, 1.1 mmol), 1,2-dimethoxyethane (5.0 mL) and water (1.0 mL). Then, in the same manner as in the step 4 in Example 1, Compound 189 (76 mg, 53%) was obtained from the resulting compound, using methanol (3.0 mL) and 1,4-dioxane solution (2.0 mL) of 4 mol/L hydrogen chloride.
$^1$H-NMR (270 MHz, CDCl$_3$) δ (ppm): 1.06 (t, J=7.4 Hz, 3H), 2.54-2.66 (m, 4H), 3.11-3.39 (m, 6H), 3.53 (m, 1H), 3.73 (s, 3H), 6.23 (s, 1H), 6.66-6.79 (m, 2H), 6.81 (m, 1H), 7.23 (t, J=7.9 Hz, 1H);
APCI-MS (m/z): 361 (M−H)$^-$.

EXAMPLE 190

5-[2-(2,3-Dihydroxypropoxy)ethyl]-6-ethyl-4-[3-(pyridin-2-ylmethyloxy)phenyl]benzene-1,3-diol (Compound 190)

3-{2-[(2,2-Dimethyl-1,3-dioxolan-4-yl)methoxy]ethyl}-4-ethyl-2-(3-hydroxyphenyl)-1,5-bis(methoxymethoxy)benzene (45 mg, 0.095 mmol) obtained in the step 4 in Example 173 was dissolved in N,N-dimethylformamide (1 mL), and potassium carbonate (50 mg, 0.36 mmol) and 2-picolyl chloride (20 mg, 0.12 mmol) were added thereto and stirred at room temperature for 48 hours. Water was added to the reaction solution, and extracted three times with ethyl acetate. The organic layer was dried over anhydrous magnesium sulfate, and then the solvent was evaporated away under reduced pressure. Methanol (1.0 mL) and 1,4-dioxane solution (1.0 mL) of 4 mol/L hydrogen chloride were added to the resulting residue, and stirred for 1 hour. The reaction solution was neutralized with aqueous saturated sodium hydrogencarbonate solution, and then extracted twice with ethyl acetate. The organic layer was dried over anhydrous magnesium sulfate, and then the solvent was evaporated away under reduced pressure. The resulting residue was purified through silica gel column chromatography (methanol/chloroform=1/50 to 1/10) to obtain Compound 190 (15 mg, 36%).
$^1$H-NMR (270 MHz, CD$_3$OD) δ (ppm): 1.07 (t, J=7.5 Hz, 3H), 2.54-2.64 (m, 4H), 3.13-3.32 (m, 4H), 3.37 (m, 2H), 3.57 (m, 1H), 5.14 (s, 2H), 6.25 (s, 1H), 6.74-6.79 (m, 2H), 6.91 (m, 1H), 7.27 (t, J=7.8 Hz, 1H), 7.31 (m, 1H), 7.59 (d, J=7.5 Hz, 1H), 7.82 (t, J=7.8, 2.1 Hz, 1H), 8.47 (m, 1H);
APCI-MS (m/z): 438 (M−H)$^-$.

EXAMPLE 191

5-[2-(2,3-Dihydroxypropoxy)ethyl]-6-ethyl-4-[3-(pyridin-3-ylmethyloxy)phenyl]benzene-1,3-diol (Compound 191)

In the same manner as in Example 190, 3-{2-[(2,2-dimethyl-1,3-dioxolan-4-yl)methoxy]ethyl}-4-ethyl-1,5-bis(methoxymethoxy)-2-[3-(pyridin-3-ylmethyloxy)phenyl]benzene was obtained from 3-{2-[(2,2-dimethyl-1,3-yl-4-yl)methoxy]ethyl}-4-ethyl-2-(3-hydroxyphenyl)-1,5-bis(methoxymethoxy)benzene (45 mg, 0.095 mmol) obtained in the step 4 in Example 173, using 3-picolyl chloride (20 mg, 0.12 mmol), potassium carbonate (50 mg, 0.36 mmol) and N,N-dimethylformamide (1.0 mL). The resulting compound was treated with methanol (1.0 mL) and 1,4-dioxane solution (1.0 mL) of 4 mol/L hydrogen chloride to obtain Compound 191 (20 mg, 48%).
$^1$H-NMR (270 MHz, CD$_3$OD) δ (ppm): 1.07 (t, J=7.4 Hz, 3H), 2.55-2.66 (m, 4H), 3.14-3.47 (m, 6H), 3.57 (m, 1H), 5.66 (s, 2H), 6.25 (s, 1H), 6.74-6.81 (m, 2H), 6.92 (dd, J=8.1, 2.4 Hz, 1H), 7.27 (t, J=7.9 Hz, 1H), 7.40 (ddd, J=7.9, 4.9, 1.2 Hz, 1H), 7.91 (dt, J=7.9, 1.2 Hz, 1H), 8.44 (dd, J=4.9, 1.2 Hz, 1H), 8.58 (br s, 1H);
APCI-MS (m/z): 439 (M+H)$^+$.

EXAMPLE 192

5-[2-(2,3-Dihydroxypropoxy)ethyl]-6-ethyl-4-[3-(pyridin-4-ylmethyloxy)phenyl]benzene-1,3-diol (Compound 192)

In the same manner as in Example 190, 3-{2-[(2,2-dimethyl-1,3-dioxolan-4-yl)methoxy]ethyl}-4-ethyl-1,5-bis(methoxymethoxy)-2-[3-(pyridin-4-ylmethyloxy)phenyl]benzene was obtained from 3-{2-[(2,2-dimethyl-1,3-dioxolan-4-yl)methoxy]ethyl}-4-ethyl-2-(3-hydroxyphenyl)-1,5-bis(methoxymethoxy)benzene (45 mg, 0.095 mmol) obtained in the step 4 in Example 173, using 4-picolyl chloride (20 mg, 0.12 mmol), potassium carbonate (50 mg, 0.36 mmol) and N,N-dimethylformamide (1.0 mL). The resulting compound was treated with methanol (1.0 mL) and 1,4-dioxane solution (1.0 mL) of 4 mol/L hydrogen chloride to obtain Compound 192 (25 mg, 60%).

$^1$H-NMR (270 MHz, CD$_3$OD) δ (ppm): 1.07 (t, J=7.5 Hz, 3H), 2.55-2.65 (m, 4H), 3.15-3.40 (m, 6H), 3.57 (m, 1H), 5.15 (s, 2H), 6.25 (s, 1H), 6.75-6.78 (m, 2H), 6.91 (dd, J=7.9, 2.5 Hz, 1H), 7.27 (t, J=7.9 Hz, 1H), 7.48 (d, J=5.8 Hz, 2H), 8.47 (d, J=5.8 Hz, 2H);

APCI-MS (m/z): 440 (M+H)$^+$.

EXAMPLE 193

5-[2-(2,3-Dihydroxypropoxy)ethyl]-6-ethyl-4-[3-(2-methyl-1,3-thiazol-4-ylmethyloxy)phenyl]benzene-1,3-diol (Compound 193)

In the same manner as in Example 190, 3-{2-[(2,2-dimethyl-1,3-dioxolan-4-yl)methoxy]ethyl}-4-ethyl-1,5-bis(methoxymethoxy)-2-[3-(2-methyl-1,3-thiazol-4-ylmethyloxy)phenyl]benzene was obtained from 3-{2-[(2,2-dimethyl-1,3-dioxolan-4-yl)methoxy]ethyl}-4-ethyl-2-(3-hydroxyphenyl)-1,5-bis(methoxymethoxy)benzene (45 mg, 0.095 mmol) obtained in the step 4 in Example 173, using 4-(chloromethyl)-2-methyl-1,3-thiazole (25 mg, 0.14 mmol), 60% sodium hydride/mineral oil dispersion (20 mg, 0.5 mmol) and N,N-dimethylformamide (1.0 mL). The resulting compound was treated with methanol (1.0 mL) and 1,4-dioxane solution (1.0 mL) of 4 mol/L hydrogen chloride to obtain Compound 193 (30 mg, 69%).

$^1$H-NMR (270 MHz, CD$_3$OD) δ (ppm): 1.07 (t, J=7.5 Hz, 3H), 2.62 (s, 3H), 2.59-2.71 (m, 4H), 3.15-3.49 (m, 6H), 3.60 (m, 1H), 5.12 (s, 2H), 6.29 (s, 1H), 6.77-6.84 (m, 2H), 6.95 (ddd, J=7.9, 2.6, 1.0 Hz, 1H), 7.30 (t, J=7.9 Hz, 1H), 7.39 (s, 1H);

APCI-MS (m/z): 458 (M−H)$^−$.

EXAMPLE 194

5-[2-(2,3-Dihydroxypropoxy)ethyl]-6-ethyl-4-[3-(2-hydroxyethoxy)phenyl]benzene-1,3-diol (Compound 194)

In the same manner as in Example 190, 3-{2-[(2,2-dimethyl-1,3-dioxolan-4-yl)methoxy]ethyl}-4-ethyl-1,5-bis(methoxymethoxy)-2-{3-[2-(tetrahydropyran-2-yloxy)ethoxy]phenyl}benzene was obtained from 3-{2-[(2,2-dimethyl-1,3-dioxolan-4-yl)methoxy]ethyl}-4-ethyl-2-(3-hydroxyphenyl)-1,5-bis(methoxymethoxy)benzene (50 mg, 0.11 mmol) obtained in the step 4 in Example 173, using 2-(2-bromoethoxy)tetrahydropyran (0.03 mL, 0.20 mmol), 60% sodium hydride/mineral oil dispersion (20 mg, 0.5 mmol) and N,N-dimethylformamide (1.0 mL). The resulting compound was treated with methanol (1.0 mL) and 1,4-dioxane solution (1.0 mL) of 4 mol/L hydrogen chloride to obtain Compound 194 (7 mg, 16%).

$^1$H-NMR (270 MHz, CD$_3$OD) δ (ppm): 1.03 (t, J=7.4 Hz, 3H), 2.49-2.63 (m, 4H), 3.07-3.39 (m, 6H), 3.51 (m, 1H), 3.77 (t, J=4.6 Hz, 2H), 3.97 (t, J=4.6 Hz, 2H), 6.19 (s, 1H), 6.64-6.68 (m, 2H), 6.82 (ddd, J=7.8, 2.7, 1.0 Hz, 1H), 7.20 (t, J=7.8 Hz, 1H);

APCI-MS (m/z): 391 (M−H)$^−$.

EXAMPLE 195

5-[2-(2,3-Dihydroxypropoxy)ethyl]-6-ethyl-4-[3-(2-morpholinoethoxy)phenyl]benzene-1,3-diol (Compound 195)

3-{2-[(2,2-Dimethyl-1,3-dioxolan-4-yl)methoxy]ethyl}-4-ethyl-2-(3-hydroxyphenyl)-1,5-bis(methoxymethoxy)benzene (50 mg, 0.11 mmol) obtained in the step 4 in Example 173 was dissolved in toluene (3.0 mL), and N-(hydroxyethyl)morpholine (0.01 mL, 0.21 mmol), triphenylphosphine (30 mg, 0.12 mmol) and toluene solution of 40 w/v % diethyl azodicarboxylate were added thereto in order, and stirred at room temperature for 112 hours. The reaction solution was concentrated under reduced pressure, and the resulting residue was purified through silica gel column chromatography (ethyl acetate/n-hexane=1/4 to 1/1) to obtain 3-{2-[(2,2-dimethyl-1,3-dioxolan-4-yl)methoxy]ethyl}-4-ethyl-2-[3-(2-morpholinoethoxy)phenyl]-1,5-bis(methoxymethoxy)benzene. The resulting compound was dissolved in methanol (1.0 mL), and 1,4-dioxane solution (1.0 mL) of 4 mol/L hydrogen chloride was added thereto and stirred for 1 hour. The reaction solution was neutralized with aqueous saturated sodium hydrogencarbonate solution, and then extracted twice with ethyl acetate. The organic layer was dried over anhydrous magnesium sulfate, and then the solvent was evaporated away under reduced pressure. The resulting residue was purified through silica gel column chromatography (methanol/chloroform=1/50 to 1/10) to obtain Compound 195 (16 mg, 36%).

$^1$H-NMR (270 MHz, CD$_3$OD) δ (ppm): 1.11 (t, J=7.5 Hz, 3H), 2.59-2.71 (m, 8H), 2.81 (t, J=5.3 Hz, 2H), 3.19-3.45 (m, 6H), 3.60 (m, 1H), 3.70 (t, J=4.7 Hz, 4H), 4.16 (t, J=5.3 Hz, 2H), 6.29 (s, 1H), 6.75-6.78 (m, 2H), 6.90 (m, 1H), 7.29 (t, J=7.9 Hz, 1H);

ESI-MS (m/z): 462 (M+H)$^+$.

EXAMPLE 196

5-[2-(2,3-Dihydroxypropoxy)ethyl]-6-ethyl-4-{3-[2-(2-oxopyrrolidin-1-yl)ethoxy]phenyl}benzene-1,3-diol (Compound 196)

In the same manner as in Example 195, 3-{2-[(2,2-dimethyl-1,3-dioxolan-4-yl)methoxy]ethyl}-4-ethyl-1,5-bis(methoxymethoxy)-2-{3-[2-(2-oxopyrrolidin-1-yl)ethoxy]phenyl}benzene was obtained from 3-{2-[(2,2-dimethyl-1,3-dioxolan-4-yl)methoxy]ethyl}-4-ethyl-2-(3-hydroxyphenyl)-1,5-bis(methoxymethoxy)benzene (50 mg, 0.11 mmol) obtained in the step 4 in Example 173, using N-(hydroxyethyl)pyrrolidone (0.02 mL, 0.18 mmol), triphenylphosphine (30 mg, 0.12 mmol), toluene solution of 40 w/v % diethyl azodicarboxylate and toluene (3.0 mL). The resulting compound was treated with methanol (1.0 mL) and 1,4-dioxane solution (1.0 mL) of 4 mol/L hydrogen chloride to obtain Compound 196 (33 mg, 65%).

¹H-NMR (270 MHz, CD₃OD) δ (ppm): 1.12 (t, J=7.5 Hz, 3H), 2.02 (m, 2H), 2.37 (t, J=8.1 Hz, 2H), 2.61-2.71 (m, 4H), 3.19-3.44 (m, 6H), 3.56-3.67 (m, 5H), 4.14 (t, J=5.3 Hz, 2H), 6.29 (s, 1H), 6.73-6.79 (m, 2H), 6.87 (ddd, J=7.9, 2.5, 1.0 Hz, 1H), 7.28 (t. J=7.9 Hz, 1H);

ESI-MS (m/z): 460 (M+H)⁺.

EXAMPLE 197

4-(3-Aminophenyl)-5-[2-(2,3-dihydroxypropoxy)ethyl]-6-ethylbenzene-1,3-diol (Compound 197)

(Step 1)

In the same manner as in the step 3 in Example 1, 3-(2-allyloxyethyl)-2-(3-aminophenyl)-4-ethyl-1,5-bis(methoxymethoxy)benzene (960 mg, 88%) was obtained from 3-(2-allyloxyethyl)-2-bromo-4-ethyl-1,5-bis(methoxymethoxy)benzene (1.1 g, 2.3 mmol) obtained in the step 2 in Example 173, using 3-aminophenylboronic acid (430 mg, 2.8 mmol), bis(tri-o-tolylphosphine)palladium(II) dichloride (150 mg, 0.19 mmol), cesium carbonate (2.1 g, 6.5 mmol), 1,2-dimethoxyethane (20 mL) and water (1.0 mL).

¹H-NMR (270 MHz, CDCl₃) δ (ppm): 1.12 (t, J=7.5 Hz, 3H), 1.35 (s, 3H), 1.40 (s, 3H), 2.65-2.80 (m, 4H), 3.15 (m, 1H), 3.27 (s, 3H), 3.29 (m, 1H), 3.39 (m, 2H), 3.51 (s, 3H), 3.56 (m, 2H), 3.96 (m, 1H), 4.98 (s, 2H), 5.20 (s, 2H), 6.65-6.53 (m, 3H), 6.84 (s, 1H), 7.15 (m, 1H).

(Step 2)

In the same manner as in the step 4 in Example 1, Compound 197 (32 mg, 71%) was obtained from 3-(2-allyloxyethyl)-2-(3-aminophenyl)-4-ethyl-1,5-bis(methoxymethoxy)benzene (60 mg, 0.13 mmol) obtained in the above, using methanol (2.0 mL) and 1,4-dioxane solution (2.0 mL) of 4 mol/L hydrogen chloride.

¹H-NMR (270 MHz, CD₃OD) δ (ppm): 1.07 (t, J=7.5 Hz, 3H), 2.58 (q, J=7.5 Hz, 2H), 2.67 (t, J=8.1 Hz, 2H), 3.17-3.42 (m, 6H), 3.57 (m, 1H), 6.23 (s, 1H), 7.10 (t, J=7.5 Hz, 1H), 6.47-6.54 (m, 2H), 6.65 (ddd, J=7.5, 2.5, 1.0 Hz, 1H);

ESI-MS (m/z): 346 (M–H)⁻.

EXAMPLE 198

2-[3-(2-Ethyl-3,5-dihydroxy-6-phenylphenyl)]-N,N-bis(2-hydroxyethyl)acetamide (Compound 198)

(Step 1)

Methyl 2-ethyl-3,5-bis(methoxymethoxy)-6-phenylphenylacetate (650 mg, 1.7 mmol) obtained in the step 2 in Example 52 was dissolved in methanol (100 mL), and aqueous 10 mol/L sodium hydroxide solution (1.0 mL) was added thereto and stirred at 60° C. for 5 hours. The reaction solution was neutralized with 1.0 mol/L hydrochloric acid, and then extracted with chloroform. The organic layer was washed with aqueous saturated sodium chloride solution, then dried over anhydrous sodium sulfate, and the solvent was evaporated away under reduced pressure. The resulting residue was purified through silica gel column chromatography (n-hexane/ethyl acetate=4/1) to obtain 2-ethyl-3,5-bis(methoxymethoxy)-6-phenylphenylacetic acid (540 mg, 87%).

APCI-MS (m/z): 361 (M+H)⁺.

(Step 2)

In an argon atmosphere, 2-ethyl-3,5-bis(methoxymethoxy)-6-phenylphenylacetic acid (86 mg, 0.27 mmol) obtained in the above was dissolved in dichloromethane (10 mL), and diethanolamine (75 mg, 0.70 mmol), 1-[3-(dimethylamino)propyl]-3-ethylcarbodiimide hydrochloride (63 mg, 0.33 mmol) and 1-hydroxybenzotriazole hydrate (50 mg, 0.33 mmol) were added thereto and stirred at room temperature for 3 hours. The reaction liquid was concentrated under reduced pressure, and purified through preparative thin-layer column chromatography (chloroform/methanol=15/1) to obtain 2-[2-ethyl-3,5-bis(methoxymethoxy)-6-phenylphenyl]-N,N-bis(2-hydroxyethyl)acetamide (56 mg, 51%).

APCI-MS (m/z): 448 (M+H)⁺.

(Step 3)

2-[2-Ethyl-3,5-bis(methoxymethoxy)-6-phenylphenyl]-N,N-bis(2-hydroxyethyl)acetamide (78 mg, 0.18 mmol) obtained in the above was dissolved in methanol (3 mL), and 4 mol/L hydrogen chloride (1 ml) was added thereto and stirred at room temperature for 2 hours. The reaction liquid was neutralized with aqueous 1.0 mol/L sodium hydroxide solution, and extracted with chloroform. The organic layer was washed with aqueous saturated sodium chloride solution, and the solvent was evaporated away under reduced pressure. The resulting residue was purified through preparative thin-layer column chromatography (n-hexane/ethyl acetate=1/1) to obtain Compound 198 (22 mg, 13%).

¹H-NMR (270 MHz, CD₃OD) δ (ppm): 1.07 (t, J=7.4 Hz, 3H), 2.53 (q, J=7.4 Hz, 2H), 3.41-3.21 (m, 8H), 3.62 (t, J=5.9 Hz, 2H), 6.35 (s, 1H), 7.16-7.13 (m, 2H), 7.37-7.27 (m, 3H);

APCI-MS (m/z): 358 (M–H)⁻.

EXAMPLE 199

6-Ethyl-5-[2,5-dihydroxy-2-(3-hydroxypropyl)pentyl]-4-phenylbenzene-1,3-diol (Compound 199)

(Step 1)

Methyl 2-ethyl-3,5-bis(methoxymethoxy)-6-phenylphenylacetate (19 mg, 0.050 mmol) obtained in the step 2 in Example 52 was dissolved in tetrahydrofuran (10 mL), and allylmagnesium bromide (0.20 mL, 1.0 mol/L) was added thereto and stirred at room temperature for 1 hour. The reaction liquid was neutralized with hydrochloric acid (1.0 mol/L), and then extracted with chloroform. The organic layer was washed with aqueous saturated sodium chloride solution, and dried over anhydrous sodium sulfate, and the solvent was evaporated away under reduced pressure. The resulting residue was purified through preparative thin-layer column chromatography (n-hexane/ethyl acetate=4/1) to obtain 4-[2-ethyl-3,5-bis(methoxymethoxy)-6-phenylphenyl]hept-1,6-dien-4-ol (32 mg, quantitative).

¹H-NMR (270 MHz, CDCl₃) δ (ppm): 1.09 (t, J=7.4 Hz, 3H), 2.01-1.97 (m, 4H), 2.84 (q, J=7.4 Hz, 2H), 2.97 (br s, 2H), 3.21 (s, 3H), 3.53 (s, 3H), 4.98-4.89 (s, 6H), 5.24 (s, 2H), 5.60-5.40 (m, 2H), 6.90 (s, 1H), 7.41-7.20 (m, 5H);

APCI-MS (m/z): 427 (M+H)⁺.

(Step 2)

In an argon atmosphere, 4-[2-ethyl-3,5-bis(methoxymethoxy)-6-phenylphenyl]hept-1,6-dien-4-ol (32 mg, 0.75 mmol) obtained in the above was dissolved in tetrahydrofuran (10 mL), and borane-tetrahydrofuran complex (0.20 mL, 1.0 mol/L) was added thereto at −78° C., then gently heated up to room temperature, and stirred for 6 hours. Aqueous saturated sodium bicarbonate solution (1.2 mL) and aqueous hydrogen peroxide (1.2 mL) were added to the reaction mixture, and stirred at the same temperature for 1 hour. Water was added to the reaction liquid, and extracted with ethyl acetate. The organic layer was washed with aqueous saturated sodium chloride solution, then dried over sodium sulfate, and the solvent was evaporated away under reduced pressure. The resulting residue was purified through preparative thin-layer column chromatography (n-hexane/ethyl acetate=1/1) to obtain 4-[2-ethyl-3,5-bis(methoxymethoxy)-6-phenylphenyl]heptane-1,4,7-triol (13 mg, 37%).

$^1$H-NMR (270 MHz, CDCl$_3$) δ (ppm): 1.10 (t, J=7.4 Hz, 3H), 1.40-1.20 (m, 4H), 1.80-1.65 (m, 4H), 2.91 (q, J=7.4 Hz, 2H), 3.10-2.95 (m, 2H), 3.59-3.48 (m, 9H), 4.93 (s, 2H), 5.24 (s, 2H), 6.91 (s, 1H), 7.32-7.26 (m, 2H), 7.42-7.36 (m, 3H);

APCI-MS (m/z): 463 (M+H)$^+$.

(Step 3)

4-[2-Ethyl-3,5-bis(methoxymethoxy)-6-phenylphenyl]heptane-1,4,7-triol (50 mg, 0.11 mmol) obtained in the above was dissolved in methanol (5.0 mL), and 1,4-dioxane solution (1.0 mL) of 4 mol/L hydrogen chloride was added thereto and stirred at room temperature for 2 hours. The reaction liquid was neutralized with aqueous 1 mol/L sodium hydroxide solution, and extracted with chloroform. The organic layer was washed with aqueous saturated sodium chloride solution, then dried over anhydrous sodium sulfate, and the solvent was evaporated away under reduced pressure. The resulting residue was purified through preparative thin-layer column chromatography (chloroform/methanol=9/1) to obtain Compound 199 (21 mg, 55%).

$^1$H-NMR (270 MHz, CD$_3$OD) δ (ppm): 1.06 (t, J=7.4 Hz, 3H), 1.50-1.10 (m, 8H), 2.92-2.81 (m, 4H), 3.35-3.31 (m, 4H), 6.34 (s, 1H), 7.24-7.15 (m, 3H), 7.38-7.32 (m, 2H);

APCI-MS (m/z): 375 (M+H)$^+$.

EXAMPLE 200

Methyl 5-[(2-ethyl-3,5-dihydroxy-6-phenylphenyl)methyl]-1,3-oxazole-4-carboxylate (Compound 200)

(Step 1)

2-Ethyl-3,5-bis(methoxymethoxy)-6-phenylphenylacetic acid (70 mg, 0.2 mmol) obtained in the step 1 in Example 198 was dissolved in N,N-dimethylacetamide (10 mL), and potassium carbonate (55 mg, 0.4 mmol) and methyl isocyanoacetate (79 mL, 0.4 mmol) were added thereto and stirred at room temperature for 5 minutes. Diphenylphosphorylamide (0.040 mL, 0.22 mmol) was added to the reaction mixture, and stirred at 0° C. for 2 hours. With heating up to room temperature, the reaction mixture was further stirred for 12 hours, and then neutralized with 1.0 mol/L hydrochloric acid, and extracted with chloroform. The organic layer was washed with aqueous saturated sodium chloride solution, then dried over anhydrous sodium sulfate, and the solvent was evaporated away under reduced pressure. The resulting residue was purified through preparative thin-layer column chromatography (n-hexane/ethyl acetate=1/1) to obtain methyl 5-{[2-ethyl-3,5-bis(methoxymethoxy)-6-phenylphenyl]methyl}-1,3-oxazole-4-carboxylate (38 mg, 48%).

APCI-MS (m/z): 442 (M+H)$^+$.

(Step 2)

Methyl 5-{[2-ethyl-3,5-bis(methoxymethoxy)-6-phenylphenyl]methyl}-1,3-oxazole-4-carboxylate (43 mg, 0.10 mmol) obtained in the above was dissolved in methanol (5.0 in), and 1,4-dioxane solution (1.0 mL) of 4.0 mol/L hydrochloric acid was added thereto and stirred at 40° C. for 2 hours. The reaction liquid was neutralized with aqueous 1.0 mol/L sodium hydroxide solution, and extracted with chloroform. The organic layer was washed with aqueous saturated sodium chloride solution, then dried over anhydrous sodium sulfate, and the solvent was evaporated away under reduced pressure. The resulting residue was purified preparative through thin-layer column chromatography (n-hexane/ethyl acetate=1/1) to obtain Compound 200 (11 mg, 31%).

$^1$H-NMR (270 MHz, CD$_3$OD) δ (ppm): 1.04 (t, J=7.5 Hz, 3H), 2.64 (q, J=7.5 Hz, 2H), 3.83 (s, 3H), 4.24 (s, 2H), 4.56 (s, 1H), 5.10 (s, 1H), 6.45 (s, 1H), 7.18-7.14 (m, 2H), 7.44-7.33 (m, 3H), 7.67 (s, 1H);

APCI-MS (m/z): 353 (M−H)$^-$.

EXAMPLE 201

Compound 201

(Step 1)

In an argon atmosphere, 2-[3,5-bis(benzyloxy)-2-ethyl-6-phenylphenyl]ethanol (44 mg, 0.10 mmol) obtained in the step 4 in Example 179 was dissolved in dichloromethane (3.0 mL), and tri-O-benzyl-D-glucal (0.62 mL, 0.15 mol/L) and triphenylphosphonium bromide (10 mg, 0.03 mmol) were added thereto and stirred at room temperature for 12 hours. Water was added to the reaction liquid, and extracted with a mixed solvent of chloroform and methanol (9/1). The organic layer was washed with aqueous saturated sodium chloride solution, and dried over anhydrous sodium sulfate, and the solvent was evaporated away under reduced pressure. The resulting residue was purified through preparative thin-layer column chromatography (n-hexane/ethyl acetate=1/1) to obtain a glycoside (42 mg, 49%).

FAB-MS (m/z): 854 (M+H)$^+$.

(Step 2)

The glycoside (42 mg, 0.049 mmol) obtained in the above was dissolved in ethyl acetate (20 mL), and in a hydrogen atmosphere, 10% palladium-carbon (42 mg) was added thereto and stirred at room temperature for 3 days. The reaction mixture was filtered through Celite, and the filtrate was concentrated under reduced pressure. The resulting residue was purified through preparative thin-layer column chromatography (chloroform/methanol=9/1) to obtain Compound 201 (21 mg, 100%).

$^1$H-NMR (CD$_3$OD, 270 MHz) δ (ppm): 1.17 (t, J=7.4 Hz, 3H), 1.49 (td, J=12.9, 3.9 Hz, 1H), 1.92 (dd, J=12.9, 3.9 Hz, 1H), 2.69-2.60 (m, 4H), 3.31-3.22 (m, 3H), 3.50 (m, 1H), 3.72-3.67 (m, 3H), 4.65 (d, J=2.6 Hz, 1H), 6.29 (s, 1H), 7.26-7.15 (m, 2H), 7.40-7.29 (m, 3H);

APCI-MS (m/z): 405 (M+H)$^+$.

EXAMPLE 202

6-Ethyl-5-[2-(2,3-dihydroxypropoxy)ethyl]-4-{3-[N-(methylsulfonyl)amino]phenyl}benzene-1,3-diol (Compound 202)

3-(2-Allyloxyethyl)-2-(3-aminophenyl)-4-ethyl-1,5-bis(methoxymethoxy)benzene (50 mg, 0.11 mmol) obtained in the step 1 in Example 197 was dissolved in dichloromethane (2.0 mL), and triethylamine (0.04 mL, 0.29 mmol) and mesyl chloride (0.02 mL, 0.26 mmol) were added thereto and stirred at room temperature for 6 hours. Water was added to the reaction solution, and extracted with chloroform. The organic layer was dried over anhydrous magnesium sulfate, and the solvent was evaporated away under reduced pressure. The resulting residue was dissolved in methanol (1.0 mL), and 1,4-dioxane solution (1.0 mL) of 4 mol/L hydrogen chloride was added thereto and stirred for 1 hour. The reaction solution was neutralized with aqueous saturated sodium hydrogencarbonate solution, and extracted twice with ethyl acetate. The organic layer was dried over anhydrous magnesium sulfate, and the solvent was evaporated away under reduced pressure. The resulting residue was purified through silica gel column chromatography (methanol/chloroform=1/50 to 1/10) to obtain Compound 202 (21 mg, 45%).

$^1$H-NMR (270 MHz, CD$_3$OD) δ (ppm): 1.12 (t, J=7.5 Hz, 3H), 2.60-2.76 (m, 4H), 3.42 (s, 3H), 3.15-3.49 (m, 6H), 3.59 (m, 1H), 6.32 (s, 1H), 7.25 (m, 1H), 7.32-7.39 (m, 2H), 7.50 (t, J=7.7 Hz, 1H);

ESI-MS (m/z): 424 (M−H)$^−$.

EXAMPLE 203

5-[2-(2,3-Dihydroxypropoxy)ethyl]-6-ethyl-4-{3-[N-(4-tolylsulfonyl)amino]phenyl}benzene-1,3-diol (Compound 203)

In the same manner as in Example 202, 3-(2-allyloxyethyl)-4-ethyl-1,5-bis(methoxymethoxy)-2-{3-[N-(4-tolylsulfonyl)amino]phenyl}benzene was obtained from 3-(2-allyloxyethyl)-2-(3-aminophenyl)-4-ethyl-1,5-bis(methoxymethoxy)benzene (50 mg, 0.11 mmol) obtained in the step 1 in Example 197, using tosyl chloride (30 mg, 0.16 mmol), triethylamine (0.04 mL, 0.29 mmol) and dichloromethane (2.0 mL). Then, the resulting compound was treated with methanol (1.0 mL) and 1,4-dioxane solution (1.0 mL) of 4 mol/L hydrogen chloride to obtain compound 203 (18 mg, 32%).

$^1$H-NMR (270 MHz, CD$_3$OD) δ (ppm): 1.10 (t, J=7.5 Hz, 3H), 2.37 (s, 3H), 2.50-2.67 (m, 4H), 3.17-3.29 (m, 4H), 3.40-3.46 (m, 2H), 3.62 (m, 1H), 6.27 (s, 1H), 6.87-6.99 (m, 2H), 7.21 (t, J=8.3 Hz, 1H), 7.28 (d, J=3.3 Hz, 2H), 7.62 (d, J=8.3 Hz, 2H);

ESI-MS (m/z): 500 (M−H)$^−$.

EXAMPLE 204

4-[3-(N-acetylamino)phenyl]-5-[2-(2,3-dihydroxypropoxy)ethyl]-6-ethylbenzene-1,3-diol (Compound 204)

In the same manner as in Example 202, 2-[3-(N-acetylamino)phenyl]-3-(2-allyloxyethyl)-4-ethyl-1,5-bis(methoxymethoxy)benzene was obtained from 3-(2-allyloxyethyl)-2-(3-aminophenyl)-4-ethyl-1,5-bis(methoxymethoxy)benzene (70 mg, 0.15 mmol) obtained in the step 1 in Example 197, using acetyl chloride (0.02 mL, 0.28 mmol), triethylamine (0.04 mL, 0.29 mmol) and dichloromethane (2.0 mL). Then, the resulting compound was treated with methanol (1.0 mL) and 1,4-dioxane solution (1.0 mL) of 4 mol/L hydrogen chloride to obtain compound 204 (25 mg, 47%).

$^1$H-NMR (270 MHz, CD$_3$OD) δ (ppm): 1.12 (s, 3H), 2.11 (s, 3H), 2.62-2.72 (m, 4H), 3.19-3.48 (m, 6H), 3.60 (m, 1H), 6.29 (s, 1H), 6.92 (dt, J=7.8, 2.7 Hz, 1H), 7.29-7.36 (m, 2H), 7.51 (ddd, J=7.8, 2.7, 1.0 Hz, 1H);

ESI-MS (m/z): 390 (M−H)$^−$.

EXAMPLE 205

4-[3-(N-benzoylamino)phenyl]-5-[2-(2,3-dihydroxypropoxy)ethyl]-6-ethylbenzene-1,3-diol (Compound 205)

In the same manner as in Example 202, 3-(2-allyloxyethyl)-2-[3-(N-benzoylamino)phenyl]-4-ethyl-1,5-bis(methoxymethoxy)benzene was obtained from 3-(2-allyloxyethyl)-2-(3-aminophenyl)-4-ethyl-1,5-bis(methoxymethoxy)benzene (70 mg, 0.15 mmol) obtained in the step 1 in Example 197, using benzoyl chloride (0.02 mL, 0.17 mmol), triethylamine (0.04 mL, 0.29 mmol) and dichloromethane (2.0 mL). Then, the resulting compound was treated with methanol (1.0 mL) and 1,4-dioxane solution (1.0 mL) of 4 mol/L hydrogen chloride to obtain compound 205 (43 mg, 64%).

$^1$H-NMR (270 MHz, CD$_3$OD) δ (ppm): 1.16 (t, J=7.6 Hz, 3H), 2.66-2.78 (m, 4H), 3.24-3.51 (m, 6H), 3.65 (s, 1H), 6.34 (s, 1H), 7.01 (dt, J=7.6, 1.3 Hz, 1H), 7.41-7.58 (m, 5H), 7.70 (m, 1H), 7.92-7.96 (m, 2H);

ESI-MS (m/z): 452 (M+H)$^+$.

EXAMPLE 206

5-[2-(2,3-Dihydroxypropoxy)ethyl]-6-ethyl-4-[3-(3-ethylureido)phenyl]benzene-1,3-diol (Compound 206)

3-(2-Allyloxyethyl)-2-(3-aminophenyl)-4-ethyl-1,5-bis(methoxymethoxy)benzene (60 mg, 0.13 mmol) obtained in the step 1 in Example 197 was dissolved in toluene (2 mL), and ethyl isocyanate (0.03 mL, 0.38 mmol) was added thereto and stirred for 1 hour. The reaction solution was concentrated under reduced pressure, and methanol (1.0 mL) and 1,4-dioxane solution (1.0 mL) of 4 mol/L hydrogen chloride were added to the resulting residue and stirred at room temperature for 1 hour. The reaction solution was neutralized with aqueous saturated sodium hydrogencarbonate solution, and extracted twice with ethyl acetate. The organic layer was dried over anhydrous magnesium sulfate, and the solvent was evaporated away under reduced pressure. The resulting residue was purified through silica gel column chromatography (methanol/chloroform=1/50 to 1/10) to obtain Compound 206 (31 mg, 57%).

$^1$H-NMR (270 MHz, CD$_3$OD) δ (ppm): 1.17-1.28 (m, 6H), 2.67-2.81 (m, 4H), 3.25-3.58 (m, 6H), 3.69 (s, 3H), 6.37 (s, 1H), 6.90 (dt, J=7.1, 2.9 Hz, 1H), 7.25 (t, J=2.9 Hz, 1H), 7.33-7.44 (m, 2H);

ESI-MS (m/z): 419 (M−H)$^−$.

EXAMPLE 207

5-[2-(2,3-Dihydroxypropoxy)ethyl]-6-ethyl-4-{3-[2-hydroxy-1-(hydroxymethyl)-1-methylethylcarbonylamino]phenyl}benzene-1,3-diol (Compound 207)

3-(2-Allyloxyethyl)-2-(3-aminophenyl)-4-ethyl-1,5-bis(methoxymethoxy)benzene (60 mg, 0.13 mmol) obtained in the step 1 in Example 197 was dissolved in chloroform (2.0 mL), and 1-[3-(dimethylamino)propyl]-3-ethylcarbodiimide hydrochloride (30 mg, 0.18 mmol), 1-hydroxybenzotriazole hydrate (25 mg, 0.16 mmol) and 2,2-bis(hydroxymethyl)propanoic acid (20 mg, 0.15 mmol) were added thereto in order, and stirred for 6 hours. Ethyl acetate and 1 mol/L hydrochloric acid were added to the reaction solution for liquid-liquid separation. The organic layer was washed with aqueous saturated sodium hydrogencarbonate solution and aqueous saturated sodium chloride solution in order, and then dried over anhydrous magnesium sulfate, and the solvent was evaporated away under reduced pressure. The resulting residue was dissolved in methanol (1.0 mL), and 1,4-dioxane solution (1.0 mL) of 4 mol/L hydrogen chloride was added thereto and stirred at room temperature for 1 hour. The organic layer was dried over anhydrous magnesium sulfate, and the solvent was evaporated away under reduced pressure. The resulting residue was purified through silica gel column chromatography (methanol/chloroform=1/50 to 1/10) to obtain Compound 207 (12 mg, 20%).

$^1$H-NMR (270 MHz, CD$_3$OD) δ (ppm): 1.11 (t, J=7.5 Hz, 3H), 1.19 (s, 3H), 2.59-2.72 (m, 2H), 3.15-3.47 (m, 6H), 3.59 (m, 1H), 3.75 (d, J=11.1 Hz, 2H), 3.76 (d, J=11.1 Hz, 2H), 6.29 (s, 1H), 6.93 (m, 1H), 7.31-7.38 (m, 2H), 7.47 (m, 1H);

ESI-MS (m/z): 464 (M+H)$^+$.

EXAMPLE 208

6-Ethyl-5-{[4-(hydroxymethyl)-1,3-oxazol-5-yl]methyl}-4-phenylbenzene-1,3-diol (Compound 208)

(Step 1)

Methyl 5-{[2-ethyl-3,5-bis(methoxymethoxy)-6-phenylphenyl]methyl}-1,3-oxazole-4-carboxylate (68 mg, 0.15 mmol) obtained in the step 1 in Example 200 was dissolved in tetrahydrofuran (5.0 mL), and with ice-cooling, lithium aluminium hydride (5.7 mg, 0.15 mol) was added thereto and stirred at the same temperature for 30 minutes. Sodium sulfate 10-hydrate (50 mg, 0.15 mol) was gradually added to the reaction solution, and stirred at room temperature for 30 minutes, and then filtered through Celite. The filtrate was concentrated under reduced pressure to obtain (5-{[2-ethyl-3,5-bis(methoxymethoxy)-6-phenylphenyl]methyl}-1,3-oxazol-4-yl)methanol (52 mg).

$^1$H-NMR (270 MHz, CDCl$_3$) δ (ppm): 1.09 (t, J=7.4 Hz, 3H), 2.74 (q, J=7.4 Hz, 2H), 3.23 (s, 3H), 3.53 (s, 3H), 3.87 (br s, 2H), 3.99 (br s, 2H), 4.95 (br s, 2H), 5.25 (br s, 2H), 6.94 (br s, 1H), 7.09-7.06 (m, 2H), 7.35-7.30 (m, 3H), 7.63 (s, 1H);

ESI-MS (m/z): 414 (M+H)$^+$.

(Step 2)

(5-{[2-Ethyl-3,5-bis(methoxymethoxy)-6-phenylphenyl]methyl}-1,3-oxazol-4-yl)methanol (52 mg) obtained in the above was dissolved in methanol (4.0 mL), and 1,4-dioxane solution (1.0 mL) of 4.0 mol/L hydrochloric acid was added thereto and stirred at room temperature for 3 hours. The reaction liquid was neutralized with aqueous 1 mol/L sodium hydroxide solution, and then extracted with chloroform. The organic layer was washed with aqueous saturated sodium chloride solution, then dried over anhydrous sodium sulfate, and the solvent was evaporated away under reduced pressure. The resulting residue was purified through preparative thin-layer column chromatography (chloroform/methanol=9/1) to obtain Compound 208 (14 mg, 29%).

$^1$H-NMR (270 MHz, CD$_3$OD) δ (ppm): 1.02 (t, J=7.4 Hz, 3H), 2.65 (q, J=7.4 Hz, 2H), 3.84 (br s, 2H); 3.90 (br s, 2H), 6.37 (br s, 1H), 7.08-7.04 (m, 2H), 7.34-7.27 (m, 3H), 7.88 (s, 1H);

ESI-MS (m/z): 326 (M+H)$^+$.

EXAMPLE 209

5-[2-(2-Ethyl-3,5-dihydroxy-6-phenylphenyl)ethyl]-1,3-oxazole-4-carboxylic acid (Compound 209)

(Step 1)

3-[2-Ethyl-3,5-bis(methoxymethoxy)-6-phenylphenyl]propanoic acid (310 mg, 0.83 mmol) obtained in the step 3 in Example 212 was dissolved in N,N-dimethylacetamide (3.0 mL), and potassium carbonate (230 mg 1.7 mmol) and methyl isocyanoacetate (0.33 mL, 3.3 mmol) were added thereto and stirred at room temperature for 5 minutes. Diphenylphosphorylazide (0.17 mL, 0.91 mmol) was added to the reaction mixture, and stirred at 0° C. for 2 hours, and then with heating up to room temperature, further stirred for 12 hours. The reaction solution was neutralized with hydrochloric acid (1.0 mol/L), and then extracted with ethyl acetate. The organic layer was washed with aqueous saturated sodium chloride solution, and dried over anhydrous sodium sulfate, and the solvent was evaporated away under reduced pressure. The resulting residue was purified through silica gel column chromatography (n-hexane/ethyl acetate=4/1) to obtain methyl 5-{2-[2-ethyl-3,5-bis(methoxymethoxy)-6-phenylphenyl]ethyl}-1,3-oxazole-4-carboxylate (270 mg, 72%).

ESI-MS (m/z): 456 (M+H)$^+$.

(Step 2)

Methyl 5-{2-[2-ethyl-3,5-bis(methoxymethoxy)-6-phenylphenyl]ethyl}-1,3-oxazole-4-carboxylate (89 mg, 0.20 mmol) obtained in the above was dissolved in methanol (5.0 mL), and 1,4-dioxane solution (1.0 mL) of 4.0 mol/L hydrochloric acid was added thereto and stirred at 40° C. for 4 hours. The reaction liquid was neutralized with aqueous 1 mol/L sodium hydroxide solution, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer column chromatography (n-hexane/ethyl acetate=1/1) to obtain Compound 209 (50 mg, 69%).

$^1$H-NMR (270 MHz, CD$_3$OD) δ (ppm): 1.22 (t, J=7.4 Hz, 3H), 2.80-2.65 (m, 4H), 3.08-3.02 (m, 2H), 3.84 (s, 3H), 4.56 (br s, 1H), 5.09 (br s, 1H), 6.40 (s, 1H), 7.26-7.24 (m, 2H), 7.53-7.39 (m, 3H), 7.63 (s, 1H);

ESI-MS (m/z): 368 (M+H)$^+$.

EXAMPLE 210

6-Ethyl-5-[2-(4-hydroxymethyl-1,3-oxazol-5-yl)ethyl]-4-phenylbenzene-1,3-diol (Compound 210)

(Step 1)

Methyl 5-{2-[2-ethyl-3,5-bis(methoxymethoxy)-6-phenylphenyl]ethyl}-1,3-oxazole-4-carboxylate (180 mg, 0.40 mmol) obtained in the step 1 in Example 209 was dissolved in tetrahydrofuran (10 mL), and with cooling with ice, lithium aluminium hydride (15 mg, 0.40 mmol) was added thereto and stirred at the same temperature for 30 minutes. Sodium sulfate 10-hydrate (130 mg, 0.40 mmol) was gradually added to the reaction solution, then stirred at room temperature for 30 minutes, and filtered through Celite. The filtrate was concentrated under reduced pressure to obtain (5-{2-[2-ethyl-3,5-bis(methoxymethoxy)-6-phenylphenyl]ethyl}-1,3-oxazol-4-yl)methanol (200 mg).

$^1$H-NMR (270 MHz, CDCl$_3$) δ (ppm): 1.18 (t, J=7.4 Hz, 3H), 2.75-2.60 (m, 6H), 3.24 (s, 3H), 3.53 (s, 3H), 4.10 (br s, 2H), 4.95 (br s, 2H), 5.24 (br s, 2H), 6.88 (br s, 1H), 7.21-7.18 (m, 2H), 7.44-7.35 (m, 3H), 7.64 (s, 1H);

ESI-MS (m/z): 428 (M+H)$^+$.

(Step 2)

(5-{2-[2-Ethyl-3,5-bis(methoxymethoxy)-6-phenylphenyl]ethyl}-1,3-oxazol-4-yl)methanol (200 mg) was dissolved in methanol (5.0 mL), and 1,4-dioxane solution (1 ml) of 4.0 mol/L hydrochloric acid was added thereto and stirred at room temperature for 3 hours. The reaction liquid was neutralized with aqueous sodium hydroxide solution (1 mol/L), and then extracted with chloroform. The organic layer was washed with aqueous saturated sodium chloride solution, then dried over anhydrous sodium sulfate, and the solvent was evaporated away under reduced pressure. The resulting residue was purified through preparative thin-layer column chromatography (chloroform/methanol=9/1) to obtain Compound 210 (53 mg, 39%).

$^1$H-NMR (270 MHz, CD$_3$OD) δ (ppm): 1.12 (t, J=7.4 Hz, 3H), 2.70-2.55 (m, 6H), 4.03 (br s, 2H), 6.32 (s, 1H), 7.18-7.14 (m, 2H), 7.43-7.28 (m, 3H), 7.89 (s, 1H);

ESI-MS (m/z): 340 (M+H)$^+$.

EXAMPLE 211

6-Ethyl-5-[(4-hydroxymethyl-1,3-dioxolan-2-yl)methyl]-4-phenylbenzene-1,3-diol (Compound 211)

(Step 1)
2-[3,5-Bis(benzyloxy)-2-ethyl-6-phenylphenyl]ethanal (120 mg, 0.28 mol) obtained in the step 1 in Example 218 was dissolved in dichloromethane (10 mL), and glycerin (0.15 mL, 1.0 mol) and p-toluenesulfonic acid (15 mg, 0.1 mol) were added thereto and stirred at room temperature for 4 hours. The reaction liquid was neutralized with aqueous saturated sodium bicarbonate solution, and then extracted with ethyl acetate. The organic layer was washed with aqueous saturated sodium chloride solution, and dried over anhydrous sodium sulfate, and the solvent was evaporated away under reduced pressure to obtain (2-{[3,5-bis(benzyloxy)-2-ethyl-6-phenylphenyl]methyl}-1,3-dioxolan-4-yl)methanol (150 mg, 100%).

ESI-MS (m/z): 511 (M+H)$^+$.

(Step 2)
(2-{[3,5-Bis(benzyloxy)-2-ethyl-6-phenylphenyl]methyl}-1,3-dioxolan-4-yl)methanol (50 mg, 0.10 mmol) obtained in the above was dissolved in ethyl acetate (5.0 mL), and in a hydrogen atmosphere, 10% palladium-carbon (20 mg) was added thereto and stirred at room temperature for 1 day. The reaction mixture was filtered through Celite, and the filtrate was concentrated under reduced pressure. The resulting residue was purified through thin-layer column chromatography (chloroform/methanol=15/1) to obtain Compound 211 (19 mg, 56%) as a diastereomeric mixture thereof (1/2).

ESI-MS (m/z): 405 (M−H)$^-$.

EXAMPLE 212

3-(2-Ethyl-3,5-dihydroxy-6-phenylphenyl)propanamide (Compound 212)

(Step 1)
In an argon atmosphere, methyl 3-[2-iodo-3,5-bis(methoxymethoxy)-6-phenylphenyl]propanoate (2.9 g, 6.0 mmol) obtained in the step 1 in Example 186 was dissolved in toluene (100 mL), and bis(tri-o-tolylphosphine)palladium(II) dichloride (940 mg, 1.2 mmol) and tributylvinyltin (3.8 g, 12 mmol) were added thereto and stirred at 100° C. for 12 hours. The reaction liquid was poured into aqueous ammonium fluoride solution, and stirred for one full day, and then filtered through Celite. Activated charcoal was added to the filtrate and stirred for 3 hours, and then filtered through Celite, and the filtrate was concentrated under reduced pressure. The resulting residue was purified through silica gel column chromatography (n-hexane/ethyl acetate=8/1) to obtain methyl 3-[3,5-bis(methoxymethoxy)-6-phenyl-2-vinylphenyl]propanoate (2.0 g, 87%).

$^1$H-NMR (270 MHz, CDCl$_3$) δ (ppm): 2.32-2.26 (m, 2H), 2.83-2.77 (m, 2H), 3.26 (s, 3H), 3.51 (s, 3H), 3.56 (s, 3H), 4.98 (s, 2H), 5.20 (s, 2H), 5.53 (dd, J=11.5, 2.1 Hz, 1H), 5.63 (dd, J=17.8, 2.1 Hz, 1H), 6.68 (dd, J=17.8, 11.5 Hz, 1H), 6.89 (S, 1H), 7.19-7.16 (m, 2H), 7.42-7.32 (m, 3H);

ESI-MS (m/z): 387 (M+H)$^+$.

(Step 2)
Methyl 3-[3,5-bis(methoxymethoxy)-6-phenyl-2-vinylphenyl]propanoate (2.0 g, 5.2 mmol) obtained in the above was dissolved in ethyl acetate (100 mL), and in a hydrogen atmosphere, 10% palladium-carbon (2.0 g) was added thereto and stirred at room temperature for 2 days. The reaction mixture was filtered through Celite, and the filtrate was concentrated under reduced pressure to obtain methyl 3-[2-ethyl-3,5-bis(methoxymethoxy)-6-phenylphenyl]propanoate (1.7 g, 84%).

$^1$H-NMR (270' MHz, CDCl$_3$) δ (ppm): 1.17 (t, J=7.4 Hz, 3H), 2.30-2.17 (m, 2H), 2.78-2.63 (m, 4H), 3.24 (s, 3H), 3.52 (s, 3H), 3.57 (s, 3H), 4.94 (s, 1H), 5.23 (s, 1H), 6.86 (s, 1H), 7.26-7.17 (m, 2H), 7.42-7.28 (m, 3H); ESI-MS (m/z): 387 (M−H)$^-$.

(Step 3)
Methyl 3-[2-ethyl-3,5-bis(methoxymethoxy)-6-phenylphenyl]propanoate (780 mg, 2.0 mmol) obtained in the above was dissolved in methanol (100 mL), and aqueous 10 mol/L sodium hydroxide solution (1.0 mL) was added thereto and stirred at 50° C. for 2 hours. The reaction solution was neutralized with 1.0 mol/L hydrochloric acid, and then extracted with chloroform. The organic layer was washed with aqueous saturated sodium chloride solution, and dried over anhydrous sodium sulfate. The solvent was evaporated away under reduced pressure to obtain 3-[2-ethyl-3,5-bis(methoxymethoxy)-6-phenylphenyl]propanoic acid (580 mg, 78%).

APCI-MS (m/z): 373 (M−H)$^-$.

(Step 4)
3-[2-Ethyl-3,5-bis(methoxymethoxy)-6-phenylphenyl]propanoic acid (250 mg, 0.67 mmol) obtained in the above was dissolved in dichloromethane (10 mL), and 1-[3-(dimethylamino)propyl]-3-ethylcarbodiimide hydrochloride (130 mg, 0.67 mmol) and 1-hydroxybenzotriazole hydrate (100 mg, 0.67 mmol) were added thereto and stirred at room temperature for 1 hour. Methanol solution (3.0 mL) of 7.0 mol/L ammonia was added to the reaction solution, and stirred at room temperature for 3 hours. Water was added to the reaction liquid, and extracted with chloroform. The organic layer was dried over anhydrous sodium sulfate, and the solvent was evaporated away under reduced pressure. The resulting residue was purified through silica gel column chromatography (ethyl acetate/n-hexane=2/1) to obtain 3-[2-ethyl-3,5-bis(methoxymethoxy)-6-phenylphenyl]propanamide (190 mg, 76%).

$^1$H-NMR (270 MHz, CDCl$_3$) δ (ppm): 1.09 (t, J=7.4 Hz, 3H), 2.74 (q, J=7.4 Hz, 2H), 3.23 (s, 3H), 3.53 (s, 3H), 3.87 (br s, 2H), 3.99 (br s, 2H), 4.95 (br s, 2H), 5.25 (br s, 2H), 6.94 (br s, 1H), 7.09-7.06 (m, 2H), 7.35-7.30 (m, 3H);

ESI-MS (m/z): 374-(M+H)$^+$.

(Step 5)
3-[2-Ethyl-3,5-bis(methoxymethoxy)-6-phenylphenyl]propanamide (190 mg, 0.51 mmol) obtained in the above was dissolved in methanol (10 mL), and 1,4-dioxane solution (2.0 mL) of 4.0 mol/L hydrochloric acid was added thereto and stirred at 40° C. for 3 hours. The reaction solution was neutralized with aqueous 1.0 mol/L sodium hydroxide solution, and extracted with chloroform. The organic layer was washed with aqueous saturated sodium chloride solution, and dried over anhydrous sodium sulfate, and the solvent was evaporated away under reduced pressure. The resulting residue was purified through thin-layer column chromatography (ethyl acetate/hexane=1/1) to obtain Compound 212 (74 mg, 51%).

$^1$H-NMR (270 MHz, CD$_3$OD) δ (ppm): 1.12 (t, J=7.4 Hz, 3H), 2.19-2.13 (m, 2H), 2.66-2.60 (m, 4H), 6.29 (s, 1H), 7.20-7.17 (m, 2H), 7.41-7.28 (m, 3H), 7.89 (s, 1H); APCI-MS (m/z): 284 (M–H)$^-$.

EXAMPLE 213

Methyl 4-(2-ethyl-3,5-dihydroxy-6-phenylphenyl)-2-(methoxycarbonyl)butanoate (Compound 213) and 6-ethyl-5-[4-hydroxy-3-(hydroxymethyl)but-1-en-1-yl]-4-phenylbenzene-1,3-diol (Compound 214)

(Step 1)

2-[2-Ethyl-3,5-bis(methoxymethoxy)-6-phenylphenyl]ethanal (88 mg, 0.26 mmol) obtained in the step 1 in Example 177 was dissolved in toluene (10 mL), and dimethyl malonate (0.059 mL, 0.52 mmol), piperidine (0.051 mL, 0.52 mmol) and acetic acid (0.060 mL, 1.0 mmol) were added thereto in order, and stirred at room temperature for 19 hours. Water was put into the reaction liquid, and extracted with ethyl acetate. The organic layer was washed with aqueous saturated sodium chloride solution, and dried over anhydrous sodium sulfate, and the solvent was evaporated away under reduced pressure. The resulting residue was purified through preparative thin-layer silica gel column chromatography (n-hexane/ethyl acetate=2/1) to obtain a mixture of methyl 4-[2-ethyl-3,5-bis(methoxymethoxy)-6-phenylphenyl]-2-(methoxycarbonyl)but-2-enoate and dimethyl 2-{2-[2-ethyl-3,5-bis(methoxymethoxy)-6-phenylphenyl]vinyl}di-propanoate (about 1/1).

ESI-MS (m/z): 459 (M+H)$^+$.

(Step 2)

The mixture (100 mg, 0.22 mmol) obtained in the above was dissolved in methanol (10 mL), and 1,4-dioxane solution (2.0 mL) of 4.0 mol/L hydrochloric acid was added thereto and stirred at 40° C. for 3 hours. The reaction solution was neutralized with aqueous 1.0 mol/L sodium hydroxide solution, and extracted with chloroform. The organic layer was washed with aqueous saturated sodium chloride solution, and dried over anhydrous sodium sulfate, and the solvent was evaporated away under reduced pressure to obtain a mixture of methyl 4-(2-ethyl-3,5-dihydroxy-6-phenylphenyl)-2-(methoxycarbonyl)but-2-enoate and dimethyl 2-{2-[2-ethyl-3,5-dihydroxy-6-phenylphenyl]vinyl}di-propanoate (about 1/1) (74 mg, 100%).

ESI-MS (m/z): 371 (M–H)$^-$.

(Step 3)

The mixture (20 mg, 0.054 mol) obtained in the above was added to diethyl ether suspension (50 mL) of lithium aluminium hydride (20 mg, 0.54 mol), and with cooling with ice, this was stirred for 1 hour, and then lithium aluminium hydride (24 mg, 0.64 mol) was added thereto and stirred at room temperature for 2 hours. 1.0 mol/L hydrochloric acid (4.0 mL) was added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer column chromatography (chloroform/methanol=9/1) to obtain Compound 213 (5.2 mg, 26%) and Compound 214 (2.0 mg, 12%).

Compound 213:
$^1$H-NMR (270 MHz, CDCl$_3$) δ (ppm): 1.18 (t, J=7.4 Hz, 3H), 1.93-1.84 (m, 2H), 2.42-2.36 (m, 2H), 2.64 (q, J=7.4 Hz, 2H), 3.14 (t, J=7.2 Hz, 1H), 3.60 (s, 6H), 4.46 (s, 1H), 4.78 (s, 1H), 6.35 (s, 1H), 7.21-7.18 (m, 2H), 7.52-7.41 (m, 3H);
APCI-MS (m/z): 371 (M–H)$^-$.

Compound 214:
$^1$H-NMR (270 MHz, CDCl$_3$) δ (ppm): 1.13 (t, J=7.4 Hz, 3H), 2.40 (m, 1H), 2.62 (q, J=7.4 Hz, 2H), 3.50-3.42 (m, 5H), 4.70 (s, 1H), 4.73 (s, 1H), 5.07 (dd, J=16.0, 8.8 Hz, 1H), 6.36 (s, J=16.0 Hz, 1H), 6.41 (s, 1H), 7.24-7.22 (m, 2H), 7.49-7.38 (m, 3H);
APCI-MS (m/z): 313 (M–H)$^-$.

EXAMPLE 214

6-Ethyl-5-[4-hydroxy-3-(hydroxymethyl)butyl]-4-phenylbenzene-1,3-diol (Compound 215)

Tetrahydrofuran solution (10 mL) of Compound 213 (82 mg) obtained in Example 213 was added to tetrahydrofuran suspension (10 mL) of lithium aluminium hydride (8.1 mg, 0.32 mmol) and stirred for 1 hour with cooling with ice, and then lithium aluminium hydride (65 mg, 2.5 mol) was added thereto and stirred at room temperature for 2 hours. 1.0 mol/L hydrochloric acid (4.0 mL) was added to the reaction mixture, and extracted with chloroform. The organic layer was washed with aqueous saturated sodium chloride solution, and dried over anhydrous sodium sulfate, and the solvent was evaporated away under reduced pressure. The resulting residue was purified through preparative thin-layer column chromatography (chloroform/methanol=9/1) to obtain Compound 215 (4.0 mg, 5.7%).

$^1$H-NMR (270 MHz, DMSO-d$_6$) δ (ppm): 1.03 (t, J=7.2 Hz, 3H), 1.20-1.10 (m, 3H), 2.23 (br s, 2H), 3.12-3.02 (m, 4H), 4.12 (t, J=5.2 Hz, 2H), 6.28 (s, 1H), 7.08-7.06 (m, 2H), 7.34-7.23 (m, 3H), 8.52 (br s, 1H), 8.92 (br s, 1H);
ESI-MS (m/z): 315 (M–H)$^-$.

EXAMPLE 215

Another method for 6-ethyl-5-[4-hydroxy-3-(hydroxymethyl)butyl]-4-phenylbenzene-1,3-diol (Compound 215)

(Step 1)

2-[3,5-Bis(benzyloxy)-2-ethyl-6-phenylphenyl]ethanal (150 mg, 0.42 mmol) obtained in the step 1 in Example 218 was dissolved in toluene (20 mL), and dimethyl malonate (0.37 mL, 3.2 mmol), piperidine (0.32 mL, 3.2 mmol) and acetic acid (0.37 mL, 6.4 mmol) were added thereto in order, and stirred at room temperature for 1 day. Water was added to the reaction solution, and extracted with ethyl acetate. The organic layer was washed with aqueous saturated sodium chloride solution, then dried over anhydrous sodium sulfate, and the solvent was evaporated away under reduced pressure. The resulting residue was dissolved in methanol (20 mL), and aqueous solution (5.0 mL) of sodium borohydride (16 mg, 0.42 mmol) was added thereto with cooling with ice, and stirred at the same temperature for 2 hours. The reaction solution was poured into diluted hydrochloric acid, and extracted with ethyl acetate, the organic layer was dried over sodium sulfate, and the solvent was evaporated away under reduced pressure. The resulting residue was purified through silica gel column chromatography (n-hexane/ethyl acetate=6/1) to obtain a mixture of methyl 4-[3,5-bis(benzyloxy)-2-ethyl-6-phenylphenyl]-2-(methoxycarbonyl)but-2-enoate and dimethyl 2-{2-[3,5-bis(benzyloxy)-2-ethyl-6-phenylphenyl]vinyl}di-propanoate (about 1:1) (150 mg, 76%).

FAB-MS (m/z): 550 (M+H)⁺.

(Step 2)

The mixture (0.44 g, 0.8 mol) obtained in the above was dissolved in tetrahydrofuran (100 mL), and lithium aluminium hydride (0.059 g, 1.6 mol) was added thereto with cooling with ice, and stirred at the same temperature for 2 hours. Sodium sulfate 10-hydrate (1.2 g, 3.7 mol) was added to the reaction solution, stirred at room temperature for 2 hours, and then filtered through Celite. The filtrate was concentrated under reduced pressure to obtain a mixture of {2-[3,5-bis(benzyloxy)-2-ethyl-6-phenylphenyl]vinyl}propane-1,3-diol and 4-[3,5-bis(benzyloxy)-2-ethyl-6-phenylphenyl]-2-(hydroxymethyl)butanol (400 mg, quantitative).

FAB-MS (m/z): 497 (M+H)⁺.

(Step 3)

The mixture (400 mg) obtained in the above was dissolved in ethyl acetate (50 mL), and in a hydrogen atmosphere, 10% palladium-carbon (300 mg) was added thereto and stirred at room temperature for 1 day. The reaction mixture was filtered through Celite, and the filtrate was concentrated under reduced pressure. The resulting residue was purified through silica gel column chromatography (chloroform/methanol=9/1) to obtain Compound 215 (150 mg, 59%).

EXAMPLE 216

Compound 216

(Step 1)

In an argon atmosphere, 2-[3,5-bis(benzyloxy)-2-ethyl-6-phenylphenyl]ethanol (88 mg, 0.20 mmol) obtained in the step 4 in Example 179 was dissolved in dichloromethane (3.0 mL), and tri-O-benzyl-D-galactal (0.92 mg, 0.15 mol/L) and triphenylphosphonium bromide (20 mg, 0.060 mmol) were added thereto and stirred at room temperature for 40 hours. Water was added to the reaction liquid, and extracted with a mixed solvent of chloroform and methanol (9/1). The organic layer was washed with aqueous saturated sodium chloride solution, and dried over anhydrous sodium sulfate, and the solvent was evaporated away under reduced pressure. The resulting residue was purified through preparative thin-layer column chromatography (n-hexane/ethyl acetate=1/1) to obtain a glycoside (100 mg, 58%).

FAB-MS (m/z): 854 (M+)⁺.

(Step 2)

The glycoside (100 mg, 0.12 mmol) obtained in the above was dissolved in ethyl acetate (10 mL), and in a hydrogen atmosphere, 10% palladium-carbon (100 mg) was added thereto and stirred at room temperature for 3 days. The reaction mixture was filtered through Celite, and the filtrate was concentrated under reduced pressure. The resulting residue was purified through preparative thin-layer column chromatography (chloroform/methanol=9/1) to obtain Compound 216 (36 mg, 81%).

¹H-NMR (270 MHz, CD₃OD) δ (ppm): 1.12 (t, J=7.4 Hz, 3H), 1.62 (dd, J=12.4, 5.1 Hz, 1H), 1.83 (td, J=12.4, 3.6 Hz, 1H), 2.68-2.61 (m, 4H), 3.32 (m, 1H), 3.51-3.49 (m, 2H), 3.64-3.61 (m, 2H), 3.72 (br s, 1H), 3.83-3.76 (m, 1H), 4.67 (d, J=2.6 Hz, 1H), 6.29 (s, 1H), 7.19-7.16 (m, 2H), 7.41-7.26 (m, 3H);

APCI-MS (m/z): 405 (M+H)⁺.

EXAMPLE 217

6-Ethyl-5-[5-hydroxy-4-(hydroxymethyl)pentyl]-4-phenylbenzene-1,3-diol (Compound 217)

(Step 1)

3-[2-Ethyl-3,5-bis(methoxymethoxy)-6-phenylphenyl]propanal (150 mg, 0.42 mmol) obtained in the step 1 in Example 169 was dissolved in toluene (15 mL), and dimethyl malonate (0.096 mL, 0.84 mmol), piperidine (0.083 mL, 0.84 mmol) and acetic acid (0.096 mL, 1.7 mmol) were added thereto in order, and stirred at room temperature for 16 hours and then at 40° C. for 2 hours. Water was added to the reaction solution, and extracted with ethyl acetate. The organic layer was washed with aqueous saturated sodium chloride solution, and then dried over anhydrous sodium sulfate, and the solvent was evaporated away under reduced-pressure. The resulting residue was purified through silica gel column chromatography (n-hexane/ethyl acetate=2/1) to obtain methyl 5-[2-ethyl-3,5-bis(methoxymethoxy)-6-phenylphenyl]-2-(methoxycarbonyl)pent-2-enoate (150 mg, 76%).

¹H-NMR (270 MHz, CDCl₃) δ (ppm): 1.16 (t, J=7.4 Hz, 3H), 2.32-2.23 (m, 2H), 2.70-2.54 (m, 4H), 3.23 (s, 3H), 3.52 (s, 3H), 3.74 (s, 3H), 3.76 (s, 3H), 4.94 (s, 2H), 5.23 (s, 2H), 6.72 (t, J=7.9 Hz, 1H), 6.86 (s, 1H), 7.20-7.16 (m, 2H), 7.42-7.32 (m, 3H);

APCI-MS (m/z): 473 (M+H)⁺.

(Step 2)

Methyl 5-[2-ethyl-3,5-bis(methoxymethoxy)-6-phenylphenyl]-2-(methoxycarbonyl)pent-2-enoate (150 mg, 0.32 mmol) obtained in the above was dissolved in ethyl acetate (30 mL), and in a hydrogen atmosphere, 10% palladium-carbon (150 mg) was added thereto and stirred at room temperature for 1 day. The reaction mixture was filtered through Celite, and the filtrate was concentrated under reduced pressure to obtain dimethyl 2-{3-[2-ethyl-3,5-bis(methoxymethoxy)-6-phenylphenyl]propyl}di-propanoate (170 mg, 100%).

APCI-MS (m/z): 475 (M+H)⁺.

(Step 3)

Dimethyl 2-{3-[2-ethyl-3,5-bis(methoxymethoxy)-6-phenylphenyl]propyl}di-propanoate (170 mg, 0.32 mmol) obtained in the above was added to diethyl ether suspension (50 mL) of lithium aluminium hydride (24 mg, 0.64 mol), and stirred for 1 hour with cooling with ice, and then lithium aluminium hydride (24 mg, 0.64 mol) was added thereto and further stirred at room temperature for 2 hours. Sodium sulfate 10-hydrate was added to the reaction solution until bubbles were not observed, and stirred for 30 minutes. The reaction mixture was filtered through Celite, and the filtrate was concentrated under reduced pressure to obtain 2-{3-[2-ethyl-3,5-bis(methoxymethoxy)-6-phenylphenyl]propyl}propane-1,3-diol (150 mg, quantitative).

APCI-MS (m/z): 419 (M+H)⁺.

(Step 4)

2-{3-[2-Ethyl-3,5-bis(methoxymethoxy)-6-phenylphenyl]propyl}propane-1,3-diol (50 mg, 0.11 mmol) obtained in the above was dissolved in methanol (5.0 mL), and 1,4-dioxane solution (1.0 mL) of 4.0 mol/L hydrochloric acid was added thereto and stirred at room temperature for 2 hours. The reaction liquid was neutralized with aqueous 1 mol/L sodium hydroxide solution, and extracted with chloroform. The organic layer was washed with aqueous saturated sodium chloride solution, and the solvent was evaporated away under reduced pressure. The resulting residue was purified through preparative thin-layer column chromatography (chloroform/methanol=9/1) to obtain Compound 217 (44 mg, 42%).

$^1$H-NMR (270 MHz, CD$_3$OD) δ (ppm): 1.06 (t, J=7.4 Hz, 3H), 1.50-1.10 (m, 8H), 2.92-2.81 (m, 3H), 3.35-3.31 (m, 4H), 6.34 (s, 1H), 7.24-7.15 (m, 3H), 7.38-7.32 (m, 2H); APCI-MS (m/z): 331 (M+H)$^+$.

EXAMPLE 218

5-{[(4R,5R)-4,5-bis(hydroxymethyl)-1,3-dioxolan-2-yl]methyl}-6-ethyl-4-phenylbenzene-1,3-diol (Compound 218)

(Step 1)

2-[3,5-bis(benzyloxy)-2-ethyl-6-phenylphenyl]ethanol (2.06 g, 5.03 mmol) obtained in the step 4 in Example 179 was dissolved in dichloromethane (40 mL), and pyridinium dichromate (5.06 g, 13.4 mmol) was added thereto and stirred at room temperature for 16 hours. The reaction mixture was filtered, and the filtrate was concentrated under reduced pressure. The residue was purified through silica gel column chromatography (n-hexane/ethyl acetate=20/1 to 9/1) to obtain 2-[3,5-bis(benzyloxy)-2-ethyl-6-phenylphenyl]ethanal (1.12 g, 54%).

$^1$H-NMR (270 MHz, CDCl$_3$) δ (ppm): 1.11 (t, J=7.5 Hz, 3H), 2.62 (q, J=7.5 Hz, 2H), 3.59 (d, J=1.5 Hz, 2H), 4.91 (s, 2H), 5.06 (s, 2H), 6.61 (s, 1H), 7.05-7.45 (m, 15H), 9.56 (t, J=1.5 Hz, 1H).

(Step 2)

2-[3,5-Bis(benzyloxy)-2-ethyl-6-phenylphenyl]ethanal (803 mg, 1.84 mmol) obtained in the above was dissolved in toluene (100 mL). (+)-1,4-di-O-benzyl-D-threitol (1.26 g, 4.17 mmol) and DL-10-camphorsulfonic acid (123 mg, 0.530 mmol) were added to the resulting solution, and stirred with heating under reflux for 8 hours. Water and aqueous saturated sodium hydrogencarbonate solution were added to the reaction mixture, and extracted with ethyl acetate. The organic layer was washed with aqueous saturated sodium chloride solution, and then dried over anhydrous sodium sulfate, and the solvent was evaporated away under reduced pressure. The residue was purified through silica gel column chromatography (n-hexane/ethyl acetate=9/1 to 4/1) to obtain 1,5-bis(benzyloxy)-3-{[(4R,5R)-4,5-bis(benzyloxy)-1,3-dioxolan-2-yl]methyl}-4-ethyl-2-phenylbenzene (1.33 g, 100%).

$^1$H-NMR (300 MHz, CDCl$_3$) δ (ppm): 1.15 (t, J=7.3 Hz, 3H), 2.82 (q, J=7.3 Hz, 2H), 2.87-3.05 (m, 2H), 3.48-3.56 (m, 4H), 3.75-4.00 (m, 2H), 4.48 (s, 2H), 4.50 (s, 2H), 4.86 (s, 2H), 5.00-5.10 (m, 1H), 5.03 (s, 2H), 6.54 (s, 1H), 7.00-7.50 (m, 25H).

(Step 3)

1,5-Bis(benzyloxy)-3-{[(4R,5R)-4,5-bis(benzyloxy)-1,3-dioxolan-2-yl]methyl}-4-ethyl-2-phenylbenzene (1.31 g, 1.82 mmol) obtained in the above was dissolved in ethyl acetate (20 mL), and 10% palladium-carbon (148 mg) was added thereto and stirred in a hydrogen atmosphere at room temperature for 6 hours. The reaction mixture was filtered, the filtrate was concentrated under reduced pressure, and the residue was purified through silica gel column chromatography (chloroform/methanol/water=100/10/1) to obtain Compound 218 (496 mg, 76%).

$^1$H-NMR (300 MHz, DMSO-d$_6$) δ (ppm): 1.00 (t, J=7.2 Hz, 3H), 2.57 (q, J=7.2 Hz, 2H), 2.65 (d, J=5.1 Hz, 2H), 3.25-3.45 (m, 4H), 3.50-3.65 (m, 2H), 4.70-4.82 (m, 3H), 6.35 (s, 1H), 7.04-7.14 (m, 2H), 7.18-7.36 (m, 3H), 8.60 (br s, 1H), 9.02 (br s, 1H); APCI-MS (m/z): 359 (M−H)$^−$.

EXAMPLE 219

6-Ethyl-4-(3-hydroxyphenyl)-5-[2-(oxiran-2-ylmethoxy)ethyl]benzene-1,3-diol (Compound 219)

(Step 1)

In the same manner as in the step 1 in Example 62, 2-[3,5-bis(benzyloxy)-2-ethylphenyl]ethanol (1.8 g, 97%) was obtained from methyl 3,5-bis(benzyloxy)-2-ethylphenylacetate (2.0 g, 5.1 mmol), using lithium aluminium hydride (200 mg, 5.3 mmol) and diethyl ether (50 mL).

$^1$H-NMR (300 MHz, CDCl$_3$) δ (ppm): 1.13 (t, J=7.4 Hz, 3H), 1.33 (br s, 1H), 2.68 (q, J=7.4 Hz, 2H), 2.89 (t, J=6.8 Hz, 2H), 3.82 (m, 2H), 5.02 (s, 2H), 5.03 (s, 2H), 6.44 (d, J=2.5 Hz, 1H), 6.51 (d, J=2.5 Hz, 1H), 7.31-7.43 (m, 10 H).

(Step 2)

In the same manner as in the step 1 in Example 64, 3,5-bis(benzyloxy)-2-ethyl-1-[2-(oxiran-2-ylmethoxy)ethyl]benzene (420 mg, 28%) was obtained from 2-[3,5-bis(benzyloxy)-2-ethylphenyl]ethanol (1.3 g, 3.6 mmol) obtained in the above, using 60% sodium hydride/mineral oil dispersion (450 mg, 11 mmol), epichlorohydrin (0.88 mL, 11 mmol) and N,N-dimethylformamide (20 mL).

$^1$H-NMR (300 MHz, CDCl$_3$) (ppm): 1.11 (t, J=7.3 Hz, 3H) 2.44 (m, 1H), 2.72-2.59 (m, 5H), 2.96 (m, 1H), 3.06 (m, 1H), 3.32 (m, 2H), 3.48 (m, 1H), 4.99 88s, 1H), 5.01 (s, 1H), 6.49-6.45 (m, 2H), 7.50-7.30 (m, 10H); APCI-MS (m/z): 419 (M−H)$^−$.

(Step 3)

In the same manner as in the step 2 in Example 1, 1,5-bis(benzyloxy)-2-bromo-4-ethyl-3-[2-(oxiran-2-ylmethoxy)ethyl]benzene (350 mg, 71%) was obtained from 3,5-bis(benzyloxy)-2-ethyl-1-[2-(oxiran-2-ylmethoxy)ethyl]benzene (410 mg, 0.98 mmol) obtained in the above, using N-bromosuccinimide (200 mg, 1.1 mmol) and N,N-dimethylformamide (10 mL).

$^1$H-NMR (300 MHz, CDCl$_3$) δ (ppm): 1.11 (t, J=7.3 Hz, 3H), 2.76 (q, J=7.3 Hz, 2H), 3.19 (m, 2H), 3.45 (m, 1H), 3.64 (m, 1H), 4.01 (m, 2H), 5.02 (s, 2H), 5.04 (s, 2H), 6.47 (s, 1H), 7.48-7.32 (m, 10H); APCI-MS (m/z): 497, 499 (M+H)$^+$.

(Step 4)

In the same manner as in the step 3 in Example 1, 1,5-bis(benzyloxy)-4-ethyl-3-[2-(oxiran-2-ylmethoxy)ethyl]-2-phenylbenzene (230 mg, 64%) was obtained from 1,5-bis(benzyloxy)-2-bromo-4-ethyl-3-[2-(oxiran-2-ylmethoxy)ethyl]benzene (350 mg, 0.7 mmol) obtained in the above, using 2-(3-hydroxyphenyl)-4,4,5,5-tetramethyl-1,3,2-dioxaborolane (260' mg, 1.2 mmol), bis(tri-o-tolylphosphine)palladium(II) dichloride (50 mg, 0.064 mmol), cesium carbonate (780 mg, 2.4 mmol), 1,2-dimethoxyethane (10 mL) and water (2.0 mL).

$^1$H-NMR (300 MHz, CDCl$_3$) δ (ppm): 1.11 (t, J=7.3 Hz, 3H), 2.82-2.63 (m, 5H), 3.17-3.04 (m, 2H), 3.62-3.38 (m, 3H), 4.98 (s, 2H), 5.02 (s, 2H), 6.51 (s, 1H), 7.43-7.10 (m, 14H).

(Step 5)

1,5-Bis(benzyloxy)-4-ethyl-3-[2-(oxiran-2-ylmethoxy)ethyl]-2-phenylbenzene (230 mg, 0.45 mmol) obtained in the above was dissolved in ethyl acetate (10 mL), and 10% palladium-carbon (50% wet., 200 mg) was added thereto and stirred in a hydrogen atmosphere at room temperature for 6 hours. The reaction mixture was filtered through Celite, and the filtrate was concentrated under reduced pressure. The resulting residue was purified through silica gel column chromatography (ethyl acetate/n-hexane=1/2 to 1/1) to obtain Compound 219 (83 mg, 56%).

$^1$H-NMR (300 MHz, CD$_3$OD) δ (ppm): 1.11 (t, J=7.3 Hz, 3H), 2.44 (m, 1H), 2.59-2.72 (m, 5H), 2.96 (m, 1H), 3.06 (ddd, J=11.4, 5.8, 2.5 Hz, 1H), 3.34-3.40 (m, 2H), 3.48 (dd, J=11.4, 2.8, 1H), 6.28 (s, 1H), 6.61-6.63 (m, 2H), 6.75 (m, 1H), 7.20 (t, J=8.1 Hz, 1H);

APCI-MS (m/z): 329 (M−H)⁻.

EXAMPLE 220

3-(2-Ethyl-3,5-dihydroxy-6-phenylphenyl)-N-(2-hydroxyethyl)propanamide (Compound 220)

(Step 1)

3-[2-Ethyl-3,5-bis(methoxymethoxy)-6-phenylphenyl] propanol (1.89 g, 5.24 mmol) obtained in the step 2 in Example 123 was dissolved in dichloromethane (50 mL), and pyridinium dichromate (5.16 g, 13.7 mmol) was added thereto and stirred at room temperature for 40 hours. The reaction mixture was filtered, and the filtrate was concentrated under reduced pressure. The residue was purified through silica gel column chromatography (n-hexane/ethyl acetate=20/1 to 9/1) to obtain 3-[2-ethyl-3,5-bis(methoxymethoxy)-6-phenylphenyl]propanal (1.36 g, 72%).

$^1$H-NMR (270 MHz, CDCl$_3$) δ (ppm): 1.16 (t, J=7.4 Hz, 3H), 2.35-2.45 (m, 2H), 2.64 (q, J=7.4 Hz, 2H), 2.70-2.80 (m, 2H), 3.24 (s, 3H), 3.52 (s, 3H), 4.94 (s, 2H), 5.23 (s, 2H), 6.86 (s, 1H), 7.14-7.4 (m, 5H), 9.49 (t, J=1.4 Hz, 1H).

(Step 2)

3-[2-Ethyl-3,5-bis(methoxymethoxy)-6-phenylphenyl] propanal (1.35 g, 3.76 mmol) obtained in the above was dissolved in tert-butyl alcohol (10 mL), and 2-methyl-2-butene (5.00 mL, 47.2 mmol), sodium chlorite (1.00 g, 11.1 mmol), sodium dihydrogenphosphate (1.00 g, 8.33 mmol) and water (5 mL) were added thereto and stirred at room temperature for 10 hours. Water and 1 mol/L hydrochloric acid were added to the reaction mixture, and extracted with ethyl, acetate. The organic layer was washed with water and aqueous saturated sodium thiosulfate solution in order, and dried over anhydrous sodium sulfate. The solvent was evaporated away under reduced pressure to obtain 3-[2-ethyl-3,5-bis(methoxymethoxy)-6-phenylphenyl]propanoic acid (1.17 g, 83%).

$^1$H-NMR (270 MHz, CDCl$_3$) δ (ppm): 1.16 (t, J=7.4 Hz, 3H), 2.20-2.36 (m, 2H), 2.60-2.80 (m, 4H), 3.23 (s, 3H), 3.52 (s, 3H), 4.94 (s, 2H), 5.22 (s, 2H), 6.85 8s, 1H), 7.15-7.45 (m, 5H).

(Step 3)

3-[2-Ethyl-3,5-bis(methoxymethoxy)-6-phenylphenyl] propanoic acid (59.5 mg, 0.159 mmol) obtained in the above was dissolved in N,N-dimethylformamide (4 mL), and 1-hydroxybenzotriazole hydrate (126 mg, 0.820 mmol), 1-[3-(dimethylamino)propyl]-3-ethylcarbodiimide hydrochloride (109 mg, 0.570 mmol) and 2-aminoethanol (0.0400 mL, 0.660 mmol) were added thereto and stirred at room temperature for 18 hours. Water was added to the reaction mixture, and extracted with ethyl acetate. The organic layer was washed three times with aqueous saturated sodium chloride solution, and dried over anhydrous sodium sulfate. The solvent was evaporated away under reduced pressure. The resulting residue was purified through preparative thin-layer chromatography (chloroform/methanol=9/1) to obtain 3-[2-ethyl-3,5-bis(methoxymethoxy)-6-phenylphenyl]-N-(2-hydroxyethyl)propanamide (73.7 mg, 100%).

$^1$H-NMR (270 MHz, CDCl$_3$) δ (ppm): 1.16 (t, J=7.5 Hz, 3H), 2.06-2.16 (m, 2H), 2.40 (br s, 1H), 2.70 (q, J=7.5 Hz, 2H), 2.75-2.85 (m, 2H), 3.17-3.27 (m, 2H), 3.24 (s, 3H), 3.52 (s, 3H), 3.58 (t, J=4.9 Hz, 2H), 5.15 (br s, 1H), 5.23 (s, 2H), 6.86 (s, 1H), 7.20-7.47 (m, 5H).

(Step 4)

3-[2-Ethyl-3,5-bis(methoxymethoxy)-6-phenylphenyl]-N-(2-hydroxyethyl)propanamide (71.2 mg, 0.154 mmol) obtained in the above was dissolved in methanol (6 mL), and concentrated hydrochloric acid (0.2 mL) was added thereto and stirred at 60° C. for 1.2 hours. The reaction mixture was concentrated under reduced pressure, and the resulting residue was purified through preparative thin-layer chromatography (chloroform/methanol=4/1) to obtain Compound 220 (12.0 mg, 24%).

$^1$H-NMR (270 MHz, CDCl$_3$) δ (ppm): 1.18 (t, J=7.6 Hz, 3H), 2.08-2.18 (m, 2H), 2.32 (br s, 1H), 2.65 (q, J=7.6 Hz, 2H), 2.70-2.80 (m, 2H), 3.27 (dt, J=5.1, 5.1 Hz, 2H), 3.61 (t, J=5.1 Hz, 2H), 4.52 (br s, 1H), 4.91 (br s, 1H), 5.32 (br s, 1H), 6.37 (s, 1H), 7.22-7.34 (m, 2H), 7.40-7.58 (m, 3H);

ESI-MS (m/z): 330 (M+H)⁺.

EXAMPLE 221

N-[2-(acetylamino)ethyl]-3-(2-ethyl-3,5-dihydroxy-6-phenylphenyl)propanamide (Compound 221)

(Step 1)

In the same manner as in the step 3 in Example 220, N-[2-(acetylamino)ethyl]-3-[2-ethyl-3,5-bis(methoxymethoxy)-6-phenylphenyl]propanamide (88.0 mg, 100%) was obtained from 3-[2-ethyl-3,5-bis(methoxymethoxy)-6-phenylphenyl]propanoic acid (69.6 mg, 0.186 mmol) obtained in the step 2 in Example 220, using 1-hydroxybenzotriazole monohydrate (138 mg, 0.898 mmol), 1-[3-(dimethylamino)propyl]-3-ethylcarbodiimide hydrochloride (120 mg, 0.626 mmol) and N-acetylethylenediamine (70.5 mg, 0.690 mmol).

$^1$H-NMR (270 MHz, CDCl$_3$) δ (ppm): 1.16 (t, J=7.4 Hz, 3H), 1.92 (s, 3H), 2.00-2.20 (m, 2H), 2.60-2.82 (m, 4H), 3.24 (s, 3H), 3.15-3.25 (m, 4H), 3.52 (s, 3H), 4.95 (s, 2H), 5.22 (s, 2H), 5.45 (br s, 1H), 6.23 (br s, 1H), 6.86 (s, 1H), 7.15-7.45 (m, 5H).

(Step 2)

N-[2-(Acetylamino)ethyl]-3-[2-ethyl-3,5-bis(methoxymethoxy)-6-phenylphenyl]propanamide (67.2 mg, 0.142 mmol) obtained in the above was dissolved in ethanol (6 mL), and concentrated hydrochloric acid (0.2 mL) was added thereto and stirred at 60° C. for 1.2 hours. The reaction mixture was concentrated under reduced pressure, and the resulting residue was purified through preparative thin-layer chromatography (chloroform/methanol=4/1) to obtain Compound 221 (47.6 mg, 90%).

$^1$H-NMR (270 MHz, CDCl$_3$) δ (ppm): 1.18 (t, J=7.4 Hz, 3H), 1.92 (s, 3H), 2.00-2.20 (m, 2H), 2.60-2.78 (m, 4H), 3.20-3.35 (m, 4H), 4.55 (br s, 1H), 5.39 (br s, 1H), 5.64 (br s, 1H), 5.98 (br s, 1H), 6.38 (s, 1H), 7.20-7.30 (m, 2H), 7.40-7.55 (m, 3H);

ESI-MS (m/z): 371 (M+H)⁺.

EXAMPLE 222

5-[2-(2-Ethyl-3,5-dihydroxy-6-phenylphenyl)ethyl]-1,3-oxazole-4-carboxamide (Compound 222)

(Step 1)

Methyl 5-{2-[2-ethyl-3,5-bis(methoxymethoxy)-6-phenylphenyl]ethyl}-1,3-oxazole-4-carboxylate (372 mg, 0.817 mmol) obtained in the step 1 in Example 209 was dissolved in methanol (10 mL), and aqueous 2 mol/L lithium hydroxide solution (2.00 mL, 4.00 mmol) was added thereto and stirred at room temperature for 24 hours. Water and 1 mol/L hydrochloric acid were added to the reaction mixture, and extracted with ethyl acetate. The organic layer was washed with aqueous saturated sodium chloride solution, and dried over anhydrous sodium sulfate. The solvent was evaporated away under reduced pressure to obtain 5-{2-[2-ethyl-3,5-bis(methoxymethoxy)-6-phenylphenyl]ethyl}-1,3-oxazole-4-carboxylic acid (353 mg, 98%).

$^1$H-NMR (270 MHz, $CDCl_3$) δ (ppm): 1.19 (t, J=7.4 Hz, 3H), 2.60-2.85 (m, 4H), 3.00-3.10 (m, 2H), 3.24 (s, 3H), 3.53 (s, 3H), 4.95 (s, 2H), 5.24 (s, 2H), 6.88 (s, 1H), 7.15-7.45 (m, 5H), 7.65 (s, 1H).

(Step 2)

5-{2-[2-Ethyl-3,5-bis(methoxymethoxy)-6-phenylphenyl]ethyl}-1,3-oxazole-4-carboxylic acid (54.2 mg, 0.123 mmol) obtained in the above was dissolved in N,N-dimethylformamide (4 mL), and 1-hydroxybenzotriazole hydrate (120 mg, 0.784 mmol), 1-[3-(dimethylamino)propyl]-3-ethylcarbodiimide hydrochloride (67.3 mg, 0.351 mmol) and aqueous 25% ammonia solution (1.00 mL, 6.49 mmol) were added thereto and stirred at room temperature for 1 hour. Water was added to the reaction mixture, and extracted with ethyl acetate. The organic layer was washed three times with aqueous saturated sodium chloride solution, and dried over anhydrous sodium sulfate, and the solvent was evaporated away under reduced pressure. The resulting residue was purified through preparative thin-layer chromatography (chloroform/methanol=9/1) to obtain 5-{2-[2-ethyl-3,5-bis(methoxymethoxy)-6-phenylphenyl]ethyl}-1,3-oxazole-4-carboxamide (34.5 mg, 64%).

$^1$H-NMR (270 MHz, $CDCl_3$) δ (ppm): 1.19 (t, J=7.3 Hz, 3H), 2.66-2.84 (m, 4H), 3.00-3.20 (m, 2H), 3.25 (s, 3H), 3.53 (s, 3H), 4.95 (s, 2H), 5.24 (s, 2H), 5.41 (br s, 1H), 6.70 (br s, 1H), 6.87 (s, 1H), 7.20-7.45 (m, 5H), 7.55 (s, 1H).

(Step 3)

In the same manner as in the step 2 in Example 25, Compound 222 (13.0 mg, 47%) was obtained from 5-{2-[2-ethyl-3,5-bis(methoxymethoxy)-6-phenylphenyl]ethyl}-1,3-oxazole-4-carboxamide (34.5 mg, 0.0783 mmol) obtained in the above, using ethanol (6 mL) and concentrated hydrochloric acid (0.2 mL).

$^1$H-NMR (270 MHz, $CDCl_3/CD_3OD$) δ (ppm): 1.20 (t, J=7.4 Hz, 3H), 2.60-2.80 (m, 4H), 3.00-3.20 (m, 2H), 6.37 (s, 1H), 7.25-7.55 (m, 5H), 7.58 (s, 1H);

ESI-MS (m/z): 353 (M+H)$^+$.

EXAMPLE 223

5-[2-(2-Ethyl-3,5-dihydroxy-6-phenylphenyl)ethyl]-N-(2-hydroxyethyl)-1,3-oxazole-4-carboxamide (Compound 223)

(Step 1)

In the same manner as in the step 2 in Example 222, 5-{2-[2-ethyl-3,5-bis(methoxymethoxy)-6-phenylphenyl]ethyl}-N-(2-hydroxyethyl)-1,3-oxazole-4-carboxamide (39.4 mg, 67%) was obtained from 5-{2-[2-ethyl-3,5-bis(methoxymethoxy)-6-phenylphenyl]ethyl}-1,3-oxazole-4-carboxylic acid (54.2 mg, 0.123 mmol) obtained in the step 1 in Example 222, using 1-hydroxybenzotriazole hydrate (99.0 mg, 0.646 mmol), 1-[3-(dimethylamino)propyl]-3-ethylcarbodiimide hydrochloride (65.6 mg, 0.342 mmol) and 2-aminoethanol (0.0180 mL, 0.300 mmol).

$^1$H-NMR (270 MHz, $CDCl_3$) δ (ppm): 1.18 (t, J=7.4 Hz, 3H), 2.70-2.85 (m, 4H), 2.98 (br s, 1H), 3.05-3.15 (m, 2H), 3.24 (s, 3H), 3.53 (s, 3H), 3.47-3.57 (m, 2H), 3.75-3.85 (m, 2H), 4.95 (s, 2H), 5.23 (s, 2H), 6.87 (s, 1H), 7.15-7.45 (m, 6H), 7.55 (s, 1H).

(Step 2)

In the same manner as in the step 2 in Example 25, Compound 223 (8.6 mg, 27%) was obtained from 5-{2-[2-ethyl-3,5-bis(methoxymethoxy)-6-phenylphenyl]ethyl}-N-(2-hydroxyethyl)-1,3-oxazole-4-carboxamide (39.4 mg, 0.0813 mmol) obtained in the above, using ethanol (6 mL) and concentrated hydrochloric acid (0.2 mL).

$^1$H-NMR (270 MHz, DMSO-$d_6$) δ (ppm): 1.04 (t, J=7.0 Hz, 3H), 2.46-2.64 (m, 4H), 2.90-3.04 (m, 2H), 3.20-3.50 (m, 4H), 4.72 (t, J=5.4 Hz, 1H), 6.35 (s, 1H), 7.04-7.36 (m, 5H), 7.87 (t, J=5.9 Hz, 1H), 8.17 (s, 1H), 8.64 (br s, 1H), 9.04 (br s, 1H);

ESI-MS (m/z): 397 (M+H)$^+$.

EXAMPLE 224

5-[2-(2-ethyl-3,5-dihydroxy-6-phenylphenyl)ethyl]-N,N-bis(2-hydroxyethyl)-1,3-oxazole-4-carboxamide (Compound 224)

(Step 1)

In the same manner as in the step 2 in Example 222, 5-{2-[2-ethyl-3,5-bis(methoxymethoxy)-6-phenylphenyl]ethyl}-N,N-bis(2-hydroxyethyl)-1,3-oxazole-4-carboxamide (36.3 mg, 56%) was obtained from 5-{2-[2-ethyl-3,5-bis(methoxymethoxy)-6-phenylphenyl]ethyl}-1,3-oxazole-4-carboxylic acid (54.2 mg, 0.123 mmol) obtained in the step 1 in Example 222, using 1-hydroxybenzotriazole hydrate (79.3 mg, 0.518 mmol), 1-[3-(dimethylamino)propyl]-3-ethylcarbodiimide hydrochloride (64.2 mg, 0.335 mmol) and diethanolamine (0.0290 mL, 0.303 mmol).

$^1$H-NMR (270 MHz, $CDCl_3$) δ (ppm): 1.16 (t, J=7.4 Hz, 3H), 2.64 (q, J=7.4 Hz, 2H), 2.75-2.85 (m, 2H), 2.90-3.00 (m, 2H), 3.24 (s, 3H), 3.52 (s, 3H), 3.54-3.66 (m, 4H), 3.74-3.88 (m, 4H), 4.95 (s, 2H), 5.13 (br s, 2H), 5.22 (s, 2H), 6.85 (s, 1H), 7.15-7.45 (m, 5H), 7.65 (s, 1H).

(Step 2)

In the same manner as in the step 2 in Example 25, Compound 224 (8.1 mg, 27%) was obtained from 5-{2-[2-ethyl-3,5-bis(methoxymethoxy)-6-phenylphenyl]ethyl}-N,N-bis(2-hydroxyethyl)-1,3-oxazole-4-carboxamide (36.3 mg, 0.687 mmol) obtained in the above, using ethanol (6 mL) and concentrated hydrochloric acid (0.2 mL).

$^1$H-NMR (270 MHz, $CDCl_3/CD_3OD$) δ (ppm): 1.11 (t, J=7.3 Hz, 3H), 2.42 (q, J=7.3 Hz, 2H), 2.75 (t, J=7.6 Hz, 2H), 3.20-2.80 (m, 2H), 3.45-3.60 (m, 4H), 3.77 (t, J=5.0 Hz, 4H), 6.32 (s, 1H), 7.20-7.50 (m, 5H), 7.71 (s, 1H);

ESI-MS (m/z): 441 (M+H)$^+$.

EXAMPLE 225

5-[2-(2-ethyl-3,5-dihydroxy-6-phenylphenyl)ethyl]-N-[2-hydroxy-1-(hydroxymethyl)ethyl]-1,3-oxazole-4-carboxamide (Compound 225)

(Step 1)

In the same manner as in the step 2 in Example 222, 5-{2-[2-ethyl-3,5-bis(methoxymethoxy)-6-phenylphenyl]ethyl}-N-[2-hydroxy-1-(hydroxymethyl)ethyl]-1,3-oxazole-4-carboxamide (39.7 mg, 64%) was obtained from 5-{2-[2-ethyl-3,5-bis(methoxymethoxy)-6-phenylphenyl]ethyl}-1,3-oxazole-4-carboxylic acid (54.2 mg, 0.123 mmol) obtained in the step 1 in Example 222, using 1-hydroxybenzotriazole hydrate (91.3 mg, 0.596 mmol), 1-[3-(dimethylamino)propyl]-3-ethylcarbodiimide hydrochloride (56.7 mg, 0.296 mmol) and 2-aminopropane-1,3-diol (31.9 mg, 0.350 mmol).

$^1$H-NMR (270 MHz, CDCl$_3$) δ (ppm): 1.17 (t, J=7.3 Hz, 3H), 2.64-2.84 (m, 4H), 2.95 (br s, 2H), 3.04-3.16 (m, 2H), 3.24 (s, 3H), 3.53 (s, 3H), 3.76-3.94 (m, 4H), 3.95-4.05 (m, 1H), 4.95 (s, 2H), 5.23 (s, 2H), 6.86 (s, 1H), 7.15-7.45 (m, 6H), 7.55 (s, 1H).

(Step 2)

In the same manner as in the step 2 in Example 25, Compound 225 (24.6 mg, 75%) was obtained from 5-{2-[2-ethyl-3,5-bis(methoxymethoxy)-6-phenylphenyl]ethyl}-N-[2-hydroxy-1-(hydroxymethyl)ethyl]-1,3-oxazole-4-carboxamide (39.7 mg, 0.0772 mmol) obtained in the above, using ethanol (6 mL) and concentrated hydrochloric acid (0.2 mL).

$^1$H-NMR (300 MHz, CDCl$_3$/CD$_3$OD) δ (ppm): 1.17 (t, J=7.4 Hz, 3H), 2.64 (q, J=7.4 Hz, 2H), 2.70-2.80 (m, 2H), 3.00-3.20 (m, 2H), 3.60-3.85 (m, 4H), 3.85-4.00 (m, 1H), 6.35 (s, 1H), 7.20-7.50 (m, 5H), 7.60 (s, 1H);

ESI-MS (m/z): 427 (M+H)$^+$.

EXAMPLE 226

N-(2,3-dihydroxypropyl)-5-[2-(2-ethyl-3,5-dihydroxy-6-phenylphenyl)ethyl]-1,3-oxazole-4-carboxamide (Compound 226)

(Step 1)

In the same manner as in the step 2 in Example 222, 5-{2-[2-ethyl-3,5-bis(methoxymethoxy)-6-phenylphenyl]ethyl}-1,3-oxazole-4-carboxylic acid (54.2 mg, 0.123 mmol) obtained in the step 1 in Example 222 was dissolved in N,N-dimethylformamide (4 mL), and 1-hydroxybenzotriazole hydrate (88.9 mg, 0.581 mmol), 1-[3-(dimethylamino)propyl]-3-ethylcarbodiimide hydrochloride (59.9 mg, 0.312 mmol) and 3-amino-1,2-propanediol (0.0230 mL, 0.297 mmol) were added thereto and stirred at room temperature for 18 hours. Water was added to the reaction mixture, and extracted with ethyl acetate. The organic layer was washed three times with aqueous saturated sodium chloride solution, and dried over anhydrous sodium sulfate, and the solvent was evaporated away under reduced pressure. The resulting residue was purified through preparative thin-layer chromatography (chloroform/methanol=9/1) to obtain N-(2,3-dihydroxypropyl)-5-{2-[2-ethyl-3,5-bis(methoxymethoxy)-6-phenylphenyl]ethyl}-1,3-oxazole-4-carboxamide (24.7 mg, 40%).

$^1$H-NMR (270 MHz, CDCl$_3$) δ (ppm): 1.18 (t, J=7.4 Hz, 3H), 2.66-2.84 (m, 4H), 3.25 (s, 3H), 3.00-3.30 (m, 4H), 3.53 (s, 3H), 3.40-3.60 (m, 2H), 3.75-3.85 (m, 1H), 4.95 (s, 2H), 5.23 (s, 2H), 6.87 (s, 1H), 7.15-7.45 (m, 6H), 7.56 (s, 1H).

(Step 2)

In the same manner as in the step 2 in Example 25, N-(2,3-dihydroxypropyl)-5-{2-[2-ethyl-3,5-bis(methoxymethoxy)-6-phenylphenyl]ethyl}-1,3-oxazole-4-carboxamide (24.7 mg, 0.0480 mmol) obtained in the above was dissolved in methanol (6 mL), and concentrated hydrochloric acid (0.2 mL) was added thereto and stirred at 60° C. for 1.2 hours. The reaction mixture was concentrated under reduced pressure, and the resulting residue was purified through preparative thin-layer chromatography (chloroform/methanol/water=90/10/1) to obtain Compound 226 (16.4 mg, 80%).

$^1$H-NMR (270 MHz, CDCl$_3$/CD$_3$OD) δ (ppm): 1.10-1.26 (m, 3H), 2.60-2.80 (m, 4H), 3.02-3.14 (m, 2H), 3.30-3.80 (m, 5H), 6.35 (s, 1H), 7.20-7.50 (m, 5H), 7.64 (s, 1H);

ESI-MS (m/z): 427 (M+H)$^+$.

EXAMPLE 227

5-{([(4S,5S)-4,5-bis(hydroxymethyl)-1,3-dioxolan-2-yl]methyl}-6-ethyl-4-phenylbenzene-1,3-diol (Compound 227)

(Step 1)

In the same manner as in the step 2 in Example 218, 1,5-bis(benzyloxy)-3-{[(4S,5S)-4,5-bis(benzyloxy)-1,3-dioxolan-2-yl]methyl}-4-ethyl-2-phenylbenzene (1.10 g, 74%) was obtained from 2-[3,5-bis(benzyloxy)-2-ethyl-6-phenylphenyl]ethanal (900 mg, 2.06 mmol) obtained in the step 1 in Example 218, using (−)-1,4-di-O-benzyl-L-threitol (1.00 g, 3.31 mmol) and DL-10-camphorsulfonic acid (151 mg, 0.649 mmol).

$^1$H-NMR (300 MHz, CDCl$_3$) δ (ppm): 1.15 (t, J=7.3 Hz, 3H), 2.82 (q, J=7.3 Hz, 2H), 2.87-3.05 (m, 2H), 3.48-3.56 (m, 4H), 3.75-4.00 (m, 2H), 4.48 (s, 2H), 4.50 (s, 2H), 4.86 (s, 2H), 5.00-5.10 (m, 1H), 5.03 (s, 2H), 6.54 (s, 1H), 7.00-7.50 (m, 25H).

(Step 2)

In the same manner as in the step 3 in Example 218, 1,5-bis(benzyloxy)-3-{[(4S,5S)-4,5-bis(benzyloxy)-1,3-dioxolan-2-yl]methyl}-4-ethyl-2-phenylbenzene (1.09 g, 1.51 mmol) obtained in the above was dissolved in ethyl acetate (20 mL), and 10% palladium-carbon (142 mg) was added thereto, and stirred in a hydrogen atmosphere at room temperature for 6 hours. The reaction mixture was filtered, and the filtrate was concentrated under reduced pressure. The resulting residue was purified through silica gel column chromatography (chloroform/methanol/water 100/10/1) to obtain Compound 227 (442 mg, 81%).

$^1$H-NMR (300 MHz, DMSO-d$_6$) δ (ppm): 1.00 (t, J=7.2 Hz, 3H), 2.57 (q, J=7.2 Hz, 2H), 2.65 (d, J=5.1 Hz, 2H), 3.25-3.45 (m, 4H), 3.50-3.65 (m, 2H), 4.70-4.82 (m, 3H), 6.35 (s, 1H), 7.04-7.14 (m, 2H), 7.18-7.36 (m, 3H), 8.60 (br s, 1H), 9.02 (br s, 1H);

APCI-MS (m/z): 359 (M−H)$^−$.

EXAMPLE 228

5-{[(4R,5R)-4,5-bis(hydroxymethyl)-1,3-dioxolan-2-yl]methyl}-6-ethyl-4-(3-methylphenyl)benzene-1,3-diol (Compound 228)

(Step 1)

Methyl 3,5-bis(benzyloxy)-2-ethylphenylacetate (2.21 g, 5.66 mmol) obtained in the step 1 in Example 179 was dissolved in chloroform (30 mL), and the solution was cooled to 0° C., and then iodine (1.82 g, 7.18 mmol) and [bis(trifluoroacetoxy)iodo]benzene (2.97 g, 6.91 mmol) were added thereto and stirred at the same temperature for 0.5 hour. Aqueous saturated sodium hydrogencarbonate solution and aqueous saturated sodium thiosulfate solution were added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through silica gel column chromatography (n-hexane/ethyl acetate=20/1 to 9/1) to obtain methyl 3,5-bis(benzyloxy)-2-ethyl-6-iodophenylacetate (1.26 g, 43%).

$^1$H-NMR (300 MHz, CDCl$_3$) δ (ppm): 1.08 (t, J=7.5 Hz, 3H), 2.73 (q, J=7.5 Hz, 2H), 3.72 (s, 3H), 4.05 (s, 2H), 5.02 (s, 2H), 5.07 (s, 2H), 6.49 (s, 1H), 7.25-7.50 (m, 5H).

(Step 2)

Methyl 3,5-bis(benzyloxy)-2-ethyl-6-iodophenylacetate (645 mg, 1.25 mmol) obtained in the above was dissolved in a mixed solvent of 1,2-dimethoxyethane (10 mL) and water (0.5 mL), and 3-methylphenylboronic acid (322 mg, 2.37 mmol), cesium carbonate (1.58 g, 4.85 mmol) and bis(tri-o-tolylphosphine)palladium(II) dichloride (101 mg, 0.129 mmol) were added thereto and stirred with heating under reflux for 15 hours. The reaction mixture was filtered, water was added to the filtrate, and extracted with ethyl acetate. The organic layer was washed with aqueous saturated sodium chloride solution, and dried over anhydrous sodium sulfate, and the solvent was evaporated away under reduced pressure. The resulting residue was purified through silica gel column chromatography (n-hexane/ethyl acetate=20/1 to 9/1) to obtain methyl 3,5-bis(benzyloxy)-2-ethyl-6-(3-methylphenyl)phenylacetate (488 mg, 81%).

$^1$H-NMR (300 MHz, CDCl$_3$) δ (ppm): 1.12 (t, J=7.4 Hz, 3H), 2.36 (s, 3H), 2.66 (q, J=7.4 Hz, 2H), 3.50 (s, 2H), 3.60 (s, 3H), 4.90 (s, 2H), 5.05 (s, 2H), 6.59 (s, 1H), 7.00-7.45 (m, 14H).

(Step 3)

Methyl 3,5-bis(benzyloxy)-2-ethyl-6-(3-methylphenyl)phenylacetate (483 mg, 1.01 mmol) obtained in the above was dissolved in tetrahydrofuran (10 mL), and the solution was cooled to 0° C., and toluene solution of 1.01 mol/L diisobutylaluminium hydride (3.00 mL, 3.03 mmol) was added thereto and stirred at the same temperature for 1.5 hours. Anhydrous sodium sulfate and aqueous saturated sodium sulfate solution were added to the reaction mixture, and stirred at room temperature for 2 hours, then filtered, and the filtrate was concentrated under reduced pressure. The resulting residue was purified through silica gel column chromatography (n-hexane/ethyl acetate=9/1 to 4/1 to 2/1) to obtain 2-[3,5-bis(benzyloxy)-2-ethyl-6-(3-methylphenyl)phenyl]ethanol (403 mg, 88%).

$^1$H-NMR (300 MHz, CDCl$_3$) δ (ppm): 1.14 (br s, 1H), 1.18 (t, J=7.3 Hz, 3H), 2.38 (s, 3H), 2.70-2.86 (m, 4H), 3.50-3.62 (m, 2H), 4.89 (s, 2H), 5.04 (s, 2H), 6.53 (s, 1H), 7.00-7.50 (m, 14H).

(Step 4)

In the same manner as in the step 1 in Example 218, 2-[3,5-bis(benzyloxy)-2-ethyl-6-(3-methylphenyl)phenyl]ethanal (202 mg, 52%) was obtained from 2-[3,5-bis(benzyloxy)-2-ethyl-6-(3-methylphenyl)phenyl]ethanol (393 mg, 0.868 mmol) obtained in the above, using pyridinium dichromate (1.01 g, 2.69 mmol).

$^1$H-NMR (300 MHz, CDCl$_3$) δ (ppm): 1.10 (t, J=7.5 Hz, 3H), 2.36 (s, 3H), 2.62 (q, J=7.5 Hz, 2H), 3.59 (d, J=1.6 Hz, 2H), 4.92 (s, 2H), 5.06 (s, 2H), 6.60 (s, 1H), 6.90-7.45 (m, 14H), 9.56 (t, J=1.6 Hz, 1H).

(Step 5)

In the same manner as in the step 2 in Example 218, 1,5-bis(benzyloxy)-3-{[(4R,5R)-4,5-bis(benzyloxy)-1,3-dioxolan-2-yl]methyl}-4-ethyl-2-(3-(methylphenyl)benzene (94.7 mg, 60%) was obtained from 2-[3,5-bis(benzyloxy)-2-ethyl-6-(3-methylphenyl)phenyl]ethanal (96.3 mg, 0.214 mmol), using (+)-1,4-di-O-benzyl-D-threitol (312 mg, 1.03 mmol) and DL-10-camphorsulfonic acid (44.5 mg, 0.192 mmol).

$^1$H-NMR (270 MHz, CDCl$_3$) δ (ppm): 1.14 (t, J=7.4 Hz, 3H), 2.26-2.36 (m, 3H), 2.82 (q, J=7.4 Hz, 2H), 2.90-3.00 (m, 2H), 3.40-3.60 (m, 4H), 3.75-4.00 (m, 2H), 4.44-4.54 (m, 4H), 4.87 (s, 2H), 5.00-5.10 (m, 1H), 5.03 (s, 2H), 6.53 (s, 1H), 7.20-7.50 (m, 24H).

(Step 6)

1,5-Bis(benzyloxy)-3-{[(4R,5R)-4,5-bis(benzyloxy)-1,3-dioxolan-2-yl]methyl}-4-ethyl-2-(3-(methylphenyl)benzene (90.4 mg, 0.123 mmol) obtained in the above was dissolved in ethyl acetate (15 mL), and 10% palladium-carbon (30.3 mg) was added thereto and stirred under hydrogen pressure (0.35 MPa) at room temperature for 48 hours. The reaction mixture was filtered, and the filtrate was concentrated under reduced pressure. The resulting residue was purified through preparative thin-layer chromatography (chloroform/methanol/water=100/10/1) to obtain Compound 228 (43.7 mg, 95%).

$^1$H-NMR (300 MHz, CD$_3$OD) δ (ppm): 1.09 (t, J=7.3 Hz, 3H), 2.35 (s, 3H), 2.70 (q, J=7.3 Hz, 2H), 2.76-2.86 (m, 2H), 3.40-3.60 (m, 4H), 3.60-3.80 (m, 2H), 4.90-5.00 (m, 1H), 6.31 (s, 1H), 6.97 (br d, J=7.5 Hz, 1H), 7.01 (br s, 1H), 7.09 (br d, J=7.5 Hz, 1H), 7.24 (br dd, J=7.5, 7.5 Hz, 1H);

APCI-MS (m/z): 373 (M−H)$^−$.

EXAMPLE 229

5-{[(4S,5S)-4,5-bis(hydroxymethyl)-1,3-dioxolan-2-yl]methyl}-6-ethyl-4-(3-methylphenyl)benzene-1,3-diol (Compound 229)

(Step 1)

In the same manner as in the step 2 in Example 218, 1,5-bis(benzyloxy)-3-{[(4S,5S)-4,5-bis(benzyloxy)-1,3-dioxolan-2-yl]methyl}-4-ethyl-2-(3-(methylphenyl)benzene (106 mg, 65%) was obtained from 2-[3,5-bis(benzyloxy)-2-ethyl-6-(3-methylphenyl)phenyl]ethanal (100 mg, 0.223 mmol) obtained in the step 4 in Example 228, using (−)-1,4-di-O-benzyl-L-threitol (318 mg, 1.05 mmol) and DL-10-camphorsulfonic acid (40.5 mg, 0.174 mmol).

$^1$H-NMR (270 MHz, CDCl$_3$) δ (ppm): 1.14 (t, J=7.4 Hz, 3H), 2.26-2.36 (m, 3H), 2.82 (q, J=7.4 Hz, 2H), 2.90-3.00 (m, 2H), 3.40-3.60 (m, 4H), 3.75-4.00 (m, 2H), 4.44-4.54 (m, 4H), 4.87 (s, 2H), 5.00-5.10 (m, 1H), 5.03 (s, 2H), 6.53 (s, 1H), 7.20-7.50 (m, 24H).

(Step 2)

1,5-Bis(benzyloxy)-3-{[(4S,5S)-4,5-bis(benzyloxy)-1,3-dioxolan-2-yl]methyl}-4-ethyl-2-(3-(methylphenyl)benzene (106 mg, 0.145 mmol) obtained in the above was dissolved in ethyl acetate (15 mL), and 10% palladium-carbon (32.3 mg) was added thereto and stirred under hydrogen pressure (0.35 MPa) at room temperature for 48 hours. The reaction mixture was filtered, and the filtrate was concentrated under reduced pressure. The resulting residue was purified through preparative thin-layer chromatography (chloroform/methanol/water=100/10/1) to obtain Compound 229 (48.7 mg, 90%).

$^1$H-NMR (300 MHz, CD$_3$OD) δ (ppm): 1.09 (t, J=7.3 Hz, 3H), 2.35 (s, 3H), 2.70 (q, J=7.3 Hz, 2H), 2.76-2.86 (m, 2H), 3.40-3.60 (m, 4H), 3.60-3.80 (m, 2H), 4.90-5.00 (m, 1H), 6.31 (s, 1H), 6.97 (br d, J=7.5 Hz, 1H), 7.01 (br s, 1H), 7.09 (br d, J=7.5 Hz, 1H), 7.24 (br dd, J=7.5, 7.5 Hz, 1H);

APCI-MS (m/z): 373 (M−H)$^−$.

EXAMPLE 230

5-{[(4R,5R)-4,5-bis(hydroxymethyl)-1,3-dioxolan-2-yl]methyl}-4-phenylbenzene-1,3-diol
(Compound 230)

(Step 1)

Compound 1 (1.81 g, 7.00 mmol) obtained in Example 1 was dissolved in acetone (50 mL), and potassium carbonate (5.88 g, 42.6 mmol) and benzyl bromide (3.33 mL, 28.0 mmol) were added thereto and stirred with heating under reflux for 1.5 hours. Water was added to the reaction mixture, and extracted with ethyl acetate. The organic layer was washed with aqueous saturated sodium chloride solution, and dried over anhydrous sodium sulfate, and the solvent was evaporated away under reduced pressure. The residue was purified through silica gel column chromatography (n-hexane/ethyl acetate=20/1 to 9/1) to obtain methyl 3,5-bis(benzyloxy)-2-phenylphenylacetate (2.58 g, 84%).

$^1$H-NMR (270 MHz, CDCl$_3$) δ (ppm): 3.43 (s, 2H), 3.58 (s, 3H), 4.96 (s, 2H), 5.05 (s, 2H), 6.59 (d, J=2.5 Hz, 1H), 6.61 (d, J=2.5 Hz, 1H), 7.05-7.50 (m, 15H).

(Step 2)

Methyl 3,5-bis(benzyloxy)-2-phenylphenylacetate (2.58 g, 5.88 mmol) obtained in the above was dissolved in tetrahydrofuran (40 mL), and the solution was cooled to 0° C., and toluene solution of 1.01 mol/L diisobutylaluminium hydride (15.0 mL, 15.2 mmol) was added thereto and stirred at the same temperature for 1 hour. Anhydrous sodium sulfate and aqueous saturated sodium sulfate solution were added to the reaction mixture, and stirred at room temperature for 2 hours. Then, the mixture was filtered, and the filtrate was concentrated under reduced pressure. The resulting residue was purified through silica gel column chromatography (n-hexane/ethyl acetate=4/1 to 2/1) to obtain 2-[3,5-bis(benzyloxy)-2-phenylphenyl]ethanol (2.38 g, 99%).

$^1$H-NMR (300 MHz, CDCl$_3$) δ (ppm): 1.21 (t, J=6.0 Hz, 1H), 2.70 (t, J=6.8 Hz, 2H), 3.63 (dt, J=6.0, 6.8 Hz, 2H), 4.95 (s, 2H), 5.06 (s, 2H), 6.56 (d, J=2.4 Hz, 1H), 6.60 (d, J=2.4 Hz, 1H), 7.05-7.50 (m, 15H).

(Step 3)

2-[3,5-Bis(benzyloxy)-2-phenylphenyl]ethanol (2.40 g, 5.84 mmol) obtained in the above was dissolved in dichloromethane (40 mL), and pyridinium dichromate (5.16 g, 13.7 mmol) was added thereto and stirred with heating under reflux for 5 hours. The reaction mixture was filtered, and the filtrate was concentrated under reduced pressure. The resulting residue was purified through silica gel column chromatography (n-hexane/ethyl acetate=20/1 to 9/1) to obtain 2-[3,5-bis(benzyloxy)-2-phenylphenyl]ethanal (725 mg, 30%).

$^1$H-NMR (300 MHz, CDCl$_3$) δ (ppm): 3.50 (d, J=2.0 Hz, 2H), 4.98 (s, 2H), 5.05 (s, 2H), 6.50 (d, J=2.4 Hz, 1H), 6.62 (d, J=2.4 Hz, 1H), 7.05-7.50 (m, 15H), 9.55 (d, J=2.0 Hz, 1H).

(Step 4)

2-[3,5-Bis(benzyloxy)-2-phenylphenyl]ethanal (721 mg, 1.77 mmol) obtained in the above was dissolved in toluene (38 mL), and (+)-1,4-di-O-benzyl-D-threitol (1.00 g, 3.31 mmol) and DL-10-camphorsulfonic acid (122 mg, 0.597 mmol) were added thereto and stirred with heating under reflux for 4 hours. Water and aqueous saturated sodium hydrogencarbonate solution were added to the reaction mixture, and extracted with ethyl acetate. The organic layer was washed with aqueous saturated sodium chloride solution, and dried over anhydrous sodium sulfate, and the solvent was evaporated away under reduced pressure. The resulting residue was purified through silica gel column chromatography (n-hexane/ethyl acetate=20/1 to 9/1) to obtain 3,5-bis(benzyloxy)-1-{[(4R,5R)-4,5-bis(benzyloxy)-1,3-dioxolan-2-yl]methyl}-2-phenylbenzene (1.01 g, 82%).

$^1$H-NMR (300 MHz, CDCl$_3$) δ (ppm): 2.75-2.82 (m, 2H), 3.40-3.60 (m, 4H), 3.90-4.10 (m, 2H), 4.52 (s, 4H), 4.93 (s, 2H), 5.02 (s, 2H), 5.12 (t, J=5.0 Hz, 1H), 6.54 (d, J=2.4 Hz, 1H), 6.73 (d, J=2.4 Hz, 1H), 7.00-7.50 (m, 25H).

(Step 5)

3,5-bis(benzyloxy)-1-{[(4R,5R)-4,5-bis(benzyloxy)-1,3-dioxolan-2-yl]methyl}-2-phenylbenzene (342 mg, 0.494 mmol) obtained in the above was dissolved in ethyl acetate (10 mL), and 10% palladium-carbon (59.7 mg) was added thereto and stirred in a hydrogen atmosphere at room temperature for 5 hours. The reaction mixture was filtered, and the filtrate was concentrated under reduced pressure. The resulting residue was purified through preparative thin-layer chromatography (chloroform/methanol/water=100/10/1) to obtain Compound 230 (139 mg, 85%).

$^1$H-NMR (300 MHz, CD$_3$OD) δ (ppm): 2.55-2.70 (m, 2H), 3.50-3.60 (m, 4H), 3.70-3.85 (m, 2H), 5.04 (t, J=5.1 Hz, 1H), 6.26 (d, J=2.4 Hz, 1H), 6.43 (d, J=2.4 Hz, 1H), 7.15-7.40 (m, 5H);

APCI-MS (m/z): 331 (M−H)$^−$.

EXAMPLE 231

5-{[(4R,5R)-4,5-bis(hydroxymethyl)-1,3-dioxolan-2-yl]methyl}-2,6-dibromo-4-phenylbenzene-1,3-diol
(Compound 231)

Compound 230 (76.3 mg, 0.230 mmol) obtained in Example 230 was dissolved in N,N-dimethylformamide (10 mL), and the solution was cooled to 0° C., and N-bromosuccinimide (46.2 mg, 0.260 mmol) was added thereto and stirred at the same temperature for 1 hour. The reaction mixture was concentrated under reduced pressure, and the resulting residue was purified through preparative thin-layer chromatography (chloroform/methanol/water=100/10/1) to obtain Compound 231 (36.1 mg, 32%) and Compound 232 (48.0 mg, 51%).

Compound 231:

$^1$H-NMR (270 MHz, CD$_3$OD) δ (ppm): 2.91 (d, J=5.4 Hz, 2H), 3.40-3.80 (m, 6H), 5.30 (t, J=5.4 Hz, 1H), 7.15-7.45 (m, 5H);

APCI-MS (m/z): 487, 489, 491 (M−H)$^−$.

EXAMPLE 232

5-{[(4R,5R)-4,5-bis(hydroxymethyl)-1,3-dioxolan-2-yl]methyl}-6-bromo-4-phenylbenzene-1,3-diol
(Compound 232)

As in Example 231, Compound 232 was obtained.

$^1$H-NMR (270 MHz, CD$_3$OD) δ (ppm): 2.93 (d, J=5.4 Hz, 2H), 3.40-3.80 (m, 6H), 5.32 (t, J=5.4 Hz, 1H), 6.46 (s, 1H), 7.15-7.40 (m, 5H);

APCI-MS (m/z): 409, 411 (M−H)$^−$.

EXAMPLE 233

5-{[(4S,5S)-4,5-Bis(hydroxymethyl)-1,3-dioxolan-2-yl]methyl}-6-ethyl-4-(3-methoxyphenyl)benzene-1,3-diol (Compound 233)

(Step 1)

Methyl 3,5-bis(benzyloxy)-2-ethylphenylacetate (8.46 g, 21.7 mmol) obtained in the step 1 in Example 179 was dissolved in tetrahydrofuran (100 mL), and the solution was cooled to 0° C., and toluene solution of 1.01 mol/L diisobutylaluminium hydride (57.0 mL, 57.6 mmol) was added thereto and stirred at the same temperature for 1 hour. Anhydrous sodium sulfate and aqueous saturated sodium sulfate solution were added to the reaction mixture, and stirred at room temperature for 2 hours, and then filtered. The filtrate was concentrated under reduced pressure. The resulting residue was purified through silica gel column chromatography (n-hexane/ethyl acetate=4/1 to 2/1) to obtain 2-[3,5-bis(benzyloxy)-2-ethylphenyl]ethanol (7.52 g, 96%).

$^1$H-NMR (270 MHz, CDCl$_3$) δ (ppm): 1.12 (t, J=7.5 Hz, 3H), 1.41 (br s, 1H), 2.68 (q, J=7.5 Hz, 2H), 2.89 (t, J=6.8 Hz, 2H), 3.83 (br dt, J=6.4, 6.8 Hz, 2H), 5.01 (s, 2H), 5.03 (s, 2H), 6.45 (d, J=2.5 Hz, 1H), 6.50 (d, J=2.5 Hz, 1H), 7.25-7.45 (m, 10H).

(Step 2)

2-[3,5-Bis(benzyloxy)-2-ethylphenyl]ethanol (630 mg, 1.74 mmol) obtained in the above was dissolved in dichloromethane (50 mL), and pyridinium dichromate (2.63 g, 6.98 mmol) was added thereto and stirred at room temperature for 48 hours. The reaction mixture was filtered, and the filtrate was concentrated under reduced pressure. The resulting residue was purified through silica gel column chromatography (n-hexane/ethyl acetate=20/1 to 9/1) to obtain 2-[3,5-bis(benzyloxy)-2-ethylphenyl]ethanal (137 mg, 22%).

$^1$H-NMR (300 MHz, CDCl$_3$) δ (ppm): 1.09 (t, J=7.5 Hz, 3H), 2.64 (q, J=7.5 Hz, 2H), 3.68 (d, J=2.3 Hz, 2H), 5.01 (s, 2H), 5.04 (s, 2H), 6.41 (d, J=2.4 Hz, 1H), 6.57 (d, J=2.4 Hz, 1H), 7.28-7.45 (m, 10H), 9.70 (t, J=2.3 Hz, 1H).

(Step 3)

2-[3,5-Bis(benzyloxy)-2-ethylphenyl]ethanal (135 mg, 0.374 mmol) obtained in the above was dissolved in toluene (20 mL), and (−)-1,4-di-O-benzyl-L-threitol (445 mg, 1.47 mmol) and DL-10-camphorsulfonic acid (34.8 mg, 0.150 mmol) were added thereto and stirred with heating under reflux for 3 hours. Water and aqueous saturated sodium hydrogencarbonate solution were added thereto and extracted with ethyl acetate. The organic layer was washed with aqueous saturated sodium chloride solution, then dried over anhydrous sodium sulfate, and the solvent was evaporated away under reduced pressure. The resulting residue was purified through silica gel column chromatography (n-hexane/ethyl acetate=20/1 to 9/1) to obtain 3,5-bis(benzyloxy)-1-{[(4S,5S)-4,5-bis(benzyloxy)-1,3-dioxolan-2-yl]methyl}-2-ethylbenzene (225 mg, 93%).

$^1$H-NMR (270 MHz, CDCl$_3$) δ (ppm): 1.09 (t, J=7.4 Hz, 3H), 2.71 (q, J=7.4 Hz, 2H), 3.01 (d, J=4.9 Hz, 2H), 3.50-3.64 (m, 4H), 4.00-4.10 (m, 2H), 4.55 (s, 2H), 4.56 (s, 2H), 4.97 (s, 2H), 5.01 (s, 2H), 5.26 (t, J=4.9 Hz, 1H), 6.49 (d, J=2.5 Hz, 1H) 6.55 (d, J=2.5 Hz, 1H), 7.20-7.45 (m, 20H).

(Step 4)

3,5-Bis(benzyloxy)-1-{[(4S,5S)-4,5-bis(benzyloxy)-1,3-dioxolan-2-yl]methyl}-2-ethylbenzene (129 mg, 0.201 mmol) obtained in the above was dissolved in chloroform (10 mL), and the solution was cooled to 0° C., and iodine (61.6 mg, 0.243 mmol) and [bis(trifluoroacetoxy)iodo]benzene (105 mg, 0.243 mmol) were added thereto and stirred at the same temperature for 0.5 hour. Aqueous saturated sodium hydrogencarbonate solution and aqueous saturated sodium thiosulfate solution were added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=20/1 to 9/1) to obtain 1,5-bis(benzyloxy)-3-{([(4S,5S)-4,5-bis(benzyloxy)-1,3-dioxolan-2-yl]methyl}-4-ethyl-2-iodobenzene (126 mg, 82%).

$^1$H-NMR (300 MHz, CDCl$_3$) δ (ppm): 1.07 (t, J=7.4 Hz, 3H), 2.88 (q, J=7.4 Hz, 2H), 3.38 (d, J=5.4 Hz, 2H), 3.50-3.70 (m, 4H), 4.00-4.20 (m, 2H), 4.55 (s, 2H), 4.58 (s, 2H), 5.00 (s, 2H), 5.05 (s, 2H), 5.41 (t, J=5.4 Hz, 1H), 6.44 (s, 1H), 7.20-7.50 (m, 20H).

(Step 5)

1,5-Bis(benzyloxy)-3-{[(4S,5S)-4,5-bis(benzyloxy)-1,3-dioxolan-2-yl]methyl}-4-ethyl-2-iodobenzene (80.5 mg, 0.104 mmol) obtained in the above was dissolved in a mixed solvent of 1,2-dimethoxyethane (10 mL) and water (0.5 mL), and 3-methoxyphenylboronic acid (43.7 mg, 0.288 mmol), cesium carbonate (212 mg, 0.650 mmol) and bis(tri-o-tolylphosphine)palladium(II) dichloride (14.9 mg, 0.0190 mmol) were added thereto and stirred with heating under reflux for 5 hours. The reaction mixture was filtered, then water was added to the filtrate and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=9/1) to obtain 1,5-bis(benzyloxy)-3-{[(4S,5S)-4,5-bis(benzyloxy)-1,3-dioxolan-2-yl]methyl}-4-ethyl-2-(3-methoxyphenyl)benzene (55.2 mg, 71%).

$^1$H-NMR (300 MHz, CDCl$_3$) δ (ppm): 1.14 (t, J=7.3 Hz, 3H), 2.75-3.05 (m, 4H), 3.40-4.00 (m, 9H), 4.49 (s, 2H), 4.51 (s, 2H), 4.88 (s, 2H), 5.00-5.10 (m, 1H), 5.03 (s, 2H), 6.53 (s, 1H), 6.75-7.45 (m, 24H).

(Step 6)

1,5-Bis(benzyloxy)-3-{[(4S,5S)-4,5-bis(benzyloxy)-1,3-dioxolan-2-yl]methyl}-4-ethyl-2-(3-methoxyphenyl)benzene (55.2 mg, 0.0736 mmol) obtained in the above was dissolved in ethyl acetate (10 mL), and 10% palladium-carbon (30.1 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=100/10/1) to obtain Compound 233 (30.5 mg, 100%).

$^1$H-NMR (300 MHz, CD$_3$OD) δ (ppm): 1.09 (t, J=7.3 Hz, 3H), 2.71 (q, J=7.3 Hz, 2H), 2.82 (d, J=5.3 Hz, 2H), 3.50-3.77 (m, 6H), 3.79 (s, 3H), 4.95-5.05 (m, 1H), 6.31 (s, 1H), 6.70-6.78 (m, 2H), 6.80-6.88 (m, 1H), 7.20-7.30 (m, 1H);

APCI-MS (m/z): 389 (M−H)$^-$.

EXAMPLE 234

1-(6-{[(4R,5R)-4,5-bis(hydroxymethyl)-1,3-dioxolan-2-yl]methyl}-2,4-dihydroxy-5-phenylphenyl)ethanone (Compound 234)

(Step 1)

3,5-Bis(benzyloxy)-1-{[(4R,5R)-4,5-bis(benzyloxy)-1,3-dioxolan-2-yl]methyl}-2-phenylbenzene (333 mg, 0.481 mmol) obtained in the step 4 in Example 230 was dissolved in chloroform (10 mL), and the solution was cooled to 0° C., and iodine (162 mg, 0.640 mmol) and [bis(trifluoroacetoxy)iodo]benzene (276 mg, 0.642 mmol) were added thereto and stirred at the same temperature for 0.5 hour. Aqueous saturated sodium hydrogencarbonate solution and aqueous saturated sodium thiosulfate solution were added to the reaction mixture and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=20/1 to 9/1) to obtain 1,5-bis(benzyloxy)-3-{[(4R,5R)-4,5-bis(benzoyloxy)-1,3-dioxolan-2-yl]methyl}-4-iodo-2-phenylbenzene (330 mg, 84%).

$^1$H-NMR (300 MHz, CDCl$_3$) δ (ppm): 3.08-3.22 (m, 2H), 3.34-3.54 (m, 4H), 3.70-3.80 (m, 1H), 3.90-4.00 (m, 1H), 4.49 (s, 2H), 4.51 (s, 2H), 4.89 (s, 2H), 5.09 (s, 2H), 5.39 (t, J=5.4 Hz, 1H), 6.48 (s, 1H), 7.00-7.55 (m, 25H).

(Step 2)

1,5-Bis(benzyloxy)-3-{[(4R,5R)-4,5-bis(benzoyloxy)-1,3-dioxolan-2-yl]methyl}-4-iodo-2-phenylbenzene (327 mg, 0.400 mmol) obtained in the above was dissolved in toluene (10 mL), and tributyl(1-ethoxyvinyl)tin (0.300 mL, 0.888 mmol) and bis(tri-o-tolylphosphine)palladium(II) dichloride (67.9 mg, 0.0864 mmol) were added thereto and stirred with heating under reflux for 60 hours. Aqueous saturated ammonium fluoride solution was added to the reaction mixture, and stirred at room temperature for 2 hours, and then filtered. Water was added to the filtrate, and extracted with ethyl acetate. The organic layer was washed with aqueous saturated sodium chloride solution, then dried over anhydrous sodium sulfate, and the solvent was evaporated away under reduced pressure. The resulting residue was dissolved in toluene (15 mL), and DL-10-camphorsulfonic acid (41.0 mg, 0.177 mmol) was added thereto and stirred at room temperature for 1.5 hours. The reaction mixture was concentrated under reduced pressure, and the resulting residue was purified through silica gel column chromatography (n-hexane/ethyl acetate=20/1 to 9/1 to 4/1) to obtain 1-(4,6-bis(benzyloxy)-2-{[(4R,5R)-4,5-bis(hydroxymethyl)-1,3-dioxolan-2-yl]methyl}-3-phenylphenyl)ethanone (96.3 mg, 33%).

$^1$H-NMR (270 MHz, CDCl$_3$) δ (ppm): 2.54 (s, 3H), 2.90-3.00 (m, 2H), 3.38-3.58 (m, 4H), 3.70-4.00 (m, 2H), 4.47 (s, 4H), 4.85-4.95 (m, 1H), 4.92 (s, 2H), 5.02 (s, 2H), 6.48 (s, 1H), 7.00-7.40 (m, 25H).

(Step 3)

1-(4,6-Bis(benzyloxy)-2-{[(4R,5R)-4,5-bis(hydroxymethyl)-1,3-dioxolan-2-yl]methyl}-3-phenylphenyl)ethanone (91.3 mg, 0.124 mmol) obtained in the Above was dissolved in tetrahydrofuran (20 mL), and 10% palladium-carbon (26.3 mg) was added thereto and stirred under hydrogen pressure (0.35 MPa) at room temperature for 72 hours. The reaction mixture was filtered, the filtrate was concentrated under reduced pressure, and the residue was purified through preparative thin-layer chromatography (chloroform/methanol/water=100/10/1) to obtain Compound 234 (20.1 mg, 43%).

$^1$H-NMR (300 MHz, CD$_3$OD) δ (ppm): 2.57 (s, 3H), 2.80-2.96 (m, 2H), 3.50-3.80 (m, 6H), 4.80-4.90 (m, 1H), 6.35 (s, 1H), 7.10-7.40 (m, 5H);

APCI-MS (m/z): 373 (M−H)$^-$.

EXAMPLE 235

5-[6-(benzyloxymethyl)-2,4-dihydroxyphenyl]furan-2-carbaldehyde (Compound 235)

(Step 1)

[2-Bromo-3,5-bis(methoxymethoxy)phenyl]methanol (3.51 mg, 11.4 mmol) obtained according to the method described in Tetrahedron, Vol. 59, pp. 7345-7355 (2003) or methods similar thereto was dissolved in N,N-dimethylformamide (20 mL), and the solution was cooled to 0° C., then 60% sodium hydride/mineral oil dispersion (594 mg, 14.9 mmol) and benzyl bromide (2.00 mL, 16.8 mmol) were added thereto, heated up to room temperature, and stirred for 1 hour. Water and methanol were added to the reaction mixture, and extracted with chloroform. The organic layer was washed with aqueous saturated sodium chloride solution, and then dried over anhydrous sodium sulfate, and the solvent was evaporated away under reduced pressure. The resulting residue was purified through silica gel column chromatography (n-hexane/ethyl acetate=20/1 to 10/1) to obtain 1-(benzyloxymethyl)-3,5-bis(methoxymethoxy)-2-bromobenzene (3.16 g, 70%).

$^1$H-NMR (270 MHz, CDCl$_3$) δ (ppm): 3.47 (s, 3H), 3.57 (s, 3H), 4.61 (s, 2H), 4.64 (s, 2H), 5.10 (s, 2H), 5.23 (s, 2H), 6.81 (d, J=2.7 Hz, 1H), 6.97 (d, J=2.7 Hz, 1H), 7.20-7.50 (m, 5H).

(Step 2)

1-(Benzyloxymethyl)-3,5-bis(methoxymethoxy)-2-bromobenzene (500 mg, 1.26 mmol) obtained in the above was dissolved in toluene (30 mL), and triphenylphosphine (129 mg, 0.325 mmol), tris(dibenzylideneacetone)dipalladium (102 mg, 0.111 mmol) and tributyl[5-(1,3-dioxolan-2-yl)furan-2-yl]tin-(572 mg, 1.33 mmol) were added thereto and stirred at 100° C. for 10 hours. Aqueous saturated potassium fluoride solution was added to the reaction mixture, and stirred at room temperature for 1.5 hours, and then filtered. Water was added to the filtrate and extracted with chloroform. The organic layer was washed with aqueous sodium chloride solution, then dried over anhydrous sodium sulfate, and the solvent was evaporated away under reduced pressure. The resulting residue was dissolved in acetone (50 mL), and 1 mol/L hydrochloric acid (2.00 mL, 2.00 mmol) was added thereto and stirred at room temperature for one and half a hours. Aqueous saturated sodium hydrogencarbonate solution was added to the reaction mixture and extracted with chloroform. The organic layer was washed with aqueous saturated sodium chloride solution, then dried over anhydrous sodium sulfate, and the solvent was evaporated away under reduced pressure. The resulting residue was purified through silica gel column chromatography (n-hexane/ethyl acetate=10/1) to obtain 5-[6-(benzyloxymethyl)-2,4-bis(methoxymethoxy)]furan-2-carbaldehyde (321 mg, 62%).

$^1$H-NMR (270 MHz, CDCl$_3$) δ (ppm): 3.42 (s, 3H), 3.49 (s, 3H), 4.51 8s, 2H), 4.58 8s, 2H), 5.15 8s, 2H), 5.21 (s, 2H), 6.70 (d, J=3.6 Hz, 1H), 6.84 (d, J=2.3 Hz, 1H), 6.98 (d, J=2.3 Hz, 1H), 7.20-7.40 (m, 6H), 9.60 (s, 1H).

(Step 3)

5-[6-(Benzyloxymethyl)-2,4-bis(methoxymethoxy)]furan-2-carbaldehyde (70.4 mg, 0.171 mmol) obtained in the above was dissolved in ethanol (8 mL), and concentrated hydrochloric acid (0.2 mL) was added thereto and stirred at 60° C. for 1.2 hours. The reaction mixture was concentrated under reduced pressure, and the resulting residue was purified through preparative thin-layer chromatography (chloroform/methanol=20/1) to obtain Compound 235 (19.2 mg, 35%).

$^1$H-NMR (270 MHz, CDCl$_3$) δ (ppm): 4.52 (s, 2H), 4.54 (s, 2H), 5.23 (br s, 1H), 6.34 (br s, 1H), 6.45 (d, J=2.5 Hz, 1H), 6.66 (d, J=2.5 Hz, 1H), 6.78 (d, J=3.6 Hz, 1H), 7.20-7.40 (m, 6H), 9.61 (s, 1H);

APCI-MS (m/z): 323 (M−H)$^-$.

EXAMPLE 236

Ethyl 3-{5-[6-(benzyloxymethyl)-2,4-dihydroxyphenyl]furan-2-yl}propanoate (Compound 236)

(Step 1)

5-[6-(Benzyloxymethyl)-2,4-bis(methoxymethoxy)]furan-2-carbaldehyde (93.1 mg, 0.226 mmol) obtained in the step 2 in Example 235 was dissolved in toluene (10 mL), and methyl triphenylphospholanylidene-acetate (186 mg, 0.556 mmol) was added thereto and stirred at 80° C. for 2 hours. The reaction mixture was concentrated under reduced pressure, and the resulting residue was purified through preparative thin-layer chromatography (n-hexane/ethyl acetate=2/1) to obtain methyl 3-{5-[6-(benzyloxymethyl)-2,4-bis(methoxymethoxy)]furan-2-yl}acrylate (90.7 mg, 86%).

$^1$H-NMR (270 MHz, CDCl$_3$) δ (ppm): 3.42 (s, 3H), 3.49 (s, 3H), 3.79 (s, 3H), 4.51 (s, 2H), 4.59 (s, 2H), 5.14 (s, 2H), 5.21 (s, 2H), 6.24 (d, J=15.6 Hz, 1H), 6.59 (d, J=3.4 Hz, 1H), 6.69 (d, J=3.4 Hz, 1H), 6.83 (d, J=2.4 Hz, 1H), 7.02 (d, J=2.4 Hz, 1H), 7.20-7.40 (m, 5H), 7.44 (d, J=15.6 Hz, 1H).

(Step 2)

Methyl 3-{5-[6-(benzyloxymethyl)-2,4-bis(methoxymethoxy)]furan-2-yl}acrylate (62.8 mg, 0.134 mmol) obtained in the above was dissolved in tetrahydrofuran (1 mL) and methanol (10 mL), and magnesium (50.4 mg, 2.07 mmol) was added thereto and stirred at room temperature for 10 hours. Water was added to the reaction mixture, and extracted with diethyl ether. The organic layer was washed with aqueous saturated sodium chloride solution, and dried over anhydrous sodium sulfate, and the solvent was evaporated away under reduced pressure to obtain methyl 3-{5-[6-(benzyloxymethyl)-2,4-bis(methoxymethoxy)furan-2-yl}propanoate (60.0 mg, 95%).

$^1$H-NMR (270 MHz, CDCl$_3$) δ (ppm): 2.65 (t, J=7.7 Hz, 2H), 2.98 (t, J=7.7 Hz, 2H), 3.41 (s, 3H), 3.49 (s, 3H), 3.68 (s, 3H), 4.50 (s, 2H), 4.51 (s, 2H), 5.10 (s, 2H), 5.20 (s, 2H), 6.10 (d, J=3.0 Hz, 1H), 6.33 (d, J=3.0 Hz, 1H), 6.80 (d, J=2.2 Hz, 1H), 6.99 (d, J=2.2 Hz, 1H), 7.24-7.38 (m, 5H).

(Step 3)

Methyl 3-{5-[6-(benzyloxymethyl)-2,4-bis(methoxymethoxy)furan-2-yl}propanoate (42.1 mg, 0.134 mmol) was dissolved in ethanol (8 mL), and concentrated hydrochloric acid (0.2 mL) was added thereto and stirred at 60° C. for 1.2 hours. The reaction solution was concentrated under reduced pressure, and the resulting residue was purified through preparative thin-layer chromatography (chloroform/methanol=20/1) to obtain Compound 236 (12.7 mg, 25%).

$^1$H-NMR (270 MHz, CDCl$_3$) δ (ppm): 1.24 (t, J=7.2 Hz, 3H), 2.68 (t, J=7.2 Hz, 2H), 3.00 (t, J=7.2 Hz, 2H), 4.15 (q, J=7.2 Hz, 2H), 4.46 (s, 2H), 4.53 (s, 2H), 6.15 (d, J=3.3 Hz, 1H), 6.39 (d, J=3.3 Hz, 1H), 6.44 (d, J=2.4 Hz, 1H), 6.64 (d, J=2.4 Hz, 1H), 7.20-7.36 (m, 5H);

FAB-MS (m/z): 419 (M+Na)$^+$.

EXAMPLE 237

Methyl 3-{5-[2,4-dihydroxy-6-(1-methoxy-1-phenylmethyl)phenyl]furan-2-yl}propanoate (Compound 237)

(Step 1)

[2-Bromo-3,5-bis(methoxymethoxy)phenyl]methanol (974 mg, 3.17 mmol) obtained according to the method described in Tetrahedron, Vol. 59, pp. 7345-7355 (2003) or methods similar thereto was dissolved in toluene (50 mL), and triphenylphosphine (214 mg, 0.697 mmol), tris(dibenzylideneacetone)dipalladium (205 mg, 0.224 mmol) and tributyl[5-(1,3-dioxolan-2-yl)furan-2-yl]tin (926 mg, 2.16 mmol) were added thereto and stirred at 100° C. for 8 hours. Aqueous saturated potassium fluoride solution was added to the reaction mixture, and stirred at room temperature for 1.5 hours, and then filtered. Water was added to the filtrate, and extracted with chloroform. The organic layer was washed with aqueous saturated sodium chloride solution, then dried over anhydrous sodium sulfate, and the solvent was extracted out under reduced pressure. The resulting residue was purified through silica gel column chromatography (n-hexane/ethyl acetate=4/1) to obtain {2-[5-(1,3-dioxolan-2-yl)furan-2-yl]-3,5-bis(methoxymethoxy)phenyl}methanol (429 mg, 54%).

$^1$H-NMR (270 MHz, CDCl$_3$) δ (ppm): 2.40 (br t, J=7.1 Hz, 1H), 3.42 (s, 3H), 3.48 8s, 3H), 3.90-4.30 (m, 4H), 4.58 (d, J=7.1 Hz, 2H), 5.13 (s, 2H), 5.20 (s, 2H), 5.94 (s, 1H), 6.53 (d, J=3.3 Hz, 1H), 6.55 (d, J=3.3 Hz, 1H), 6.82 (d, J=2.5 Hz, 1H), 6.90 (d, J=2.5 Hz, 1H).

(Step 2)

{2-[5-(1,3-Dioxolan-2-yl)furan-2-yl]-3,5-bis(methoxymethoxy)phenyl}methanol (151 mg, 0.413 mmol) obtained in the above was dissolved in dichloromethane (20 mL), and manganese dioxide (486 mg, 5.58 mmol) was added thereto and stirred at room temperature for 24 hours. The reaction mixture was filtered, and the filtrate was concentrated under reduced pressure to obtain 2-[5-(1,3-dioxolan-2-yl)furan-2-yl]-3,5-bis(methoxymethoxy)benzaldehyde (143 mg, 96%).

$^1$H-NMR (270 MHz, CDCl$_3$) δ (ppm): 3.45 (s, 3H), 3.49 (s, 3H), 3.90-4.20 (m, 4H), 5.18 (s, 2H), 5.23 (s, 2H), 5.96 (s, 1H), 6.58 (d, J=3.4 Hz, 1H), 6.61 (d, J=3.4 Hz, 1H), 7.08 (d, J=2.5 Hz, 1H), 7.29 (d, J=2.5 Hz, 1H), 10.00 (s, 1H).

(Step 3)

2-[5-(1,3-Dioxolan-2-yl)furan-2-yl]-3,5-bis(methoxymethoxy)benzaldehyde (135 mg, 0.374 mmol) was dissolved in diethyl ether (10 mL), and the solution was cooled to −78° C., and then cyclohexane/diethyl ether solution of 1.06 mol/L phenyllithium (0.54 mL, 0.57 mmol) was added thereto and stirred at the same temperature for 1 hour. Water was added to the reaction mixture, and extracted with diethyl ether. The organic layer was washed with aqueous saturated sodium chloride solution, then dried over anhydrous sodium sulfate, and the solvent was extracted out under reduced pressure. The resulting residue was purified through preparative thin-layer chromatography (chloroform/methanol=50/1) to obtain 1-{2-[5-(1,3-dioxolan-2-yl)furan-2-yl]-3,5-bis(methoxymethoxy)phenyl}-1-phenylmethanol (93.9 mg, 57%).

¹H-NMR (270 MHz, CDCl₃) δ (ppm): 2.46 (d, J=4.3 Hz, 1H), 3.39 (s, 3H), 3.46 (s, 3H), 3.80-4.20 (m, 4H), 5.08 (s, 2H), 5.16 (s, 2H), 5.89 (d, J=4.3 Hz, 1H), 5.90 (s, 1H), 6.22 (d, J=3.3 Hz, 1H), 6.47 (d, J=3.3 Hz, 1H), 6.80 (d, J=2.4 Hz, 1H), 6.94 (d, J=2.4 Hz, 1H), 7.10-7.40 (m, 5H).

(Step 4)

1-{2-[5-(1,3-Dioxolan-2-yl)furan-2-yl]-3,5-bis(methoxymethoxy)phenyl}-1-phenylmethanol (92.9 mg, 0.211 mmol) obtained in the above was dissolved in acetone (10 mL), and 1.0 mol/L hydrochloric acid (0.500 mL, 0.500 mmol) was added thereto and stirred at room temperature for 1 hour. Water was added to the reaction mixture, and extracted with chloroform. The organic layer was washed with aqueous saturated sodium chloride solution, then dried over anhydrous sodium sulfate, and the solvent was evaporated away under reduced pressure to obtain 5-[6-(1-hydroxy-1-phenylmethyl)-2,4-bis(methoxymethoxy)phenyl]furan-2-carbaldehyde (92.8 mg, 100%).

¹H-NMR (270 MHz, CDCl₃) δ (ppm): 2.58 (br s, 1H), 3.39 (s, 3H), 3.48 (s, 3H), 5.11 (s, 2H), 5.20 (s, 2H), 5.96 (br s, 1H), 6.43 (d, J=3.6 Hz, 1H), 6.84 (d, J=2.3 Hz, 1H), 7.07 (d, J=2.3 Hz, 1H), 7.15-7.25 (m, 6H), 9.55 (s, 1H).

(Step 5)

5-[6-(1-Hydroxy-1-phenylmethyl)-2,4-bis(methoxymethoxy)phenyl]furan-2-carbaldehyde (78.7 mg, 0.199 mmol) obtained in the above was dissolved in toluene (10 mL), and methyl triphenylphospholanylidene-acetate (199 mg, 0.594 mmol) was added thereto and stirred at 80° C. for 1 hour. The reaction mixture was concentrated under reduced pressure, and the resulting residue was purified through preparative thin-layer chromatography (n-hexane/ethyl acetate=1/1) to obtain methyl 3-{5-[6-(1-hydroxy-1-phenylmethyl)-2,4-bis(methoxymethoxy)phenyl]furan-2-yl]acrylate (99.5 mg, 100%).

¹H-NMR (270 MHz, CDCl₃) δ (ppm): 2.25 (d, J=4.1 Hz, 1H), 3.39 (s, 3H), 3.49 (s, 3H), 3.77 (s, 3H), 5.10 (s, 2H), 5.20 (s, 2H), 5.94 (d, J=4.1 Hz, 1H), 6.02 (d, J=15.7 Hz, 1H), 6.34 (d, J=3.4 Hz, 1H), 6.62 (d, J=3.4 Hz, 1H), 6.83 (d, J=2.4 Hz, 1H), 7.06 (d, J=2.4 Hz, 1H), 7.13-7.30 (m, 5H), 7.38 (d, J=15.7 Hz, 1H).

(Step 6)

Methyl 3-{5-[6-(1-hydroxy-1-phenylmethyl)-2,4-bis(methoxymethoxy)phenyl]furan-2-yl}acrylate (98.5 mg, 0.197 mmol) obtained in the above was dissolved in methanol (10 mL), and magnesium (105 mg, 4.30 mmol) was added thereto and stirred at room temperature for 5 hours. Water was added to the reaction mixture, and extracted with diethyl ether. The organic layer was washed with aqueous saturated sodium chloride solution, then dried over anhydrous sodium sulfate, and the solvent was evaporated away under reduced pressure to obtain methyl 3-{5-[6-(1-hydroxy-1-phenylmethyl)-2,4-bis(methoxymethoxy)phenyl]furan-2-yl}propanoate (51.1 mg, 57%).

¹H-NMR (270 MHz, CDCl₃) δ (ppm): 2.46 (d, J=4.3 Hz, 1H), 2.60 (t, J=7.4 Hz, 2H), 2.94 (t, J=7.4 Hz, 2H), 3.39 (s, 3H), 3.46 (s, 3H), 3.67 (s, 3H), 5.08 (s, 2H), 5.15 (s, 2H), 5.87 (d, J=4.3 Hz, 1H), 6.08 (d, J=3.3 Hz, 1H), 6.19 (d, J=3.3 Hz, 1H), 6.80 (d, J=2.3 Hz, 1H), 6.89 (d, J=2.3 Hz, 1H), 7.15-7.30 (m, 5H).

(Step 7)

Methyl 3-{5-[6-(1-hydroxy-1-phenylmethyl)-2,4-bis(methoxymethoxy)phenyl]furan-2-yl}propanoate (51.1 mg, 0.113 mmol) obtained in the above was dissolved in methanol (8 mL), and concentrated hydrochloric acid (0.2 mL) was added thereto and stirred at 60° C. for 1.2 hours. The reaction mixture was concentrated under reduced pressure, and the resulting residue was purified through preparative thin-layer chromatography (chloroform/methanol=20/1) to obtain Compound 237 (8.1 mg, 20%).

¹H-NMR (270 MHz, CDCl₃) δ (ppm): 2.65 (t, J=7.3 Hz, 2H), 3.00 (t, J=7.3 Hz, 2H), 3.30 (s, 3H), 3.67 (s, 3H), 5.27 (s, 1H), 6.14 (d, J=3.1 Hz, 1H), 6.21 (d, J=3.1 Hz, 1H), 6.42 (d, J=2.5 Hz, 1H), 6.60 (d, J=2.5 Hz, 1H), 7.10-7.35 (m, 5H); APCI-MS (m/z): 381 (M−H)⁻.

EXAMPLE 238

Methyl 2-bromo-6-(furan-2-yl)-3,5-dihydroxyphenylacetate (Compound 238)

(Step 1)

Methyl 2-bromo-3,5-bis(methoxymethoxy)phenylacetate (1.32 g, 3.78 mmol) obtained in the step 2 in Example 1 was dissolved in carbon tetrachloride (20 mL), and N-bromosuccinimide (960 mg, 5.39 mmol) was added thereto and stirred at room temperature for 4 days. Water was added to the reaction mixture, and extracted with chloroform. The organic layer was washed with aqueous saturated sodium sulfate solution and aqueous saturated sodium chloride solution in order, then dried over anhydrous sodium sulfate, and the solvent was evaporated away under reduced pressure. The resulting residue was purified through silica gel column chromatography (n-hexane/ethyl acetate=6/1 to 2/1) to obtain methyl 2,6-dibromo-3,5-bis(methoxymethoxy)phenylacetate (1.49 g, 92%).

¹H-NMR (270 MHz, CDCl₃) δ (ppm): 3.52 (s, 6H), 3.73 (s, 3H), 4.20 (s, 2H), 5.23 (s, 4H), 7.02 (s, 1H).

(Step 2)

Methyl 2,6-dibromo-3,5-bis(methoxymethoxy)phenylacetate (571 mg, 1.33 mmol) obtained in the above was dissolved in toluene (20 mL), and triphenylphosphine (97.6 mg, 0.372 mmol), tris(dibenzylidene-acetone)dipalladium (135 mg, 0.147 mmol) and tributyl(furan-2-yl)tin (2.00 mL, 6.35 mmol) was added thereto and stirred at 80° C. for 15 hours. Aqueous saturated potassium fluoride solution was added to the reaction mixture, and stirred at room temperature for 1.5 hours, and then filtered. Water was added to the filtrate, and extracted with chloroform. The organic layer was washed with aqueous saturated sodium chloride solution, then dried over anhydrous sodium sulfate, and the solvent was evaporated away under reduced pressure. The resulting residue was purified through silica gel column chromatography (n-hexane/ethyl acetate=10/1 to 5/1) to obtain methyl 2-bromo-6-(furan-2-yl)-3,5-bis(methoxymethoxy)phenylacetate (259 mg, 47%).

¹H-NMR (270 MHz, CDCl₃) δ (ppm): 3.39 (s, 3H), 3.53 (s, 3H), 3.69 (s, 3H), 3.78 (s, 2H), 5.09 (s, 2H), 5.27 (s, 2H), 6.38 (dd, J=0.8, 3.3 Hz, 1H), 6.47 (dd, J=1.9, 3.3 Hz, 1H), 7.01 (s, 1H), 7.48 (dd, J=0.8, 1.9 Hz, 1H).

(Step 3)

Methyl 2-bromo-6-(furan-2-yl)-3,5-bis(methoxymethoxy)phenylacetate (27.5 mg, 0.0662 mmol) obtained in the above was dissolved in ethanol (8 mL), and concentrated hydrochloric acid (0.2 mL) was added thereto and stirred at 60° C. for 1.2 hours. The reaction solution was concentrated under reduced pressure, and the resulting residue was purified through preparative thin-layer chromatography (chloroform/methanol=20/1) to obtain Compound 238 (8.6 mg, 40%).

¹H-NMR (270 MHz, CDCl₃) δ (ppm): 3.71 (s, 3H), 3.75 (s, 2H), 5.77 (br s, 2H), 6.48 (dd, J=0.7, 3.3 Hz, 1H), 6.54 (dd, J=1.8, 3.3 Hz, 1H), 6.67 (s, 1H), 7.57 (dd, J=0.7, 1.8 Hz, 1H);
APCI-MS (m/z): 325, 327 (M−H)⁻.

EXAMPLE 239

2-[2-Bromo-6-(furan-2-yl)-3,5-dihydroxyphenyl]-N-propylacetamide (Compound 239)

(Step 1)
Methyl 2-bromo-6-(furan-2-yl)-3,5-bis(methoxymethoxy)phenylacetate (58.6 mg, 0.141 mmol) obtained in the step 2 in Example 238 was dissolved in a mixed solvent of tetrahydrofuran (2 mL) and methanol (4 mL), and aqueous 1 mol/L lithium hydroxide solution (1.00 mL, 1.00 mmol) was added thereto and stirred at 60° C. for 5 hours. Water and 1 mol/L hydrochloric acid were added to the reaction mixture, and extracted with ethyl acetate. The organic layer was washed with aqueous saturated sodium chloride solution, and then dried over anhydrous sodium sulfate. The solvent was evaporated away under reduced pressure to obtain 2-bromo-6-(furan-2-yl)-3,5-bis(methoxymethoxy)phenylacetic acid (49.7 mg, 88%).
¹H-NMR (270 MHz, CDCl₃) δ (ppm): 1.75 (br s, 1H), 3.39 (s, 3H), 3.53 (s, 3H), 3.83 (s, 2H), 5.09 (s, 2H), 5.27 (s, 2H), 6.42 (br d, J=3.3 Hz, 1H), 6.48 (dd, J=1.8, 3.3 Hz, 1H), 7.02 (s, 1H), 7.50 (br d, J=1.8 Hz, 1H).

(Step 2)
2-Bromo-6-(furan-2-yl)-3,5-bis(methoxymethoxy)phenylacetic acid (27.4 mg, 0.0683 mmol) obtained in the above was dissolved in tetrahydrofuran (2 mL), and 1-hydroxybenzotriazole hydrate (35.0 mg, 0.229 mmol), 1-[3-(dimethylamino)propyl]-3-ethylcarbodiimide hydrochloride (60.3 mg, 0.315 mmol) and propylamine (0.0120 mL, 0.146 mmol) were added thereto and stirred at room temperature for 3 hours. The reaction mixture was concentrated under reduced pressure, and the resulting residue was purified through preparative thin-layer chromatography (n-hexane/ethyl acetate=4/1) to obtain 2-[2-bromo-6-(furan-2-yl)-3,5-bis(methoxymethoxy)phenyl]-N-propylacetamide (20.0 mg, 66%).
¹H-NMR (270 MHz, CDCl₃) δ (ppm): 0.87 (t, J=7.0 Hz, 3H), 1.48 (tq, J=7.0, 7.0 Hz, 2H), 3.19 (dt, J=7.0, 7.0 Hz, 2H), 3.40 8s, 3H), 3.55 (s, 3H), 3.68 (s, 2H), 5.11 (s, 2H), 5.29 (s, 2H), 5.39 (br s, 1H), 6.40 (dd, J=0.8, 3.3 Hz, 1H), 6.48 (dd, J=1.9, 3.3 Hz, 1H), 7.03 (s, 1H), 7.48 (dd, J=0.8, 1.9 Hz, 1H).

(Step 3)
2-[2-Bromo-6-(furan-2-yl)-3,5-bis(methoxymethoxy)phenyl]-N-propylacetamide (18.8 mg, 0.0425 mmol) obtained in the above was dissolved in ethanol (6 mL), and concentrated hydrochloric acid (0.2 mL) was added thereto and stirred at 60° C. for 1.2 hours. The reaction solution was concentrated under reduced pressure, and the resulting residue was purified through preparative thin-layer chromatography (chloroform/methanol=20/1) to obtain Compound 239 (8.5 mg, 56%).
¹H-NMR (270 MHz, CDCl₃) δ (ppm): 0.88 (t, J=7.0 Hz, 3H), 1.49 (tq, J=7.0, 7.0 Hz, 2H), 3.21 (dt, J=7.0, 7.0 Hz, 2H), 3.66 (s, 2H), 5.48 (br s, 1H), 6.12 (br s, 1H), 6.29 (br s, 1H), 6.51 (dd, J=0.7, 3.3 Hz, 1H), 6.54 (dd, J=1.6, 3.3 Hz, 1H), 6.67 (s, 1H), 7.56 (dd, J=0.7, 1.6 Hz, 1H);
APCI-MS (m/z): 352, 354 (M−H)⁻.

EXAMPLE 240

2-[2-Bromo-6-(furan-2-yl)-3,5-dihydroxyphenyl]-1-(pyrrolidin-1-yl)ethanone (Compound 240)

(Step 1)
2-Bromo-6-(furan-2-yl)-3,5-bis(methoxymethoxy)phenylacetic acid (51.6 mg, 0.124 mmol) obtained in the step 1 in Example 239 was dissolved in tetrahydrofuran (4 mL), and 1-hydroxybenzotriazole hydrate (80.9 mg, 0.528 mmol), 1-[3-(dimethylamino)propyl]-3-ethylcarbodiimide hydrochloride (150 mg, 0.781 mmol) and pyrrolidine (0.0250 mL, 0.292 mmol) were added thereto, and stirred at room temperature for 6 hours. Water was added to the reaction mixture, and extracted with chloroform. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=1/1) to obtain 2-[2-bromo-6-(furan-2-yl)-3,5-bis(methoxymethoxy)phenyl]-1-(pyrrolidin-1-yl)ethanone (57.7 mg, 91%).
¹H-NMR (270 MHz, CDCl₃) δ (ppm): 1.75-2.05 (m, 4H), 3.37 (s, 3H), 3.38 (t, J=6.7 Hz, 2H), 3.48 (t, J=6.7 Hz, 2H), 3.52 (s, 3H), 3.69 (s, 2H), 5.07 (s, 2H), 5.26 (s, 2H), 6.42 (dd, J=0.8, 3.3 Hz, 1H), 6.45 (dd, J=1.8, 3.3 Hz, 1H), 6.98 (s, 1H), 7.48 (dd, J=0.8, 1.8 Hz, 1H).

(Step 2)
2-[2-Bromo-6-(furan-2-yl)-3,5-bis(methoxymethoxy)phenyl]-1-(pyrrolidin-1-yl)ethanone (55.9 mg, 0.119 mmol) obtained in the above was dissolved in ethanol (6 mL), and concentrated hydrochloric acid (0.2 mL) was added thereto and stirred at 60° C. for 1.2 hours. The reaction solution was concentrated under reduced pressure, and the resulting residue was purified through preparative thin-layer chromatography (chloroform/methanol=9/1) to obtain Compound 240 (47.6 mg, 100%).
¹H-NMR (270 MHz, CDCl₃) δ (ppm): 01.80-2.05 (m, 4H), 3.42 (t, J=6.7 Hz, 2H), 3.51 (t, J=6.7 Hz, 2H), 3.70 (s; 2H), 6.05 (br s, 1H), 6.50 (br s, 1H), 6.51 (dd, J=1.9, 3.3 Hz, 1H), 6.54 (dd, J=0.8, 3.3 Hz, 1H), 6.64 (br s, 1H), 7.53 (dd, J=0.8, 1.9 Hz, 1H);
APCI-MS (m/z): 366, 368 (M+H)⁺.

EXAMPLE 241

2-[2-Bromo-6-(furan-2-yl)-3,5-dihydroxyphenyl]-N,N-diethylacetamide (Compound 241)

(Step 1)
2-Bromo-6-(furan-2-yl)-3,5-bis(methoxymethoxy)phenylacetic acid (51.6 mg, 0.124 mmol) obtained in the step 1 in Example 239 was dissolved in tetrahydrofuran (4 mL), and 1-hydroxybenzotriazole hydrate (73.2 mg, 0.478 mmol), 1-[3-(dimethylamino)propyl]-3-ethylcarbodiimide hydrochloride (140 mg, 0.728 mmol) and diethylamine (0.0300 mL, 0.290 mmol) were added thereto and stirred at room temperature for 6 hours. Water was added to the reaction mixture, and extracted with chloroform. The organic layer was washed with aqueous saturated sodium chloride solution, then dried over anhydrous sodium sulfate, and the solvent was evaporated away under reduced pressure. The resulting residue was purified through preparative thin-layer chromatography (chloroform/methanol=100/1) to obtain 2-[2-bromo-6-

(furan-2-yl)-3,5-bis(methoxymethoxy)phenyl]-N,N-diethylacetamide (59.1 mg, 100%).

¹H-NMR (270 MHz, CDCl₃) δ (ppm): 1.13 (t, J=7.1 Hz, 3H), 1.14 (t, J=7.1 Hz, 3H), 3.29 (q, J=7.1 Hz, 2H), 3.38 (s, 3H), 3.39 (q, J=7.1 Hz, 2H), 3.52 (s, 3H), 3.73 (s, 2H), 5.07 (s, 2H), 5.26 (s, 2H), 6.39 (dd, J=0.8, 3.3 Hz, 1H), 6.44 (dd, J=1.8, 3.3 Hz, 1H), 6.98 (s, 1H), 7.47 (dd, J=0.8, 1.8 Hz, 1H).

(Step 2)

2-[2-Bromo-6-(furan-2-yl)-3,5-bis(methoxymethoxy) phenyl]-N,N-diethylacetamide (57.9 mg, 0.123 mmol) obtained in the above was dissolved in ethanol (6 mL), and concentrated hydrochloric acid (0.2 mL) was added thereto and stirred at 60° C. for 1.2 hours. The reaction solution was concentrated under reduced pressure, and the resulting residue was purified through preparative thin-layer chromatography (chloroform/methanol=9/1) to obtain Compound 241 (41.6 mg, 92%).

¹H-NMR (270 MHz, CDCl₃) δ (ppm): 1.16 (t, J=7.0 Hz, 3H), 1.18 (t, J=7.0 Hz, 3H), 3.33 (q, J=7.0 Hz, 2H), 3.42 (q, J=7.0 Hz, 2H), 3.75 (s, 2H), 6.09 (br s, 1H), 6.40-6.50 (m, 3H), 6.79 (br s, 1H), 7.52 (dd, J=0.8, 1.8 Hz, 1H);

APCI-MS (m/z): 368, 370 (M+H)⁺.

EXAMPLE 242

2-[2-Bromo-6-(furan-2-yl)-3,5-dihydroxyphenyl]-N-(3,5-dimethoxyphenyl)acetamide (Compound 242)

(Step 1)

2-Bromo-6-(furan-2-yl)-3,5-bis(methoxymethoxy)phenylacetic acid (52.9 mg, 0.127 mmol) obtained in the step 1 in Example 239 was dissolved in tetrahydrofuran (4 mL), and 1-hydroxybenzotriazole hydrate (86.1 mg, 0.562 mmol), 1-[3-(dimethylamino)propyl]-3-ethylcarbodiimide hydrochloride (169 mg, 0.882 mmol) and 3,5-dimethoxyaniline (58.2 mg, 0.380 mmol) were added thereto and stirred at room temperature for 6 hours. Water was added to the reaction mixture, and extracted with chloroform. The organic layer was washed with aqueous saturated sodium chloride solution, then dried over anhydrous sodium sulfate, and the solvent was evaporated away under reduced pressure. The resulting residue was purified through preparative thin-layer chromatography (chloroform/methanol=100/1) to obtain 2-[2-bromo-6-(furan-2-yl)-3,5-bis(methoxymethoxy)phenyl]-N-(3,5-dimethoxyphenyl)acetamide (77.7 mg, 100%).

¹H-NMR (270 MHz, CDCl₃) δ (ppm): 3.41 (s, 3H), 3.55 (s, 3H), 3.74 (s, 3H), 3.76 (s, 3H), 3.82 (s, 2H), 5.12 (s, 2H), 5.30 (s, 2H), 6.22 (t, J=2.3 Hz, 1H), 6.45 (br d, J=3.3 Hz, 1H), 6.49 (dd, J=1.6, 3.0 Hz, 1H), 6.69 (d, J=2.3 Hz, 2H), 7.06 (s, 1H), 7.08 (br s, 1H), 7.50 (dd, J=0.7, 1.6 Hz, 1H).

(Step 2)

2-[2-Bromo-6-(furan-2-yl)-3,5-bis(methoxymethoxy) phenyl]-N-(3,5-dimethoxyphenyl)acetamide (77.2 mg, 0.140 mmol) obtained in the above was dissolved in ethanol (6 mL), and concentrated hydrochloric acid (0.2 mL) was added thereto and stirred at 60° C. for 1.2 hours. The reaction solution was concentrated under reduced pressure, and the resulting residue was purified through preparative thin-layer chromatography (chloroform/methanol=9/1) to obtain Compound 242 (35.6 mg, 63%).

¹H-NMR (270 MHz, CDCl₃) δ (ppm): 3.77 (s, 6H), 3.83 (s, 2H), 5.86 (br s, 1H), 5.89 (br s, 1H), 6.23 (t, J=2.1 Hz, 1H), 6.56 (d, J=1.3 Hz, 2H), 6.68 (d, J=2.1 Hz, 1H), 6.72 (s, 1H), 7.07 (br s, 1H), 7.59 (t, J=1.3 Hz, 1H);

APCI-MS (m/z): 446, 448 (M−H)⁻.

EXAMPLE 243

6-Bromo-4-(furan-2-yl)-5-(2-methoxyethyl)benzene-1,3-diol (Compound 243)

(Step 1)

Methyl 2-bromo-6-(furan-2-yl)-3,5-bis(methoxymethoxy)phenylacetate (195 mg, 0.470 mmol) obtained in the step 2 in Example 238 was dissolved in tetrahydrofuran (15 mL), then the solution was cooled to 0° C., and lithium aluminium hydride (28.3 mg, 0.746 mol) was added thereto and stirred at the same temperature for 3 hour. Anhydrous sodium sulfate and aqueous saturated sodium sulfate solution were added to the reaction mixture, then stirred at room temperature for 1 hour, and filtered. The filtrate was concentrated under reduced pressure, and the resulting residue was purified through preparative thin-layer chromatography (n-hexane/ethyl acetate=2/1) to obtain 2-[2-bromo-6-(furan-2-yl)-3,5-bis(methoxymethoxy)phenyl]ethanol (118 mg, 65%).

¹H-NMR (270 MHz, CDCl₃) δ (ppm): 1.43 (t, J=6.1 Hz, 1H), 2.99 (t, J=7.3 Hz, 2H), 3.37 (s, 3H), 3.54 (s, 3H), 3.80 (dt, J=6.1, 7.3 Hz, 2H), 5.06 (s, 2H), 5.27 (s, 2H), 6.37 (dd, J=0.8, 3.3 Hz, 1H), 6.50 (dd, J=1.8, 3.3 Hz, 1H), 6.94 (s, 1H), 7.52 (dd, J=0.8, 1.8 Hz, 1H).

(Step 2)

2-[2-Bromo-6-(furan-2-yl)-3,5-bis(methoxymethoxy) phenyl]ethanol (117 mg, 0.303 mmol) obtained in the above was dissolved in N,N-dimethylformamide (5 mL), and the solution was cooled to 0° C., then 60% sodium hydride/mineral oil dispersion (64.9 mg, 1.62 mmol) and methyl iodide (0.0570 mL, 0.916 mmol) were added thereto, then heated up to room temperature and stirred for 8 hours. Water and methanol were added to the reaction mixture, and extracted with chloroform. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=2/1) to obtain 4-bromo-2-(furan-2-yl)-3-(2-methoxyethyl)-1,5-bis(methoxymethoxy)benzene (97.0 mg, 80%).

¹H-NMR (270 MHz, CDCl₃) δ (ppm): 2.90-3.10 (m, 2H), 3.29 (s, 3H), 3.36 (s, 3H), 3.40-3.60 (m, 2H), 3.53 (s, 3H), 5.05 (s, 2H), 5.26 (s, 2H), 6.36 (dd, J=0.7, 3.3 Hz, 1H), 6.49 (dd, J=1.6, 3.3 Hz, 1H), 6.93 (s, 1H), 7.51 (dd, J=0.7, 1.6 Hz, 1H).

(Step 3)

4-Bromo-2-(furan-2-yl)-3-(2-methoxyethyl)-1,5-bis (methoxymethoxy)benzene (46.1 mg, 0.115 mmol) obtained in the above was dissolved in ethanol (6 mL), and concentrated acid (0.2 mL) was added thereto and stirred at 60° C. for 1.2 hours. The reaction solution was concentrated under reduced pressure, and the resulting residue was purified through preparative thin-layer chromatography (chloroform/methanol=20/1) to obtain Compound 243 (24.8 mg, 69%).

¹H-NMR (270 MHz, CDCl₃) δ (ppm): 2.96 (t, J=7.9 Hz, 2H), 3.30 (s, 3H), 3.52 (t, J=7.9 Hz, 2H), 5.59 (br s, 1H), 5.77 (br s, 1H), 6.52 (dd, J=0.7, 3.3 Hz, 1H), 6.56 (dd, J=1.8, 3.3 Hz, 1H), 6.61 (s, 1H), 7.60 (dd, J=0.7, 1.6 Hz, 1H);

APCI-MS (m/z): 311, 313 (M−H)⁻.

EXAMPLE 244

6-Ethyl-4-(furan-2-yl)-5-(2-methoxyethyl)benzene-1,3-diol (Compound 244)

(Step 1)

4-Bromo-2-(furan-2-yl)-3-(2-methoxyethyl)-1,5-bis(methoxymethoxy)benzene (50.0 mg, 0.125 mmol) obtained in the step 2 in Example 243 was dissolved in toluene (5 mL), and tributylvinyltin (0.100 mL, 0.342 mmol) and bis(tri-o-tolylphosphine)palladium(II) dichloride (10.4 mg, 0.0130 mmol) were added thereto and stirred with heating under reflux for 36 hours. Aqueous saturated ammonium fluoride solution was added to the reaction mixture and stirred at room temperature for 2 hours, and then filtered. Water was added to the filtrate, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (chloroform) to obtain 2-(furan-2-yl)-3-(2-methoxyethyl)-1,5-bis(methoxymethoxy)-4-vinylbenzene (39.3 mg, 90%).

$^1$H-NMR (270 MHz, CDCl$_3$) δ (ppm): 2.82-2.92 (m, 2H), 3.24 (s, 3H), 3.36 (s, 3H), 3.35-3.45 (m, 2H), 3.49 (s, 3H), 5.06 (s, 2H), 5.20 (s, 2H), 5.53 (dd, J=2.2, 11.7 Hz, 1H), 5.61 (dd, J=2.2, 17.8 Hz, 1H), 6.33 (dd, J=1.0, 3.3 Hz, 1H), 6.48 (dd, J=1.8, 3.3 Hz, 1H), 6.71 (dd, J=11.7, 17.8 Hz, 1H), 6.88 (s, 1H), 7.51 (dd, J=1.0, 1.8 Hz, 1H).

(Step 2)

2-(Furan-2-yl)-3-(2-methoxyethyl)-1,5-bis(methoxymethoxy)-4-vinylbenzene (39.3 mg, 0.125 mmol) obtained in the above was dissolved in ethanol (10 mL), and 10% palladium-carbon (34.2 mg) was added thereto and stirred in a hydrogen atmosphere at room temperature for 48 hours. The reaction mixture was filtered, and the filtrate was concentrated under reduced pressure. The resulting residue was purified through preparative thin-layer chromatography (n-hexane/ethyl acetate=2/1) to obtain 4-ethyl-2-(furan-2-yl)-3-(2-methoxyethyl)-1,5-bis(methoxymethoxy)benzene (19.6 mg, 45%).

$^1$H-NMR (270 MHz, CDCl$_3$) δ (ppm): 1.14 (t, J=7.5 Hz, 3H), 2.70 (q, J=7.5 Hz, 2H), 2.76-2.90 (m, 2H), 3.25 (s, 3H), 3.35 (s, 3H), 3.30-3.45 (m, 2H), 3.50 (s, 3H), 5.02 (s, 2H), 5.22 (s, 2H), 6.32 (dd, J=0.8, 3.3 Hz, 1H), 6.48 (dd, J=1.8, 3.3 Hz, 1H), 6.84 (s, 1H), 7.50 (dd, J=0.8, 1.8 Hz, (Step 3)

4-Ethyl-2-(furan-2-yl)-3-(2-methoxyethyl)-1,5-bis(methoxymethoxy)benzene (17.0 mg, 0.0485 mmol) obtained in the above was dissolved in ethanol (6 mL), and concentrated acid (0.2 mL) was added thereto and stirred at 60° C. for 1.2 hours. The reaction solution was concentrated under reduced pressure, and the resulting residue was purified through preparative thin-layer chromatography (chloroform/methanol=20/1) to obtain Compound 244 (8.2 mg, 64%).

$^1$H-NMR (270 MHz, CDCl$_3$) δ (ppm): 1.16 (t, J=7.5 Hz, 3H), 2.66 (q, J=7.5 Hz, 2H), 2.70-2.90 (m, 2H), 3.27 (s, 3H), 3.36-3.50 (m, 2H), 4.91 (br s, 1H), 5.37 (br s, 1H), 6.34 (s, 1H), 6.47 (dd, J=0.8, 3.3 Hz, 1H), 6.54 (dd, J=1.8, 3.3 Hz, 1H), 7.58 (dd, J=0.8, 1.8 Hz, 1H);

APCI-MS (m/z): 261 (M−H)$^-$.

EXAMPLE 245

Methyl 3,5-dihydroxy-2-[5-(morpholinomethyl)furan-2-yl]phenylacetate (Compound 245)

(Step 1)

Methyl 3,5-dihydroxyphenylacetate (5.0 g, 27 mmol) was dissolved in dichloromethane (0.15 L), and N,N-diisopropylethylamine (14 mL, 80 mmol) and chloromethyl methyl ether (5.6 mL, 60 mmol) were added thereto and stirred for 12 hours. Water (0.10 L) was added to the reaction solution for liquid-liquid separation. The organic layer was washed with aqueous saturated sodium hydrogencarbonate solution (0.10 L), then dried over anhydrous sodium sulfate, and the solvent was evaporated a w a y under reduced pressure. The resulting residue was purified through silica gel column chromatography (ethyl acetate/n-hexane=1/4 to 2/1) to obtain methyl 3,5-bis(methoxymethoxy)phenylacetate (4.1 g, 56%).

$^1$H-NMR (270 MHz, CDCl$_3$) δ (ppm): 3.47 (s, 6H), 3.56 (s, 2H), 3.69 (s, 3H), 5.14 (s, 4H), 6.62-6.66 (m, 3H);

APCI-MS (m/z): 269 (M−H)$^-$.

(Step 2)

Methyl 3,5-bis(methoxymethoxy)phenylacetate (3.0 g, 11 mmol) obtained in the above was dissolved in carbon tetrachloride (0.15 L), and N-bromosuccinimide (2.0 g, 11 mmol) was added thereto and heated under reflux for 8 hours. The reaction solution was cooled to room temperature and then concentrated under reduced pressure. The resulting residue was purified through silica gel column chromatography (n-hexane to ethyl acetate/n-hexane=1/2) to obtain methyl 2-bromo-3,5-bis(methoxymethoxy)phenylacetate (3.7 g, 97%).

$^1$H-NMR (270 MHz, CDCl$_3$) δ (ppm): 3.47 (s, 3H), 3.51 (s, 3H), 3.71 (s, 3H), 3.78 (s, 2H), 5.14 (s, 2H), 5.22 (s, 2H), 6.69 (d, J=2.6 Hz, 1H), 6.81 (d, J=2.6 Hz, 1H);

APCI-MS (m/z): 349 ($^{79}$Br), 351 ($^{81}$Br) (M+H)$^+$.

(Step 3)

Tetrahydrofuran (10 mL) solution of 2-(1,3-dioxolan-2-yl)furan (1.0 g, 7.1 mmol) was cooled to −78° C., and n-hexane solution of 1.6 mol/L n-butyllithium (4.5 mL, 7.2 mmol) was dropwise added thereto, and stirred for 3 hours. Tributyltin chloride (2.6 g, 7.9 mmol) was dropwise added to the reaction mixture, and stirred for 5 hours with heating up to room temperature. Water (10 mL) was added to the reaction mixture, and extracted with ethyl acetate (50 mL). The organic layer was dried over anhydrous sodium sulfate, and the solvent was evaporated away under reduced pressure. The resulting residue was purified through silica gel column chromatography (n-hexane to ethyl acetate/n-hexane=1/20) to obtain tributyl[5-(1,3-dioxolan-2-yl)furan-2-yl]tin (2.3 g, 75%).

$^1$H-NMR (270 MHz, CDCl$_3$) δ (ppm): 0.89 (t, J=7.3 Hz, 9H), 1.07 (t, J=7.9 Hz, 6H), 1.26-1.61 (m, 12H), 3.98-4.16 (m, 4H), 5.99 (s, 1H), 6.43 (d, J=3.0 Hz, 1H), 6.48 (d, J=3.0 Hz, 1H).

(Step 4)

Methyl 2-bromo-3,5-bis(methoxymethoxy)phenylacetate (3.7 g, 11 mmol) obtained in the step 2 was dissolved in toluene (0.20 L), and tributyl[5-(1,3-dioxolan-2-yl)furan-2-yl]tin (4.6 g, 11 mmol) obtained in the step 3, tris(dibenzylideneacetone)dipalladium (0.92 g, 1.0 mmol) and triphenylphosphine (1.1 g, 4.0 mmol) were added thereto and stirred at room temperature for 0.5 hour, and then further stirred with heating under reflux for 6 hours. The reaction mixture was cooled to room temperature, then aqueous potassium fluoride solution (1.1 L) was added thereto and stirred for 0.5 hour. The reaction mixture was filtered, and the filtrate was concentrated under reduced pressure. The resulting residue was dissolved in acetone (50 mL), and 3 mol/L (1.0 mL) hydrochloric acid was added thereto and stirred for 1 hour. Aqueous saturated sodium hydrogencarbonate solution (10 mL) was added to the reaction solution, then concentrated under reduced pressure, and the residue was extracted with ethyl acetate (0.10 L). The organic layer was washed with aqueous saturated sodium hydrogencarbonate solution (50 mL), then dried over anhydrous sodium sulfate, and the solvent was evaporated away under reduced pressure. The resulting residue was purified through silica gel column chromatography (ethyl acetate/n-hexane=1/10 to ethyl acetate) to obtain methyl 2-(5-formylfuran-2-yl)-3,5-bis(methoxymethoxy)phenylacetate (2.3 g, 64%).

$^1$H-NMR (270 MHz, CDCl$_3$) δ (ppm): 3.43 (s, 3H), 3.49 (s, 3H), 3.66 (s, 3H), 3.70 (s, 2H), 5.16 (s, 2H), 5.20 (s, 2H), 6.69 (d, J=2.3 Hz, 1H), 6.74 (d, J=3.6 Hz, 1H), 6.84 (d, J=2.3 Hz, 1H), 7.31 (d, J=3.6 Hz, 1H), 9.58 (s, 1H);

APCI-MS (m/z): 365 (M+H)$^+$.

(Step 5)

Methyl 2-(5-formylfuran-2-yl)-3,5-bis(methoxymethoxy)phenylacetate (53 mg, 0.15 mmol) obtained in the step 4 was dissolved in 1,2-dichloroethane (2.0 mL), and morpholine (0.03 mL, 0.34 mmol) was added thereto and stirred with heating under reflux for 2 hours. The reaction solution was cooled to room temperature, then sodium triacetoxyborohydride (130 mg, 0.60 mmol) was added thereto and stirred for 13 hours. The reaction mixture was cooled to 0° C., then water was added thereto with stirring, and the reaction mixture was extracted with ethyl acetate. The organic layer was washed with a 1 mol/L hydrochloric acid, aqueous saturated sodium hydrogencarbonate solution and aqueous saturated sodium chloride solution in order, then dried over anhydrous sodium sulfate, and the solvent was evaporated away under reduced pressure to obtain methyl 3,5-bis(methoxymethoxy)-2-[5-(morpholinomethyl)furan-2-yl]phenylacetate. The resulting compound was dissolved in methanol (1.0 mL), and 1,4-dioxane solution (1.0 mL) of 4 mol/L hydrogen chloride was added thereto with cooling with ice, and stirred for 2 hours. The reaction solution was neutralized with aqueous saturated sodium hydrogencarbonate, and then extracted three times with ethyl acetate. The organic layer was dried over anhydrous sodium sulfate, then the solvent was evaporated away under reduced pressure, and the resulting residue was purified through preparative thin-layer chromatography (methanol/chloroform=1/4) to obtain Compound 245 (23 mg, 44%).

$^1$H-NMR (270 MHz, CD$_3$OD) δ (ppm): 3.26 (m, 2H), 3.39 (m, 2H), 3.53 (s, 5H), 3.72 (m, 2H), 4.01 (m, 4H), 4.39 (s, 2H), 6.27 (d, J=2.3 Hz, 1H), 6.30 (d, J=2.3 Hz, 1H), 6.40 (d, J=3.3 Hz, 1H), 6.75 (d, J=3.3 Hz, 1H);

APCI-MS (m/z): 348 (M+H)$^+$.

EXAMPLE 246

Methyl 3,5-dihydroxy-2-(5-{N-[3-(imidazol-1-yl) propyl]aminomethyl}furan-2-yl)phenylacetate (Compound 246)

In the same manner as in 245, methyl 2-(5-{N-[3-(imidazol-1-yl)propyl]aminomethyl)furan-2-yl)-3,5-bis(methoxymethoxy)phenylacetate was obtained from methyl 2-(5-formylfuran-2-yl)-3,5-bis(methoxymethoxy)phenylacetate (53 mg, 0.15 mmol) obtained in the step 4 in Example 245, using 1-(3-aminopropyl)imidazole (0.03 mL, 0.25 mmol), sodium triacetoxyborohydride (72 mg, 0.34 mmol) and 1,2-dichloroethane (3.0 mL). The resulting compound was treated with methanol (1.0 mL) and 1,4-dioxane solution (1.0 mL) of 4 mol/L hydrogen chloride to obtain Compound 246 (20 mg, 35%).

$^1$H-NMR (270 MHz, CD$_3$OD) δ (ppm): 2.31 (m, 2H), 3.52 (s, 3H), 3.72 (m, 4H), 4.26 (s, 2H), 6.26 (d, J=2.1 Hz, 1H), 6.32 (d, J=2.1 Hz, 1H), 4.38 (m, 2H), 6.36 (d, J=3.3 Hz, 1H), 6.67 (d, J=3.3 Hz, 1H), 7.52 (m, 1H), 7.67 (m, 1H), 9.01 (m, 1H);

APCI-MS (m/z): 386 (M+H)$^+$.

EXAMPLE 247

Methyl 3,5-dihydroxy-2-{5-[N-(3-morpholinopropyl)aminomethyl]furan-2-yl}phenylacetate (Compound 247)

In the same manner as in Example 245, methyl 3,5-bis(methoxymethoxy)-2-{5-[N-(3-morpholinopropyl)aminomethyl]furan-2-yl}phenylacetate was obtained from methyl 2-(5-formylfuran-2-yl)-3,5-bis(methoxymethoxy)phenylacetate (64 mg, 0.17 mmol) obtained in the step 4 in Example 245, using 4-(3-aminopropyl)morpholine (0.05 mL, 0.34 mmol), sodium triacetoxyborohydride (150 mg, 0.71 mmol) and 1,2-dichloroethane (2.0 mL). The resulting compound was treated with methanol (1.0 mL) and 1,4-dioxane solution (1.0 mL) of 4 mol/L hydrogen chloride to obtain Compound 247 (35 mg, 51%).

$^1$H-NMR (270 MHz, CD$_3$OD) δ (ppm): 2.18 (m, 2H), 3.23 (s, 2H), 3.27 (s, 3H), 3.54 (m, 4H), 3.80 (m, 4H), 3.98 (m, 4H), 4.27 (s, 2H), 6.24 (d, J=2.1 Hz, 1H), 6.27 (d, J=2.1 Hz, 1H), 6.35 (d, J=3.3 Hz, 1H), 6.66 (d, J=3.3 Hz, 1H);

APCI-MS (m/z): 405 (M+H)$^+$.

EXAMPLE 248

Methyl 2-{5-[N-acetyl-N-(3-morpholinopropyl)aminomethyl]furan-2-yl}-3,5-dihydroxyphenylacetate (Compound 248)

(Step 1)

Methyl 3,5-bis(methoxymethoxy)-2-{5-[N-(3-morpholinopropyl)aminomethyl]furan-2-yl}phenylacetate (46 mg, 0.094 mmol) obtained in Example 247 was dissolved in dichloromethane (1.0 mL), and dimethylaminopyridine (20 mg, 0.16 mmol) and acetic anhydride (0.1 mL, 1.1 mmol) were added thereto and stirred for 20 hours. Chloroform was added to the reaction solution for liquid-liquid separation. The organic layer was washed with 2 mol/L hydrochloric acid, aqueous saturated carbonic acid solution and aqueous saturated sodium chloride solution in order, then dried over anhydrous sodium sulfate, and the solvent was evaporated away under reduced pressure. The resulting residue was purified through preparative thin-layer chromatography (methanol/chloroform=1/9) to obtain methyl 2-{5-[N-acetyl-N-(3-morpholinopropyl)aminomethyl]furan-2-yl}-3,5-bis(methoxymethoxy)phenylacetate (45 mg, 89%).

APCI-MS (m/z): 535 (M+H)$^+$.

(Step 2)

In the same manner as in the step 4 in Example 1, Compound 248 (25 mg, 67%) was obtained from methyl 2-{5-[N-acetyl-N-(3-morpholinopropyl)aminomethyl]furan-2-yl}-3,5-bis(methoxymethoxy)phenylacetate (45 mg, 0.084 mmol), using 1,4-dioxane solution (1.0 mL) of 4 mol/L hydrogen chloride and methanol (1.6 mL).

¹H-NMR (270 MHz, CD₃OD) δ (ppm): 2.10 (m, 2H), 2.24 (s, 3H), 3.25 (s, 5H), 3.54 (m, 4H), 3.80 (m, 4H), 3.98 (m, 4H), 4.59 (s, 2H), 6.24 (d, J=2.1 Hz, 1H), 6.27 (d, J=2.1 Hz, 1H), 6.35 (d, J=3.2 Hz, 1H), 6.66 (d, J=3.2 Hz, 1H);
APCI-MS (m/z): 447 (M+H)⁺.

EXAMPLE 249

Methyl 3,5-dihydroxy-2-(5-{N-[3-(2-oxopyrrolidin-1-yl)propyl]aminomethyl}furan-2-yl)phenylacetate (Compound 249)

In the same manner as in Example 245, methyl 3,5-bis(methoxymethoxy)-2-(5-(N-[3-(2-oxopyrrolidin-1-yl)propyl]aminomethyl}furan-2-yl)phenylacetate was obtained from methyl 2-(5-formylfuran-2-yl)-3,5-bis(methoxymethoxy)phenyl acetate (70 mg, 0.19 mmol) obtained in the step 4 in Example 245, using 1-(3-aminopropyl)-2-pyrrolidine (0.05 mL, 0.36 mmol), sodium triacetoxyborohydride (150 mg, 0.71 mmol) and 1,2-dichloroethane (3.0 mL). The resulting compound was treated with methanol (1.0 mL), and 1,4-dioxane solution (1.0 mL) of 4 mol/L hydrogen chloride to obtain Compound 249 (49 mg, 59%).
¹H-NMR (270 MHz, CD₃OD) δ (ppm): 2.20 (m, 4H), 2.43 (br s, 2H), 3.00 (br s, 2H), 3.50 (s, 2H), 3.52 (s, 2H), 3.63-3.50 (m, 4H), 4.20 (br s, 2H), 6.31 (d, J=2.2 Hz, 1H), 6.69 (d, J=3.3 Hz, 1H), 6.41 (d, J=3.2 Hz, 1H), 6.35 (d, J=2.2 Hz, 1H);
APCI-MS (m/z): 403 (M+H)⁺.

EXAMPLE 250

Methyl 2-[5-(2-benzoylethyl)furan-2-yl]-3,5-dihydroxyphenylacetate (Compound 250)

(Step 1)
Methyl 2-(5-formylfuran-2-yl)-3,5-bis(methoxymethoxy)phenyl acetate (250 mg, 0.69 mmol) obtained in the step 4 in Example 245 was dissolved in toluene (7.0 mL), and (benzoylmethylene)triphenylphospholane (520 mg, 1.4 mmol) was added thereto and stirred with heating under reflux for 5 hours. The reaction solution was concentrated under reduced pressure, and the resulting residue was purified through silica gel column chromatography (ethyl acetate/n-hexane=1/4 to 1/2) to obtain methyl 3,5-bis(methoxymethoxy)-2-[5-(3-oxo-3-phenylprop-1-en-1-yl)furan-2-yl]phenylacetate (310 mg, 96%).
¹H-NMR (270 MHz, CDCl₃) δ (ppm): 3.44 (s, 3H), 3.49 (s, 3H), 3.60 (s, 3H), 3.79 (s, 2H), 5.18 (s, 2H), 5.20 (s, 2H), 6.71-6.73 (m, 2H), 6.81 (d, J=3.6 Hz, 1H), 6.87 (d, J=2.3 Hz, 1H), 7.42-7.63 (m, 5H), 8.06-8.09 (m, 2H).

(Step 2)
Methyl 3,5-bis(methoxymethoxy)-2-[5-(3-oxo-3-phenylprop-1-en-1-yl)furan-2-yl]phenylacetate (310 mg, 0.66 mmol) obtained in the above was dissolved in toluene (10 mL), and tris(triphenylphosphine)rhodium(I) chloride (45 mg, 0.049 mmol) and triethylsilane (0.81 mL, 4.9 mmol) were added thereto and stirred at room temperature for 10 hours. The reaction mixture was filtered through Celite, and the filtrate was concentrated under reduced pressure. The resulting residue was purified through silica gel column chromatography (ethyl acetate/n-hexane=1/9 to 1/4) to obtain methyl 2-[5-(2-benzoylethyl)furan-2-yl]-3,5-bis(methoxymethoxy)phenylacetate (210 mg, 68%).
¹H-NMR (270 MHz, CDCl₃) (ppm): 3.09 (t, J=7.5 Hz, 2H), 3.36 (t, J=7.5 Hz, 2H), 3.40 (s, 3H), 3.48 (s, 3H), 3.61 (s, 3H), 3.63 (s, 2H), 5.10 (s, 2H), 5.17 (s, 2H), 6.13 (d, J=3.1 Hz, 1H), 6.37 (d, J=3.1 Hz, 1H), 6.67 (d, J=2.5 Hz, 1H), 6.81 (d, J=2.5 Hz, 1H), 7.43-7.56 (m, 3H), 7.97-8.00 (m, 2H).

(Step 3)
In the same manner as in the step 4 in Example 1, Compound 250 (50 mg, 88%) was obtained from methyl 2-[5-(2-benzoylethyl)furan-2-yl]-3,5-bis(methoxymethoxy)phenylacetate (70 mg, 0.15 mmol) obtained in the above, using methanol (1.0 mL) and 1,4-dioxane solution (1.0 mL) of 4 mol/L hydrogen chloride.
¹H-NMR (270 MHz, CD₃OD) δ (ppm): 2.78 (t, J=7.3 Hz, 2H), 2.96 (t, J=7.3 Hz, 2H), 3.2.8 (s, 2H), 3.51 (s, 3H), 6.39 (d, J=2.5 Hz, 1H), 6.41 (d, J=2.5 Hz, 1H), 7.37-7.51 (m, 5H), 7.92-7.94 (m, 2H);
APCI-MS (m/z): 379 (M−H)⁻.

EXAMPLE 251

Methyl 3,5-dihydroxy-2-[5-(4-methylpiperazin-1-ylmethyl)furan-2-yl]phenylacetate (Compound 251)

In the same manner as in Example 245, methyl 3,5-bis(methoxymethoxy)-2-[5-(4-methylpiperazin-1-ylmethyl)furan-2-yl]phenylacetate was obtained from methyl 2-(5-formylfuran-2-yl)-3,5-bis(methoxymethoxy)phenylacetate (67 mg, 0.18 mmol) obtained in the step 4 in Example 245, using N-methylpiperazine (0.03 mL, 0.26 mmol), sodium triacetoxyborohydride (150 mg, 0.71 mmol) and 1,2-dichloroethane (3.0 mL). The resulting compound was treated with methanol (1.0 mL) and 1,4-dioxane solution (1.0 mL) of 4 mol/L hydrogen chloride to obtain Compound 251 (28 mg, 43%).
¹H-NMR (270 MHz, CD₃OD) δ (ppm): 2.96 (s, 3H), 3.02 (br s, 2H), 3.29 (br s, 3H), 3.62-4.00 (m, 8H), 4.56 (s, 2H), 6.30 (m, 2H), 6.43 (br s, 1H), 6.81 (br s 1H);
APCI-MS (m/z): 361 (M+H)⁺.

EXAMPLE 252

Methyl 2-[5-(N,N-diethylaminomethyl)furan-2-yl]-3,5-dihydroxyphenylacetate (Compound 252)

In the same manner as in Example 245, methyl 2-[5-(N,N-diethylaminomethyl)furan-2-yl]-3,5-bis(methoxymethoxy)phenylacetate was obtained from methyl 2-(5-formylfuran-2-yl)-3,5-bis(methoxymethoxy)phenylacetate (58 mg, 0.16 mmol) obtained in the step 4 in Example 245, using diethylamine (0.03 mL, 0.41 mmol), sodium triacetoxyborohydride (150 mg, 0.71 mmol) and 1,2-dichloroethane (3.0 mL). The resulting compound was processed with methanol (1.0 mL) and 1,4-dioxane solution (1.0 mL) of 4 molIfL hydrogen chloride to obtain Compound 252 (21 mg, 39%).
¹H-NMR (270 MHz, CD₃OD) δ (ppm): 1.33 (t, J=7.3 Hz, 6H), 3.19 (q, J=7.3 Hz, 4H), 3.51 (s, 2H), 3.55 (s, 3H), 4.38 (s, 2H), 6.26 (d, J=2.3 Hz, 1H), 6.73 (d, J=3.3 Hz, 1H), 6.28 (d, J=2.3 Hz, 1H), 6.40 (d, J=3.3 Hz, 1H);
APCI-MS (m/z): 334 (M+H)⁺.

EXAMPLE 253

Methyl 3,5-dihydroxy-2-[5-(hydroxyiminomethyl)furan-2-yl]phenylacetate (Compound 253)

(Step 1)
Methyl 2-(5-formylfuran-2-yl)-3,5-bis(methoxymethoxy)phenylacetate (50 mg, 0.14 mmol) obtained in the step 4 in Example 245 was dissolved in pyridine (2.0 mL), and hydroxyamine hydrochloride (15 mg, 0.20 mmol) was added thereto and stirred at room temperature for 1 hour. The reaction solution was distilled under reduced pressure, and the resulting residue was purified through silica gel column chromatography (ethyl acetate/n-hexane=1/4 to 1/1) to obtain methyl 2-[5-(hydroxyiminomethyl)furan-2-yl]-3,5-bis(methoxymethoxy)phenylacetate (52 mg, 98%).

$^1$H-NMR (270 MHz, CDCl$_3$) δ (ppm): 3.41 (s, 3H), 3.49 (s, 3H), 5.13 (s, 1.4H), 3.71-3.63 (m, 5H), 5.14 (s, 0.6H), 7.98 (s, 1H), 5.18 (s, 1.4H), 5.19 (s, 0.6H), 6.83-6.54 (m, 4H);

APCI-MS (m/z): 380 (M+H)$^+$.

(Step 2)

In the same manner as in the step 4 in Example 1, Compound 253 (27 mg, 71%) was obtained from methyl 2-[5-(hydroxyiminomethyl)furan-2-yl]-3,5-bis(methoxymethoxy)phenylacetate (52 mg, 0.13 mmol) obtained in the above, using methanol (1.0 mL) and 1,4-dioxane solution (1.0 mL) of 4 mol/L hydrogen chloride.

$^1$H-NMR (270 MHz, CD$_3$OD) δ (ppm): 3.30 (s, 2H), 3.52 (s, 3H), 6.23 (m, 1H), 6.27 (d, J=2.3 Hz, 0.3H), 6.30 (d, J=2.3 Hz, 0.7H), 6.25 (d, J=3.3 Hz, 0.7H), 6.46 (d, J=3.3 Hz, 0.3H), 6.65 (d, J=3.6 Hz, 0.3H), 7.26 (d, J=3.6 Hz, 0.7H), 7.30 (s, 0.7H), 7.88 (s, 0.3H);

APCI-MS (m/z): 290 (M−H)$^-$.

EXAMPLE 254

Methyl 3,5-dihydroxy-2-[5-(methoxyiminomethyl)furan-2-yl]phenylacetate (Compound 254)

(Step 1)

In the same manner as in the step 1 in Example 253, methyl 2-[5-(methoxyiminomethyl)furan-2-yl]-3,5-bis(methoxymethoxy)phenylacetate (75 mg, 95%) was obtained from methyl 2-(5-formylfuran-2-yl)-3,5-bis(methoxymethoxy)phenylacetate (72 mg, 0.20 mmol) obtained in the step 4 in Example 245, using pyridine (2.0 mL) and O-methylhydroxyamine hydrochloride (20 mg, 0.24 mmol).

$^1$H-NMR (270 MHz, CDCl$_3$) δ (ppm): 3.41 (s, 2.1H), 3.42 (s, 0.9H), 3.48 (s, 2.1H), 3.49 (s, 0.9H), 3.64-3.63 (m, 5H), 3.94 (s, 2.1H), 4.05 (s, 0.9H), 5.13 (s, 1.4H), 5.13 (s, 0.6H), 5.17 (s, 1.4H), 5.18 (s, 0.6H), 6.51-6.83 (m, 4H), 7.37 (s, 0.3H), 7.92 (s, 0.7H);

APCI-MS (m/z): 394 (M+H)$^+$.

(Step 2)

In the same manner as in the step 4 in Example 1, Compound 254 (55 mg, 94%) was obtained from methyl 2-[5-(methoxyiminomethyl)furan-2-yl]-3,5-bis(methoxymethoxy)phenylacetate (75 mg, 0.19 mmol) obtained in the above, using methanol (1.0 mL) and 1,4-dioxane solution (1.0 mL) of 4 mol/L hydrogen chloride.

$^1$H-NMR (270 MHz, CD$_3$OD) δ (ppm): 3.30 (s, 2H), 3.83 (s, 1H), 3.94 (s, 2H), 5.33 (s, 3H), 6.23 (m, 1H), 6.29 (m, 1H), 6.52 (d, J=3.6 Hz, 0.3H), 6.63 (d, J=3.3 Hz, 0.7H), 6.69 (d, J=3.6 Hz, 0.3H), 7.16 (d, J=3.3 Hz, 0.7H), 7.29 (s, 0.7H), 7.87 (s, 0.3H);

APCI-MS (m/z): 306 (M+H)$^+$.

EXAMPLE 255

Methyl 2-(furan-2-yl)-3,5-dihydroxyphenylacetate (Compound 255)

(Step 1)

Methyl 2-bromo-3,5-bis(methoxymethoxy)phenylacetate (120 mg, 0.35 mmol) obtained in the step 2 in Example 1 was dissolved in toluene (4.0 mL), and tributyl(furan-2-yl)tin (250 mg, 0.71 mmol), tris(dibenzylideneacetone)palladium (32 mg, 0.035 mmol) and triphenylphosphine (37 mg, 0.14 mmol) were added thereto and stirred with heating under reflux for 6 hours. The reaction mixture was cooled to room temperature, then aqueous saturated ammonium fluoride solution was added thereto, and further stirred for 2 hours. The reaction mixture was filtered through Celite, and the filtrate was extracted twice with ethyl acetate. The organic layer was washed with aqueous saturated sodium chloride solution, the dried over anhydrous sodium sulfate, and the solvent was evaporated away under reduced pressure. The resulting residue was purified through preparative thin-layer chromatography (ethyl acetate/n-hexane=1/2) to obtain methyl 2-(furan-2-yl)-3,5-bis(methoxymethoxy)phenylacetate (73 mg, 62%).

$^1$H-NMR (270 MHz, CDCl$_3$) δ (ppm): 3.39 (s, 3H), 3.48 (s, 3H), 3.59 (s, 2H), 3.63 (s, 3H), 5.10 (s, 2H), 5.17 (s, 2H), 6.43 (dd, J=3.3, 0.7 Hz, 1H), 6.46 (dd, J=3.3, 2.0 Hz, 1H), 6.68 (d, J=2.7 Hz, 1H), 6.82 (d, J=2.7 Hz, 1H), 7.46 (dd, J=2.0, 0.7 Hz, 1H);

APCI-MS (m/z): 337 (M+H)$^+$.

(Step 2)

In the same manner as in the step 4 in Example 1, Compound 255 (28 mg, 53%) was obtained from methyl 2-(furan-2-yl)-3,5-bis(methoxymethoxy)phenylacetate (73 mg, 0.21 mmol) obtained in the above, using methanol (1.0 mL) and 1,4-dioxane solution (1.0 mL) of 4 mol/L hydrogen chloride.

$^1$H-NMR (270 MHz, CD$_3$OD) δ (ppm): 3.50 (s, 2H), 3.59 (s, 3H), 6.27 (d, J=2.5 Hz, 1H), 6.30 (d, J=2.5 Hz, 1H), 6.38 (dd, J=3.3, 0.82 Hz, 1H), 6.44 (dd, J=3.3, 1.8 Hz, 1H), 7.46 (dd, J=1.8, 0.82 Hz, 1H);

APCI-MS (m/z): 249 (M+H)$^+$.

EXAMPLE 256

6-Ethyl-4-(furan-2-yl)-5-[2-(2-hydroxyethoxy)ethyl]benzene-1,3-diol (Compound 256)

(Step 1)

In the same manner as in the step 1 in Example 243, 2-[2-ethyl-3,5-bis(methoxymethoxy)phenyl]ethanol (3.8 g, 94%) was obtained from methyl 2-ethyl-3,5-bis(methoxymethoxy)phenylacetate (4.5 g, 17 mmol), using lithium aluminium hydride (640 mg, 17 mmol) and diethyl ether (100 mL).

$^1$H-NMR (270 MHz, CDCl$_3$) δ (ppm): 1.39 (br s, 1H), 2.81 (t, J=6.3 Hz, 2H), 3.48 (s, 6H), 3.85 (m, 2H), 5.14 (s, 4H), 6.57 (d, J=2.3 Hz, 2H), 6.62 (t, J=2.3 Hz, 1H).

(Step 2)

In the same manner as in the step 2 in Example 243, 2-ethyl-3,5-bis(methoxymethoxy)-1-{2-[2-(tetrahydropyran-2-yloxy)ethoxy]ethyl}benzene (2.1 g, 60%) was obtained from 2-[2-ethyl-3,5-bis(methoxymethoxy)phenyl]ethanol (2.4 g, 8.8 mmol) obtained in the above, using 60% sodium hydride/mineral oil dispersion (1.0 g, 25 mmol), 2-(2-bromoethoxy)tetrahydro-2H-pyran (2.9 mL, 19 mmol) and N,N-dimethylformamide (50 mL).

$^1$H-NMR (270 MHz, CDCl$_3$) δ (ppm): 1.10 (t, J=7.5 Hz, 3H), 1.49-1.83 (m, 6H), 2.63 (q, J=7.5 Hz, 2H), 2.92 (t, J=7.5 Hz, 2H), 3.48 (s, 3H), 3.48 (s, 3H), 3.51 (m, 2H), 3.58-3.67 (m, 4H), 3.86 (m, 2H), 4.64 (dd, J=7.0, 3.1 Hz, 1H), 5.12 (s, 2H), 5.16 (s, 2H), 6.56 (d, J=2.4 Hz, 1H), 6.67 (d, J=2.4 Hz, 1H);

ESI-MS (m/z): 416 (M+NH$_4$)$^+$.

(Step 3)

In the same manner as in the step 2 in Example 1, 2-bromo-4-ethyl-1,5-bis(methoxymethoxy)-3-{2-[2-(tetrahydropyran-2-yloxy)ethoxy]ethyl}benzene (2.1 g, 89%) was obtained from 2-ethyl-3,5-bis(methoxymethoxy)-1-{2-[2-(tetrahydropyran-2-yloxy)ethoxy]ethyl}benzene (2.1 g, 5.3 mmol) obtained in the above, using N-bromosuccinimide (1.0 g, 5.6 mmol) and N,N-dimethylformamide (50 mL).

$^1$H-NMR (270 MHz, CDCl$_3$) δ (ppm): 1.10 (t, J=7.5 Hz, 3H), 1.86-1.49 (m, 6H), 2.72 (q, J=7.5 Hz, 2H), 3.18 (t, J=7.5 Hz, 2H), 3.47 (s, 3H), 3.52 (s, 3H), 3.60-3.71 (m, 6H), 3.90 (m, 2H), 5.17 (s, 2H), 5.19 (s, 2H), 6.86 (s, 1H).

(Step 4)

In the same manner as in the step 2 in Example 235, 4-ethyl-2-(furan-2-yl)-1,5-bis(methoxymethoxy)-3-{2-[2-(tetrahydropyran-2-yloxy)ethoxy]ethyl}benzene (92 mg, 58%) was obtained from 2-bromo-4-ethyl-1,5-bis(methoxymethoxy)-3-{2-[2-(tetrahydropyran-2-yloxy)ethoxy]ethyl}benzene (150 mg, 0.34 mmol) obtained in the above, using bistriphenylphosphine-palladium(II) dichloride (200 mg, 0.29 mmol) and tributyl(furan-2-yl)tin (0.3 mL, 0.96 mmol).

$^1$H-NMR (270 MHz, CDCl$_3$) δ (ppm): 1.15 (t, J=7.3 Hz, 3H), 1.48-1.90 (m, 6H), 2.70 (q, J=7.3 Hz, 2H), 2.82 (t, J=7.9 Hz, 2H), 3.34 (s, 3H), 3.49 (s, 3H), 3.49-3.52 (m, 6H), 3.80 (m, 2H), 4.60 (m, 1H), 5.02 (s, 2H), 5.21 (s, 2H), 6.32 (dd, J=3.3, 0.7 Hz, 1H), 6.47 (dd, J=3.3, 2.0 Hz, 1H), 6.83 (s, 1H), 7.49 (dd, J=20, 0.7 Hz, 1H).

(Step 5)

In the same manner as in the step 4 in Example 1, Compound 256 (43 mg, 73%) was obtained from 4-ethyl-2-(furan-2-yl)-1,5-bis(methoxymethoxy)-3-{2-[2-(tetrahydropyran-2-yloxy)ethoxy]ethyl}benzene (92 mg, 0.20 mmol) obtained in the above, using methanol (1.0 mL) and 1,4-dioxane solution (1.0 mL) of 4 mol/L hydrogen chloride.

$^1$H-NMR (270 MHz, CD$_3$OD) δ (ppm): 1.10 (t, J=7.4 Hz, 3H), 2.62 (q, J=7.4 Hz, 2H), 2.73 (t, J=8.2 Hz, 2H), 3.38-3.48 (m, 4H), 3.59 (t, J=5.0 Hz, 2H), 6.28 (s, 1H), 6.29 (dd, J=3.1, 0.55 Hz, 1H), 6.47 (dd, J=3.1, 1.8 Hz, 1H), 7.53 (dd, J=1.8, 0.55 Hz, 1H);

APCI-MS (m/z): 293 (M+H)$^+$.

EXAMPLE 257

2-[2-Ethyl-6-(furan-2-yl)-3,5-dihydroxyphenyl]-N-(2-methoxyethyl)-N-methylacetamide (Compound 257)

(Step 1)

Methyl 2-ethyl-3,5-bis(methoxymethoxy)phenylacetate (370 mg, 1.2 mmol) was dissolved in methanol (6.0 mL), and aqueous 2 mol/L sodium hydroxide solution (6.0 mL) was added thereto and stirred at room temperature for 1 hour. The reaction mixture was made acidic with 2 mol/L hydrochloric acid, and extracted twice with ethyl acetate. The organic layer was dried over anhydrous sodium sulfate, and the solvent was evaporated away under reduced pressure to obtain 2-bromo-3,5-bis(methoxymethoxy)phenylacetic acid. The resulting compound was dissolved in chloroform (12 mL), and 1-[3-(dimethylamino)propyl]-3-ethylcarbodiimide hydrochloride (230 mg, 1.2 mmol), 1-hydroxybenzotriazole hydrate (190 mg, 1.2 mmol) and N-(2-methoxyethyl)methylamine (0.13 mL, 1.2 mmol) were added thereto, in order, and stirred at room temperature for 3 hours. Water was added to the reaction mixture, and extracted twice with chloroform. The organic layer was dried over anhydrous sodium sulfate, and the solvent was evaporated away under reduced pressure. The resulting residue was purified through silica gel column chromatography (ethyl acetate/n-hexane=1/4 to 1/1) to obtain 2-[2-ethyl-3,5-bis(methoxymethoxy)phenyl]-N-(2-methoxyethyl)-N-methylacetamide (390 mg, 92%).

$^1$H-NMR (270 MHz, CDCl$_3$) δ (ppm): 1.01 (m, 3H), 2.58 (m, 2H), 2.99 (m, 3H), 3.35 (s, 3H), 3.33-3.47 (m, 6H), 3.58 (m, 2H), 3.76 (m, 2H), 5.14 (s, 2H), 5.17 (s, 2H), 6.50 (m, 1H), 6.7.1 (m, 1H).

(Step 2)

2-[2-Ethyl-3,5-bis(methoxymethoxy)phenyl]-N-(2-methoxyethyl)-N-methylacetamide (390 mg, 1.1 mmol) obtained in the above was dissolved in chloroform, and with stirring at −30° C., iodine (310 mg, 1.2 mmol) and [bis(trifluoroacetoxy)iodo]benzene (520 mg, 1.2 mmol) were added thereto, and stirred for 1 hour. Aqueous saturated sodium thiosulfate was added to the reaction mixture, and stirred for 2 hours with heating up to room temperature. The reaction mixture was extracted twice with ethyl acetate, and the organic layer was washed with aqueous saturated sodium hydrogencarbonate solution and aqueous saturated sodium chloride solution in order, then dried over anhydrous sodium sulfate, and the solvent was evaporated away under reduced pressure. The resulting residue was purified through silica gel column chromatography (ethyl acetate/n-hexane=1/4 to 1/1) to obtain 2-[2-ethyl-6-iodo-3,5-bis(methoxymethoxy)phenyl]-N-(2-methoxyethyl)-N-methylacetamide (310 mg, 59%).

$^1$H-NMR (270 MHz, CDCl$_3$) δ (ppm): 1.08 (m, 3H), 2.67 (m, 2H), 3.28-3.66 (m, 15H), 5.17 (s, 2H), 5.18 (s, 2H), 6.86 (s, 1H);

FAB-MS (m/z): 482 (M+H)$^+$.

(Step 3)

In the same manner as in the step 2 in Example 235, 2-[2-ethyl-6-(furan-2-yl)-3,5-bis(methoxymethoxy)phenyl]-N-(2-methoxyethyl)-N-methylacetamide (240 mg, 87%) was obtained from 2-[2-ethyl-6-iodo-3,5-bis(methoxymethoxy) phenyl]-N-(2-methoxyethyl)-N-methylacetamide (310 mg, 0.62 mmol) obtained in the above, using bis(triphenylphosphine)palladium(II) dichloride (50 mg, 0.07 mmol) and tributyl(furan-2-yl)tin (0.3 mL, 0.96 mmol).

$^1$H-NMR (270 MHz, CDCl$_3$) δ (ppm): 1.10 (m, 3H), 2.67 (m, 2H), 2.97 (m, 3H), 3.32-3.40 (m, 8H), 3.49-3.58 (m, 7H), 5.04 (s, 2H), 5.21 (s, 2H), 6.32 (m, 1H), 6.44 (m, 1H), 6.88 (m, 1H), 7.47 (m, 1H);

APCI-MS (m/z): 422 (M+H)$^+$.

(Step 4)

In the same manner as in the step 4 in Example 1, Compound 257 (110 mg, 61%) was obtained from 2-[2-ethyl-6-(furan-2-yl)-3,5-bis(methoxymethoxy)phenyl]-N-(2-methoxyethyl)-N-methylacetamide (240 mg, 0.54 mmol) obtained in the above, using methanol (2.0 mL) and 1,4-dioxane solution (2.0 mL) of 4 mol/L hydrogen chloride.

$^1$H-NMR (270 MHz, CDCl$_3$) δ (ppm): 1.04 (m, 3H), 2.49 (m, 2H), 3.01 (s, 1H), 3.03 (s, 2H), 3.34 (s, 1H), 3.38 (s, 2H), 3.46-3.62 (m, 6H), 5.47 (br s, 1H), 6.05 (s, 1H), 6.42 (m, 1H), 6.48 (m, 1H), 7.51 (m, 1H), 7.82 (br s, 1H);

APCI-MS (m/z): 332 (M−H)$^-$.

EXAMPLE 258

Methyl 3,5-dihydroxy-2-[5-(hydroxymethyl)furan-2-yl]phenylacetate (Compound 258)

(Step 1)

Methyl 2-(5-formylfuran-2-yl)-3,5-bis(methoxymethoxy) phenylacetate (0.44 g, 1.2 mmol) obtained in the step 4 in Example 245 was dissolved in tetrahydrofuran (10 mL), then the solution was cooled to 4° C., and sodium borohydride (45 mg, 1.2 mmol) was added thereto and stirred for 3 hours with heating up to room temperature. 1 mol/L hydrochloric acid (10 mL) was added to the reaction mixture, and extracted with chloroform (0.10 L). The organic layer was dried over anhydrous sodium sulfate, and the solvent was evaporated away under reduced pressure. The resulting residue was purified through silica gel column chromatography (ethyl acetate/n-hexane=1/4 to 1/1) to obtain methyl 2-[5-(hydroxymethyl)furan-2-yl]-3,5-bis(methoxymethoxy)phenylacetate (0.36 g, 82%).

$^1$H-NMR (270 MHz, CDCl$_3$) δ (ppm): 2.62 (t, J=5.1 Hz, 1H), 3.44 (s, 3H), 3.50 (s, 3H), 3.63 (s, 2H), 3.66 (s, 3H), 4.57 (d, J=5.1 Hz, 2H), 5.15 (s, 2H), 5.19 (s, 2H), 6.35 (d, J=2.3 Hz, 1H), 6.48 (d, J=2.3 Hz, 1H), 6.69 (d, J=3.3 Hz, 1H), 6.83 (d, J=3.3 Hz, 1H);

FAB-MS (m/z): 349 (M-OH)$^+$.

(Step 2)

Methyl 2-[5-(hydroxymethyl)furan-2-yl]-3,5-bis(methoxymethoxy)phenylacetate (70 mg, 0.19 mmol) obtained in the above was dissolved in 2-propanol (3.0 mL), and 1,4-dioxane solution (3.0 mL) of 4 mol/L hydrogen chloride was added thereto and stirred at room temperature for 20 minutes. The reaction liquid was concentrated under reduced pressure, and the resulting residue was purified through partitioning thin-layer chromatography (methanol/chloroform=1/9) to obtain Compound 258 (52 mg, 98%).

$^1$H-NMR (270 MHz, CDCl$_3$) δ (ppm): 3.55 (s, 2H), 3.57 (s, 3H), 4.04 (br s, 2H), 6.29 (d, J=2.3 Hz, 1H), 6.33 (d, J=2.3 Hz, 1H), 6.39 (d, J=3.3 Hz, 1H), 6.54 (d, J=3.3 Hz, 1H);

APCI-MS (m/z): 261 (M-OH)$^+$.

EXAMPLE 259

Methyl 3,5-dihydroxy-2-[5-(3-hydroxy-3-phenylpropyl)furan-2-yl]phenylacetate (Compound 259)

(Step 1)

Methyl 2-(5-formylfuran-2-yl)-3,5-bis(methoxymethoxy)phenylacetate (0.13 g, 0.36 mmol) obtained in the step 4 in Example 245 was dissolved in toluene (3.0 mL), and (benzoylmethylene)triphenylphospholane (0.18 g, 0.47 mmol) was added thereto and stirred at 110° C. for 10 hours. The reaction solution was cooled to room temperature, and then concentrated under reduced pressure. The resulting residue was purified through silica gel column chromatography (ethyl acetate/n-hexane=1/9 to 1/2) to obtain methyl 3,5-bis(methoxymethoxy)-2-[5-(3-oxo-3-phenylprop-1-en-1-yl)furan-2-yl]phenylacetate (0.16 g, 96%).

APCI-MS (m/z): 467 (M+H)$^+$.

(Step 2)

Methyl 3,5-bis(methoxymethoxy)-2-[5-(3-oxo-3-phenylprop-1-en-1-yl)furan-2-yl]phenylacetate (0.11 g, 0.23 mmol) obtained in the above was dissolved in ethyl acetate (10 mL), and 10% palladium-carbon (50 mg) was added thereto and stirred under hydrogen pressure (0.3 MPa) at room temperature for 0.5 hour. The reaction mixture was filtered, and the filtrate was concentrated under reduced pressure. The resulting residue was purified through preparative thin-layer chromatography (methanol/chloroform/acetic acid=2/10/0.1) to obtain methyl 2-[5-(3-hydroxy-3-phenylpropyl)furan-2-yl]-3,5-bis(methoxymethoxy)phenylacetate (69 mg, 65%).

$^1$H-NMR (270 MHz, CDCl$_3$) (ppm): 2.04-2.15 (m, 2H), 2.74 (t, J=7.5 Hz, 2H), 3.40 (s, 3H), 3.48 (s, 3H), 3.60 (s, 3H), 3.62 (s, 2H), 4.73 (t, J=6.4 Hz, 1H), 5.11 (s, 2H), 5.17 (s, 2H), 6.09 (d, J=3.1 Hz, 1H), 6.36 (d, J=3.1 Hz, 1H), 6.67 (d, J=2.4 Hz, 1H), 6.81 (d, J=2.4 Hz, 1H), 7.25-7.36 (m, 5H);

APCI-MS (m/z): 471 (M+H)$^+$.

(Step 3)

Methyl 2-[5-(3-hydroxy-3-phenylpropyl)furan-2-yl]-3,5-bis(methoxymethoxy)phenylacetate (68 mg, 0.15 mmol) obtained in the above was dissolved in methanol (2.5 mL), then the solution was cooled to 4° C., and methanol solution (2.5 mL) of 10% hydrochloric acid was added thereto and stirred for 1 hour with heating up to room temperature. Then, 1,4-dioxane solution of 4 mol/L hydrogen chloride was added to the reaction mixture, and stirred at room temperature for 1 hour. The reaction solution was concentrated under reduced pressure, and the resulting residue was purified through preparative thin-layer chromatography (methanol/chloroform=1/9) to obtain Compound 259 (21 mg, 38%).

$^1$H-NMR (270 MHz, CD$_3$OD) δ (ppm): 2.00-2.07 (m, 2H), 2.60-2.70 (m, 2H), 3.53 (s, 5H), 3.67 (m, 1H), 6.08 (s, 1H), 6.27 (s, 1H), 6.31 (br s, 2H), 7.24-7.35 (m, 5H);

APCI-MS (m/z): 383 (M+H)$^+$.

EXAMPLE 260

Methyl 3-{5-[2,4-dihydroxy-6-(methoxycarbonylmethyl)phenyl]furan-2-yl}propanoate (Compound 260)

(Step 1)

Methyl 2-(5-formylfuran-2-yl)-3,5-bis(methoxymethoxy)phenylacetate (0.19 g, 0.52 mmol) obtained in the step 4 in Example 245 was dissolved in toluene (5.0 mL), and (carbomethoxymethylene)triphenylphospholane (0.21 g, 0.63 mmol) was added thereto, and stirred with heating at 80° C. for 5 hours. The reaction mixture was cooled to room temperature, and then concentrated under reduced pressure. The resulting residue was purified through silica gel column chromatography (n-hexane to ethyl acetate/n-hexane=1/2) to obtain methyl 3-{5-[6-(methoxycarbonylmethyl)-2,4-bis(methoxymethoxy)phenyl]furan-2-yl}acrylate (0.12 g, 56%).

$^1$H-NMR (270 MHz, CDCl$_3$) δ (ppm): 3.44 (s, 3H), 3.49 (s, 3H), 3.66 (s, 3H), 3.73 (s, 2H), 3.78 (s, 3H), 5.16 (s, 2H), 5.20 (s, 2H), 6.26 (d, J=15.2 Hz, 1H), 6.65 (d, J=3.3 Hz, 1H), 6.69 (d, J=2.6 Hz, 1H), 6.70 (d, J=3.3 Hz, 1H), 6.84 (d, J=2.6 Hz, 1H), 7.43 (d, J=15.2 Hz, 1H);

FAB-MS (m/z): 421 (M+H)$^+$.

(Step 2)

Methyl 3-{5-[6-(methoxycarbonylmethyl)-2,4-bis(methoxymethoxy)phenyl]furan-2-yl}acrylate (0.12 g, 0.29 mmol) obtained in the above was dissolved in ethyl acetate (20 mL), and 10% palladium-carbon (46 mg) was added thereto and stirred under hydrogen pressure (0.3 MPa) at room temperature for 0.5 hour. The reaction mixture was filtered, and the filtrate was concentrated under reduced pressure. The resulting residue was purified through preparative thin-layer chromatography (ethyl acetate/n-hexane=1/2) to obtain methyl 3-{5-[6-(methoxycarbonyl)-2,4-bis(methoxymethoxy)phenyl]furan-2-yl}propanoate (0.12 g, 89%).

$^1$H-NMR (CDCl$_3$, 270 MHz): δ (ppm) 2.68 (dd, J=7.3, 8.3 Hz, 2H), 2.98 (dd, J=7.3, 8.3 Hz, 2H), 3.42 (s, 3H), 3.48 (s, 3H), 3.62 (s, 2H), 3.65 (s, 3H), 3.69 (s, 3H), 5.11 (s, 2H), 5.17 (s, 2H), 6.10 (d, J=3.1 Hz, 1H), 6.36 (d, J=3.1 Hz, 1H), 6.67 (d, J=2.3 Hz, 1H), 6.81 (d, J=2.3 Hz, 1H);

APCI-MS (m/z): 391 (M-OMe)$^-$.

(Step 3)

Methyl 3-{5-[6-(methoxycarbonyl)-2,4-bis(methoxymethoxy)phenyl]furan-2-yl}propanoate (0.12 g, 0.28 mmol) obtained in the above was dissolved in methanol (3.0 mL), and methanol solution (7.0 mL) of 10% hydrochloric acid was added thereto and stirred at room temperature for 6 hours. The reaction solution was concentrated under reduced pressure, and the resulting residue was purified through preparative thin-layer chromatography (methanol/chloroform=1/9) to obtain Compound 260 (65 mg, 68%).

$^1$H-NMR (270 MHz, CDCl$_3$) δ (ppm): 2.69 (t, J=7.4 Hz, 2H), 3.00 (t, J=7.4 Hz, 2H), 3.55 (s, 2H), 3.66 (s, 3H), 3.69 (s, 3H), 6.15 (d, J=3.1 Hz, 1H), 6.36 (d, J=3.1 Hz, 1H), 6.38 (br s, 2H);

APCI-MS (m/z): 335 (M+H)$^+$.

EXAMPLE 261

Methyl 3,5-dihydroxy-2-[5-(3-oxobutyl)furan-2-yl]phenylacetate (Compound 261)

(Step 1)

Methyl 2-(5-formylfuran-2-yl)-3,5-bis(methoxymethoxy)phenylacetate (0.14 g, 0.39 mmol) obtained in the step 4 in Example 245 was dissolved in toluene (5.0 mL), and (acetylmethylene)triphenylphospholane (0.15 g, 0.46 mmol) was added thereto and stirred at 80° C. for 5 hours. The reaction solution was cooled to room temperature, and concentrated under reduced pressure. The resulting residue was purified through silica gel column chromatography (ethyl acetate/n-hexane=1/9 to 1/2) to obtain methyl 3,5-bis(methoxymethoxy)-2-[5-(3-oxobut-1-en-1-yl)furan-2-yl]phenylacetate (0.13 g, 83%).

$^1$H-NMR (270 MHz, CDCl$_3$) δ (ppm): 2.33 (s, 3H), 3.43 (s, 3H), 3.49 (s, 3H), 3.65 (s, 3H), 3.73 (s, 2H), 5.16 (s, 2H), 5.19 (s, 2H), 6.56 (d, J=15.9 Hz, 1H), 6.66 (d, J=3.5 Hz, 1H), 6.69 (d, J=2.2 Hz, 1H), 6.76 (d, J=3.5 Hz, 1H), 6.84 (d, J=2.2 Hz, 1H), 7.26 (d, J=15.9 Hz, 1H);

APCI-MS (m/z): 405 (M+H)$^+$.

(Step 2)

Methyl 3,5-bis(methoxymethoxy)-2-[5-(3-oxobut-1-en-1-yl)furan-2-yl]phenylacetate (0.13 g, 0.32 mmol) obtained in the above was dissolved in ethyl acetate (20 mL), and 10% palladium-carbon (46 mg) was added thereto and stirred under hydrogen pressure (0.3 MPa) at room temperature for 0.5 hour. The reaction mixture was filtered, and the filtrate was concentrated under reduced pressure. The resulting residue was purified through preparative thin-layer chromatography (ethyl acetate/n-hexane=1/2) to obtain methyl 3,5-bis(methoxymethoxy)-2-[5-(3-oxobutyl)furan-2-yl]phenylacetate (0.12 g, 89%).

$^1$H-NMR (270 MHz, CDCl$_3$) δ (ppm): 2.17 (s, 3H), 2.77-2.94 (m, 4H), 3.42 (s, 3H), 3.48 (s, 3H), 3.62 (s, 2H), 3.64 (s, 3H), 5.11 (s, 2H), 5.18 (s, 2H), 6.07 (d, J=3.1 Hz, 1H), 6.34 (d, J=3.1 Hz, 1H), 6.67 (d, J=2.3 Hz, 1H), 6.81 (d, J=2.3 Hz, 1H);

APCI-MS (m/z): 405 (M+H)$^+$.

(Step 3)

Methyl 3,5-bis(methoxymethoxy)-2-[5-(3-oxobutyl)furan-2-yl]phenylacetate (0.11 g, 0.27 mmol) obtained in the above was dissolved in methanol (2.0 mL), and methanol solution (2.0 mL) of 10% hydrochloric acid was added thereto and stirred at room temperature for 2 hours. The reaction solution was concentrated under reduced pressure, and the resulting residue was dissolved in chloroform, and water (30 mL) was added thereto for liquid-liquid separation. The solvent was evaporated away under reduced pressure, and the resulting residue was purified through preparative thin-layer chromatography (methanol/chloroform=1/9) and then crystallized (diisopropyl ether) to obtain Compound 261 (65 mg, 60%).

$^1$H-NMR (270 MHz, CDCl$_3$) δ (ppm): 2.18 (s, 3H), 2.79-2.96 (m, 4H), 3.55 (s, 2H), 3.65 (s, 3H), 6.10 (d, J=3.1 Hz, 1H), 6.35 (d, J=3.1 Hz, 1H), 6.37 (d, J=3.1 Hz, 1H), 6.38 (d, J=3.1 Hz, 1H);

APCI-MS (m/z): 317 (M−H)$^-$.

EXAMPLE 262

3,5-Dihydroxy-2-[5-(3-oxobutyl)furan-2-yl]phenylacetic acid (Compound 262)

Compound 261 (20 mg, 0.063 mmol) obtained in Example 261 was dissolved in acetonitrile (2.0 mL), and aqueous 4 mol/L sodium hydroxide solution (2.0 mL, 4.0 mmol) was added thereto and stirred at 60° C. for 3 hours. 3 mol/L hydrochloric acid (4.0 mL) was added to the reaction solution, and extracted twice with chloroform (50 mL). The organic layer was dried over anhydrous sodium sulfate, and the solvent was evaporated away under reduced pressure. The resulting residue was purified through preparative thin-layer chromatography (methanol/chloroform=1/6) to obtain Compound 262 (10 mg, 52%).

$^1$H-NMR (270 MHz, CDCl$_3$) δ (ppm): 2.15 (s, 3H), 2.86 (br s, 4H), 3.49 (s, 2H), 6.07 (d, J=3.1 Hz, 1H), 6.27 (d, J=2.3 Hz, 1H), 6.29 (d, J=2.3 Hz, 1H), 6.32 (d, J=3.1 Hz, 1H).

EXAMPLE 263

Methyl 2-[5-(aminomethyl)furan-2-yl]-3,5-dihydroxyphenylacetate (Compound 263)

(Step 1)

Methyl 2-[5-(hydroxymethyl)furan-2-yl]-3,5-bis(methoxymethoxy)phenylacetate (0.37 g, 1.0 mmol) obtained in the step 1 in Example 258 was dissolved in toluene (10 mL), and N-(allyloxycarbonyl)-2-nitrobenzenesulfonamide (0.44 g, 1.5 mmol), triphenylphosphine (0.39 g, 1.5 mmol) and diisopropyl azodicarboxylate (0.30 mL, 1.5 mmol) were added thereto and stirred at room temperature for 12 hours. The reaction solution was concentrated under reduced pressure, and the resulting residue was purified through silica gel column chromatography (n-hexane to ethyl acetate/n-hexane=1/1) to obtain methyl 2-{5-[N-(allyloxycarbonyl)-N-(2-nitrobenzenesulfonyl)aminomethyl]furan-2-yl}-3,5-bis(methoxymethoxy)phenylacetate (0.60 g, 93%).

$^1$H-NMR (270 MHz, CDCl$_3$) δ (ppm): 3.42 (s, 3H), 3.49 (s, 3H), 3.63 (s, 3H), 3.68 (s, 2H), 4.60-4.63 (m. 2H), 5.04 (s, 2H), 5.12 (s, 2H), 5.18 (s, 2H), 5.16-5.27 (m, 2H), 5.78 (m, 1H), 6.41 (d, J=3.2 Hz, 1H), 6.48 (d, J=3.2 Hz, 1H), 6.67 (d, J=2.3 Hz, 1H), 6.81 (d, J=2.3 Hz, 1H), 7.69-7.90 (m, 3H), 8.30-8.33 (m, 1H);

FAB-MS (m/z): 635 (M+H)$^+$.

(Step 2)

Methyl 2-{5-[N-(allyloxycarbonyl)-N-(2-nitrobenzenesulfonyl)aminomethyl]furan-2-yl}-3,5-bis(methoxymethoxy)phenylacetate (0.60 g, 0.95 mmol) obtained in the above was dissolved in N,N-dimethylformamide (10 mL), and potassium carbonate (0.26 g, 1.9 mmol) and thiophenol (0.13 mL, 1.2 mmol) were added thereto and stirred at room temperature for 4 hours. Water (0.10 L) was added to the reaction solution, and extracted with ethyl acetate (0.10 L).

The organic layer was dried over anhydrous sodium sulfate, and the solvent was evaporated away under reduced pressure. The resulting residue was purified through silica gel column chromatography (n-hexane to ethyl acetate/n-hexane=1/1) to obtain methyl 2-{5-[N-(allyloxycarbonyl)aminomethyl]furan-2-yl}-3,5-bis(methoxymethoxy)phenylacetate (0.34 g, 80%).

$^1$H-NMR (270 MHz, CDCl$_3$) δ (ppm): 3.42 (s, 3H), 3.49 (s, 3H), 3.62 (s, 2H), 3.64 (s, 3H), 4.35 (d, J=5.6 Hz, 2H), 4.58 (d, J=5.6 Hz, 2H), 5.13 (s, 2H), 5.18 (s, 2H), 5.19 (dd, J=3.0, 10.2 Hz, 1H), 5.30 (dd, J=3.0, 17.1 Hz, 1H), 5.57 (br s, 1H), 5.91 (ddt, J=10.2, 17.1, 5.6 Hz, 1H), 6.31 (d, J=3.3 Hz, 1H), 6.43 (d, J=3.3 Hz, 1H), 6.68 (d, J=2.3 Hz, 1H); 6.82 (d, J=2.3 Hz, 1H);

FAB-MS (m/z): 450 (M+H)$^+$.

(Step 3)

Methyl 2-{5-[N-(allyloxycarbonyl)aminomethyl]furan-2-yl}-3,5-bis(methoxymethoxy)phenylacetate (0.34 g, 0.76 mmol) obtained in the above was dissolved in dichloromethane (10 mL), and tetrakis(triphenylphosphine)palladium(II) (44 mg, 0.038 mmol), triphenylphosphine (53 mg, 0.20 mmol) and piperidine (0.32 mL, 3.8 mmol) were added thereto and stirred at room temperature for 4 hours. The reaction solution was concentrated under reduced pressure, and the resulting residue was purified through preparative thin-layer chromatography (methanol/chloroform=1/9) to obtain methyl 2-[5-(aminomethyl)furan-2-yl]-3,5-bis(methoxymethoxy)phenylacetate (0.20 g, 72%).

$^1$H-NMR (270 MHz, CDCl$_3$) δ (ppm): 3.43 (s, 3H), 3.49 (s, 3H), 3.63 (s, 2H), 3.66 (s, 3H), 3.81 (s, 2H), 5.12 (s, 2H), 5.18 (s, 2H), 6.21 (d, J=3.3 Hz, 1H), 6.41 (d, J=3.3 Hz, 1H), 6.68 (d, J=2.3 Hz, 1H), 6.82 (d, J=2.3 Hz, 1H);

FAB-MS (m/z): 349 (M-NH$_2$)$^+$.

(Step 4)

Methyl 2-[5-(aminomethyl)furan-2-yl]-3,5-bis(methoxymethoxy)phenylacetate (0.18 g, 0.49 mmol) obtained in the above was dissolved in methanol solution (10 mL) of 5% hydrochloric acid, and stirred at room temperature for 5 hours. The reaction solution was concentrated under reduced pressure, and the resulting residue was purified through preparative thin-layer chromatography (methanol/chloroform=1/6) to obtain Compound 263 (67 mg, 67%).

$^1$H-NMR (270 MHz, CDCl$_3$) δ (ppm): 3.55 (s, 2H), 3.61 (s, 3H), 4.16 (s, 2H), 6.32 (d, J=2.3 Hz, 1H), 6.34 (d, J=2.3 Hz, 1H), 6.40 (d, J=3.3 Hz, 1H), 6.60 (d, J=3.3 Hz, 1H);

APCI-MS (m/z): 276 (M-H)$^-$.

EXAMPLE 264

Methyl 2-[5-(N-acetylaminomethyl)furan-2-yl]-3,5-dihydroxyphenylacetate (Compound 264)

Methyl 2-{5-[N-(allyloxycarbonyl)aminomethyl]furan-2-yl}-3,5-bis(methoxymethoxy)phenylacetate (30 mg, 0.067 mmol) obtained in the step 2 in Example 263 was dissolved in dichloromethane (2.0 mL), and tetrakis(triphenylphosphine)palladium(II) (4.5 mg, 0.0039 mmol), triphenylphosphine (6.0 mg, 0.023 mmol) and piperidine (0.032 mL, 0.38 mmol) were added thereto and stirred at room temperature for 5 hours. Then, acetic anhydride (0.10 mL, 1.1 mmol) and pyridine (0.10 mL, 1.2 mmol) were added to the reaction mixture, and stirred for 4 hours, and methanol was added thereto and stirred for 1 hour. The reaction solution was concentrated under reduced pressure, and the resulting residue was dissolved in chloroform (50 mL), and 1 mol/L hydrochloric acid (4.0 mL) was added thereto for liquid-liquid separation. The organic layer was dried over anhydrous sodium sulfate, and the solvent was evaporated away under reduced pressure. The resulting residue was purified through preparative thin-layer chromatography (ethyl acetate/n-hexane=2/1) to obtain methyl 2-[5-(N-acetylaminomethyl)furan-2-yl]-3,5-bis(methoxymethoxy)phenylacetate. The resulting compound was dissolved in methanol solution (2.0 mL) of 5% hydrochloric acid, then stirred at room temperature for 4 hours, and concentrated under reduced pressure. The resulting residue was purified through preparative thin-layer chromatography (methanol/chloroform=1/9) to obtain Compound 264 (4.0 mg, 19%).

$^1$H-NMR (270 MHz, CDCl$_3$) δ (ppm): 1.97 (s, 3H), 3.55 (s, 2H), 3.60 (s, 3H), 4.33 (s, 2H), 6.26 (d, J=2.3 Hz, 1H), 6.28 (d, J=3.3 Hz, 1H), 6.30 (d, J=2.3 Hz, 1H), 6.34 (d, J=3.3 Hz, 1H);

APCI-MS (m/z): 318 (M-H)$^-$.

EXAMPLE 265

Methyl 2-bromo-3,5-dihydroxy-6-[5-(3-oxobutyl)furan-2-yl]phenylacetate (Compound 265)

(Step 1)

Methyl 3,5-bis(methoxymethoxy)phenylacetate (0.10 g, 0.37 mmol) obtained in the step 2 in Example 1 was dissolved in toluene (3.0 mL), and N-bromosuccinimide (0.20 g, 1.1 mmol) was added thereto and stirred with heating under reflux for 4 hours. Then, N-bromosuccinimide (0.29 g, 1.6 mmol) was added thereto and stirred at 60° C. for 4 hours. The reaction solution was cooled to room temperature, and then concentrated under reduced pressure. The resulting residue was purified through preparative thin-layer chromatography (ethyl acetate/n-hexane=1/2) to obtain methyl 2,6-dibromo-3,5-bis(methoxymethoxy)phenylacetate (0.10 g, 70%).

$^1$H-NMR (270 MHz, CDCl$_3$) δ (ppm): 3.52 (s, 6H), 3.73 (s, 3H), 4.20 (s, 2H), 5.23 (s, 4H), 7.02 (s, 1H).

(Step 2)

Methyl 2,6-dibromo-3,5-bis(methoxymethoxy)phenylacetate (0.28 g, 0.66 mmol) obtained in the above was dissolved in toluene (3.5 mL), and tributyl[5-(1,3-dioxolan-2-yl)furan-2-yl]tin (0.30 g, 0.70 mmol), tris(dibenzylideneacetone)dipalladium (60 mg, 0.066 mmol) and triphenylphosphine (70 mg, 0.27 mmol) were added thereto, then stirred at room temperature for 0.5 hour, and further stirred with heating under reflux for 5 hours. The reaction mixture was cooled to room temperature, and ethyl acetate (0.10 L) and aqueous saturated potassium fluoride solution (5.0 mL) were added thereto, then stirred for 0.5 hours, and filtered. The filtrate was subjected to liquid-liquid separation, and the organic layer was washed with 3 mol/L hydrochloric acid (50 mL) and water (50 mL) in order, then dried over anhydrous sodium sulfate. The solvent was evaporated away under reduced pressure, and the resulting residue was purified through preparative thin-layer chromatography (ethyl acetate/n-hexane=1/2) to obtain methyl 2-bromo-6-(5-formylfuran-2-yl)-3,5-bis(methoxymethoxy)phenylacetate (0.13 g, 45%).

$^1$H-NMR (270 MHz, CDCl$_3$) δ (ppm): 3.41 (s, 3H), 3.53 (s, 3H), 3.73 (s, 3H), 3.83 (s, 2H), 5.13 (s, 2H), 5.29 (s, 2H), 6.65 (d, J=3.4 Hz, 1H), 7.03 (s, 1H), 7.32 (d, J=3.4 Hz, 1H), 9.63 (s, 1H);

FAB-MS (m/z): 443 ($^{79}$Br), 445 ($^{81}$Br) (M+H)$^+$.

(Step 3)

Methyl 2-bromo-6-(5-formylfuran-2-yl)-3,5-bis(methoxymethoxy)phenylacetate (0.14 g, 0.31 mmol) obtained in the above was dissolved in tetrahydrofuran (5.0 mL), and (acetylmethylene)triphenylphospholane (0.19 g, 0.61 mmol) was added thereto and stirred at 60° C. for 4 hours. The reaction solution was cooled to room temperature, and then concentrated under reduced pressure. The resulting residue was purified through silica gel column chromatography (ethyl acetate/n-hexane=1/9 to 1/2) to obtain methyl 2-bromo-3,5-bis(methoxymethoxy)-6-[5-(3-oxobut-1-en-1-yl)furan-2-yl]phenylacetate (0.14 g, 95%).

$^1$H-NMR (270 MHz, CDCl$_3$) δ (ppm): 2.32 (s, 3H), 3.41 (s, 3H), 3.54 (s, 3H), 3.72 (s, 3H), 3.86 (s, 2H), 5.13 (s, 2H), 5.29 (s, 2H), 6.52 (d, J=15.8 Hz, 1H), 6.56 (d, J=3.3 Hz, 1H), 6.75 (d, J=3.3 Hz, 1H), 7.03 (s, 1H), 7.26 (d, J=15.8 Hz, 1H);

FAB-MS (m/z): 483 ($^{79}$Br), 485 ($^{81}$Br) (M+H)$^+$.

(Step 4)

In an argon atmosphere, methyl 2-bromo-3,5-bis(methoxymethoxy)-6-[5-(3-oxobut-1-en-1-yl)furan-2-yl]phenylacetate (0.11 g, 0.23 mmol) obtained in the above was dissolved in toluene (2.0 mL), and triethylsilane (0.15 mL, 0.94 mmol) and tris(triphenylphosphine)rhodium(I) chloride (30 mg, 0.032 mmol) were added thereto and stirred at room temperature for 10 hours. The reaction solution was concentrated under reduced pressure, and the residue was purified through silica gel column chromatography (ethyl acetate/n-hexane=1/4 to ethyl acetate) to obtain methyl 2-bromo-3,5-bis(methoxymethoxy)-6-[5-(3-oxobutyl)furan-2-yl]phenylacetate. The resulting compound was dissolved in methanol solution (5.0 mL) of 10% hydrochloric acid, then stirred at room temperature for 4 hours, and concentrated under reduced pressure. The resulting residue was purified through preparative thin-layer chromatography (methanol/chloroform=1/9) to obtain Compound 265 (33 mg, 36%).

$^1$H-NMR (270 MHz, CDCl$_3$) δ (ppm): 2.28 (s, 3H), 2.78-2.97 (m, 4H), 3.70 (s, 3H), 3.75 (s, 2H), 5.71 (s, 1H), 5.87 (s, 1H), 6.14 (d, J=3.3 Hz, 1H), 6.35 (d, J=3.3 Hz, 1H), 6.66 (s, 1H);

APCI-MS (m/z): 395 ($^{79}$Br), 397 ($^{81}$Br) (M–H)$^-$.

EXAMPLE 266

2-[5-(N-acetylaminomethyl)furan-2-yl]-3,5-dihydroxyphenylacetic acid (Compound 266)

Methyl 2-[5-(N-acetylaminomethyl)furan-2-yl]-3,5-bis(methoxymethoxy)phenylacetate (45 mg, 0.15 mmol) obtained in Example 264 was dissolved in dichloromethane (1.0 mL), and acetic anhydride (0.20 mL, 2.12 mmol) and pyridine (0.20 mL, 2.5 mmol) were added thereto and stirred at room temperature for 3 hours. Methanol (5.0 mL) was added to the reaction solution, then stirred for 0.5 hours, and concentrated under reduced pressure. The resulting residue was dissolved in acetonitrile (1.0 mL), and aqueous 4 mol/L sodium hydroxide solution (1.0 mL, 4.0 mmol) was added thereto and stirred at 40° C. for 4 hours. 3 mol/L hydrochloric acid (3.0 mL) was added to the reaction solution, and concentrated under reduced pressure, and the resulting residue was purified through HP-20 (Mitsubishi Chemical Industry; water to acetonitrile/water=1/4) to obtain Compound 266 (23 mg, 23%).

$^1$H-NMR (270 MHz, CD$_3$OD) δ (ppm): 1.93 (s, 3H), 3.48 (br s, 2H), 4.15 (br s, 2H), 6.22 (d, J=2.0 Hz, 1H), 6.31 (d, J=2.0 Hz, 1H), 6.46 (d, J=2.6 Hz, 1H), 6.57 (d, J=2.6 Hz, 1H);

APCIMS (m/z): 304 (M–H)$^-$.

EXAMPLE 267

Methyl 3-{5-[5-bromo-2,4-dihydroxy-6-(methoxycarbonylmethyl)phenyl]furan-2-yl}propanoate (Compound 267)

(Step 1)

(Carbomethoxymethylene)triphenylphospholane (0.17 g, 0.51 mmol) was added to toluene (4.0 mL) solution of methyl 2-bromo-6-(5-formylfuran-2-yl)-3,5-bis(methoxymethoxy) phenylacetate (0.11 g, 0.25 mmol) obtained in the step 3 in Example 265, and stirred at 60° C. for 4 h ours. The reaction solution was cooled to room temperature, and then concentrated under reduced pressure. The resulting residue was purified through silica gel column chromatography (n-hexane to ethyl acetate/n-hexane=1/2) to obtain methyl 3-{5-[3-bromo-2-(methoxycarbonylmethyl)-4,6-bis(methoxymethoxy)phenyl]furan-2-yl}acrylate (0.12 g, 93%).

$^1$H-NMR (270 MHz, CDCl$_3$) δ (ppm): 3.41 (s, 3H), 3.53 (s, 3H), 3.73 (s, 3H), 3.77 (s, 3H), 3.86 (s, 2H), 5.13 (s, 2H), 5.29 (s, 2H), 6.21 (d, J=15.8 Hz, 1H), 6.54 (d, J=3.3 Hz, 1H), 6.69 (d, J=3.3 Hz, 1H), 7.03 (s, 1H), 7.42 (d, J=15.8 Hz, 1H);

FAB-MS (m/z): 499 ($^{79}$Br), 501 ($^{81}$Br) (M+H)$^+$.

(Step 2)

In an argon atmosphere, triethylsilane (0.15 mL, 0.94 mmol) and tris(triphenylphosphine)rhodium(I) chloride (30 mg, 0.032 mmol) were added to toluene (2.0 mL) solution of methyl 3-{5-[3-bromo-2-(methoxycarbonylmethyl)-4,6-bis (methoxymethoxy)phenyl]furan-2-yl}acrylate (89 mg, 0.18 mmol) obtained in the above, and stirred at 50° C. for 3 hours. The reaction solution was concentrated, and the residue was purified through silica chromatography (n-hexane to ethyl acetate/n-hexane=1/2) to obtain methyl 3-{5-[3-bromo-2-(methoxycarbonylmethyl)-4,6-bis(methoxymethoxy)phenyl]furan-2-yl}propanoate. Then, the resulting compound was dissolved in methanol solution (5.0 mL) of 10% hydrochloric acid, stirred at room temperature for 2 hours, and then concentrated under reduced pressure. The resulting residue was purified through preparative thin-layer chromatography (methanol/chloroform=1/9) to obtain Compound 267 (35 mg, 48%).

$^1$H-NMR (270 MHz, CDCl$_3$) δ (ppm): 2.68 (t, J=7.3 Hz, 2H), 3.00 (t, J=7.3 Hz, 2H), 3.69 (s, 3H), 3.71 (s, 3H), 3.76 (s, 2H), 5.86 (s, 1H), 5.99 (s, 1H), 6.17 (d, J=3.1 Hz, 1H) 6.36 (d, J=3.1 Hz, 1H), 6.64 (s, 1H);

APCI-MS (m/z): 411 ($^{79}$Br), 413 ($^{81}$Br) (M–H)$^-$.

EXAMPLE 268

Methyl 3,5-dihydroxy-2-[5-(3-hydroxyiminobutyl) furan-2-yl]phenylacetate (Compound 268)

(Step 1)

In the same manner as in the step 1 in Example 253, methyl 2-[5-(3-hydroxyiminobutyl)furan-2-yl]-3,5-bis(methoxymethoxy)phenylacetate (96 mg, 96%) was obtained from methyl 3,5-bis(methoxymethoxy)-2-[5-(3-oxobutyl)furan-2-yl]phenylacetate (100 mg, 0.24 mmol) obtained in the step 2 in Example 261, using pyridine (2.0 mL) and hydroxylamine hydrochloride (30 mg, 0.40 mmol).

APCI-MS (m/z): 422 (M+H)$^+$.

(Step 2)

In the same manner as in the step 4 in Example 1, Compound 268 (60 mg, 82%) was obtained from methyl 2-[5-(3-hydroxyiminobutyl)furan-2-yl]-3,5-bis(methoxymethoxy)

phenylacetate (96 mg, 0.22 mmol) obtained in the above, using methanol (1.0 mL) and 1,4-dioxane solution (1.0 mL) of 4 mol/L hydrogen chloride.

$^1$H-NMR (270 MHz, CD$_3$OD) δ (ppm): 1.79 (s, 1.2H), 1.80 (s, 1.8H), 2.43-2.50 (m, 2H), 2.64-2.80 (m, 2H), 3.30 (s, 2H), 3.56 (s, 3H), 6.04-6.06 (m, 1H), 6.22-6.27 (m, 3H);

APCI-MS (m/z): 334 (M+H)$^+$.

EXAMPLE 269

Methyl 3,5-dihydroxy-2-[5-(3-methoxyiminobutyl)furan-2-yl]phenylacetate (Compound 269)

(Step 1)

In the same manner as in the step 1 in Example 253, methyl 2-[5-(3-methoxyiminobutyl)furan-2-yl]-3,5-bis(methoxymethoxy)phenylacetate (53 mg, 94%) was obtained from methyl 3,5-bis(methoxymethoxy)-2-[5-(3-oxobutyl)furan-2-yl]phenylacetate (53 mg, 0.13 mmol) obtained in the step 2 in Example 261, using pyridine (2.0 mL) and O-methylhydroxylamine hydrochloride (20 mg, 0.24 mmol).

APCI-MS (m/z): 436 (M+H)$^+$.

(Step 2)

In the same manner as in the step 4 in Example 1, Compound 269 (35 mg, 84%) was obtained from methyl 2-[5-(3-methoxyiminobutyl)furan-2-yl]-3,5-bis(methoxymethoxy)phenylacetate (53 mg, 0.12 mmol) obtained in the above, using methanol (1.0 mL) and 1,4-dioxane solution (1.0 mL) of 4 mol/L hydrogen chloride.

$^1$H-NMR (270 MHz, CD$_3$OD) δ (ppm): 1.80 (s, 1.5H), 1.82 (s, 1.5H), 2.48-2.52 (m, 2H), 2.78-2.89 (m, 2H), 3.54 (s, 2H), 3.60 (s, 1.5H), 3.61 (s, 1.5H), 3.76 (s, 3H), 6.05-6.09 (m, 1H), 6.18-6.31 (m, 3H);

APCI-MS (m/z): 348 (M+H)$^+$.

EXAMPLE 270

Methyl-3,5-dihydroxy-2-(2-naphthyl)phenylacetate (Compound 270)

In the same manner as in the step 3 in Example 1, methyl 3,5-bis(methoxymethoxy)-2-(2-naphthyl)phenylacetate was obtained from methyl 2-bromo-3,5-bis(methoxymethoxy)phenylacetate (93 mg, 0.27 mmol) obtained in the step 2 in Example 1, using 2-naphthaleneboronic acid (70 mg, 0.41 mmol), tetrakis(triphenylphosphine)palladium(II) (15 mg, 0.013 mmol), aqueous 2 mol/L sodium carbonate solution (0.4 mL) and 1,2-dimethoxyethane (3.0 mL). Then, in the same manner as in the step 4 in Example 1, Compound 270 (39 mg, 46%) was obtained from the resulting compound, using methanol (2.0 mL) and 1,4-dioxane solution (1.0 mL) of 4 mol/L hydrogen chloride.

$^1$H-NMR (270 MHz, CDCl$_3$) δ (ppm): 3.33 (s, 3H), 3.45 (s, 2H), 6.35 (d, J=2.3 Hz, 1H), 6.36 (d, J=2.3 Hz, 1H), 7.29 (dd, J=8.4, 1.8 Hz, 1H), 7.43 (t, J=3.1 Hz, 1H), 7.46 (t, J=3.1 Hz, 1H), 7.62 (br s, 1H), 7.75-7.85 (m, 3H);

APCI-MS (m/z): 307 (M−H)$^-$.

EXAMPLE 271

Methyl 3,5-dihydroxy-2-(dibenzofuran-4-yl)phenylacetate (Compound 271)

In the same manner as in the step 3 in Example 1, methyl 2-(dibenzofuran-4-yl)-3,5-bis(methoxymethoxy)phenylacetate was obtained from methyl 2-bromo-3,5-bis(methoxymethoxy)phenylacetate (94 mg, 0.27 mmol) obtained in the step 2 in Example 1, using 4-dibenzofuranboronic acid (85 mg, 0.40 mmol), tetrakis(triphenylphosphine)palladium (II) (15 mg, 0.013 mmol), aqueous 2 mol/L sodium carbonate solution (0.4 mL) and 1,2-dimethoxyethane (3 mL). Then, in the same manner as in the step 4 in Example 1, Compound 271 (67 mg, 72%) was obtained from the resulting compound, using methanol (2.0 mL) and 1,4-dioxane solution (1.0 mL) of 4 mol/L hydrogen chloride.

$^1$H-NMR (270 MHz, CDCl$_3$) δ (ppm): 3.33 (s, 5H), 6.33 (d, J=2.5 Hz, 1H), 6.40 (d, J=2.5 Hz, 1H), 7.24-7.50 (m, 5H), 7.96-8.04 (m, 2H);

APCI-MS (m/z): 347 (M−H)$^-$.

EXAMPLE 272

Methyl 3,5-dihydroxy-2-(1-naphthyl)phenylacetate (Compound 272)

In the same manner as in the step 3 in Example 1, methyl 3,5-bis(methoxymethoxy)-2-(1-naphthyl)phenylacetate was obtained from methyl 2-bromo-3,5-bis(methoxymethoxy)phenylacetate (95 mg, 0.27 mmol) obtained in the step 2 in Example 1, using 1-naphthaleneboronic acid (70 mg, 0.41 mmol), tetrakis(triphenylphosphine)palladium(II) (15 mg, 0.013 mmol), aqueous 2 mol/L sodium carbonate solution (0.4 mL) and 1,2-dimethoxyethane (3.0 mL). Then, in the same manner as in the step 4 in Example 1, Compound 272 (39 mg, 46%) was obtained from the resulting compound, using methanol (2.0 mL) and 1,4-dioxane solution (1.0 mL) of 4 mol/L hydrogen chloride.

$^1$H-NMR (270 MHz, CDCl$_3$) δ (ppm): 3.30 (d, J=15.1 Hz, 1H), 3.20 (d, J=15.6 Hz, 1H), 3.27 (s, 3H), 6.38 (d, J=2.5 Hz, 1H), 6.40 (d, J=2.5 Hz, 1H), 7.22-7.50 (m, 5H), 7.84 (m, 2H);

FAB-MS (m/z): 308 (M+H)$^+$.

EXAMPLE 273

Methyl 2-(1,3-benzodioxolan-5-yl)-3,5-dihydroxyphenylacetate (Compound 273)

In the same manner as in the step 3 in Example 1, methyl 2-(1,3-benzodioxolan-5-yl)-3,5-bis(methoxymethoxy)phenylacetate was obtained from methyl 2-bromo-3,5-bis(methoxymethoxy)phenylacetate (100 mg, 0.29 mmol) obtained in the step 2 in Example 1, using 3,4-(methylenedioxy)phenylboronic acid (73 mg, 0.44 mmol), bis(tri-o-tolylphosphine)palladium(II) dichloride (10 mg, 0.017 mmol), cesium carbonate (300 mg, 0.92 mmol), 1,2-dimethoxyethane (3.0 mL) and water (0.5 mL). Then, in the same manner as in the step 4 in Example 1, Compound 273 (61 mg, 69%) was obtained from the resulting compound, using methanol (2.0 mL) and 1,4-dioxane solution (1.0 mL) of 4 mol/L hydrogen chloride.

$^1$H-NMR (270 MHz, DMSO-d$_6$) δ (ppm): 3.27 (s, 2H), 3.30 (s, 3H), 5.60 (s, 2H), 6.17 (d, J=2.4 Hz, 1H), 6.27 (d, J=2.4 Hz, 1H), 6.49 (dd, J=7.8, 1.6 Hz, 1H), 6.57 (d, J=1.6 Hz, 1H), 6.86 (d, J=7.8 Hz, 1H), 8.98 (s, 1H), 9.19 (s, 1H);

FAB-MS (m/z): 302 (M+H)$^+$.

EXAMPLE 274

Methyl 3,5-dihydroxy-2-(2-thienyl)phenylacetate (Compound 274)

(Step 1)

In the same manner as in the step 2 in Example 1, methyl 3,5-bis(methoxymethoxy)-2-(2-thienyl)phenylacetate (130 mg, 66%) was obtained from methyl 2-bromo-3,5-bis(methoxymethoxy)phenylacetate (190 mg, 0.56 mmol), using tris(dibenzylideneacetone)dipalladium (51 mg, 0.056 mmol) and tributyl(2-thienyl)tin (0.36 mL, 1.1 mmol).

$^1$H-NMR (270 MHz, CDCl$_3$) δ (ppm): 3.27 (s, 3H), 3.41 (s, 3H), 3.43 (s, 2H), 3.54 (s, 3H), 4.98 (s, 2H), 5.11 (s, 2H), 6.63 (d, J=2.5 Hz, 1H), 6.73 (d, J=2.5 Hz, 1H), 6.80 (dd, J=3.3, 1.3 Hz, 1H), 6.98 (dd, J=5.0, 3.3 Hz, 1H), 7.29 (dd, J=5.0, 1.3 Hz, 1H);

APCI-MS (m/z): 352 (M+H)$^+$.

(Step 2)

In the same manner as in the step 4 in Example 1, Compound 274 (63 mg, 64%) was obtained from methyl 3,5-bis(methoxymethoxy)-2-(2-thienyl)phenylacetate (130 mg, 0.37 mmol) obtained in the above, using methanol (2.0 mL) and 1,4-dioxane solution (2.0 mL) of 4 mol/L hydrogen chloride.

$^1$H-NMR (270 MHz, CDCl$_3$) δ (ppm): 3.46 (s, 2H), 3.62 (s, 3H), 5.37 (br s, 1H), 6.38 (J=2.5 Hz, 1H), 6.40 (d, J=2.5 Hz, 1H), 6.51 (br s, 1H), 6.98 (dd, J=3.6, 1.3 Hz, 1H), 7.13 (dd, J=5.0, 3.6, Hz, 1H), 7.46 (dd, J=5.0, 1.3 Hz, 1H);

APCI-MS (m/z): 263 (M−H)$^−$.

EXAMPLE 275

6-Ethyl-5-[2-(2-hydroxyethoxy)ethyl]-4-(2-thienyl)benzene-1,3-diol (Compound 275)

(Step 1)

In the same manner as in the step 2 in Example 235, 4-ethyl-1,5-bis(methoxymethoxy)-3-{2-[2-(tetrahydropyran-2-yloxy)ethoxy]ethyl}-2-(2-thienyl)benzene (92 mg, 66%) was obtained from 2-bromo-4-ethyl-1,5-bis(methoxymethoxy)-3-{2-[2-(tetrahydropyran-2-yloxy)ethoxy]ethyl}benzene (140 mg, 0.29 mmol) obtained in the step 2 in Example 174, using bis(triphenylphosphine)palladium(II) dichloride (200 mg, 0.29 mmol) and tributyl(2-thienyl)tin (0.3 mL, 0.95 mmol).

$^1$H-NMR (270 MHz, CDCl$_3$) δ (ppm): 7.35 (dd, J=5.1, 1.1 Hz, 1H), 7.06 (dd, J=5.1, 3.3 Hz, 1H), 6.88 (dd, J=3.3, 1.1 Hz, 1H), 6.84 (s, 1H), 5.22 (s, 2H), 5.01 (s, 2H), 4.58 (m, 1H), 3.87-3.60 (m, 6H), 3.58 (s, 3H), 3.32 (s, 3H), 2.85 (t, J=8.0 Hz, 2H), 2.70 (q, J=7.3 Hz, 2H), 1.74-1.47 (m, 6H), 1.15 (t, J=7.3 Hz, 3H).

(Step 2)

In the same manner as in the step 4 in Example 1, Compound 275 (56 mg, 70%) was obtained from 4-ethyl-1,5-bis(methoxymethoxy)-3-{2-[2-(tetrahydropyran-2-yloxy)ethoxy]ethyl}-2-(2-thienyl)benzene (90 mg, 0.18 mmol) obtained in the above, using methanol (3.0 mL) and 1,4-dioxane solution (1.0 mL) of 4 mol/L hydrogen chloride.

$^1$H-NMR (270 MHz, CDCl$_3$) δ (ppm): 1.06 (t, J=7.3 Hz, 3H), 2.57 (q, J=7.3 Hz, 2H), 2.72 (t, J=8.3 Hz, 2H), 3.30 (t, J=5.0 Hz, 2H), 3.39 (t, J=8.3 Hz, 2H), 3.51 (t, J=5.0 Hz, 2H), 6.24 (s, 1H), 6.80 (d, J=3.5 Hz, 1H), 7.02 (d, J=4.3 Hz, 1H), 7.37 (d, J=4.2 Hz, 1H);

APCI-MS (m/z): 307 (M−H)$^−$.

EXAMPLE 276

6-Ethyl-4-(6-methoxy-1H-indazol-3-yl)benzene-1,3-diol (Compound 276)

(Step 1)

4-Ethylresorcinol (3.1 g, 22 mmol) was dissolved in dichloromethane (100 mL), and diisopropylethylamine (10 mL, 57 mmol) and methoxymethyl chloride (3.8 mL, 50 mmol) were added thereto and stirred at room temperature for 8 hours. Water was added to the reaction solution, and extracted with chloroform. The organic layer was washed with aqueous saturated sodium chloride solution, then dried over anhydrous sodium sulfate, and the solvent was evaporated away under reduced pressure. The resulting residue was purified through silica gel column chromatography (ethyl acetate/n-hexane=1/4 to 1/2) to obtain 1-ethyl-2,4-bis(methoxymethoxy)benzene (3.0 g, 60%).

$^1$H-NMR (270 MHz, CDCl$_3$) δ (ppm): 1.17 (t, J=7.5 Hz, 3H), 2.59 (q, J=7.5 Hz, 2H), 3.47 (s, 3H), 3.48 (s, 3H), 5.13 (s, 2H), 5.17 (s, 2H), 6.65 (dd, J=8.3, 2.5 Hz, 1H), 6.77 (d, J=2.5 Hz, 1H), 7.04 (d, J=8.3 Hz, 1H).

(Step 2)

1-Ethyl-2,4-bis(methoxymethoxy)benzene (2.9 g, 13 mmol) obtained in the above was dissolved in N,N-dimethylformamide (50 mL), and N-bromosuccinimide (2.5 g, 14 mmol) was added thereto and stirred at room temperature for 1 hour. The reaction solution was concentrated under reduced pressure, and the resulting residue was purified through silica gel column chromatography (ethyl acetate/n-hexane=1/9 to 1/4) to obtain 5-bromo-1-ethyl-2,4-bis(methoxymethoxy)benzene (3.7 g, 93%).

$^1$H-NMR (300 MHz, CDCl$_3$) δ (ppm): 1.17 (t, J=7.5 Hz, 3H), 2.54 (q, J=7.5 Hz, 2H), 3.47 (s, 3H), 3.52 (s, 3H), 5.16 (s, 2H), 5.19 (s, 2H), 6.92 (s, 1H), 7.28 (s, 1H).

(Step 3)

5-Bromo-1-ethyl-2,4-bis(methoxymethoxy)benzene (570 mg, 1.9 mmol) obtained in the above was dissolved in tetrahydrofuran (15 mL), and with stirring at −78° C., n-hexane solution of 1.5 mol/L n-butyllithium (1.9 mL, 2.9 mmol) was added thereto and stirred for 30 minutes. 2-Fluoro-4-methoxybenzaldehyde (430 mg, 2.8 mmol) was added to the reaction liquid, and stirred for 1 hour. Aqueous saturated animonium chloride solution was added to the reaction liquid, heated up to room temperature, and then extracted twice with ethyl acetate. The organic layer was washed with aqueous saturated sodium chloride solution, then dried over anhydrous sodium sulfate, and the solvent was evaporated away under reduced pressure. Dichloromethane (30 mL) and pyridinium dichromate (1.0 g, 2.7 mmol) were added to the resulting residue, and stirred at room temperature for 18 hours. The reaction mixture was diluted with ether, and filtered through Celite. The filtrate was concentrated under reduced pressure, and the resulting residue was purified through silica gel column chromatography (ethyl acetate/n-hexane=1/4 to 1/2) to obtain 5-ethyl-2,4-bis(methoxymethoxy)phenyl 2-fluoro-4-methoxyphenyl ketone (450 mg, 65%).

$^1$H-NMR (270 MHz, CDCl$_3$) δ (ppm): 1.19 (t, J=7.6 Hz, 3H), 2.62 (q, J=7.6 Hz, 2H), 3.31 (s, 3H), 3.50 (s, 3H), 3.84 (s, 3H), 4.96 (s, 2H), 5.24 (s, 2H), 6.56 (dd, J=13.5, 2.5 Hz, 1H), 6.73 (dd, J=8.6, 2.5 Hz, 1H), 6.86 (s, 1H), 7.37 (s, 1H), 7.66 (t, J=8.6 Hz, 1H).

(Step 4)

5-Ethyl-2,4-bis(methoxymethoxy)phenyl 2-fluoro-4-methoxyphenyl ketone (20 mg, 0.069 mmol) obtained in the above was dissolved in ethanol (2.0 mL), and hydrazine hydrate (0.05 mL, 1.0 mmol) was added thereto and stirred with heating under reflux for 12 hours. The reaction solution was concentrated under reduced pressure, and the resulting residue was purified through preparative thin-layer chromatography (ethyl acetate/n-hexane=1/1) to obtain 1-ethyl-5-(6-methoxy-1H-indazol-3-yl)-2,4-bis(methoxymethoxy)benzene (14 mg, 55%).

$^1$H-NMR (300 MHz, CDCl$_3$) δ (ppm): 1.20 (t, J=7.5 Hz, 3H), 2.65 (q, J=7.5 Hz, 2H), 3.34 (s, 3H), 3.53 (s, 3H), 3.85 (s, 3H), 5.09 (s, 2H), 5.26 (s, 2H), 6.70-6.81 (m, 2H), 7.05 (s, 1H), 7.47 (s, 1H), 7.67 (d, J=8.8 Hz, 1H).

(Step 5)

1-Ethyl-5-(6-methoxy-1H-indazol-3-yl)-2,4-bis(methoxymethoxy)benzene (14 mg, 0.037 mmol) obtained in the above was dissolved in methanol (1.0 mL), and 1,4-dioxane solution (1.0 mL) of 4 mol/L hydrogen chloride was added thereto and stirred at room temperature for 1 hour. The reaction solution was neutralized with aqueous saturated sodium hydrogencarbonate solution, then the aqueous layer was extracted twice with ethyl acetate, and dried over anhydrous sodium sulfate. The solvent was evaporated away under reduced pressure, and the resulting residue was crystallized from chloroform to obtain Compound 276 (10 mg, 95%).

$^1$H-NMR (270 MHz, CD$_3$OD) δ (ppm): 1.12 (t, J=7.6 Hz, 3H), 2.63 (q, J=7.6 Hz, 2H), 3.94 (s, 3H), 6.56 (s, 1H), 7.01 (d, J=2.2 Hz, 1H), 7.05 (dd, J=9.2, 2.2 Hz, 1H), 7.54 (s, 1H), 8.02 (d, J=9.2 Hz, 1H);

ESI-MS (m/z): 285 (M+H)$^+$.

EXAMPLE 277

6-Ethyl-4-(5-nitro-1H-indazol-3-yl)benzene-1,3-diol
(Compound 277)

(Step 1)

In the same manner as in the step 3 in Example 276, 5-bromo-1-ethyl-2,4-bis(methoxymethoxy)benzene (420 mg, 1.4 mmol) obtained in the step 2 in Example 276 was treated with n-hexane solution of 1.5 mol/L n-butyllithium (1.4 mL, 2.1 mmol), 2-fluoro-5-nitrobenzaldehyde (280 mg, 1.7 mmol) and tetrahydrofuran (15 mL). Then, the resulting compound was treated with pyridinium dichromate (750 mg, 2.0 mmol) and dichloromethane (15 mL) to obtain 5-ethyl-2,4-bis(methoxymethoxy)phenyl 2-fluoro-3-nitrophenyl ketone (160 mg, 29%).

$^1$H-NMR (270 MHz, CDCl$_3$) δ (ppm): 1.22 (t, J=7.5 Hz, 3H), 2.64 (q, J=7.5 Hz, 2H), 3.23 (s, 3H), 3.50 (s, 3H), 4.88 (s, 2H), 5.26 (s, 2H), 6.85 (s, 1H), 7.23 (t, J=8.9 Hz, 1H), 7.61 (s, 1H), 8.33 (m, 1H), 8.46 (dd, J=5.7, 2.7 Hz, 1H).

(Step 2)

In the same manner as in the step 4 in example 276, 1-ethyl-2,4-bis(methoxymethoxy)-5-(5-nitro-1H-indazol-3-yl)benzene (37 mg, 68%) was obtained from 5-ethyl-2,4-bis(methoxymethoxy)phenyl 2-fluoro-3-nitrophenyl ketone (55 mg, 0.14 mmol) obtained in the above, using hydrazine hydrate (0.05 mL, 1.0 mmol), toluene (1.0 mL) and ethanol (1.0 mL).

$^1$H-NMR (270 MHz, CDCl$_3$) δ (ppm): 1.16 (t, J=7.4 Hz, 3H), 2.66 (q, J=7.4 Hz, 2H), 3.41 (s, 3H), 3.57 (s, 3H), 5.15 (s, 2H), 5.32 (s, 2H), 7.15 (s, 1H), 7.20 (d, J=9.2 Hz, 1H), 7.51 (s, 1H), 8.20 (dd, J=9.2, 2.2H, 1H), 8.88 (d, J=2.2 Hz, 1H).

(Step 3)

In the same manner as in the step 4 in Example 1, Compound 277 (25 mg, 87%) was obtained from 1-ethyl-2,4-bis(methoxymethoxy)-5-(5-nitro-1H-indazol-3-yl)benzene (37 mg, 0.096 mmol) obtained in the above, using 1,4-dioxane solution (1.0 mL) of 4 mol/L hydrogen chloride and methanol (1.0 mL).

$^1$H-NMR (300 MHz, DMSO-d$_6$) δ (ppm): 1.13 (t, J=7.5 Hz, 3H), 2.51 (q, J=7.5 Hz, 2H), 6.56 (s, 1H), 7.35 (s, 1H), 7.68 (d, J=8.4 Hz, 1H), 8.16 (dd, J=8.4, 1.6 Hz, 1H), 8.89 (d, J=1.6 Hz, 1H);

ESI-MS (m/z): 300 (M+H)$^+$.

EXAMPLE 278

4-Benzimidazol-2-yl-6-ethylbenzene-1,3-diol
(Compound 278)

(Step 1)

4-Ethylresorcinol (10 g, 73 mmol) was dissolved in acetone (250 mL), and potassium carbonate (30 g, 220 mmol) and allyl bromide (15 mL, 170 mmol) were added thereto and heated under reflux for 4 hours. The reaction mixture was cooled to room temperature, then filtered through Celite, and the filtrate was concentrated under reduced pressure. The resulting residue was purified through silica gel column chromatography (ethyl acetate/n-hexane=1/9) to obtain 2,4-bis(allyloxy)-1-ethylbenzene (15 g, 95%).

$^1$H-NMR (300 MHz, CDCl$_3$) δ (ppm): 1.17 (t, J=7.5 Hz, 3H), 2.60 (q, J=7.5 Hz, 2H), 4.49-4.53 (m, 4H), 5.24-5.30 (m, 2H), 5.37-5.46 (m, 2H), 5.99-6.31 (m, 2H), 6.42-6.46 (m, 2H), 7.03 (d, J=7.8 Hz, 1H).

(Step 2)

2,4-Bis(allyloxy)-1-ethylbenzene (10 g, 47 mmol) obtained in the above was dissolved in N,N-dimethylformamide (50 mL), and phosphorus oxychloride (8.0 mL, 86 mmol) was added thereto and stirred at 80° C. for 12 hours. The reaction solution was concentrated under reduced pressure, then ground ice was added to the residue, and neutralized with aqueous saturated sodium hydrogencarbonate solution, and the mixture was extracted with ethyl acetate. The organic layer was washed with aqueous saturated sodium chloride solution, then dried over anhydrous sodium sulfate, and the solvent was evaporated away under reduced pressure. The resulting residue was purified through silica gel column chromatography (ethyl acetate/n-hexane=1/9 to 1/4) to obtain 2,4-bis(allyloxy)-5-ethylbenzaldehyde (10 g, 89%).

$^1$H-NMR (270 MHz, CDCl$_3$) δ (ppm): 1.18 (t, J=7.5 Hz, 3H), 2.60 (q, J=7.5 Hz, 2H), 4.14-4.64 (m, 4H), 5.30-5.35 (m, 2H), 5.40-5.48 (m, 2H), 6.00-6.12 (m, 2H), 6.39 (s, 1H), 7.65 (s, 1H), 10.4 (s, 1H).

(Step 3)

2,4-Bis(allyloxy)-5-ethylbenzaldehyde (4.0 g, 16 mmol) obtained in the above was dissolved in a mixed solution of tert-butanol (50 mL), dichloromethane (10 mL) and water (10 mL), and sodium hydrogenphosphate (3.9 g, 33 mmol), 2-methyl-2-butene (8.0 mL, 76 mmol) and chlorous acid (4.5 g, 50 mmol) were added thereto in order, and stirred for 36 hours. The reaction solution was concentrated under reduced pressure, and the resulting residue was made acidic by adding 1 mol/L hydrochloric acid thereto, and then extracted with ethyl acetate. The organic layer was washed with aqueous saturated sodium chloride solution, then dried over anhydrous sodium sulfate, and the solvent was evaporated away under reduced pressure. The resulting residue was triturated (ethyl acetate/n-hexane=1/4) to obtain 2,4-bis(allyloxy)-5-ethylbenzoic acid (3.8 g, 90%).

$^1$H-NMR (270 MHz, CDCl$_3$) δ (ppm): 1.18 (t, J=7.5 Hz, 3H), 2.62 (q, J=7.5 Hz, 2H), 4.61-4.58 (m, 2H), 4.74-4.77 (m, 2H), 5.31-5.51 (m, 4H), 5.98-6.13 (m, 2H), 6.46 (s, 1H), 7.94 (s, 1H).

(Step 4)

2,4-Bis(allyloxy)-5-ethylbenzoic acid (300 mg, 1.1 mmol) obtained in the above was dissolved in phosphorus oxychloride (5.0 mL), and o-phenylenediamine (150 mg, 1.4 mmol) was added thereto and stirred for 2 hours. Phosphorus oxychloride was evaporated away under reduced pressure, and then the residue was extracted with ethyl acetate. The organic layer was washed with water, aqueous saturated sodium hydrogencarbonate solution and aqueous saturated sodium chloride solution in order, then dried over anhydrous sodium sulfate, and the solvent was evaporated away under reduced pressure. The resulting residue was purified through silica gel column chromatography (ethyl acetate/n-hexane=1/9 to 1/4) to obtain 2,4-bis(allyloxy)-5-(benzimidazol-2-yl)-1-ethylbenzene (311 mg, 86%).

$^1$H-NMR (300 MHz, CDCl$_3$) δ (ppm): 1.21 (t, J=7.5 Hz, 3H), 2.68 (q, J=7.5 Hz, 2H), 4.57 (m, 2H), 4.74 (m, 2H), 5.29-5.54 (m, 4H), 6.01-6.21 (m, 2H), 6.50 (s, 1H), 7.18-7.21 (m, 2H), 7.51-7.54 (m, 2H), 8.34 (s, 1H).

(Step 5)

2,4-Bis(allyloxy)-5-(benzimidazol-2-yl)-1-ethylbenzene (47 mg, 0.14 mmol) obtained in the above was dissolved in dichloromethane (3.0 mL), and with stirring at −78° C., n-hexane solution of 1.0 mol/L borane bromide (0.5 mL, 0.5 mmol) was added thereto and stirred for 20 minutes. Water was added to the reaction solution, then neutralized with aqueous saturated sodium hydrogencarbonate solution, and extracted twice with chloroform. The organic layer was dried over anhydrous sodium sulfate, and the solvent was evaporated away under reduced pressure. The resulting residue was purified through preparative thin-layer chromatography (ethyl acetate/n-hexane=1/2) to obtain Compound 278 (29 mg, 82%).

$^1$H-NMR (300 MHz, CD$_3$OD) δ (ppm): 1.25 (t, J=7.5 Hz, 3H), 2.62 (q, J=7.5 Hz, 2H), 6.43 (s, 1H), 7.21-7.18 (m, 2H), 7.54-7.51 (m, 2H), 7.63 (s, 1H);

APCI-MS (m/z): (M+H)$^+$.

EXAMPLE 279

6-Ethyl-4-(1-phenylbenzimidazol-2-yl)benzene-1,3-diol (Compound 279)

(Step 1)

In the same manner as in the step 4 in Example 278, 2,4-bis(allyloxy)-1-ethyl-5-(1-phenylbenzimidazol-2-yl)benzene (140 mg, 69%) was obtained from 2,4-bis(allyloxy)-5-ethylbenzoic acid (130 mg, 0.50 mmol) obtained in the step 3 in Example 278, using N-phenyl-o-phenylenediamine (110 mg, 0.60 mmol) and phosphorus oxychloride (5.0 mL).

$^1$H-NMR (300 MHz, CDCl$_3$) δ (ppm): 1.19 (t, J=7.5 Hz, 3H), 2.65 (q, J=7.5 Hz, 2H), 4.05 (m, 2H), 4.47 (m, 2H), 4.97-5.07 (m, 2H), 5.27 (m, 1H), 5.40 (m, 1H), 5.57 (m, 1H), 6.02 (m, 1H), 6.22 (s, 1H), 7.22-7.40 (m, 8H), 7.46 (s, 1H), 7.88 (m, 1H).

(Step 2)

In the same manner as in the step 5 in Example 278, Compound 279-(83 mg, 73%) was obtained from 2,4-bis(allyloxy)-1-ethyl-5-(1-phenylbenzimidazol-2-yl)benzene (140 mg, 0.34 mmol) obtained in the above, using n-hexane solution of 1.0 mol/L borane bromide (1.0 mL, 1.0 mmol) and dichloromethane (5.0 mL).

$^1$H-NMR (300 MHz, CDCl$_3$) δ (ppm): 1.21 (t, J=7.3 Hz, 3H), 2.20 (q, J=7.3 Hz, 2H), 6.37 (s, 1H), 6.62 (s, 1H), 7.00 (d, J=7.6 Hz, 1H), 7.13-7.27 (m, 2H), 7.33-7.36 (m, 2H), 7.55-7.66 (m, 4H);

APCI-MS (m/z): 331 (M+H)$^+$.

EXAMPLE 280

5-{[(4R,5R)-4,5-bis(hydroxymethyl)-1,3-dioxolan-2-yl]methyl}-6-chloro-4-phenylbenzene-1,3-diol (Compound 280)

Compound 230 (79.6 mg, 0.240 mmol) obtained in Example 230 was dissolved in tetrahydrofuran (10 mL), and sodium chlorite (48.7 mg, 0.538 mmol) and sulfamic acid (102 mg, 1.05 mmol) were added thereto and stirred at room temperature for 2 hours. Aqueous saturated sodium hydrogencarbonate solution and aqueous saturated sodium thiosulfate were added to the reaction solution, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (chloroform/methanol/water=100/10/1) to obtain Compound 280 (22.7 mg, 26%).

$^1$H-NMR (300 MHz, CD$_3$OD) δ (ppm): 2.88 (d, J=5.4 Hz, 1H), 3.40-3.60 (m, 5H), 3.70-3.80 (m, 1H), 5.28 (t, J=5.4 Hz, 1H), 6.45 (s, 1H), 7.16-7.42 (m, 5H);

APCI-MS (m/z): 365 (M−H)$^-$.

EXAMPLE 281

5-{[(4S,5S)-4,5-bis(hydroxymethyl)-1,3-dioxolan-2-yl]methyl}-6-ethyl-4-(3-hydroxyphenyl)benzene-1,3-diol (Compound 281)

(Step 1)

In the same manner as in the step 3 in Example 1, 1,5-bis(benzyloxy)-3-{[(4S,5S)-4,5-bis(benzyloxy)-1,3-dioxolan-2-yl]methyl}-4-ethyl-2-(3-hydroxyphenyl)benzene (330 mg, 64%) was obtained, using 1,5-bis(benzyloxy)-3-{[(4S,5S)-4,5-bis(benzyloxy)-1,3-dioxolan-2-yl]methyl}-4-ethyl-2-iodobenzene (540 mg, 0.70 mmol) obtained in the step 4 in Example 233, 2-(3-hydroxyphenyl)-4,4,5,5-tetramethyl-1,3,2-dioxaborolane (32 mg, 1.5 mmol), cesium carbonate (98 mg, 3.0 mmol) and bis(tri-o-tolylphosphine)palladium(II) dichloride (30 mg, 0.038 mmol).

APCI-MS (m/z): 737 (M+H)$^+$.

(Step 2)

In the same manner as in the step 3 in Example 218, 1,5-bis(benzyloxy)-3-{[(4S,5S)-4,5-bis(benzyloxy)-1,3-dioxolan-2-yl]methyl}-4-ethyl-2-(3-hydroxyphenyl)benzene (330 mg, 0.45 mmol) obtained in the above was dissolved in tetrahydrofuran (10 mL), and 10% palladium-carbon (110 mg) was added thereto and stirred under hydrogen pressure (0.35 MPa) at room temperature for 11 hours. The reaction mixture was filtered, and the filtrate was concentrated under reduced pressure. The resulting residue was purified through middle-pressure column chromatography (chloroform/methanol=1/0 to 20/1) to obtain Compound 281 (129 mg, 76%).

$^1$H-NMR (300 MHz, DMSO-d$_6$) δ (ppm): 0.99 (t, J=7.2 Hz, 3H), 2.57 (q, J=7.2 Hz, 2H), 2.62-2.70 (m, 2H), 3.30-3.44 (m, 4H), 3.54-3.64 (m, 2H), 4.70-4.84 (m, 2H), 6.33 (s, 1H), 6.44-6.54 (m, 2H), 6.58-6.66 (m, 1H), 7.09 (t, J=8.0 Hz, 1H), 8.54 (s, 1H), 8.99 (s, 1H), 9.17 (s, 1H);

APCI-MS (m/z): 375 (M−H)$^-$.

EXAMPLE 282

5-{[(4S,5S)-4,5-bis(hydroxymethyl)-1,3-dioxolan-2-yl]methyl}-6-ethyl-4-(3-fluorophenyl)benzene-1,3-diol (Compound 282)

(Step 1)

In the same manner as in the step-3 in Example 1, 1,5-bis(benzyloxy)-3-{[(4S,5S)-4,5-bis(benzyloxy)-1,3-dioxolan-2-yl]methyl}-4-ethyl-2-(3-fluorophenyl)benzene (142 mg, 55%) was obtained from 1,5-bis(benzyloxy)-3-{[(4S,5S)-4,5-bis(benzyloxy)-1,3-dioxolan-2-yl]methyl}-4-ethyl-2-iodobenzene (270 mg, 0.351 mmol) obtained in the step 4 in Example 233, using 3-fluorophenylboronic acid (103 mg, 0.736 mmol), cesium carbonate (492 mg, 1.51 mmol) and bis(tri-o-tolylphosphine)palladium(II) dichloride (15.0 mg, 0.0191 mmol).

APCI-MS (m/z): 739 (M+H)$^+$.

(Step 2)

1,5-Bis(benzyloxy)-3-{[(4S,5S)-4,5-bis(benzyloxy)-1,3-dioxolan-2-yl]methyl}-4-ethyl-2-(3-fluorophenyl)benzene (141 mg, 0.191 mmol) obtained in the above was dissolved in tetrahydrofuran (10 mL), and 10% palladium-carbon (60 mg) was added thereto and stirred under hydrogen pressure (0.35 MPa) at room temperature for 11 hours. The reaction mixture was filtered, and the filtrate was concentrated under reduced pressure. The resulting residue was purified through preparative thin-layer chromatography (chloroform/methanol/water=100/10/1) to obtain Compound 282 (45.5 mg, 65%).

$^1$H-NMR (300 MHz, DMSO-d$_6$) δ (ppm): 1.02 (t, J=7.4 Hz, 3H), 2.45-2.62 (m, 2H), 2.66 (d, J=5.4 Hz, 2H), 3.25-3.50 (m, 4H), 3.50-3.75 (m, 2H), 4.70-4.80 (m, 2H), 4.84 (t, J=5.4 Hz, 1H), 6.37 (s, 1H), 6.80-7.20 (m, 3H), 7.25-7.40 (m, 1H), 8.74 (s, 1H), 9.10 (s, 1H);

APCI-MS (m/z): 363 (M−H)$^−$.

EXAMPLE 283

5-{[(4S,5S)-4,5-bis(hydroxymethyl)-1,3-dioxolan-2-yl]methyl}-4-(3,5-dimethylphenyl)-6-ethylbenzene-1,3-diol (Compound 283)

(Step 1)

In the same manner as in the step 3 in Example 1, 1,5-bis(benzyloxy)-3-{[(4S,5S)-4,5-bis(benzyloxy)-1,3-dioxolan-2-yl]methyl}-2-(3,5-dimethylphenyl)-4-ethylbenzene (161 mg, 61%) was obtained from 1,5-bis(benzyloxy)-3-{[(4S,5S)-4,5-bis(benzyloxy)-1,3-dioxolan-2-yl]methyl}-4-ethyl-2-iodobenzene (270 mg, 0.351 mmol) obtained in the step 4 in Example 233, using 3,5-dimethylphenylboronic acid (111 mg, 0.740 mmol), cesium carbonate (492 mg, 1.51 mmol) and bis(tri-o-tolylphosphine)palladium(II) dichloride (15.0 mg, 0.0191 mmol).

APCI-MS (m/z): 749 (M+H)$^+$.

(Step 2)

1,5-Bis(benzyloxy)-3-{[(4S,5S)-4,5-bis(benzyloxy)-1,3-dioxolan-2-yl]methyl}-4-ethyl-2-(3,5-dimethylphenyl)benzene (161 mg, 0.215 mmol) obtained in the above was dissolved in tetrahydrofuran (10 mL), and 10% palladium-carbon (60 mg) was added thereto and stirred under hydrogen pressure (0.35 MPa) at room temperature for 11 hours. The reaction mixture was filtered, and the filtrate was concentrated under reduced pressure. The resulting residue was purified through preparative thin-layer chromatography (chloroform/methanol/water=100/10/1) to obtain Compound 283 (77.4 mg, 93%).

APCI-MS (m/z): 387 (M−H)$^−$.

EXAMPLE 284

4-[3-(acetylamino)phenyl]-5-{[(4S,5S)-4,5-bis(hydroxymethyl)-1,3-dioxolan-2-yl]methyl}-6-ethylbenzene-1,3-diol (Compound 284)

(Step 1)

In the same manner as in the step 3 in Example 1, 2-[3-(acetylamino)phenyl]-1,5-bis(benzyloxy)-3-{[(4S,5S)-4,5-bis(benzyloxy)-1,3-dioxolan-2-yl]methyl}-4-ethylbenzene (233 mg, 64%) was obtained from 1,5-bis(benzyloxy)-3-{[(4S,5S)-4,5-bis(benzyloxy)-1,3-dioxolan-2-yl]methyl}-4-ethyl-2-iodobenzene (360 mg, 0.468 mmol) obtained in the step 4 in Example 233, using 3-acetylaminophenylboronic acid (176 mg, 0.983 mmol), cesium carbonate (661 mg, 2.03 mmol) and bis(tri-o-tolylphosphine)palladium(II) dichloride (18.0 mg, 0.0229 mmol).

APCI-MS (m/z): 778 (M+H)$^+$.

(Step 2)

2-[3-(Acetylamino)phenyl]-1,5-bis(benzyloxy)-3-{[(4S,5S)-4,5-bis(benzyloxy)-1,3-dioxolan-2-yl]methyl}-4-ethylbenzene (233 mg, 0.300 mmol) obtained in the above was dissolved in tetrahydrofuran (10 mL), and 10% palladium-carbon (54 mg) was added thereto and stirred under hydrogen pressure (0.35 MPa) at room temperature for 11 hours. The reaction mixture was filtered, and the filtrate was concentrated under reduced pressure. The resulting residue was purified through preparative thin-layer chromatography (chloroform/methanol/water=100/10/1) to obtain Compound 284 (80.4 mg, 64%).

$^1$H-NMR (300 MHz, DMSO-d$_6$) δ (ppm): 1.01 (t, J=7.2 Hz, 3H), 2.03 (s, 3H), 2.40-2.80 (m, 4H), 3.20-3.50 (m, 4H), 3.50-3.60 (m, 2H), 4.70-4.85 (m, 3H), 6.35 (s, 1H), 6.70-6.80 (m, 1H), 7.15-7.35 (m, 2H), 7.40-7.60 (m, 1H), 8.62 (s, 1H), 9.03 (s, 1H), 9.83 (s, 1H);

APCI-MS (m/z): 418 (M+H)$^+$.

EXAMPLE 285

5-{[(4S,5S)-4,5-bis(hydroxymethyl)-1,3-dioxolan-2-yl]methyl}-6-chloro-4-phenylbenzene-1,3-diol (Compound 285)

(Step 1)

In the same manner as in the step 2 in Example 218, 3,5-bis(benzyloxy)-1-{[(4S,5S)-4,5-bis(benzyloxy)-1,3-dioxolan-2-yl]methyl}-2-phenylbenzene (2.64 g, 66%) was obtained from 2-[3,5-bis(benzyloxy)-2-phenylphenyl]ethanal (2.35 g, 5.76 mmol) obtained in the step 3 in Example 230, using (−)-1,4-di-O-benzyl-L-threitol (2.61 g, 8.64 mmol) and DL-10-camphorsulfonic acid (401 mg, 1.73 mmol).

APCI-MS (m/z): 693 (M+H)$^+$.

(Step 2)

3,5-Bis(benzyloxy)-1-{[(4S,5S)-4,5-bis(benzyloxy)-1,3-dioxolan-2-yl]methyl}-2-phenylbenzene (868 mg, 1.25 mmol) obtained in the above was dissolved in tetrahydrofuran (5 mL), and 10% palladium-carbon (400 mg) was added thereto and stirred under hydrogen pressure (0.35 MPa) at room temperature for 11 hours. The reaction mixture was filtered, and the filtrate was concentrated under reduced pressure. The resulting residue was purified through preparative thin-layer chromatography (chloroform/methanol/water=100/10/1) to obtain 5-{[(4S,5S)-4,5-bis(hydroxymethyl)-1,3-dioxolan-2-yl]methyl}-4-phenylbenzene-1,3-diol (154 mg, 37%).

APCI-MS (m/z): 331 (M−H)⁻.

(Step 3)

5-{[(4S,5S)-4,5-bis(hydroxymethyl)-1,3-dioxolan-2-yl]methyl}-4-phenylbenzene-1,3-diol (154 mg, 0.463 mmol) obtained in the above was dissolved in tetrahydrofuran (10 mL) and water (4 mL), and sodium chlorite (88.9 mg, 0.983 mmol) and sulfamic acid (138 mg, 1.42 mmol) were added thereto and stirred at room temperature for 15 minutes. Aqueous saturated sodium hydrogencarbonate solution and aqueous saturated sodium thiosulfate solution were added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (chloroform/methanol/water=100/10/1) to obtain Compound 285 (80.4 mg, 47%).

$^1$H-NMR (270 MHz, DMSO-$d_6$) δ (ppm): 2.60-2.85 (m, 2H), 3.20-3.70 (m, 6H), 4.65-4.85 (m, 2H), 5.12 (t, J=5.3 Hz, 1H), 6.54 (s, 1H), 7.20-7.40 (m, 5H), 9.20 (br s, 1H), 9.91 (br s, 1H);

APCI-MS (m/z): 365 (M−H)⁻.

EXAMPLE 286

5-{[(4R,5R)-4,5-bis(hydroxymethyl)-1,3-dioxolan-2-yl]methyl}-6-ethyl-4-(3-methoxyphenyl)benzene-1,3-diol (Compound 286)

(Step 1)

In the same manner as in the step 2 in Example 218, 3,5-bis(benzyloxy)-1-{[(4R,5R)-4,5-bis(benzyloxy)-1,3-dioxolan-2-yl]methyl}-2-ethylbenzene (1.35 g, 36%) was obtained from 2-[3,5-bis(benzyloxy)-2-ethylphenyl]ethanal (2.10 g, 5.82 mmol) obtained in the step 2 in Example 233, using (+)-1,4-di-O-benzyl-D-threitol (2.64 g, 8.73 mmol) and DL-10-camphorsulfonic acid (406 mg, 1.75 mmol).

APCI-MS (m/z): 645 (M+H)⁺.

(Step 2)

In the same manner as in the step 4 in Example 233, 1,5-bis(benzyloxy)-3-{[(4R,5R)-4,5-bis(benzyloxy)-1,3-dioxolan-2-yl]methyl}-4-ethyl-2-iodobenzene (1.01 g, 63%) was obtained from 3,5-bis(benzyloxy)-1-{[(4R,5R)-4,5-bis(benzyloxy)-1,3-dioxolan-2-yl]methyl}-2-ethylbenzene (1.35 g, 2.10 mmol) obtained in the above, using iodine (640 mg, 2.52 mmol) and [bis(trifluoroacetoxy)iodo]benzene (1.10 g, 2.56 mmol).

APCI-MS (m/z): 771 (M+H)⁺.

(Step 3)

In the same manner as in the step 3 in Example 1, 1,5-bis(benzyloxy)-3-{[(4R,5R)-4,5-bis(benzyloxy)-1,3-dioxolan-2-yl]methyl}-4-ethyl-2-(3-methoxyphenyl)benzene (290 mg, 59) was obtained from 1,5-bis(benzyloxy)-3-{[(4R,5R)-4,5-bis(benzyloxy)-1,3-dioxolan-2-yl]methyl}-4-ethyl-2-iodobenzene (500 mg, 0.649 mmol) obtained in the above, using 3-methoxyphenylboronic acid (207 mg, 1.36 mmol), cesium carbonate (910 mg, 2.79 mmol) and bis(tri-o-tolylphosphine)palladium(II) dichloride (26.0 mg, 0.0331 mmol).

APCI-MS (m/z): 751 (M+H)⁺.

(Step 4)

1,5-Bis(benzyloxy)-3-{[(4R,5R)-4,5-bis(benzyloxy)-1,3-dioxolan-2-yl]methyl}-4-ethyl-2-(3-methoxyphenyl)benzene (290 mg, 0.386 mmol) obtained in the above was dissolved in tetrahydrofuran (5 mL), and 10% palladium-carbon (100 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=100/10/1) to obtain Compound 286 (104 mg, 69%).

$^1$H-NMR (300 MHz, DMSO-$d_6$) δ (ppm): 1.01 (t, J=7.2 Hz, 3H), 2.50-2.70 (m, 4H), 3.26-3.46 (m, 4H), 3.54-3.70 (m, 2H), 3.73 (s, 3H), 4.70-4.88 (m, 3H), 6.35 (s, 1H), 6.75-6.85 (m, 1H), 7.23 (t, J=7.7 Hz, 1H), 8.60 (s, 1H), 9.03 (s, 1H);

APCI-MS (m/z): 389 (M−H)⁻.

EXAMPLE 287

6-Acetyl-5-{[(4S,5S)-4,5-bis(hydroxymethyl)-1,3-dioxolan-2-yl]methyl}-4-phenylbenzene-1,3-diol (Compound 287)

(Step 1)

In the same manner as in the step 4 in Example 233, 1,5-bis(benzyloxy)-3-{[(4S,5S)-4,5-bis(benzyloxy)-1,3-dioxolan-2-yl]methyl}-4-iodo-2-phenylbenzene (1.52 g, 78%) was obtained from 1,5-bis(benzyloxy)-3-{[(4S,5S)-4,5-bis(benzyloxy)-1,3-dioxolan-2-yl]methyl}-2-phenylbenzene (1.76 g, 2.54 mmol) obtained in the step 1 in Example 285, using iodine (840 mg, 3.30 mmol) and [bis(trifluoroacetoxy)iodo]benzene (1.42 g, 3.30 mmol).

APCI-MS (m/z): 819 (M+H)⁺.

(Step 2)

1,5-bis(benzyloxy)-3-{[(4S,5S)-4,5-bis(benzyloxy)-1,3-dioxolan-2-yl]methyl}-4-iodo-2-phenylbenzene (1.21 g, 1.48 mmol) obtained in the above was dissolved in diethyl ether (15 mL), and the solution was cooled to −78° C. Hexane solution of 1.56 mol/L n-butyllithium (1.42 mL, 2.22 mmol) was added to the resulting solution, and stirred at the same temperature for 5 minutes. Then, acetyl chloride (0.210 mL, 2.96 mmol) was added thereto, and stirred at the same temperature for 2 hours. Aqueous saturated sodium hydrogencarbonate solution was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through silica gel column chromatography (n-hexane/ethyl acetate=20/1 to 9/1) to obtain 4-acetyl-1,5-bis(benzyloxy)-3-{[(4S,5S)-4,5-bis(benzyloxy)-1,3-dioxolan-2-yl]methyl}-2-phenylbenzene (190 mg, 17%).

APCI-MS (m/z): 735 (M+H)⁺.

(Step 3)

4-Acetyl-1,5-bis(benzyloxy)-3-{[(4S,5S)-4,5-bis(benzyloxy)-1,3-dioxolan-2-yl]methyl}-2-phenylbenzene (190 mg, 0.259 mmol) obtained in the above was dissolved in tetrahydrofuran (10 mL), and 10% palladium-carbon (140 mg) was added thereto and stirred under hydrogen pressure (0.35 MPa) at room temperature for 24 hours. The reaction mixture was filtered, and the filtrate was concentrated under reduced pressure. The resulting residue was purified through preparative thin-layer chromatography (chloroform/methanol/water=100/10/1) to obtain Compound 287 (106 mg, 100%).

¹H-NMR (300 MHz, DMSO-D₆) δ (ppm): 2.45 (s, 3H), 2.50-2.80 (m, 2H), 3.20-3.65 (m, 6H), 4.60-4.90 (m, 3H), 7.06-7.40 (m, 5H), 9.41 (br. s, 1H), 9.84 (br s 1H);
APCI-MS (m/z): 373 (M–H)⁻.

EXAMPLE 288

5-{[(4S,5S)-4,5-Bis(hydroxymethyl)-1,3-dioxolan-2-yl]methyl}-6-ethyl-4-(3-carbamoylphenyl)benzene-1,3-diol (Compound 288)

(Step 1)
In the same manner as in the step 3 in Example 1, 4-ethyl-1,5-bis(benzyloxy)-3-{[(4S,5S)-4,5-bis(benzyloxy)-1,3-dioxolan-2-yl]methyl}-2-(3-formylphenyl)benzene (622 mg, 53%) was obtained from 1,5-bis(benzyloxy)-3-{[(4S,5S)-4,5-bis(benzyloxy)-1,3-dioxolan-2-yl]methyl}-4-ethyl-2-iodobenzene (1.20 g, 1.56 mmol) obtained in the step 4 in Example 233, using 3-formylphenylboronic acid (490 mg, 3.28 mmol), cesium carbonate (2.19 g, 6.71 mmol) and bis(tri-o-tolylphosphine)palladium(II) dichloride (62.0 mg, 0.0780 mmol).
APCI-MS (m/z): 749 (M+H)⁺.

(Step 2)
1,5-Bis(benzyloxy)-3-{[(4S,5S)-4,5-bis(benzyloxy)-1,3-dioxolan-2-yl]methyl}-4-ethyl-2-(3-formylphenyl)benzene (640 mg, 0.856 mmol) obtained in the above was dissolved in a mixed solvent of tert-butyl alcohol (5 mL) and 2-methyl-2-butene (5 mL), and sodium chlorite (1.00 g, 11.1 mmol), sodium dihydrogenphosphate (1.00 g, 10.3 mmol) and water (1.0 mL) were added thereto and stirred at room temperature for 10 hours. Water was added to the reaction mixture, and extracted with ethyl acetate. The organic layer was washed with aqueous saturated sodium chloride solution, then dried over anhydrous sodium sulfate, and the solvent was evaporated away under reduced pressure to obtain 1,5-bis(benzyloxy)-3-{[(4S,5S)-4,5-bis(benzyloxy)-1,3-dioxolan-2-yl]methyl}-2-(3-carboxyphenyl)-4-ethylbenzene (657 mg, 100%).
APCI-MS (m/z): 765 (M+H)⁺.

(Step 3)
1,5-Bis(benzyloxy)-3-{[(4S,5S)-4,5-bis(benzyloxy)-1,3-dioxolan-2-yl]methyl}-2-(3-carboxyphenyl)-4-ethylbenzene (217 mg, 0.284 mmol) obtained in the above was dissolved in N,N-dimethylformamide (5 mL), and 1-hydroxybenzotriazole hydrate (192 mg, 1.42 mmol), 1-[3-(dimethylamino)propyl]-3-ethylcarbodiimide hydrochloride (109 mg, 0.568 mmol) and aqueous concentrated ammonia (0.067 mL, 0.966 mmol) were added thereto and stirred at room temperature for 1 hour. Water was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (hexane/ethyl acetate=1/1) to obtain 1,5-bis(benzyloxy)-3-{[(4S,5S)-4,5-bis(benzyloxy)-1,3-dioxolan-2-yl]methyl}-2-(3-carbamoylphenyl)-4-ethylbenzene (130 mg, 60%).
APCI-MS (m/z): 764 (M+H)⁺.

(Step 4)
1,5-Bis(benzyloxy)-3-{[(4S,5S)-4,5-bis(benzyloxy)-1,3-dioxolan-2-yl]methyl}-2-(3-carbamoylphenyl)-4-ethylbenzene (130 mg, 0.170 mmol) obtained in the above was dissolved in tetrahydrofuran (5 mL), and 10% palladium-carbon (90.0 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol=4/1) to obtain Compound 288 (54.2 mg, 79%).
¹H-NMR (270 MHz, DMSO-d₆) δ (ppm): 1.02 (t, J=7.1 Hz, 3H), 2.50-2.75 (m, 4H), 3.20-3.45 (m, 4H), 3.45-3.70 (m, 2H), 4.60-4.85 (m, 3H), 6.38 (s, 1H), 7.20-7.45 (m, 3H), 7.64 (br s, 1H), 7.70-7.80 (m, 1H), 7.91 (br s, 1H), 8.70 (s, 1H), 9.07 (s, 1H);
APCI-MS (m/z): 404 (M+H)⁺.

EXAMPLE 289

5-{[(4S,5S)-4,5-Bis(hydroxymethyl)-1,3-dioxolan-2-yl]methyl}-6-ethyl-4-[3-(methylcarbamoyl)phenyl]benzene-1,3-diol (Compound 289)

(Step 1)
In the same manner as in the step 3 in Example 288, 1,5-bis(benzyloxy)-3-{[(4S,5S)-4,5-bis(benzyloxy)-1,3-dioxolan-2-yl]methyl}-4-ethyl-2-[3-(methylcarbamoyl)phenyl]benzene (153 mg, 69%) was obtained from 1,5-bis(benzyloxy)-3-{[(4S,5S)-4,5-bis(benzyloxy)-1,3-dioxolan-2-yl]methyl}-2-(3-carboxyphenyl)-4-ethylbenzene (217 mg, 0.284 mmol) obtained in the step 2 in Example 288, using 1-hydroxybenzotriazole hydrate (192 mg, 1.42 mmol), 1-[3-(dimethylamino)propyl]-3-ethylcarbodiimide hydrochloride (109 mg, 0.568 mmol) and methanol solution of 40% methylamine (0.042 mL, 0.852 mmol).
APCI-MS (m/z): 778 (M+H)⁺.

(Step 2)
1,5-Bis(benzyloxy)-3-{[(4S,5S)-4,5-bis(benzyloxy)-1,3-dioxolan-2-yl]methyl}-4-ethyl-2-[3-(methylcarbamoyl)phenyl]benzene (153 mg, 0.197 mmol) obtained in the above was dissolved in tetrahydrofuran (5 mL), and 10% palladium-carbon (100 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol=4/1) to obtain Compound 289 (59.3 mg, 72%).
¹H-NMR (270 MHz, DMSO-d₆) δ (ppm): 1.02 (t, J=7.3 Hz, 3H), 2.50-2.70 (m, 4H), 2.77 (d, J=4.0 Hz, 3H), 3.00-3.70 (m, 6H), 4.60-4.80 (m, 3H), 6.38 (s, 1H), 7.20-7.30 (m, 3H), 7.34-7.44 (m, 1H), 7.56-7.62 (m, 1H), 7.68-7.76 (m, 1H), 8.35 (t, J=4.0 Hz, 1H), 8.70 (br s, 1H), 9.07 (br s, 1H);
APCI-MS (m/z): 418 (M+H)⁺.

EXAMPLE 290

5-{[(4S,5S)-4,5-Bis(hydroxymethyl)-1,3-dioxolan-2-yl]methyl}-4-[3-(dimethylcarbamoyl)phenyl]-6-ethylbenzene-1,3-diol (Compound 290)

(Step 1)
In the same manner as in the step 3 in Example 288, 1,5-bis(benzyloxy)-3-{[(4S,5S)-4,5-bis(benzyloxy)-1,3-dioxolan-2-yl]methyl}-2-[3-(dimethylcarbamoyl)phenyl]-4-ethylbenzene (156 mg, 69%) was obtained from 1,5-bis(benzyloxy)-3-{[(4S,5S)-4,5-bis(benzyloxy)-1,3-dioxolan-2-yl]methyl}-2-[3-(dimethylcarbamoyl)phenyl]-4-ethylbenzene (217 mg, 0.284 mmol) obtained in the step 2 in Example 288, using 1-hydroxybenzotriazole hydrate (192 mg, 1.42 mmol), 1-[3-(dimethylamino)propyl]-3-ethylcarbodiimide hydrochloride (109 mg, 0.568 mmol) and aqueous 50% dimethylamine solution (0.077 mL, 0.852 mmol).

APCI-MS (m/z): 792 (M+H)$^+$.

(Step 2)

1,5-Bis(benzyloxy)-3-{[(4S,5S)-4,5-bis(benzyloxy)-1,3-dioxolan-2-yl]methyl}-4-ethyl-2-(3-dimethylcarbamoylphenyl)benzene (156 mg, 0.197 mmol) obtained in the above was dissolved in tetrahydrofuran (5 mL), and 10% palladium-carbon (100 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol=4/1) to obtain Compound 290 (44.9 mg, 53%).

$^1$H-NMR (300 MHz, DMSO-d$_6$) δ (ppm): 1.02 (t, J=7.4 Hz, 3H), 2.50-2.75 (m, 4H), 2.85-3.00 (m, 6H), 3.25-3.45 (m, 4H), 3.50-3.70 (m, 2H), 4.70-4.85 (m, 3H), 6.38 (s, 1H), 7.05-7.45 (m, 4H), 8.74 (s, 1H), 9.10 (s, 1H);

APCI-MS (m/z): 432 (M+H)$^+$.

EXAMPLE 291

5-{[(4R,5R)-4,5-bis(hydroxymethyl)-1,3-dioxolan-2-yl]methyl}-6-ethyl-4-(4-fluoro-3-methylphenyl)benzene-1,3-diol (Compound 291)

(Step 1)

3,5-Bis(benzyloxy)-1-{[(4R,5R)-4,5-bis(benzyloxy)-1,3-dioxolan-2-yl]methyl}-2-ethylbenzene (3.00 g, 4.63 mmol) obtained in the step 1 in Example 286 was dissolved in N,N-dimethylformamide (30 mL), and the solution was cooled to 0° C., then N-bromosuccinimide (906 mg, 5.09 mmol) was added thereto and stirred at the same temperature for 2.5 hours. Aqueous saturated sodium hydrogencarbonate solution and aqueous saturated sodium thiosulfate were added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through middle-pressure column chromatography (n-hexane/ethyl acetate=1/0 to 10/1) to obtain 1,5-bis(benzyloxy)-3-{[(4R,5R)-4,5-bis(benzyloxy)-1,3-dioxolan-2-yl]methyl}-2-bromo-4-ethylbenzene (3.08 g, 92%).

$^1$H-NMR (270 MHz, CDCl$_3$) δ (ppm): 1.07 (t, J=7.3 Hz, 3H), 2.84 (q, J=7.3 Hz, 2H), 3.24-3.38 (m, 2H), 3.52-3.69 (m, 4H), 4.01-4.16 (m, 2H), 4.54 (s, 2H), 4.58 (s, 2H), 4.94 (s, 2H), 5.05 (s, 2H), 5.40 (t, J=5.0 Hz, 1H), 6.49 (s, 1H), 7.16-7.46 (m, 20H).

(Step 2)

In the same manner as in the step 3 in Example 1, 1,5-bis(benzyloxy)-3-{[(4R,5R)-4,5-bis(benzyloxy)-1,3-dioxolan-2-yl]methyl}-4-ethyl-2-(4-fluoro-3-methylphenyl)benzene (516 mg, 83%) was obtained from 1,5-bis(benzyloxy)-3-{([(4R,5R)-4,5-bis(benzyloxy)-1,3-dioxolan-2-yl]methyl}-2-bromo-4-ethylbenzene (600 mg, 0.831 mmol) obtained in the above, using 4-fluoro-3-methylphenylboronic acid (207 mg, 1.34 mmol), cesium carbonate (1.17 g, 3.59 mmol) and bis(tri-o-tolylphosphine)palladium(II) dichloride (32.0 mg, 0.0407 mmol).

APCI-MS (m/z): 753 (M+H)$^+$.

(Step 3)

1,5-Bis(benzyloxy)-3-{[(4R,5R)-4,5-bis(benzyloxy)-1,3-dioxolan-2-yl]methyl}-4-ethyl-2-(4-fluoro-3-methylphenyl)benzene (500 mg, 0.665 mmol) obtained in the above was dissolved in tetrahydrofuran (10 mL), and 10% palladium-carbon (200 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=90/10/1) to obtain Compound 291 (252 mg, 64%).

$^1$H-NMR (300 MHz, DMSO-d$_6$) δ (ppm): 1.01 (t, J=7.6 Hz, 3H), 2.20-2.25 (m, 3H), 2.40-2.70 (m, 4H), 3.20-3.70 (m, 6H), 4.70-4.90 (m, 3H), 6.35 (s, 1H), 6.80-7.10 (m, 3H), 8.61 (s, 1H), 9.03 (s, 1H);

APCI-MS (m/z): 393 (M+H)$^+$.

EXAMPLE 292

5-{[(4R,5R)-4,5-bis(hydroxymethyl)-1,3-dioxolan-2-yl]methyl}-4-[3-(dimethylcarbamoyl)phenyl]-6-ethylbenzene-1,3-diol (Compound 292)

(Step 1)

In the same manner as in the step 3 in Example 1, 1,5-bis(benzyloxy)-3-{[(4R,5R)-4,5-bis(benzyloxy)-1,3-dioxolan-2-yl]methyl}-4-ethyl-2-(3-formylphenyl)benzene (2.47 g, 95%) was obtained from 1,5-bis(benzyloxy)-3-{[(4R,5R)-4,5-bis(benzyloxy)-1,3-dioxolan-2-yl]methyl}-2-bromo-4-ethylbenzene (2.50 g, 3.46 mmol) obtained in the step 1 in Example 291, using 3-formylphenylboronic acid (1.09 g, 7.27 mmol), cesium carbonate (4.85 g, 14.9 mmol) and bis(tri-o-tolylphosphine)palladium(II) dichloride (140 mg, 0.178 mmol).

APCI-MS (m/z): 749 (M+H)$^+$.

(Step 2)

1,5-Bis(benzyloxy)-3-{[(4R,5R)-4,5-bis(benzyloxy)-1,3-dioxolan-2-yl]methyl}-4-ethyl-2-(3-formylphenyl)benzene (2.47 g, 3.30 mmol) obtained in the above was dissolved in a mixed solvent of tert-butyl alcohol (19 mL) and 2-methyl-2-butene (19 mL), and sodium chlorite (3.00 g, 33.3 mmol), sodium dihydrogenphosphate (3.00 g, 30.9 mmol) and water (15.0 mL) were added thereto and stirred at room temperature for 10 hours. Water was added to the reaction mixture, and extracted with ethyl acetate. The organic layer was washed with aqueous saturated sodium chloride solution, then dried over anhydrous sodium sulfate, and the solvent was evaporated away under reduced pressure to obtain 1,5-bis(benzyloxy)-3-{[(4R,5R)-4,5-bis(benzyloxy)-1,3-dioxolan-2-yl]methyl}-2-(3-carboxyphenyl)-4-ethylbenzene (3.20 g, 100%).

APCI-MS (m/z): 765 (M+H)$^+$.

(Step 3)

In the same manner as in the step 3 in Example 288, 1,5-bis(benzyloxy)-3-{[(4R,5R)-4,5-bis(benzyloxy)-1,3-dioxolan-2-yl]methyl}-2-[3-(dimethylcarbamoyl)phenyl]-4-ethylbenzene (590 mg, 68%) was obtained from 1,5-bis(benzyloxy)-3-{[(4R,5R)-4,5-bis(benzyloxy)-1,3-dioxolan-2-yl]methyl}-2-(3-carboxyphenyl)-4-ethylbenzene (841 mg, 1.10 mmol) obtained in the above, using 1-hydroxybenzotriazole hydrate (743 mg, 5.50 mmol), 1-[3' (dimethylamino)propyl]-3-ethylcarbodiimide hydrochloride (422 mg, 2.20 mmol) and aqueous 50% dimethylamine solution (0.300 mL, 3.74 mmol).

APCI-MS (m/z): 792 (M+H)$^+$.

(Step 4)

1,5-Bis(benzyloxy)-3-{[(4R,5R)-4,5-bis(benzyloxy)-1,3-dioxolan-2-yl]methyl}-2-[3-(dimethylcarbamoyl)phenyl]-4-ethylbenzene (590 mg, 0.746 mmol) obtained in the above was dissolved in tetrahydrofuran (10 mL), and 10% palladium-carbon (200 mg) was added thereto and stirred, under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=90/10/1) to obtain Compound 292 (212 mg, 66%).

$^1$H-NMR (300 MHz, DMSO-$d_6$) δ (ppm): 1.02 (t, J=7.2 Hz, 3H), 2.58 (q, J=7.2 Hz, 2H), 2.69 (d, J=5.1 Hz, 2H), 2.96 (br s, 6H), 3.25-3.70 (m, 6H), 4.70-4.90 (m, 3H), 6.38 (s, 1H), 7.05-7.50 (m, 4H), 8.73 (s, 1H), 9.09 (s, 1H);

APCI-MS (m/z): 432 (M+H)$^+$.

EXAMPLE 293

5-{[(4R,5R)-4,5-bis(hydroxymethyl)-1,3-dioxolan-2-yl]methyl}-4-(3-chloro-4-fluorophenyl)-6-ethylbenzene-1,3-diol (Compound 293)

(Step 1)

In the same manner as in the step 3 in Example 1, 1,5-bis(benzyloxy)-3-{[(4R,5R)-4,5-bis(benzyloxy)-1,3-dioxolan-2-yl]methyl}-2-(3-chloro-4-fluorophenyl)-4-ethylbenzene (316 mg, 79%) was obtained from 3,5-is(benzyloxy)-1-{[(4R,5R)-4,5-bis(benzyloxy)-1,3-dioxolan-2-yl]methyl}-2-ethyl-4-iodobenzene (400 mg, 0.520 mmol) obtained in the step 2 in Example 286, using 3-chloro-4-fluorophenylboronic acid (191 mg, 1.10 mmol), cesium carbonate (730 mg, 2.24 mmol) and bis(tri-o-tolylphosphine)palladium(II) dichloride (20 mg, 0.0254 mmol).

APCI-MS (m/z): 773 (M+H)$^+$.

(Step 2)

1,5-Bis(benzyloxy)-3-{[(4R,5R)-4,5-bis(benzyloxy)-1,3-dioxolan-2-yl]methyl}-2-(3-chloro-4-fluorophenyl)-4-ethylbenzene (316 mg, 0.665 mmol) obtained in the above was dissolved in tetrahydrofuran (10 mL), and 10% palladium-carbon (200 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=90/10/1) to obtain Compound 293 (58.4 mg, 21%).

$^1$H-NMR (300 MHz, DMSO-$d_6$) δ (ppm): 1.02 (t, J=7.2 Hz, 3H), 2.45-2.75 (m, 4H), 3.25-3.75 (m, 6H), 4.70-4.95 (m, 3H), 6.38 (s, 1H), 7.00-7.20 (m, 1H), 7.25-7.40 (m, 2H), 8.83 (s, 1H), 9.15 (s, 1H);

APCI-MS (m/z): 413 (M+H)$^+$.

EXAMPLE 294

5-{[(4R,5R)-4,5-Bis(hydroxymethyl)-1,3-dioxolan-2-yl]methyl}-6-ethyl-4-[3-(methylcarbamoyl)phenyl]benzene-1,3-diol (Compound 294)

(Step 1)

In the same manner as in the step 3 in Example 288, 1,5-bis(benzyloxy)-3-{[(4R,5R)-4,5-bis(benzyloxy)-1,3-dioxolan-2-yl]methyl}-4-ethyl-2-[3-(methylcarbamoyl)phenyl]benzene (590 mg, 69%) was obtained from 1,5-bis(benzyloxy)-3-{[(4R,5R)-4,5-bis(benzyloxy)-1,3-dioxolan-2-yl]methyl}-4-ethyl-2-(3-carboxyphenyl)benzene (841 mg, 1.10 mmol) obtained in the step 2 in Example 292, using 1-hydroxybenzotriazole hydrate (743 mg, 5.50 mmol), 1-[3-(dimethylamino)propyl]-3-ethylcarbodiimide hydrochloride (422 mg, 2.20 mmol) and methanol solution of 40% methylamine (0.170 mL, 3.74 mmol).

APCI-MS (m/z): 778 (M+H)$^+$.

(Step 2)

1,5-Bis(benzyloxy)-3-{[(4R,5R)-4,5-bis(benzyloxy)-1,3-dioxolan-2-yl]methyl}-4-ethyl-2-[3-(methylcarbamoyl)phenyl]benzene (590 mg, 0.746 mmol) obtained in the above was dissolved in tetrahydrofuran (10 mL), and 10% palladium-carbon (200 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol=4/1) to obtain Compound 294 (259 mg, 83%).

$^1$H-NMR (300 MHz, DMSO-$d_6$) δ (ppm): 1.02 (t, J=7.2 Hz, 3H), 2.50-2.70 (m, 4H), 2.77 (d, J=4.3 Hz, 3H), 3.25-3.65 (m, 6H), 4.70-4.85 (m, 3H), 6.38 (s, 1H), 7.20-7.30 (m, 1H), 7.35-7.45 (m, 1H), 7.55-7.65 (m, 1H), 7.70-7.80 (m, 1H), 8.36 (t, J=4.3 Hz, 1H), 8.71 (s, 1H), 9.08 (s, 1H);

APCI-MS (m/z): 418 (M+H)$^+$.

EXAMPLE 295

5-{[(4R,5R)-4,5-bis(hydroxymethyl)-1,3-dioxolan-2-yl]methyl}-4-(3-carbamoylphenyl)-6-ethylbenzene-1,3-diol (Compound 295)

(Step 1)

In the same manner as in the step 3 in Example 288, 1,5-bis(benzyloxy)-3-{[(4R,5R)-4,5-bis(benzyloxy)-1,3-dioxolan-2-yl]methyl}-2-(3-carbamoylphenyl)-4-ethylbenzene (665 mg, 79%) was obtained from 1,5-bis(benzyloxy)-3-{[(4R,5R)-4,5-bis(benzyloxy)-1,3-dioxolan-2-yl]methyl}-4-ethyl-2-(3-carboxyphenyl)benzene (841 mg, 1.10 mmol) obtained in the step 2 in Example 292 and 1-hydroxybenzotriazole hydrate (743 mg, 5.50 mmol), using 1-[3-(dimethylamino)propyl]-3-ethylcarbodiimide hydrochloride (422 mg, 2.20 mmol) and aqueous concentrated ammonia (0.260 mL, 3.74 mmol).

APCI-MS (m/z): 764 (M+H)$^+$.

(Step 2)

1,5-Bis(benzyloxy)-3-{[(4R,5R)-4,5-bis(benzyloxy)-1,3-dioxolan-2-yl]methyl}-2-(3-carbamoylphenyl)-4-ethylbenzene (665 mg, 0.871 mmol) obtained in the above was dissolved in tetrahydrofuran (10 mL), and 10% palladium-carbon (200 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol=4/1) to obtain Compound 295 (286 mg, 81%).

$^1$H-NMR (270 MHz, DMSO-$d_6$) δ (ppm): 1.03 (t, J=7.2 Hz, 3H), 2.50-2.80 (m, 4H), 3.25-3.65 (m, 6H), 4.65-4.90 (m, 3H), 6.38 (s, 1H), 7.20-7.50 (m, 3H), 7.64 (br s, 1H), 7.70-7.85 (m, 2H), 7.92 (br s, 1H), 8.70 (s, 1H), 9.07 (s, 1H);

APCI-MS (m/z): 404 (M+H)$^+$.

EXAMPLE 296

5-{[(4R,5R)-4,5-bis(hydroxymethyl)-1,3-dioxolan-2-yl]methyl}-6-ethyl-4-(3-fluorophenyl)benzene-1,3-diol (Compound 296)

(Step 1)

In the same manner as in the step 3 in Example 1, 1,5-bis(benzyloxy)-3-{[(4R,5R)-4,5-bis(benzyloxy)-1,3-dioxolan-2-yl]methyl}-4-ethyl-2-(3-fluorophenyl)benzene (623 mg, 100%) was obtained from 1,5-bis(benzyloxy)-3-{[(4R,5R)-4,5-bis(benzyloxy)-1,3-dioxolan-2-yl]methyl}-2-bromo-4-ethylbenzene (600 mg, 0.831 mmol) obtained in the step 1 in Example 291, using 3-fluorophenylboronic acid (244 mg, 1.74 mmol), cesium carbonate (1.16 g, 3.56 mmol) and bis(tri-o-tolylphosphine)palladium(II) dichloride (33.0 mg, 0.0420 mmol).

APCI-MS (m/z): 739 $(M+H)^+$.

(Step 2)

1,5-Bis(benzyloxy)-3-{[(4R,5R)-4,5-bis(benzyloxy)-1,3-dioxolan-2-yl]methyl}-4-ethyl-2-(3-fluorophenyl)benzene (600 mg, 0.813 mmol) obtained in the above was dissolved in tetrahydrofuran (10 mL), and 10% palladium-carbon (100 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=90/10/1) to obtain Compound 296 (242 mg, 79%).

$^1$H-NMR (300 MHz, DMSO-$d_6$) δ (ppm): 1.02 (t, J=7.3 Hz, 3H), 2.57 (q, J=7.3 Hz, 2H), 2.67 (d, J=5.3 Hz, 2H), 3.25-3.75 (m, 6H), 4.70-4.80 (m, 2H), 4.85 (t, J=5.3 Hz, 1H), 6.37 (s, 1H), 6.70-7.10 (m, 3H), 7.30-7.40 (m, 1H), 8.74 (s, 1H), 9.10 (s, 1H);

APCI-MS (m/z): 379 $(M+H)^+$.

EXAMPLE 297

5-{[(4R,5R)-4,5-bis(hydroxymethyl)-1,3-dioxolan-2-yl]methyl}-4-(3,4-difluorophenyl-6-ethylbenzene-1,3-diol (Compound 297)

(Step 1)

In the same manner as in the step 3 in Example 1, 1,5-bis(benzyloxy)-3-{[(4R,5R)-4,5-bis(benzyloxy)-1,3-dioxolan-2-yl]methyl}-2-(3,4-difluorophenyl)-4-ethylbenzene (260 mg, 66%) was obtained from 1,5-bis(benzyloxy)-3-{[(4R,5R)-4,5-bis(benzyloxy)-1,3-dioxolan-2-yl]methyl}-4-ethyl-2-iodobenzene (400 mg, 0.520 mmol) obtained in the step 2 in Example 286, using 3,4-difluorophenylboronic acid (153 mg, 1.09 mmol), cesium carbonate (730 mg, 2.24 mmol) and bis(tri-o-tolylphosphine)palladium(II) dichloride (20.0 mg, 0.0254 mmol).

APCI-MS (m/z): 757 $(M+H)^+$.

(Step 2)

1,5-Bis(benzyloxy)-3-{[(4R,5R)-4,5-bis(benzyloxy)-1,3-dioxolan-2-yl]methyl}-2-(3,4-difluorophenyl)-4-ethylbenzene (260 mg, 0.344 mmol) obtained in the above was dissolved in tetrahydrofuran (5 mL), and 10% palladium-carbon (50.0 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=100/10/1) to obtain Compound 297 (76.1 mg, 56%).

$^1$H-NMR (300 MHz, DMSO-$d_6$) δ (ppm): 1.02 (t, J=7.2 Hz, 3H), 2.50-2.75 (m, 4H), 3.25-3.75 (m, 6H), 4.70-4.80 (m, 2H), 4.87 (t, J=5.1 Hz, 1H), 6.37 (s, 1H), 6.85-7.40 (m, 3H), 8.81 (s, 1H), 9.13 (s, 1H);

APCI-MS (m/z): 397 $(M+H)^+$.

EXAMPLE 298

5-{[(4R,5R)-4,5-Bis(hydroxymethyl)-1,3-dioxolan-2-yl]methyl}-6-ethyl-4-(3-hydroxyphenyl)benzene-1,3-diol (Compound 298)

(Step 1)

In the same manner as in the step 3 in Example 1, 1,5-bis(benzyloxy)-3-{[(4R,5R)-4,5-bis(benzyloxy)-1,3-dioxolan-2-yl]methyl}-4-ethyl-2-(3-hydroxyphenyl)benzene (116 mg, 30%) was obtained from 1,5-bis(benzyloxy)-3-{[(4R,5R)-4,5-bis(benzyloxy)-1,3-dioxolan-2-yl]methyl}-4-ethyl-2-iodobenzene (400 mg, 0.520 mmol) obtained in the step 2 in Example 286, using 4,4,5,5-tetramethyl-2-(3-hydroxyphenyl)-1,3,2-dioxaborolane (240 mg, 1.09 mmol), cesium carbonate (730 mg, 2.24 mmol) and bis(tri-o-tolylphosphine)palladium(II) dichloride (20.0 mg, 0.0254 mmol).

APCI-MS (m/z): 737 $(M+H)^+$.

(Step 2)

1,5-Bis(benzyloxy)-3-{[(4R,5R)-4,5-bis(benzyloxy)-1,3-dioxolan-2-yl]methyl}-4-ethyl-2-(3-hydroxyphenyl)benzene (116 mg, 0.157 mmol) obtained in the above was dissolved in tetrahydrofuran (5 mL), and 10% palladium-carbon (60.0 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=100/10/1) to obtain Compound 298 (46.4 mg, 79%).

$^1$H-NMR (300 MHz, DMSO-$d_6$) δ (ppm): 1.00 (t, J=7.2 Hz, 3H), 2.58 (q, J=7.2 Hz, 2H), 2.65-2.80 (m, 2H), 3.20-3.70 (m, 6H), 4.70-4.90 (m, 3H), 6.33 (s, 1H), 6.45-6.70 (m, 3H), 7.05-7.15 (m, 1H), 8.54 (s, 1H), 9.00 (s, 1H), 9.19 (s, 1H);

APCI-MS (m/z): 375 $(M-H)^-$.

EXAMPLE 299

5-{[(4S,5S)-4,5-bis(hydroxymethyl)-1,3-dioxolan-2-yl]methyl}-4-(3,4-difluorophenyl)-6-ethylbenzene-1,3-diol (Compound 299)

(Step 1)

In the same manner as in the step 1 in Example 291, 1,5-bis(benzyloxy)-3-{[(4S,5S)-4,5-bis(benzyloxy)-1,3-dioxolan-2-yl]methyl}-2-bromo-4-ethylbenzene (1.32 g, 80%) was obtained from 3,5-bis(benzyloxy)-1-{[(4S,5S)-4,5-bis(benzyloxy)-1,3-dioxolan-2-yl]methyl}-2-ethylbenzene (1.48 g, 2.28 mmol) obtained in the step 3 in Example 233, using N-bromosuccinimide (450 mg, 2.51 mmol).

$^1$H-NMR (270 MHz, CDCl$_3$) δ (ppm): 1.09 (t, J=7.4 Hz, 3H), 2.84 (q, J=7.4 Hz, 2H), 3.24-3.33 (m, 2H), 3.54-3.65 (m, 4H), 4.00-4.16 (m, 2H), 4.54 (s, 2H), 4.58 (s, 2H), 5.00 (s, 2H), 5.05 (s, 2H), 5.40 (t, J=4.9 Hz, 1H), 6.49 (s, 1H), 7.16-7.46 (m, 20H).

(Step 2)

In the same manner as in the step 3 in Example 1, 1,5-bis(benzyloxy)-3-{[(4S,5S)-4,5-bis(benzyloxy)-1,3-dioxolan-2-yl]methyl}-2-(3,4-difluorophenyl)-4-ethylbenzene (240 mg, 76%) was obtained from 1,5-bis(benzyloxy)-3-{[(4S,5S)-4,5-bis(benzyloxy)-1,3-dioxolan-2-yl]methyl}-2-bromo-4-ethylbenzene (300 mg, 0.416 mmol) obtained in the above, using 3,4-difluorophenylboronic acid (122 mg, 0.872 mmol), cesium carbonate (583 mg, 1.79 mmol) and bis(tri-o-tolylphosphine)palladium(II) dichloride (16.0 mg, 0.0204 mmol).

APCI-MS (m/z): 757 (M+H)$^+$.

(Step 3)

1,5-Bis(benzyloxy)-3-{[(4S,5S)-4,5-bis(benzyloxy)-1,3-dioxolan-2-yl]methyl}-2-(3,4-difluorophenyl)-4-ethylbenzene (240 mg, 0.317 mmol) obtained in the above was dissolved in tetrahydrofuran (5 mL), and 10% palladium-carbon (100 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=100/10/1) to obtain Compound 299 (110 mg, 87%).

$^1$H-NMR (270 MHz, DMSO-d$_6$) δ (ppm): 1.02 (t, J=7.1 Hz, 3H), 2.50-2.72 (m, 4H), 3.25-3.45 (m, 4H), 3.50-3.70 (m, 2H), 4.70-4.80 (m, 2H), 4.87 (t, J=5.1 Hz, 1H), 6.37 (s, 1H), 6.85-7.45 (m, 3H), 8.78 (s, 1H), 9.12 (s, 1H);

APCI-MS (m/z): 395 (M−H)$^−$.

EXAMPLE 300

5-{[(4S,5S)-4,5-Bis(hydroxymethyl)-1,3-dioxolan-2-yl]methyl}-6-ethyl-4-(4-fluoro-3-methylphenyl)benzene-1,3-diol (Compound 300)

(Step 1)

In the same manner as in the step 3 in Example 1, 1,5-bis(benzyloxy)-3-{[(4S,5S)-4,5-bis(benzyloxy)-1,3-dioxolan-2-yl]methyl}-4-ethyl-2-(4-fluoro-3-methylphenyl)benzene (310 mg, 99%) was obtained from 1,5-bis(benzyloxy)-3-{[(4S,5S)-4,5-bis(benzyloxy)-1,3-dioxolan-2-yl]methyl}-2-bromo-4-ethylbenzene (300 mg, 0.416 mmol) obtained the step 1 in Example 299, using 4-fluoro-3-methylphenylboronic acid (135 mg, 0.872 mmol), cesium carbonate (583 mg, 1.79 mmol) and bis(tri-o-tolylphosphine)palladium(II) dichloride (16.0 mg, 0.0204 mmol).

APCI-MS (m/z): 753 (M+H)$^+$.

(Step 2)

1,5-Bis(benzyloxy)-3-{[(4S,5S)-4,5-bis(benzyloxy)-1,3-dioxolan-2-yl]methyl}-4-ethyl-2-(4-fluoro-3-methylphenyl)benzene (310 mg, 0.412 mmol) obtained in the above was dissolved in tetrahydrofuran (10 mL), and 10% palladium-carbon (150 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=100/10/1) to obtain Compound 300 (101 mg, 62%).

$^1$H-NMR (270 MHz, DMSO-d$_6$) δ (ppm): 1.01 (t, J=7.3 Hz, 3H), 2.22 (s, 3H), 2.50-2.70 (m, 4H), 3.25-3.70 (m, 6H), 4.70-4.90 (m, 3H), 6.35 (s, 1H), 6.85-7.10 (m, 3H), 8.61 (s, 1H), 9.02 (s, 1H);

APCI-MS (m/z): 391 (M−H)$^−$.

EXAMPLE 301

5-{[(4S,5S)-4,5-Bis(hydroxymethyl)-1,3-dioxolan-2-yl]methyl}-4-(3-chloro-4-fluorophenyl)-6-ethylbenzene-1,3-diol (Compound 301)

(Step 1)

In the same manner as in the step 3 in Example 1, 1,5-bis(benzyloxy)-3-{[(4S,5S)-4,5-bis(benzyloxy)-1,3-dioxolan-2-yl]methyl}-2-(3-chloro-4-fluorophenyl)-4-ethylbenzene (320 mg, 99%) was obtained by dissolving 1,5-bis(benzyloxy)-3-{[(4S,5S)-4,5-bis(benzyloxy)-1,3-dioxolan-2-yl]methyl}-2-bromo-4-ethylbenzene (300 mg, 0.416 mmol) obtained the step 1 in Example 299 in a mixed solvent of 1,2-dimethoxyethane (5 mL) and water (2 mL) and using 3-chloro-4-fluorophenylboronic acid (152 mg, 0.872 mmol), cesium carbonate (583 mg, 1.79 mmol) and bis(tri-o-tolylphosphine)palladium(II) dichloride (16.0 mg, 0.0204 mmol).

APCI-MS (m/z): 773 (M+H)$^+$.

(Step 2)

1,5-Bis(benzyloxy)-3-{[(4S,5S)-4,5-bis(benzyloxy)-1,3-dioxolan-2-yl]methyl}-2-(3-chloro-4-fluorophenyl)-4-ethylbenzene (320 mg, 0.414 mmol) obtained in the above was dissolved in tetrahydrofuran (6 mL), and 10% palladium-carbon (20 mg) was added thereto and stirred in a hydrogen atmosphere at room temperature for 4 hours. The reaction mixture was filtered, and the filtrate was concentrated under reduced pressure. The resulting residue was purified through preparative thin-layer chromatography (chloroform/methanol/water=100/10/1) to obtain Compound 301 (121 mg, 71%).

$^1$H-NMR (270 MHz, DMSO-d$_6$) δ (ppm): 1.02 (t, J=7.4 Hz, 3H), 2.50-2.75 (m, 4H), 3.25-3.75 (m, 6H), 4.70-4.94 (m, 3H), 6.37 (s, 1H), 7.00-7.40 (m, 3H), 8.82 (s, 1H), 9.15 (s, 1H);

APCI-MS (m/z): 413 (M+H)$^+$.

EXAMPLE 302

5-{[meso-4,5-Bis(hydroxymethyl)-1,3-dioxolan-2-yl]methyl}-6-ethyl-4-phenylbenzene-1,3-diol (Compound 302)

(Step 1)

Cis-1,4-dibenzyloxy-2-butene (2.00 mL, 7.80 mmol) was dissolved in acetonitrile (20 mL) and water (5 mL). N-methylmorpholine-N-oxide (2.74 g, 23.4 mmol) and tert-butyl alcohol solution of 2.5 wt. % osmium tetroxide (0.100 mL, 0.00799 mmol) were added to the resulting solution, and stirred in a nitrogen atmosphere at room temperature for 14 hours. Water and aqueous saturated sodium hydrogencarbonate solution were added to the reaction mixture, and extracted with ethyl acetate. The organic layer was washed with aqueous saturated sodium chloride solution, then dried over anhydrous sodium sulfate, and the solvent was evaporated away under reduced pressure to obtain meso-1,4-dibenzyloxybutane-2,3-diol (2.11 g, 89%).

APCI-MS (m/z): 303 (M+H)$^+$.

(Step 2)

In the same manner as in the step 2 in Example 218, 1,5-bis(benzyloxy)-3-{[meso-4,5-bis(benzyloxy)-1,3-dioxolan-2-yl]methyl}-4-ethyl-2-phenylbenzene (693 mg, 96%) was obtained from 2-[3,5-bis(benzyloxy)-2-ethyl-6-phenylphenyl]ethanal (428 mg, 0.979 mmol) obtained in the step 1 in Example 218, using meso-1,4-dibenzyloxybutane-2,3-diol (620 mg, 2.05 mmol) obtained in the above and DL-10-camphorsulfonic acid (71.6 mg, 0.308 mmol).

APCI-MS (m/z): 721 (M+H)$^+$.

(Step 3)

1,5-Bis(benzyloxy)-3-{[meso-4,5-bis(benzyloxy)-1,3-dioxolan-2-yl]methyl}-4-ethyl-2-phenylbenzene (683 mg, 0.947 mmol) obtained in the above was dissolved in tetrahydrofuran (16 mL), and 10% palladium-carbon (280 mg) was added thereto and stirred in a hydrogen atmosphere at room temperature for 18 hours. The reaction mixture was filtered, and the filtrate was concentrated under reduced pressure. The resulting residue was purified through silica gel column chromatography (chloroform/methanol=20/1 to 9/1) to obtain Compound 302 (208 mg, 61%).

$^1$H-NMR (300 MHz, DMSO-d$_6$) δ (ppm): 0.98-1.08 (m, 3H), 2.50-2.80 (m, 4H), 3.25-3.50 (m, 4H), 3.76-3.90 (m, 4H), 4.58-4.67 (m, 2H), 4.68-5.02 (m, 1H), 6.36 (s, 1H), 7.00-7.50 (m, 5H), 8.59-8.63 (m, 1H), 9.02 (s, 1H);

APCI-MS (m/z): 359 (M−H)$^-$.

EXAMPLE 303

5-{[(4R,5R)-4,5-Bis(hydroxymethyl)-1,3-dioxolan-2-yl]methyl}-6-ethyl-4-[3-(2-methoxyethyl)carbamoylphenyl]benzene-1,3-diol (Compound 303)

(Step 1)

In the same manner as in the step 3 in Example 288, 1,5-bis(benzyloxy)-3-{[(4R,5R)-4,5-bis(benzyloxy)-1,3-dioxolan-2-yl]methyl}-4-ethyl-2-[3-(2-methoxyethyl)carbamoylphenyl]benzene (170 mg, 52%) was obtained from 1,5-bis(benzyloxy)-3-{[(4R,5R)-4,5-bis(benzyloxy)-1,3-dioxolan-2-yl]methyl}-4-ethyl-2-(3-carboxyphenyl)benzene (306 mg, 0.400 mmol) obtained in the step 2 in Example 292, using 1-hydroxybenzotriazole hydrate (270 mg, 2.00 mmol), 1-[3-(dimethylamino)propyl]-3-ethylcarbodiimide hydrochloride (154 mg, 0.800 mmol) and 2-methoxyethylamine (0.105 mL, 1.20 mmol).

APCI-MS (m/z): 822 (M+H)$^+$.

(Step 2)

1,5-Bis(benzyloxy)-3-{[(4R,5R)-4,5-bis(benzyloxy)-1,3-dioxolan-2-yl]methyl}-4-ethyl-2-[3-(2-methoxyethyl)carbamoylphenyl]benzene (171 mg, 0.208 mmol) obtained in the above was dissolved in tetrahydrofuran (10 mL), and 10% palladium-carbon (62.4 mg) was added thereto and stirred under hydrogen pressure (0.35 MPa) at room temperature for 16 hours. The reaction mixture was filtered, and the filtrate was concentrated under reduced pressure. The resulting residue was purified through preparative thin-layer chromatography (chloroform/methanol=4/1) to obtain compound 303 (45.0 mg, 47%).

$^1$H-NMR (270 MHz, CD$_3$OD) δ (ppm): 1.10 (t, J=7.4 Hz, 3H), 2.64-2.82 (m, 4H), 3.56 (s, 3H), 3.20-3.75 (m, 10H), 4.50-5.02 (m, 1H), 6.33 (s, 1H), 7.30-7.50 (m, 2H), 7.64-7.78 (m, 2H);

APCI-MS (m/z): 462 (M+H)$^+$.

EXAMPLE 304

5-{[(4R,5R)-4,5-Bis(hydroxymethyl)-1,3-dioxolan-2-yl]methyl}-6-ethyl-4-[3-(2-hydroxyethyl)carbamoylphenyl]benzene-1,3-diol (Compound 304)

(Step 1)

In the same manner as in the step 3 in Example 288, 1,5-bis(benzyloxy)-3-{[(4R,5R)-4,5-bis(benzyloxy)-1,3-dioxolan-2-yl]methyl}-4-ethyl-2-[3-(2-hydroxyethyl)carbamoylphenyl]benzene (170 mg, 53%) was obtained from 1,5-bis(benzyloxy)-3-{[(4R,5R)-4,5-bis(benzyloxy)-1,3-dioxolan-2-yl]methyl}-2-(3-carboxyphenyl)-4-ethylbenzene (306 mg, 0.400 mmol) obtained in the step 2 in Example 292, using 1-hydroxybenzotriazole hydrate (270 mg, 2.00 mmol), 1-[3-(dimethylamino)propyl]-3-ethylcarbodiimide hydrochloride (154 mg, 0.800 mmol) and ethanolamine (0.073 mL, 1.20 mmol).

APCI-MS (m/z): 808 (M+H)$^+$.

(Step 2)

1,5-Bis(benzyloxy)-3-{[(4R,5R)-4,5-bis(benzyloxy)-1,3-dioxolan-2-yl]methyl}-4-ethyl-2-[3-(2-hydroxyethyl)carbamoylphenyl]benzene (160 mg, 0.198 mmol) obtained in the above was dissolved in tetrahydrofuran (10 mL), and 10% palladium-carbon (26.4 mg) was added thereto and stirred under hydrogen pressure (0.35 MPa) at room temperature for 16 hours. The reaction mixture was filtered, and the filtrate was concentrated under reduced pressure. The resulting residue was purified through preparative thin-layer chromatography (chloroform/methanol/water=100/10/1) to obtain compound 304 (80.2 mg, 91%).

$^1$H-NMR (270 MHz, DMSO-d$_6$) δ (ppm): 1.02 (t, J=7.4 Hz, 3H), 2.50-2.75 (m, 4H), 3.20-3.70 (m, 10H), 4.65-4.85 (m, 4H), 6.38 (s, 1H), 7.22-7.45 (m, 2H), 7.60-7.80 (m, 2H), 8.36 (brq, J=4.2 Hz, 1H), 8.71 (s, 1H), 9.08 (s, 1H);

APCI-MS (m/z): 448 (M+H)$^+$.

EXAMPLE 305

5-{[(4R,5R)-4,5-Bis(hydroxymethyl)-1,3-dioxolan-2-yl]methyl}-4-[3-(2-cyclopropylcarbamoyl)phenyl]-6-ethylbenzene-1,3-diol (Compound 305)

(Step 1)

In the same manner as in the step 3 in Example 288, 1,5-bis(benzyloxy)-3-{[(4R,5R)-4,5-bis(benzyloxy)-1,3-dioxolan-2-yl]methyl}-2-[3-cyclopropylcarbamoyl)phenyl]-4-ethylbenzene (90.0 mg, 28%) was obtained from 1,5-bis(benzyloxy)-3-{[(4R,5R)-4,5-bis(benzyloxy)-1,3-dioxolan-2-yl]methyl}-4-ethyl-2-(3-carboxyphenyl)benzene (306 mg, 0.400 mmol) obtained in the step 2 in Example 292, using 1-hydroxybenzotriazole hydrate (270 mg, 2.00 mmol), 1-[3-(dimethylamino)propyl]-3-ethylcarbodiimide hydrochloride (154 mg, 0.800 mmol) and cyclopropylamine (0.083 mL, 1.20 mmol).

APCI-MS (m/z): 804 (M+H)$^+$.

(Step 2)

1,5-Bis(benzyloxy)-3-{[(4R,5R)-4,5-bis(benzyloxy)-1,3-dioxolan-2-yl]methyl}-2-[3-cyclopropylcarbamoyl)phenyl]-4-ethylbenzene (99.4 mg, 0.124 mmol) obtained in the above was dissolved in tetrahydrofuran (10 mL), and 10% palladium-carbon (28.6 mg) was added thereto and stirred under hydrogen pressure (0.35 MPa) at room temperature for 16 hours. The reaction mixture was filtered, and the filtrate was concentrated under reduced pressure. The resulting residue was purified through preparative thin-layer chromatography (chloroform/methanol=4/1) to obtain compound 305 (35.1 mg, 64%).

$^1$H-NMR (300 MHz, DMSO-d$_6$) δ (ppm): 0.52-0.74 (m, 4H), 1.02 (t, J=7.4 Hz, 3H), 2.50-2.70 (m, 4H), 2.80-2.90 (m, 1H), 4.70-4.90 (m, 3H), 6.38 (s, 1H), 7.20-7.80 (m, 4H), 8.37 (brd, J=3.9 Hz, 1H), 8.71 (s, 1H), 9.08 (s, 1H); APCI-MS (m/z): 444 (M+H)$^+$.

EXAMPLE 306

5-{[(4R,5R)-4,5-Bis(hydroxymethyl)-1,3-dioxolan-2-yl]methyl}-6-ethyl-4-[3-(propylcarbamoyl)phenyl]benzene-1,3-diol (Compound 306)

(Step 1)

In the same manner as in the step 3 in Example 288, 1,5-bis(benzyloxy)-3-{[(4R,5R)-4,5-bis(benzyloxy)-1,3-dioxolan-2-yl]methyl}-4-ethyl-2-[3-(propylcarbamoyl)phenyl]benzene (140 mg, 43%) was obtained from 1,5-bis(benzyloxy)-3-{[(4R,5R)-4,5-bis(benzyloxy)-1,3-dioxolan-2-yl]methyl}-4-ethyl-2-[3-(propylcarbamoyl)phenyl]benzene (306 mg, 0.400 mmol) obtained in the step 2 in Example 292, using 1-hydroxybenzotriazole hydrate (270 mg, 2.00 mmol), 1-[3-(dimethylamino)propyl]-3-ethylcarbodiimide hydrochloride (154 mg, 0.800 mmol) and propylamine (0.099 mL, 1.20 mmol).

APCI-MS (m/z): 806 (M+H)$^+$.

(Step 2)

1,5-Bis(benzyloxy)-3-{[(4R,5R)-4,5-bis(benzyloxy)-1,3-dioxolan-2-yl]methyl}-4-ethyl-2-[3-(propylcarbamoyl)phenyl]benzene (133 mg, 0.165 mmol) obtained in the above was dissolved in tetrahydrofuran (10 mL), and 10% palladium-carbon (28.6 mg) was added thereto and stirred under hydrogen pressure (0.35 MPa) at room temperature for 16 hours. The reaction mixture was filtered, and the filtrate was concentrated under reduced pressure. The resulting residue was purified through preparative thin-layer chromatography (chloroform/methanol=4/1) to obtain compound 306 (23.4 mg, 32%).

$^1$H-NMR (270 MHz, DMSO-d$_6$) δ (ppm): 0.96 (t, J=7.3 Hz, 3H), 1.09 (t, J=7.3 Hz, 3H), 1.63 (tq, J=7.3, 7.3 Hz, 2H), 2.60-2.90 (m, 4H), 3.25-3.75 (m, 8H), 4.94-5.03 (m, 1H), 6.33 (s, 1H), 7.30-7.50 (m, 2H), 7.62-7.78 (m, 2H), 8.41 (brt, J=5.1 Hz, 1H);

APCI-MS (m/z): 446 (M+H)$^+$.

EXAMPLE 307

5-{[(4R,5R)-4,5-Bis(methoxymethyl)-1,3-dioxolan-2-yl]methyl}-6-ethyl-4-(3-hydroxyphenyl)benzene-1,3-diol (Compound 307)

(Step 1)

In the same manner as in the step 2 in Example 218, 3,5-bis(benzyloxy)-1-{[(4R,5R)-4,5-bis(methoxymethyl)-1,3-dioxolan-2-yl]methyl}-2-ethylbenzene (674 mg, 32%) was obtained from 2-[3,5-bis(benzyloxy)-2-ethylphenyl]ethanal (1.56 g, 4.33 mmol) obtained in the step 2 in Example 233, using (R,R)-(+)-1,4-dimethylbutane-2,3-diol (466 mg, 3.10 mmol) and DL-10-camphorsulfonic acid (148 mg, 0.642 mmol).

APCI-MS (m/z): 493 (M+H)$^+$.

(Step 2)

In the same manner as in the step 1 in Example 291, 3,5-bis(benzyloxy)-1-{[(4R,5R)-4,5-bis(methoxymethyl)-1,3-dioxolan-2-yl]methyl}-2-bromo-4-ethylbenzene (580 mg, 70%) was obtained from 3,5-bis(benzyloxy)-1-{[(4R,5R)-4,5-bis(methoxymethyl)-1,3-dioxolan-2-yl]methyl}-2-ethylbenzene (650 mg, 1.32 mmol) obtained in the above, using N-bromosuccinimide (259 mg, 1.45 mmol).

APCI-MS (m/z): 571 (M+H)$^+$.

(Step 3)

In the same manner as in the step 3 in Example 1, 1,5-bis(benzyloxy)-3-{[(4R,5R)-4,5-bis(methoxymethyl)-1,3-dioxolan-2-yl]methyl}-4-ethyl-2-(3-hydroxyphenyl)benzene (215 mg, 75%) was obtained from 3,5-bis(benzyloxy)-1-{[(4R,5R)-4,5-bis(methoxymethyl)-1,3-dioxolan-2-yl]methyl}-2-bromo-4-ethylbenzene (280 mg, 0.490 mmol) obtained in the above, using 4,4,5,5-tetramethyl-2-(3-hydroxyphenyl)-1,3,2-dioxaborolane (220 mg, 1.03 mmol), cesium carbonate (680 mg, 2.09 mmol) and bis(tri-o-tolylphosphine)palladium(II) dichloride (19 mg, 0.0242 mmol).

APCI-MS (m/z): 585 (M+H)$^+$.

(Step 4)

1,5-Bis(benzyloxy)-3-{[(4R,5R)-4,5-bis(methoxymethyl)-1,3-dioxolan-2-yl]methyl}-4-ethyl-2-(3-hydroxyphenyl)benzene (195 mg, 0.334 mmol) obtained in the above was dissolved in tetrahydrofuran (15 mL), and 10% palladium-carbon (55.4 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=100/10/1) to obtain compound 307 (115 mg, 85%).

$^1$H-NMR (300 MHz, DMSO-d$_6$) δ (ppm): 1.00 (t, J=7.2 Hz, 3H), 2.45-2.75 (m, 4H), 3.21 (s, 3H), 3.23 (s, 3H), 3.20-3.40 (m, 4H), 3.60-3.80 (m, 2H), 4.75-4.84 (m, 1H), 6.34 (s, 1H), 6.45-6.70 (m, 3H), 7.05-7.15 (m, 1H), 8.56 (s, 1H), 9.01 (s, 1H), 9.17 (s, 1H);

APCI-MS (m/z): 403 (M−H)$^-$.

EXAMPLE 308

5-{[(4R,5R)-4,5-Bis(methoxymethyl)-1,3-dioxolan-2-yl]methyl}-6-ethyl-4-phenylbenzene-1,3-diol (Compound 308)

(Step 1)

In the same manner as in the step 3 in Example 1, 1,5-bis(benzyloxy)-3-{[(4R,5R)-4,5-bis(methoxy-1,3-dioxolan-2-yl]methyl}-4-ethyl-2-phenylbenzene (252 mg, 91%) was obtained from 3,5-bis(benzyloxy)-1-{[(4R,5R)-4,5-bis(methoxymethyl)-1,3-dioxolan-2-yl]methyl}-2-bromo-4-ethylbenzene (280 mg, 0.490 mmol) obtained in the step 2 in Example 307, using phenylboronic acid (122 mg, 0.996 mmol), cesium carbonate (748 mg, 2.30 mmol) and bis(tri-o-tolylphosphine)palladium(II) dichloride (20.0 mg, 0.0249 mmol).

APCI-MS (m/z): 569 (M+H)$^+$.

(Step 2)

1,5-Bis(benzyloxy)-3-{[(4R,5R)-4,5-bis(methoxy)-1,3-dioxolan-2-yl]methyl}-4-ethyl-2-phenylbenzene (237 mg, 0.416 mmol) obtained in the above was dissolved in tetrahydrofuran (10 mL), and 10% palladium-carbon (46.7 mg) was added thereto and stirred under hydrogen pressure (0.35 MPa) at room temperature for 21 hours. The reaction mixture was filtered, and the filtrate was concentrated under reduced pressure. The resulting residue was purified through preparative thin-layer chromatography (chloroform/methanol/water=100/10/1) to obtain compound 308 (118 mg, 73%).

$^1$H-NMR (300 MHz, DMSO-d$_6$) δ (ppm): 1.01 (t, J=7.3 Hz, 3H), 2.57 (q, J=7.3 Hz, 2H), 2.67 (d, J=5.2 Hz, 2H), 3.20 (s, 3H), 3.23 (s, 3H), 3.20-3.40 (m, 4H), 3.60-3.75 (m, 2H), 4.77 (t, J=5.2 Hz, 1H), 6.37 (s, 1H), 7.00-7.40 (m, 5H), 8.64 (s, 1H), 9.05 (s, 1H);

APCI-MS (m/z): 387 (M−H)$^-$.

EXAMPLE 309

6-Ethyl-5-[2-(2-hydroxyethoxy)ethyl]-4-(3,4-dimethoxyphenyl)benzene-1,3-diol (Compound 309)

(Step 1)

2-[3,5-Bis(benzyloxy)-2-ethylphenyl]ethanol (4.7 g, 13 mmol) obtained in the step 1 in Example 219 was dissolved in N,N-dimethylformamide (50 mL), and in an argon atmosphere, 60% sodium hydride/mineral oil dispersion (1.5 g, 38 mmol) was gradually added thereto with stirring with cooling with ice. The reaction mixture was stirred at room temperature for 1 hour, and then 2-(2-bromoethoxy)tetrahydro-2H-pyran (3.9 mL, 26 mmol) was dropwise added thereto, and further stirred at room temperature for 12 hours. The reaction mixture was cooled with ice, then saturated ammonium chloride was dropwise added thereto, and extracted with ethyl acetate. The organic layer was washed with aqueous saturated sodium chloride solution, then dried over anhydrous sodium sulfate, and the solvent was evaporated away under reduced pressure. The resulting residue was purified through silica gel column chromatography (ethyl acetate/hexane=1/10 to 1/4) to obtain 3,5-bis(benzyloxy)-2-ethyl-1-[2-(2-tetrahydropyran-2-yloxyethoxy)ethyl]benzene (4.3 g, 68%).

$^1$H-NMR (300 MHz, CDCl$_3$) δ (ppm): 1.12 (t, J=7.5 Hz, 3H), 1.48-1.83 (m, 6H), 2.70 (q, J=7.5 Hz, 2H), 2.92 (t, J=7.3 Hz, 2H), 3.48-3.71 (m, 6H), 3.83-3.89 (m, 2H), 4.63 (t, J=3.3 Hz, 1H), 4.99 (s, 2H), 5.01 (s, 2H), 6.46 (d, J=2.4 Hz, 1H), 6.49 (d, J=2.4 Hz, 1H), 7.25-7.46 (m, 10H).

(Step 2)

In the same manner as in the step 2 in Example 1, 1,5-bis(benzyloxy)-2-bromo-4-ethyl-3-[2-(2-tetrahydropyran-2-yloxyethoxy)ethyl]benzene (1.6 g, 62%) was obtained from 3,5-bis(benzyloxy)-2-ethyl-1-[2-(2-tetrahydropyran-2-yloxyethoxy)ethyl]benzene (2.1 g, 4.5 mmol) obtained in the above, using N-bromosuccinimide (0.89 g, 5.0 mmol) and N,N-dimethylformamide (20 mL).

$^1$H-NMR (270 MHz, CDCl$_3$) δ (ppm): 1.11 (t, J=7.5 Hz, 3H), 1.48-1.83 (m, 6H), 2.75 (q, J=7.5 Hz, 2H), 3.20 (t, J=7.3 Hz, 2H), 3.48-3.71 (m, 6H), 3.84-3.91 (m, 2H), 4.64 (t, J=3.3 Hz, 1H), 4.99 (s, 2H), 5.05 (s, 2H), 6.47 (s, 1H), 7.25-7.46 (m, 10H).

(Step 3)

In the same manner as in the step 3 in Example 1, 1,5-bis(benzyloxy)-2-(3,4-dimethoxyphenyl)-4-ethyl-3-[2-(2-tetrahydropyran-2-yloxyethoxy)ethyl]benzene was obtained from 1,5-bis(benzyloxy)-2-bromo-4-ethyl-3-[2-(2-tetrahydropyran-2-yloxyethoxy)ethyl]benzene (510 mg, 0.89 mmol) obtained in the above, using 3,4-dimethoxyphenylboronic acid (200 mg, 1.1 mmol), bis(tri-o-tolylphosphine)palladium(II) dichloride (70 mg, 0.089 mmol), cesium carbonate (880 mg, 2.7 mmol), 1,2-dimethoxyethane (5.0 mL) and water (1.0 mL). Then, in the same manner as in the step 4 in Example 1, 1,5-bis(benzyloxy)-2-(3,4-dimethoxyphenyl)-4-ethyl-3-[2-(2-hydroxyethoxy)ethyl]benzene (320 mg, 70%) was obtained from the resulting compound, using methanol (6.0 mL) and 1,4-dioxane solution (2.0 mL) of 4 mol/L hydrogen chloride.

$^1$H-NMR (270 MHz, CDCl$_3$) δ (ppm): 1.19 (t, J=7.2 Hz, 3H), 2.74-2.87 (m, 4H), 3.34 (t, J=4.8 Hz, 2H), 3.42 (t, J=8.2 Hz, 2H), 3.61 (t, J=4.8 Hz, 2H), 3.84 (s, 3H), 3.93 (s, 3H), 4.91 (s, 2H), 5.05 (s, 2H), 6.53 (s, 1H), 6.77-6.80 (m, 2H), 6.93 (d, J=8.4 Hz, 1H), 7.09-7.46 (m, 10H);

APCI-MS (m/z): 543 (M+H)$^+$.

(Step 4)

1,5-Bis(benzyloxy)-2-(3,4-dimethoxyphenyl)-4-ethyl-3-[2-(2-hydroxyethoxy)ethyl]benzene (320 mg, 0.59 mmol) obtained in the above was dissolved in ethyl acetate (5.0 mL), and 10% palladium-carbon (50% wet., 50 mg) was added thereto and stirred in a hydrogen atmosphere at room temperature for 8 hours. The reaction mixture was filtered through Celite, and the filtrate was concentrated under reduced pressure. The resulting residue was purified through silica gel column chromatography (ethyl acetate/hexane=1/1 to 9/1) to obtain Compound 309 (140 mg, 65%).

$^1$H-NMR (300 MHz, CD$_3$OD) δ (ppm): 1.12 (t, J=7.5 Hz, 3H), 2.56-2.74 (m, 4H), 3.28-3.40 (m, 2H), 3.37 (t, J=8.0 Hz, 2H), 3.53 (t, J=4.8 Hz, 2H), 3.81 (s, 3H), 3.86 (s, 3H), 6.28 (s, 1H), 6.73 (dd, J=8.4, 2.0 Hz, 1H), 6.77 (d, J=2.0 Hz, 1H), 7.00 (d, J=8.4 Hz, 1H);

APCI-MS (m/z): 363 (M+H)$^+$.

EXAMPLE 310

1-{2,4-Dihydroxy-6-[2-(2-hydroxyethoxy)ethyl]-5-(3-hydroxyphenyl)phenyl}ethanone (Compound 310)

(Step 1)

In the same manner as in the step 1 in Example 179, methyl 3,5-bis(benzyloxy)phenylacetate was quantitatively obtained from methyl 3,5-dihydroxyphenylacetate (25 g, 0.15 mmol), using potassium carbonate (75 g, 0.54 mmol), benzyl bromide (35 mL, 0.29 mmol) and acetone (200 mL).

$^1$H-NMR (300 MHz, CDCl$_3$) δ (ppm): 3.55 (s, 2H), 3.68 (s, 3H), 5.01 (s, 4H), 6.53 (s, 3H), 7.35-7.42 (s, 10H).

(Step 2)

In the same manner as in the step 1 in Example 62, 2-[3,5-bis(benzyloxy)phenyl]ethanol was obtained from methyl 3,5-bis(benzyloxy)phenylacetate (10 g, 29 mmol) obtained in the above, using lithium aluminium hydride (1.5 g, 40 mmol) and tetrahydrofuran (100 mL). Then, in the same manner as in the step 1 in Example 309, 1,3-bis(benzyloxy)-5-[2-(2-tetrahydropyran-2-yloxyethoxy)ethyl]benzene (7.6 g, 59%) was obtained from 2-[3,5-bis(benzyloxy)phenyl]ethanol (9.4 g, 28 mmol) obtained in the above, using 60% sodium hydride/mineral oil dispersion (3.3 g, 83 mmol), 2-(2-bromoethoxy)tetrahydro-2H-pyran (8.3 mL, 55 mmol) and N,N-dimethylformamide (100 mL).

$^1$H-NMR (300 MHz, CDCl$_3$) δ (ppm): 1.46-1.83 (m, 6H), 2.84 (t, J=7.2 Hz, 2H), 3.40-3.72 (m, 6H), 3.82-3.86 (m, 2H), 4.61 (t, J=3.9 Hz, 1H), 5.01 (s, 4H), 6.48 (s, 3H), 7.31-7.43 (m, 10H);

APCI-MS (m/z): 463 (M+H)$^+$.

(Step 3)

In the same manner as in the step 1 in Example 13, 3,5-bis(benzyloxy)-2-iodo-1-[2-(2-tetrahydropyran-2-yloxyethoxy)ethyl]benzene (7.1 g, 94%) was obtained from 1,3-bis(benzyloxy)-5-[2-(2-tetrahydropyran-2-yloxyethoxy)ethyl]benzene (5.9 g, 13 mmol) obtained in the above, using iodine (1.7 g, 13 mmol), [bis(trifluoroacetoxy)iodo]benzene (5.5 g, 13 mmol) and chloroform (50 mL).

$^1$H-NMR (300 MHz, CDCl$_3$) δ (ppm): 1.46-1.83 (m, 6H), 3.08 (t, J=6.9 Hz, 2H), 3.40-3.72 (m, 6H), 3.82-3.86 (m, 2H), 4.62 (t, J=4.2 Hz, 1H), 5.06 (s, 2H), 5.08 (s, 2H), 6.42 (d, J=2.7 Hz, 1H), 6.63 (d, J=2.7 Hz, 1H), 7.31-7.43 (m, 10H);

APCI-MS (m/z): 589 (M+H)$^+$.

(Step 4)

In the same manner as in the step 1 in Example 69, 3,5-bis(benzyloxy)-2-iodo-1-[2-(2-tetrahydropyran-2-yloxyethoxy)ethyl]benzene (7.1 g, 13 mmol) obtained in the above was treated with tributyl(1-ethoxyvinyl)tin (5.2 mL, 15 mmol), bis(triphenylphosphine)palladium(II) dichloride (0.9 g, 1.3 mmol) and toluene (100 mL), and then treated with tetrahydrofuran (50 mL) and 1 mol/L hydrochloric acid (30 mL) to obtain 1-{2,4-bis(benzyloxy)-6-[2-(2-hydroxyethoxy)ethyl]phenyl}ethanone (4.0 g, 73%).

$^1$H-NMR (300 MHz, CDCl$_3$) δ (ppm): 2.48 (s, 3H), 2.82 (t, J=6.9 Hz, 2H), 3.49-3.69 (m, 6H), 5.03 (s, 2H), 5.04 (s, 2H), 6.48 (s, 2H), 7.31-7.43 (m, 10H).

(Step 5)

In the same manner as in the step 2 in Example 1, 1-{4,6-bis(benzyloxy)-3-bromo-2-[2-(2-hydroxyethoxy)ethyl]phenyl}ethanone (1.0 g, 21%) was obtained from 1-{2,4-bis(benzyloxy)-6-[2-(2-hydroxyethoxy)ethyl]phenyl}ethanone (4.0 g, 9.5 mmol) obtained in the above, using N-bromosuccinimide (1.7 g, 9.5 mmol) and N,N-dimethylformamide (50 mL).

$^1$H-NMR (300 MHz, CDCl$_3$) δ (ppm): 2.04 (s, 3H), 3.03 (t, J=6.9 Hz, 2H), 3.55 (t, J=4.9 Hz, 2H), 3.66-3.71 (m, 4H), 5.06 (s, 2H), 5.10 (s, 2H), 6.47 (s, 1H), 7.25-7.44 (m, 10H);
APCI-MS (m/z): 499, 501 (M+H)$^+$.

(Step 6)

In the same manner as in the step 3 in Example 1, 1-{4,6-bis(benzyloxy)-2-[2-(2-hydroxyethoxy)ethyl]-3-(3-hydroxyphenyl)phenyl}ethanone (540 mg, 99%) was obtained from 1-{4,6-bis(benzyloxy)-3-bromo-2-[2-(2-hydroxyethoxy)ethyl]phenyl}ethanone (500 mg, 1.0 mmol) obtained in the above, using 2-(3-hydroxyphenyl)-4,4,5,5-tetramethyl-1,3,2-dioxaborolane (270 mg, 1.2 mmol), bis(tri-o-tolylphosphine)palladium(II) dichloride (50 mg, 0.07 mmol), cesium carbonate (1.0 g, 3.1 mmol), 1,2-dimethoxyethane (10 mL) and water (2.0 mL).

$^1$H-NMR (300 MHz, CDCl$_3$) δ (ppm): 2.53 (s, 3H), 2.71 (t, J=7.2 Hz, 2H), 3.32 (dt, J=1.5, 4.9 Hz, 2H), 3.43 (t, J=7.2 Hz, 2H), 3.61 (br s, 2H), 4.94 (s, 2H), 5.02 (s, 2H), 6.00 (br s, 1H), 6.48 (s, 1H), 6.74-6.83 (m, 2H), 7.08-7.11 (m, 1H), 7.22-7.38 (m, 11H).

(Step 7)

In the same manner as in the step 4 in Example 309, Compound 310 (160 mg, 58%) was obtained from 1-{4,6-bis(benzyloxy)-2-[2-(2-hydroxyethoxy)ethyl]-3-(3-hydroxyphenyl)phenyl}ethanone (540 mg, 1.0 mmol) obtained in the above, using 10% palladium-carbon (50% wet., 50 mg) and ethyl acetate (5.0 mL).

$^1$H-NMR (300 MHz, CD$_3$OD) δ (ppm): 2.54 (s, 3H), 2.66 (t, J=7.2 Hz, 2H), 3.25 (t, J=4.9 Hz, 2H), 3.36 (t, J=7.2 Hz, 2H), 3.50 (t, J=4.9 Hz, 2H), 6.31 (s, 1H), 6.60-6.65 (m, 2H), 6.43-6.77 (m, 1H), 7.20 (t, J=8.1 Hz, 1H);
APCI-MS (m/z): 333 (M+H)$^+$.

EXAMPLE 311

1-{2,4-Dihydroxy-5-(3-hydroxyphenyl)-6-[2-(2-methoxyethoxy)ethyl]phenyl}ethanone
(Compound 311)

(Step 1)

In the same manner as in the step 3 in Example 1, 1-{4,6-bis(benzyloxy)-2-[2-(2-hydroxyethoxy)ethyl]-3-(3-methoxyphenyl)phenyl}ethanone (480 mg, 94%) was obtained from 1-{4,6-bis(benzyloxy)-3-bromo-2-[2-(2-hydroxyethoxy)ethyl]phenyl}ethanone (500 mg, 1.00 mmol) obtained in the step 5 in Example 310, using 3-methoxyphenylboronic acid (200 mg, 1.3 mmol), bis(tri-o-tolylphosphine)palladium(II) dichloride (50 mg, 0.07 mmol), cesium carbonate (1.0 g, 3.1 mmol), 1,2-dimethoxyethane (10 mL) and water (2.0 mL).

$^1$H-NMR (300 MHz, CDCl$_3$) δ (ppm): 2.57 (s, 3H), 2.72 (t, J=7.1 Hz, 2H), 3.31 (t, J=4.9 Hz, 2H), 3.39 (t, J=7.1 Hz, 2H), 3.57-3.65 (m, 2H), 3.79 (s, 3H), 4.94 (s, 2H), 5.03 (s, 2H), 6.48 (s, 1H), 6.76-6.79 (m, 2H), 6.81-6.90 (m, 1H), 7.72-7.38 (m, 11H).

(Step 2)

In the same manner as in the step 4 in Example 309, Compound 311 (200 mg, 56%) was obtained from 1-(4,6-bis(benzyloxy)-2-[2-(2-hydroxyethoxy)ethyl]-3-(3-methoxyphenyl)phenyl}ethanone (480 mg, 9.4 mmol) obtained in the above, using 10% palladium-carbon (50% wet., 50 mg) and ethyl acetate (5.0 mL).

$^1$H-NMR (300 MHz, CD$_3$OD) δ (ppm): 2.54 (s, 3H), 2.67 (t, J=7.2 Hz, 2H), 3.25 (t, J=4.9 Hz, 2H), 3.36 (t, J=7.2 Hz, 2H), 3.50 (t, J=4.9 Hz, 2H), 3.79 (s, 3H), 6.33 (s, 1H), 6.72-6.76 (m, 2H), 6.86-6.90 (m, 1H), 7.30 (t, J=8.3 Hz, 1H);

EXAMPLE 312

4-(3-Chloro-4-fluorophenyl)-6-ethyl-5-[2-(2-hydroxyethoxy)ethyl]benzene-1,3-diol
(Compound 312)

(Step 1)

In the same manner as in the step 3 in Example 1, 1,5-bis(benzyloxy)-2-(3-chloro-4-fluorophenyl)-4-ethyl-3-[2-(2-tetrahydropyran-2-yloxyethoxy)ethyl]benzene was obtained from 1,5-bis(benzyloxy)-2-bromo-4-ethyl-3-[2-(2-tetrahydropyran-2-yloxyethoxy)ethyl]benzene (510 mg, 0.89 mmol) obtained in the step 2 in Example 309, using 3-chloro-4-fluorophenylboronic acid (230 mg, 1.3 mmol), bis(tri-o-tolylphosphine)palladium(II) dichloride (50 mg, 0.069 mmol), cesium carbonate (900 mg, 2.8 mmol), 1,2-dimethoxyethane (10 mL) and water (2.0 mL). Then, in the same manner as in the step 4 in Example 1, 1,5-bis(benzyloxy)-2-(3-chloro-4-fluorophenyl)-4-ethyl-3-[2-(2-hydroxyethoxy)ethyl]benzene (460 mg, 95%) was obtained from the resulting compound, using methanol (8.0 mL) and 1,4-dioxane solution (2.0 mL) of 4 mol/L hydrogen chloride.

$^1$H-NMR (300 MHz, CD$_3$OD) δ (ppm): 1.11 (t, J=7.5 Hz, 3H), 2.72-2.80 (m, 4H), 3.36-3.39 (m, 4H), 3.62 (m, 2H), 4.90 (s, 2H), 5.05 (s, 2H), 6.52 (s, 1H), 7.07-7.27 (m, 13H);
APCI-MS (m/z): 535, 537 (M+H)$^+$.

(Step 2)

In the same manner as in the step 4 in Example 309, Compound 312 (200 mg, 66%) was obtained from 1,5-bis(benzyloxy)-2-(3-chloro-4-fluorophenyl)-4-ethyl-3-[2-(2-hydroxyethoxy)ethyl]benzene (460 mg, 0.86 mmol) obtained in the above, using 10% palladium-carbon (50% wet., 50 mg) and ethyl acetate (10 mL).

$^1$H-NMR (270 MHz, CD$_3$OD) δ (ppm): 1.11 (t, J=7.5 Hz, 3H), 2.59-2.71 (m, 4H), 3.27-3.36 (m, 4H), 3.54 (t, J=4.8 Hz, 2H), 6.30 (s, 1H), 7.11 (m, 1H), 7.20-7.27 (m, 2H);
APCI-MS (m/z): 355, 357 (M+H)$^+$.

EXAMPLE 313

Methyl 2-[2-ethyl-3,5-dihydroxy-6-phenylphenyl)methyl]-4,5-dihydroxazole-4-carboxylate
(Compound 313)

(Step 1)

In the same manner as in the step 2 in Example 9, 3,5-bis(benzyloxy)-2-ethyl-6-phenylphenylacetic acid was quantitatively obtained from methyl 3,5-bis(benzyloxy)-2-ethyl-6- phenylphenylacetate (1.0 g, 2.2 mmol) obtained in the step 3 in Example 179, using aqueous 2 mol/L sodium hydroxide solution (20 mL) and acetonitrile (20 mL).

$^1$H-NMR (270 MHz, CDCl$_3$) δ (ppm): 1.11 (t, J=7.5 Hz, 3H), 2.67 (q, J=7.5 Hz, 2H), 3.59 (s, 2H), 4.89 (s, 2H), 5.05 (s, 2H), 6.60 (s, 1H), 7.06-7.41 (m, 15H);

APCI-MS (m/z): 453 (M+H)$^+$.

(Step 2)

In the same manner as in the step 1 in Example 48, methyl 2-[2-(3,5-bis(benzyloxy)-2-ethyl-6-phenylphenyl)acetylamino]-3-hydroxypropionate (530 mg, 97%) was obtained from 3,5-bis(benzyloxy)-2-ethyl-6-phenylphenylacetic acid (0.99 g, 2.2 mmol) obtained in the above, using methyl 2-amino-3-hydroxypropionate (350 mg, 2.3 mmol), 1-[3-(dimethylamino)propyl]-3-ethylcarbodiimide hydrochloride (620 mg, 3.3 mmol), 1-hydroxybenzotriazole hydrate (500 mg, 3.3 mmol) and chloroform (20 mL).

$^1$H-NMR (300 MHz, CDCl$_3$) δ (ppm): 1.11 (t, J=7.5 Hz, 3H), 2.53 (br s, 1H), 2.67 (q, J=7.5 Hz, 2H), 3.52 (s, 2H), 3.72 (s, 3H), 3.79-3.85 (m, 2H), 4.52-4.57 (m, 1H), 4.90 (s, 2H), 5.06 (s, 2H), 6.23 (brd, J=7.2 Hz, 1H), 6.62 (s, 1H), 7.06-7.41 (m, 15H);

APCI-MS (m/z): 554 (M+H)$^+$.

(Step 3)

Methyl 2-[2-(3,5-bis(benzyloxy)-2-ethyl-6-phenylphenyl)acetylamino]-3-hydroxypropionate (500 mg, 0.90 mmol) obtained in the above was dissolved in chloroform (10 mL), and with stirring with cooling with ice, thionyl chloride (0.5 mL, 6.9 mmol) was dropwise added thereto. The mixture was stirred at room temperature for 4 hours, and then concentrated under reduced pressure to obtain methyl 2-[2-(3,5-bis(benzyloxy)-2-ethyl-6-phenylphenyl)acetylamino]-3-chloropropionate. The resulting methyl 2-[2-(3,5-bis(benzyloxy)-2-ethyl-6-phenylphenyl)acetylamino]-3-chloropropionate was dissolved in toluene (5.0 mL), and with stirring at room temperature, calcium carbonate (120 mg, 1.2 mmol) and silver trifluoromethanesulfonate (300 mg, 1.2 mmol) were added thereto in order, and stirred with heating under reflux for 30 minutes. Water was added to the reaction mixture, and extracted with ethyl acetate. The organic layer was washed with 1.0 mol/L hydrochloric acid, aqueous saturated sodium hydrogencarbonate solution and aqueous saturated sodium chloride solution in order, then dried over anhydrous sodium sulfate, and the solvent was evaporated away under reduced pressure. The resulting residue was purified through silica gel column chromatography (ethyl acetate/hexane=1/4 to 1/1) to obtain methyl 2-[2-(3,5-bis(benzyloxy)-2-ethyl-6-phenylphenyl)methyl]-4,5-dihydro-1,3-oxazole-4-carboxylate (180 mg, 36%).

$^1$H-NMR (300 MHz, CD$_3$OD) δ (ppm): 1.10-1.15 (m, 3H), 2.66-2.76 (m, 2H), 3.52 (s, 2H), 3.72 (s, 3H), 4.27-4.43 (m, 2H), 4.63-4.69 (m, 1H), 4.88 (s, 2H), 5.03 (s, 2H), 6.59 (s, 1H), 7.06-7.41 (m, 15H);

APCI-MS (m/z): 535 (M+H)$^+$.

(Step 4)

In the same manner as in the step 4 in Example 309, Compound 313 (70 mg, 70%) was obtained from methyl 2-[2-ethyl-3,5-dihydroxy-6-phenylphenyl)methyl]-4,5-dihydro-1,3-oxazole-4-carboxylate (150 mg, 0.28 mmol) obtained in the above, using 10% palladium-carbon (50% wet., 50 mg) and ethyl acetate (5 mL).

$^1$H-NMR (300 MHz, CDCl$_3$) δ (ppm): 1.10 (t, J=7.5 Hz, 3H), 2.46-2.70 (m, 2H), 3.31-3.47 (m, 2H), 3.80 (s, 3H), 4.34 (dd. J=11, 8.8 Hz, 1H), 4.46 (t, J=8.8 Hz, 1H), 4.59 (br s, 1H), 4.79-4.72 (m, 1H), 6.17 (s, 1H), 7.25-7.46 (m, 5H), 7.72 (br s, 1H);

APCI-MS (m/z): 356 (M+H)$^+$.

EXAMPLE 314

6-Ethyl-4-(4-fluoro-3-methylphenyl)-5-[2-(2-hydroxyethoxy)ethyl]benzene-1,3-diol (Compound 314)

(Step 1)

In the same manner as in the step 3 in Example 1, 1,5-bis(benzyloxy)-4-ethyl-2-(4-fluoro-3-methylphenyl)-3-[2-(2-tetrahydropyran-2-yloxyethoxy)ethyl]benzene was obtained from 1,5-bis(benzyloxy)-2-bromo-4-ethyl-3-[2-(2-tetrahydropyran-2-yloxyethoxy)ethyl]benzene (420 mg, 0.74 mol) obtained in the step 2 in Example 309, using 4-fluoro-3-methylphenylboronic acid (140 mg, 0.92 mmol), bis(tri-o-tolylphosphine)palladium(II) dichloride (50 mg, 0.069 mmol), cesium carbonate (750 mg, 2.3 mmol), 1,2-dimethoxyethane (10 mL) and water (2.0 mL). Then, in the same manner as in the step 4 in Example 1, 1,5-bis(benzyloxy)-4-ethyl-2-(4-fluoro-3-methylphenyl)-3-[2-(2-hydroxyethoxy)ethyl]benzene (260 mg, 53%) was obtained from the resulting compound, using methanol (10.0 mL) and 1,4-dioxane solution (2.0 mL) of 4 mol/L hydrogen chloride.

$^1$H-NMR (300 MHz, CDCl$_3$) δ (ppm): 1.11 (t, J=7.5 Hz, 3H), 2.28 (d, J=2.2 Hz, 3H), 2.72-2.80 (m, 4H), 3.36-3.39 (m, 4H), 3.62 (m, 2H), 4.85 (s, 2H), 5.05 (s, 2H), 6.52 (s, 1H), 6.96-7.40 (m, 13H).

(Step 2)

In the same manner as in the step 4 in Example 309, Compound 314 (120 mg, 71%) was obtained from 1,5-bis(benzyloxy)-4-ethyl-2-(4-fluoro-3-methylphenyl)-3-[2-(2-hydroxyethoxy)ethyl]benzene (260 mg, 0.51 mmol) obtained in the above, using 10% palladium-carbon (50% wet., 50 mg) and ethyl acetate (10 mL).

$^1$H-NMR (300 MHz, CD$_3$OD) δ (ppm): 1.11 (t, J=7.5 Hz, 3H), 2.27 (d, J=1.5 Hz, 3H), 2.59-2.70 (m, 4H), 3.27-3.36 (m, 4H), 3.25 (t, J=4.8 Hz, 2H), 6.28 (s, 1H), 6.97-7.06 (m, 3H);

APCI-MS (m/z): 333 (M−H)$^-$.

EXAMPLE 315

5-[(2-ethyl-3,5-dihydroxy-6-phenylphenyl)methyl]-3H-1,3,4-oxadiazol-2-one (Compound 315)

(Step 1)

In the same manner as in the step 1 in Example 48, 2-[3,5-bis(benzyloxy)-2-ethyl-6-phenylphenyl]acetohydrazide was quantitatively obtained from 3,5-bis(benzyloxy)-2-ethyl-6-phenylphenylacetic acid (200 mg, 0.44 mmol) obtained in the step 1 in Example 313, using hydrazine hydrate (0.06 mL, 0.90 mmol), 1-[3-(dimethylamino)propyl]-3-ethylcarbodiimide hydrochloride (130 mg, 0.68 mmol), 1-hydroxybenzotriazole hydrate (110 mg, 0.68 mmol) and chloroform (5 mL).

$^1$H-NMR (270 MHz, CDCl$_3$) δ (ppm): 1.11 (t, J=7.5 Hz, 3H), 2.67 (q, J=7.5 Hz, 2H), 3.59 (s, 2H), 4.89 (s, 2H), 5.05 (s, 2H), 6.60 (s, 1H), 7.06-7.41 (m, 15H);

APCI-MS (m/z): 467 (M+H)$^+$.

(Step 2)

2-[3,5-Bis(benzyloxy)-2-ethyl-6-phenylphenyl]acetohydrazide (210 mg, 0.44 mmol) obtained in the above was dissolved in tetrahydrofuran (5.0 mL), and N,N'-carbonyldiimidazole (90 mg, 0.56 mmol) was added thereto and stirred at room temperature for 1 hour. The reaction solution was concentrated under reduced pressure, and the resulting residue was purified through silica gel column chromatography (ethyl acetate/hexane=1/4 to 1/1) to obtain 5-{[3,5-bis(benzyloxy)-2-ethyl-6-phenylphenyl]methyl}-3H-1,3,4-oxadiazol-2-one (140 mg, 65%).

$^1$H-NMR (300 MHz, CDCl$_3$) δ (ppm): 1.11 (t, J=7.5 Hz, 3H), 2.70 (q, J=7.5 Hz, 2H), 3.72 (s, 2H), 4.89 (s, 2H), 5.05 (s, 2H), 6.62 (s, 1H), 7.06-7.41 (m, 15H), 8.71 (br s, 1H);

ESI-MS (m/z): 491 (M−H)$^-$.

(Step 3)

In the same manner as in the step 4 in Example 309, Compound 315 (62 mg, 81%) was obtained from 5-{[3,5-bis(benzyloxy)-2-ethyl-6-phenylphenyl]methyl}-3H-1,3,4-oxadiazol-2-one (120 mg, 0.24 mmol) obtained in the above, using 10% palladium-carbon (50% wet., 20 mg) and ethyl acetate (2 mL).

$^1$H-NMR (300 MHz, CD$_3$OD) δ (ppm): 1.04 (t, J=7.5 Hz, 3H), 2.60 (q, J=7.5 Hz, 2H), 3.63 (s, 2H), 6.40 (s, 1H), 7.12-7.28 (m, 5H), 8.71 (br s, 1H);

ESI-MS (m/z): 311 (M−H)$^-$.

EXAMPLE 316

6-Ethyl-5-{2-[2-(hydroxymethyl)pyrrolidin-1-yl]ethyl}-4-phenylbenzene-1,3-diol (Compound 316)

(Step 1)

2-[3,5-Bis(benzyloxy)-2-ethyl-6-phenylphenyl]ethanal (150 mg, 0.34 mmol) obtained in the step 1 in Example 218 was dissolved in 1,2-dichloroethane (3.0 mL), and with stirring at room temperature, acetic acid (0.3 mL), pyrrolidin-2-ylmethanol (0.05 mL, 0.73 mmol) and sodium triacetoxyborohydride (150 mg, 0.71 mmol) were added thereto in order, and stirred at room temperature for 5 hours. Aqueous saturated sodium hydrogencarbonate was added to the reaction mixture, and extracted with chloroform. The organic layer was washed with aqueous saturated sodium chloride solution, then dried over-anhydrous sodium sulfate, and the solvent was evaporated away under reduced pressure. The resulting residue was purified through silica gel column chromatography (chloroform/methanol=4/1) to quantitatively obtain 1,5-bis(benzyloxy)-4-ethyl-3-{2-[2-(hydroxymethyl)pyrrolidin-1-yl]ethyl}-2-phenylbenzene.

$^1$H-NMR (300 MHz, CDCl$_3$) δ (ppm): 1.14 (t, J=7.5 Hz, 3H), 1.57-1.84 (m, 4H), 2.13-2.31 (m, 1H), 2.31-2.36 (m, 1H), 2.52-2.68 (m, 4H), 2.73-2.82 (m. 2H), 3.37-3.39 (m, 1H), 3.46-3.66 (m, 1H), 3.69-3.74 (m, 1H), 4.89 (s, 2H), 5.04 (s, 2H), 6.52 (s, 1H), 7.12-7.44 (m, 15H);

APCI-MS (m/z): 522 (M+H)$^+$.

(Step 2)

In the same manner as in the step 4 in Example 309, Compound 316 (67 mg, 57%) was obtained from 1,5-bis(benzyloxy)-4-ethyl-3-{2-[2-(hydroxymethyl)pyrrolidin-1-yl]ethyl}-2-phenylbenzene (180 mg, 0.34 mmol) obtained in the above, using 10% palladium-carbon (50% wet., 20 mg) and ethyl acetate (3 mL).

$^1$H-NMR (300 MHz, CD$_3$OD) δ (ppm): 1.14 (t, J=7.5 Hz, 3H), 1.54-1.64 (m, 2H), 1.78-1.88 (m, 2H), 2.13-2.31 (m, 1H), 2.31-2.36 (m, 1H), 2.52-2.68 (m, 4H), 2.73-2.82 (m. 2H), 3.22-3.42 (m, 3H), 6.30 (s, 1H), 7.12-7.28 (m, 5H);

APCI-MS (m/z): 342 (M+H)$^+$.

EXAMPLE 317

5-[(2-Ethyl-3,5-dihydroxy-6-phenylphenyl)methyl]-3-(2-methoxyethyl)-3H-1,3,4-oxadiazol-2-one (Compound 317)

(Step 1)

5-{[3,5-Bis(benzyloxy)-2-ethyl-6-phenylphenyl]methyl}-3H-1,3,4-oxadiazol-2-one (200 mg, 0.41 mmol) obtained in the step 2 in Example 315 was dissolved in N,N-dimethylformamide (3.0 mL), and with stirring at room temperature, potassium carbonate (150 mg, 1.1 mmol) and 2-bromoethyl methyl ether (0.06 mL, 0.64 mmol) were added thereto in order, and stirred at room temperature for 5 hours. Water was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through silica gel column chromatography (ethyl acetate/hexane=1/1) to obtain 5-{[3,5-bis(benzyloxy)-2-ethyl-6-phenylphenyl]methyl}-3-(2-methoxyethyl)-3H-1,3,4-oxadiazol-2-one (210 mg, 93%).

$^1$H-NMR (270 MHz, CDCl$_3$) δ (ppm): 1.10 (t, J=7.5 Hz, 3H), 2.71 (q, J=7.5 Hz, 2H), 3.35 (s, 3H), 3.59 (t, J=5.4 Hz, 2H), 3.72 (s, 2H), 3.79 (t, J=5.4 Hz, 2H), 4.90 (s, 2H), 5.01 (s, 2H), 6.61 (s, 1H), 7.05-7.42 (m, 15H);

APCI-MS (m/z): 551 (M+H)$^+$.

(Step 2)

In the same manner as in the step 4 in Example 309, Compound 317 (120 mg, 84%) was obtained from 5-{[3,5-bis(benzyloxy)-2-ethyl-6-phenylphenyl]methyl}-3-(2-methoxyethyl)-3H-1,3,4-oxadiazol-2-one (210 mg, 0.38 mmol) obtained in the above, using 10% palladium-carbon (50% wet., 20 mg) and ethyl acetate (3 mL).

$^1$H-NMR (270 MHz, CD$_3$OD) δ (ppm): 1.05 (t, J=7.3 Hz, 3H), 2.61 (q, J=7.3 Hz, 2H), 3.30 (s, 3H), 3.57 (t, J=5.2 Hz, 2H), 3.64 (s, 2H), 3.73 (t, J=5.2 Hz, 2H), 6.41 (s, 1H), 7.12-7.34 (m, 5H);

APCI-MS (m/z): 371 (M+H)$^+$.

EXAMPLE 318

5-[(2-Ethyl-3,5-dihydroxy-6-phenylphenyl)methyl]-3-(2-hydroxyethyl)-3H-1,3,4-oxadiazol-2-one (Compound 318)

(Step 1)

In the same manner as in the step 1 in Example 317, 5-{[3,5-bis(benzyloxy)-2-ethyl-6-phenylphenyl]methyl}-3-(2-tetrahydropyran-2-yloxyethyl)-3H-1,3,4-oxadiazol-2-one was obtained from 5-{[3,5-bis(benzyloxy)-2-ethyl-6-phenylphenyl]methyl}-3H-1,3,4-oxadiazol-2-one (280 mg, 0.57 mmol) obtained in the step 2 in Example 315, using potassium carbonate (200 ng, 1.4 mmol), 2-(2-bromoethoxy)tetrahydro-2H-pyran (0.13 mL, 0.86 mmol) and N,N-dimethylformamide (3.0 mL). The resulting 5-{[3,5-bis(benzyloxy)-2-ethyl-6-phenylphenyl]methyl}-3-(2-tetrahydropyran-2-yloxyethyl)-3H-1,3,4-oxadiazol-2-one was dissolved in methanol (3.0 mL), and methanol solution (2.0 mL) of 10% hydrogen chloride was added thereto and stirred at room temperature for 30 minutes. The reaction solution was neutralized with aqueous saturated sodium hydrogencarbonate solution added thereto, and then extracted with ethyl acetate. The organic layer was washed with aqueous saturated sodium chloride solution, then dried over anhydrous sodium sulfate, and the solvent was evaporated away under reduced pressure. The resulting residue was purified through silica gel column chromatography (ethyl acetate/hexane=1/1 to 1/0) to obtain 5-{[3,5-bis(benzyloxy)-2-ethyl-6-phenylphenyl]methyl}-3-(2-hydroxyethyl)-3H-1,3,4-oxadiazol-2-one (260 mg, 85%).

$^1$H-NMR (300 MHz, CDCl$_3$) δ (ppm): 1.10 (t, J=7.2 Hz, 3H), 2.33 (br s, 1H), 2.71 (q, J=7.2 Hz, 2H), 3.73-3.76 (m, 4H), 3.82 (t, J=4.7 Hz, 2H), 4.90 (s, 2H), 5.01 (s, 2H), 6.61 (s, 1H), 7.05-7.42 (m, 15H);

APCI-MS (m/z): 537 (M+H)$^+$.

(Step 2)

In the same manner as in the step 4 in Example 309, Compound 318 (110 mg, 63%) was obtained from 5-{[3,5-bis(benzyloxy)-2-ethyl-6-phenylphenyl]methyl}-3-(2-hydroxyethyl)-3H-1,3,4-oxadiazol-2-one (260 mg, 0.49 mmol) obtained in the above, using 10% palladium-carbon (50% wet., 20 mg) and ethyl acetate (3 mL).

$^1$H-NMR (300 MHz, CD$_3$OD) δ (ppm): 1.06 (t, J=7.2 Hz, 3H), 2.62 (q, J=7.2 Hz, 2H), 3.66-3.73 (m, 6H), 6.41 (s, 1H), 7.14-7.38 (m, 5H);

APCI-MS (m/z): 357 (M+H)$^+$.

EXAMPLE 319

Methyl 3-[2-(2-ethyl-3,5-dihydroxy-6-phenylphenyl)ethyl]-2-oxo-1,3-oxazolidine-4-carboxylate (Compound 319)

(Step 1)

In the same manner as in the step 1 in Example 316, methyl 3-{2-[3,5-bis(benzyloxy)-2-ethyl-6-phenylphenyl]ethylamino}-3-hydroxypropionate was obtained from 2-[3,5-bis(benzyloxy)-2-ethyl-6-phenylphenyl]ethanal (280 mg, 0.64 mmol) obtained in the step 1 in Example 218, using acetic acid (0.6 mL), methyl 3-amino-3-hydroxypropionate (150 mg, 0.97 mmol), sodium triacetoxyborohydride (270 mg, 1.3 mmol) and 1,2-dichloroethane (6.0 mL). Then, in the same manner as in the step 2 in Example 315, methyl 3-{2-[3,5-bis(benzyloxy)-2-ethyl-6-phenylphenyl]ethyl}-2-oxo-1,3-oxazolidine-4-carboxylate (230 mg, 63%) was obtained from methyl 3-{2-[3,5-bis(benzyloxy)-2-ethyl-6-phenylphenyl]ethylamino}-3-hydroxypropionate obtained in the above.

$^1$H-NMR (300 MHz, CDCl$_3$) δ (ppm): 1.12 (t, J=7.3 Hz, 3H), 2.69-2.80 (m, 4H), 2.92-3.03 (m, 1H), 3.52-3.60 (m, 1H), 3.72 (s, 3H), 3.65-3.69 (m, 1H), 4.07-4.21 (m, 1H), 4.25 (t, J=9.8 Hz, 1H), 4.88 (s, 2H), 5.05 (s, 2H), 6.33 (s, 1H), 7.04-7.44 (m, 15H);

APCI-MS (m/z): 566 (M+H)$^+$.

(Step 2)

In the same manner as in the step 4 in Example 309, Compound 319 (62 mg, 80%) was obtained from methyl 3-{2-[3,5-bis(benzyloxy)-2-ethyl-6-phenylphenyl]ethyl}-2-oxo-1,3-oxazolidine-4-carboxylate (120 mg, 0.21 mmol)-obtained in the above, using 10% palladium-carbon (50% wet., 20 mg) and ethyl acetate (2 mL).

$^1$H-NMR (300 MHz, CD$_3$OD) δ (ppm): 1.12 (t, J=7.3 Hz, 3H), 2.57-2.74 (m, 4H), 2.87-2.97 (m, 1H), 3.34-3.43 (m, 1H), 3.72 (s, 3H), 3.90 (dd, J=9.8, 4.5 Hz, 1H), 4.19 (dd, J=7.2, 4.5 Hz, 1H), 4.35 (t, J=9.8 Hz, 1H), 6.33 (s, 1H), 7.14-7.41 (m, 5H);

APCI-MS (m/z): 386 (M+H)$^+$.

EXAMPLE 320

6-Ethyl-1,3-dihydroxy-5-[4-(hydroxymethyl)-1,3-oxazol-2-ylmethyl]biphenyl (Compound 320)

(Step 1)

Methyl 2-[2-(3,5-bis(benzyloxy)-2-ethyl-6-phenylphenyl)methyl]-4,5-dihydro-1,3-oxazole-4-carboxylate (370 mg, 0.72 mmol) obtained in the step 3 in Example 313 was dissolved in dichloromethane (10 mL), and with stirring at room temperature, bromotrichloromethane (0.2 mL, 2.0 mmol) and 1,8-diazabicyclo-[5,4,0]-undec-7-ene (0.3 mL, 2.3 mmol) were added thereto in order. The mixture was stirred at room temperature for 8 hours, and the solvent was concentrated under reduced pressure. The resulting residue was purified through silica gel column chromatography (ethyl acetate/hexane=1/1) to obtain methyl 2-[2-(3,5-bis(benzyloxy)-2-ethyl-6-phenylphenyl)methyl]-1,3-oxazole-4-carboxylate (350 mg, 92%).

$^1$H-NMR (300 MHz, CDCl$_3$) δ (ppm): 0.94 (t, J=7.5 Hz, 3H), 2.70 (q, J=7.5 Hz, 2H), 3.87 (s, 3H), 4.03 (s, 2H), 4.91 (s, 2H), 5.05 (s, 2H), 6.61 (s, 1H), 7.01-7.44 (m, 15H), 8.01 (s, 1H);

APCI-MS (m/z): 534 (M+H)$^+$.

(Step 2)

Methyl 2-[2-(3,5-bis(benzyloxy)-2-ethyl-6-phenylphenyl)methyl]-1,3-oxazole-4-carboxylate (350 mg, 0.65 mmol) obtained in the above was dissolved in tetrahydrofuran (10 mL), and with stirring with cooling with ice, lithium aluminium hydride (50 mg, 2.2 mmol) was added thereto. The reaction mixture was stirred at room temperature for 1 hour, and then sodium sulfate 10-hydrate was added thereto. The reaction mixture was filtered through Celite. The filtrate was concentrated under reduced pressure to obtain 1,5-bis(benzyloxy)-4-ethyl-3-[4-(hydroxymethyl)-1,3-oxazol-2-ylmethyl]-2-phenylbenzene (290 mg, 88%).

$^1$H-NMR (300 MHz, CDCl$_3$) δ (ppm): 0.99 (t, J=7.5 Hz, 3H), 2.70 (q, J=7.5 Hz, 2H), 3.94 (s, 2H), 4.46 (s, 2H), 4.91 (s, 2H), 5.05 (s, 2H), 6.61 (s, 1H), 7.01-7.44 (m, 16H), 8.01 (s, 1H);

APCI-MS (m/z): 506 (M+H)$^+$.

(Step 3)

In the same manner as in the step 4 in Example 309, Compound 320 (120 mg, 80%) was obtained from 1,5-bis(benzyloxy)-4-ethyl-3-[4-(hydroxymethyl)-1,3-oxazol-2-ylmethyl]-2-phenylbenzene (290 mg, 0.58 mmol) obtained in the above, using 10% palladium-carbon (50% wet., 20 mg) and tetrahydrofuran (10 mL).

$^1$H-NMR (300 MHz, DMSO-d$_6$) δ (ppm): 0.83 (t, J=7.2 Hz, 3H), 2.41 (q, J=7.2 Hz, 2H), 3.69 (s, 2H), 4.24 (d, J=5.4 Hz, 2H), 5.06 (t, J=5.4 Hz, 1H), 6.42 (s, 1H), 7.14-7.41 (m, 5H), 7.65 (s, 1H), 8.78 (s, 1H), 9.14 (s, 1H);

APCI-MS (m/z): 326 (M+H)$^+$.

EXAMPLE 321

6-Ethyl-5-[2-(3-hydroxypyrrolidin-1-yl)ethyl]-4-phenylbenzene-1,3-diol (Compound 321)

(Step 1)

In the same manner as in the step 1 in Example 316, 3,5-bis(benzyloxy)-2-ethyl-1-[2-(3-hydroxypyrrolidin-1-yl)ethyl]-6-phenylbenzene (260 mg, 73%) was obtained from 2-[3,5-bis(benzyloxy)-2-ethyl-6-phenylphenyl]ethanal (310 mg, 0.70 mmol) obtained in the step 1 in Example 218, using 3-pyrrolidinol (92 mg, 1.1 mmol), sodium triacetoxyborohydride (300 mg, 1.4 mmol), acetic acid (0.7 mL) and 1,2-dichloroethane (7.0 mL).

$^1$H-NMR (270 MHz, CD$_3$OD) δ (ppm): 1.16 (t, J=7.5 Hz, 3H), 1.55-1.61 (m, 1H), 1.93-2.01 (m, 1H), 2.22 (dd, J=10, 3.5 Hz, 1H), 2.24-2.45 (m, 4H), 2.45-2.66 (m, 5H), 4.21-4.28 (m, 1H), 4.87 (s, 2H), 5.07 (s, 2H), 6.65 (s, 1H), 7.03-7.45 (m, 15H);

ESI-MS (m/z): 508 (M+H)$^+$.

(Step 2)

In the same manner as in the step 4 in Example 309, Compound 321 (110 mg, 66%) was obtained from 3,5-bis(benzyloxy)-2-ethyl-1-[2-(3-hydroxypyrrolidin-1-yl)ethyl]-6-phenylbenzene (260 mg, 0.51 mmol) obtained in the above, using 10% palladium-carbon (50% wet., 20 mg) and tetrahydrofuran (10 mL).

$^1$H-NMR (300 MHz, CD$_3$OD) δ (ppm): 1.13 (t, J=7.4 Hz, 3H), 1.52-1.61 (m, 1H), 1.90-2.02 (m, 1H), 2.18 (dd, J=11, 3.9 Hz, 1H), 2.24-2.45 (m, 4H), 2.45-2.66 (m, 5H), 4.16-4.23 (m, 1H), 6.29 (s, 1H), 7.27-7.41 (m, 5H);

APCI-MS (m/z): 328 (M+H)$^+$.

EXAMPLE 322

2-(2-Ethyl-3,5-dihydroxy-6-phenylphenyl)-N-(2-hydroxyethyl)-N-(3-methoxypropyl)acetamide (Compound 322)

(Step 1)

In the same manner as in the step 1 in Example 48, 2-(3,5-bis(benzyloxy)-2-ethyl-6-phenylphenyl)-N-(2-hydroxyethyl)-N-(3-methoxypropyl)acetamide (230 mg, 46%) was obtained from 3,5-bis(benzyloxy)-2-ethyl-6-phenylphenylacetic acid (400 mg, 0.88 mmol) obtained in the step 1 in Example 313, using 2-(3-methoxypropylamino)ethanol (230 mg, 1.7 mmol), 1-[3-(dimethylamino)propyl]-3-ethylcarbodiimide hydrochloride (250 mg, 1.3 mmol), 1-hydroxybenzotriazole hydrate (210 mg, 1.3 mmol) and chloroform (10 mL).

$^1$H-NMR (300 MHz, CDCl$_3$) δ (ppm): 1.11 (t, J=7.5 Hz, 3H), 1.39-1.46 (m, 1.5H), 1.78-1.81 (m, 0.5H), 2.63-2.71 (m, 2H), 3.07-3.25 (m, 4H), 3.25-3.45 (m, 6H), 3.67-3.81 (m, 4H), 4.88 (s, 2H), 5.05 (s, 2H), 6.58 (s, 1H), 7.01-7.44 (m, 15H);

APCI-MS (m/z): 568 (M+H)$^+$.

(Step 2)

In the same manner as in the step 4 in Example 309, Compound 322 (120 mg, 78%) was obtained from 2-(3,5-bis(benzyloxy)-2-ethyl-6-phenylphenyl)-N-(2-hydroxyethyl)-N-(3-methoxypropyl)acetamide (230 mg, 0.40 mmol) obtained in the above, using 10% palladium-carbon (50% wet., 20 mg) and ethyl acetate (10 mL).

$^1$H-NMR (300 MHz, CD$_3$OD) δ (ppm): 1.04-1.11 (m, 3H), 1.35-1.46 (m, 1H), 1.69-1.79 (m, 1H), 2.54 (q, J=7.5 Hz, 2H), 3.12-3.18 (m, 4H), 3.25-3.61 (m, 10H), 6.34 (s, 1H), 7.13-7.37 (m, 5H);

APCI-MS (m/z): 388 (M+H)$^+$.

EXAMPLE 323

5-{[2-Ethyl-3,5-dihydroxy-6-(3-methoxyphenyl)phenyl]methyl}-3-(2-hydroxyethyl)-3H-1,3,4-oxadiazol-2-one (Compound 323)

(Step 1)

In the same manner as in the step 4 in Example 141, 3,5-bis(benzyloxy)-6-bromo-2-ethylphenylacetic acid was quantitatively obtained from methyl 3,5-bis(benzyloxy)-6-bromo-2-ethylphenylacetate (6.2 g, 13 mmol) obtained in the step 2 in Example 179, using aqueous 2 mol/L sodium hydroxide solution (30 mL) and tetrahydrofuran (60 mL).

$^1$H-NMR (270 MHz, DMSO-d$_6$) δ (ppm): 0.99 (t, J=7.3 Hz, 3H), 2.60 (q, J=7.3 Hz, 2H), 3.80 (s, 2H), 5.15 (s, 2H), 5.18 (s, 2H), 6.94 (s, 1H), 7.30-7.50 (m, 10H);

APCI-MS (m/z): 455, 457 (M+H)$^+$.

(Step 2)

In the same manner as in the step 1 in Example 48, 2-[3,5-bis(benzyloxy)-6-bromo-2-ethylphenyl]acetohydrazide was quantitatively obtained from 3,5-bis(benzyloxy)-6-bromo-2-ethylphenylacetic acid (6.5 g, 14 mmol) obtained in the above, using hydrazine hydrate (1.4 mL, 28 mmol), 1-[3-(dimethylamino)propyl]-3-ethylcarbodiimide hydrochloride (4.1 g, 21 mmol), 1-hydroxybenzotriazole hydrate (3.3 g, 21 mmol) and chloroform (50 mL).

$^1$H-NMR (270 MHz, DMSO-d$_6$) δ (ppm): 0.99 (t, J=7.3 Hz, 3H), 2.60 (q, J=7.3 Hz, 2H), 3.80 (s, 2H), 5.15 (s, 2H), 5.18 (s, 2H), 6.92 (s, 1H), 7.30-7.50 (m, 10H);

APCI-MS (m/z): 469, 471 (M+H)$^+$.

(Step 3)

In the same manner as in the step 2 in Example 315, 5-[3,5-bis(benzyloxy)-6-bromo-2-ethylphenylmethyl]-3H-1,3,4-oxadiazol-2-one (3.9 g, 59%) was obtained from 2-[3,5-bis(benzyloxy)-6-bromo-2-ethylphenyl]acetohydrazide (6.2 g, 13 mmol) obtained in the above, using N,N'-carbonyldiimidazole (2.6 g, 16 mmol) and tetrahydrofuran (50 mL).

$^1$H-NMR (270 MHz, CD$_3$OD) δ (ppm): 1.01 (t, J=7.3 Hz, 3H), 2.75 (q, J=7.3 Hz, 2H), 4.18 (s, 2H), 5.05 (s, 2H), 5.09 (s, 2H), 6.75 (s, 1H), 7.30-7.45 (m, 10H);

APCI-MS (m/z): 493, 495 (M−H)$^-$.

(Step 4)

In the same manner as in the step 1 in Example 317, a crude product of 5-[3,5-bis(benzyloxy)-6-bromo-2-ethylphenylmethyl]-3-(2-tetrahydropyran-2-yloxyethyl)-3H-1,3,4-oxadiazol-2-one was obtained from 5-[3,5-bis(benzyloxy)-6-bromo-2-ethylphenylmethyl]-3H-1,3,4-oxadiazol-2-one (1.1 g, 2.1 mmol) obtained in the above, using potassium carbonate (740 mg, 5.4 mmol), 2-(2-bromoethoxy)tetrahydro-2H-pyran (0.49 mL, 3.2 mmol) and N,N-dimethylformamide (15 mL). Thus obtained, 5-[3,5-bis(benzyloxy)-6-bromo-2-ethylphenylmethyl]-3-(2-tetrahydropyran-2-yloxyethyl)-3H-1,3,4-oxadiazol-2-one was dissolved in methanol (30 mL), then treated with methanol solution (10 mL) of 10% hydrogen chloride, and the reaction solution was concentrated under reduced pressure. The resulting residue was purified through silica gel column chromatography (ethyl acetate/hexane=1/1) to obtain 5-[3,5-bis(benzyloxy)-6-bromo-2-ethylphenylmethyl]-3-(2-hydroxyethyl)-3H-1,3,4-oxadiazol-2-one (0.85 g, 75%).

$^1$H-NMR (300 MHz, CDCl$_3$) δ (ppm): 1.10 (t, J=7.3 Hz, 3H), 2.26 (t, J=6.0 Hz, 1H), 2.75 (q, J=7.3 Hz, 2H), 3.91-3.81 (m, 4H), 4.19 (s, 2H), 5.01 (s, 2H), 5.08 (s, 2H), 6.57 (s, 1H), 7.26-7.46 (m, 10H);

APCI-MS (m/z): 539, 541 (M+H)$^+$.

(Step 5)

In the same manner as in the step 3 in Example 1, 5-{[3,5-bis(benzyloxy)-2-ethyl-6-(3-methoxyphenyl)phenyl]methyl}-3-)2-hydroxyethyl)-3H-1,3,4-oxadiazol-2-one (520 mg, 58%) was obtained from 5-[3,5-bis(benzyloxy)-6-bromo-2-ethylphenylmethyl]-3-(2-hydroxyethyl)-3H-1,3,4-oxadiazol-2-one (850 mg, 1.6 mmol) obtained in the above, using 3-methoxyphenylboronic acid (290 mg, 1.9 mmol), bis(tri-o-tolylphosphine)palladium(II) dichloride (120 mg, 0.16 mmol), cesium carbonate (1.5 g, 4.6 mmol), 1,2-dimethoxyethane (20 mL) and water (4.0 mL).

$^{1}$H-NMR (300 MHz, CDCl$_{3}$) δ (ppm): 1.08-1.17 (m, 3H), 2.71-2.81 (m, 2H), 3.52 (s, 1H), 3.66-3.80 (m, 5H), 3.96 (s, 1H), 4.32-4.39 (m, 2H); 4.92 (s, 1H), 5.02 (s, 1H), 5.05 (s, 1H), 5.08 (s, 1H), 6.56 (s, 0.5H), 6.60 (s, 0.5H), 6.78-6.90 (m, 1H), 7.09-7.12 (m, 1H), 7.26-7.46 (m, 12H);

APCI-MS (m/z): 567 (M+H)$^{+}$.

(Step 6)

In the same manner as in the step 4 in Example 309, Compound 323 (320 mg, 90%) was obtained from 5-{[3,5-bis(benzyloxy)-2-ethyl-6-(3-methoxyphenyl)phenyl]methyl}-3-(2-hydroxyethyl)-3H-1,3,4-oxadiazol-2-one (520 mg, 0.92 mmol) obtained in the above, using 10% palladium-carbon (50% wet., 50 mg) and ethyl acetate (10 mL).

$^{1}$H-NMR (270 MHz, CD$_{3}$OD) δ (ppm): 1.09 (t, J=7.3 Hz, 3H), 2.59 (q, J=7.3 Hz, 2H), 3.64 (t, J=5.6 Hz, 2H), 3.92 (s, 2H), 3.76 (s, 3H), 4.35 (t, J=5.6 Hz, 2H), 6.39 (s, 1H), 6.78-6.85 (m, 3H), 7.27 (t, J=8.1 Hz, 1H);

APCI-MS (m/z): 387 (M+H)$^{+}$.

EXAMPLE 324

5-{[2-Ethyl-3,5-dihydroxy-6-(3-hydroxyphenyl)phenyl]methyl}-3-(2-methoxyethyl)-3H-1,3,4-oxadiazol-2-one (Compound 324)

(Step 1)

In the same manner as in the step 1 in Example 317, 5-{[3,5-bis(benzyloxy)-6-bromo-2-ethylphenyl]methyl}-3-(2-methoxyethyl)-3H-1,3,4-oxadiazol-2-one (0.82 g, 71%) was obtained from 5-[3,5-bis(benzyloxy)-6-bromo-2-ethylphenylmethyl]-3H-1,3,4-oxadiazol-2-one (1.0 g, 2.1 mmol) obtained in the step 3 in Example 323, using potassium carbonate (740 mg, 5.4 mmol), 2-bromomethyl ethyl ether (0.30 mL; 3.2 mmol) and N,N-dimethylformamide (15 mL).

$^{1}$H-NMR (270 MHz, CDCl$_{3}$) δ (ppm): 1.09 (t, J=7.5 Hz, 3H), 2.75 (q, J=7.5 Hz, 2H), 3.33 (s, 3H), 3.61 (t, J=5.4 Hz, 2H), 3.83 (t, J=5.4 Hz, 1H), 4.18 (s, 2H), 5.01 (s, 2H), 5.07 (s, 2H), 6.56 (s, 1H), 7.31-7.46 (m, 10H);

APCI-MS (m/z): 553, 555 (M+H)$^{+}$.

(Step 2)

In the same manner as in the step 3 in Example 1, 5-{[3,5-bis(benzyloxy)-2-ethyl-6-(3-hydroxyphenyl)phenyl]methyl}-3-(2-methoxyethyl)-3H-1,3,4-oxadiazol-2-one (730 mg, 91%) was obtained from 5-{[3,5-bis(benzyloxy)-6-bromo-2-ethylphenyl]methyl}-3-(2-methoxyethyl)-3H-1,3,4-oxadiazol-2-one (780 mg, 1.4 mmol) obtained in the above, using 2-(3-hydroxyphenyl)-4,4,5,5-tetramethyl-1,3,2-dioxaborolane (380 mg, 1.7 mmol), bis(tri-o-tolylphosphine)palladium(II) dichloride (100 mg, 0.13 mmol), cesium carbonate (1.4 g, 4.3 mmol), 1,2-dimethoxyethane (20 mL) and water (4.0 mL).

$^{1}$H-NMR (270 MHz, CDCl$_{3}$) δ (ppm): 1.12 (t, J=7.5 Hz, 3H), 2.56-2.84 (m, 2H), 3.41 (s, 3H), 3.53-4.00 (m, 6H), 4.92 (s, 2H), 5.05 (s, 2H), 6.55-6.56 (m, 1H), 6.56 (s, 1H), 6.69 (br s 1H), 6.73-6.77 (m, 1H), 6.81-6.85 (m, 1H), 7.31-7.46 (m, 11H);

APCI-MS (m/z): 567 (M+H)$^{+}$.

(Step 3)

In the same manner as in the step 4 in Example 309, Compound 324 (360 mg, 71%) was obtained from 5-{[3,5-bis(benzyloxy)-2-ethyl-6-(3-hydroxyphenyl)phenyl]methyl}-3-(2-methoxyethyl)-3H-1,3,4-oxadiazol-2-one (730 mg, 1.3 mmol) obtained in the above, using 10% palladium-carbon (50% wet., 50 mg) and ethyl acetate (10 mL).

$^{1}$H-NMR (270 MHz, CDCl$_{3}$) δ (ppm): 1.04 (t, J=7.3 Hz, 3H), 2.59 (q, J=7.3 Hz, 2H), 3.33 (s, 3H), 3.58 (t, J=5.1 Hz, 2H), 3.61 (s, 2H), 3.75 (t, J=5.1 Hz, 2H), 6.38 (s, 1H), 6.58-6.61 (m, 2H), 6.70-6.74 (m, 1H), 7.15 (t, J=7.8 Hz, 1H);

APCI-MS (m/z): 387 (M+H)$^{+}$.

EXAMPLE 325

1,5-Bis(ethoxycarbonyloxy)-4-ethyl-3-[2-(2-methoxyethoxy)ethyl]-2-phenylbenzene (Compound 325)

Compound 113 (33.2 mg, 0.105 mmol) obtained in Example 113 was dissolved in dichloromethane (4 mL), and ethyl chloroformate (0.100 mL, 1.05 mmol), 4-dimethylaminopyridine (18.3 mg, 0.150 mmol) and triethylamine (0.100 mL, 0.720 mmol) were added thereto and stirred at room temperature for 5 hours. Water was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=2/1) to obtain Compound 325 (31.6 mg, 65%).

$^{1}$H-NMR (300 MHz, CDCl$_{3}$) δ (ppm): 1.11 (t, J=7.1 Hz, 3H), 1.18 (t, J=7.5 Hz, 3H), 1.41 (t, J=7.1 Hz, 3H), 2.70 (q, J=7.5 Hz, 2H), 2.76-2.88 (m, 2H), 3.31 (s, 3H), 3.25-3.45 (m, 6H), 4.03 (q, J=7.1 Hz, 2H), 4.34 (q, J=7.1 Hz, 2H), 6.97 (s, 1H), 7.15-7.25 (m, 2H), 7.30-7.45 (m, 3H);

APCI-MS (m/z): 461 (M+H)$^{+}$.

EXAMPLE 326

1,5-Bis(dimethylcarbamoyloxy)-4-ethyl-3-[2-(2-methoxyethoxy)ethyl]-2-phenylbenzene (Compound 326)

(Step 1)

Compound 113 (35.0 mg, 0.111 mmol) obtained in Example 113 was dissolved in dichloromethane (4 mL), and N,N-dimethylcarbamoyl chloride (0.100 mL, 0.369 mmol) and 4-dimethylaminopyridine (54.0 mg, 0.442 mmol) were added thereto and stirred at room temperature for 18 hours. Water was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (n-hexane/ethyl acetate=1/1) to obtain Compound 326 (44.0 mg, 86%).

$^{1}$H-NMR (300 MHz, CDCl$_{3}$) δ (ppm): 1.18 (t, J=7.5 Hz, 3H), 2.46 (br s, 3H), 2.66 (q, J=7.5 Hz, 2H), 2.74 (br s, 3H), 2.75-2.85 (m, 2H), 3.03 (br s, 3H), 3.12 (br s, 3H), 3.31 (s, 3H), 3.27-3.45 (m, 6H), 6.93 (s, 1H), 7.15-7.40 (m, 5H);

APCI-MS (m/z): 459 (M+H)$^{+}$.

EXAMPLE 327

4-Ethyl-3-[2-(2-methoxyethoxy)ethyl]-5-(4-methylpiperazin-1-ylcarbonyloxy)-2-phenylbenzen-1-ol (Compound 327)

Compound 113 (33.1 mg, 0.105 mmol) obtained in Example 113 was dissolved in dichloromethane (2 mL), and carbonyldiimidazole (139 mg, 0.858 mmol) was added thereto and stirred at room temperature for 18 hours. Then, 4-methylpiperazine (0.200 mL, 1.80 mmol) was added thereto; and further stirred at room temperature for 5 hours. Water was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (chloroform/methanol=9/1) to obtain Compound 327 (12.9 mg, 28%).

$^1$H-NMR (300 MHz, CDCl$_3$) δ (ppm): 1.09 (t, J=7.3 Hz, 3H), 1.80-1.96 (m, 2H), 2.15-2.25 (m, 5H), 2.58 (q, J=7.3 Hz, 2H), 2.68-2.80 (m, 2H), 3.02-3.16 (m, 2H), 3.32 (s, 3H), 3.27-3.44 (m, 8H), 6.47 (s, 1H), 7.11-7.23 (m, 2H), 7.25-7.40 (m, 3H);

APCI-MS (m/z): 443 (M+H)$^+$.

EXAMPLE 328

1,5-Bis(acetyloxy)-4-ethyl-3-[2-(2-methoxyethoxy)ethyl]-2-phenylbenzene (Compound 328)

Compound 113 (32.1 mg, 0.101 mmol) obtained in Example 113 was dissolved in chloroform (1 mL), and acetic anhydride (0.020 mL, 0.21 mmol) and 4-dimethylaminopyridine (32.1 mg, 0.260 mmol) were added thereto and stirred at room temperature for 18 hours. Water was added to the reaction mixture, and extracted with ethyl acetate. The organic layer was washed with aqueous saturated sodium chloride solution, then dried over anhydrous sodium sulfate, and the solvent was evaporated away under reduced pressure. The resulting residue was purified through preparative thin-layer chromatography (hexane/ethyl acetate=2/1) to obtain Compound 328 (40.7 mg, 100%).

$^1$H-NMR (270 MHz, CDCl$_3$) δ (ppm): 1.16 (t, J=7.5 Hz, 3H), 1.80 (s, 3H), 2.34 (s, 3H), 2.64 (q, J=7.5 Hz, 2H), 2.76-2.87 (m, 2H), 3.31 (s, 3H), 3.27-3.42 (m, 6H), 6.78 (s, 1H), 7.12-7.20 (m, 2H), 7.30-7.42 (m, 3H);

APCI-MS (m/z): 401 (M+H)$^+$.

EXAMPLE 329

Methyl 2-ethyl-3,5-dihydroxy-6-(5-phenyl-1,3-oxazol-2-yl)phenylacetate (Compound 329)

(Step 1)
Ethyl 3-oxohexanoate (20 mL, 0.13 mol) was dissolved in toluene (100 mL), and triethylamine (28 mL, 0.20 mol) and chlorotrimethylsilane (24 mL, 0.19 mol) were added thereto and stirred at room temperature for 4 hours. Hexane (200 mL) and aqueous 0.5 mol/L sodium hydrogencarbonate solution were added to the reaction mixture, and extracted three times with hexane. The organic layers were combined, and washed with aqueous saturated sodium hydrogencarbonate solution and aqueous saturated sodium chloride solution in order, then dried over anhydrous sodium sulfate, and the solvent was evaporated away under reduced pressure. The resulting residue was dissolved in tetrahydrofuran (100 mL), and the solution was cooled to −78° C. Tetrahydrofuran solution of 2.0 mol/L lithium diisopropylamide (78 mL, 0.16 mol) was added to the resulting solution, and stirred at −78° C. for 1 hour, and then chlorotrimethylsilane (18 mL, 0.14 mol) was added thereto and further stirred at −78° C. for 8 hours. Hexane (200 mL) and water were added to the reaction mixture, and extracted three times with hexane. The organic layers were combined, and washed with aqueous 0.5 mol/L sodium hydrogencarbonate solution and aqueous saturated sodium chloride solution in order, then dried over anhydrous sodium sulfate, and the solvent was evaporated away under reduced pressure to obtain 1-ethoxy-1,3-bis(trimethylsiloxy)hexa-1,3-diene (41 g, 100%).

$^1$H-NMR (270 MHz, CDCl$_3$) δ (ppm): 0.17 (s, 9H), 0.24 (s, 9H), 0.94 (t, J=7.1 Hz, 3H), 1.29 (t, J=6.5 Hz, 3H), 2.07 (dq, J=6.8, 7.1 Hz, 2H), 3.73 (q, J=6.5 Hz, 2H), 3.86 (s, 1H), 4.85 (t, J=6.8 Hz, 1H).

(Step 2)
Dimethyl 3-oxodipentanoate (11 mL, 75 mmol) was dissolved in dichloromethane (100 mL), and the solution was cooled to 0° C. 2-Chloro-1,3-dimethylimidazolium chloride (14 g, 83 mmol) and triethylamine (31 mL, 0.23 mol) were added to the resulting solution, and stirred at room temperature for 4 hours. Hexane (200 mL) and water were added to the reaction mixture, and extracted three times with hexane. The organic layers were combined, and washed with water and aqueous saturated sodium chloride solution in order, then dried over anhydrous sodium sulfate, and the solvent was evaporated away under reduced pressure. The resulting residue was purified through silica gel column chromatography (hexane/ethyl acetate=2/1) to obtain dimethyl penta-2,3-dienoate (4.7 g, 40%).

$^1$H-NMR (270 MHz, CDCl$_3$) δ (ppm): 3.78 (s, 6H), 6.05 (s, 2H).

(Step 3)
Dimethyl penta-2,3-dienoate (4.6 g, 30 mmol) obtained in the above was mixed with 1-ethoxy-1,3-bis(trimethylsiloxy)hexa-1,3-diene (13 g, 41 mmol), and stirred at room temperature for 1.5 hours. Ethanol (100 mL) and ammonium fluoride (5.4 g) were added to the reaction mixture, and further stirred at room temperature for 2 hours. Water was added to the reaction mixture, and extracted three times with ethyl acetate. The organic layers were combined, then washed with water and aqueous saturated sodium chloride solution in order, then dried over anhydrous sodium sulfate, and the solvent was evaporated away under reduced pressure. The resulting residue was triturated with hexane (50 mL) to obtain methyl 3-ethyl-4,6-dihydroxy-2-(methoxycarbonylmethyl)benzoate (3.2 g, 40%).

$^1$H-NMR (270 MHz, CDCl$_3$) δ (ppm): 1.06 (t, J=7.5 Hz, 3H), 2.61 (q, J=7.5 Hz, 2H), 3.71 (s, 3H), 3.85 (s, 3H), 3.95 (s, 2H), 6.35 (s, 1H);

APCI-MS (m/z): 269 (M+H)$^+$.

(Step 4)
Methyl 3-ethyl-4,6-dihydroxy-2-(methoxycarbonylmethyl)benzoate (2.0 g, 7.5 mmol) obtained in the above was dissolved in acetone (50 mL), and potassium carbonate (5.0 g 36 mmol) and chloromethyl methyl ether (2.5 mL, 33 mmol) were added thereto, and stirred at 60° C. for 4 hours. Water was added to the reaction mixture, and extracted three times with chloroform. The organic layers were combined, washed with aqueous saturated sodium chloride solution, then dried over anhydrous sodium sulfate, and the solvent was evaporated away under reduced pressure. The resulting residue was purified through silica gel column chromatography (hexane/ethyl acetate=9/1) to obtain methyl 3-ethyl-2-(methoxycarbonylmethyl)-4,6-bis(methoxymethoxy)benzoate (1.6 g, 61%).

$^1$H-NMR (270 MHz, CDCl$_3$) δ (ppm): 1.07 (t, J=7.5 Hz, 3H), 2.64 (q, J=7.5 Hz, 2H), 3.47 (s, 6H), 3.68 (s, 3H), 3.70 (s, 2H), 3.86 (s, 3H), 5.14 (s, 2H), 5.20 (s, 2H), 6.88 (s, 1H).

(Step 5)

Methyl 3-ethyl-2-(methoxycarbonylmethyl)-4,6-bis(methoxymethoxy)benzoate (1.1 g, 3.0 mmol) obtained in the above was dissolved in methanol (3 mL), and aqueous 4.0 mol/L lithium hydroxide solution (15 mL, 60 mmol) was added thereto and stirred at 60° C. for 30 hours. Water and 6.0 mol/L hydrochloric acid were added to the reaction mixture until the mixture was adjusted to pH 3, and then the mixture was extracted three times with ethyl acetate. The organic layers were combined, dried over anhydrous sodium sulfate, and the solvent was evaporated away under reduced pressure to obtain 2-(carboxymethyl)-3-ethyl-4,6-bis(methoxymethoxy)benzoic acid (0.91 g, 94%).

$^1$H-NMR (270 MHz, CDCl$_3$) δ (ppm): 1.09 (t, J=7.5 Hz, 3H), 2.77 (q, J=7.5 Hz, 2H), 3.49 (s, 3H), 3.52 (s, 3H), 3.95 (s, 2H), 5.24 (s, 2H), 5.26 (s, 2H), 6.96 (s, 1H).

(Step 6)

2-(Carboxymethyl)-3-ethyl-4,6-bis(methoxymethoxy)benzoic acid (0.38 g, 1.2 mmol) obtained in the above was dissolved in toluene (20 mL), and acetic anhydride (0.20 mL, 2.1 mmol) was added thereto and stirred at 100° C. for 4 hours. Water was added to the reaction mixture, and extracted three times with diethyl ether. The organic layers were combined, washed with aqueous saturated sodium chloride solution, then dried over anhydrous sodium sulfate, and the solvent was evaporated away under reduced pressure. The resulting residue was dissolved in methanol (20 mL), and sodium methoxide (0.22 g, 4.2 mmol) was added to the resulting solution, and stirred at room temperature for 7 hours. Water was added to the reaction mixture, and then extracted three times with ethyl acetate. The organic layers were combined, washed with aqueous saturated sodium chloride solution, then dried over anhydrous sodium sulfate, and the solvent was evaporated away under reduced pressure to obtain 3-ethyl-2-(methoxycarbonylmethyl)-4,6-bis(methoxymethoxy)benzoic acid (0.52 g, 100%).

$^1$H-NMR (270 MHz, CDCl$_3$) δ (ppm): 1.07 (t, J=7.5 Hz, 3H), 2.65 (q, J=7.5 Hz, 2H), 3.49 (s, 3H), 3.52 (s, 3H), 3.72 (s, 3H), 3.96 (s, 2H), 5.24 (s, 2H), 5.26 (s, 2H), 6.96 (s, 1H).

(Step 7)

In the same manner as in the step 1 in Example 48, methyl 2-ethyl-3,5-bis(methoxymethoxy)-6-(2-oxo-2-phenylethylcarbamoyl)phenylacetate (120 mg, 41%) was obtained from 3-ethyl-2-(methoxycarbonylmethyl)-4,6-bis(methoxymethoxy)benzoic acid (150 mg, 0.42 mmol) obtained in the above, using 1-[3-(dimethylamino)propyl]-3-ethylcarbodiimide hydrochloride (90 mg, 0.67 mmol), 1-hydroxybenzotriazole hydrate (120 mg, 0.63 mmol), triethylamine (0.1 mL, 0.72 mmol) and α-aminoacetophenone hydrochloride (110 mg, 0.63 mmol).

$^1$H-NMR (270 MHz, CDCl$_3$) δ (ppm): 1.07 (t, J=7.3 Hz, 3H), 2.62 (q, J=7.3 Hz, 2H), 3.49 (s, 6H), 3.71 (s, 3H), 3.84 (s, 2H), 4.95 (d, J=4.6 Hz, 2H), 5.17 (s, 2H), 5.21 (s, 2H), 6.92 (s, 1H), 7.23-7.25 (m, 1H), 7.46-7.52 (m, 2H), 7.58-7.64 (m, 1H), 7.97-8.01 (m, 2H).

(Step 8)

Methyl 2-ethyl-3,5-bis(methoxymethoxy)-6-(2-oxo-2-phenylethylcarbamoyl)phenylacetate (90 mg, 0.25 mmol) obtained in the above was dissolved in dichloromethane (3.0 mL), and triethylamine (0.15 mL, 1.1 mmol), triphenylphosphine (140 mg, 0.53 mmol) and iodine (63 mg, 0.50 mmol) were added thereto in order, and stirred with heating under reflux for 30 minutes. Aqueous saturated sodium thiosulfate solution was added to the reaction solution, and the aqueous layer was extracted twice with ethyl acetate. The organic layers were combined, dried over anhydrous sodium sulfate, and the solvent was evaporated away under reduced pressure. The resulting residue was purified through silica gel column chromatography (ethyl acetate/hexane=1/4 to 1/1) to obtain methyl 2-ethyl-3,5-bis(methoxymethoxy)-6-(5-phenyloxazol-2-yl)phenylacetate (4 mg, 7%).

$^1$H-NMR (270 MHz, CDCl$_3$) δ (ppm): 1.10 (t, J=7.3 Hz, 3H), 2.68 (q, J=7.3 Hz, 2H), 3.41 (s, 3H), 3.51 (s, 3H), 3.57 (s, 3H), 3.75 (s, 2H), 5.12 (s, 2H), 5.2.5 (s, 2H), 6.97 (s, 1H), 7.31-7.43 (m, 3H), 7.46 (s, 1H), 7.67-7.64 (m, 2H).

(Step 9)

In the same manner as in the step 4 in Example 1, Compound 329 (3 mg, 71%) was obtained from methyl 2-ethyl-3,5-bis(methoxymethoxy)-6-(5-phenyloxazol-2-yl)phenylacetate (7 mg, 0.016 mmol) obtained in the above, using methanol (2.0 mL) and 1,4-dioxane solution (1.0 mL) of 4 mol/L hydrogen chloride.

$^1$H-NMR (270 MHz, CD$_3$OD) δ (ppm): 1.09 (t, J=7.3 Hz, 3H), 2.66 (q, J=7.3 Hz, 2H), 3.64 (s, 3H), 4.23 (s, 2H), 6.54 (s, 1H), 7.55-7.45 (m, 3H), 7.76-7.80 (m, 2H), 7.92 (s, 1H);

APCI-MS m/z 352 (M−H)$^-$.

EXAMPLE 330

5-[2-(2,3-Dihydroxypropoxy)ethyl]-6-ethyl-4-(6-methoxy-1H-indazol-3-yl)benzene-1,3-diol (Compound 330)

(Step 1)

2-Bromo-3-{2-[(2,2-dimethyl-1,3-dioxolan-4-yl)methoxy]ethyl}-4-ethyl-1,5-bis(methoxymethoxy)benzene (390 mg, 0.84 mmol) obtained in the step 3 in Example 173 was dissolved in tetrahydrofuran (10 mL), and with stirring at −78° C., tetrahydrofuran solution of 1.5 mol/L n-butyllithium (1.0 mL, 1.5 mmol) was dropwise added thereto. The resulting mixture was stirred at −78° C. for 30 minutes, then 2-fluoro-4-methoxybenzaldehyde (130 mg, 0.8 mmol) was dropwise added thereto and further stirred for 30 minutes. Aqueous saturated ammonium chloride solution was added to the reaction mixture, and extracted twice with ethyl acetate. The organic layers were combined, washed with aqueous saturated sodium chloride solution, then dried over anhydrous sodium sulfate, and the solvent was evaporated away to obtain 1-(6-{2-[(2,2-dimethyl-1,3-dioxolan-4-yl)methoxy]ethyl}-5-ethyl-2,4-bis(methoxymethoxy)phenyl)-1-(3-fluoro-4-methoxyphenyl)methanol. Thus obtained, 1-(6-{2-[(2,2-dimethyl-1,3-dioxolan-4-yl)methoxy]ethyl}-5-ethyl-2,4-bis(methoxymethoxy)phenyl)-1-(3-fluoro-4-methoxyphenyl)methanol was dissolved in dichloromethane (10 mL), and pyridinium dichromate (160 m, 0.43 mmol) was added thereto and stirred at room temperature for 8 hours. The reaction mixture was diluted with diethyl ether, filtered through Celite, and the filtrate was concentrated under reduced pressure. The resulting residue was purified through silica gel column chromatography (ethyl acetate/hexane=1/4 to 1/1) to obtain 6-{2-[(2,2-dimethyl-1,3-dioxolan-4-yl)methoxy]ethyl}-5-ethyl-2,4-bis(methoxymethoxy)phenyl 3-fluoro-4-methoxyphenyl ketone (210 mg, 46%).

$^1$H-NMR (300 MHz, CDCl$_3$) δ (ppm): 1.14 (t, J=7.3 Hz, 3H), 1.33 (s, 3H), 1.38 (s, 3H), 2.68 (q, J=7.3 Hz, 2H), 2.73 (dd, J=8.8, 6.8 Hz, 2H), 3.25 (s, 3H), 3.30 (dd, J=9.9, 5.9 Hz, 1H), 3.40 (dd, J=9.9, 5.9 Hz, 1H), 3.51 (s, 3H), 3.47-3.51 (m, 2H), 3.61 (dd, J=8.3, 6.6 Hz, 3H), 3.94 (s, 3H), 3.97 (dd, J=8.3, 6.6 Hz, 1H), 4.13 (m, 1H), 4.97 (s, 2H), 5.23 (s, 2H), 6.84 (s, 1H), 6.95 (t, J=8.3 Hz, 1H), 7.57-7.61 (m, 2H).

(Step 2)

6-{2-[(2,2-Dimethyl-1,3-dioxolan-4-yl)methoxy]ethyl}-5-ethyl-2,4-bis(methoxymethoxy)phenyl=3-fluoro-4-methoxyphenyl=ketone (80 mg, 0.15 mmol) obtained in the above was dissolved in ethanol (2.0 mL), and hydrazine hydrate (0.02 mL, 0.41 mmol) was added thereto and stirred with heating under reflux for 12 hours. The reaction solution was concentrated under reduced pressure, and the resulting residue was purified through silica gel column chromatography (methanol/chloroform=1/15 to 1/9) to obtain 3-{2-[(2,2-dimethyl-1,3-dioxolan-4-yl)methoxy]ethyl}-4-ethyl-2-(6-methoxy-1H-indazol-3-yl)-1,5-bis(methoxymethoxy)benzene (60 mg, 75%).

$^1$H-NMR (270 MHz, CDCl$_3$) δ (ppm): 1.16 (t, J=7.3 Hz, 3H), 1.29 (s, 3H), 1.33 (s, 3H), 2.74 (q, J=7.3 Hz, 2H), 3.17 (s, 3H), 3.53 (s, 3H), 3.84 (s, 3H), 3.00-4.00 (m, 8H), 4.04 (m, 1H), 4.92 (s, 2H), 5.25 (s, 2H), 6.73-6.76 (m, 2H), 6.92 (s, 1H), 7.24 (d, J=9.4 Hz, 1H).

(Step 3)

In the same manner as in the step 4 in Example 1, Compound 330 (28 mg, 63%) was obtained from 3-{2-[(2,2-dimethyl-1,3-dioxolan-4-yl)methoxy]ethyl}-4-ethyl-2-(6-methoxy-1H-indazol-3-yl)-1,5-bis(methoxymethoxy)benzene (60 mg, 0.11 mmol) obtained in the above, using methanol (2.0 mL) and 1,4-dioxane solution (1.0 mL) of 4 mol/L hydrogen chloride.

$^1$H-NMR (270 MHz, CD$_3$OD) δ (ppm): 1.10 (t, J=7.7 Hz, 3H), 2.61-2.67 (m, 4H), 3.13 (dd, J=6.5, 4.9 Hz, 2H), 3.29-3.39 (m, 4H), 3.51 (m, 1H), 3.83 (s, 3H), 6.34 (s, 1H), 6.74 (dd, J=8.9, 1.9 Hz, 1H), 6.91 (d, J=1.9 Hz, 1H), 7.27 (d, J=8.9 Hz, 1H):

APCI-MS m/z 403 (M+H)$^+$.

INDUSTRIAL APPLICABILITY

According to the invention, there are provided Hsp90 family protein inhibitors comprising, as an active ingredient, a benzene derivative or a prodrug thereof, or a pharmaceutically acceptable salt thereof, and the like.

The invention claimed is:

1. A benzene derivative represented by general formula (IA):

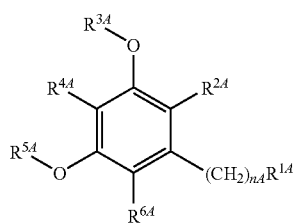

{wherein nA represents an integer of 0 to 5;

$R^{2A}$ represents phenyl optionally substituted with one to four groups selected from substituent (D);

$R^{3A}$ and $R^{5A}$ are the same and represent a hydrogen atom, lower alkenyl optionally substituted with one to three groups selected from substituent (B), lower alkanoyl optionally substituted with one to three groups selected from substituent (B), carbamoyl, sulfamoyl, lower alkylsulfonyl optionally substituted with one to three groups selected from substituent (B), lower alkylaminocarbonyl optionally substituted with one to three groups selected from substituent (B), di-lower alkylaminocarbonyl optionally substituted with one to three groups selected from substituent (B), lower alkoxycarbonyl optionally substituted with one to three groups selected from substituent (B), heterocyclic-carbonyl, or aroyl optionally substituted with one to three groups selected from substituent (C);

$R^{4A}$ represents a hydrogen atom;

provided that;

(1) when nA is 0, then $R^{1A}$ is hydroxy, methoxy, carboxy, methoxycarbonyl, carbamoyl, —CONHCH$_3$, —CON(CH$_3$)$_2$, —CONHCH$_2$Ph, propionyl, benzoyl, 1,3-dioxolan-2-yl, vinyl optionally substituted with one to three groups selected from substituent (B), or prop-1-en-1-yl optionally substituted with one to three groups selected from substituent (B); and $R^{6A}$ is halogen; and (2) when nA is an integer of 1 to 5, then $R^{1A}$ is hydroxy, cyano, carboxy, halogen, lower alkyl substituted with one to three groups selected from substituent (A), lower alkenyl optionally substituted with one to three groups selected from substituent (B), lower alkynyl optionally substituted with one to three groups selected from substituent (B), cycloalkyl optionally substituted with one to three groups selected from substituent (C), lower alkanoyl optionally substituted with one to three groups selected from substituent (B), lower alkoxycarbonyl optionally substituted with one to three groups selected from substituent (B), aryl optionally substituted with one to four groups selected from substituent (D), aroyl optionally substituted with one to three groups selected from substituent (C), heterocyclic-alkyl optionally substituted with one to three groups selected from substituent (C), aralkyl optionally substituted with one to three groups selected from substituent (C), arylsulfonyl optionally substituted with one to three groups selected from substituent (C), a heterocyclic group optionally substituted with one to four groups selected from substituent (D), —CONR$^7$R$^8$ [wherein R$^7$ and R$^8$ independently represent a hydrogen atom, lower alkyl optionally substituted with one to three groups selected from substituent (A), cycloalkyl optionally substituted with one to three groups selected from substituent (C), lower alkanoyl optionally substituted with one to three groups selected from substituent (B), aryl optionally substituted with one to four groups selected from substituent (D), a heterocyclic group optionally substituted with one to four groups selected from substituent (D), aralkyl optionally substituted with one to three groups selected from substituent (C), heterocyclic-alkyl optionally substituted with one to three groups selected from substituent (C) or aroyl optionally substituted with one to three groups selected from substituent (C), or R$^7$ and R$^8$ form a heterocyclic group together with the adjacent nitrogen atom, which is optionally substituted with one to three groups selected from substituent (C)], —NR$^9$R$^{10}$ [wherein R$^9$ and R$^{10}$ independently represent a hydrogen atom, lower alkylsulfonyl optionally substituted with one to three groups selected from substituent (B), lower alkyl optionally substituted with one to three groups selected from substituent (A), cycloalkyl optionally substituted with one to three groups selected from substituent (C), lower alkanoyl optionally substituted with one to three groups selected from substituent (B), aryl optionally substituted with one to four groups selected from substituent (D), a heterocyclic group optionally substituted with one to four groups selected from substituent (D), aralkyl optionally substituted with one to three groups selected from substituent (C), heterocyclic-alkyl optionally substituted with one to three groups selected from substituent (C), aroyl optionally substituted with one to three groups selected from substituent (C), or —CONR$^{11}$R$^{12}$ (wherein R$^{11}$ and R$^{12}$ have the same meanings as the above R$^7$ and R$^8$, respectively)], or —OR$^{13}$ [wherein R$^{13}$ represents lower alkyl optionally substituted with one to three groups selected from substituent (A), lower alkenyl optionally substituted with one to three groups selected from substituent (B), lower alkanoyl optionally substituted with one to three groups selected from substituent (B), aryl optionally substituted with one to four groups selected from substituent (D), a heterocyclic group optionally substituted with one to four groups selected from substituent (D), aralkyl optionally substituted with one to three groups selected from substituent (C), or heterocyclic-alkyl optionally substituted with one to three groups selected from substituent (C)]; and R$^{64}$ is a hydrogen atom, halogen, cyano, nitro, lower alkyl optionally substituted with one to three groups selected from substituent (A), lower alkenyl optionally substituted with one to three groups selected from substituent (B), lower alkynyl optionally substituted with one to three groups selected from substituent (B), lower alkoxy optionally substituted with one to three groups selected from substituent (B), cycloalkyl optionally substituted with one to three groups selected from substituent (C), lower alkanoyl optionally substituted with one to three groups selected from substituent (B), amino, lower alkylamino, di-lower alkylamino, carboxy, lower alkoxycarbonyl optionally substituted with one to three groups selected from substituent (B), aryloxy optionally substituted with one to three groups selected from substituent (C), aryl optionally substituted with one to four groups selected from substituent (D), aralkyl optionally substituted with one to three groups selected from substituent (C), or heterocyclic-alkyl optionally substituted with one to three groups selected from substituent (C);

wherein substituent (A) independently represents hydroxy, oxo, cyano, nitro, carboxy, carbamoyl, amino, hydroxyimino, lower alkoxyimino, halogen, lower alkoxy optionally substituted with one to three groups selected from substituent (a), cycloalkyl, lower alkanoyl, lower alkoxycarbonyl, lower alkylaminocarbonyl optionally substituted with one to three groups selected from substituent (a), di-lower alkylaminocarbonyl optionally substituted with one to three groups selected from substituent (a), lower alkylamino, di-lower alkylamino, or lower alkanoylamino optionally substituted with one to three groups selected from substituent (B);

substituent (B) independently represents hydroxy, cyano, nitro, carboxy, amino, halogen, lower alkoxy optionally substituted with one to three groups selected from substituent (c), cycloalkyl, lower alkanoyl, lower alkoxycarbonyl, lower alkylamino, or di-lower alkylamino;

substituent (C) independently represents hydroxy, halogen, nitro, cyano, amino, carboxy, carbamoyl, lower alkyl optionally substituted with one to three groups selected from substituent (a), lower alkoxy optionally substituted with one to three groups selected from substituent (a), aralkyloxy, lower alkylsulfonyl, cycloalkyl, lower alkoxycarbonyl, heterocyclic-carbonyl, lower alkylamino, di-lower alkylamino, lower alkanoyl, a heterocyclic group optionally substituted with one to three groups selected from substituent (d), heterocyclic-alkyl optionally substituted with one to three groups selected from substituent (d), or aryl optionally substituted with one to three groups selected from substituent (d);

substituent (D) independently represents hydroxy, halogen, nitro, cyano, amino, carboxy, carbamoyl, lower alkyl optionally substituted with one to three groups selected from substituent (e), lower alkenyl optionally substituted with one to three groups selected from substituent (f), lower alkoxy optionally substituted with one to three groups selected from substituent (a), aryloxy optionally substituted with one to three groups selected from substituent (d), aralkyloxy optionally substituted with one to three groups selected from substituent (d), heterocyclic-alkyloxy optionally substituted with one to three groups selected from substituent (d), lower alkylsulfonyl optionally substituted with one to three groups selected from substituent (a), cycloalkyl optionally substituted with one to three groups selected from substituent (a), lower alkoxycarbonyl optionally substituted with one to three groups selected from substituent (a), lower alkylaminocarbonyl optionally substituted with one to three groups selected from substituent (a), di-lower alkylaminocarbonyl optionally substituted with one to three groups selected from substituent (a), cycloalkylaminocarbonyl optionally substituted with one to three groups selected from substituent (a), lower alkylamino optionally substituted with one to three groups selected from substituent (a), di-lower alkylamino optionally substituted with one to three groups selected from substituent (a), lower alkylsulfonylamino optionally substituted with one to thee groups selected from substituent (a), arylsulfonylamino optionally substituted with one to three groups selected from substituent (d), lower alkanoylamino optionally substituted with one to three groups selected from substituent (a), aroylamino optionally substituted with one to three groups selected from substituent (d), lower alkylaminocarbonylamino optionally substituted with one to three groups selected from substituent (a), di-lower alkylaminocarbonylamino optionally substituted with one to three groups selected from substituent (a), lower alkanoyl optionally substituted with one to thee groups selected from substituent (a), a heterocyclic group optionally substituted with one to three groups selected from substituent (d), aryl optionally substituted with one to three groups selected from substituent (d), aralkyl optionally substituted with one to three groups selected from substituent (d), or heterocyclic-alkyl optionally substituted with one to three groups selected from substituent (d);

substituent (a) independently represents hydroxy, halogen, or lower alkoxy, substituent (c) independently represents hydroxy, or halogen;

substituent (d) independently represents hydroxy, cyano, halogen, lower alkyl, or lower alkoxy;

substituent (e) independently represents hydroxy, halogen, lower alkoxy, lower alkanoyl, aroyl, lower alkoxycarbonyl, carboxy, cyano, hydroxyimino, lower alkoxyimino, or —NR$^{14}$R$^{15}$ (wherein R$^{14}$ and R$^{15}$ independently represent a hydrogen atom, lower alkyl, lower alkanoyl or heterocyclic-alkyl); and substituent (f) independently represents hydroxy, halogen, lower alkoxy, lower alkanoyl, aroyl, lower alkoxycarbonyl, carboxy, or cyano} or a pharmaceutically acceptable salt thereof.

2. The benzene derivative according to claim 1, wherein $R^{2A}$ is phenyl substituted with one to four groups selected from substituent (D), or a pharmaceutically acceptable salt thereof.

3. The benzene derivative according to claim 1, wherein $R^{2A}$ is phenyl, or a pharmaceutically acceptable salt thereof.

4. The benzene derivative according to any of claims 1 to 3, wherein $R^{3A}$ and $R^{5A}$ are the same and are a hydrogen atom, lower alkanoyl optionally substituted with one to three groups selected from substituent (B), aroyl optionally substituted with one to three groups selected from substituent (C), lower alkenyl optionally substituted with one to three groups selected from substituent (B), lower alkylaminocarbonyl optionally substituted with one to three groups selected from substituent (B), di-lower alkylaminocarbonyl optionally substituted with one to three groups selected from substituent (B), lower alkoxycarbonyl optionally substituted with one to three groups selected from substituent (B), or heterocyclic-carbonyl, or a pharmaceutically acceptable salt thereof.

5. The benzene derivative according to any of claims 1 to 3, wherein $R^{3A}$ and $R^{5A}$ are hydrogen atoms, or a pharmaceutically acceptable salt thereof.

6. The benzene derivative according to any of claims 1 to 3, wherein nA is an integer of 1 to 5, or a pharmaceutically acceptable salt thereof.

7. A pharmaceutical composition comprising, as an active ingredient, the benzene derivative according to any of claims 1 to 3 or a pharmaceutically acceptable salt thereof together with a pharmaceutically acceptable carrier.

8. The benzene derivative according to claim 5, wherein $R^{6A}$ is halogen, lower alkyl optionally substituted with one to three groups selected from substituent (A), or lower alkanoyl optionally substituted with one to three groups selected from substituent (B), or a pharmaceutically acceptable salt thereof.

9. The benzene derivative according to claim 8, wherein nA is an integer of 1 to 5, and
$R^{1A}$ is hydroxy, carboxy, lower alkyl substituted with one to three groups selected from substituent (A), cycloalkyl optionally substituted with one to three groups selected from substituent (C), lower alkoxycarbonyl optionally substituted with one to three groups selected from substituent (B), heterocyclic-alkyl optionally substituted with one to three groups selected from substituent (C), a heterocyclic group optionally substituted with one to four groups selected from substituent (D), —CONR$^7$R$^8$, —NR$^9$R$^{10}$, or —OR$^{13}$, or a pharmaceutically acceptable salt thereof.

10. The benzene derivative according to claim 8, wherein nA is an integer of 1 to 5, and
$R^{1A}$ is a heterocyclic group optionally substituted with one to four groups selected from substituent (D), or a pharmaceutically acceptable salt thereof.

11. The benzene derivative according to claim 8, wherein nA is an integer of 1 to 5, and
$R^{1A}$ is an alicyclic heterocyclic group optionally substituted with one to four groups selected from substituent (D), or a pharmaceutically acceptable salt thereof.

12. The benzene derivative according to claim 5, wherein nA is an integer of 1 to 5,
$R^{6A}$ is ethyl, or acetyl, and
$R^{1A}$ is an alicyclic heterocyclic group optionally substituted with one to four groups selected from substituent (D), or a pharmaceutically acceptable salt thereof.

13. A pharmaceutical composition comprising, as an active ingredient, the benzene derivative according to claim 4 or a pharmaceutically acceptable salt thereof, together with a pharmaceutically acceptable carrier.

14. A pharmaceutical composition comprising, as an active ingredient, the benzene derivative according to claim 5 or a pharmaceutically acceptable salt thereof, together with a pharmaceutically acceptable carrier.

15. A pharmaceutical composition comprising, as an active ingredient, the benzene derivative according to claim 6 or a pharmaceutically acceptable salt thereof, together with a pharmaceutically acceptable carrier.

16. A pharmaceutical composition comprising, as an active ingredient, the benzene derivative according to claim 8 or a pharmaceutically acceptable salt thereof, together with a pharmaceutically acceptable carrier.

17. A pharmaceutical composition comprising, as an active ingredient, the benzene derivative according to claim 9 or a pharmaceutically acceptable salt thereof, together with a pharmaceutically acceptable carrier.

18. A pharmaceutical composition comprising, as an active ingredient, the benzene derivative according to claim 10 or a pharmaceutically acceptable salt thereof, together with a pharmaceutically acceptable carrier.

19. A pharmaceutical composition comprising, as an active ingredient, the benzene derivative according to claim 11 or a pharmaceutically acceptable salt thereof, together with a pharmaceutically acceptable carrier.

20. A pharmaceutical composition comprising, as an active ingredient, the benzene derivative according to claim 12 or a pharmaceutically acceptable salt thereof, together with a pharmaceutically acceptable carrier.

* * * * *

UNITED STATES PATENT AND TRADEMARK OFFICE
CERTIFICATE OF CORRECTION

PATENT NO. : 7,538,241 B2
APPLICATION NO. : 10/584234
DATED : May 26, 2009
INVENTOR(S) : Yushi Kitamura et al.

It is certified that error appears in the above-identified patent and that said Letters Patent is hereby corrected as shown below:

ON COVER PAGE AT (56) FOREIGN PATENT DOCUMENTS

"52151133" should read --52-151133--.

COLUMN 5

Line 10, "that;" should read --that:--; and
Line 59, "that;" should read --that:--.

COLUMN 6

Line 3, "Then" should read --then--.

COLUMN 14

Line 41, "alkanoyla" should read --alkanoyl,--.

COLUMN 77

Line 34, "to," should read --to--; and
Line 65, "1/10and" should read --1/10 and--.

COLUMN 80

Line 66, "1.8 mmol)-obtained" should read --1.8 mmol) obtained--.

COLUMN 87

Line 6, "APCI-MS" should read --¶APCI-MS--.

COLUMN 90

Line 7, "447 449" should read --447, 449--; and
Line 29, "380/382" should read --380, 382--.

UNITED STATES PATENT AND TRADEMARK OFFICE
CERTIFICATE OF CORRECTION

PATENT NO. : 7,538,241 B2
APPLICATION NO. : 10/584234
DATED : May 26, 2009
INVENTOR(S) : Yushi Kitamura et al.

It is certified that error appears in the above-identified patent and that said Letters Patent is hereby corrected as shown below:

COLUMN 97

Line 59, "0.65 8 mmol)" should read --0.658 mmol)--.

COLUMN 98

Line 13, "(276 MHz," should read --(270 MHz,--.

COLUMN 128

Line 25, "(s, 3H, 2.29" should read --(s, 3H) 2.29--;
Line 26, "s, 1H) m," should read --s, 1H),--; and
Line 38, "APCI-MS" should read --¶APCI-MS--.

COLUMN 129

Line 7, "9.38 br s, 1H)," should read --9.38 (br s, 1H),--.

COLUMN 131

Line 41, "-3-(methoxyethyl)-11,5-bis(meth-" should read
-- -3-(methoxyethyl)-1,5-bis(meth- --.

COLUMN 133

Line 29, "APCI-MS" should read --¶APCI-MS--.

COLUMN 135

Line 8, "(t J=7.3 Hz," should read --(t, J=7.3 Hz,--.

COLUMN 140

Line 35, "(53 mg, 18%)" should read --(53 mg, 18%).--.

UNITED STATES PATENT AND TRADEMARK OFFICE
CERTIFICATE OF CORRECTION

| | | |
|---|---|---|
| PATENT NO. | : 7,538,241 B2 | |
| APPLICATION NO. | : 10/584234 | |
| DATED | : May 26, 2009 | |
| INVENTOR(S) | : Yushi Kitamura et al. | |

It is certified that error appears in the above-identified patent and that said Letters Patent is hereby corrected as shown below:

COLUMN 141

Line 44, "(t, J=7.0 HZ," should read --(t, J=7.0 Hz,--.

COLUMN 146

Line 13, "step-1" should read --step 1--; and
Line 17, "for 11" should read --for 1--.

COLUMN 158

Line 9, "6.84 8s, 1H)," should read --6.84 (s, 1H),--.

COLUMN 161

Line 26, "N,N-dimethylfonnamide" should read --N,N-dimethylformamide--.

COLUMN 162

Line 39, "7.20 (&, J=8.0 Hz, 1H)," should read --7.20 (d, J=8.0 Hz, 1H),--.

COLUMN 164

Line 48, "concentrated acid" should read --concentrated hydrochloric acid--.

COLUMN 167

Line 43, "(Step 2) in" should read --(Step 2) ¶In--.

COLUMN 168

Line 12, "6.84 8s, 1H), 7.16-7.25 8m, 2H)," should read --6.84 (s, 1H),
    7.16-7.25 (m, 2H),--; and
Line 51, "88%)" should read --88%).--.

UNITED STATES PATENT AND TRADEMARK OFFICE
CERTIFICATE OF CORRECTION

| | | |
|---|---|---|
| PATENT NO. | : 7,538,241 B2 | |
| APPLICATION NO. | : 10/584234 | |
| DATED | : May 26, 2009 | |
| INVENTOR(S) | : Yushi Kitamura et al. | |

It is certified that error appears in the above-identified patent and that said Letters Patent is hereby corrected as shown below:

COLUMN 171

Line 40, "7.30-7.45 8m, 3H)." should read --7.30-7.45 (m, 3H).--; and
    Line 52, "7.24-7.50 8m, 5H);" should read --7.24-7.50 (m, 5H);--.

COLUMN 172

Line 26, "8m, 4H), 3.74 8s, 2H)," should read --(m, 4H), 3.74 (s, 2H),--.

COLUMN 173

Line 4, "2.38-2.65 8m," should read --2.38-2.65 (m,--; and
    Line 31, "3.24 8s, 3H)," should read --3.24 (s, 3H),--.

COLUMN 174

Line 59, "(12g, 97%" should read --(12g, 97%)--.

COLUMN 176

Line 18, "3.47 (S," should read --3.47 (s,--.

COLUMN 177

Line 18, "$CD_3OD$) 6, (ppm):" should read --$CD_3OD$) δ (ppm):--; and
    Line 45, "ESI-MS 416 $(M+NH_4)^+$ ." should read --ESI-MS (m/z): 416 $(M+NH_4)^+$.--.

COLUMN 178

Line 1, "cerium" should read --cesium--;
    Line 51, "2360-2.76 (m, 4H)," should read --2.36-2.76 (m, 4H),--; and
    Line 52, "6.34 8s, 1H)," should read --6.34 (s, 1H),--.

UNITED STATES PATENT AND TRADEMARK OFFICE
CERTIFICATE OF CORRECTION

PATENT NO. : 7,538,241 B2
APPLICATION NO. : 10/584234
DATED : May 26, 2009
INVENTOR(S) : Yushi Kitamura et al.

It is certified that error appears in the above-identified patent and that said Letters Patent is hereby corrected as shown below:

COLUMN 179

Line 6, "3018-3.38 (m, 6H)," should read --3.18-3.38 (m, 6H),--.

COLUMN 180

Line 28, "2.00-2.10 8m, 2H)," should read --2.00-2.10 (m, 2H),--.

COLUMN 181

Line 11, "ad" should read --and--.

COLUMN 188

Line 26, "6.66 mmol)" should read --0.66 mmol)--.

COLUMN 190

Line 39, "(t, J=7.8," should read --(td, J=7.8,--.

COLUMN 195

Line 61, "in)," should read --m),--.

COLUMN 196

Line 1, "preparative" should be deleted; and
Line 2, "through" should read --through preparative--.

COLUMN 202

Line 18, "ESI-MS" should read --¶ESI-MS--; and
Line 56, "374-(M+H)$^+$." should read --374 (M+H)$^+$.--.

UNITED STATES PATENT AND TRADEMARK OFFICE
CERTIFICATE OF CORRECTION

PATENT NO.         : 7,538,241 B2
APPLICATION NO. : 10/584234
DATED                  : May 26, 2009
INVENTOR(S)        : Yushi Kitamura et al.

It is certified that error appears in the above-identified patent and that said Letters Patent is hereby corrected as shown below:

COLUMN 203

Line 6, "APCI-MS" should read --¶APCI-MS--.

COLUMN 205

Line 2, "(about 111)" should read --(about 1/1)--; and
  Line 41, "liquid," should read --solution,--.

COLUMN 206

Line 17, "reduced-pressure." should read --reduced pressure.--.

COLUMN 208

Line 27, "4.99 88s, 1H)," should read --4.99 (s, 1H),--; and
  Line 51, "(260' mg," should read --(260 mg,--.

COLUMN 209

Line 42, "ethyl, acetate." should read --ethyl acetate.--; and
  Line 50, "6.85 8s, 1H)," should read --6.85 (s, 1H),--.

COLUMN 214

Line 48, "(chloroform/methanol/water 100/10/1)" should read
       --(chloroform/methanol/water = 100/10/1)--.

COLUMN 222

Line 53, "half a" should read --a half--; and
  Line 65, "4.51 8s, 2H), 4.58 8s, 2H), 5.15 8s, 2H)," should read
       --4.51 (s, 2H), 4.58 (s, 2H), 5.15 (s, 2H),--.

UNITED STATES PATENT AND TRADEMARK OFFICE
CERTIFICATE OF CORRECTION

PATENT NO. : 7,538,241 B2
APPLICATION NO. : 10/584234
DATED : May 26, 2009
INVENTOR(S) : Yushi Kitamura et al.

It is certified that error appears in the above-identified patent and that said Letters Patent is hereby corrected as shown below:

COLUMN 224

Line 33, "3.48 8s, 3H)," should read --3.48 (s, 3H),--.

COLUMN 227

Line 47, "3.40 8s, 3H)," should read --3.40 (s, 3H),--.

COLUMN 230

Line 13, "3 hour." should read --3 hours.--.

COLUMN 231

Line 50, "7.50 (dd, J=0.8, 1.8 Hz," should read --7.50 (dd, J=0.8, 1.8 Hz, 1H).--.

COLUMN 232

Line 15, "a w a y" should read --away--.

COLUMN 233

Line 61, "245," should read --Example 245,--.

COLUMN 235

Line 65, "(270 MHz, $CDCl_3$) (ppm):" should read --(270 MHz, $CDCl_3$) $\delta$ (ppm):--.

COLUMN 241

Line 25, "partitioning" should read --preparative--; and
Line 65, "(270 MHz, CDCl3) (ppm):" should read --(270 MHz, CDCl3) $\delta$ (ppm):--.

UNITED STATES PATENT AND TRADEMARK OFFICE
CERTIFICATE OF CORRECTION

PATENT NO. : 7,538,241 B2
APPLICATION NO. : 10/584234
DATED : May 26, 2009
INVENTOR(S) : Yushi Kitamura et al.

It is certified that error appears in the above-identified patent and that said Letters Patent is hereby corrected as shown below:

COLUMN 247

Line 66, "APCIMS" should read --APCI-MS--.

COLUMN 248

Line 12, "4 h ours." should read --4 hours.--; and
Line 53, "silica" should read --silica gel--.

COLUMN 252

Line 36, "liquid," should read --solution,--; and
Line 37, "liquid," should read --solution,--.

COLUMN 254

Line 22, "(10 g, 47 mmol)" should read --(10g, 47 mmol)--.

COLUMN 259

Line 60, "mg, 59)" should read --mg, 59 mmol)--.

COLUMN 269

Line 44, "obtained the" should read --obtained in the--.

COLUMN 270

Line 14, "obtained the" should read --obtained in the--.

COLUMN 272

Line 66, "APCI-MS" should read --¶APCI-MS--.

UNITED STATES PATENT AND TRADEMARK OFFICE
CERTIFICATE OF CORRECTION

PATENT NO.       : 7,538,241 B2
APPLICATION NO.  : 10/584234
DATED            : May 26, 2009
INVENTOR(S)      : Yushi Kitamura et al.

It is certified that error appears in the above-identified patent and that said Letters Patent is hereby corrected as shown below:

COLUMN 282

Line 57, "(200 ng," should read --(200 mg,--.

COLUMN 292

Line 21, "APCI-MS m/z 352 $(M-H)^-$." should read --APCI-MS (m/z) 352 $(M-H)^-$.--.

COLUMN 293

Line 32, "APCI-MS m/z 403 $(M+H)^+$." should read --APCI-MS (m/z) 403 $(M+H)^+$.--.

COLUMN 294

Line 8, "that;" should read --that:--.

COLUMN 297

Line 35, "claim 8 ," should read --claim 8,--.

Signed and Sealed this

Seventeenth Day of November, 2009

David J. Kappos
*Director of the United States Patent and Trademark Office*